US009175315B2

(12) United States Patent
Anton et al.

(10) Patent No.: US 9,175,315 B2
(45) Date of Patent: Nov. 3, 2015

(54) PRODUCTION OF ALCOHOL ESTERS AND IN SITU PRODUCT REMOVAL DURING ALCOHOL FERMENTATION

(75) Inventors: Douglas Robert Anton, Wilmington, DE (US); Stephane Francois Bazzana, Wilmington, DE (US); Keith H Burlew, Middletown, DE (US); Jelena Cirakovic, Bel Air, MD (US); Robert Dicosimo, Chadds Ford, PA (US); Bruce A Diner, Chadds Ford, PA (US); Michael Charles Grady, Oaklyn, NJ (US); Brian Michael Roesch, Middletown, DE (US); Francis J Woerner, Bear, DE (US)

(73) Assignee: BUTAMAX ADVANCED BIOFUELS LLC, Wilmington, DE (US)

( * ) Notice: Subject to any disclaimer, the term of this patent is extended or adjusted under 35 U.S.C. 154(b) by 35 days.

(21) Appl. No.: 13/162,868

(22) Filed: Jun. 17, 2011

(65) Prior Publication Data

US 2012/0156738 A1    Jun. 21, 2012

Related U.S. Application Data

(60) Provisional application No. 61/356,290, filed on Jun. 18, 2010, provisional application No. 61/368,451, filed on Jul. 28, 2010, provisional application No. 61/368,436, filed on Jul. 28, 2010, provisional application No. 61/368,444, filed on Jul. 28, 2010, provisional application No. 61/368,429, filed on Jul. 28, 2010, provisional application No. 61/379,546, filed on Sep. 2, 2010, provisional application No. 61/440,034, filed on Feb. 7, 2011.

(51) Int. Cl.

| C12P 7/62 | (2006.01) |
|---|---|
| C12P 7/22 | (2006.01) |
| C12P 7/16 | (2006.01) |
| C12N 1/00 | (2006.01) |
| C12N 1/12 | (2006.01) |
| C07H 21/04 | (2006.01) |
| B01D 3/00 | (2006.01) |
| B01D 21/26 | (2006.01) |
| C07C 29/86 | (2006.01) |
| C11B 1/02 | (2006.01) |
| C11B 13/00 | (2006.01) |
| C12M 1/00 | (2006.01) |
| C12P 7/64 | (2006.01) |
| C12P 7/18 | (2006.01) |

(52) U.S. Cl.

CPC . *C12P 7/16* (2013.01); *B01D 3/002* (2013.01); *B01D 21/26* (2013.01); *C07C 29/86* (2013.01); *C11B 1/025* (2013.01); *C11B 13/00* (2013.01); *C12M 1/00* (2013.01); *C12M 21/12* (2013.01); *C12M 45/04* (2013.01); *C12M 45/09* (2013.01); *C12P 7/18* (2013.01); *C12P 7/6418* (2013.01); *B01D 21/262* (2013.01); *Y02E 50/10* (2013.01); *Y02E 50/16* (2013.01); *Y02E 50/17* (2013.01); *Y02W 30/74* (2015.05)

(58) Field of Classification Search

None
See application file for complete search history.

(56) References Cited

U.S. PATENT DOCUMENTS

| 5,036,005 A | 7/1991 | Tedder |
|---|---|---|
| 5,071,754 A | 12/1991 | Walkup et al. |
| 5,514,583 A | 5/1996 | Picataggio et al. |
| 5,710,030 A | 1/1998 | Anderson |
| 5,712,133 A | 1/1998 | Picataggio et al. |
| 5,723,639 A | 3/1998 | Datta et al. |
| 5,780,275 A | 7/1998 | Oda |
| 6,242,015 B1 | 6/2001 | Egi et al. |
| 6,291,708 B1 | 9/2001 | Cockrem |
| 6,398,707 B1 | 6/2002 | Wu et al. |
| 6,509,051 B1 | 1/2003 | Wills |
| 6,613,551 B2 | 9/2003 | Davies et al. |
| 6,646,146 B1 | 11/2003 | Sinnema et al. |
| 6,664,413 B1 | 12/2003 | Cockrem et al. |
| 6,703,227 B2 | 3/2004 | Jakel et al. |
| 6,732,454 B2 | 5/2004 | Anderson et al. |
| 6,766,595 B2 | 7/2004 | Anderson |
| 6,996,917 B2 | 2/2006 | Anderson |
| 7,083,954 B2 | 8/2006 | Jakel et al. |
| 7,223,575 B2 | 5/2007 | Zhang et al. |

(Continued)

FOREIGN PATENT DOCUMENTS

| CN | 1248617 A | 3/2000 |
|---|---|---|
| CN | 101058740 A | 10/2007 |

(Continued)

OTHER PUBLICATIONS

Ishizaki et al. Extractive Acetone-Butanol-Ethanol Fermentation Using Methylated Crude Palm Oil as Extractant in Batch Culture of Clostridium Saccharo perbutylacetonicum NI-4 (ATCC 13564), Journal of Bioscience and Bioengineering, (1999), 87(3): 352-356.*

(Continued)

Primary Examiner — Iqbal H Chowdhury

(57) ABSTRACT

An alcohol fermentation process and composition that includes production of alcohol esters by esterification of product alcohol in a fermentation medium with a carboxylic acid (e.g., fatty acid) and a catalyst (e.g., lipase) capable of esterifying the product alcohol, such as butanol, with the carboxylic acid to form the alcohol esters. The alcohol esters can be extracted from the fermentation medium, and the product alcohol recovered from the alcohol esters. The carboxylic acid can also serve as an extractant for removal of the alcohol esters from the fermentation medium.

19 Claims, 8 Drawing Sheets

(56) References Cited

U.S. PATENT DOCUMENTS

| | | |
|---|---|---|
| 7,378,549 B2 | 5/2008 | Ayoub |
| 7,501,062 B2 | 3/2009 | Den Boestert et al. |
| 7,507,562 B2 | 3/2009 | Verser et al. |
| 7,612,221 B2 | 11/2009 | Haas et al. |
| 7,666,282 B2 | 2/2010 | Sylvester et al. |
| 7,741,119 B2 | 6/2010 | Viitanen et al. |
| 7,799,544 B2 | 9/2010 | Schorken et al. |
| 8,076,110 B2 | 12/2011 | Chou |
| 8,373,008 B2 | 2/2013 | Grady et al. |
| 8,373,009 B2 | 2/2013 | Grady et al. |
| 8,409,834 B2 | 4/2013 | Burlew et al. |
| 8,426,173 B2 | 4/2013 | Bramucci et al. |
| 8,426,174 B2 | 4/2013 | Bramucci et al. |
| 8,460,439 B2 | 6/2013 | Parten |
| 8,476,047 B2 | 7/2013 | Burlew et al. |
| 8,557,540 B2 | 10/2013 | Burlew et al. |
| 8,563,788 B2 | 10/2013 | Grady et al. |
| 8,569,552 B2 | 10/2013 | Grady et al. |
| 8,574,406 B2 | 11/2013 | Grady et al. |
| 8,617,861 B2 | 12/2013 | Grady et al. |
| 8,628,643 B2 | 1/2014 | Grady et al. |
| 8,697,404 B2 | 4/2014 | Anton et al. |
| 8,759,044 B2 | 6/2014 | Dicosimo et al. |
| 8,765,425 B2 | 7/2014 | Dicosimo et al. |
| 8,828,695 B2 | 9/2014 | Grady et al. |
| 8,865,443 B2 | 10/2014 | Burlew et al. |
| 8,906,204 B2 | 12/2014 | Xu |
| 8,968,522 B2 | 3/2015 | Xu et al. |
| 8,968,523 B2 | 3/2015 | Xu et al. |
| 8,969,055 B2 | 3/2015 | Grady et al. |
| 9,012,190 B2 | 4/2015 | Dauner et al. |
| 2001/0004462 A1 | 6/2001 | Sugiura et al. |
| 2004/0063184 A1 | 4/2004 | Grichko |
| 2005/0084941 A1* | 4/2005 | Abe et al. .............. 435/135 |
| 2006/0024801 A1 | 2/2006 | Holtzapple et al. |
| 2007/0031918 A1 | 2/2007 | Dunson et al. |
| 2007/0077635 A1 | 4/2007 | Brunner et al. |
| 2007/0092957 A1 | 4/2007 | Donaldson et al. |
| 2007/0259410 A1 | 11/2007 | Donaldson et al. |
| 2007/0292927 A1 | 12/2007 | Donaldson et al. |
| 2008/0051592 A1 | 2/2008 | McNeff et al. |
| 2008/0113419 A1 | 5/2008 | Abo et al. |
| 2008/0153143 A1 | 6/2008 | Schorken et al. |
| 2008/0182308 A1 | 7/2008 | Donaldson et al. |
| 2008/0199924 A1 | 8/2008 | Holm et al. |
| 2008/0261230 A1 | 10/2008 | Liao et al. |
| 2008/0271364 A1 | 11/2008 | Wiesman et al. |
| 2008/0274526 A1 | 11/2008 | Bramucci et al. |
| 2008/0289248 A1 | 11/2008 | Gao |
| 2008/0293109 A1 | 11/2008 | Berka et al. |
| 2009/0056201 A1 | 3/2009 | Morgan |
| 2009/0133322 A1 | 5/2009 | Basheer et al. |
| 2009/0163376 A1 | 6/2009 | Li et al. |
| 2009/0171129 A1 | 7/2009 | Evanko et al. |
| 2009/0203098 A1 | 8/2009 | Verser |
| 2009/0203099 A1 | 8/2009 | Caimi et al. |
| 2009/0246846 A1 | 10/2009 | Viitanen et al. |
| 2009/0269823 A1 | 10/2009 | Bramucci et al. |
| 2009/0305363 A1 | 12/2009 | Anthony et al. |
| 2009/0305370 A1 | 12/2009 | Grady et al. |
| 2010/0043281 A1 | 2/2010 | DeAngelis |
| 2010/0058649 A1 | 3/2010 | Bootsma |
| 2010/0071259 A1 | 3/2010 | Hu et al. |
| 2010/0081154 A1 | 4/2010 | Flint et al. |
| 2010/0092603 A1 | 4/2010 | Bruinsma et al. |
| 2010/0124773 A1 | 5/2010 | Yang |
| 2010/0143995 A1 | 6/2010 | Erdner-Tindall et al. |
| 2010/0146843 A1 | 6/2010 | Dumenil |
| 2010/0146844 A1 | 6/2010 | Dumenil |
| 2010/0147771 A1 | 6/2010 | McNeff et al. |
| 2010/0159538 A1 | 6/2010 | Both et al. |
| 2010/0197519 A1 | 8/2010 | Li et al. |
| 2010/0199548 A1 | 8/2010 | DelCardayre et al. |
| 2010/0209968 A1 | 8/2010 | Akers |
| 2010/0221802 A1 | 9/2010 | Grady et al. |
| 2010/0234458 A1 | 9/2010 | Dubreucq et al. |
| 2011/0097773 A1 | 4/2011 | Grady et al. |
| 2011/0124060 A1 | 5/2011 | Anthony et al. |
| 2011/0136193 A1 | 6/2011 | Grady et al. |
| 2011/0244536 A1 | 10/2011 | Nagarajan |
| 2011/0294179 A1 | 12/2011 | Grady et al. |
| 2011/0312044 A1 | 12/2011 | Anton et al. |
| 2011/0312053 A1 | 12/2011 | Burlew et al. |
| 2012/0208246 A1 | 8/2012 | Anton et al. |
| 2013/0164795 A1 | 6/2013 | Lowe et al. |
| 2013/0217060 A1 | 8/2013 | Bramucci et al. |
| 2013/0224728 A1 | 8/2013 | Bramucci et al. |
| 2013/0252297 A1 | 9/2013 | Parten |
| 2013/0295661 A1 | 11/2013 | Roesch et al. |
| 2013/0309738 A1 | 11/2013 | Barr et al. |
| 2014/0018581 A1 | 1/2014 | Grady et al. |
| 2014/0024064 A1 | 1/2014 | Burlew et al. |
| 2014/0073021 A1 | 3/2014 | Bazzana et al. |
| 2014/0073820 A1 | 3/2014 | Bazzana et al. |
| 2014/0093931 A1 | 4/2014 | Dauner et al. |
| 2014/0094630 A1 | 4/2014 | Anton et al. |
| 2014/0099688 A1 | 4/2014 | Grady et al. |
| 2014/0106419 A1 | 4/2014 | Bazzana et al. |
| 2014/0142352 A1 | 5/2014 | Dauner et al. |
| 2014/0162344 A1 | 6/2014 | Dicosimo et al. |
| 2014/0178529 A1 | 6/2014 | Anton et al. |
| 2014/0234929 A1 | 8/2014 | Barr et al. |
| 2014/0256020 A1 | 9/2014 | Dicosimo et al. |
| 2014/0273127 A1 | 9/2014 | Fuchs et al. |
| 2014/0273130 A1 | 9/2014 | Anthony et al. |
| 2014/0303408 A1 | 10/2014 | Zaher |
| 2014/0311889 A1 | 10/2014 | Zaher et al. |
| 2014/0363865 A1 | 12/2014 | Burlew et al. |
| 2015/0010975 A1 | 1/2015 | Burlew et al. |
| 2015/0010984 A1 | 1/2015 | Bhalla et al. |
| 2015/0060259 A1 | 3/2015 | Xu et al. |

FOREIGN PATENT DOCUMENTS

| | | |
|---|---|---|
| CN | 101285078 A | 10/2008 |
| CN | 101412989 A | 4/2009 |
| CN | 101532038 A | 9/2009 |
| DE | 10231029 A1 | 1/2003 |
| DE | 60317699 T2 | 10/2008 |
| EP | 0216221 B1 | 4/1987 |
| EP | 0305901 A2 | 6/1988 |
| EP | 0614983 A2 | 9/1994 |
| EP | 0789079 A2 | 8/1997 |
| EP | 1775344 A2 | 4/2007 |
| EP | 1556475 B1 | 11/2007 |
| EP | 1905821 A1 | 4/2008 |
| EP | 2189535 A1 | 5/2010 |
| FR | 2831886 A1 | 5/2003 |
| GB | 2146638 A | 4/1985 |
| IN | 201474 A1 | 2/2007 |
| IT | 1337648 B1 | 1/2007 |
| JP | 1986192291 | 8/1986 |
| JP | 1997071594 | 3/1997 |
| JP | 2009106274 | 5/2009 |
| KR | 20100097543 A | 9/2010 |
| WO | 9528476 A1 | 10/1995 |
| WO | 9911752 A1 | 3/1999 |
| WO | 0005395 A1 | 2/2000 |
| WO | 2004092392 A2 | 10/2004 |
| WO | 2005014765 A1 | 2/2005 |
| WO | 2005077485 A1 | 8/2005 |
| WO | 2007050671 A2 | 5/2007 |
| WO | 2007130521 A2 | 11/2007 |
| WO | 2008092207 A1 | 8/2008 |
| WO | 2008111941 A2 | 9/2008 |
| WO | 2008125574 A1 | 10/2008 |
| WO | 2009009320 A1 | 1/2009 |
| WO | 2009009322 A1 | 1/2009 |
| WO | 2009009323 A1 | 1/2009 |
| WO | 2009009391 A9 | 1/2009 |
| WO | 2009029344 A1 | 3/2009 |
| WO | 2009042950 A1 | 4/2009 |
| WO | 2009063296 A2 | 5/2009 |
| WO | 2009079213 A2 | 6/2009 |

(56) References Cited

FOREIGN PATENT DOCUMENTS

| | | |
|---|---|---|
| WO | 2009100434 A1 | 8/2009 |
| WO | 2009149270 A2 | 12/2009 |
| WO | 2010005391 A8 | 1/2010 |
| WO | 2010021711 A1 | 2/2010 |
| WO | 2010022090 A1 | 2/2010 |
| WO | 2010043013 A2 | 4/2010 |
| WO | 2010049491 A1 | 5/2010 |
| WO | 2010057996 A2 | 5/2010 |
| WO | 2010063402 | 5/2010 |
| WO | 2010075241 A1 | 7/2010 |

OTHER PUBLICATIONS

Akada et al., "PCR-mediated seamless gene deletion and marker recycling in saccharomyces cerevisiae", Yeast (2006) 23, pp. 399-405.
Bellion et al., Microb. Growth C1 Compd., [Int. Symp.], 7th (1993), 415 32, Editor(s): Murrell, J. Collin; Kelly, Don P. Publisher: Intercept, Andover, UK.
Bligh et al., A Rapid Method of Total Lipid Extraction and Purification, Canadian Journal of Biochemistry and Physiology, 1959, 911-917, 37.
Barros et al., Integration of Enzyme Catalysis in an Extraction Fermentation Process, Studies in Organic Chemistry 29, 1986.
Chen et al., Regeneration of Immobilized Candida Antarctica Lipase for Transesterification, Journal of Bioscience and Bioengineering, 2003, 466-469, 95 (5).
Deng et al., Enzymatic Production of Alkyl Esters Through Alcoholysis: A Critical Evaluation of Lipases and Alcohols, 2005, 341, 82 (5).
Elias et al., Role of Hydrodynamic Shear on Activity and Structure of Proteins, Advances in Biochemical Engineering/Biotechnology, 1998, 59.
Enfors et al., Physiological Responses to Mixing in Large Scale Bioreactors, Journal of Biotechnology, 2001, 175-187, 85.
Feldmann et al., Pentose Metalbolism in Zymomonas Mobilis Wild-type and Recombinant Strains, Applied Microbiology and Biotechnology, 1992, 354-361, 38.
Ghadge et al, Enzyme deactiviation in a Bubble Column, a Stirred Vessel and an Inclined Plane, Chemical Engineering Science, 2003, 58, 5125-5134.
Hahnai et al., Engineered Synthetic Pathway for Isopropanol Production in *Escherichia coli*, Applied and Environmental Microbiology, 2007, 7814-7818, 73(24).
Horton et al., Engineering Hybrid Genes without the use of Restriction Enzymes: Gene Splicing by Overlap Extension, Gene, 1989, 61-68, 77.
Iso et al., Production of Biodiesel Fuel from Triglycerides and Alcohol Using Immobolized Lipase, Journal of Molecular Catalysis B: Enzymatic, 2001, 53-58, 16.
Kalscheuer et al., Microdiesel: *Escherichia coli* Engineered for Fuel Production, Microbiology, 2006, 2529-2536, 152.
Kim et al., Extractive Recovery of Products from Fermentation Broths, Biotechnology and Bioprocess Engineering, 1999, 1-11, 4.
Lara et al., Potential Application of Waste Activated Bleaching Earth on the Production of Fatty Acid Alkyl Esters using Candida Cylindracea Lipase in organic Solvent System, Enzyme and Microbial Technology, 34 (2004) 270-277.
Lee et al., The Kinetics and Mechanism of Shear Inactivation of Lipase from Candida Cylindracea, Biotechnology and Bioengineering, 1989, 183-190, 33.
Leung et al, A Review on Biodiesel Production using Catalyzed Transesterification, Applied Energy, 2010, 1083-1095, 87.
Lynd et al., Microbial Cellulose Utilization: Fundamentals and Biotechnology, Microbiology and Molecular Biology Reviews, 2002, 506-577, 66(3).
Malinowski, Two-phase Bioreactors in Fermentation Technology, Biotechnology Advances, 2001, 525-538, 19.
Ohta et al., Genetic Improvement of *Escherichia coli* for Ethanol Production: Chromosomal Integration of Zymomonas mobilis Genes Encoding Pyruvate Decarboxylase and Alcohol Dehydrogenase II, Applied and Environmental Microbiology, 1991, 893-900, 57(4).
Oliveira et al., Production and Extractive Biocatalysis of Ethanol Using Microencapsulated Yeast Cells and Lipase System, Journal of Chemical Technology and Biotechnology, 1991, 219-225, 52.
Oliveira et al., Immobilization of Saccharomyces cerevisiae Cells and Rhizomucor miehi Lipase for the Production and Extractive Biocatalysis of Ethanol, Bioprocess Engineering, 1997, 349-353, 16.
Oliveira et al., Improvement f Alcoholic Fermentations by Simultaneous Extraction and Enzymatic Esterification of Ethanol, Journal of Molecular Catalysis B: Enzymatic, 1998, 29-33, 5.
Oliveira et al., Effect of extraction and Enzymatic Esterification of Ethanol on glucose Consumption by Two Saccharomyces cerevisiae Strains: A comparative study, Journal of Chemical Technology and Biotechnology, 2001, 285-290, 76.
Ognajanovic et al, Lipases as Biocatalysts for Biodiesel Production, Hemijska Industria, 2010, 1-8, 64(1) (Abstract Only).
Rothstein, Targeting, Disruption, Replacement, and Allele Rescue: Integrative DNA Transformation in Yeast, Methods in Enzymology, 1991, 281-301, 194.
Rodrigues et al., Enzymatic Synthesis of Biodiesel from Transesterification Reactions of Vegetable Oils and Short Chain Alcohols, Journal of the American Oil Chemists Society, 2008, 925-930, 85(10).
Ross et al., Organic Solvent Functional Group Effect on Enzyme Inactivation by the Interfacial Mechanism, Journal of Molecular Catalysis B: Enzymatic, 2000, 183-192, 8.
Roffler, Extractive fermentation—Lactic Acid and Acetone/Butanol Production, University of California dissertation 1986.
Saravanan et al., An Experimental Comparison of Transesterification Process with Different Alcohols using Acid Catalysts, Biomass and Bioenergy, 2010, 999-1005, 34.
Shen et al., Metabolic Engineering of *Escherichia coli* for 1-butanol and 1-propanol Production via the keto-acid Pathways, Metabolic Engineering, 2008, 312-320, 10.
Schugerl, Integrated Processing of Biotechnology Products, Biotechnology Advances, 2000, 581-599, 18.
Singh et al., American Society of Agricultural Engineers, 1998, 1775-1777, 41(6).
Stahmann et al., Regulation and Properties of a Fungal Lipase Showing Interfacial Inactivation by Gas Bubbles, or Droplets of Lipid or Fatty Acid, European Journal of Biochemistry, 1997, 220-225, 244.
Sulter et al., Proliferation and Metabolic Significance of Peroxisomes in Candida Boidinii during growth on D-alanine or oleic acid as the Sole Carbon Source, Archives of Microbiology, 1990, 485-489, 153.
Talukder et al., Two-step Lipase Catalysis for Production of Biodiesel, Biochemical Engineering Journal, 2010, 207-212, 49.
Van Dijken et al., An Interlaboratory Comparison of Physiological and Genetic Properties of Four Saccharomyces Cerevisiae Strains, Enzyme and Microbial Technology, 2000, 706-714, 26.
Van Hoek et al., Fermentative Capacity in High-Cell-Density Fed-Batch Cultures of Baker's Yeast, Biotechnology and Bioengineering, 2000, 517-523, 68(5).
Underwood et al., Flux through Citrate synthase Limits the Growth of Ethanlogenic *Escherichia coli* KO11 during Xylose Fermentation, Applied and Environmental Microbiology, 2002, 1071-1081, 68(3).
Zhang et al., Metabolic Engineering of a Pentose Metabolism Pathway in Ethanologenic Zymomonas Mobilis, Science, 1995, 24, 267.
Narasimharao et al., Catalysts in Production of Biodiesel: A Review, Journal of Biobased Materials and Bioenergy, 2007, 19-30, 1(1).
Methods in Yeast Genetics, 2005, Cold Spring Harbor Laboratory Press, Cold Spring Harbor, NY, pp. 201-202.
Patil et al., Lipase Deactivation at Gas-Liquid Interface and Its Subsequent Reactivation, AIChE Journal, 2000, 1280-1283, 46.
Barros et al., Production of ethanol by immobilized saccharomyces bayanus in an extractive fermentation system, Biotechnology and Bioengineering, vol. XXIX, pp. 1097-1104 (1987).
International Search Report and Written Opinion of copending PCT/US2011/040856 mailed Dec. 29, 2011.
U.S. Appl. No. 13/163,243, filed Jun. 17, 2011.
U.S. Appl. No. 13/227,016, filed Sep. 7, 2011.
U.S. Appl. No. 13/161,168, filed Jun. 15, 2011.

(56) References Cited

OTHER PUBLICATIONS

Groot, et al., Technologies for Butanol Recovery Integrated with Fermentation, Process Biochemistry 27:61-75, 1992.

Gupta, et al., Bacterial lipases: an overview of production, purification and biochemical properties, Appl. Microbiol. Biotechnol. 64:763-781, 2004.

Roffler, et al., In-situ recovery of butanol during fermentation, part 1: Batch extractive fermentation, Bioprocess Engineering 2:1-12, 1987.

Yoo, et al., Enzymatic Synthesis of Sugar Fatty Acid Esters, J. Ind. Eng. Chem. 13:1-6, 2007.

Mu et al., "A Combined Bioprocess of Biodiesel Production by Lipase With Microbial Production of 1,3-propanediol by Klebsiella pneumoniae", Biochemical Engineering Journal 40 (2008) 537-541.

U.S. Pat. No. 8,487,149; entitled "Renewable Compositions"; including Inter Partes Review (IPR2014-00144), 2013.

U.S. Appl. No. 13/326,660; entitled "Enzymatic Production of Alcohol Esters for Recovery of Diols Produced by Fermentation"; Dec. 15, 2011.

U.S. Appl. No. 13/193,147, filed Jul. 28, 2011.

U.S. Appl. No. 13/326,660, filed Dec. 15, 2011.

9.9.7 Corn Wet Milling; US Environmental Protection Agency; <http://www.epa.gov/ttnchie1/ap42/ch09/final/c9s09-7.pdf>; Feb. 1, 2001; pp. 9.9.7-1-9.

* cited by examiner

PRODUCTION OF ALCOHOL ESTERS AND IN SITU PRODUCT REMOVAL DURING ALCOHOL FERMENTATION

This application claims the benefit of U.S. Provisional Application No. 61/356,290, filed on Jun. 18, 2010; U.S. Provisional Application No. 61/368,451, filed on Jul. 28, 2010; U.S. Provisional Application No. 61/368,436, filed on Jul. 28, 2010; U.S. Provisional Application No. 61/368,444, filed on Jul. 28, 2010; U.S. Provisional Application No. 61/368,429, filed on Jul. 28, 2010; U.S. Provisional Application No. 61/379,546, filed on Sep. 2, 2010; and U.S. Provisional Application No. 61/440,034, filed on Feb. 7, 2011; the entire contents of which are all herein incorporated by reference.

The Sequence Listing associated with this application is filed in electronic form via EFS-Web and hereby incorporated by reference into the specification in its entirety.

FIELD OF THE INVENTION

The present invention relates to the fermentative production of alcohols including ethanol and butanol, and all related co-products, and processes for improving alcohol fermentation employing in situ product removal methods.

BACKGROUND OF THE INVENTION

Alcohols have a variety of applications in industry and science such as a beverage (i.e., ethanol), fuel, reagents, solvents, and antiseptics. For example, butanol is an alcohol that is an important industrial chemical and drop-in fuel component with a variety of applications including use as a renewable fuel additive, as a feedstock chemical in the plastics industry, and as a food-grade extractant in the food and flavor industry. Accordingly, there is a high demand for alcohols such as butanol, as well as for efficient and environmentally-friendly production methods.

Production of alcohol utilizing fermentation by microorganisms is one such environmentally-friendly production method. In the production of butanol, in particular, some microorganisms that produce butanol in high yields also have low butanol toxicity thresholds. Removal of butanol from the fermentation vessel as it is being produced is a means to manage these low butanol toxicity thresholds. Thus, there is a continuing need to develop efficient methods and systems for producing butanol in high yields despite low butanol toxicity thresholds of the butanol-producing microorganisms in the fermentation medium.

In situ product removal (ISPR) (also referred to as extractive fermentation) can be used to remove butanol (or other fermentative alcohol) from the fermentation vessel as it is produced, thereby allowing the microorganism to produce butanol at high yields. One ISPR method for removing fermentative alcohol that has been described in the art is liquid-liquid extraction (U.S. Patent Application Publication No. 2009/0305370). In general, with regard to butanol fermentation, the fermentation medium which includes the microorganism is contacted with an organic extractant at a time before the butanol concentration reaches a toxic level. The organic extractant and the fermentation medium form a biphasic mixture. The butanol partitions into the organic extractant phase decreasing the concentration of butanol in the aqueous phase containing the microorganism, thereby limiting the exposure of the microorganism to the inhibitory butanol. In order to be technically and economically viable, liquid-liquid extraction requires contact between the extractant and the fermentation broth for efficient mass transfer of the product alcohol into the extractant; phase separation of the extractant from the fermentation broth (during an/or after fermentation); efficient recovery and recycle of the extractant; and minimal decrease of the partition coefficient of the extractant over a long-term operation.

The extractant can become contaminated over time with each recycle, for example, by the build-up of lipids present in the biomass that is fed to the fermentation vessel as feedstock of hydrolyzable starch. As an example, during the conversion of glucose to butanol, a liquified corn mash loaded to a fermentation vessel at 30 wt % dry corn solids can result in a fermentation broth that contains about 1.2 wt % corn oil generated by simultaneous saccharification and fermentation (with saccharification of the liquified mash occurring during fermentation by the addition of glucoamylase to produce glucose). The dissolution of the corn oil lipids into oleyl alcohol (OA) serving as an extractant during ISPR can result in build-up of lipid concentration with each OA recycle decreasing the partition coefficient for the product alcohol in OA as the lipid concentration in OA increases with each recycle of OA.

In addition, the presence of the undissolved solids during extractive fermentation can negatively affect the efficiency of the alcohol production. For example, the presence of the undissolved solids may lower the mass transfer coefficient inside the fermentation vessel, impede phase separation in the fermentation vessel, result in the accumulation of corn oil from the undissolved solids in the extractant leading to reduced extraction efficiency over time, increase the loss of solvent because it becomes trapped in solids and ultimately removed as Dried Distillers' Grains with Solubles (DDGS), slow the disengagement of extractant drops from the fermentation broth, and/or result in a lower fermentation vessel volume efficiency.

Several approaches for reducing the degradation of the partition coefficient of the extractant used in extractive fermentation have included wet milling, fractionation, and removal of solids. Wet milling is an expensive, multi-step process that separates a biomass (e.g., corn) into its key components (germ, pericarp fiber, starch, and gluten) in order to capture value from each co-product separately. This process gives a purified starch stream; however, it is costly and includes the separation of the biomass into its non-starch components which is unnecessary for fermentative alcohol production. Fractionation removes fiber and germ, which contains a majority of the lipids present in ground whole corn resulting in a fractionated corn that has a higher starch (endosperm) content. Dry fractionation does not separate the germ from fiber and therefore, it is less expensive than wet milling. However, fractionation does not remove the entirety of the fiber or germ, and does not result in total elimination of solids. Furthermore, there is some loss of starch in fractionation. Wet milling of corn is more expensive than dry fractionation, but dry fractionation is more expensive than dry grinding of unfractionated corn. Removal of solids including germ containing lipids, from liquefied mash prior to use in fermentation can substantially eliminate undissolved solids as described, for example, in co-pending, commonly owned U.S. Provisional Application Ser. No. 61/356,290, filed Jun. 18, 2010. However, it would be advantageous if the degradation of the partition coefficient of the extractant caused by contamination by lipid can be reduced even without fractionation or removal of substantially all undissolved solids. Converting the lipids present in a liquefied mash into an extractant that can be used in ISPR is another method of decreasing the amount of lipids that are fed to the fermentation vessel as described, for example, in co-pending, commonly owned U.S. Provisional Application Ser. No. 61/368,436 and U.S. Provisional Application Ser. No. 61/368,444, both filed on Jul. 28, 2010.

There is a continuing need for alternative extractive fermentation methods which do not necessitate the partitioning of the product alcohol between the fermentation medium and the ISPR extractant as a means to reduce the toxic effect of the product alcohol such as butanol on the microorganism, and which can also reduce the degradation of the partition coefficient of a fermentation product extractant.

BRIEF SUMMARY OF THE INVENTION

Conversion of alcohol such as butanol produced from a microorganism in a fermentation medium into a substance less toxic to the microorganism can allow increased production of alcohol such as butanol for a given fermentation vessel volume. Alcohol esters can be formed by contacting the alcohol in a fermentation medium with a carboxylic acid (e.g., fatty acids) and a catalyst capable of esterifying the alcohol with the carboxylic acid. Moreover, the carboxylic acid can serve as an ISPR extractant into which the alcohol esters partition. The carboxylic acid can be supplied to the fermentation vessel and/or derived from the biomass supplying fermentable carbon feed to the fermentation vessel. Lipids present in the feedstock can be catalytically hydrolyzed to carboxylic acid and the same catalyst (e.g., enzymes) can esterify the carboxylic acid with the alcohol (e.g., butanol); lipids can also be directly transesterified by the catalyst to produce alcohol esters. The catalyst can be supplied to the feedstock prior to fermentation or can be supplied to the fermentation vessel before or contemporaneously with the supplying of the feedstock. When the catalyst is supplied to the fermentation vessel, alcohol esters can be obtained by hydrolysis of the lipids into carboxylic acid and concurrent esterification of carboxylic acid with butanol present in the fermentation vessel; lipids can also be directly transesterified with butanol by the catalyst to produce alcohol esters. Carboxylic acid and/or native oil not derived from the feedstock can also be fed to the fermentation vessel, with the native oil being hydrolyzed into carboxylic acid. Carboxylic acid and/or native oil not derived from the feedstock can be fed into the fermentation vessel in an amount sufficient such that a two-phase mixture comprising an organic phase and an aqueous phase is formed. As such, in some embodiments, any carboxylic acid not esterified with the alcohol can serve as the ISPR extractant or as a part thereof. The extractant containing alcohol esters can be separated from the fermentation medium, and the alcohol can be recovered from the extractant. The extractant can be recycled to the fermentation vessel. Thus, in the case of butanol production, for example, the conversion of butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to carboxylic acid, thereby decreasing the rate of build-up of lipids in the ISPR extractant.

The present invention is directed to a method for producing butyl esters comprising contacting butanol produced in a fermentation process with at least one carboxylic acid and at least one catalyst capable of esterifying the carboxylic acid with the butanol to form butyl esters of the carboxylic acid; wherein the carboxylic acid in the fermentation process is present at a concentration sufficient to produce a two-phase mixture. In one embodiment, the production of butanol and the production of butyl esters occur simultaneously or sequentially. In one embodiment, a feedstock in the fermentation process comprises one or more fermentable sugars. In another embodiment, the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof. In one embodiment, the method further comprises providing a native oil and converting at least a portion of the native oil into carboxylic acid by contacting the oil with one or more enzymes. In one embodiment, the carboxylic acid comprises fatty acids. In another embodiment, the carboxylic acid comprises 12 to 22 carbons. In one embodiment, the carboxylic acid is a mixture of carboxylic acids. In another embodiment, the butyl esters of the carboxylic acid are butyl esters of fatty acids. In one embodiment, the catalyst is an enzyme capable of esterifying the carboxylic acid with the butanol to form butyl esters of the carboxylic acid. In another embodiment, the enzyme is an esterase, lipase, phospholipase, or lysophospholipase.

The present invention is also directed to a method for producing butanol and butyl esters from a feedstock comprising: (a) providing a feedstock; (b) liquefying the feedstock to create a liquefied biomass comprising oligosaccharides; (c) separating the feedstock slurry to produce a product comprising an aqueous stream comprising oligosaccharides, an oil stream, and solids; (d) adding the aqueous stream to a fermentation vessel containing a fermentation broth; (e) saccharifying the oligosaccharides of the aqueous stream; (f) fermenting the products of the oligosaccharide saccharification present in the aqueous stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; and optionally steps (e) and (f) occur concurrently. In one embodiment, the method further comprises obtaining an oil from the oil stream and converting at least a portion of the oil into carboxylic acid. In one embodiment, the feedstock slurry is separated by decanter bowl centrifugation, Tricanter® (three-phase centrifuge) centrifugation, disk stack centrifugation, filtering centrifugation, decanter centrifugation, filtration, vacuum filtration, beltfilter, pressure filtration, screen filtration, screen separation, grating, porous grating, flotation, hydroclone, filter press, screwpress, gravity settler, vortex separator, or combination thereof. In another embodiment, the carboxylic acid comprises fatty acids. In one embodiment, the carboxylic acid comprises 12 to 22 carbons. In one embodiment, the method further comprises adding the oil to the fermentation vessel prior to the step of converting at least a portion of the oil into carboxylic acid. In one embodiment, the method further comprises adding additional carboxylic acid to the fermentation vessel. In one embodiment, the oil is converted to carboxylic acid after the step of adding the additional carboxylic acid. In another embodiment, the carboxylic acid is corn oil fatty acid, soya oil fatty acid, or a mixture of corn oil fatty acid and soya oil fatty acid. In one embodiment, the oil obtained from the oil stream comprises glycerides and the one or more catalysts hydrolyze the glycerides into fatty acids. In another embodiment, the butyl esters of carboxylic acid are butyl esters of fatty acids. In one embodiment, the catalyst is an enzyme capable of esterifying the carboxylic acid with the butanol to form butyl esters of the carboxylic acid. In one embodiment, the enzyme is an esterase, lipase, phospholipase, or lysophospholipase. In one embodiment, the method further comprises the step of washing the solids with a solvent. In one embodiment, the solvent is select from hexane, isobutanol, isohexane, ethanol, petroleum distillates such as petroleum ether, or mixtures thereof. In another embodiment, the solids are processed to form an animal feed product. In one embodiment, the solids are processed to form an animal feed product. In one embodiment, the animal feed product comprises one or more crude protein, crude fat, triglycerides, fatty acid, fatty acid isobutyl ester, lysine, neutral detergent fiber (NDF), and acid detergent fiber (ADF). In another embodiment, the animal feed product further comprises one or more vitamins, minerals, flavoring, or coloring. In one embodiment, the animal feed product comprises 20-35 wt % crude protein, 1-20 wt % crude fat, 0-5 wt % triglycerides, 4-10 wt % fatty acids, and 2-6 wt % fatty acid isobutyl esters. In one embodiment, the step of separating the solids from the feedstock slurry increases the efficiency of the butanol production by increasing a liquid-liquid mass transfer coefficient of the butanol from the fermentation broth to the extractant; increases the efficiency of the butanol production by increasing an extraction efficiency of the butanol with an extractant; increases the efficiency of the butanol production by increasing a rate of phase separation between the fermentation broth and an extractant; increases the efficiency of the butanol production by increasing recovery and recycling of an extractant; or increases the efficiency of the butanol production by decreasing a flow rate of an extractant.

The present invention is also directed to a method for producing butanol and butyl esters from a feedstock comprising: (a) providing a feedstock; (b) liquefying the feedstock to create a liquefied biomass comprising oligosaccharides; (c) separating the feedstock slurry to produce a stream comprising oligosaccharides and oil, and solids; (d) adding the stream to a fermentation vessel containing a fermentation broth; (e) saccharifying the oligosaccharides of the stream; (f) fermenting the products of the oligosaccharide saccharification present in the stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; and optionally steps (e) and (f) occur concurrently. In one embodiment, the method further comprising converting at least a portion of the oil into carboxylic acid. In one embodiment, the feedstock slurry is separated by decanter bowl centrifugation, Tricanter® (three-phase centrifuge) centrifugation, disk stack centrifugation, filtering centrifugation, decanter centrifugation, filtration, vacuum filtration, beltfilter, pressure filtration, screen filtration, screen separation, grating, porous grating, flotation, hydroclone, filter press, screwpress, gravity settler, vortex separator, or combination thereof. In another embodiment, the carboxylic acid comprises fatty acids. In one embodiment, the carboxylic acid comprises 12 to 22 carbons. In one embodiment, the method further comprises adding oil to the fermentation vessel. In one embodiment, the method further comprising adding additional carboxylic acid to the fermentation vessel. In one embodiment, the oil is converted to carboxylic acid after the step of adding the additional carboxylic acid. In one embodiment, the carboxylic acid is corn oil fatty acid, soya oil fatty acid, or a mixture of corn oil fatty acid and soya oil fatty acid. In one embodiment, the oil comprises glycerides and the one or more catalysts hydrolyze the glycerides into fatty acids. In one embodiment, the butyl esters of carboxylic acid are butyl esters of fatty acids. In one embodiment, the catalyst is an enzyme capable of esterifying the carboxylic acid with the butanol to form butyl esters of the carboxylic acid. In one embodiment, the enzyme is an esterase, lipase, phospholipase, or lysophospholipase. In one embodiment, the method further comprises the step of washing the solids with a solvent. In one embodiment, the solvent is select from hexane, isobutanol, isohexane, ethanol, petroleum distillates such as petroleum ether, or mixtures thereof. In one embodiment, the solids are processed to form an animal feed product. In one embodiment, the solids are processed to form an animal feed product. In some embodiments, the animal feed product comprises one or more crude protein, crude fat, triglycerides, fatty acid, fatty acid isobutyl ester, lysine, neutral detergent fiber (NDF), and acid detergent fiber (ADF). In some embodiments, the animal feed product further comprises one or more vitamins, minerals, flavoring, or coloring. In some embodiments, the animal feed product comprises 20-35 wt % crude protein, 1-20 wt % crude fat, 0-5 wt % triglycerides, 4-10 wt % fatty acids, and 2-6 wt % fatty acid isobutyl esters. In some embodiments, the step of separating the solids from the feedstock slurry increases the efficiency of the butanol production by increasing a liquid-liquid mass transfer coefficient of the butanol from the fermentation broth to the extractant; increases the efficiency of the butanol production by increasing an extraction efficiency of the butanol with an extractant; increases the efficiency of the butanol production by increasing a rate of phase separation between the fermentation broth and an extractant; increases the efficiency of the butanol production by increasing recovery and recycling of an extractant; or increases the efficiency of the butanol production by decreasing a flow rate of an extractant.

The present invention is also directed to a method for producing butanol comprising (a) contacting butanol produced in a fermentation process with at least one carboxylic acid and at least one catalyst capable of esterifying the carboxylic acid with the butanol to form butyl esters of the carboxylic acid; wherein the carboxylic acid in the fermentation process is present at a concentration sufficient to produce a two-phase mixture comprising an aqueous phase and a butyl ester-containing organic phase; (b) separating the butyl ester-containing organic phase from the aqueous phase; and (c) recovering butanol from the butyl esters. In some embodiments, recovering butanol from the butyl esters comprises hydrolyzing the esters into carboxylic acid and butanol. In some embodiments, the butyl esters are hydrolyzed in the presence of a hydrolysis catalyst. In some embodiments, the butyl esters are hydrolyzed in the presence of water and wherein the hydrolysis catalyst comprises an acid catalyst, an organic acid, an inorganic acid, a water soluble acid, or water insoluble acid. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, enzyme reaction conditions favor enzymatic hydrolysis over esterification. In some embodiments, the enzyme reaction conditions comprise a cosolvent. In some embodiments, fatty acid butyl esters, fatty acids, isobutanol, and water are soluble in the cosolvent, and wherein free fatty acids do not react with the cosolvent. In some embodiments, the cosolvent is selected from acetone, tert-butanol, 2-Me-2-butanol, 2-Me-2-pentanol, and 3-Me-3-pentanol. In some embodiments, the enzyme reaction conditions comprise end-product removal. In some embodiments, the end-product is isobutanol or fatty acids. In some embodiments, isobutanol is removed by vacuum distillation, pervaporation, permselective filtration, or gas sparging. In some embodiments, the fatty acids are removed by precipitation, permselective filtration, or electrophorectically. In some embodiments, the hydrolysis reaction occurs in a reaction vessel. In some embodiments, recovering butanol from the butyl esters comprises transesterifying the butyl esters into butanol and fatty acid alkyl esters or acyl glycerides. In some embodiments, the fatty acid alkyl esters comprise fatty acid methyl esters, fatty acid ethyl esters, or fatty acid propyl esters. In some embodiments, the method further comprises providing a native oil and converting at least a portion of the native oil into carboxylic acid by contacting the oil with one or more enzymes. In some embodiments, the enzyme is an enzyme capable of hydrolyzing or transesterifying the butyl esters to form butanol. In some embodiments, the enzyme is an esterase, lipase, phospholipase, or lysophospholipase. In some embodiments, the carboxylic acid comprises fatty acids. In some embodiments, the carboxylic acid has carbon chain lengths ranging from 12 to 22 carbons. In some embodiments, at least about 10% of butanol is recovered from the butyl esters. In some embodiments, at least about 50% of butanol is recovered from the butyl esters. In some embodiments, at least about 90% of butanol is recovered from the butyl esters. In some embodiments, carboxylic acid is recovered from the butyl esters. In some embodiments, the method further comprising the steps of removing butanol from the fermentor as extractant stream; and adding the extractant stream to two or more distillation columns. In some embodiments, the distillation column is a super-atmospheric distillation column with a steam heated reboiler. In some embodiments, the method further comprises the steps of recovering water and solvent from the distillation columns; and recycling the water and solvent. In some embodiments, the method further comprises the steps of recovering heat from the distillation process; and recycling the heat to evaporate water.

The present invention is also directed to method for producing butanol from a feedstock comprising (a) providing a feedstock; (b) liquefying the feedstock to create a feedstock slurry; (c) separating the feedstock slurry to produce a product comprising an aqueous stream, an oil stream, and solids; (d) adding the aqueous stream to a fermentation vessel containing a fermentation broth; (e) saccharifying the aqueous stream; (f) fermenting the saccharified aqueous stream to produce butanol and concurrently contacting the butanol with at least one carboxylic acid and at least one catalyst capable of esterifying the carboxylic acid with the butanol to form butyl esters of the carboxylic acid wherein the carboxylic acid is present at a concentration sufficient to produce a two-phase mixture; (g) separating the butyl ester-containing organic phase from the aqueous phase; and (h) recovering butanol from the butyl esters; and optionally steps (e) and (f) occur concurrently. In some embodiments, the method further comprises obtaining an oil from the oil stream and converting at least a portion of the oil into carboxylic acid. In some embodiments, the feedstock slurry is separated by centrifugation, filtration, or decantation. In some embodiments, the carboxylic acid comprises fatty acids. In some embodiments, the carboxylic acid has carbon chain lengths ranging from 12 to 22 carbons. In some embodiments, the method further comprises adding the oil to the fermentation vessel prior to the step of converting at least a portion of the oil into carboxylic acid. In some embodiments, the method further comprises adding additional carboxylic acid to the fermentation vessel. In some embodiments, the oil is converted to carboxylic acid after the step of adding the additional carboxylic acid. In some embodiments, the carboxylic acid is corn oil fatty acid, soya oil fatty acid, or a mixture of corn oil fatty acid and soya oil fatty acid. In some embodiments, the oil obtained from the oil stream comprises glycerides and the one or more catalysts hydrolyze the glycerides into fatty acids. In some embodiments, the butyl esters of carboxylic acid are butyl esters of fatty acids. In some embodiments, the catalyst is an enzyme capable of esterifying the carboxylic acid with the butanol to form butyl esters of the carboxylic acid. In some embodiments, the enzyme is an esterase, lipase, phospholipase, or lysophospholipase. In some embodiments, the solids are processed to form to an animal feed product. In some embodiments, recovering butanol from the butyl esters comprises hydrolyzing the esters into carboxylic acid and butanol. In some embodiments, the butyl esters are hydrolyzed in the presence of a hydrolysis catalyst. In some embodiments, the butyl esters are hydrolyzed in the presence of water and wherein the hydrolysis catalyst comprises an acid catalyst, an organic acid, an inorganic acid, a water soluble acid, or water insoluble acid. In some embodiments, the hydrolysis catalyst comprises an enzyme capable of hydrolyzing the butyl esters to form a carboxylic acid and butanol. In some embodiments, the enzyme is an esterase, lipase, phospholipase, or lysophospholipase. In some embodiments, the hydrolysis reaction occurs in a reaction vessel. In some embodiments, recovering butanol from the butyl esters comprises transesterifying the butyl esters into butanol and fatty acid alkyl esters or acyl glycerides. In some embodiments, the fatty acid alkyl esters comprise fatty acid methyl esters, fatty acid ethyl esters, or fatty acid propyl esters. In some embodiments, the method further comprises providing a native oil and converting at least a portion of the native oil into carboxylic acid by contacting the oil with one or more enzymes. In some embodiments, the enzyme is an enzyme capable of hydrolyzing or transesterifying the butyl esters to form butanol. In some embodiments, the enzyme is an esterase, lipase, phospholipase, or lysophospholipase.

In other embodiments, a fermentation method may include: providing an aqueous feedstream obtained from biomass where the aqueous feedstream includes water, fermentable carbon source derived from the biomass, and oil; contacting the aqueous feedstream with a catalyst whereby at least a portion of the oil is hydrolyzed into free fatty acids to form a catalyst-treated feedstream including the free fatty acids and the catalyst; contacting the catalyst-treated feedstream with a fermentation broth in a fermentation vessel; fermenting the fermentable carbon source in the fermentation vessel to produce a product alcohol; and contacting the product alcohol with the free fatty acids and the catalyst during fermentation so as to catalyze the esterification of the free fatty acids and the product alcohol in the fermentation vessel to produce alcohol esters of fatty acids. In some embodiments, the steps of contacting the feedstream with catalyst and fermentation broth and the steps of fermenting and contacting the product alcohol with the free fatty acids and the catalyst may occur simultaneously. In some embodiments, the product alcohol is butanol and the alcohol esters of fatty acids are butyl esters of fatty acids.

The present invention provides methods for removing alcohol from a fermentation medium during fermentation including: providing a fermentation medium including a microorganism that produces alcohol in the fermentation medium; and contacting the fermentation medium during fermentation with a carboxylic acid and a catalyst capable of esterifying the alcohol with the carboxylic acid to form an alcohol ester. In some embodiments, the alcohol that is produced by the microorganism is butanol, and the alcohol ester is butyl ester. In some embodiments, the fermentation medium is contacted with a carboxylic acid that is substantially insoluble in the fermentation medium and with a catalyst capable of esterifying the alcohol with the carboxylic acid to form an alcohol ester.

The present invention also provides methods for producing alcohol esters of fatty acids during a fermentation process including: providing a fermentation medium comprising alcohol, fermentable carbon source, and free fatty acids; and contacting the fermentation medium with one or more enzymes capable of esterifying the free fatty acids with the alcohol whereby the free fatty acids are esterified with the alcohol to form alcohol esters of fatty acids. In some embodiments, the fermentable carbon source is derived from biomass. In some embodiments, the microorganism of the fermentation medium is a recombinant microorganism. In some embodiments, the alcohol is butanol and the alcohol esters of fatty acids are butyl esters of fatty acids.

In another embodiment, a method for producing a product alcohol may include providing a biomass feedstock including water, fermentable carbon source, and oil where the oil includes acyl glycerides; liquefying the biomass feedstock to create a liquefied biomass comprising oligosaccharides; contacting the biomass feedstock or the liquefied biomass with a composition comprising one or more enzymes capable of converting at least a portion of the acyl glycerides into free fatty acids whereby the free fatty acids form an extractant, the one or more enzymes also being capable of esterifying free fatty acids with product alcohol into alcohol esters of fatty acids; contacting the liquefied biomass with a saccharification enzyme capable of converting oligosaccharides into fermentable sugar; contacting the liquefied biomass with a recombinant microorganism capable of converting the fermentable sugar to product alcohol whereby a fermentation product comprising product alcohol is produced; contacting the product alcohol with the free fatty acids and the one or more enzymes so as to catalyze the esterification of the free fatty acids and the product alcohol to produce alcohol esters of fatty acids; and contacting the fermentation product with extractant. In embodiments, the contacting with extractant results in the formation of a two-phase mixture including an aqueous phase and an extractant phase and the alcohol esters of fatty acids partition into the extractant phase to form an ester-containing extractant phase. In some embodiments, the product alcohol is butanol and the alcohol esters of fatty acids are butyl esters of fatty acids.

In another embodiment, a method for producing a product alcohol may include providing a biomass feedstock including water, fermentable carbon source, and oil where the oil includes acyl glycerides; liquefying the biomass feedstock to create a liquefied biomass comprising oligosaccharides; contacting the liquefied biomass with a composition comprising one or more enzymes capable of converting at least a portion of the acyl glycerides into free fatty acids, the one or more enzymes also being capable of esterifying free fatty acids with product alcohol into alcohol esters of fatty acids; contacting the liquefied biomass with a saccharification enzyme capable of converting oligosaccharides into fermentable sugar; contacting the saccharified biomass with a recombinant microorganism capable of converting the fermentable sugar to product alcohol during fermentation whereby a fermentation medium comprising product alcohol is produced; contacting the fermentation medium during fermentation with a carboxylic acid extractant, where the fermentation medium comprises one or more enzymes capable of esterifying free fatty acids with product alcohol to form alcohol esters of fatty acids. In additional embodiments of this method, the fermentation medium is contacted with a carboxylic acid that is substantially insoluble in the fermentation medium and with a catalyst capable of esterifying the alcohol with the carboxylic acid to form an alcohol ester. In other embodiments of this method, the alcohol that is produced by the microorganism is butanol and the alcohol ester is butyl ester.

The present invention also provides a process to produce a product alcohol from a feedstock including: liquefying starch or a fermentable carbon source in a feedstock to create a slurry having oligosaccharides; centrifuging the feedstock slurry to produce a centrifuge product comprising (i) an aqueous layer comprising oligosaccharides, (ii) an oil layer, and (iii) solids; feeding the aqueous layer to a fermentation vessel containing a fermentation broth; and fermenting the aqueous layer to produce the product alcohol. The product alcohol is then contacted with the carboxylic acid and the catalyst whereby the carboxylic acid is esterified with the product alcohol to form the alcohol esters. In some embodiments, the oil is plant-derived oil. In other embodiments, the product alcohol is butanol and the alcohol esters of carboxylic acids are butyl esters of fatty acids.

In some embodiments, a method for producing a product alcohol includes providing a fractionated biomass feedstock including water, starch, and/or a fermentable carbon source, and only residual amounts of oil remaining after fractionation of the biomass, the residual oil including acyl glycerides; liquefying the fractionated biomass feedstock to create a liquefied fractionated biomass comprising oligosaccharides; contacting the liquefied fractionated biomass with a composition comprising one or more enzymes capable of converting at least a portion of the residual acyl glycerides into free fatty acids, the one or more enzymes also being capable of esterifying free fatty acids with product alcohol to form alcohol esters of fatty acids; contacting the liquefied fractionated biomass with a saccharification enzyme capable of converting oligosaccharides into fermentable sugar; contacting the saccharified biomass with a recombinant microorganism capable of converting the fermentable sugar to product alcohol during fermentation whereby a fermentation medium comprising product alcohol is produced; contacting the fermentation medium during fermentation with a carboxylic acid extractant, where the fermentation medium comprises one or more enzymes capable of esterifying free fatty acids with product alcohol to form alcohol esters of fatty acids. In additional embodiments of this method, the fermentation medium is contacted with a carboxylic acid in the fermentation medium and with a catalyst capable of esterifying the alcohol with the carboxylic acid to form an alcohol ester. In a further embodiment, the carboxylic acid may be substantially insoluble in the fermentation medium. In other embodiments of this method, the alcohol that is produced by the microorganism is butanol and the alcohol ester is butyl ester.

The present invention also provides a composition including: a mash formed from biomass and including water and fermentable sugar; a catalyst capable of esterifying free fatty acids with alcohol into fatty acid alkyl esters and optionally capable of hydrolyzing acyl glycerides into free fatty acids; alcohol; free fatty acids; and fatty acid alcohol esters formed in situ from esterification of the free fatty acids with the alcohol by the catalyst. In some embodiments, the alcohol is butanol and the fatty acid alcohol esters are fatty acid butyl esters.

The present invention also provides a fermentation broth including: a recombinant microorganism capable of producing alcohol; a fermentable carbon source; and fatty acid alcohol esters, wherein the fatty acid alcohol esters are produced during the fermentation. In some embodiments, the recombinant microorganism is capable of producing butanol. In some embodiments, the fatty acid alcohol esters are fatty acid butyl esters. In some embodiments, the fermentable carbon source comprises sugar. In some embodiments, the fermentable carbon source comprises methane, the recombinant microorganism is capable of producing methanol, and the fatty acid alcohol esters are fatty acid methyl esters.

Also provided herein are recombinant yeast cells useful for production of product alcohols. In embodiments, the recombinant host cells disclosed herein can be any bacteria, yeast or fungi host useful for genetic modification and recombinant gene expression. In other embodiments, a recombinant host cell can be a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula, Issatchenkia,* or *Saccharomyces.* In other embodiments, the host cell can be *Saccharomyces cerevisiae, Schizosaccharomyces pombe, Kluyveromyces lactis, Kluyveromyces thermotolerans, Kluyveromyces marxianus, Candida glabrata, Candida albicans, Pichia stipitis, Yarrowia lipolytica, E. coli,* or *L. plantarum.* In still other embodiments, the host cell is a yeast host cell. In some embodiments, the host cell is a member of the genera *Saccharomyces.* In some embodiments, the host cell is *Kluyveromyces lactis, Candida glabrata* or *Schizosaccharomyces pombe.* In some embodiments, the host cell is *Saccharomyces cerevisiae. S. cerevisiae* yeast are known in the art and are available from a variety of sources, including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Gert Strand Prestige Turbo yeast, Ferm Pro™ yeast, Bio-Ferm® XR yeast, Gert Strand Distillers Yeast, FerMax™ Green yeast, FerMax™ Gold yeast, Thermosacc® yeast, BG-1, PE-2, CAT-1, CBS7959, CBS7960, and CBS7961.

Also provided are methods of producing isobutanol including: providing a recombinant host cell comprising an isobutanol biosynthetic pathway wherein at least one of the enzyme that catalyzes the substrate to product conversion α-ketoisovalerate to isobutyraldehyde or the enzyme that catalyzes the substrate to product conversion isobutyraldehyde to isobutanol are encoded by heterologous polynucleotides integrated into the chromosome; and contacting the recombinant host cell with a fermentable carbon source to form a fermentation broth under conditions whereby isobutanol is produced. In some embodiments, the methods further include: adding an extractant to form a two-phase mixture. In other embodiments, the extractant comprises a carboxylic acid. In some embodiments, the extractant comprises fatty acids. In other embodiments, the methods further include: adding an esterification enzyme capable of catalyzing the esterification of isobutanol with the carboxylic acid.

Also provided herein are methods including: providing a fermentation medium comprising product alcohol, water, fermentable carbon source, and a microorganism that produces the product alcohol; contacting the fermentation medium during fermentation with an extractant to form a two-phase mixture comprising an aqueous phase and an organic phase; and contacting the fermentation medium with a carboxylic acid and an enzyme capable of esterifying the carboxylic acid with the product alcohol. In some embodiments, the extractant comprises the carboxylic acid. In some embodiments, the carboxylic acid is produced by hydrolysis of oil from a biomass feedstock. In some embodiments, the fermentable carbon and the carboxylic acid are derived from the same biomass feedstock source. In some embodiments, the carboxylic acid comprises saturated, mono-unsaturated, poly-unsaturated carboxylic acids having 12 to 22 carbons, and mixtures thereof. In some embodiments, contacting the fermentation medium with an extractant and a carboxylic acid and an enzyme occur contemporaneously. In some embodiments, the microorganism is a genetically modified microorganism (e.g., a recombinant microorganism or host cell such as recombinant yeast cells).

Also provided herein are compositions comprising: PNY1504, PNY2205, or a recombinant host cell; an extractant; and optionally an esterification enzyme. Also provided herein are compositions comprising PNY1504, PNY2205, or a recombinant host cell and butyl ester.

Further provided herein are uses of PNY1504, PNY2205, or other recombinant yeast cells, and compositions comprising recombinant yeast cells for the production of isobutanol.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 1 schematically illustrates an exemplary method and system of the present invention, in which a catalyst for alcohol esterification is supplied to a fermentation vessel along with carboxylic acid and/or native oil.

FIG. 2 schematically illustrates an exemplary method and system of the present invention, in which native oil is converted into carboxylic acid using a catalyst, and the carboxylic acid and the catalyst are supplied to a fermentation vessel.

FIG. 3 schematically illustrates an exemplary method and system of the present invention, in which a liquefied biomass is contacted with a catalyst for lipid hydrolysis before fermentation.

FIG. 4 schematically illustrates an exemplary method and system of the present invention, in which a liquefied and saccharified biomass is contacted with a catalyst for lipid hydrolysis before fermentation.

FIG. 5 schematically illustrates an exemplary method and system of the present invention, in which an amount of lipids and undissolved solids are removed from a liquefied biomass before fermentation, and in which the removed lipids are converted into carboxylic acid using a catalyst, and the carboxylic acid and the catalyst are supplied to the fermentation vessel.

FIG. 6 shows the aqueous and solvent phase concentrations of isobutanol produced by fermentation with sucrose as a carbon source. Aqueous phase titer (Panel A) is reported in g/L and the solvent phase species (isobutanol, Panel B and isobutanol as FABE, Panel C. Panel D is the total isobutanol in the solvent phase) in weight percent.

DETAILED DESCRIPTION OF THE INVENTION

Figure 1:
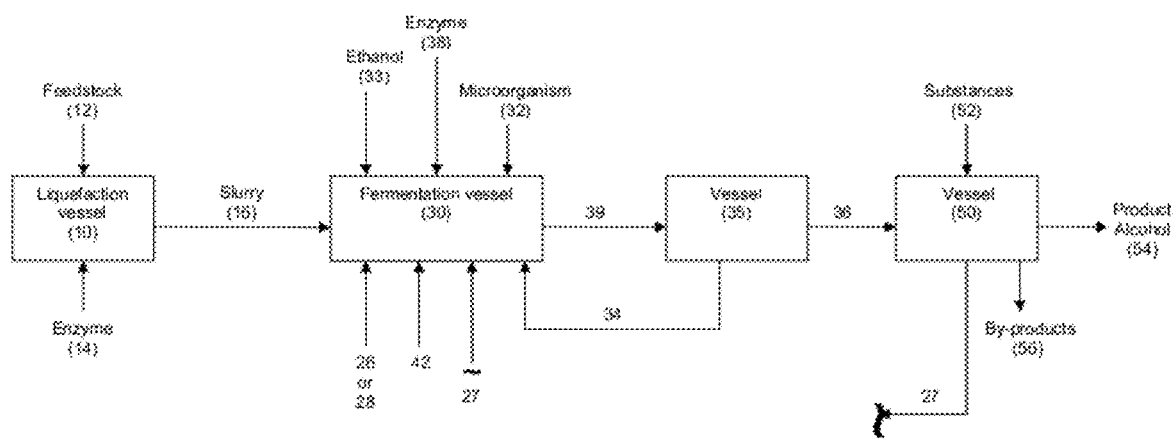

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents, and other references mentioned herein are incorporated by reference in their entireties for all purposes.

Unless otherwise specified, when the following abbreviations are used herein, they have the following meaning:

| | |
|---|---|
| ADH | alcohol dehydrogenase |
| ALS | acetolactate synthase |
| AQ | aqueous fraction |
| BuO-COFA | butyl ester(s) of corn oil fatty acid(s) |
| CALB | *Candida antarctica* lipase B |
| COFA | corn oil fatty acid(s) |
| DDGS | Dried Distillers' Grains with Solubles |
| DG | diglyceride(s) |
| DHAD | dihydroxyacid dehydratase |
| EOR | end of run |
| EtOH | ethanol |
| EtO-COFA | ethyl ester(s) of corn oil fatty acid(s) |
| FABE | fatty acid butyl ester(s) |
| FAEE | fatty acid ethyl ester(s) |
| FAME | fatty acid methyl ester(s) |
| FFA | free fatty acid(s) |
| FOA | fluoro-orotic acid |
| HADH | horse liver alcohol dehydrogenase |
| IBA | isobutanol |
| i-BuOH | isobutanol |
| i-BuO-COFA | isobutyl ester(s) of corn oil fatty acid(s) |
| i-BuO-oleate | iso-butyl oleate |
| i-PrOH | isopropanol |
| i-PrO-COFA | isopropyl ester(s) of corn oil fatty acid(s) |
| ISPR | in situ product removal |
| KARI | ketol-acid reductoisomerase |
| KivD | ketoisovalerate decarboxylase |
| MAG | monoacylglyceride(s) |
| MeBOH | 2-methyl-1-butanol |
| MeBO-COFA | 2-methyl-1-butyl ester(s) of corn oil fatty acid(s) |
| MeOH | methanol |
| MeO-COFA | methyl ester(s) of corn oil fatty acid(s) |
| MG | monoglyceride(s) |
| n-BuOH | n-butanol |
| OA | oleyl alcohol |
| ORG | organic fraction |
| PenOH | 1-pentanol |
| PenO-COFA | 1-pentyl ester(s) of corn oil fatty acid(s) |
| PrOH | 1-propanol |
| PrO-COFA | 1-propyl ester(s) of corn oil fatty acid(s) |
| SOFA | soya oil fatty acids |
| SSF | simultaneous saccharification and fermentation |
| t-BuOH | tert-butyl alcohol |
| TG | triglyceride(s) |
| 3M3P | 3-Me-3-pentanol |

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, that is, occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

"Biomass" as used herein refers to a natural product containing hydrolyzable polysaccharides that provide fermentable sugars including any sugars and starch derived from natural resources such as corn, cane, wheat, cellulosic or lignocellulosic material and materials comprising cellulose, hemicellulose, lignin, starch, oligosaccharides, disaccharides and/or monosaccharides, and mixtures thereof. Biomass may also comprise additional components such as protein and/or lipids. Biomass may be derived from a single source or biomass can comprise a mixture derived from more than one source. For example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, waste sugars, wood and forestry waste. Examples of biomass include, but are not limited to, corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, trees, branches, roots, leaves, wood chips, sawdust, shrubs and bushes, vegetables, fruits, flowers, animal manure, and mixtures thereof. For example, mash, juice, molasses, or hydrolysate may be formed from biomass by any processing known in the art for processing the biomass for purposes of fermentation such as by milling, treating, and/or liquefying and comprises fermentable sugar and may comprise water. For example, cellulosic and/or lignocellulosic biomass may be processed to obtain a hydrolysate containing fermentable sugars by any method known to one skilled in the art. Particularly useful is a low ammonia pretreatment as disclosed U.S. Patent Application Publication No. 2007/0031918A1, which is herein incorporated by reference. Enzymatic saccharification of cellulosic and/or lignocellulosic biomass typically makes use of an enzyme consortium for breaking down cellulose and hemicellulose to produce a hydrolysate containing sugars including glucose, xylose, and arabinose. (Saccharification enzymes suitable for cellulosic and/or lignocellulosic biomass are reviewed in Lynd, et al. (Microbiol. Mol. Biol. Rev. 66:506-577, 2002).

Mash, juice, molasses, or hydrolysate may include feedstock 12 and feedstock slurry 16 as described herein. An aqueous feedstream may be derived or formed from biomass by any processing known in the art for processing the biomass for purposes of fermentation such as by milling, treating, and/or liquefying and comprises fermentable carbon substrate (e.g., sugar) and may comprise water. An aqueous feedstream may include feedstock 12 and feedstock slurry 16 as described herein.

"Biomass yield" as used herein refers to the grams of biomass produced (i.e., cell biomass production) per gram of carbon substrate produced.

"Feedstock" as used herein means a feed in a fermentation process, the feed containing a fermentable carbon source with or without undissolved solids, and where applicable, the feed containing the fermentable carbon source before or after the fermentable carbon source has been liberated from starch or obtained from the break down of complex sugars by further processing such as by liquefaction, saccharification, or other process. Feedstock includes or is derived from a biomass. Suitable feedstocks include, but are not limited to, rye, wheat, corn, corn mash, cane, cane mash, barley, cellulosic material, lignocellulosic material, or mixtures thereof. Where reference is made to "feedstock oil," it will be appreciated that the term encompasses the oil produced from a given feedstock.

"Fermentation medium" as used herein means the mixture of water, sugars, dissolved solids, optionally microorganisms producing alcohol, product alcohol, and all other constituents of the material held in the fermentation vessel in which product alcohol is being made by the reaction of sugars to alcohol, water, and carbon dioxide ($CO_2$) by the microorganisms present. From time to time, as used herein the term "fermentation broth" and "fermented mixture" can be used synonymously with "fermentation medium."

"Fermentable carbon source" or "fermentable carbon substrate" as used herein means a carbon source capable of being metabolized by the microorganisms disclosed herein for the production of fermentative alcohol. Suitable fermentable carbon sources include, but are not limited to, monosaccharides such as glucose or fructose; disaccharides such as lactose or sucrose; oligosaccharides; polysaccharides such as starch or cellulose; C5 sugars such as xylose and arabinose; one carbon substrates including methane; and mixtures thereof.

"Fermentable sugar" as used herein refers to one or more sugars capable of being metabolized by the microorganisms disclosed herein for the production of fermentative alcohol.

"Fermentation vessel" as used herein means the vessel in which the fermentation reaction is carried out whereby product alcohol such as butanol is made from sugars.

"Liquefaction vessel" as used herein means the vessel in which liquefaction is carried out. Liquefaction is the process in which oligosaccharides are liberated from the feedstock. In some embodiments where the feedstock is corn, oligosaccharides are liberated from the corn starch content during liquefaction.

"Saccharification vessel" as used herein means the vessel in which saccharification (i.e., the break down of oligosaccharides into monosaccharides) is carried out. Where fermentation and saccharification occur simultaneously, the saccharification vessel and the fermentation vessel may be one in the same vessel.

"Sugar" as used herein refers to oligosaccharides, disaccharides, monosaccharides, and/or mixtures thereof. The term "saccharide" also includes carbohydrates including starches, dextrans, glycogens, cellulose, pentosans, as well as sugars.

As used herein, "saccharification enzyme" means one or more enzymes that are capable of hydrolyzing polysaccharides and/or oligosaccharides, for example, alpha-1,4-glucosidic bonds of glycogen, or starch. Saccharification enzymes may include enzymes capable of hydrolyzing cellulosic or lignocellulosic materials as well.

"Undissolved solids" as used herein means non-fermentable portions of feedstock, for example, germ, fiber, and gluten. For example, the non-fermentable portions of feedstock include the portion of feedstock that remains as solids and can absorb liquid from the fermentation broth.

Dried Distillers' Grains with Solubles (DDGS) as used herein refers to a co-product or by-product from a fermentation of a feedstock or biomass (e.g., fermentation of grain or grain mixture that produces a product alcohol). In some embodiments, DDGS may also refer to an animal feed product produced from a process of making a product alcohol (e.g., butanol, isobutanol, etc.).

"Product alcohol" as used herein refers to any alcohol that can be produced by a microorganism in a fermentation process that utilizes biomass as a source of fermentable carbon substrate. Product alcohols include, but are not limited to, $C_1$ to $C_8$ alkyl alcohols. In some embodiments, the product alcohols are $C_2$ to $C_8$ alkyl alcohols. In other embodiments, the product alcohols are $C_2$ to $C_5$ alkyl alcohols. It will be appreciated that $C_1$ to $C_8$ alkyl alcohols include, but are not limited to, methanol, ethanol, propanol, butanol, and pentanol. Likewise $C_2$ to $C_8$ alkyl alcohols include, but are not limited to, ethanol, propanol, butanol, and pentanol. "Alcohol" is also used herein with reference to a product alcohol.

"Butanol" as used herein refers with specificity to the butanol isomers 1-butanol (1-BuOH), 2-butanol (2-BuOH), tert-butanol (t-BuOH), and/or isobutanol (iBuOH or i-BuOH or I-BUOH, also known as 2-methyl-1-propanol), either individually or as mixtures thereof. From time to time, when referring to esters of butanol, the terms "butyl esters" and "butanol esters" may be used interchangeably.

"Propanol" as used herein refers to the propanol isomers isopropanol or 1-propanol.

"Pentanol" as used herein refers to the pentanol isomers 1-pentanol, 3-methyl-1-butanol, 2-methyl-1-butanol, 2,2-dimethyl-1-propanol, 3-pentanol, 2-pentanol, 3-methyl-2-butanol, or 2-methyl-2-butanol.

The term "alcohol equivalent" as used herein refers to the weight of alcohol that would be obtained by a perfect hydrolysis of an alcohol ester and the subsequent recovery of the alcohol from an amount of alcohol ester.

The term "aqueous phase titer" as used herein refers to the concentration of a particular alcohol (e.g., butanol) in the fermentation broth.

The term "effective titer" as used herein refers to the total amount of a particular alcohol (e.g., butanol) produced by fermentation or alcohol equivalent of the alcohol ester produced by alcohol esterification per liter of fermentation medium. For example, the effective titer of butanol in a unit volume of a fermentation includes: (i) the amount of butanol in the fermentation medium; (ii) the amount of butanol recovered from the organic extractant; (iii) the amount of butanol recovered from the gas phase, if gas stripping is used; and (iv) the alcohol equivalent of the butyl ester in either the organic or aqueous phase.

The term "effective rate" as used herein is the effective titer divided by the fermentation time.

The term "effective yield" as used herein is the total grams of product alcohol produced per gram of glucose consumed.

"In Situ Product Removal (ISPR)" as used herein means the selective removal of a specific fermentation product from a biological process such as fermentation, to control the product concentration in the biological process as the product is produced.

"Extractant" or "ISPR extractant" as used herein means an organic solvent used to extract any product alcohol such as butanol or used to extract any product alcohol ester produced by a catalyst from a product alcohol and a carboxylic acid or lipid. From time to time, as used herein the term "solvent" may be used synonymously with "extractant." For the processes described herein, extractants are water-immiscible.

The terms "water-immiscible" or "insoluble" refer to a chemical component such as an extractant or solvent, which is incapable of mixing with an aqueous solution such as a fermentation broth, in such a manner as to form one liquid phase.

The term "aqueous phase" as used herein refers to the aqueous phase of a biphasic mixture obtained by contacting a fermentation broth with a water-immiscible organic extractant. In an embodiment of a process described herein that includes fermentative extraction, the term "fermentation broth" then specifically refers to the aqueous phase in biphasic fermentative extraction.

The term "organic phase" as used herein refers to the non-aqueous phase of a biphasic mixture obtained by contacting a fermentation broth with a water-immiscible organic extractant.

The term "carboxylic acid" as used herein refers to any organic compound with the general chemical formula —COOH in which a carbon atom is bonded to an oxygen atom by a double bond to make a carbonyl group (—C=O) and to a hydroxyl group (—OH) by a single bond. A carboxylic acid may be in the form of the protonated carboxylic acid, in the form of a salt of a carboxylic acid (e.g., an ammonium, sodium, or potassium salt), or as a mixture of protonated carboxylic acid and salt of a carboxylic acid. The term carboxylic acid may describe a single chemical species (e.g., oleic acid) or a mixture of carboxylic acids as can be produced, for example, by the hydrolysis of biomass-derived fatty acid esters or triglycerides, diglycerides, monoglycerides, and phospholipids.

The term "fatty acid" as used herein refers to a carboxylic acid (e.g., aliphatic monocarboxylic acid) having $C_4$ to $C_{28}$ carbon atoms (most commonly $C_{12}$ to $C_{24}$ carbon atoms), which is either saturated or unsaturated. Fatty acids may also be branched or unbranched. Fatty acids may be derived from, or contained in esterified form, in an animal or vegetable fat, oil, or wax. Fatty acids may occur naturally in the form of glycerides in fats and fatty oils or may be obtained by hydrolysis of fats or by synthesis. The term fatty acid may describe a single chemical species or a mixture of fatty acids. In addition, the term fatty acid also encompasses free fatty acids.

The term "fatty alcohol" as used herein refers to an alcohol having an aliphatic chain of $C_4$ to $C_{22}$ carbon atoms, which is either saturated or unsaturated.

The term "fatty aldehyde" as used herein refers to an aldehyde having an aliphatic chain of $C_4$ to $C_{22}$ carbon atoms, which is either saturated or unsaturated.

The term "fatty amide" as used herein refers to an amide having a long, aliphatic chain of $C_4$ to $C_{22}$ carbon atoms, which is either saturated or unsaturated The term "fatty ester" as used herein refers to an ester having a long aliphatic chain of $C_4$ to $C_{22}$ carbon atoms, which is either saturated or unsaturated.

"Native oil" as used herein refers to lipids obtained from plants (e.g., biomass) or animals. "Plant-derived oil" as used herein refers to lipids obtain from plants in particular. From time to time, "lipids" may be used synonymously with "oil" and "acyl glycerides." Native oils include, but are not limited to, tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, and vegetable oil blends.

The term "separation" as used herein is synonymous with "recovery" and refers to removing a chemical compound from an initial mixture to obtain the compound in greater purity or at a higher concentration than the purity or concentration of the compound in the initial mixture.

The term "butanol biosynthetic pathway" as used herein refers to an enzyme pathway to produce 1-butanol, 2-butanol, or isobutanol.

The term "1-butanol biosynthetic pathway" as used herein refers to an enzyme pathway to produce 1-butanol from acetyl-coenzyme A (acetyl-CoA).

The term "2-butanol biosynthetic pathway" as used herein refers to an enzyme pathway to produce 2-butanol from pyruvate.

The term "isobutanol biosynthetic pathway" as used herein refers to an enzyme pathway to produce isobutanol from pyruvate.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene (i.e., it is modified from its native state or is from another source) comprising regulatory and coding sequences that are not found together in nature. Accordingly, a chimeric gene may comprise regulatory sequences and coding sequences that are derived from different sources or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found as a native gene in the host organism, but that is introduced into the host organism by gene transfer. Foreign genes can comprise native genes inserted into a non-native organism or chimeric genes.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site, and stem-loop structure.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Codon optimization is within the ordinary skill in the art.

The term "polynucleotide" is intended to encompass a singular nucleic acid as well as plural nucleic acids, and refers to a nucleic acid molecule or construct, for example, messenger RNA (mRNA) or plasmid DNA (pDNA). As used herein, a "gene" is a polynucleotide. A polynucleotide can contain the nucleotide sequence of the full-length cDNA sequence or a fragment thereof, including the untranslated 5' and 3' sequences and the coding sequences. The polynucleotide can be composed of any polyribonucleotide or polydeoxyribonucleotide, which may be unmodified RNA or DNA or modified RNA or DNA (e.g., heterologous DNA). For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. "Polynucleotide" embraces chemically, enzymatically, or metabolically modified forms.

A polynucleotide sequence may be referred to as "isolated," in which it has been removed from its native environment. For example, a heterologous polynucleotide encoding a polypeptide or polypeptide fragment having dihydroxy-acid dehydratase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA may be comprised of one or more segments of cDNA, genomic DNA, or synthetic DNA.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposes of the invention, as are native or recombinant polypeptides which have been separated, fractionated, or partially or substantially purified by any suitable technique.

As used herein, "recombinant microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

The present invention satisfies the need for alternative extractive fermentation methods which do not necessitate the partitioning of the product alcohol between the fermentation medium and the ISPR extractant as a means to reduce the toxic effect of the product alcohol (such as butanol) on the microorganism. It also satisfies the need to reduce the degradation of the partition coefficient of a fermentation product ISPR extractant by providing methods for producing alcohol such as butanol in which the product alcohol is converted into alcohol esters which can be less toxic to the microorganism and where there is realized a concomitant reduction in the degradation of the partition coefficient of a fermentation product extractant, resulting in improved production yields of alcohol (as a combination of free alcohol and alcohol esters that can be converted back to alcohol after separation from the fermentation medium). Moreover, the present invention offers solutions to disadvantages of alternative alcohol product removal processes such that the methods herein can be combined with existing processes (e.g., solids removal) to provide increased product removal at economic and environmental advantage. As such, the present invention provides further related advantages, as will be made apparent by the description of the embodiments that follow.

The present invention provides methods for removing alcohol from a fermentation medium by esterifying the alcohol with carboxylic acid and extracting the resulting alcohol ester from the fermentation medium, whereafter the alcohol can be recovered from the alcohol ester. The acid may be added to the fermentation medium directly as free fatty acid or may be derived from oil. The present invention also provides methods for removing or reducing oil from an alcohol fermentation process by hydrolyzing the oil derived from a feedstock into carboxylic acid which can be used for the esterification of alcohol and/or serve as an ISPR extractant or a component of the ISPR extractant for extracting the alcohol ester.

Decreasing the amount of water present in a reaction system, or employing a reaction system that uses only one or more non-aqueous solvents, has typically been necessary for esterification of alcohols by carboxylic acids when catalyzed by enzymes such as lipases. Described herein is the surprising finding that lipase enzymes can efficiently catalyze the esterification of a product alcohol with a carboxylic acid during fermentation of a fermentable carbon source to produce product alcohol. Also described herein is the surprising finding that esterification of a product alcohol with a carboxylic acid during a fermentation can provide improvements in the fermentation performance. For example, by capturing the product alcohol (e.g., butanol) as produced in ester form it effectively reduces the concentration of the product alcohol in the aqueous phase and thus, mitigates the toxic effects of the product alcohol on glucose consumption and product production.

The present invention will be described with reference to the Figures. FIG. 1 illustrates an exemplary process flow diagram for production of fermentative alcohol such as ethanol or butanol, according to an embodiment of the present invention. As shown, a feedstock 12 can be introduced to an inlet in a liquefaction vessel 10 and liquefied to produce a feedstock slurry 16. Feedstock 12 contains hydrolysable polysaccharides that supplies a fermentable carbon substrate (e.g., fermentable sugar such as glucose), and can be a biomass such as, but not limited to, rye, wheat, cane or corn, or can otherwise be derived from a biomass. In some embodiments, feedstock 12 can be one or more components of a fractionated biomass, and in other embodiments, feedstock 12 can be a milled, unfractionated biomass. In some embodiments, feedstock 12 can be corn, such as dry milled, unfractionated corn kernels, and the undissolved particles can include germ, fiber, and gluten. The undissolved solids are non-fermentable portions of feedstock 12. For purposes of the discussion herein with reference to the embodiments shown in the Figures, feedstock 12 will often be described as constituting milled, unfractionated corn in which the undissolved solids have not been separated therefrom. However, it should be understood that the exemplary methods and systems described herein can be modified for different feedstocks whether fractionated or not, as apparent to one of skill in the art. Furthermore, as one skilled in the art can appreciate, maximizing feedstock content (e.g., corn content) can maximize sugar content as well as product titer. In some embodiments, feedstock 12 can be high-oleic corn, such that corn oil derived therefrom is a high-oleic corn oil having an oleic acid content of at least about 55 wt % oleic acid. In some embodiments, the oleic acid content in high-oleic corn oil can be up to about 65 wt %, as compared with the oleic acid content in normal corn oil which is about 24 wt %. High-oleic oil can provide some advantages for use in the methods of the present invention, as hydrolysis of the oil provides free fatty acids having a high oleic acid content for contacting with a fermentation broth.

The process of liquefying feedstock 12 involves hydrolysis of polysaccharides in feedstock 12 into sugars including, for example, dextrins and oligosaccharides, and is a conventional process. Any known liquefying processes as well as the corresponding liquefaction vessel, normally utilized by the industry can be used including, but not limited to, the acid process, the acid-enzyme process, or the enzyme process. Such processes can be used alone or in combination. In some embodiments, the enzyme process can be utilized and an appropriate enzyme 14, for example, alpha-amylase, is introduced to an inlet in liquefaction vessel 10. Water can also be introduced to liquefaction vessel 10. In some embodiments, a saccharification enzyme, for example, glucoamylase, may also be introduced to liquefaction vessel 10. In additional embodiments, a lipase may also be introduced to liquefaction vessel 10 to catalyze the conversion of one or more components of the oil to free fatty acids.

Feedstock slurry 16 produced from liquefying feedstock 12 comprises fermentable carbon substrate (e.g., sugar), oil, and undissolved solids derived from the feedstock. Feedstock slurry 16 can be discharged from an outlet of liquefaction vessel 10. In some embodiments, feedstock 12 is corn or corn kernels and therefore, feedstock slurry 16 is a corn mash slurry. In some embodiments, feedstock 12 is a lignocellulosic feedstock and therefore, feedstock slurry 16 may be a lignocellulosic hydrolysate. In some embodiments, feedstock 12 is sugar cane.

Feedstock slurry 16 is introduced into a fermentation vessel 30 along with a microorganism 32. Fermentation vessel 30 is configured to ferment slurry 16 to produce alcohol. In particular, microorganism 32 metabolizes the fermentable sugar in slurry 16 and excretes a product alcohol. Microorganism 32 is selected from the group of bacteria, cyanobacteria, filamentous fungi, and yeasts. In some embodiments, microorganism 32 can be a bacteria such as E. coli. In some embodiments, microorganism 32 can be a fermentative recombinant microorganism. The slurry can include sugar, for example, in the form of oligosaccharides, and water, and in some embodiments, can comprise less than about 20 g/L of monomeric glucose, less than about 10 g/L, or less than about 5 g/L of monomeric glucose. Suitable methodology to determine the amount of monomeric glucose is well known in the art. Such suitable methods known in the art include HPLC.

In some embodiments, slurry 16 is subjected to a saccharification process in order to break the complex sugars (e.g., oligosaccharides) in slurry 16 into monosaccharides that can be readily metabolized by microorganism 32. Any known saccharification process, normally utilized by the industry can be used including, but not limited to, the acid process, the acid-enzyme process, or the enzyme process. In some embodiments, simultaneous saccharification and fermentation (SSF) can occur inside fermentation vessel 30 as shown in FIG. 1. In some embodiments, an enzyme 38 such as glucoamylase, can be introduced to an inlet in fermentation vessel 30 in order to breakdown the starch or oligosaccharides to glucose capable of being metabolized by microorganism 32.

Carboxylic acid 28 and/or native oil 26 are introduced into fermentation vessel 30, along with a catalyst 42. Catalyst 42 can be introduced before, after, or contemporaneously with enzyme 38. Thus, in some embodiments, addition of enzyme 38 and catalyst 42 can be stepwise (e.g., catalyst 42, then enzyme 38, or vice versa) or substantially simultaneous (i.e., at exactly the same time as in the time it takes for a person or a machine to perform the addition in one stroke, or one enzyme/catalyst immediately following the other catalyst/enzyme as in the time it takes for a person or a machine to perform the addition in two strokes). Catalyst 42 is capable of esterifying the product alcohol with carboxylic acid 28 to form an alcohol ester. For example, in the case of butanol production, catalyst 42 is capable of esterifying butanol with carboxylic acid 28 to form a butyl ester.

In the instance that native oil 26 is supplied to fermentation vessel 30, at least a portion of the acyl glycerides in oil 26 can be hydrolyzed to carboxylic acid 28 by contacting oil 26 with catalyst 42. The resulting acid/oil composition from hydrolyzing oil 26 is typically at least about 17 wt % carboxylic acid 28 (as free fatty acids). In some embodiments, the resulting acid/oil composition from hydrolyzing oil 26 is at least about 20 wt % carboxylic acid, at least about 25 wt % carboxylic acid, at least about 30 wt % carboxylic acid, at least about 35 wt % carboxylic acid, at least about 40 wt % carboxylic acid, at least about 45 wt % carboxylic acid, at least about 50 wt % carboxylic acid, at least about 55 wt % carboxylic acid, at least about 60 wt % carboxylic acid, at least about 65 wt % carboxylic acid, at least about 70 wt % carboxylic acid, at least about 75 wt % carboxylic acid, at least about 80 wt % carboxylic acid, at least about 85 wt % carboxylic acid, at least about 90 wt % carboxylic acid, at least about 95 wt % carboxylic acid, or at least about 99 wt % carboxylic acid. In some embodiments, the resulting acid/oil composition includes monoglycerides and/or diglycerides from the partial hydrolysis of the acyl glycerides in the oil. In some embodiments, the resulting acid/oil composition includes glycerol, a by-product of acyl glyceride hydrolysis. In some additional embodiments, the resulting acid/oil composition includes lysophospholipids from the partial hydrolysis of phospholipids in the oil.

In some embodiments, after hydrolysis of the acyl glycerides in oil 26, the remaining acyl glycerides from oil 26 are from about 0 wt % to at least about 2 wt % of the fermentation broth composition. In some additional embodiments, after hydrolysis of the acyl glycerides in oil 26, the remaining acyl glycerides from oil 26 are at least about 0.5 wt % of the fermentation broth composition. Thus, in some embodiments, the acyl glycerides from oil 26 can be catalytically hydrolyzed to carboxylic acid 28 using catalyst 42, and catalyst 42 can also esterify carboxylic acid 28 with the product alcohol. In some embodiments, a second catalyst (not shown) can be introduced to the fermentation vessel for hydrolysis of the acyl glycerides. In addition, the acyl glycerides in the oil derived from feedstock 12 and present in slurry 16 can also be hydrolyzed to carboxylic acid 28' (see, e.g., the embodiment of FIG. 3). In some embodiments, the concentration of the carboxylic acid (such as fatty acid) in the fermentation vessel exceeds the solubility limit in the aqueous phase and results in the production a two-phase fermentation mixture comprising an organic phase and an aqueous phase. In some embodiments, the concentration of carboxylic acids in the fermentation broth is typically not greater than about 0.8 g/L and is limited by the solubility of the carboxylic acid in the broth.

In some embodiments, catalyst 42 and the second catalyst, if used, can be one or more enzymes, for example, lipase enzymes. In some embodiments, catalyst 42 can be one or more enzymes, for example, hydrolase enzymes such as lipase enzymes. Lipase enzymes used may be derived from any source including, for example, *Absidia, Achromobacter, Aeromonas, Alcaligenes, Alternaria, Aspergillus, Achromobacter, Aureobasidium, Bacillus, Beauveria, Brochothrix, Candida, Chromobacter, Coprinus, Fusarium, Geotricum, Hansenula, Humicola, Hyphozyma, Lactobacillus, Metarhizium, Mucor, Nectria, Neurospora, Paecilomyces, Penicillium, Pseudomonas, Rhizoctonia, Rhizomucor, Rhizopus, Rhodosporidium, Rhodotorula, Saccharomyces, Sus, Sporobolomyces, Thermomyces, Thiarosporella, Trichoderma, Verticillium*, and/or a strain of *Yarrowia*. In a preferred aspect, the source of the lipase is selected from the group consisting of *Absidia blakesleena, Absidia corymbifera, Achromobacter iophagus, Alcaligenes* sp., *Alternaria brassiciola, Aspergillus flavus, Aspergillus niger, Aspergillus tubingensis, Aureobasidium pullulans, Bacillus pumilus, Bacillus strearothermophilus, Bacillus subtilis, Brochothrix thermosohata, Candida cylindracea (Candida rugosa), Candida paralipolytica, Candida antarctica* lipase A, *Candida antarctica* lipase B, *Candida ernobii, Candida deformans, Chromobacter viscosum, Coprinus cinerius, Fusarium oxysporum, Fusarium solani, Fusarium solani pisi, Fusarium roseum culmorum, Geotricum penicillatum, Hansenula anomala, Humicola brevispora, Humicola brevis* var. *thermoidea, Humicola insolens, Lactobacillus curvatus, Rhizopus oryzae, Penicillium cyclopium, Penicillium crustosum, Penicillium expansum, Penicillium* sp. I, *Penicillium* sp. II, *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri*, and *Pseudomonas wisconsinensis, Rhizoctonia solani, Rhizomucor miehei, Rhizopus japonicus, Rhizopus microsporus, Rhizopus nodosus, Rhodosporidium toruloides, Rhodotorula glutinis, Saccharomyces cerevisiae, Sporobolomyces shibatanus, Sus scrofa, Thermomyces lanuginosus* (formerly *Humicola lanuginose*), *Thiarosporella phaseolina, Trichoderma harzianum, Trichoderma reesei*, and *Yarrowia lipolytica*. In a further preferred aspect, the lipase is selected from the group consisting of *Thermomcyces lanuginosus* lipase, *Aspergillus* sp. lipase, *Aspergillus niger* lipase, *Aspergillus tubingensis* lipase, *Candida antarctica* lipase B, *Pseudomonas* sp. lipase, *Penicillium roqueforti* lipase, *Penicillium camembertii* lipase, *Mucor javanicus* lipase, *Burkholderia cepacia* lipase, *Alcaligenes* sp. lipase, *Candida rugosa* lipase, *Candida parapsilosis* lipase, *Candida deformans* lipase, lipases A and B from *Geotrichum candidum, Neurospora crassa* lipase, *Nectria haematococca* lipase, *Fusarium heterosporum* lipase *Rhizopus delemar* lipase, *Rhizomucor miehei* lipase, *Rhizopus arrhizus* lipase, and *Rhizopus oryzae* lipase. Suitable commercial lipase preparations suitable as catalyst 42 include, but are not limited to, Lipolase® 100 L, Lipex® 100L, Lipoclean® 2000T, Lipozyme® CALB L, Novozyme® CALA L, and Palatase 20000L, available from Novozymes, or from *Pseudomonas fluorescens, Pseudomonas cepacia, Mucor miehei, hog pancreas, Candida cylindracea, Candida rugosa, Rhizopus niveus, Candida antarctica, Rhizopus arrhizus* or *Aspergillus* available from SigmaAldrich.

Phospholipases are enzymes that hydrolyze the ester bonds of phospholipids, but many phospholipases also can hydrolyze triglycerides, diglycerides, and monoglycerides (lipid acyl hydrolase (LAH) activity). As used herein, the term "phospholipase" encompasses enzymes having any phospholipase activity, for example, cleaving a glycerolphosphate ester linkage (catalyzing hydrolysis of a glycerolphosphate ester linkage), for example, in an oil, such as a crude oil or a vegetable oil. The phospholipase activity of the invention can generate a water extractable phosphorylated base and a diglyceride. The phospholipase activity can comprise a phospholipase C (PLC) activity; a PI-PLC activity, a phospholipase A (PLA) activity such as a phospholipase A1 or phospholipase A2 activity; a phospholipase B (PLB) activity such as a phospholipase B1 or phospholipase B2 activity, including lysophospholipase (LPL) activity and/or lysophospholipase-transacylase (LPT A) activity; a phospholipase D (PLD) activity such as a phospholipase DI or a phospholipase D2 activity; and/or a patatin activity or any combination thereof.

The term "phospholipase" also encompasses enzymes having lysophospholipase activity, where the two substrates of this enzyme are 2-lysophosphatidylcholine and $H_2O$, and where its two products are glycerophosphocholine and carboxylate. Phospholipase A1 (PLA1) enzymes remove the 1-position fatty acid to produce free fatty acid and 1-lyso-2-acylphospholipid. Phospholipase A2 (PLA2) enzymes remove the 2-position fatty acid to produce free fatty acid and I-acyl-2-lysophospholipid. PLA1 and PLA2 enzymes can be intra- or extra-cellular, membrane-bound or soluble. Phospholipase C (PLC) enzymes remove the phosphate moiety to produce 1,2 diacylglycerol and a phosphate ester. Phospholipase D (PLD) enzymes produce 1,2-diacylglycerophosphate and base group. A phospholipase useful in the present invention may be obtained from a variety of biological sources, for example, but not limited to, filamentous fungal species within the genus *Fusarium*, such as a strain of *F. culmorum, F. heterosporum, F. solani*, or *F. oxysporum*; or a filamentous fungal species within the genus *Aspergillus*, such as a strain of *Aspergillus awamori, Aspergillus foetidus, Aspergillus japonicus, Aspergillus niger* or *Aspergillus oryzae*. Also useful in the present invention are *Thermomyces lanuginosus* phospholipase variants such as the commercial product Lecitase® Ultra (Novozymes A'S, Denmark). One or more phospholipases may be applied as lyophilized powder, immobilized or in aqueous solution.

An alcohol (e.g., butanol) that is produced by fermentation of one or more fermentable sugars may be converted to a carboxylic acid ester by an enzyme-catalyzed reaction where the carboxylic acid is esterified with the alcohol. Enzymes such as lipase, phospholipase, and lysophospholipase may catalyzed this reaction; however, these enzymes may be inactivated due to one or more factors including, but not limited to, hydrodynamic shear or inactivation at gas-liquid and liquid-liquid interfaces. In fermentations where oligosaccharides are additionally converted to one or more fermentable sugars, the enzyme that converts oligosaccharides to fermentable sugars (e.g., glucoamylase) may also be inactivated by one or more of these same factors.

Inactivation of enzymes at a gas-liquid interface (e.g., may occur at the interface of bubbles with the fermentation broth) that results from aeration of the fermentation broth and/or is produced by the evolution of gaseous carbon dioxide in the broth during fermentation of one or more fermentable sugars, is well-known in the art. Inactivation of Hen egg white lysozyme and *Thermomyces lanuginosus* lipase produced in *Aspergillus oryzae* (Novozymes Lipolase®) was observed at the gas-liquid interface in three different reactor configurations: bubble column, stirred vessel with baffles (with no aeration by gas sparging), and falling film (Ghadge, et al., Chem. Eng. Sci. 58:5125-5134, 2003). The mechanism of inactivation of *Thermomyces lanuginosus* lipase (produced in *Aspergillus oryzae*; Novozymes Lipolase 100L®) at the gas-liquid interface in a baffled stirred-tank reactor (with no aeration by gas sparging) has been reported (Patil, et al., AIChE J. 46:1280-1283, 2000).

Stahmann, et al. (Eur. J. Biochem. 244:220-225, 1997) have reported that *Ashbya gossypii* lipase was inactivated within minutes in stirred gas/water, trioleoylglycerol/water or oleic acid/water mixtures, due to interfacial inactivation at either a gas/liquid or liquid/liquid interface. Elias, et al. (Adv. Biochem. Engineering/Biotechnology 59:47-71, 1998) have reported that: (i) some enzymes are inactivated by hydrodynamic shear even in the absence of a gas-liquid interface; (ii) for enzymes that are inactivated by hydrodynamic shear, the rate of inactivation increases in the presence of gas-liquid interface; (iii) some enzymes are not inactivated in the absence of gas-liquid interface regardless of the applied hydrodynamic shear; and (iv) for enzymes that require a gas-liquid interface for inactivation, the rate of inactivation increases with an increase in hydrodynamic shear. Ross, et al. (J. Mol. Catal. B: Enzymatic 8:183-192, 2000) have described the interfacial inactivation of α-chymotrypsin, β-chymotrypsin, papain, and pig liver esterase in a variety of aqueous/organic solvent mixtures by passing solvent droplets up through an aqueous enzyme solution in a bubble column apparatus. The kinetics and mechanism of shear inactivation of *Candida cylindracea* lipase in a stirred tank reactor has also been reported, where the mechanism of inactivation was found to be due to a shear-induced gas-liquid interface effect (Lee, et al., Biotechnol. Bioeng. 33:183-190, 1989).

Under the fermentation conditions employed in some methods described herein, hydrodynamic shear and gas-liquid and liquid-liquid interfaces are each present over the course of the fermentation, and capable of causing enzyme inactivation. The potential effect of each of these factors on the stability and activity of one or more of the enzymes (e.g., glucoamylase, lipase, phospholipase, and lysophospholipase) present in the two-phase mixture (e.g., fermentation broth and carboxylic acid) during fermentation under the conditions described herein could not have been anticipated based on the prior art. Although each of these factors could have resulted in the inactivation of one or more enzymes in the fermentation mixture, sufficient enzyme activity to catalyze esterification of the product alcohol by carboxylic acid to produce carboxylic acid esters was maintained over the course of the fermentation. In reactions where glucoamylase was also present in the two-phase fermentation mixture of fermentation broth and carboxylic acid, sufficient enzyme activity (i.e., to convert oligosaccharide to fermentable sugars) was also maintained.

Carboxylic acid 28 can be any carboxylic acid capable of esterifying with a product alcohol such as butanol or ethanol, to produce an alcohol ester of the carboxylic acid. For example, in some embodiments, carboxylic acid 28 can be free fatty acid, and in some embodiments, the carboxylic acid or free fatty acid has 4 to 28 carbons, 4 to 22 carbons in other embodiments, 8 to 22 carbons in other embodiments, 10 to 28 carbons in other embodiments, 7 to 22 carbons in other embodiments, 12 to 22 carbons in other embodiments, 4 to 18 carbons in other embodiments, 12 to 22 carbons in other embodiments, and 12 to 18 carbons in still other embodiments. In some embodiments, carboxylic acid 28 is one or more of the following fatty acids: azaleic, capric, caprylic, castor, coconut (i.e., as a naturally-occurring combination of fatty acids including lauric, myrisitic, palmitic, caprylic, capric, stearic, caproic, arachidic, oleic, and linoleic, for example), isostearic, lauric, linseed, myristic, oleic, palm oil, palmitic, palm kernel, pelargonic, ricinoleic, sebacic, soya, stearic acid, tall oil, tallow, and #12 hydroxy stearic. In some embodiments, carboxylic acid 28 is one or more of diacids.

In some embodiments, carboxylic acid 28 can be a mixture of two or more different fatty acids. In some embodiments, carboxylic acid 28 comprises free fatty acid derived from hydrolysis of acyl glycerides by any method known in the art including chemical or enzymatic hydrolysis. In some embodiments as noted above, carboxylic acid 28 can be derived from native oil 26 by enzymatic hydrolysis of the oil glycerides using an enzyme as catalyst 42. In some embodiments, the fatty acids or mixtures thereof comprise unsaturated fatty acids. The presence of unsaturated fatty acids decreases the melting point, providing advantages for handling. Of the unsaturated fatty acids, those which are monounsaturated, that is, possessing a single carbon-carbon double bond, may provide advantages with respect to melting point without sacrificing suitable thermal and oxidative stability for process considerations.

In some embodiments, native oil 26 can be tallow, corn, canola, capric/caprylic triglycerides, castor, coconut, cottonseed, fish, jojoba, lard, linseed, neetsfoot, oiticica, palm, peanut, rapeseed, rice, safflower, soya, sunflower, tung, jatropha, pumpkin, grape seed, and vegetable oil blends (or oils that can be purified into higher concentrations of different chain length and levels of unsaturation (i.e., 18:1)). In some embodiments, native oil 26 is a mixture of two or more native oils such as a mixture of palm and soybean oils, for example. In some embodiments, native oil 26 is a plant-derived oil. In some embodiments, the plant-derived oil can be, though not necessarily, derived from biomass that can be used in a fermentation process. The biomass can be the same or different source from which feedstock 12 is obtained. Thus, for example, in some embodiments, oil 26 can be derived from corn, whereas feedstock 12 can be cane. For example, in some embodiments, oil 26 can be derived from corn, and the biomass source of feedstock 12 is also corn. Any possible combination of different biomass sources for oil 26 versus feedstock 12 can be used, as should be apparent to one of skill in the art. In some embodiments, oil 26 is derived from the biomass used in the fermentation process. Thus, in some embodiments, as later described with reference to FIG. 3, oil 26 is derived directly from feedstock 12 as oil 26'. For example, when feedstock 12 is corn, then oil 26' is the feedstock's constituent corn oil.

Optionally, ethanol 33 may be supplied to fermentation vessel 30 to be included in the fermentation broth. In some embodiments, when a recombinant microorganism having a butanol biosynthetic pathway and/or reduced or eliminated expression of pyruvate decarboxylase is used as microorganism 32, microorganism 32 may require supplementation of a 2-carbon substrate, for example, ethanol, for survival and growth. Thus, in some embodiments, ethanol 33 may be supplied to fermentation vessel 30.

However, it has been surprisingly found that methods of the present invention, in which carboxylic acid such as fatty acid, is present in the fermentation vessel, can allow reduction of the amount of ethanol 33 typically supplied for a given recombinant microorganism without detriment to the vitality of the recombinant microorganism. Further, in some embodiments of the methods of the present invention, the alcohol (e.g., butanol) production rate without ethanol supplementation can be comparable with the production rate that can be realized when ethanol 33 is supplemented. As further demonstrated by the comparative examples presented in the Examples 1-14 below, the butanol production rate when fatty acid but not ethanol is in the fermentation vessel can be comparable to or greater than the butanol production rate when neither fatty acid nor ethanol is in the fermentation vessel. Thus, in some embodiments, the amount of ethanol 33 supplementation is reduced compared to conventional processes. For example, a typical amount of ethanol added to a fermentation vessel for microorganisms requiring supplementation of a 2-carbon substrate is about 5 g/L anhydrous ethanol (i.e., 5 g anhydrous ethanol per liter of fermentation medium). In some embodiments, the fermentation is not supplemented with any ethanol 33. In the latter case, the stream of ethanol 33 is entirely omitted from the fermentation vessel. Thus, in some embodiments of the present invention, it is possible to reduce or eliminate the cost associated with supplemental ethanol 33, as well as the inconvenience associated with storing vats of ethanol 33 and supplying it to the fermentation vessel during butanol fermentation or other alcohol fermentation that employs a microorganism that may require supplementation of a 2-carbon substrate to survive and grow.

Moreover, regardless of ethanol supplementation, in some embodiments, the methods of the present invention can provide a higher rate of glucose uptake by microorganism 32 by virtue of the presence of fatty acids during the fermentation. The fatty acids can be introduced into fermentation vessel 30 as carboxylic acid 28, hydrolyzed from supplied oil 26, and/or derived from hydrolysis of constituent biomass oil of slurry 16. Methods for producing a product alcohol from a fermentation process in which free fatty acids are produced at a step in the process and are contacted with microorganism cultures in a fermentation vessel for improving microorganism growth rate and glucose consumption are described in co-pending, commonly owned U.S. Provisional Application Ser. No. 61/368,451, filed on Jul. 28, 2010, which is incorporated herein in its entirety by reference thereto.

In fermentation vessel 30, alcohol produced by microorganism 32 is esterified with carboxylic acid 28 using catalyst 42 to form alcohol esters. For example, in the case of butanol production, butanol produced by microorganism 32 is esterified with carboxylic acid 28 using catalyst 42 to form butyl esters. In situ product removal (ISPR) can be utilized to remove the alcohol esters from the fermentation broth. As demonstrated herein, using catalyst to form esters in conjunction with ISPR can improve the performance of the fermentation. In some embodiments, using catalyst to form esters in conjunction with ISPR (such as, for example, liquid-liquid extraction) can increase the effective titer by at least about 10%, at least about 20%, at least about 30%, at least about 40%, at least about 50%, at least about 60%, at least about 70%, at least about 80%, at least about 90%, or at least about 100% as compared to the effective titer in an analogous fermentation using ISPR without a catalyst forming esters. Similarly, in some embodiments, using a catalyst to form esters in conjunction with ISPR (such as, for example, liquid-liquid extraction) can increase the effective rate by at least about 10%, at least about 20%, at least about 30%, at least about 40%, at least about 50%, at least about 60%, at least about 70%, at least about 80%, at least about 90%, or at least about 100% as compared to the effective rate in an analogous fermentation using ISPR without a catalyst forming esters (see, e.g., Examples 9 and 11-14, Table 3). In some embodiments, the effective yield is increased by at least about 10%, at least about 20%, at least about 30%, at least about 40%, or at least about 50%. In some embodiments, the resulting fermentation broth after alcohol esterification can comprise free (i.e., unesterified) alcohol and in some embodiments, the concentration of free alcohol in the fermentation broth after alcohol esterification is not greater than 1, 3, 6, 10, 15, 20, 25, 30 25, 40, 45, 50, 55, or 60 g/L when the product alcohol is butanol, or when the product alcohol is ethanol, the concentration of free alcohol in the fermentation broth after alcohol esterification is not greater than 15, 20, 25, 30 25, 40, 45, 50, 55, 60, 65, 70, 75, 80, 85, 90, 95, or 100 g/L. In some embodiments, the ratio of alcohol ester to alcohol in the fermentation vessel may be about 1:1. In some embodiments, at least about 20%, at least about 30%, at least about 40%, at least about 50%, at least about 60%, at least about 70%, at least about 80%, or at least about 90% of the effective titer of alcohol is converted to alcohol ester.

In some embodiments, a grain load on water at a sufficient concentration to achieve a final effective titer of at least about 50 g/L, at least about 75 g/L, or at least about 100 g/L may be used in a grain mash fermentation comprising a microorganism capable of producing an alcohol such as butanol. In other embodiments, the grain mash fermentation may use simultaneous saccharification and fermentation (SSF), and the concentration of glucose may remain relatively low, for example, at least about 75 g/L glucose in the fermentation broth phase over the course of the fermentation.

In some embodiments, fatty acids may be added to the fermentor in an amount that is less than about 70% of the volume of the fermentor, less than about 50% of the volume of the fermentor, or less than about 30% of the volume of the fermentor. The amount of fatty acid added to the fermentor may be a means to maintain the aqueous phase titer of butanol during fermentation. In other embodiments, the aqueous phase titer of butanol may be maintained at a level less than about 35 g/L of fermentation broth, less than about 25 g/L of fermentation broth, or less than about 20 g/L of fermentation broth. In other embodiments, the amount of active esterification enzyme in the fermentation broth may be less than about 100 ppm, less than about 50 ppm, or less than about 10 ppm active enzyme. In some embodiments, the cell mass employed in a fermentation broth may be less than about 50 g dcw/L, less than about 20 g dcw/L, or less than about 10 g dcw/L. In other embodiments, the fermentation process may run at least about 30 hours to at least about 100 hours, at least about 40 hours to at least about 80 hours, or at least about 50 hours to at least about 70 hours.

In some embodiments, a brix on water at a sufficient concentration to achieve a final effective titer of at least about 30 g of butanol per liter of fermentation broth phase, at least about 45 g of butanol per liter of fermentation broth phase, or at least about 60 g of butanol per liter of fermentation broth phase may be used in a sugarcane fermentation comprising a microorganism capable of producing butanol. In some embodiments, fatty acids may be added to the fermentor in an amount that is less than about 70% of the volume of the fermentor, less than about 50% of the volume of the fermentor, or less than about 30% of the volume of the fermentor. The amount of fatty acid added to the fermentor may be a means to maintain the aqueous phase titer of butanol during fermentation. In other embodiments, the aqueous phase titer of butanol may be maintained at a level less than about 35 g/L of fermentation broth, less than about 25 g/L of fermentation broth, or less than about 15 g/L of fermentation broth. In other embodiments, the amount of active esterification enzyme in the fermentation broth may be less than about 200 ppm, less than about 100 ppm, or less than about 20 ppm active enzyme. In some embodiments, the cell mass employed in a fermentation broth may initially be at least about 100 g of cell per liter of broth in the initial charge occupying at least about 30% of the fermentor volume. After 3-7 hours of fermentation, the cell mass may be diluted to at least about 25 g of cell per liter of fermentation broth by the addition of a sugarcane feed. The cells may continue to grow to at least about 30 g of cell per liter of fermentation broth over the 8 to 15 hours of total fermentation time.

In some embodiments, the fermentation broth is contacted during fermentation with an extractant to form a two-phase mixture comprising an aqueous phase and an organic phase. In such embodiments, ISPR including liquid-liquid extraction may be conveniently carried out. Liquid-liquid extraction can be performed according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water-immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, $C_{12}$ to $C_{22}$ fatty amides, and mixtures thereof. The extractant may also be an organic extractant selected from the group consisting of saturated, mono-unsaturated, poly-unsaturated (and mixtures thereof) $C_4$ to $C_{22}$ fatty alcohols, $C_4$ to $C_{28}$ fatty acids, esters of $C_4$ to $C_{28}$ fatty acids, $C_4$ to $C_{22}$ fatty aldehydes, and mixtures thereof. For use with the processes described herein, the extractant(s) for ISPR are typically non-alcohol extractants, so as to avoid consuming carboxylic acid 28 in fermentation vessel 30 by catalytic esterification of carboxylic acid 28 with an alcohol extractant, whereby less carboxylic acid would be available for esterification with the product alcohol. For example, if oleyl alcohol is used as an ISPR extractant, then oleyl alcohol esters of the carboxylic acid can be produced in fermentation vessel due to the presence of active catalyst 42, as further demonstrated in the Example 24 below.

With reference to the embodiment of FIG. 1, the carboxylic acid 28 can also serve as an ISPR extractant 28 or a component thereof. As earlier noted, carboxylic acid 28 can be supplied, and/or formed in situ in the case when native oil 26 is supplied to fermentation vessel 30, and/or formed in situ in the case when feedstock 16 includes oil that can be hydrolyzed. In some embodiments, ISPR extractant 28 includes free fatty acids. In some embodiments, ISPR extractant 28 includes corn oil fatty acids (COFA). In some embodiments, oil 26 is corn oil, whereby ISPR extractant 28 is COFA. ISPR extractant (carboxylic acid) 28 contacts the fermentation broth and forms a two-phase mixture comprising an aqueous phase 34 and an organic phase. The product alcohol ester formed in the fermentation vessel preferentially partitions into the organic phase to form an ester-containing organic phase 36. That is, the product alcohol esters are produced at a concentration in excess of the equilibrium concentration of alcohol ester present in the aqueous phase 34 and therefore, preferentially partition into the organic phase. Any free product alcohol in the fermentation broth also preferentially partitions into the ester-containing organic phase. The biphasic mixture can be removed from fermentation vessel 30 as stream 39 and introduced into a vessel 35, in which the ester-containing organic phase 36 is separated from aqueous phase 34. Separation of biphasic mixture 39 into ester-containing organic phase 36 and aqueous phase 34 can be achieved using any methods known in the art, including but not limited to, siphoning, aspiration, decantation, centrifugation, using a gravity settler, membrane-assisted phase splitting, hydroclyclone, and the like. All or part of aqueous phase 34 can be recycled into fermentation vessel 30 as fermentation medium (as shown), or otherwise discarded and replaced with fresh medium, or treated for the removal of any remaining product alcohol and then recycled to fermentation vessel 30.

With reference to FIG. 1, ester-containing organic phase 36 is introduced into vessel 50 in which the alcohol esters are reacted with one or more substances 52 to recover product alcohol 54. Product alcohol 54 can be recovered using any method known in the art for obtaining an alcohol from an alcohol ester. For example, in some embodiments, the product alcohol can be recovered from the alcohol ester by hydrolysis with base followed by acidification. In other embodiments the product alcohol esters can be hydrolyzed by water in the presence of a hydrolysis catalyst as substance 52. For example, in some embodiments, hydrolysis of the product alcohol esters to alcohol and carboxylic acid 28 (e.g., fatty acid when carboxylic acid 28 is a fatty acid) can be achieved using a lipase, a water soluble acid, an inorganic acid, an organic acid, or a solid acid catalyst as substance 52. For example, sulfuric acid can be used as an inorganic acid catalyst for alcohol ester hydrolysis. Some suitable hydrolysis catalysts are lipase enzymes; esterase enzymes; strong inorganic acids such as sulfuric acid, hydrochloric acid, or phosphoric acid; strong organic acids such as toluenesulfonic acid or naphthalenesulfonic acid; or solid acid catalysts such as Amberlyst® sulfonated polystyrene resins, or zeolites. In some embodiments, hydrolysis of the alcohol esters can be achieved using steam as substance 52, by increasing temperature, and/or by application of pressure. In some embodiments, hydrolysis of the alcohol esters can be carried out in a column, for example, a reactive distillation column. Examples 45 to 54 and 56 to 58 demonstrate several methods to recover the product alcohol from an alcohol ester. In some embodiments, by-products 56 are obtained from recovering product alcohol 54. By-products 56 do not include carboxylic acid 28 that can be recovered from hydrolysis of the alcohol esters.

In some embodiments, hydrolysis of the alcohol esters of fatty acids present in the ester-containing organic phase 36 into the product alcohol and free fatty acids occurs at a fatty acid to water ratio from about 10:1 to about 1:10 or in other embodiments, at a fatty acid to water ratio from about 100:1 to about 1:100. In some embodiments, the alcohol esters of fatty acids are hydrolyzed with water at a temperature less than about 100° C. In some embodiments, the hydrolysis occurs at a temperature greater than 100° C., greater than 150° C., greater than 200° C., or greater than 250° C.

For example, in some embodiments, the alcohol esters can be transesterified to produce product alcohol 54 and in some embodiments, a second alcohol ester 56, for example, fatty acid alkyl esters, can also be produced as by-product 56. To achieve such transesterification, the alcohol esters can be contacted with catalysts capable of transesterifying the alcohol esters to release butanol. In some embodiments, the alcohol esters can be transesterified using glycerol to produce product alcohol 54 and acyl glycerides as by-product 56. The acyl glycerides produced may comprise mono- and diacylglycerides. Some suitable catalysts for transesterification reactions are, for example, lipase enzymes, alkoxide salts particularly of the second alcohol, alkyl titanates, soluble inorganic acids such as sulfuric acid and phosphoric acid, soluble organic acids such as toluenesulfonic acid and naphthalenesulfonic acid, and solid acids such as Amberlyst® sulfonated polystyrene resins, or zeolites. Suitable lipases for transesterifications or hydrolysis include, but are not limited to, lipases derived from *Burkholderia cepacia, Thermomyces lanuginosa*, or *Candida antarctica*. In some embodiments, the lipases are immobilized on a soluble or insoluble support using methods well-known to those skilled in the art (see, e.g., Immobilization of Enzymes and Cells; Gordon F. Bickerstaff, Editor; Humana Press, Totowa, N.J., USA, 1997). The immobilization of enzymes may be performed using a variety of techniques including 1) binding of the enzyme to a porous or non-porous carrier support, via covalent support, physical adsorption, electrostatic binding, or affinity binding; 2) crosslinking with bifunctional or multifunctional reagents; 3) entrapment in gel matrices, polymers, emulsions, or some form of membrane; and 4) a combination of any of these methods. In other embodiments, the lipases may not be immobilized. In some embodiments, the lipases are soluble. Fatty acid alkyl esters 56 can include fatty acid methyl esters, for example. Other fatty acid alkyl esters 56 can include $C_2$ to $C_{12}$ linear, branched, and cyclic alcohol esters, for example. Product alcohol 54 can then be separated from the reaction mixture including by-products 56 using any separation means known in the art such as distillation, for example. Other suitable separation mechanisms can include extraction and membrane separation, for example.

In some embodiments, at least about 5%, at least about 10%, at least about 20%, at least about 30%, at least about 40%, at least about 50%, at least about 60%, at least about 70%, at least about 80%, at least about 90%, or at least about 99% of the product alcohol is recovered from the alcohol esters.

ISPR extractant (carboxylic acid) 28 can be separated from the alcohol esters before reaction of the alcohol esters for recovery of product alcohol 54. Alternatively, ISPR extractant 28 can be separated from the product alcohol and any by-products after the reaction of the alcohol esters. The resulting recovered lean extractant 27 can then be recycled back into fermentation vessel 30, usually in combination with fresh make-up extractant 28 (which can be derived from oil 26, if supplied) for further production and/or extraction of alcohol esters. Alternatively, fresh extractant 28 (or oil 26) can be continuously added to the fermentation vessel to replace the extractant removed in biphasic mixture stream 39.

In some embodiments, catalyst 42 can be recovered from biphasic mixture 39 and reused at a step in the fermentation process such as in the fermentation itself or in recovery of the product alcohol.

In some embodiments, one or more additional ISPR extractants 29 (see FIG. 2) can be introduced into fermentation vessel 30 to form a two-phase mixture comprising an aqueous phase and an organic phase. In such embodiments, ISPR extractant 29 can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof. However, for the reasons noted above, ISPR extractant 29 is preferably not an alcohol. Rather, ISPR extractant 29 is preferably a carboxylic acid (e.g. free fatty acids). In some embodiments, ISPR extractant 29 is COFA. In some embodiments, ISPR extractant 29 is linseed oil fatty acid, soybean oil fatty acid, jatropha oil fatty acid, or fatty acids derived from palm oil, castor oil, olive oil, coconut oil, peanut oil, or any seed oil. In some embodiments, ISPR extractant 29 can be a fatty acid extractant selected from the group consisting of fatty acids, fatty alcohols, fatty amides, fatty esters (particularly those comprising 1 to 8 carbon atoms in the alcohol portion, e.g., fatty acid methyl esters and lower alcohol esters of fatty acids), fatty acid glycol esters, hydroxylated triglycerides, and mixtures thereof, obtained from chemical conversion of native oil such as biomass lipids as described, for example, in co-pending, commonly owned U.S. Provisional Application Ser. No. 61/368,436, filed on Jul. 28, 2010, herein incorporated by reference. In some embodiments, ISPR extractant 29 is free fatty acids obtained by chemical hydrolysis of biomass lipids. In some embodiments, ISPR extractant 29 can be free fatty acids produced from enzymatic hydrolysis of native oil such as biomass lipids as described, for example, in co-pending, commonly owned U.S. Provisional Application Ser. No. 61/368,444, filed on Jul. 28, 2010, herein incorporated by reference.

In situ product removal can be carried out in a batch mode or a continuous mode in fermentation vessel 30. In a continuous mode of in situ product removal, product is continually removed from the vessel (or reactor). In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth which can be determined by measuring the optical density of the culture. Further, the organic extractant can contact the fermentation medium at a time at which the product alcohol level in the fermentation medium reaches a preselected level. In the case of butanol production according to some embodiments of the present invention, at a time before the butanol concentration reaches a toxic level, the carboxylic acid extractant can contact the fermentation medium to esterify the butanol with the carboxylic acid to produce butyl esters and in some embodiments, produce a two-phase mixture comprising an aqueous phase and an organic phase comprising the butyl esters. Consequently, the concentration of butanol is reduced in the fermentation vessel and as a result, minimizes the toxic effects of butanol on the microorganism. The ester-containing organic phase can then be removed from the fermentation vessel (and separated from the fermentation broth which constitutes the aqueous phase) after a desired effective titer of the butyl esters is achieved. For example, in some embodiments, the ester-containing organic phase can be separated from the fermentation broth after the effective titer of butyl esters is greater than about 10 g/kg of fermentation broth. In other embodiments, the ester-containing organic phase can be separated from the fermentation medium after the effective titer of butyl esters is greater than about 230 g/kg fermentation broth, greater than about 300 g/kg fermentation broth, greater than about 400 g/kg fermentation broth, greater than about 500 g/kg fermentation broth, or greater than about 600 g/kg fermentation broth. In another embodiment, the ester-containing organic phase can be separated from the fermentation medium after the % conversion of COFA is at least about 10%, at least about 25%, at least about 50%, at least about 75%, or at least about 100%. In some embodiments, the ester-containing organic phase is separated from the aqueous phase after fermentation of the available fermentable sugar in the fermentation vessel is substantially complete.

In the example embodiment depicted in FIG. 1, the alcohol ester is extracted from the fermentation broth in situ, with the separation of the biphasic mixture 39 occurring in a separate vessel 35. In some embodiments, separation of the biphasic mixture can occur in the fermentation vessel, as shown in the example embodiments of later described FIGS. 3 and 4 in which the ester-containing organic phase stream 36 exits directly from fermentation vessel 30. Aqueous phase stream 34 can also exit directly from fermentation vessel 30, be treated for the removal of any remaining alcohol ester or product alcohol, and recycled, or discarded and replaced with fresh fermentation medium. The extraction of the alcohol ester and the product alcohol by the organic extractant can be done with or without the removal of microorganism 32 from the fermentation broth. Microorganism 32 can be removed from the fermentation broth by means known in the art including, but not limited to, filtration or centrifugation. For example, aqueous phase stream 34 can include microorganism 32 such as yeast. Microorganism 32 can be easily separated from the aqueous phase stream, for example, in a centrifuge (not shown). Microorganism 32 can then be recycled to fermentation vessel 30 which over time can increase the production rate of alcohol production, thereby resulting in an increase in the efficiency of the alcohol production.

Figure 4:
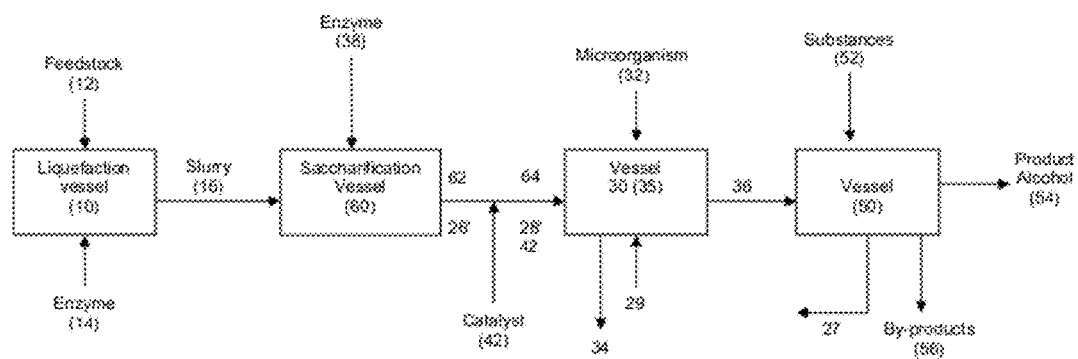

In some embodiments, the system and processes of FIG. 1 can be modified such that simultaneous saccharification and fermentation in fermentation vessel 30 is replaced with a separate saccharification vessel 60 prior to fermentation vessel 30, as should be apparent to one of skill in the art (see, e.g., the embodiment of FIG. 4).

Figure 2:
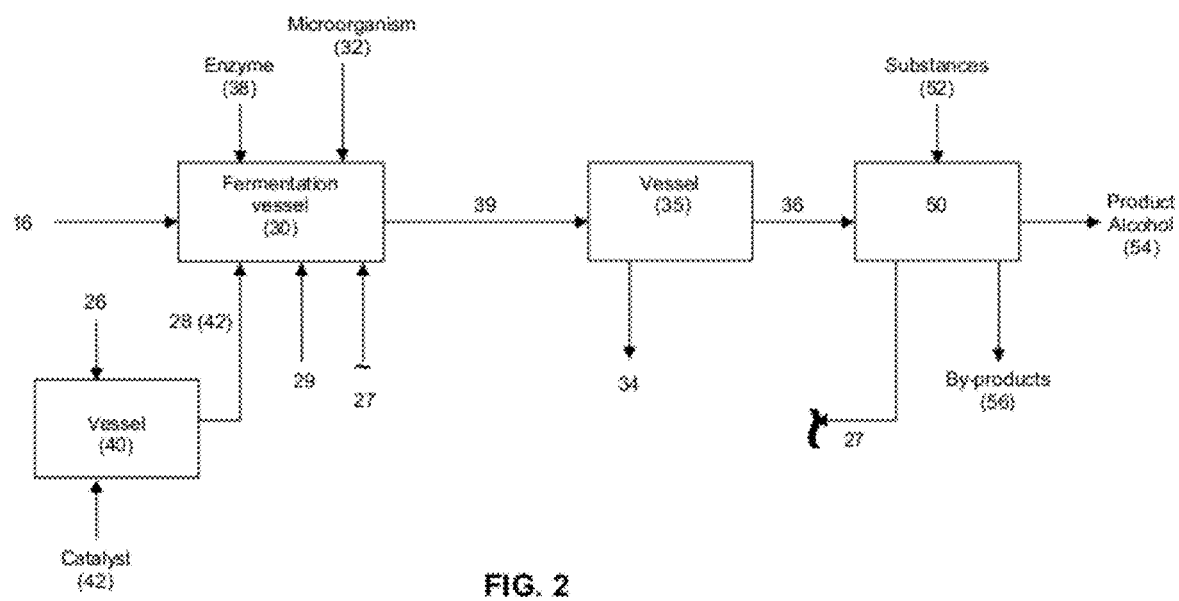

In still other embodiments, as shown, for example, in the example embodiment of FIG. 2, native oil 26 (instead of being supplied directly to fermentation vessel 30) is supplied to a vessel 40 to which catalyst 42 is also supplied, whereby at least a portion of the acyl glycerides in oil 26 are hydrolyzed to form carboxylic acid 28. A product stream from vessel 40 containing carboxylic acid 28 and catalyst 42 are then introduced into fermentation vessel 30. Carboxylic acid 28 and catalyst 42 contact the product alcohol produced in the fermentation medium whereby alcohol esters of the product alcohol are formed in situ from catalyzed esterification of the carboxylic acid with the product alcohol, in a same manner as described above with reference to FIG. 1. Carboxylic acid 28 can also serve as an ISPR extractant and in some embodiments, sufficient carboxylic acid 28 and/or one or more additional ISPR extractants 29 can be introduced into fermentation vessel 30 to form a two-phase mixture comprising an aqueous phase and an organic phase, with the alcohol ester partitioning into the organic phase. The remaining process operations of the embodiment of FIG. 2 are identical to FIG. 1 and therefore, will not be described in detail again.

Figure 3:
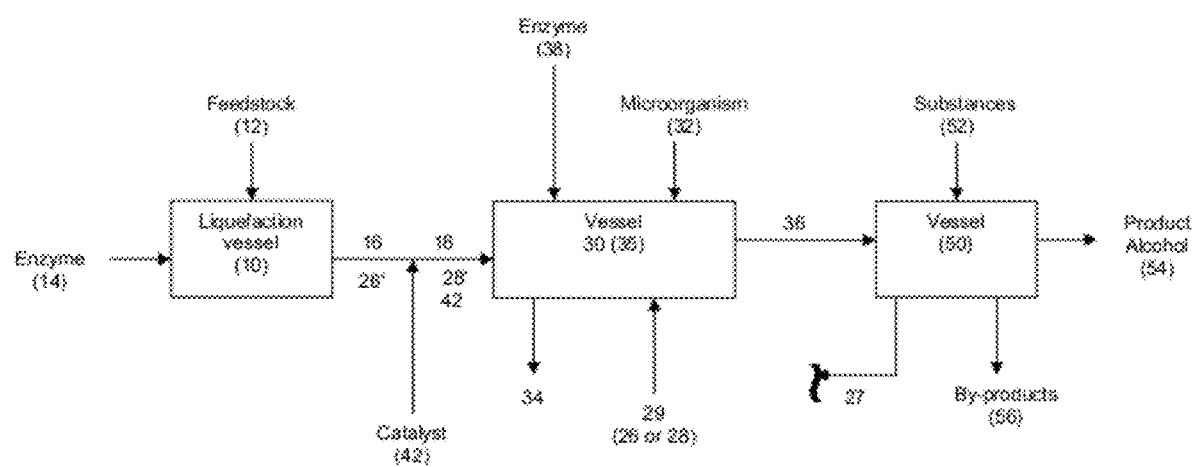

In some embodiments of the present invention, as shown, for example, in the embodiment of FIG. 3, catalyst 42 can be added to feedstock slurry 16 comprising oil 26' derived from the biomass from which feedstock 12 was formed. In the embodiment shown, catalyst 42 is capable of hydrolyzing the glycerides in oil 26' to free fatty acids 28'. Thus, after introduction of catalyst 42 to feedstock slurry 16, at least a portion of the glycerides in oil 26' are hydrolyzed, resulting in a feedstock slurry 18 having free fatty acids 28' and catalyst 42. For example, when feedstock 12 is corn, then oil 26' is the feedstock's constituent corn oil and the free fatty acids 28' are corn oil fatty acids (COFA).

Feedstock slurry 18 is introduced to fermentation vessel 30 along with alcohol-producing microorganism 32 to be included in a fermentation medium. In some embodiments, an enzyme 38 such as glucoamylase, can also be introduced into fermentation vessel for simultaneous saccharification of sugars in slurry 18 and fermentation of alcohol inside fermentation vessel 30. The presence of catalyst 42 in fermentation vessel (introduced via slurry 18) catalyzes the esterification of the alcohol with the free fatty acids 28' (introduced via slurry 18) to form fatty acid alcohol esters in situ, in a same manner as described above with reference to FIG. 1. In some embodiments, for butanol production, butanol-producing microorganism 32 is introduced in fermentation vessel 30 along with feedstock slurry 18. Catalyst 42 in fermentation vessel (introduced via slurry 18) catalyzes the esterification of the butanol with the free fatty acids 28' (introduced via slurry 18) to form fatty acid butyl esters (FABE) in situ. Free fatty acids 28' can also serve as an ISPR extractant. For example, when free fatty acids 28' are COFA, then alcohol esters of COFA are formed in situ, and COFA serves as an ISPR extractant or a portion thereof.

In some embodiments, one or more additional ISPR extractants 29 can be introduced into fermentation vessel 30 for preferentially partitioning the alcohol ester (and any free alcohol) from the aqueous phase. In some embodiments, ISPR extractant 29 can be carboxylic acid 28 described with reference to the embodiments of FIGS. 1 and 2. In some embodiments, ISPR extractant 29 is introduced in fermentation vessel 30 as oil 26 which is then hydrolyzed into fatty acids by catalyst 42 so as to become ISPR extractant 29. In some embodiments, oil 26 is corn oil, whereby ISPR extractant 29 is COFA. In some embodiments, ISPR extractant 29 can be a fatty acid extractant selected from the group consisting of fatty acids, fatty alcohols, fatty amides, fatty esters (particularly those comprising 1 to 8 carbon atoms in the alcohol portion, e.g., fatty acid methyl esters and lower alcohol esters of fatty acids), fatty acid glycol esters, hydroxylated triglycerides, and mixtures thereof, as described above with reference to the embodiments of FIGS. 1 and 2. In still other embodiments, ISPR extractant 29 can be free fatty acids obtained by chemical or enzymatic hydrolysis of biomass lipids. In such embodiments, the biomass lipids for producing extractant 29 can be from a same or different biomass source from which feedstock 12 is obtained. For example, in some embodiments, the biomass lipids for producing extractant 29 can be derived from soya, whereas the biomass source of feedstock 12 is corn. Any possible combination of different biomass sources for extractant 29 versus feedstock 12 can be used, as should be apparent to one of skill in the art. The remaining process operations of the embodiment of FIG. 2 are identical to FIG. 1 and therefore, will not be described in detail again.

As a non-limiting prophetic example, with reference to the embodiment of FIG. 3, an aqueous suspension of ground whole corn (as feedstock 12) which can nominally contain ca. 4 wt % corn oil, can be treated with amylase (as liquefaction enzyme 14) at ca. 85° C. to 120° C. for 30 minutes to 2 hours, and the resulting liquefied mash 16 cooled to between 65° C. and 30° C. and treated with 0.1 ppm to 10 ppm (in some embodiments, 0.5 ppm to 1.0 ppm) of lipase (as catalyst 42) at pH 4.5 to 7.5 (in some embodiments, between pH 5.5 and 6.5) for sufficient time to produce from at least 30% to as high as at least 99% conversion of the available fatty acid content in lipids to free fatty acids. The liquefied and lipase-treated mash 18 can be cooled to ca. 30° C. (e.g., using a heat-exchanger) and loaded to fermentation vessel 30 at ca. 25% to 30 wt % dry corn solids. Saccharification of the liquefied mash 18 during fermentation by the addition of glucoamylase (as saccharification enzyme 38) can result in the production of glucose. The resulting fermentation broth can contain significantly less than the amount of corn oil (e.g., about 1.2 wt % corn oil) that can be present in a broth using a liquefied mash that has not been treated with lipase 42. In particular, the lipase treatment 42 can result in the conversion of corn oil lipids 26' (triglycerides (TG)) into COFA 28' (and some diglycerides (DG) or monoglycerides (MG)), decreasing the rate of build-up of lipids 26' in the COFA ISPR extraction solvent 28' or 29. The lipase treatment 42 can also result in the conversion of butanol produced during fermentation to butyl esters of COFA, where the butyl esters of COFA have a high partition coefficient for dissolution into the COFA phase 36 during liquid-liquid extraction ISPR. At the end of fermentation, the COFA phase 36 containing butyl esters of COFA can be separated from the fermentation broth (at vessel 30/35), and the butanol 54 can be recovered (at vessel 50) from this organic mixture 36 using one of several methods including, but not limited to, hydrolysis of the ester using, for example, a lipase 52, a solid acid catalyst 52, or steam 52, to produce butanol 54 and COFA 27.

In still other embodiments, as shown, for example, in the embodiment of FIG. 4, the system and processes of FIG. 3 can be modified such that simultaneous saccharification and fermentation (SSF) in fermentation vessel 30 is replaced with a separate saccharification vessel 60 prior to fermentation vessel 30. FIG. 4 is substantially identical to FIG. 3 except for the inclusion of a separate saccharification vessel 60 receiving enzyme 38, with catalyst 42 being introduced to a liquefied, saccharified feedstock stream 62. Feedstock slurry 16 is introduced into saccharification vessel 60 along with enzyme 38 such as glucoamylase, whereby sugars in the form of oligosaccharides in slurry 16 can be broken down into monosaccharides. A liquefied, saccharified feedstock stream 62 exits saccharification vessel 60 to which catalyst 42 is introduced. Feedstock stream 62 includes monosaccharides, and oil 26' and undissolved solids derived from the feedstock. Oil 26' is hydrolyzed by the introduction of catalyst 42, resulting in a liquefied, saccharified feedstock slurry 64 having free fatty acids 28' and catalyst 42.

Alternatively, in some embodiments, catalyst 42 can be added along with saccharification enzyme 38 to simultaneously produce glucose and hydrolyze oil lipids 26' to free fatty acids 28', in a like manner as the introduction of catalyst 42 with enzyme 38 to the fermentation vessel 30 for SSF in the embodiment of FIG. 1. The addition of enzyme 38 and catalyst 42 can be stepwise (e.g., catalyst 42, then enzyme 38, or vice versa), or simultaneous. However, in contrast with the embodiment of FIG. 1 in which the addition of catalyst 42 into fermentation vessel 30 during SSF also substantially simultaneously converts the product alcohol to the alcohol esters, alcohol esters are not formed until slurry 64 containing catalyst 42 is introduced to fermentation vessel 30. Alternatively, in some embodiments, slurry 62 can be introduced to fermentation vessel 30, with catalyst 42 being added directly to the fermentation vessel 30.

In the embodiment of FIG. 4, slurry 64 is introduced to fermentation vessel 30 along with alcohol-producing microorganism 32 which metabolizes the monosaccharides to produce product alcohol. The presence of catalyst 42 in fermentation vessel (introduced via slurry 64) catalyzes the esterification of the alcohol with the free fatty acids 28' (introduced via slurry 62) to form fatty acid alcohol esters in situ, in the same manner as described above with reference to FIG. 1. Free fatty acids 28' can also serve as an ISPR extractant for preferentially partitioning the alcohol ester (and any free alcohol) from the aqueous phase. In some embodiments, one or more additional ISPR extractants 29 can also be introduced into fermentation vessel 30 as described above with reference to FIG. 3. The remaining process operations of the embodiment of FIG. 4 are identical to FIG. 3 and therefore, will not be described in detail again.

Figure 5:
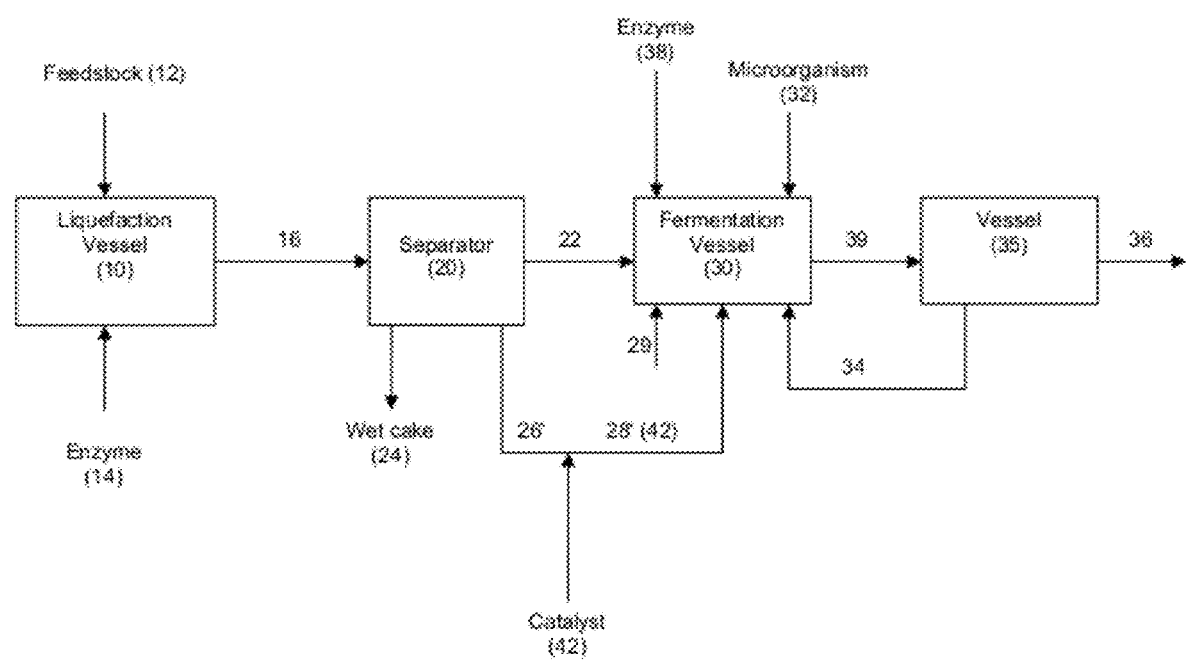

In some embodiments, including any of the earlier described embodiments with respect to FIGS. 1-4, undissolved solids can be removed from feedstock slurry 16 prior to introduction into fermentation vessel 30. For example, as shown in the embodiment of FIG. 5, feedstock slurry 16 is introduced into an inlet of a separator 20 which is configured to discharge the undissolved solids as a solid phase or wet cake 24. For example, in some embodiments, separator 20 can include a filter press, vacuum filtration, mechanical pressure filtration, or a centrifuge (e.g., decanter centrifuge) for separating the undissolved solids from feedstock slurry 16. In some embodiments, any conventional centrifuge utilized in the industry, including, for example, a decanter bowl centrifuge, Tricanter® (three-phase centrifuge) centrifuge, disk stack centrifuge, filtering centrifuge, or decanter centrifuge may be used to separate the undissolved solids. In some embodiments, removal of the undissolved solids from feedstock slurry 16 can be accomplished by filtration, vacuum filtration, beltfilter, pressure filtration, filtration using a screen, screen separation, grates or grating, porous grating, flotation, hydroclone, filter press, screwpress, gravity settler, vortex separator, or any method that may be used to separate solids from liquids. Optionally, in some embodiments, separator 20 can also be configured to remove some or substantially all of oil 26' present in feedstock slurry 16. In such embodiments, separator 20 can be any suitable separator known in the art for removing oil from an aqueous feedstream including, but not limited to, siphoning, decantation, centrifugation, using a gravity settler, membrane-assisted phase splitting, and the like. The remaining feedstock including sugar and water is discharged as an aqueous stream 22 to fermentation vessel 30.

For example, in some embodiments, separator 20 includes a Tricanter® (three-phase centrifuge) centrifuge 20 that agitates or spins feedstock slurry 16 to produce a centrifuge product comprising an aqueous layer containing sugar and water (i.e., stream 22), a solids layer containing the undissolved solids (i.e., wet cake 24), and an oil layer (i.e., oil stream 26'). In such a case, catalyst 42 can be contacted with the removed oil 26' to produce a stream of free fatty acid 28' and catalyst 42. The stream of free fatty acid 28' and catalyst 42 can then be introduced into fermentation vessel 30 to contact with the fermentation medium, whereby catalytic esterification of product alcohol in the fermentation medium into fatty acid alcohol esters can be achieved in situ, in a same manner as described above with reference to FIG. 1.

Free fatty acids 28' can also serve as an ISPR extractant 28', and one or more additional ISPR extractants 29 can also be introduced into fermentation vessel 30. Thus, feedstock oil 26' can be catalytically hydrolyzed to carboxylic acid, thereby decreasing the amount of lipids present in an ISPR extractant while also producing an ISPR extractant. The ester-containing organic phase 36 can be separated from the aqueous phase 34 of the biphasic mixture 39 at vessel 35, and the product alcohol can be recovered from the alcohol esters in vessel 50 (see FIG. 1). The remaining process operations of the embodiment of FIG. 5 are identical to FIG. 3 and therefore, will not be described in detail again.

When wet cake 24 is removed via centrifuge 20, in some embodiments, a portion of the oil from feedstock 12, such as corn oil when the feedstock is corn, remains in wet cake 24. Wet cake 24 can be washed with additional water in the centrifuge once aqueous solution 22 has been discharged from the centrifuge 20. Washing wet cake 24 will recover the sugar (e.g., oligosaccharides) present in the wet cake and the recovered sugar and water can be recycled to the liquefaction vessel 10. After washing, wet cake 24 may be combined with solubles and then dried to form Dried Distillers' Grains with Solubles (DDGS) through any suitable known process. The formation of the DDGS from wet cake 24 formed in centrifuge 20 has several benefits. Since the undissolved solids do not go to the fermentation vessel, the DDGS does not have trapped extractant and/or product alcohol such as butanol, it is not subjected to the conditions of the fermentation vessel, and it does not contact the microorganisms present in the fermentation vessel. All these benefits make it easier to process and sell DDGS, for example, as animal feed. In some embodiments, oil 26' is not discharged separately from wet cake 24, but rather oil 26' is included as part of wet cake 24 and is ultimately present in the DDGS. In such instances, the oil can be separated from the DDGS and converted to an ISPR extractant 29 for subsequent use in the same or different alcohol fermentation process. Methods and systems for removing undissolved solids from feedstock slurry 16 via centrifugation are described in detail in co-pending, commonly owned U.S. Provisional Application Ser. No. 61/356,290, filed Jun. 18, 2010, which is incorporated herein in its entirety by reference thereto.

As described above, oil 26' may be separated from DDGS using any suitable known process including, for example, a solvent extraction process. In one embodiment of the invention, DDGS are loaded into an extraction vessel and washed with a solvent such as hexane to remove oil 26'. Other solvents that may be utilized include, for example, isobutanol, isohexane, ethanol, petroleum distillates such as petroleum ether, or mixtures thereof. After oil 26' extraction, DDGS may be treated to remove any residual solvent. For example, DDGS may be heated to vaporize any residual solvent using any method known in the art. Following solvent removal, DDGS may be subjected to a drying process to remove any residual water. The processed DDGS may be used as a feed supplement for animals such as poultry, livestock, and domestic pets.

After extraction from DDGS, the resulting oil 26' and solvent mixture may be collected for separation of oil 26' from the solvent. In one embodiment, the oil 26'/solvent mixture may be processed by evaporation whereby the solvent is evaporated and may be collected and recycled. The recovered oil may be converted to an ISPR extractant 29 for subsequent use in the same or different alcohol fermentation process.

In addition to the recovery of solids, it may be desired to recover other by-products of the fermentation process. In one embodiment, fatty acid esters (e.g., fatty acid isobutyl esters) may be recovered, for example, to increase the yield of carbohydrate to product alcohol (e.g., butanol). This may be accomplished, for example, by using a solvent to extract fatty acid isobutyl esters from, for example, the by-product formed by combining and mixing several by-product streams and drying the product of the combining and mixing steps. Such a solvent-based extraction system for recovering corn oil triglyceride from DDGS is described in U.S. Patent Application Publication No. 2010/0092603, the teachings of which are incorporated by reference herein.

In one embodiment of solvent extraction of fatty acid esters, solids may be separated from whole stillage ("separated solids") since that stream would contain the largest portion, by far, of fatty acid esters in uncombined byproduct streams. These separated solids may then be fed into an extractor and washed with solvent. In one embodiment, the separated solids are turned at least once in order to ensure that all sides of the separated solids are washed with solvent. After washing, the resulting mixture of lipid and solvent, known as miscella, is collected for separation of the extracted lipid from the solvent. For example, the resulting mixture of lipid and solvent may be deposited to a separator for further processing. During the extraction process, as the solvent washes over the separated solids, the solvent not only brings lipid into solution, but it collects fine, solid particles. These "fines" are generally undesirable impurities in the miscella and in one embodiment, the miscella may be discharged from the extractor or separator through a device that separates or scrubs the fines from the miscella.

In order to separate the lipid and the solvent contained in the miscella, the miscella may be subjected to a distillation step. In this step, the miscella can, for example, be processed through an evaporator which heats the miscella to a temperature that is high enough to cause vaporization of the solvent, but is not sufficiently high to adversely affect or vaporize the extracted lipid. As the solvent evaporates, it may be collected, for example, in a condenser, and recycled for future use. Separation of the solvent from the miscella results in a stock of crude lipid which may be further processed to separate water, fatty acid esters (e.g., fatty acid isobutyl esters), fatty acids, and triglycerides.

After extraction of the lipids, the solids may be conveyed out of the extractor and subjected to a stripping process that removes residual solvent. Recovery of residual solvent is important to process economics. In one embodiment, the wet solids can be conveyed in a vapor tight environment to preserve and collect solvent that transiently evaporates from the wet solids as it is conveyed into the desolventizer. As the solids enter the desolventizer, they may be heated to vaporize and remove the residual solvent. In order to heat the solids, the desolventizer may include a mechanism for distributing the solids over one or more trays, and the solids may be heated directly, such as through direct contact with heated air or steam, or indirectly, such as by heating the tray carrying the meal. In order to facilitate transfer of the solids from one tray to another, the trays carrying the solids may include openings that allow the solids to pass from one tray to the next. From the desolventizer, the solids may be conveyed to, optionally, a mixer where the solids are mixed with other by-products before being conveyed into a dryer. An example of solids extraction is described in Example 63. In this example, the solids are fed to a desolventizer where the solids are contacted by steam. In one embodiment, the flows of steam and solids in the desolventizer may be countercurrent. The solids may then exit the desolventizer and may be fed to a dryer or optionally a mixer where various by-products may be mixed. Vapor exiting the desolventizer may be condensed and optionally mixed with miscella and then fed to a decanter. The water-rich phase exiting the decanter may be fed to a distillation column where hexane is removed from the water-rich stream. In one embodiment, the hexane-depleted water rich stream exits the bottom of the distillation column and may be recycled back to the fermentation process, for example, it may be used to slurry the ground corn solids. In another embodiment, the overhead and bottom products may be recycled to the fermentation process. For example, the lipid-rich bottoms may be added to the feed of a hydrolyzer. The overheads may be, for example, condensed and fed to a decanter. The hexane rich stream exiting this decanter can optionally be used as part of the solvent feed to the extractor. The water-rich phase exiting this decanter may be fed to the column that strips hexane out of water. As one skilled in the art can appreciate, the methods of the present invention may be modified in a variety of ways to optimize the fermentation process for the production of a product alcohol such as butanol.

In another embodiment of solvent extraction of fatty acid esters, solids may be separated from beer and solvent discharged from fermentation before they are introduced into a preflash column as a heterogeneous mixture. A wet cake of these solids can be formed using a separation device such as a screen filter or a centrifuge. A screened cake of solids can be displacement washed using hydrous isobutanol to remove fatty acid esters that were retained in the wet solids. Alternatively, a centrifuged cake of solids can be re-pulped in hydrous isobutanol and separated again to effect the removal of fatty acid esters that were retained in the wet solids. An example of this embodiment of solids extraction is described in Example 63.

In a further embodiment, by-products (or co-products) may be derived from the mash used in the fermentation process. For example, corn oil may be separated from mash and this corn oil may contain triglycerides, free fatty acids, diglycerides, monoglycerides, and phospholipids (see, e.g., Example 66). The corn oil may optionally be added to other by-products (or co-products) at different rates and thus, for example, creating the ability to vary the amount of triglyceride in the resulting byproduct. In this manner, the fat content of the resulting by-product could be controlled, for example, to yield a lower fat, high protein animal feed that would better suit the needs of dairy cows compared to a high fat product.

In one embodiment, crude corn oil separated from mash may be further processed into edible oil for consumer use, or it could also be used as a component of animal feed because its high triglyceride content would make it an excellent source of metabolizable energy. In another embodiment, it could also be used as feedstock for biodiesel or renewable diesel.

In one embodiment, extractant by-product may be used, all or in part, as a component of an animal feed by-product or it can be used as feedstock for biodiesel or renewable diesel.

In a further embodiment, solids may be separated from mash and may comprise triglycerides and free fatty acids. These solids (or stream) may be used as an animal feed, either recovered as discharge from centrifugation or after drying. The solids (or wet cake) may be particularly suited as feed for ruminants (e.g., dairy cows) because of its high content of available lysine and by-pass or rumen undegradable protein. For example, these solids may be of particular value in a high protein, low fat feed. In another embodiment, these solids may be used as a base, that is, other by-products such as syrup may be added to the solids to form a product that may be used as an animal feed. In another embodiment, different amounts of other by-products may be added to the solids to tailor the properties of the resulting product to meet the needs of a certain animal species.

The composition of solids separated from whole stillage as described in Example 62 may include, for example, crude protein, fatty acid, and fatty acid isobutyl esters. In one embodiment, this composition (or by-product) may be used, wet or dry, as an animal feed where, for example, a high protein (e.g., high lysine), low fat, and high fiber content is desired. In another embodiment, fat may be added to this composition, for example, from another by-product stream if a higher fat, low fiber animal feed is desired. In one embodiment, this higher fat, low fiber animal feed may be used for swine or poultry. In a further embodiment, a non-aqueous composition of Condensed Distillers Solubles (CDS) (see, e.g., Example 66) may include, for example, protein, fatty acids, and fatty acid isobutyl esters as well as other dissolved and suspended solids such as salts and carbohydrates. This CDS composition may be used, for example, as animal feed, either wet or dry, where a high protein, low fat, high mineral salt feed component is desired. In one embodiment, this composition may be used as a component of a dairy cow ration.

In another embodiment, oil from the fermentation process may be recovered by evaporation. This non-aqueous composition may comprise fatty acid isobutyl esters and fatty acids (see, e.g., Example 66) and this composition (or stream) may be fed to a hydrolyser to recover isobutanol and fatty acids. In a further embodiment, this stream may be used as feedstock for biodiesel production.

The various streams generated by the production of an alcohol (e.g., butanol) via a fermentation process may be combined in many ways to generate a number of co-products. For example, if crude corn from mash is used to generate fatty acids to be utilized as extractant and lipid is extracted by evaporators for other purposes, then the remaining streams may be combined and processed to create a co-product composition comprising crude protein, crude fat, triglycerides, fatty acid, and fatty acid isobutyl ester. In one embodiment, this composition may comprise at least about 20-35 wt % crude protein, at least about 1-20 wt % crude fat, at least about 0-5 wt % triglycerides, at least about 4-10 wt % fatty acid, and at least about 2-6 wt % fatty acid isobutyl ester. In one particular embodiment, the co-product composition may comprise about 25 wt % crude protein, about 10 wt % crude fat, about 0.5 wt % triglycerides, about 6 wt % fatty acid, and about 4 wt % fatty acid isobutyl ester.

In another embodiment, the lipid is extracted by evaporators and the fatty acids are used for other purposes and about 50 wt % of the crude corn from mash and the remaining streams are combined and processed, the resulting co-product composition may comprise crude protein, crude fat, triglycerides, fatty acid, and fatty acid isobutyl ester. In one embodiment, this composition may comprise at least about 25-31 wt % crude protein, at least about 6-10 wt % crude fat, at least about 4-8 wt % triglycerides, at least about 0-2 wt % fatty acid, and at least about 1-3 wt % fatty acid isobutyl ester. In one particular embodiment, the co-product composition may comprise about 28 wt % crude protein, about 8 wt % crude fat, about 6 wt % triglycerides, about 0.7 wt % fatty acid, and about 1 wt % fatty acid isobutyl ester.

In another embodiment, the solids separated from whole stillage and 50 wt % of the corn oil extracted from mash are combined and the resulting co-product composition may comprise crude protein, crude fat, triglycerides, fatty acid, fatty acid isobutyl ester, lysine, neutral detergent fiber (NDF), and acid detergent fiber (ADF). In one embodiment, this composition may comprise at least about 26-34 wt % crude protein, at least about 15-25 wt % crude fat, at least about 12-20 wt % triglycerides, at least about 1-2 wt % fatty acid, at least about 2-4 wt % fatty acid isobutyl ester, at least about 1-2 wt % lysine, at least about 11-23 wt % NDF, and at least about 5-11 wt % ADF. In one particular embodiment, the co-product composition may comprise about 29 wt % crude protein, about 21 wt % crude fat, about 16 wt % triglycerides, about 1 wt % fatty acid, about 3 wt % fatty acid isobutyl ester, about 1 wt % lysine, about 17 wt % NDF, and about 8 wt % ADF. The high fat, triglyceride, and lysine content and the lower fiber content of this co-product composition may be desirable as feed for swine and poultry.

As described above, the various streams generated by the production of an alcohol (e.g., butanol) via a fermentation process may be combined in many ways to generate a co-product composition comprising crude protein, crude fat, triglycerides, fatty acid, and fatty acid isobutyl ester. For example, a composition comprising at least about 6% crude fat and at least about 28% crude protein may be utilized as an animal feed product for dairy animals. A composition comprising at least about 6% crude fat and at least about 26% crude protein may be utilized as an animal feed product for feedlot cattle whereas a composition comprising at least about 1% crude fat and at least about 27% crude protein may be utilized as an animal feed product for wintering cattle. A composition comprising at least about 13% crude fat and at least about 27% crude protein may be utilized as an animal feed product for poultry. A composition comprising at least about 18% crude fat and at least about 22% crude protein may be utilized as an animal feed product for monogastric animals. Thus, the various streams may be combined in such a way as to customize a feed product for a specific animal species.

In one embodiment, one or more streams generated by the production of an alcohol (e.g., butanol) via a fermentation process may be combined in many ways to generate a composition comprising at least about 90% COFA which may be used as fuel source such as biodiesel.

As an example of one embodiment of the methods of the invention, milled grain (e.g., corn processed by hammer mill) and one or more enzymes are combined to generate a slurried grain. This slurried grain is cooked, liquified, and optionally flashed with flash vapor resulting in a cooked mash. The cooked mash is then filtered to remove suspended solids, generating a wet cake and a filtrate. The filtration may be accomplished by several methods such as centrifugation, screening, or vacuum filtration and this filtration step may remove at least about 80% to at least about 99% of the suspended solids from the mash.

The wet cake is reslurried with water and refiltered to remove additional starch, generating a washed filter cake. The reslurry process may be repeated a number of times, for example, one to five times. The water used to reslurry the wet cake may be recycled water generated during the fermentation process. The filtrate produced by the reslurry/refiltration process may be returned to the initial mix step to form a slurry with the milled grain. The filtrate may be heated or cooled prior to the mix step.

The washed filter cake may be reslurried with beer at a number of stages during the production process. For example, the washed filter cake may be reslurried with beer after the fermentor, before the preflash column, or at the feedpoint to the distillers grain dryer. The washed filter cake may be dried separately from other by-products or may be used directly as wet cake for generation of DDGS or an animal feed product.

The filtrate produced as a result of the initial mix step may be further processed as described herein. For example, the filtrate may be heated with steam or process to process heat exchange. A saccharification enzyme may be added to the filtrate and the dissolved starch of the filtrate may be partially or completely saccharified. The saccharified filtrate may be cooled by a number of means such as process to process exchange, exchange with cooling water, or exchange with chilled water.

The cooled filtrate may then be added to a fermentor as well as a microorganism that is suitable for alcohol production, for example, a recombinant yeast capable of producing butanol. In addition, ammonia and recycle streams may also be added to the fermentor. This process may include at least one fermentor, at least two fermentors, at least three fermentors, or at least four fermentors. Carbon dioxide generated during the fermentation may be vented to a scrubber in order to reduce air emissions (e.g., butanol air emissions) and to increase product yield.

Solvent may be added to the fermentor via a recycled loop or may be added directly into the fermentor. The solvent may be one or more organic compounds which have the ability to dissolve or react with the alcohol (e.g., butanol) and may have limited solubility in water. The solvent may be taken from the fermentor continually as a single liquid phase or as a two liquid phase material, or the solvent may be withdrawn batchwise as a single or two liquid phase material.

Beer may be degassed. The beer may be heated before degassing, for example, by process to process exchange with hot mash or process to process exchange with preflash column overheads. Vapors may be vented to a condenser and then, to a scrubber. Degassed beer may be heated further, for example, by process to process heat exchange with other streams in the distillation area.

Preheated beer and solvent may enter a preflash column which may be retrofit from a beer column of a conventional dry grind fuel ethanol plant. This column may be operated at sub-atmospheric pressure, driven by water vapor taken from an evaporator train or from the mash cook step. The overheads of the preflash column may be condensed by heat exchange with some combination of cooling water and process to process heat exchange including heat exchange with the preflash column feed. The liquid condensate may be directed to an alcohol/water decanter (e.g., butanol/water decanter).

The preflash column bottoms may be advanced to a solvent decanter. The preflash column bottoms may be substantially stripped of free alcohol (e.g., butanol). The decanter may be a still well, a centrifuge, or a hydroclone. Water is substantially separated from the solvent phase in this decanter, generating a water phase. The water phase including suspended and dissolved solids may be centrifuged to produce a wet cake and thin stillage. The wet cake may be combined with other streams and dried to produce DDGS, it may be dried and sold separate from other streams which produce DDGS, or it may be sold as a wet cake. The water phase may be split to provide a backset which is used in part to reslurry the filter cake described above. The split also provides thin stillage which may be pumped to evaporators for further processing.

The organic phase produced in the solvent decanter may be an ester of an alcohol (e.g., butanol). The solvent may be hydrolyzed to regenerate reactive solvent and to recover additional alcohol (e.g., butanol). Alternatively, the organic phase may be filtered and sold as a product. Hydrolysis may be thermally driven, homogeneously catalyzed, or heterogeneously catalyzed. Hydrolysis may also occur by enzymatic reaction. The heat input to this process may be a fired heater, hot oil, electrical heat input, or high pressure steam. Water added to drive the hydrolysis may be from a recycled water stream, fresh water, or steam.

Cooled hydrolyzed solvent may be pumped into a sub-atmospheric solvent column where it may be substantially stripped of alcohol (e.g., butanol) with steam. This steam may be water vapor from evaporators, it may be steam from the flash step of the mash process, or it may be steam from a boiler (see, e.g., U.S. Patent Application Publication No. 2009/0171129, incorporated herein by reference). A rectifier column from a conventional dry grind ethanol plant may be suitable as a solvent column. The rectifier column may be modified to serve as a solvent column. The bottoms of the solvent column may be cooled, for example, by cooling water or process to process heat exchange. The cooled bottoms may be decanted to remove residual water and this water may be recycled to other steps with the process or recycled to the mash step.

The solvent column overheads may be cooled by exchange with cooling water or by process to process heat exchange, and the condensate may be directed to a vented alcohol/water decanter (e.g., butanol/water decanter) which may be shared with the preflash column overheads. Other mixed water and alcohol (e.g., butanol) streams may be added to this decanter including the scrubber bottoms and condensate from the degas step. The vent which comprises carbon dioxide, may be directed to a water scrubber. The aqueous layer of this decanter may also be fed to the solvent column or may be stripped of alcohol (e.g., butanol) in a small dedicated distillation column. The aqueous layer may be preheated by process to process exchange with the preflash column overheads, solvent column overheads, or solvent column bottoms. This dedicated column may be modified from the side stripper of a conventional dry grind fuel ethanol process.

The organic layer of the alcohol/water decanter (e.g., butanol/water decanter) may be pumped to an alcohol (e.g., butanol) column. This column may be a super-atmospheric column and may be driven by steam condensation within a reboiler. The feed to the column may be heated by process to process heat exchange in order to reduce the energy demand to operate the column. This process to process heat exchanger may include a partial condenser of the preflash column, a partial condenser of a solvent column, the product of the hydrolyzer, water vapor from the evaporators, or the butanol column bottoms. The condensate of the alcohol (e.g., butanol) column vapor may be cooled and may be returned to the alcohol/water decanter (e.g., butanol/water decanter). The alcohol (e.g., butanol) column bottoms may be cooled by process to process heat exchange including exchange with the alcohol (e.g., butanol) column feed and may be further cooled with cooling water, filtered, and are sold as product alcohol (e.g., butanol).

Thin stillage generated from the preflash column bottoms as described above may be directed to a multiple effect evaporator. This evaporator may have two, three, or more stages. The evaporator may have a configuration of four bodies by two effects similar to the conventional design of a fuel ethanol plant, it may have three bodies by three effects, or it may have other configurations. Thin stillage may enter at any of the effects. At least one of the first effect bodies may be heated with vapor from the super-atmospheric alcohol (e.g., butanol) column. The vapor may be taken from the lowest pressure effect to provide heat in the form of water vapor to the sub-atmospheric preflash column and solvent column. Syrup from the evaporators may be added to the distiller's grain dryer.

Carbon dioxide emissions from the fermentor, degasser, alcohol/water decanter (e.g., butanol/water decanter) and other sources may be directed to a water scrubber. The water supplied to the top of this scrubber may be fresh makeup water or may be recycled water. The recycled water may be treated (e.g., biologically digested) to remove volatile organic compounds and may be chilled. Scrubber bottoms may be sent to the alcohol/water decanter (e.g., butanol/water decanter), to the solvent column, or may be used with other recycled water to reslurry the wet cake described above. Condensate from the evaporators may be treated with anaerobic biological digestion or other processes to purify the water before recycling to reslurry the filter cakes.

If corn is used as the source of the milled grain, corn oil may be separated from the process streams at any of several points. For example, a centrifuge may be operated to produce a corn oil stream following filtration of the cooked mash or the preflash column water phase centrifuge may be operated to produce a corn oil stream. Intermediate concentration syrup for final syrup may be centrifuged to produce a corn oil stream.

In another example of an embodiment of the methods of the invention, the material discharged from the fermentor may be processed in a separation system that involves devices such as a centrifuge, settler, hydrocyclone, etc., and combinations thereof to effect the recovery of live yeast in a concentrated form that can be recycled for reuse in a subsequent fermentation batch either directly or after some re-conditioning. This separation system may also produce an organic stream that comprises fatty esters (e.g. isobutyl fatty esters) and an alcohol (e.g., isobutanol) produced from the fermentation and an aqueous stream containing only trace levels of immiscible organics. This aqueous stream may be used either before or after it is stripped of the alcohol (e.g., isobutanol) content to re-pulp and pump the low starch solids that was separated and washed from liquefied mash. This has the advantage of avoiding what might otherwise be a long belt-driven conveying system to transfer these solids from the liquefaction area to the grain drying and syrup blend area. Furthermore, this whole stillage that results after the alcohol (e.g., isobutanol) has been stripped will need to be separated into thin stillage and wet cake fractions either using existing or new separation devices and this thin stillage will form in part the backset that returns to combine with cook water for preparing a new batch of fermentable mash. Another advantage of this embodiment is that any residual dissolved starch that was retained in the moisture of the solids separated from the liquefied mash would in part be captured and recovered through this backset. Alternatively, the yeast contained in the solids stream may be considered nonviable and may be redispersed in the aqueous stream and this combined stream distilled of any alcohol (e.g., butanol) content remaining from fermentation. Non viable organisms may further be separated for use as a nutrient in the propagation process.

In another embodiment, the multi-phase material may leave the bottom of the pre-flash column and may be processed in a separation system as described above. The concentrated solids may be redispersed in the aqueous stream and this combined stream may be used to re-pulp and pump the low starch solids that were separated and washed from liquefied mash.

The process described above as well as other processes described herein may be demonstrated using computational modeling such as Aspen modeling (see, e.g., U.S. Pat. No. 7,666,282). For example, the commercial modeling software Aspen Plus® (Aspen Technology, Inc., Burlington, Mass.) may be use in conjunction with physical property databases such as DIPPR, available from American Institute of Chemical Engineers, Inc. (New York, N.Y.) to develop an Aspen model for an integrated butanol fermentation, purification, and water management process. This process modeling can perform many fundamental engineering calculations, for example, mass and energy balances, vapor/liquid equilibrium, and reaction rate computations. In order to generate an Aspen model, information input may include, for example, experimental data, water content and composition of feedstock, temperature for mash cooking and flashing, saccharification conditions (e.g., enzyme feed, starch conversion, temperature, pressure), fermentation conditions (e.g., microorganism feed, glucose conversion, temperature, pressure), degassing conditions, solvent columns, preflash columns, condensers, evaporators, centrifuges, etc.

The present invention provides systems and methods for producing a fermentative product such as a product alcohol, through fermentation as well as increasing biomass processing productivity and cost effectiveness. In some embodiments, the product alcohol is butanol. A feedstock can be liquefied to create a feedstock slurry, wherein the feedstock slurry includes soluble sugar and undissolved solids. If the feedstock slurry is fed directly to the fermentor, the undissolved solids may interfere with efficient removal and recovery of a product alcohol such as butanol from the fermentor. In particular, when liquid-liquid extraction is utilized to extract butanol from the fermentation broth, the presence of the undissolved particulates may cause system inefficiencies including, but not limited to, decreasing the mass transfer rate of the butanol to the extractant by interfering with the contact between the extractant and the fermentation broth; creating an emulsion in the fermentor and thereby interfering with good phase separation of the extractant and the fermentation broth; reducing the efficiency of recovering and recycling the extractant because at least a portion of the extractant and butanol becomes "trapped" in the solids which are ultimately removed as DDGS; a lower fermentor volume efficiency because there are solids taking up volume in the fermentor and because there is a slower disengagement of the extractant from the fermentation broth; and shortening the life cycle of the extractant by contamination with corn oil. All of these effects result in higher capital and operating costs. In addition, the extractant "trapped" in the DDGS may detract from DDGS value and qualification for sale as animal feed. Thus, in order to avoid and/or minimize these problems, at least a portion of the undissolved particles (or solids) are removed from the feedstock slurry prior to the addition of sugar present in the feedstock slurry to the fermentor. Extraction activity and the efficiency of the butanol production are increased when extraction is performed on a fermentation broth containing an aqueous solution wherein undissolved particles have been removed relative to extraction performed on a fermentation broth containing an aqueous solution wherein undissolved particles have not been removed.

Extractive fermentation without the presence of the undissolved solids can lead to higher mass transfer rate of the product alcohol from the fermentation broth to the extractant, better phase separation of the extractant from the fermentation inside or external to the fermentor, and lower hold up of the extractant as a result of higher extractant droplet rise velocities. Also, for example, the extractant droplets held up in the fermentation broth during fermentation will disengage from the fermentation broth faster and more completely, thereby resulting in less free extractant in the fermentation broth and can decrease the amount of extractant lost in the process. In addition, for example, the microorganism can be recycled and additional equipment in the downstream processing can be eliminated, such as for example, a beer column and/or some or all of the whole stillage centrifuges. Further, for example, the possibility of extractant being lost in the DDGS is removed. Also, for example, the ability to recycle the microorganism can increase the overall rate of product alcohol production, lower the overall titer requirement, and/or lower the aqueous titer requirement, thereby leading to a healthier microorganism and a higher production rate. In addition, for example, it can be possible to eliminate an agitator in the fermentor to reduce capital costs; to increase the fermentor productivity since the volume is used more efficiently because the extractant hold up is minimized and the undissolved solids are not present; and/or to use continuous fermentation or smaller fermentors in a greenfield plant.

Examples of increased extraction efficiency can include, for example, a stabilized partition coefficient, enhanced (e.g., quicker or more complete) phase separation, enhanced liquid-liquid mass transfer coefficient, operation at a lower titer, increased process stream recyclability, increased fermentation volume efficiency, increased feedstock (e.g., corn) load feeding, increased butanol titer tolerance of the microorganism (e.g., a recombinant microorganism), water recycling, reduction in energy, increased recycling of extractant, and/or recycling of the microorganism.

For example, the volume of the fermentor taken up by solids will be decreased. Thus, the effective volume of the fermentor available for the fermentation can be increased. In some embodiments, the volume of the fermentor available for the fermentation is increased by at least about 10%.

For example, there can be a stabilization in partition coefficient. Because the corn oil in the fermentor can be reduced by removing the solids from the feedstock slurry prior to fermentation, the extractant is exposed to less corn oil which combines with the extractant and may lower the partition coefficient if present in sufficient amount. Therefore, reduction of the corn oil introduced into the fermentor results in a more stable partition coefficient of the extractant phase in the fermentor. In some embodiments, the partition coefficient is decreased by less than about 10% over 10 fermentation cycles.

For example, there can be an increase in the extraction efficiency of the butanol with extractant because there will be a higher mass transfer rate (e.g., in the form of a higher mass transfer coefficient) of the product alcohol from the fermentation broth to the extractant, thereby resulting in an increased efficiency of product alcohol production. In some embodiments, the mass transfer coefficient is increased at least 2-fold (see Examples 4 and 5).

In addition, there can be an increase in phase separation between the fermentation broth and the extractant that reduces the likelihood of the formation of an emulsion, thereby resulting in an increased efficiency of product alcohol production. For example, the phase separation can occur more quickly or can be more complete. In some embodiments, a phase separation may occur where previously no appreciable phase separation was observed in 24 hours. In some embodiments, the phase separation occurs at least about 2× as quickly, at least about 5× as quickly, or at least about 10× as quickly as compared to the phase separation where solids have not been removed (see Examples 6 and 7).

Further, there can be an increase in the recovery and recycling of the extractant. The extractant will not be "trapped" in the solids which may ultimately be removed as DDGS, thereby resulting in an increased efficiency of product alcohol production (see Examples 8 and 9). Also, there will be less dilution of the extractant with corn oil, and there may be less degradation of the extractant (see Example 10).

Also, the flow rate of the extractant can be reduced which will lower operating costs, thereby resulting in an increased efficiency of product alcohol production.

Further still, hold up of the extractant will be decreased as a result of extractant droplets rising at a higher velocity, thereby resulting in an increased efficiency of product alcohol production. Reducing the amount of undissolved solids in the fermentor will also result in an increased efficiency of product alcohol production.

In addition, an agitator can be removed from the fermentor because it is no longer needed to suspend the undissolved solids, thereby reducing capital costs and energy, and increasing the efficiency of the product alcohol production.

FIGS. 1-5 provide various non-limiting embodiments of methods and systems involving fermentation processes in which alcohol esters are produced in situ, extracted from the fermentation medium, and reacted to recover product alcohol. FIGS. 1-5 also provide various non-limiting embodiments of methods and systems of using carboxylic acid that can be esterified with product alcohol and can contemporaneously serve as an ISPR extractant. FIGS. 1-5 also provide various non-limiting embodiments of methods and systems of converting lipids in a feedstock to carboxylic acid that can be esterified with product alcohol and can contemporaneously serve as an ISPR extractant.

In some embodiments, including any of the aforementioned embodiments described with reference to FIGS. 1-5, the fermentation broth in fermentation vessel 30 includes at least one recombinant microorganism 32 which is genetically modified (that is, genetically engineered) to produce butanol via a biosynthetic pathway from at least one fermentable carbon source. In particular, recombinant microorganisms can be grown in a fermentation broth which contains suitable carbon substrates. Additional carbon substrates may include, but are not limited to, monosaccharides such as fructose and galactose; oligosaccharides such as lactose maltose, or sucrose; polysaccharides such as starch or cellulose; or mixtures thereof and unpurified mixtures from renewable feedstocks such as cheese whey permeate, cornsteep liquor, sugar beet molasses, and barley malt. Other carbon substrates may include ethanol, lactate, succinate, or glycerol.

Additionally, the carbon substrate may also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C*1 *Compd.*, [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., Arch. Microbiol. 153:485-489, 1990). Hence, it is contemplated that the source of carbon utilized in the present invention may encompass a wide variety of carbon containing substrates and will only be limited by the choice of organism.

Although it is contemplated that all of the above mentioned carbon substrates and mixtures thereof are suitable, in some embodiments, the carbon substrates are glucose, fructose, and sucrose, or mixtures of these with C5 sugars such as xylose and/or arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch-based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, U.S. Patent Application Publication No. 2007/0031918 A1, which is herein incorporated by reference. In addition to an appropriate carbon source (from aqueous stream 22), fermentation broth must contain suitable minerals, salts, cofactors, buffers, and other components, known to those skilled in the art, suitable for the growth of the cultures and promotion of an enzymatic pathway for production of a product alcohol.

From the above discussion and the Examples, one skilled in the art can ascertain essential characteristics of the present invention and can make various changes and modifications of the invention to adapt to various uses and conditions without departing from the present invention. For example, in some embodiments, alcohol esterification and extraction according to the present invention can be employed pre-fermentation, that is, during seed culturing of microorganisms 32 prior to fermentation in fermentation vessel 30. Typically, microorganisms 32 such as yeast can be grown from a seed culture to a desired cell concentration before being harvested and inoculated into fermentation vessel 30, as known in the art.

The carbon source feedstock is an important cost factor in microorganism production such as yeast production and consequently, the biomass yield on sugar is an important optimization criterion. Because the ATP yield from the alcoholic fermentation is much lower than that from the respiratory sugar dissimilation, occurrence of alcoholic fermentation negatively affects the biomass yield and is sought to be avoided during the yeast production (i.e., seed culturing). Nonetheless, the culturing of microorganisms in a seed culture medium can produce an amount of fermentation product including alcohol. For example, in *S. cerevisiae* yeast, the alcoholic fermentation and respiration occur simultaneously whenever the specific growth rate ($\mu$) and/or the sugar concentration in aerobic cultures exceed a critical value (see, e.g., van Hoek, et al., Biotechnol. Bioeng. 68:517-523, 2000). In order to achieve high biomass yield, the yeast growth is typically controlled, for example, by respiratory conditions using fed-batch fermentation technology for seed culturing. For example, sugar is fed at a low rate resulting in a low sugar concentration in the culture and a low rate of sugar uptake such that sugar metabolism can be substantially respiratory. Under these conditions, high biomass yields can be obtained and accumulation of toxic products can be minimized. In practice, in large scale fed-batch industrial processes, the cells can be exposed to concentration gradients due to an inefficient mixing (see, e.g., Enfors, et al., J. Biotechnol. 85:175-185, 2001). Production and reassimilation of fermentation by-products can be one of the reasons for reduction of biomass yield per glucose in large scale bioreactors compared to laboratory scale.

However, at these conditions, when culturing butanol-producing yeast, for example, the fermentation product including butanol cannot be reassimilated and may accumulate in the culture medium which can be toxic to the microorganisms at high concentration. If product accumulation exceeds critical cell growth inhibitory concentrations (e.g., cell growth is lower than the growth that may be limited by the feed), then a loss of fed-batch control may occur. According to the present invention, using alcohol esterification and extraction to remove butanol from the culture medium can allow the fed-batch fermentation to proceed despite the problems with inefficient mixing and butanol toxicity.

Thus, according to some embodiments, the seed culture medium can be contacted with catalyst 42 and carboxylic acid 28 leading to the production of alcohol esters by esterification of the product alcohol and ultimately, an improved biomass yield per glucose in large scale bioreactors. Furthermore, the concentration of product alcohol in the culture medium can be controlled by alcohol esterification and thus, minimizing or avoiding the deleterious effects of the product alcohol on the microorganisms. In some embodiments, alcohol esters can be extracted from the seed culture medium and the alcohol recovered from the alcohol esters in the same manner as described above with respect to extraction of alcohol esters from fermentation vessel 30 and recovery of product alcohol 54. In some embodiments, alcohol esterification according to the present invention can be employed to esterify the product alcohol in both the seed culture medium and the fermentation medium. In such embodiments, a higher yield of product alcohol can be achieved for the fermentation process as a whole by recovering not only alcohol esters (and free product alcohol) from the fermentation medium, but also recovering alcohol esters produced during the seed culturing (e.g., recovering alcohol esters and/or product alcohol from a propagation tank). In some embodiments, alcohol esterification according to the present invention can be employed pre-fermentation for removal of alcohol from the seed culture medium, while conventional ISPR of product alcohol can be employed for removal of product alcohol during fermentation in fermentation vessel 30.

Thus, it should be apparent that alcohol esterification and extraction according to the present invention can be employed at various stages in an alcohol fermentation process without departing from the present invention.

The alcohol products produced by the methods of the present invention have a number of applications, for example, as reagents, solvents, and fuel. Butanol produced by the claimed methods may be used directly as a fuel (e.g., biofuel), a fuel additive, an alcohol used for the production of esters that can be used as diesel or biodiesel fuel, a feedstock chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids. Thus, the present invention provides alternative methods to produce alcohols including butanol, which can support the high demand for these industrial chemicals.

Recombinant Microorganisms and Butanol Biosynthetic Pathways

While not wishing to be bound by theory, it is believed that the processes described herein are useful in conjunction with any alcohol producing microorganism, particularly recombinant microorganisms which produce alcohol at titers above their tolerance levels.

Alcohol-producing microorganisms are known in the art. For example, fermentative oxidation of methane by methanotrophic bacteria (e.g., *Methylosinus trichosporium*) produces methanol, and contacting methanol (a $C_1$ alkyl alcohol) with a carboxylic acid and a catalyst capable of esterifying the carboxylic acid with methanol forms a methanol ester of the carboxylic acid. The yeast strain CEN.PK113-7D (CBS 8340, the Centraal Buro voor Schimmelculture; van Dijken, et al., Enzyme Microb. Techno. 26:706-714, 2000) can produce ethanol, and contacting ethanol with a carboxylic acid and a catalyst capable of esterifying the carboxylic acid with the ethanol forms ethyl ester (see, e.g., Example 36).

Recombinant microorganisms which produce alcohol are also known in the art (e.g., Ohta, et al., Appl. Environ. Microbiol. 57:893-900, 1991; Underwood, et al., Appl. Environ. Microbiol. 68:1071-1081, 2002; Shen and Liao, Metab. Eng. 10:312-320, 2008; Hahnai, et al., Appl. Environ. Microbiol. 73:7814-7818, 2007; U.S. Pat. No. 5,514,583; U.S. Pat. No. 5,712,133; PCT Application Publication No. WO 1995/028476; Feldmann, et al., Appl. Microbiol. Biotechnol. 38: 354-361, 1992; Zhang, et al., Science 267:240-243, 1995; U.S. Patent Application Publication No. 2007/0031918 A1; U.S. Pat. No. 7,223,575; U.S. Pat. No. 7,741,119; U.S. Patent Application Publication No. 2009/0203099 A1; U.S. Patent Application Publication No. 2009/0246846 A1; and PCT Application Publication No. WO 2010/075241, which are herein incorporated by reference).

Suitable recombinant microorganisms capable of producing butanol are known in the art, and certain suitable microorganisms capable of producing butanol are described herein. Recombinant microorganisms to produce butanol via a biosynthetic pathway can include a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Klebsiella, Paenibacillus, Arthrobacter, Corynebacterium, Brevibacterium, Schizosaccharomyces, Kluyveromyces, Yarrowia, Pichia, Candida, Hansenula, Issatchenkia*, or *Saccharomyces*. In one embodiment, recombinant microorganisms can be selected from the group consisting of *Escherichia coli, Lactobacillus plantarum, Kluyveromyces lactis, Kluyveromyces marxianus*, and *Saccharomyces cerevisiae*. In one embodiment, the recombinant microorganism is yeast. In one embodiment, the recombinant microorganism is crabtree-positive yeast selected from *Saccharomyces, Zygosaccharomyces, Schizosaccharomyces, Dekkera, Torulopsis, Brettanomyces*, and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Zygosaccharomyces rouxii*, and *Candida glabrata*.

In some embodiments, the host cell is *Saccharomyces cerevisiae*. *S. cerevisiae* yeast are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

The production of butanol utilizing fermentation with a microorganism, as well as microorganisms which produce butanol, is disclosed, for example, in U.S. Patent Application Publication No. 2009/0305370, herein incorporated by reference. In some embodiments, microorganisms comprise a butanol biosynthetic pathway. In some embodiments, at least one, at least two, at least three, or at least four polypeptides catalyzing substrate to product conversions of a pathway are encoded by heterologous polynucleotides in the microorganism. In some embodiments, all polypeptides catalyzing substrate to product conversions of a pathway are encoded by heterologous polynucleotides in the microorganism. In some embodiments, the microorganism comprises a reduction or elimination of pyruvate decarboxylase activity. Microorganisms substantially free of pyruvate decarboxylase activity are described in US Application Publication No. 2009/0305363, herein incorporated by reference. Microorganisms substantially free of an enzyme having NAD-dependent glycerol-3-phosphate dehydrogenase activity such as GPD2 are also described therein.

Suitable biosynthetic pathways for production of butanol are known in the art, and certain suitable pathways are described herein. In some embodiments, the butanol biosynthetic pathway comprises at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Certain suitable proteins having the ability to catalyze indicated substrate to product conversions are described herein and other suitable proteins are provided in the art. For example, U.S. Patent Application Publication Nos. 2008/0261230, 2009/0163376, and 2010/0197519, incorporated herein by reference, describe acetohydroxy acid isomeroreductases; U.S. Patent Application Publication No. 2010/0081154, incorporated by reference, describes dihydroxyacid dehydratases; an alcohol dehydrogenase is described in U.S. Patent Application Publication No. 2009/0269823, incorporated herein by reference.

It is well understood by one skilled in the art that many levels of sequence identity are useful in identifying polypeptides from other species, wherein such polypeptides have the same or similar function or activity and are suitable for use in the recombinant microorganisms described herein. Useful examples of percent identities include, but are not limited to, 75%, 80%, 85%, 90%, or 95%, or any integer percentage from 75% to 100% may be useful in describing the present invention such as 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

1-Butanol Biosynthetic Pathway

A biosynthetic pathway for the production of 1-butanol as well as suitable polypeptides and polynucleotides encoding such polypeptides that may be used is described by Donaldson, et al., in U.S. Patent Application Publication No. 2008/0182308 A1, incorporated herein by reference. This biosynthetic pathway comprises the following substrate to product conversions:

a) acetyl-CoA to acetoacetyl-CoA, which may be catalyzed, for example, by acetyl-CoA acetyltransferase;

b) acetoacetyl-CoA to 3-hydroxybutyryl-CoA, which may be catalyzed, for example, by 3-hydroxybutyryl-CoA dehydrogenase;

c) 3-hydroxybutyryl-CoA to crotonyl-CoA, which may be catalyzed, for example, by crotonase;

d) crotonyl-CoA to butyryl-CoA, which may be catalyzed, for example, by butyryl-CoA dehydrogenase;

e) butyryl-CoA to butyraldehyde, which may be catalyzed, for example, by butyraldehyde dehydrogenase; and f) butyraldehyde to 1-butanol, which may be catalyzed, for example, by 1-butanol dehydrogenase In some embodiments, the 1-butanol biosynthetic pathway comprises at least one gene, at least two genes, at least three genes, at least four genes, or at least five genes that is/are heterologous to the yeast cell. In some embodiments, the recombinant host cell comprises a heterologous gene for each substrate to product conversion of a 1-butanol biosynthetic pathway.

2-Butanol Biosynthetic Pathway

Biosynthetic pathways for the production of 2-butanol as well as suitable polypeptides and polynucleotides encoding such polypeptides that may be used are described by Donaldson, et al., in U.S. Patent Application Publication Nos. 2007/0259410 A1 and 2007/0292927A1, and in PCT Application Publication No. WO 2007/130521, all of which are incorporated herein by reference. One 2-butanol biosynthetic pathway comprises the following substrate to product conversions:

a) pyruvate to alpha-acetolactate, which may be catalyzed, for example, by acetolactate synthase;

b) alpha-acetolactate to acetoin, which may be catalyzed, for example, by acetolactate decarboxylase;

c) acetoin to 2,3-butanediol, which may be catalyzed, for example, by butanediol dehydrogenase;

d) 2,3-butanediol to 2-butanone, which may be catalyzed, for example, by butanediol dehydratase; and e) 2-butanone to 2-butanol, which may be catalyzed, for example, by 2-butanol dehydrogenase.

In some embodiments, the 2-butanol biosynthetic pathway comprises at least one gene, at least two genes, at least three genes, or at least four genes that is/are heterologous to the yeast cell. In some embodiments, the recombinant host cell comprises a heterologous gene for each substrate to product conversion of a 2-butanol biosynthetic pathway.

Isobutanol Biosynthetic Pathway

Biosynthetic pathways for the production of isobutanol as well as suitable polypeptides and polynucleotides encoding such polypeptides that may be used are described in U.S. Patent Application Publication No. 2007/0092957 A1 and PCT Application Publication No. WO 2007/050671, incorporated herein by reference. One isobutanol biosynthetic pathway comprises the following substrate to product conversions:

a) pyruvate to acetolactate, which may be catalyzed, for example, by acetolactate synthase;

b) acetolactate to 2,3-dihydroxyisovalerate, which may be catalyzed, for example, by acetohydroxy acid reductoisomerase;

c) 2,3-dihydroxyisovalerate to α-ketoisovalerate, which may be catalyzed, for example, by acetohydroxy acid dehydratase;

d) α-ketoisovalerate to isobutyraldehyde, which may be catalyzed, for example, by a branched-chain keto acid decarboxylase; and e) isobutyraldehyde to isobutanol, which may be catalyzed, for example, by a branched-chain alcohol dehydrogenase.

Suitable polypeptide sequences that encode enzymes which catalyze the substrate to product conversions of the isobutanol biosynthetic pathway as well as E.C. numbers corresponding to suitable enzymes for the indicated pathway steps include, but are not limited to, those in Tables AA and BB. Suitable enzymes associated with the given E.C. numbers will be readily available to those of skill in the art, for example, through the BRENDA database (http://www-.brenda-enzymes.org/).

TABLE AA

Example polypeptides

| Pathway step | Enzyme | SEQ ID NO: |
|---|---|---|
| a) pyruvate to acetolactate | *Bacillus subtilis* alsS (acetolactate synthase, "ALS") | 144 |
| b) acetolactate to 2,3-dihydroxyisovalerate | *Lactococcus lactis* ilvC (ketol-acid reductoisomerase, "KARI") | 145 |
| c) 2,3-dihydroxyisovalerate to α-ketoisovalerate | *Streptococcus mutans* ilvD (dihydroxyacid dehydratase, "DHAD") | 146 |
| d) α-ketoisovalerate to isobutyraldehyde | *Lactococcus lactis* kivD (branched-chain α-keto acid decarboxylase), codon optimized | 147 |
| e) isobutyraldehyde to isobutanol | horse liver alcohol dehydrogenase ("ADH") | 148 |
| e) isobutyraldehyde to isobutanol | *Achromobacter xylosoxidans* sadB | 149 |

TABLE BB

E.C. numbers

| Pathway step | E.C. Number: |
|---|---|
| a) pyruvate to acetolactate | 2.2.1.6 |
| b) acetolactate to 2,3-dihydroxyisovalerate | 1.1.1.86 |
| c) 2,3-dihydroxyisovalerate to α-ketoisovalerate | 4.2.1.9 |

TABLE BB-continued

| Pathway step | E.C. Number: |
|---|---|
| d) α-ketoisovalerate to isobutyraldehyde | 4.1.1.72 or 4.1.1.1 |
| e) isobutyraldehyde to isobutanol | 1.1.1.265, 1.1.1.1 or 1.1.1.2 |

Provided herein are recombinant microorganisms comprising an isobutanol biosynthetic pathway comprising steps a)-e) (above) wherein at least one of the enzymes selected from the group of the enzyme catalyzing step c) and the enzyme catalyzing step e) is encoded by a heterologous polynucleotide integrated into the chromosome of the microorganism. In some embodiments, both an enzyme catalyzing step c) is encoded by a heterologous polynucleotide integrated into the chromosome of the microorganism, and enzyme catalyzing step e) is encoded by a heterologous polynucleotide integrated into the chromosome of the microorganism.

Provided herein are polynucleotides suitable for recombinant microorganisms comprising a butanol biosynthetic pathway such as an isobutanol biosynthetic pathway. Such polynucleotides include the coding region of the alsS gene from *Bacillus subtilis* (nt position 457-2172 of SEQ ID NO: 1) and the ilvC gene from *Lactococcus lactis* (nt 3634-4656 of SEQ ID NO: 1) as well as plasmids comprising either or both. Also suitable is a chimeric gene having the coding region of the alsS gene from *Bacillus subtilis* (nt position 457-2172 of SEQ ID NO: 1) expressed from the yeast CUP1 promoter (nt 2-449 of SEQ ID NO: 1) and followed by the CYC1 terminator (nt 2181-2430 of SEQ ID NO: 1) for expression of ALS, and a chimeric gene having the coding region of the ilvC gene from *Lactococcus lactis* (nt 3634-4656 of SEQ ID NO: 1) expressed from the yeast ILV5 promoter (2433-3626 of SEQ ID NO: 1) and followed by the ILV5 terminator (nt 4682-5304 of SEQ ID NO: 1) for expression of KARI, as well as plasmids comprising either or both chimeric genes.

Suitable polynucleotides include the coding region of the ilvD gene from *Streptococcus mutans* (nt position 3313-4849 of SEQ ID NO: 2), the coding region of codon optimized horse liver alcohol dehydrogenase (nt 6286-7413 of SEQ ID NO: 2), the coding region of the codon-optimized kivD gene from *Lactococcus lactis* (nt 9249-10895 of SEQ ID NO: 2) as well as plasmids comprising any or all or any combination thereof. Also suitable is a chimeric gene having the coding region of the ilvD gene from *Streptococcus mutans* (nt position 3313-4849 of SEQ ID NO: 2) expressed from the *S. cerevisiae* FBA1 promoter (nt 2109-3105 of SEQ ID NO: 2) followed by the FBA1 terminator (nt 4858-5857 of SEQ ID NO: 2) for expression of DHAD; a chimeric gene having the coding region of codon optimized horse liver alcohol dehydrogenase (nt 6286-7413 of SEQ ID NO: 2) expressed from the *S. cerevisiae* GPM1 promoter (nt 7425-8181 of SEQ ID NO: 2) followed by the ADH1 terminator (nt 5962-6277 of SEQ ID NO: 2) for expression of ADH; and a chimeric gene having the coding region of the codon-optimized kivD gene from *Lactococcus lactis* (nt 9249-10895 of SEQ ID NO: 2) expressed from the TDH3 promoter (nt 10896-11918 of SEQ ID NO: 2) followed by the TDH3 terminator (nt 8237-9235 of SEQ ID NO: 2) for expression of KivD as well as plasmids containing any, all, or any combination of such chimeric genes. In addition, suitable polynucleotides include those having at least about 75% identity to the coding regions and chimeric genes specified, as well as plasmids comprising such polynucleotides.

In some embodiments, the isobutanol biosynthetic pathway comprises at least one gene, at least two genes, at least three genes, or at least four genes that is/are heterologous to the yeast cell. In some embodiments, the recombinant host cell comprises a heterologous gene for each substrate to product conversion of an isobutanol biosynthetic pathway.

Suitable strains include those described in certain applications cited and incorporated by reference herein as well as in U.S. Provisional Application Ser. No. 61/380,563, filed on Sep. 7, 2010. Construction of certain suitable strains including those used in the Examples, is provided herein.

Construction of *Saccharomyces cerevisiae* Strain BP1083 ("NGCI-070"; PNY1504)

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 1, described in U.S. Provisional Application Ser. No. 61/246,844) and pLH468 (SEQ ID NO: 2) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3,500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3,500 bp. Upon excision, the 3,500 bp region of the gene was also deleted. For integration of genes using this method, the gene to be integrated was included in the PCR cassette between fragments A and B.

URA3 Deletion

To delete the endogenous URA3 coding region, a ura3::loxP-kanMX-loxP cassette was PCR-amplified from pLA54 template DNA (SEQ ID NO: 3). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 4 and 5). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 μg/mL) at 30° C. Transformants were screened to verify correct integration by PCR using primers LA468 and LA492 (SEQ ID NOs: 6 and 7) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 14) and primer oBP453 (SEQ ID NO: 15) containing a 5' tail with homology to the 5' end of HIS3 Fragment B. HIS3 Fragment B was amplified with primer oBP454 (SEQ ID NO: 16) containing a 5' tail with homology to the 3' end of HIS3 Fragment A, and primer oBP455 (SEQ ID NO: 17) containing a 5' tail with homology to the 5' end of HIS3 Fragment U. HIS3 Fragment U was amplified with primer oBP456 (SEQ ID NO: 18) containing a 5' tail with homology to the 3' end of HIS3 Fragment B, and primer oBP457 (SEQ ID NO: 19) containing a 5' tail with homology to the 5' end of HIS3 Fragment C. HIS3 Fragment C was amplified with primer oBP458 (SEQ ID NO: 20) containing a 5' tail with homology to the 3' end of HIS3 Fragment U, and primer oBP459 (SEQ ID NO: 21). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 14) and oBP455 (SEQ ID NO: 17). HIS3 Fragment UC was created by overlapping PCR by mixing HIS3 Fragment U and HIS3 Fragment C and amplifying with primers oBP456 (SEQ ID NO: 18) and oBP459 (SEQ ID NO: 21). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 14) and oBP459 (SEQ ID NO: 21). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 22) and oBP461 (SEQ ID NO: 23) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 66, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+ G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 24) and oBP451 (SEQ ID NO: 25) for Δura3 and primers oBP460 (SEQ ID NO: 22) and oBP461 (SEQ ID NO: 23) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 26) and primer oBP441 (SEQ ID NO: 27) containing a 5' tail with homology to the 5' end of PDC6 Fragment B. PDC6 Fragment B was amplified with primer oBP442 (SEQ ID NO: 28), containing a 5' tail with homology to the 3' end of PDC6 Fragment A, and primer oBP443 (SEQ ID NO: 29) containing a 5' tail with homology to the 5' end of PDC6 Fragment U. PDC6 Fragment U was amplified with primer oBP444 (SEQ ID NO: 30) containing a 5' tail with homology to the 3' end of PDC6 Fragment B, and primer oBP445 (SEQ ID NO: 31) containing a 5' tail with homology to the 5' end of PDC6 Fragment C. PDC6 Fragment C was amplified with primer oBP446 (SEQ ID NO: 32) containing a 5' tail with homology to the 3' end of PDC6 Fragment U, and primer oBP447 (SEQ ID NO: 33). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 26) and oBP443 (SEQ ID NO: 29). PDC6 Fragment UC was created by overlapping PCR by mixing PDC6 Fragment U and PDC6 Fragment C and amplifying with primers oBP444 (SEQ ID NO: 30) and oBP447 (SEQ ID NO: 33). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 26) and oBP447 (SEQ ID NO: 33). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 34) and oBP449 (SEQ ID NO:

35) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 34) and oBP449 (SEQ ID NO: 35) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 36) and oBP555 (SEQ ID NO: 37). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from *Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 genomic DNA as template, prepared with a Gentra® Puregene® Yeast/Bact. kit (Qiagen, Valencia, Calif.). NYLA83 is a strain (construction described in U.S. Patent Application Publication No. 2011/0124060, incorporated herein by reference in its entirety) which carries the PDC1 deletion-ilvDSm integration described in U.S. Patent Application Publication No. 2009/0305363, herein incorporated by reference in its entirety). PDC1 Fragment A-ilvDSm (SEQ ID NO: 141) was amplified with primer oBP513 (SEQ ID NO: 38) and primer oBP515 (SEQ ID NO: 39) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 40) containing a 5' tail with homology to the 3' end of PDC1 Fragment A-ilvDSm, and primer oBP517 (SEQ ID NO: 41) containing a 5' tail with homology to the 5' end of PDC1 Fragment U. PDC1 Fragment U was amplified with primer oBP518 (SEQ ID NO: 42) containing a 5' tail with homology to the 3' end of PDC1 Fragment B, and primer oBP519 (SEQ ID NO: 43) containing a 5' tail with homology to the 5' end of PDC1 Fragment C. PDC1 Fragment C was amplified with primer oBP520 (SEQ ID NO: 44), containing a 5' tail with homology to the 3' end of PDC1 Fragment U, and primer oBP521 (SEQ ID NO: 45). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 38) and oBP517 (SEQ ID NO: 41). PDC1 Fragment UC was created by overlapping PCR by mixing PDC1 Fragment U and PDC1 Fragment C and amplifying with primers oBP518 (SEQ ID NO: 42) and oBP521 (SEQ ID NO: 45). The resulting PCR products were purified on an agarose gel followed by a Gel Extraction kit (Qiagen, Valencia, Calif.). The PDC1 A-ilvDSm-BUC cassette (SEQ ID NO: 142) was created by overlapping PCR by mixing PDC1 Fragment A-ilvDSm-B and PDC1 Fragment UC and amplifying with primers oBP513 (SEQ ID NO: 38) and oBP521 (SEQ ID NO: 45). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 48) and oBP551 (SEQ ID NO: 49). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 46) and oBP512 (SEQ ID NO: 47) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccharomyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccharomyces cerevisiae* CEN.PK 113-7D genomic DNA was amplified with primers oBP438 (SEQ ID NO: 12) containing BamHI, AscI, PmeI, and FseI restriction sites, and oBP439 (SEQ ID NO: 13) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 (SEQ ID NO: 150) were ligated with T4 DNA ligase after digestion with BamHI and XbaI to create vector pUC19-URA3MCS. The vector was confirmed by PCR and sequencing with primers oBP264 (SEQ ID NO: 10) and oBP265 (SEQ ID NO: 11).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 67) as template with primer oBP530 (SEQ ID NO: 50) containing an AscI restriction site, and primer oBP531 (SEQ ID NO: 51) containing a 5' tail with homology to the 5' end of PDC5 Fragment B. PDC5 Fragment B was amplified with primer oBP532 (SEQ ID NO: 52) containing a 5' tail with homology to the 3' end of sadB, and primer oBP533 (SEQ ID NO: 53) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 50) and oBP533 (SEQ ID NO: 53). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 54) and oBP546 (SEQ ID NO: 55) containing a 5' tail with homology to the 5' end of PDC5 Fragment C. PDC5 Fragment C was amplified with primer oBP547 (SEQ ID NO: 56) containing a 5' tail with homology to the 3' end of PDC5 sadB-Fragment B-Fragment U, and primer oBP539 (SEQ ID NO: 57). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 54) and oBP539 (SEQ ID NO: 57). The resulting PCR product was purified on an agarose gel followed by a Gel Extraction kit (Qiagen, Valencia, Calif.). The PDC5 A-sadB-BUC cassette (SEQ ID NO: 143) was created by amplifying PDC5 sadB-Fragment B-Fragment U-Fragment C with primers oBP542 (SEQ ID NO: 58) containing a 5' tail with homology to the 50 nucleotides immediately upstream of the native PDC5 coding sequence, and oBP539 (SEQ ID NO: 57). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 61) and oBP553 (SEQ ID NO: 62). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 59) and oBP541 (SEQ ID NO: 60) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette (SEQ ID NO: 151) was PCR-amplified using loxP-URA3-loxP (SEQ ID NO: 68) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 8 and 9). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 63 and 64).

The URA3 marker was recycled by transformation with pRS423::PGAL1-cre (SEQ ID NO: 66) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 63) and oBP591 (SEQ ID NO: 65). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 1) and pLH468 (SEQ ID NO: 2) to create strain NGCI-070 (BP1083; PNY1504).

Construction of *Saccharomyces cerevisiae* Strain PNY2205

The strain, PNY2205, was derived from PNY1503 (BP1064) which is described above.

Deletions, which generally removed the entire coding sequence, were created by homologous recombination with PCR fragments containing regions of homology upstream and downstream of the target gene and the URA3 gene for selection of transformants. The URA3 gene was removed by homologous recombination to create a scarless deletion. Gene integrations were generated in a similar manner.

The scarless deletion procedure was adapted from Akada et al., (Yeast, 23:399, 2006). In general, the PCR cassette for each scarless deletion was made by combining four fragments, A-B-U-C, by overlapping PCR. In some instances, the individual fragments were first cloned into a plasmid prior to the entire cassette being amplified by PCR for the deletion/integration procedure. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene) regions. Fragments A and C, each generally 500 bp long, corresponded to the 500 bp immediately upstream of the target gene (Fragment A) and the 3,500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome.

Using the PCR product ABUC cassette, the URA3 marker was first integrated into and then excised from the chromosome by homologous recombination. The initial integration deleted the gene, excluding the 3,500 bp. Upon excision, the 3,500 bp region of the gene was also deleted. For integration of genes using this method, the gene to be integrated was included in the PCR cassette between fragments A and B.

FRA2 Deletion

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). FRA2 Fragment A was amplified with primer oBP594 (SEQ ID NO: 152) and primer oBP595 (SEQ ID NO: 153), containing a 5' tail with homology to the 5' end of FRA2 Fragment B. FRA2 Fragment B was amplified with primer oBP596 (SEQ ID NO: 154), containing a 5' tail with homology to the 3' end of FRA2 Fragment A, and primer oBP597 (SEQ ID NO: 155), containing a 5' tail with homology to the 5' end of FRA2 Fragment U. FRA2 Fragment U was amplified with primer oBP598 (SEQ ID NO: 156), containing a 5' tail with homology to the 3' end of FRA2 Fragment B, and primer oBP599 (SEQ ID NO: 157), containing a 5' tail with homology to the 5' end of FRA2 Fragment C. FRA2 Fragment C was amplified with primer oBP600 (SEQ ID NO: 158), containing a 5' tail with homology to the 3' end of FRA2 Fragment U, and primer oBP601 (SEQ ID NO: 159). PCR products were purified with a PCR Purification kit (Qiagen, Valencia, Calif.). FRA2 Fragment AB was created by overlapping PCR by mixing FRA2 Fragment A and FRA2 Fragment B and amplifying with primers oBP594 (SEQ ID NO: 152) and oBP597 (SEQ ID NO: 155). FRA2 Fragment UC was created by overlapping PCR by mixing FRA2 Fragment U and FRA2 Fragment C and amplifying with primers oBP598 (SEQ ID NO: 156) and oBP601 (SEQ ID NO: 159). The resulting PCR products were purified on an agarose gel followed by a Gel Extraction kit (Qiagen, Valencia, Calif.). The FRA2 ABUC cassette was created by overlapping PCR by mixing FRA2 Fragment AB and FRA2 Fragment UC and amplifying with primers oBP594 (SEQ ID NO: 152) and oBP601 (SEQ ID NO: 159). The PCR product was purified with a PCR Purification kit (Qiagen, Valencia, Calif.).

Competent cells of PNY1503 were made and transformed with the FRA2 ABUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol at 30° C. Transformants with a fra2 knockout were screened for by PCR with primers oBP602 (SEQ ID NO: 160) and oBP603 (SEQ ID NO: 161) using genomic DNA prepared with a Gentra® Puregene® Yeast/Bact. kit (Qiagen, Valencia, Calif.). A correct transformant was grown in YPE (yeast extract, peptone, 1% ethanol) and plated on synthetic complete medium containing 5-fluoro-orotic acid (0.1%) at 30° C. to select for isolates that lost the URA3 marker. The deletion and marker removal were confirmed by PCR with primers oBP602 (SEQ ID NO: 160) and oBP603 (SEQ ID NO: 161) using genomic DNA prepared with a Gentra® Puregene® Yeast/Bact. kit (Qiagen, Valencia, Calif.). The absence of the FRA2 gene from the isolate was demonstrated by a negative PCR result using primers specific for the deleted coding sequence of FRA2, oBP605 (SEQ ID NO: 162) and oBP606 (SEQ ID NO: 163). The correct isolate was selected as strain CEN.PK 113-7D MATa ura3Δ::loxP his3Δ pdc6Δ pdc1Δ::P[PDC1]-DHAD|ilvD_Sm-PDC1t pdc5Δ::P[PDC5]-ADH|sadB_Ax-PDC5t gpd2Δ::loxP fra2Δ and designated as PNY1505 (BP1135).

ADH1 Deletion and kivD_LI(y) Integration

The ADH1 gene was deleted and replaced with the kivD coding region from *Lactococcus lactis* codon optimized for expression in *Saccharomyces cerevisiae*. The scarless cassette for the ADH1 deletion-kivD_LI(y) integration was first cloned into plasmid pUC19-URA3MCS, as described in U.S. Provisional Application Ser. No. 61/356,379, filed Jun. 18, 2010, incorporated herein by reference. The vector is pUC19 based and contains the sequence of the URA3 gene from *Saccharomyces cerevisiae* CEN.PK 113-7D situated within a multiple cloning site (MCS). pUC19 contains the pMB1 replicon and a gene coding for beta-lactamase for replication and selection in *Escherichia coli*. In addition to the coding sequence for URA3, the sequences from upstream (250 bp) and downstream (150 bp) of this gene are present for expression of the URA3 gene in yeast.

The kivD coding region from *Lactococcus lactis* codon optimized for expression in *Saccharomyces cerevisiae* was amplified using pLH468 (U.S. Provisional Application Ser. No. 61/246,709, filed Sep. 29, 2009) as template with primer oBP562 (SEQ ID NO: 164), containing a PmeI restriction site, and primer oBP563 (SEQ ID NO: 165), containing a 5' tail with homology to the 5' end of ADH1 Fragment B. ADH1 Fragment B was amplified from genomic DNA prepared as above with primer oBP564 (SEQ ID NO: 166), containing a 5' tail with homology to the 3' end of kivD_LI(y), and primer oBP565 (SEQ ID NO: 167), containing a FseI restriction site. PCR products were purified with a PCR Purification kit (Qiagen, Valencia, Calif.). kivD_LI(y)-ADH1 Fragment B was created by overlapping PCR by mixing the kivD_LI(y) and ADH1 Fragment B PCR products and amplifying with primers oBP562 (SEQ ID NO: 164) and oBP565 (SEQ ID NO: 167). The resulting PCR product was digested with PmeI and FseI and ligated with T4 DNA ligase into the corresponding sites of pUC19-URA3MCS after digestion with the appropriate enzymes. ADH1 Fragment A was amplified from genomic DNA with primer oBP505 (SEQ ID NO: 168) containing a SacI restriction site, and primer oBP506 (SEQ ID NO: 169), containing an AscI restriction site. The ADH1 Fragment A PCR product was digested with SacI and AscI and ligated with T4 DNA ligase into the corresponding sites of the plasmid containing kivD_LI(y)-ADH1 Fragment B. ADH1 Fragment C was amplified from genomic DNA with primer oBP507 (SEQ ID NO: 170), containing a PacI restriction site, and primer oBP508 (SEQ ID NO: 171), containing a SalI restriction site. The ADH1 Fragment C PCR product was digested with PacI and SalI and ligated with T4 DNA ligase into the corresponding sites of the plasmid containing ADH1 Fragment A-kivD_LI(y)-ADH1 Fragment B. The hybrid promoter UAS(PGK1)-P$_{FBA1}$ was amplified from vector pRS316-UAS(PGK1)-P$_{FBA1}$-GUS (SEQ ID NO: 172) with primer oBP674 (SEQ ID NO: 173), containing an AscI restriction site, and primer oBP675 (SEQ ID NO: 174), containing a PmeI restriction site. The UAS(PGK1)-P$_{FBA1}$ PCR product was digested with AscI and PmeI and ligated with T4 DNA ligase into the corresponding sites of the plasmid containing kivD_LI(y)-ADH1 Fragments ABC. The entire integration cassette was amplified from the resulting plasmid with primers oBP505 (SEQ ID NO: 168) and oBP508 (SEQ ID NO: 171) and purified with a PCR Purification kit (Qiagen, Valencia, Calif.).

Competent cells of PNY1505 were made and transformed with the ADH1-kivD_LI(y) PCR cassette constructed above using a Frozen-EZ Yeast Transformation II™ kit (Zymo Research Corporation, Irvine, Calif.). Transformation mixtures were plated on synthetic complete media lacking uracil supplemented with 1% ethanol at 30° C. Transformants were grown in YPE (1% ethanol) and plated on synthetic complete medium containing 5-fluoro-orotic acid (0.1%) at 30° C. to select for isolates that lost the URA3 marker. The deletion of ADH1 and integration of kivD_LI(y) were confirmed by PCR with external primers oBP495 (SEQ ID NO: 175) and oBP496 (SEQ ID NO: 176) and with kivD_LI(y) specific primer oBP562 (SEQ ID NO: 164) and external primer oBP496 (SEQ ID NO: 176) using genomic DNA prepared with a Gentra® Puregene® Yeast/Bact. kit (Qiagen, Valencia, Calif.). The correct isolate was selected as strain CEN.PK 113-7D MATa ura3Δ::loxP his3Δ pdc6Δ pdc1Δ::P[PDC1]-DHAD|ilvD_Sm-PDC1tpdc5Δ::P[PDC5]-ADH|sadB_Ax-PDC5t gpd2Δ::loxP fra2Δ adh1Δ::UAS(PGK1)P[FBA1]-kivD_LI(y)-ADH1t and designated as PNY1507 (BP1201). PNY1507 was transformed with isobutanol pathway plasmids pYZ090 (SEQ ID NO: 1) and pBP915 (described below).

Construction of the pRS316-UAS(PGK1)-FBA1p-GUS Vector

To clone a cassette UAS(PGK1)-FBA1p (SEQ ID NO: 177, first a 602 bp FBA1 promoter (FBA1p) was PCR-amplified from genomic DNA of CEN.PK with primers T-FBA1 (SalI) (SEQ ID NO: 178) and B-FBA1(SpeI) (SEQ ID NO: 179), and cloned into SalI and SpeI sites on the plasmid pWS358-PGK1p-GUS (SEQ ID NO: 180) after the PGK1p promoter was removed with a SalI/SpeI digest of the plasmid, yielding pWS358-FBA1p-GUS. The pWS358-PGK1p-GUS plasmid was generated by inserting a PGK1p and beta-glucuronidase gene (GUS) DNA fragments into multiple cloning site of pWS358, which was derived from pRS423 vector (Christianson, et al., Gene 110:119-122, 1992). Secondly, the resulting pWS358-FBA1p-GUS plasmid was digested with SalI and SacI, a DNA fragment containing a FBA1p promoter, GUS gene, and FBAt terminator gel-purified, and cloned into SalI/SacI sites on pRS316 to create pRS316-FBA1p-GUS. Thirdly, a 118 bp DNA fragment containing an upstream activation sequence (UAS) located between positions −519 and −402 upstream of the 3-phosphoglycerate kinase (PGK1) open reading frame, namely UAS(PGK1), was PCR-amplified from genomic DNA of CEN.PK with primers T-U/PGK1(KpnI) (SEQ ID NO: 181) and B-U/PGK1 (SalI) (SEQ ID NO: 182). The PCR product was digested with KpnI and SalI and cloned into KpnI/SalI sites on pRS316-FBA1p-GUS to create pRS316-UAS(PGK1)-FBA1p-GUS.

Construction of Integration Vector pUC19-kan::pdc1::FBA-alsS::TRX1

The FBA-alsS-CYCt cassette was constructed by moving the 1.7 kb BbvCI/PacI fragment from pRS426::GPD::alsS::CYC (U.S. Patent Application Publication No. 2007/0092957) to pRS426::FBA::ILV5::CYC (U.S. Patent Application Publication No. 2007/0092957, previously digested with BbvCI/PacI to release the ILV5 gene). Ligation reactions were transformed into E. coli TOP10 cells and transformants were screened by PCR using primers N98SeqF1 (SEQ ID NO: 183) and N99SeqR2 (SEQ ID NO: 184). The FBA-alsS-CYCt cassette was isolated from the vector using BglII and NotI for cloning into pUC19-URA3::ilvD-TRX1 (as described in U.S. Provisional Application Ser. No. 61/356,379, filed Jun. 18, 2010, incorporated herein by reference, clone "B") at the AflII site (Klenow fragment was used to make ends compatible for ligation). Transformants containing the alsS cassette in both orientations in the vector were obtained and confirmed by PCR using primers N98SeqF4 (SEQ ID NO: 185) and N1111 (SEQ ID NO: 186) for configuration "A" and N98SeqF4 (SEQ ID NO: 185) and N1110 (SEQ ID NO: 187) for configuration "B". A geneticin selectable version of the "A" configuration vector was then made by removing the URA3 gene (1.2 kb NotI/NaeI fragment) and adding a geneticin cassette previously described (SEQ ID NO: 655 of U.S. Provisional Application Ser. No. 61/356,379, filed Jun. 18, 2010, incorporated herein by reference). Klenow fragment was used to make all ends compatible for ligation, and transformants were screened by PCR to select a clone with the geneticin resistance gene in the same orientation as the previous URA3 marker using primers BK468 (SEQ ID NO: 188) and N160SeqF5 (SEQ ID NO: 189). The resulting clone was called pUC19-kan::pdc1::FBA-alsS::TRX1 (clone A) (SEQ ID NO: 190).

The pUC19-kan::pdc1::FBA-alsS integration vector described above was linearized with PmeI and transformed into PNY1507 (described above). PmeI cuts the vector within the cloned pdc1-TRX1 intergenic region and thus, leads to targeted integration at that location (Rothstein, Methods Enzymol. 194:281-301, 1991). Transformants were selected on YPE plus 50 µg/ml G418. Patched transformants were screened by PCR for the integration event using primers N160SeqF5 (SEQ ID NO: 189) and oBP512 (SEQ ID NO: 47). Two transformants were tested indirectly for acetolactate synthase function by evaluating the strains ability to make isobutanol. To do this, additional isobutanol pathway genes were supplied on E. coli-yeast shuttle vectors (pYZ090ΔalsS and pBP915, described below). One clone, strain MATa ura3Δ::loxP his3Δ pdc6Δ pdc1Δ::P[PDC1]-DHAD|ilvD_Sm-PDC1t-pUC19-loxP-kanMX-loxP-P[FBA1]-ALS|alsS_Bs-CYC1t pdc5Δ::P[PDC5]-ADH|sadB_Ax-PDC5t gpd2Δ::loxP fra2Δ adh1Δ::UAS(PGK1)P [FBA1]-kivD_LI(y)-ADH1t was designated as PNY2204. PNY2205 is PNY2204 transformed with pYZ090ΔalsS and pBP915 plasmids.

Isobutanol Pathway Plasmids (pYZ090ΔalsS and pBP915)

pYZ090 (SEQ ID NO: 1) was digested with SpeI and NotI to remove most of the CUP1 promoter and all of the alsS coding sequence and CYC terminator. The vector was then self-ligated after treatment with Klenow fragment and transformed into E. coli Stbl3 cells, selecting for ampicillin resistance. Removal of the DNA region was confirmed for two independent clones by DNA sequencing across the ligation junction by PCR using primer N191 (SEQ ID NO: 191). The resulting plasmid was named pYZ090ΔalsS (SEQ ID NO: 192).

pBP915 was constructed from pLH468 (SEQ ID NO: 2; U.S. Provisional Application Ser. No. 61/246,709, filed Sep. 29, 2009) by deleting the kivD gene and 957 base pairs of the TDH3 promoter upstream of kivD. pLH468 was digested with SwaI and the large fragment (12896 bp) was purified on an agarose gel followed by a Gel Extraction kit (Qiagen, Valencia, Calif.). The isolated fragment of DNA was self-ligated with T4 DNA ligase and used to transform electrocompetent TOP10 Escherichia coli (Invitrogen, Carlsbad, Calif.). Plasmids from transformants were isolated and checked for the proper deletion by restriction analysis with the SwaI restriction enzyme. Isolates were also sequenced across the deletion site with primers oBP556 (SEQ ID NO: 193) and oBP561 (SEQ ID NO: 194). A clone with the proper deletion was designated pBP915 (pLH468ΔkivD) (SEQ ID NO: 195).

Construction of Strains NYLA74, NYLA83, and NYLA84

Insertion-inactivation of endogenous PDC1 and PDC6 genes of S. cerevisiae. PDC1, PDC5, and PDC6 genes encode the three major isozymes of pyruvate decarboxylase is described as follows:

Construction of pRS425::GPM-sadB

A DNA fragment encoding a butanol dehydrogenase (SEQ ID NO: 70) from *Achromobacter xylosoxidans* (disclosed in U.S. Patent Application Publication No. 2009/0269823) was cloned. The coding region of this gene called sadB for secondary alcohol dehydrogenase (SEQ ID NO: 69) was amplified using standard conditions from *A. xylosoxidans* genomic DNA, prepared using a Gentra® Puregene® kit (Qiagen, Valencia, Calif.) following the recommended protocol for gram negative organisms using forward and reverse primers N473 and N469 (SEQ ID NOs: 74 and 75), respectively. The PCR product was TOPO®-Blunt cloned into pCR®4 BLUNT (Invitrogen™, Carlsbad, Calif.) to produce pCR4Blunt::sadB, which was transformed into *E. coli* Mach-1 cells. Plasmid was subsequently isolated from four clones, and the sequence verified.

The sadB coding region was PCR amplified from pCR4Blunt::sadB. PCR primers contained additional 5' sequences that would overlap with the yeast GPM1 promoter and the ADH1 terminator (N583 and N584, provided as SEQ ID NOs: 76 and 77). The PCR product was then cloned using "gap repair" methodology in *Saccharomyces cerevisiae* (Ma, et al., Gene 58:201-216, 1987) as follows. The yeast-*E. coli* shuttle vector pRS425::GPM::kivD::ADH which contains the GPM1 promoter (SEQ ID NO: 72), kivD coding region from *Lactococcus lactis* (SEQ ID NO: 71), and ADH1 terminator (SEQ ID NO: 73) (described in U.S. Patent Application Publication No. 2007/0092957 A1, Example 17) was digested with BbvCI and PacI restriction enzymes to release the kivD coding region. Approximately 1 μg of the remaining vector fragment was transformed into *S. cerevisiae* strain BY4741 along with 1 μg of sadB PCR product. Transformants were selected on synthetic complete medium lacking leucine. The proper recombination event, generating pRS425::GPM-sadB, was confirmed by PCR using primers N142 and N459 (SEQ ID NOs: 108 and 109).

Construction of pdc6::PGPM1-sadB Integration Cassette and PDC6 Deletion:

A pdc6::PGPM1-sadB-ADH1t-URA3r integration cassette was made by joining the GPM-sadB-ADHt segment (SEQ ID NO: 79) from pRS425::GPM-sadB (SEQ ID NO: 78) to the URA3r gene from pUC19-URA3r. pUC19-URA3r (SEQ ID NO: 80) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England BioLabs Inc., Ipswich, Mass.) and primers 114117-11A through 114117A-11D (SEQ ID NOs: 81, 82, 83, and 84), and 114117-13A and 114117-13B (SEQ ID NOs: 85 and 86).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 112590-34G and 112590-34H (SEQ ID NOs: 87 and 88), and 112590-34F and 112590-49E (SEQ ID NOs: 89 and 90) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain has the genotype: BY4700 pdc6::PGPM1-sadB-ADH 1t.

Construction of pdc1::PPDC1-ilvD Integration Cassette and PDC1 Deletion:

A pdc1::PPDC1-ilvD-FBA1t-URA3r integration cassette was made by joining the ilvD-FBA1t segment (SEQ ID NO: 91) from pLH468 (SEQ ID NO: 2) to the URA3r gene from pUC19-URA3r by SOE PCR (as described by Horton, et al., Gene 77:61-68, 1989) using as template pLH468 and pUC19-URA3r plasmid DNAs, with Phusion® DNA polymerase (New England BioLabs Inc., Ipswich, Mass.) and primers 114117-27A through 114117-27D (SEQ ID NOs: 111, 112, 113, and 114).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::PGPM1-sadB-ADH1t and transformants were maintained on synthetic complete media lacking uracil and supplemented with 2% glucose at 30° C. using standard genetic techniques (Methods in Yeast Genetics, 2005, Cold Spring Harbor Laboratory Press, Cold Spring Harbor, N.Y., pp. 201-202). Transformants were screened by PCR using primers 114117-36D and 135 (SEQ ID NOs: 92 and 93), and primers 112590-49E and 112590-30F (SEQ ID NOs: 90 and 94) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6::PGPM1-sadB-ADH1t pdc1::PPDC1-ilvD-FBA1t.

HIS3 Deletion

To delete the endogenous HIS3 coding region, a his3::URA3r2 cassette was PCR-amplified from URA3r2 template DNA (SEQ ID NO: 95). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England BioLabs Inc., Ipswich, Mass.) and primers 114117-45A and 114117-45B (SEQ ID NOs: 96 and 97) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6::PGPM1-sadB-ADH1t pdc1::PPDC1-ilvD-FBA1t Δhis3.

Construction of pdc5::kanMX Integration Cassette and PDC5 Deletion:

A pdc5::kanMX4 cassette was PCR-amplified from strain YLR134W chromosomal DNA (ATCC No. 4034091) using Phusion® DNA polymerase (New England BioLabs Inc., Ipswich, Mass.) and primers PDC5::KanMXF and PDC5::KanMXR (SEQ ID NOs: 98 and 99) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on YP media supplemented with 1% ethanol and geneticin (200 µg/mL) at 30° C. Transformants were screened by PCR to verify correct integration at the PDC locus with replacement of the PDC5 coding region using primers PDC5kofor and N175 (SEQ ID NOs: 100 and 101). The identified correct transformants have the genotype: BY4700 pdc6::PGPM1-sadB-ADH1t pdc1::PPDC1-ilvD-FBA1t Δhis3 pdc5::kanMX4. The strain was named NYLA74.

Plasmid vectors pRS423::CUP1-alsS+FBA-budA and pRS426::FBA-budC+GPM-sadB were transformed into NYLA74 to create a butanediol producing strain (NGCI-047).

Plasmid vectors pLH475-Z4B8 (SEQ ID NO: 140) and pLH468 were transformed into NYLA74 to create an isobutanol producing strain (NGCI-049).

Deletion of HXK2 (Hexokinase II):

A hxk2::URA3r cassette was PCR-amplified from URA3r2 template (described above) using Phusion® DNA polymerase (New England BioLabs Inc., Ipswich, Mass.) and primers 384 and 385 (SEQ ID NOs: 102 and 103) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (Methods in Yeast Genetics, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 104 and 105). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 106 and 107). The resulting identified strain named NYLA83 has the genotype: BY4700 pdc6::PGPM1-sadB-ADH1t pdc1::PPDC1-ilvD-FBA1t Δhis3 Δhxk2.

Construction of pdc5::kanMX Integration Cassette and PDC5 Deletion:

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6::PGPM1-sadB-ADH1t pdc1::PPDC1-ilvD-FBA1t Δhis3 Δhxk2 pdc5::kanMX4.

Plasmid vectors pLH468 and pLH532 were simultaneously transformed into strain NYLA84 (BY4700 pdc6::PGPM1-sadB-ADH1t pdc1::PPDC1-ilvD-FBA1t Δhis3 Δhxk2 pdc5::kanMX4) using standard genetic techniques (Methods in Yeast Genetics, 2005, Cold Spring Harbor Laboratory Press, Cold Spring Harbor, N.Y.) and the resulting "butanologen NYLA84" was maintained on synthetic complete media lacking histidine and uracil, and supplemented with 1% ethanol at 30° C.

Expression Vector pLH468

The pLH468 plasmid (SEQ ID NO: 2) was constructed for expression of DHAD, KivD, and HADH in yeast and is described in U.S. Patent Application Publication No. 2009/0305363, herein incorporated by reference. pLH486 was constructed to contain: a chimeric gene having the coding region of the ilvD gene from *Streptococcus mutans* (nt position 3313-4849) expressed from the *S. cerevisiae* FBA1 promoter (nt 2109-3105) followed by the FBA1 terminator (nt 4858-5857) for expression of DHAD; a chimeric gene having the coding region of codon optimized horse liver alcohol dehydrogenase (nt 6286-7413) expressed from the *S. cerevisiae* GPM1 promoter (nt 7425-8181) followed by the ADH1 terminator (nt 5962-6277) for expression of ADH; and a chimeric gene having the coding region of the codon-optimized kivD gene from *Lactococcus lactis* (nt 9249-10895) expressed from the TDH3 promoter (nt 10896-11918) followed by the TDH3 terminator (nt 8237-9235) for expression of KivD.

Coding regions for *Lactococcus lactis* ketoisovalerate decarboxylase (KivD) and horse liver alcohol dehydrogenase (HADH) were synthesized by DNA2.0, Inc. (Menlo Park, Calif.) based on codons that were optimized for expression in *Saccharomyces cerevisiae* (SEQ ID NO: 71 and 118, respectively) and provided in plasmids pKivDy-DNA2.0 and pHadhy-DNA2.0. The encoded proteins are SEQ ID NOs: 117 and 119, respectively. Individual expression vectors for KivD and HADH were constructed. To assemble pLH467 (pRS426::PTDH3-kivDy-TDH3t), vector pNY8 (SEQ ID NO: 121; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 122) from pNY8 was PCR amplified to add an AscI site at the 5' end and an SpeI site at the 3' end, using 5' primer OT1068 and 3' primer OT1067 (SEQ ID NOs: 123 and 124). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::PTDH3-kivDy-TDH3t). pLH467 was verified by restriction mapping and sequencing.

pLH435 (pRS425::PGPM1-Hadhy-ADH1t) was derived from vector pRS425::GPM-sadB (SEQ ID NO: 78) which is described in U.S. Provisional Application Ser. No. 61/058, 970, Example 3, which is herein incorporated by reference. pRS425::GPM-sadB is the pRS425 vector (ATCC No. 77106) with a chimeric gene containing the GPM1 promoter (SEQ ID NO: 72), coding region from a butanol dehydrogenase of *Achromobacter xylosoxidans* (sadB; DNA SEQ ID NO: 69; protein SEQ ID NO: 70: disclosed in U.S. Patent Application Publication No. 2009/0269823), and ADH1 terminator (SEQ ID NO: 73). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NOs: 126 and 127) to generate vector pRS425-GPMp-sadB-NheI, which was verified by sequencing. pRS425::PGPM1-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the PTDH3-kivDy-TDH3t cassette together with the SalI-NotI fragment from pLH435 that contains the PGPM1-Hadhy-ADH1t cassette in a triple ligation reaction. This yielded the vector pRS411::PTDH3-kivDy-PGPM1-Hadhy (pLH441) which was verified by restriction mapping.

In order to generate a co-expression vector for all three genes in the lower isobutanol pathway: ilvD, kivDy, and Hadhy, pRS423 FBA ilvD(Strep) (SEQ ID NO: 128) which is described in U.S. Patent Application Publication No. 2010/0081154 as the source of the IlvD gene, was used. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 120) and FBA terminator (nt 4861 to 5860; SEQ ID NO: 129). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 115; protein SEQ ID NO: 116) from *Streptococcus mutans* UA159 (ATCC No. 700610) is between the FBA promoter and FBA terminator forming a chimeric gene for expression. In addition, there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD (*Streptococcus mutans*)-Lumio. This generated vector pLH468 (pRS423::PFBA1-ilvD(Strep) Lumio-FBA1t-PTDH3-kivDy-TDH3t-PGPM1-hadhy-ADH1t) which was confirmed by restriction mapping and sequencing.

pLH532 Construction

The pLH532 plasmid (SEQ ID NO: 130) was constructed for expression of ALS and KARI in yeast. pLH532 is a pHR81 vector (ATCC No. 87541) containing the following chimeric genes: 1) the CUP1 promoter (SEQ ID NO: 139), acetolactate synthase coding region from *Bacillus subtilis* (AlsS; SEQ ID NO: 137; protein SEQ ID NO: 138) and CYC1 terminator2 (SEQ ID NO: 133); 2) an ILV5 promoter (SEQ ID NO: 134), Pf5.IlvC coding region (SEQ ID NO: 132) and ILV5 terminator (SEQ ID NO: 135); and 3) the FBA1 promoter (SEQ ID NO: 136), *S. cerevisiae* KARI coding region (ILV5; SEQ ID NO: 131); and CYC1 terminator.

The Pf5.IlvC coding region is a sequence encoding KARI derived from *Pseudomonas fluorescens* that was described in U.S. Patent Application Publication No. 2009/0163376, which is herein incorporated by reference.

The Pf5.IlvC coding region was synthesized by DNA2.0, Inc. (Menlo Park, Calif.; SEQ ID NO: 132) based on codons that were optimized for expression in *Saccharomyces cerevisiae*.

pYZ090 Construction pYZ090 (SEQ ID NO: 1) is based on the pHR81 (ATCC No. 87541) backbone and was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4682-5304) for expression of KARI.

pYZ067 Construction pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of dihydroxy acid dehydratase (DHAD), 2) the coding region for horse liver ADH (nt 4680-5807) expressed from the yeast GPM promoter (nt 5819-6575) followed by the ADH1 terminator (nt 4356-4671) for expression of alcohol dehydrogenase, and 3) the coding region of the KivD gene from *Lacrococcus lactis* (nt 7175-8821) expressed from the yeast TDH3 promoter (nt 8830-9493) followed by the TDH3 terminator (nt 5682-7161) for expression of ketoisovalerate decarboxylase.

pRS423::CUP1-alsS+FBA-budA and pRS426::FBA-budC+GPM-sadB and pLH475-Z4B8 Construction Construction of pRS423::CUP1-alsS+FBA-budA and pRS426::FBA-budC+GPM-sadB and pLH475-Z4B8 is described in U.S. Patent Application Publication No. 2009/0305363, incorporated herein by reference.

Construction of *Saccharomyces cerevisiae* Strain PNY2242

Strain PNY2242 was constructed in several steps from PNY1507 (described above). First, a chimeric gene comprised of the FBA1 promoter, the alsS coding region, and the CYC1 terminator was integrated into Chromosome XII, upstream of the TRX1 gene. The sequence of the modified locus is provided as SEQ ID NO: 196. Next, two copies of a gene encoding horse liver alcohol dehydrogenase were integrated into Chromosomes VII and XVI. On Chromosome VII, a chimeric gene comprised of the PDC1 promoter, the hADH coding region, and the ADH1 terminator were placed into the fra2Δ locus (the original deletion of FRA2 is described above). The sequence of the modified locus is provided as SEQ ID NO: 197. On Chromosome XVI, a chimeric gene comprised of the PDC5 promoter, the hADH coding region, and the ADH1 terminator were integrated in the region formerly occupied by the long term repeat element YPRCdelta15. The sequence of the modified locus is provided as SEQ ID NO: 198. Then the native genes YMR226c and ALD6 were deleted. Elimination of YMR226c was a scarless deletion of only the coding region. The sequence of the modified locus is provided as SEQ ID NO: 199. The ALD6 coding region plus 700 bp of upstream sequence were deleted using CRE-lox mediated marker removal (methodology described above), so the resulting locus contains one loxP site. The sequence of the modified locus is provided as SEQ ID NO: 200. Finally, plasmids were introduced into the strain for expression of KARI (pLH702, SEQ ID NO: 201) and DHAD (pYZ067DkivDDhADH, SEQ ID NO: 202), resulting in strain PNY2242.

Where the recombinant microorganism produces isobutanol, under certain embodiments, microorganisms show higher specific productivity. Further, the volumetric rate was improved by about 50%.

While not wishing to be bound by theory, it is believed that the methods described herein provide extractive fermentation methods with improved production yields of product alcohol. As discussed above, alcohol production utilizing fermentation by microorganisms may be inefficient due to the alcohol toxicity thresholds of the microorganism. In some embodiments, the methods herein provide a means to convert the product alcohol into a substance less toxic to the microorganism. For example, the product alcohol may be contacted with carboxylic acid in the presence of a catalyst which esterifies the alcohol with the carboxylic acid and thereby, produces alcohol esters which are less toxic to the microorganism. In addition, the generation of alcohol esters from the product alcohol results in a lower concentration of the product alcohol in the fermentation medium. The reduced concentration of product alcohol minimizes the toxic effects of the product alcohol on the microorganism and thus, leads to improved production yields of product alcohol.

Carboxylic acid may serve as an extractant, and alcohol esters can partition into the extractant. However, the partition coefficient of the extractant may be degraded by lipid contamination. To reduce the degradation of the partition coefficient of the extractant, lipids present in the fermentation medium may be converted to extractant and consequently, minimize lipid contamination. In some embodiments, the methods herein provide a means to convert the lipids present in the feedstock or biomass into an extractant by catalytically hydrolyzing the lipids to carboxylic acid. The carboxylic acid produced by this hydrolysis may serve as an extractant or esterified with the product alcohol to form alcohol esters. Thus, the methods described herein provide a means to preserve the partition coefficient of the extractant (e.g., lipid hydrolysis) as well as minimize the toxic effects of the product alcohol (e.g., esterification of the product alcohol).

Carboxylic acid may be supplied to the fermentation vessel or derived by hydrolysis from lipids (e.g., biomass) supplied to the fermentation vessel. The amount of carboxylic acid should be sufficient to form a two-phase mixture comprising an organic phase and an aqueous phase. That is, carboxylic acid (i.e., extractant) in an appropriate concentration contacts the fermentation broth and forms the two-phase mixture. The alcohol esters formed in the fermentation broth will preferentially partition into the organic phase because these esters are formed at a concentration in excess of the equilibrium concentration of the aqueous phase. The alcohol ester-containing organic phase may be separated from the fermentation broth, the product alcohol may be recovered from organic phase, and the extractant may be recycled to the fermentation vessel.

Further, while various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the claims and their equivalents.

All publications, patents, and patent applications mentioned in this specification are indicative of the level of skill of those skilled in the art to which this invention pertains, and are herein incorporated by reference to the same extent as if each individual publication, patent, or patent application was specifically and individually indicated to be incorporated by reference.

EXAMPLES

The following nonlimiting examples will further illustrate the invention. It should be understood that, while the following examples involve corn as feedstock and COFA as carboxylic acid, other biomass sources can be used for feedstock and acids other than COFA can serve as carboxylic acid, without departing from the present invention. Moreover, while the following examples involve butanol and butyl ester production, other alcohols including ethanol, and alcohol esters can be produced without departing from the present invention.

As used herein, the meaning of abbreviations used was as follows: "g" means gram(s), "kg" means kilogram(s), "L" means liter(s), "mL" means milliliter(s), "µL" means microliter(s), "mL/L" means milliliter(s) per liter, "mL/min" means milliliter(s) per min, "DI" means deionized, "uM" means micrometer(s), "nm" means nanometer(s), "w/v" means weight/volume, "OD" means optical density, "$OD_{600}$" means optical density at a wavelength of 600 nM, "dcw" means dry cell weight, "rpm" means revolutions per minute, "° C." means degree(s) Celsius, "° C./min" means degrees Celsius per minute, "slpm" means standard liter(s) per minute, "ppm" means part per million, "pdc" means pyruvate decarboxylase enzyme followed by the enzyme number.

General Methods

Seed Flask Growth

A *Saccharomyces cerevisiae* strain that was engineered to produce isobutanol from a carbohydrate source, with pdc1 deleted, pdc5 deleted, and pdc6 deleted, was grown to 0.55-1.1 g/L dcw ($OD_{600}$ 1.3-2.6—Thermo Helios α Thermo Fisher Scientific Inc., Waltham, Mass.) in seed flasks from a frozen culture. The culture was grown at 23-26° C. in an incubator rotating at 300 rpm. The frozen culture was previously stored at −80° C. The composition of the first seed flask medium was:

3.0-5.0 g/L dextrose 3.0-3.5 g/L ethanol, anhydrous 3.7 g/L ForMedium™ Synthetic Complete Amino Acid (Kaiser) Drop-Out: without HIS, without URA (Reference # DSCK162CK)

6.7 g/L Difco Yeast Nitrogen Base without amino acids (No. 291920).

Eight to twelve milliliters from the first seed flask culture was transferred to a 2 L flask and grown at 30° C. in an incubator rotating at 300 rpm. The second seed flask has 220 mL of the following medium:

30.0 g/L dextrose 5.0 g/L ethanol, anhydrous 3.7 g/L ForMedium™ Synthetic Complete Amino Acid (Kaiser) Drop-Out: without HIS, without URA (Reference # DSCK162CK)

6.7 g/L Difco Yeast Nitrogen Base without amino acids (No. 291920)

0.2 M MES Buffer titrated to pH 5.5-6.0.

The culture was grown to 0.55-1.1 g/L dcw ($OD_{600}$ 1.3-2.6). An addition of 30 mL of a solution containing 200 g/L peptone and 100 g/L yeast extract was added at this cell concentration. Then, an addition of 250-300 mL of 0.2 uM filter sterilized HD OCENOL® 90/95 oleyl alcohol (Cognis, Monheim, Del.) was added to the flask. The culture continues to grow to >4 g/L dcw ($OD_{600}$>10) before being harvested and added to the fermentation.

Fermentation Preparation
Initial Fermentation Vessel Preparation

A glass jacked, 2 L fermentation vessel (Sartorius A G, Goettingen, Germany) was charged with house water to 66% of the liquefaction weight. A pH probe (Hamilton Easyferm Plus K8, part number: 238627, Hamilton Bonaduz A G, Bonaduz, Switzerland) was calibrated through the Sartorius DCU-3 Control Tower Calibration menu. The zero was calibrated at pH=7. The span was calibrated at pH=4. The probe was then placed into the fermentation vessel through the stainless steel head plate. A dissolved oxygen probe ($pO_2$ probe) was also placed into the fermentation vessel through the head plate. Tubing used for delivering nutrients, seed culture, extracting solvent, and base were attached to the head plate and the ends were foiled. The entire fermentation vessel was placed into a Steris (Steris Corporation, Mentor, Ohio) autoclave and sterilized in a liquid cycle for 30 minutes.

The fermentation vessel was removed from the autoclave and placed on a load cell. The jacket water supply and return line was connected to the house water and clean drain, respectively. The condenser cooling water in and water out lines were connected to a 6-L recirculating temperature bath running at 7° C. The vent line that transfers the gas from the fermentation vessel was connected to a transfer line that was connected to a Thermo mass spectrometer (Prima dB, Thermo Fisher Scientific Inc., Waltham, Mass.). The sparger line was connected to the gas supply line. The tubing for adding nutrients, extract solvent, seed culture, and base was plumbed through pumps or clamped closed.

The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 29-30% (dry corn solids weight) of the liquefaction reaction mass.

Lipase Treatment Pre-Liquefaction

A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the lipase treatment was complete, liquefaction was performed as described below (Liquefaction).

Liquefaction

An alpha-amylase was added to the fermentation vessel per its specification sheet while the fermentation vessel was mixing at 300-1200 rpm, with sterile, house $N_2$ being added at 0.3 slpm through the sparger. The temperature set-point was changed from 55° C. to 85° C. When the temperature was >80° C., the liquefaction cook time was started and the liquefaction cycle was held at >80° C. for 90-120 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

Lipase Treatment Post-Liquefaction

The fermentation vessel temperature was set to 55° C. instead of 30° C. after the liquefaction cycle was complete (Liquefaction). The pH was manually controlled at pH=5.8 by making bolus additions of acid or base when needed. A lipase enzyme stock solution was added to the fermentation vessel to a final lipase concentration of 10 ppm. The fermentation vessel was held at 55° C., 300 rpm, and 0.3 slpm $N_2$ overlay for >6 hrs. After the Lipase Treatment was complete, the fermentation vessel temperature was set to 30° C.

Lipase Heat Inactivation Treatment (Heat Kill Treatment Method)

The fermentation vessel temperature was held at >80° C. for >15 minutes to inactivate the lipase. After the Heat Inactivation Treatment was complete, the fermentation vessel temperature was set to 30° C.

Nutrient Addition Prior to Inoculation

Ethanol (7 mL/L, post-inoculation volume, 200 proof, anhydrous) was added to the fermentation vessel just prior to inoculation. Thiamine was added to a final concentration of 20 mg/L and 100 mg/L nicotinic acid was also added just prior to inoculation.

Oleyl Alcohol or Corn Oil Fatty Acids Addition Prior to Inoculation

Added 1 L/L (post-inoculation volume) of oleyl alcohol or corn oil fatty acids immediately after inoculation.

Fermentation Operation
Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated after the second seed flask with >4 g/L dcw. The shake flask was removed from the incubator/shaker for 5 minutes allowing a phase separation of the oleyl alcohol phase and the aqueous phase. The aqueous phase (110 mL) was transferred to a sterile, inoculation bottle. The inoculum was pumped into the fermentation vessel through a peristaltic pump.

Fermentation Vessel Operating Conditions

The fermentation vessel was operated at 30° C. for the entire growth and production stages. The pH was allowed to drop from a pH between 5.7-5.9 to a control set-point of 5.2 without adding any acid. The pH was controlled for the remainder of the growth and production stage at a pH=5.2 with ammonium hydroxide. Sterile air was added to the fermentation vessel, through the sparger, at 0.3 slpm for the remainder of the growth and production stages. The $pO_2$ was set to be controlled at 3.0% by the Sartorius DCU-3 Control Box PID control loop, using stir control only, with the stirrer minimum being set to 300 rpm and the maximum being set to 2000 rpm. The glucose was supplied through simultaneous saccharification and fermentation of the liquified corn mash by adding a α-amylase (glucoamylase). The glucose was kept excess (1-50 g/L) for as long as starch was available for saccharification.

Analytical
Gas Analysis

Process air was analyzed on a Thermo Prima (Thermo Fisher Scientific Inc., Waltham, Mass.) mass spectrometer. This was the same process air that was sterilized and then added to each fermentation vessel. Each fermentation vessel's off-gas was analyzed on the same mass spectrometer. This Thermo Prima dB has a calibration check run every Monday morning at 6:00 am. The calibration check was scheduled through the Gas Works v1.0 (Thermo Fisher Scientific Inc., Waltham, Mass.) software associated with the mass spectrometer. The gas calibrated for were:

| GAS | Calibration Concentration mole % | Cal Frequency |
|---|---|---|
| Nitrogen | 78% | weekly |
| Oxygen | 21% | weekly |
| Isobutanol | 0.2% | yearly |

| GAS | Calibration Concentration mole % | Cal Frequency |
|---|---|---|
| Argon | 1% | weekly |
| Carbon Dioxide | 0.03% | weekly |

Carbon dioxide was checked at 5% and 15% during calibration cycle with other known bottled gases. Oxygen was checked at 15% with other known bottled gases. Based on the analysis of the off-gas of each fermentation vessel, the amount of isobutanol stripped, oxygen consumed, and carbon dioxide respired into the off-gas was measured by using the mass spectrometer's mole fraction analysis and gas flow rates (mass flow controller) into the fermentation vessel. Calculate the gassing rate per hour and then integrating that rate over the course of the fermentation.

Cell Mass Measurement

A 0.08% Trypan Blue solution was prepared from a 1:5 dilution of 0.4% Trypan Blue in NaCl (VWR BDH8721-0) with 1×PBS. A 1.0 mL sample was pulled from a fermentation vessel and placed in a 1.5 mL Eppendorf centrifuge tube and centrifuged in an Eppendorf, 5415C at 14,000 rpm for 5 minutes. After centrifugation, the top solvent layer was removed with an m200 Variable Channel BioHit pipette with 20-200 µL BioHit pipette tips. Care was made not to remove the layer between the solvent and aqueous layers. Once the solvent layer was removed, the sample was re-suspended using a Vortex-Genie® set at 2700 rpm.

A series of dilutions was required to prepare the ideal concentration for hemacytometer counts. If the OD was 10, a 1:20 dilution would be performed to achieve 0.5 OD which would give the ideal amount of cells to be counted per square, 20-30. In order to reduce inaccuracy in the dilution due to corn solids, multiple dilutions with cut 100-1000 µL BioHit pipette tips were required. Approximately, 1 cm was cut off the tips to increase the opening which prevented the tip from clogging. For a 1:20 final dilution, an initial 1:1 dilution of fermentation sample and 0.9% NaCl solution was prepared. Then, a 1:1 dilution of the previous solution (i.e., the initial 1:1 dilution) and 0.9% NaCl solution (the second dilution) was generated followed by a 1:5 dilution of the second dilution and Trypan Blue Solution. Samples were vortexed between each dilution and cut tips were rinsed into the 0.9% NaCl and Trypan Blue solutions.

The cover slip was carefully placed on top of the hemacytometer (Hausser Scientific Bright-Line 1492). An aliquot (10 µL) was drawn of the final Trypan Blue dilution with an m20 Variable Channel BioHit pipette with 2-20 µL BioHit pipette tips and injected into the hemacytometer. The hemacytometer was placed on the Zeis Axioskop 40 microscope at 40× magnification. The center quadrant was broken into 25 squares and the four corner and center squares in both chambers were then counted and recorded. After both chambers were counted, the average was taken and multiplied by the dilution factor (20), then by 25 for the number for squares in the quadrant in the hemacytometer, and then divided by 0.0001 mL which is the volume of the quadrant that was counted. The sum of this calculation is the number cells per mL.

LC Analysis of Fermentation Products in the Aqueous Phase

Samples were refrigerated until ready for processing. Samples were removed from refrigeration and allowed to reach room temperature (about one hour). Approximately 300 µL of sample was transferred with a m1000 Variable Channel BioHit pipette with 100-1000 µL BioHit pipette tips into a 0.2 um centrifuge filter (Nanosep® MF modified nylon centrifuge filter), then centrifuged using a Eppendorf, 5415C for five minutes at 14,000 rpm. Approximately 200 µL of filtered sample was transferred into a 1.8 auto sampler vial with a 250 µL glass vial insert with polymer feet. A screw cap with PTFE septa was used to cap the vial before vortexing the sample with a Vortex-Genie® set at 2700 rpm.

Sample was then run on Agilent 1200 series LC equipped with binary, isocratic pumps, vacuum degasser, heated column compartment, sampler cooling system, UV DAD detector and RI detector. The column used was an Aminex HPX-87H, 300×7.8 with a Bio-Rad Cation H refill, 30×4.6 guard column. Column temperature was 40° C., with a mobile phase of 0.01 N sulfuric acid at a flow rate of 0.6 mL/min for 40 minutes. Results are shown in Table 1.

TABLE 1

Retention times of fermentation products in aqueous phase

| HPLC 302/310 Normalized to 10 µL injections | FW | RID Retention Time, min | Range of Standards, g/L | UV Retention Time, min |
|---|---|---|---|---|
| citric acid | 192.12 | 8.025 | 0.3-17 | 7.616 |
| glucose | 180.16 | 8.83 | 0.5-71 | |
| pyruvic acid (Na) | 110.04 | 9.388 | 0.1-5.2 | 8.5 |
| A-Kiv (Na) | 138.1 | 9.91 | 0.07-5.0 | 8.55 |
| 2,3-dihydroxyisovaleric acid (Na) | 156.1 | 10.972 | 0.2-8.8 | 10.529 |
| succinic acid | 118.09 | 11.561 | 0.3-16 | 11.216 |
| lactic acid (Li) | 96.01 | 12.343 | 0.3-17 | 11.948 |
| glycerol | 92.09 | 12.974 | 0.8-39 | |
| formic acid | 46.03 | 13.686 | 0.2-13 | 13.232 |
| acetate (Na) | 82.03 | 14.914 | 0.5-16 | 14.563 |
| meso-butanediol | 90.12 | 17.583 | 0.1-19 | |
| (+/−)-2,3-butanediol | 90.12 | 18.4 | 0.2-19 | |
| isobutyric acid | 88.11 | 19.685 | 0.1-8.0 | 19.277 |
| ethanol | 46.07 | 21.401 | 0.5-34 | |
| isobutyraldehyde | 72.11 | 27.64 | 0.01-0.11 | |
| isobutanol | 74.12 | 32.276 | 0.2-15 | |
| 3-OH-2-butanone (acetoin) | 88.11 | | 0.1-11 | 17.151 |

GC Analysis of Fermentation Products in the Solvent Phase

Samples were refrigerated until ready for processing. Samples were removed from refrigeration and allowed to reach room temperature (about one hour). Approximately 150 µL of sample was transferred using a m1000 Variable Channel BioHit pipette with 100-1000 µL BioHit pipette tips into a 1.8 auto sampler vial with a 250 µL glass vial insert with polymer feet. A screw cap with PTFE septa was used to cap the vial.

Sample was then run on Agilent 7890A GC with a 7683B injector and a G2614A auto sampler. The column was a HP-InnoWax column (30 m×0.32 mm ID, 0.25 µm film). The carrier gas was helium at a flow rate of 1.5 mL/min measured at 45° C. with constant head pressure; injector split was 1:50 at 225° C.; oven temperature was 45° C. for 1.5 minutes, 45° C. to 160° C. at 10° C./min for 0 minutes, then 230° C. at 35° C./min for 14 minutes for a run time of 29 minutes. Flame ionization detection was used at 260° C. with 40 mL/min helium makeup gas. Results are shown in Table 2.

TABLE 2

| Retention times of fermentation products in solvent phase | | | |
|---|---|---|---|
| GC 302/310 Normalized to 10 μL injections | FW | Solvent Retention Time, min | Range of Standards, g/L |
| isobutyraldehyde | 72.11 | 2.75 | 0.7-10.4 |
| ethanol | 46.07 | 3.62 | 0.5-34 |
| isobutanol | 74.12 | 5.53 | 0.2-16 |
| 3-OH-2-butanone (acetoin) | 88.11 | 8.29 | 0.1-11 |
| (+/−)-2,3-butanediol | 90.12 | 10.94 | 0.1-19 |
| isobutyric acid | 88.11 | 11.907 | 0.1-7.9 |
| meso-butanediol | 90.12 | 11.26 | 0.1-6.5 |
| glycerol | 92.09 | 16.99 | 0.8-9 |

Samples analyzed for fatty acid butyl esters were run on Agilent 6890 GC with a 7683B injector and a G2614A auto sampler. The column was a HP-DB-FFAP column (15 meters×0.53 mm ID (Megabore), 1-micron film thickness column (30 m×0.32 mm ID, 0.25 μm film). The carrier gas was helium at a flow rate of 3.7 mL/min measured at 45° C. with constant head pressure; injector split was 1:50 at 225° C.; oven temperature was 100° C. for 2.0 minutes, 100° C. to 250° C. at 10° C./min, then 250° C. for 9 minutes for a run time of 26 minutes. Flame ionization detection was used at 300° C. with 40 mL/min helium makeup gas. The following GC standards (Nu-Chek Prep; Elysian, Minn.) were used to confirm the identity of fatty acid isobutyl ester products: iso-butyl palmitate, iso-butyl stearate, iso-butyl oleate, iso-butyl linoleate, iso-butyl linolenate, iso-butyl arachidate.

Examples 1-14 describe various fermentation conditions that may be used for the claimed methods. As an example, some fermentations were subjected to Lipase Treatment pre-liquefaction and others were subjected to Lipase Treatment post-liquefaction. In other examples, the fermentation was subjected to Heat inactivation Treatment. Following fermentation, the effective isobutanol titer (Eff Iso Titer) was measured, that is, the total grams of isobutanol produced per liter aqueous volume. Results are shown in Table 3.

Example 1

Control

Experiment identifier 2010Y014 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 2

Experiment identifier 2010Y015 included: Seed Flask Growth method, Initial Fermentation Vessel Preparation method, Liquefaction method, Lipase Treatment Post-Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 3

Experiment identifier 2010Y016 included: Seed Flask Growth method, Initial Fermentation Vessel Preparation method, Liquefaction method, Lipase Treatment Post-Liquefaction method, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 4

Experiment identifier 2010Y017 included: Seed Flask Growth method, Initial Fermentation Vessel Preparation method, Liquefaction method, Heat Kill Treatment method Post-Liquefaction, Nutrient Addition Prior to Inoculation method with the exception of the exclusion of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 5

Experiment identifier 2010Y018 included: Seed Flask Growth method, Initial Fermentation Vessel Preparation method, Liquefaction method, Lipase Treatment Post-Liquefaction method with the exception of only adding 7.2 ppm lipase after liquefaction, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 6

Control

Experiment identifier 2010Y019 included: Seed Flask Growth method, Initial Fermentation Vessel Preparation method, Liquefaction method, Heat Kill Treatment method Post-Liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 7

Control

Experiment identifier 2010Y021 included: Seed Flask Growth method, Initial Fermentation Vessel Preparation method, Lipase Treatment Pre-Liquefaction method, Liquefaction method, the Heat Kill Treatment during liquefaction, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 8

Experiment identifier 2010Y022 included: Seed Flask Growth method, Initial Fermentation Vessel Preparation method, Liquefaction method, Nutrient Addition Prior to Inoculation method, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 9

Experiment identifier 2010Y023 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 10

Experiment identifier 2010Y024 included: Seed Flask Growth method, Initial Fermentation Vessel Preparation method, Lipase Treatment Pre-Liquefaction method, Liquefaction method, Heat Kill Treatment during liquefaction, the Nutrient Addition Prior to Inoculation method with the exception of there being no addition of ethanol, Fermentation Vessel Inoculation method, Fermentation Vessel Operating Conditions method, and all of the Analytical methods. Oleyl alcohol was added in a single batch between 0.1-1.0 hr after inoculation. The butanologen was NGCI-070.

Example 11

Experiment identifier 2010Y029 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 12

Experiment identifier 2010Y030 included: Seed Flask Growth method, Initial Fermentation Vessel Preparation method, Lipase Treatment Pre-Liquefaction method, Liquefaction method, Heat Kill Treatment during liquefaction, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 13

Control

Experiment identifier 2010Y031 included: Seed Flask Growth method, Initial Fermentation Vessel Preparation method, Liquefaction method, Lipase Treatment Post Liquefaction method, no Heat Kill Treatment, Nutrient Addition Prior to Inoculation method with the exception of there being no addition of ethanol, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

Example 14

Experiment identifier 2010Y032 included: Seed Flask Growth method, Initial Fermentation Vessel Preparation method, Liquefaction method, Lipase Treatment Post-Liquefaction method, no Heat Kill Treatment, Nutrient Addition Prior to Inoculation method, Fermentation Vessel Inoculation method, Fermentation Vessel Operating Conditions method, and all of the Analytical methods. Corn oil fatty acids made from crude corn oil was added in a single batch between 0.1-1.0 hr after inoculation. The butanologen was NGCI-070.

TABLE 3

Fermentation conditions for Examples 1-14

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 1 | 2010Y014 | none | 27.2 | 5 | Oleyl alcohol | none | 56.0 | 0.79 |
| 2 | 2010Y015 | 10 ppm | 31.5 | 5 | Oleyl alcohol | none | 52.4 | 0.74 |
| 3 | 2010Y016 | 10 ppm | 6.7 | 0 | Oleyl alcohol | none | 25.9 | 0.36 |
| 4 | 2010Y017 | none | 7.9 | 0 | Oleyl alcohol | post-liquefaction | 17.2 | 0.25 |
| 5 | 2010Y018 | 7.2 ppm | 16.2 | 5 | Oleyl alcohol | post-liquefaction | 45.8 | 0.66 |
| 6 | 2010Y019 | none | 17.5 | 5 | Oleyl alcohol | post-liquefaction | 48.1 | 0.69 |
| 7 | 2010Y021 | 10 ppm | 21.2 | 5 | Oleyl alcohol | during liquefaction | 46.8 | 0.82 |
| 8 | 2010Y022 | none | 9 | 5 | Oleyl alcohol | during liquefaction | 56.2 | 0.87 |
| 9 | 2010Y023 | 10 ppm | 12.8 | 5 | Corn Oil Fatty Acids | none | 60.3 | 1.3 |
| 10 | 2010Y024 | 10 ppm | 25.3 | 0 | Oleyl alcohol | during liquefaction | 19.8 | 0.33 |

TABLE 3-continued

Fermentation conditions for Examples 1-14

| Example # | Experimental Identifier | Lipase | Max cell Count × $10^7$ | Ethanol g/L | Solvent | Heat Kill Lipase | Eff Iso Titer g/L* | max Eff Iso rate g/L/h |
|---|---|---|---|---|---|---|---|---|
| 11 | 2010Y029 | 10 ppm | 21.2 | 5 | Corn Oil Fatty Acids | during liquefaction | 28.36 | 0.52 |
| 12 | 2010Y030 | 10 ppm | 9 | 0 | Corn Oil Fatty Acids | during liquefaction | 12.71 | 0.24 |
| 13 | 2010Y031 | 10 ppm | 12.8 | 0 | Corn Oil Fatty Acids | none | 18.86 | 0.35 |
| 14 | 2010Y032 | 10 ppm | 25.3 | 5 | Corn Oil Fatty Acids | none | 53.36 | 0.92 |

*The "Eff Iso Titer g/L" = total grams of isobutanol produced per liter aqueous volume Examples 15 and 16 represent a comparison of fermentation and isobutanol production in the presence and absence of post-liquefaction lipase treatment. Results are shown in Tables 4 and 5.

Example 15

Experiment identifier 2010Y026 included: Seed Flask Growth method, Initial Fermentation vessel Preparation method, the Liquefaction method, the Lipase Treatment Post-Liquefaction method, the Nutrient Addition Prior to Inoculation method, Fermentation vessel Inoculation method, Fermentation vessel Operating Conditions method, and all of the Analytical methods. Corn oil fatty acids made from crude corn oil was added in a single batch between 0.1-1.0 hr after inoculation. The corn oil fatty acids extracting solvent was added in equal volume to the broth volume. The butanologen was PNY2205. Between 46 hrs and 61 hrs fermentation time, the addition of 274 g of a 50% w/w sterile, glucose solution was made because the glucose made from corn mash had been all but depleted.

Example 16

Experiment identifier 2010Y027 included: Seed Flask Growth method, Initial Fermentation vessel Preparation method, the Liquefaction method, the Nutrient Addition Prior to Inoculation method, Fermentation vessel Inoculation method, Fermentation vessel Operating Conditions method, and all of the Analytical methods. HD OCENOL® 90/95 (oleyl alcohol, CAS No. 143-28-2, Cognis, Monheim, Del.) was added in a single batch between 0.1-1.0 hr after inoculation. The oleyl alcohol extracting solvent was added in equal volume to the broth volume. The butanologen was PNY2205.

TABLE 4

| Experimental ID | Lipase Addition | Extracting Solvent | Glucose Consumed (g) | Biomass produced (cfu/mL) |
|---|---|---|---|---|
| 2010Y026 | Yes | corn oil fatty acids | 326.3 | 34.2 × $10^7$ |
| 2010Y027 | No | oleyl alcohol | 234.9 | 33.0 × $10^7$ |

TABLE 5

| Exp. ID | Lipase Addition | Maximum residual i-BuOH in aqueous (g/L) | Effective i-BuOH titer (g/L) | Maximum effective i-BuOH production rate g/L/hr (aqueous volume) | Yield g i-BuOH/ g glucose |
|---|---|---|---|---|---|
| 2010Y026 | Yes | 4.7 | 72.2 | 1.41 | 0.26 |
| 2010Y026 | No | 10.0 | 55.4 | 1.19 | 0.25 |

Examples 17 to 22 represent a comparison of the effect of fresh extractant versus recycled extractant on fermentation and isobutanol production. Results are shown in Table 6. For these examples, 2 L and 10 L fermentations were prepared as described below.

10 L Pre-Seed Flask Growth

A *Saccharomyces cerevisiae* strain (strain PNY2242 described above) that was engineered to produce isobutanol from a carbohydrate source, with pdc1 deleted, pdc5 deleted, and pdc6, deleted was grown to 0.6-0.7 g/L dcw ($OD_{600}$ 1.5-2.5—Thermo Helios α Thermo Fisher Scientific Inc., Waltham, Mass.) in seed flasks (10 mL synthetic medium in a 125 mL, vented flask) from a frozen culture. The culture was grown at 29-31° C. in an incubator rotating at 260 rpm. The frozen culture was previously stored at −80° C. The composition synthetic seed flask medium was:
- 10.0 g/L dextrose
- 3.5 mL/L ethanol, anhydrous
- 3.7 g/L ForMedium™ Synthetic Complete Amino Acid (Kaiser) Drop-Out: without HIS, without URA (Reference No. DSCK162CK)
- 6.7 g/L Difco Yeast Nitrogen Base without amino acids (No. 291920)
- 1% Ergersterol in 1:1::Tween 80:Ethanol Two milliliters from the first seed flask culture was transferred to 25 mL in a 250 mL, vented flask and grown at 29-31° C. in an incubator rotating at 260 rpm. The second seed flask uses the same synthetic medium as used above.

The culture was grown to 0.6-0.7 g/L dcw ($OD_{600}$ 1.0-3.0). Then, 8 mL of this second flask culture was added to three flasks (2 L, vented, baffled flasks) with 200 mL of synthetic medium. The culture was grown in an incubator at 29-31° C. for 18-24 hrs. The three seed flasks use the same synthetic medium as used in the first two seed flasks. These three flasks (600 mL of flask broth) are used to inoculate the propagation tank at a final aqueous volume of 6 L.

10 L Propagation Tank Liquefaction

A 10 L, B. Braun BioStat C fermentor was prepared for use. An inline pH probe was placed in the fermentor. The zero was calibrated at pH=7. The span was calibrated at pH=4. The probe was then placed into the fermentation vessel, through a side port. A dissolved oxygen probe ($pO_2$ probe) was also placed into the fermentor through a side port. Tubing used for delivering nutrients, seed culture, extracting solvent, and base were attached to the head plate and the ends were foiled. The valve for harvesting and sampling were sterilized with low pressure steam and a steam trap at >121° C. for >20 minutes.

The fermentation vessel temperature was controlled at 30° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 10-20% (dry corn solids weight) of the liquefaction reaction mass. Difco Yeast Extract was added to the fermentor at 0.5% w/w of the total batch weight.

An alpha-amylase was added to the fermentation vessel per its specification sheet while the fermentation vessel was mixing at 300-1500 rpm, with sterile, house $N_2$ being added at 1-2 slpm through the sparger. The temperature set-point was changed from 55° C. to 95° C. in 5° C. step changes with a 5-15 minute hold at each step to ensure good mixing. When the temperature was >90° C., the liquefaction cook time was started and the liquefaction cycle was held at >90° C. for 60 minutes. The fermentation vessel temperature set-point was set to the fermentation temperature of 30° C. after the liquefaction cycle was complete. $N_2$ was redirected from the sparger to the head space to prevent foaming without the addition of a chemical antifoaming agent.

10 L Propagation Tank Operation

The fermentation vessels $pO_2$ probe was calibrated to zero while $N_2$ was being added to the fermentation vessel. The fermentation vessels $pO_2$ probe was calibrated to its span with sterile air sparging at 400 rpm. The fermentation vessel was inoculated from the final stage of the Pre-Seed Flask Growth step. The three shake flasks were removed from the incubator/shaker and added to a sterile vessel. The content of the sterile vessel was added to 5.3-5.5 L of the liquefied mash that was made during the Propagation Tank Liquefaction method.

The fermentation temperature was controlled between 29-31° C. The agitation speed was fixed at 400 rpm. Air was sparged for the entire fermentation at 2.0 slpm. The pH was controlled at 5.4-5.5 by using $NH_4OH$ and the PID control loop for the fermentor. There was 0.3-0.5 bar of back pressure set on the fermentor, controlled by a PID loop that controlled a back pressure control valve.

At 16-20 hrs after inoculation, a glucoamylase (1.8 mL of Distillase® L-400, Genencor, Palo Alto, Calif.) was added to start simultaneous saccharification and fermentation, releasing glucose from the dissolved starch. Also, 5.5 L of HD OCENOL® 90/95 (oleyl alcohol, Cognis, Monheim, Del.) was added to the fermentor. At 34-36 hrs, the agitator speed was reduced to 100 rpm. After 10 minutes, the agitator was turned off and the airflow to the fermentor was changed from sparge mode to overlay mode.

10 L Production Tank Liquefaction

A 10 L Production Tank Liquefaction was performed as described above. The fermentation vessel temperature was controlled at 30° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 25-35% (dry corn solids weight) of the liquefaction reaction mass. A 75 mL addition of a 100× Vitamin Solution (2 g/L thiamine and 10 g/L nicotinic acid) was made to the fermentor. An alpha-amylase was added to the fermentation vessel was added as described above. Also, an addition of 6-7 mL/L anhydrous ethanol was made to the fermentor after the fermentor was returned to 30° C.

10 L Production Tank Operation

The fermentation vessels $pO_2$ probe was calibrated to zero while $N_2$ was being added to the fermentation vessel. The fermentation vessels $pO_2$ probe was calibrated to its span with sterile air sparging at 400 rpm. The fermentation vessel was inoculated from Propagation Tank. An aseptic transfer was made from the Propagation Tank after 36 hrs of growth time in the propagation tank and the fermentation agitation was turned off for >10 minutes. This allowed for significant separation of the oleyl alcohol and the aqueous phase. The aseptic transfer was made from the harvest valve on the Propagation Tank, which is located at the bottom of this fermentor. Approximately 10% v/v was added to the Production Tank, based on the tanks final non-solvent volume after transfer.

The fermentation temperature was controlled between 29-31° C. The agitation speed was fixed at 400 rpm. Air was sparged for the entire fermentation at 2.0 slpm. The pH was controlled at 5.2-5.3 by using $NH_4OH$ and the PID control loop for the fermentor. There was 0.3-0.5 bar of back pressure set on the fermentor, controlled by a PID loop that controlled a back pressure control valve.

Just prior to inoculation, 25-35% v/v Cognis Emery® 610 SOYA Fatty Acid was aseptically added to the fermentor. The fermentor was inoculated with 10% v/v fermentation broth after the completion of the 10 L Propagation Tank Operation method. Just after inoculation, a glucoamylase (Distillase® L-400) was added to release glucose from the starch. Additional glucoamylase additions were made when needed to maintain the glucose excess. Just after inoculation, a lipase (Novozymes Lipolase® 100L) was added to the fermentor at 4-15 ppm.

2 L Pre-Seed Flask Growth

A 2 L pre-seed flask growth was prepared using a *Saccharomyces cerevisiae* strain (strain PNY2242 described above) and was grown to 0.6-0.7 g/L dcw ($OD_{600}$ 1.5-2.5—Thermo Helios α Thermo Fisher Scientific Inc., Waltham, Mass.) in seed flasks (10 mL synthetic medium in a 125 mL, vented flask) from a frozen culture. The culture was grown at 29-31° C. in an incubator rotating at 260 rpm. The frozen culture was previously stored at −80° C. The composition synthetic seed flask medium was:

- 10.0 g/L dextrose
- 3.5 mL/L ethanol, anhydrous
- 3.7 g/L ForMedium Synthetic Complete Amino Acid (Kaiser) Drop-Out: without HIS, without URA (Reference No. DSCK162CK)
- 6.7 g/L Difco Yeast Nitrogen Base without amino acids (No. 291920)
- 1% Ergersterol in 1:1::Tween 80:Ethanol.

Two milliliters from the first seed flask culture was transferred to 25 mL in a 250 mL, vented flask and grown at 29-31° C. in an incubator rotating at 260 rpm. The second seed flask uses the same synthetic medium as used above.

The culture was grown to 0.6-0.7 g/L dcw ($OD_{600}$ 1.0-3.0). Then 4 mL of this second flask culture was added to 100 mL of corn mash centrate in a 2 L flask. The culture was grown in an incubator at 29-31° C. for 18-24 hrs. Then 500 mL of HD OCENOL® 90/95 (oleyl alcohol, Cognis, Monheim, Del.) was added to the flask. The flask was allowed to grow for 6-8 hrs. Then 2 mL of a 1.2 g Distillase® L-400, (Genencor, Palo Alto, Calif.) in 80 mL of deionized water was added to the centrate to release glucose from the dissolved starch in the centrate. The culture continued to grow for 18-24 hrs. The final biomass concentration was 6-12 g/L dcw.

The corn mash centrate was made by liquefying corn in the following recipe:

1150 g tap water
340.5 g 1 mm screened ground corn
13.5 g yeast extract (Difco No. 9102333, low dusting)
27 g peptone
4.1 g urea
40.5 mg nicotinic acid
40.5 mg thiamine.

Then the material was centrifuged for 30 minutes in a Sorval RC5C centrifuge. The supernatant was separated from the solids pellet. The supernatant was heated in a Steris autoclave for a 5 minute liquid cycle and is defined as centrate.

2 L Fermentation Preparation
2 L Initial Fermentation Vessel Preparation

A 2 L Initial Fermentation Vessel Preparation was prepared as described above. The fermentation vessel temperature was controlled at 55° C. with a thermocouple and house water circulation loop. Wet corn kernels (#2 yellow dent) were ground using a hammer mill with a 1.0 mm screen, and the resulting ground whole corn kernels were then added to the fermentation vessel at a charge that was 25-30% (dry corn solids weight) of the liquefaction reaction mass. In addition, Liquefaction was conducted as described above. An alpha-amylase was added to the fermentation vessel per its specification sheet while the fermentation vessel was mixing at 300-1200 rpm, with sterile, house $N_2$ being added at 0.3 slpm through the sparger.

2 L Additions Prior to Inoculation

The following nutrients were added to the fermentation vessel prior to inoculation, after liquefaction, on a post-inoculation volume basis:

30 mg/L of nicotinic acid
30 mg/L of thiamine
1 mL/L of a 1% ergersterol w/v solution in 1:1:Tween 80:Ethanol
6.3 mL/L ethanol
2 g/L urea.

2 L Fermentation Vessel Inoculation

The fermentation vessels $pO_2$ probe was calibrated to zero while $N_2$ was being added to the fermentation vessel. The fermentation vessels $pO_2$ probe was calibrated to its span with sterile air sparging at 300 rpm. The fermentation vessel was inoculated from the final stage of the Pre-Seed Flask Growth step. The shake flask was removed from the incubator/shaker and centrifuged for 30 minutes. The liquid (oleyl alcohol and aqueous supernatant) was discarded and the cell pellet was re-suspended in the Pre-Seed Flask Growth medium (synthetic medium). The 100 mL of the aqueous phase was transferred to a sterile inoculation bottle. The inoculum was pumped into the fermentation vessel through a peristaltic pump.

2 L Lipase Addition After Inoculation

A Lipolase® solution (100 L stock solution) was prepared to an enzyme concentration of 1.2-1.4 mg/mL. The solution was added to the fermentation after inoculating the fermentor to the desired part per million concentration based on the non-solvent volume. The addition time occurred <1 hr after inoculating the fermentor.

2 L Soy Bean Oil Fatty Acid Addition

To the fermentation vessel was added 0.1-0.5 L/L (post-inoculation volume) of either virgin Cognis Emery® 610 SOYA Fatty Acid or recycled Cognis Emery® 610 SOYA Fatty Acids that contains 0-30 weight percent fatty acid butyl ester.

2 L Fermentation Vessel Operating Conditions

The fermentation vessel was operated at 30° C. for the entire growth and production stages. The pH was allowed to drop from a pH between 5.7-5.9 to a control set-point of 5.25 without adding any acid. The pH was controlled for the remainder of the growth and production stage at a pH=5.2 with ammonium hydroxide. Sterile air was added to the fermentation vessel, through the sparger, at 0.2-0.3 slpm for the remainder of the growth and production stages. The $pO_2$ was not controlled. The agitator was set to a fixed rpm at 300 rpm. The stir shaft had two Rushton impellers below the aqueous level and one pitched blade impeller above the aqueous level. The glucose was supplied through simultaneous saccharification and fermentation of the liquified corn mash by adding a glucoamylase. The glucose was kept excess (1-50 g/L) for as long as starch was available for saccharification.

A 5-20 mL sample was pulled from a fermentation vessel and placed in a centrifuge tube and centrifuged for cell mass measurement using the procedure described above. In addition, Analytical methods such as gas analyses as well as LC analyses of fermentation products in the aqueous phase and GC analyses of fermentation products in the solvent phase were conducted as described above.

The fermentation conditions for Examples 17 to 22 are provided below and a summary of the results (virgin soy bean oil fatty acids and recycled soy bean fatty acids with fatty acid butyl esters) are shown in Table 6.

Example 17

Experimental Identifier GLNOR1050 included: 10 L Pre-Seed Flask Growth, 10 L Propagation Tank Liquefaction, 10 L Propagation Tank Operation, 10 L Production Tank Liquefaction, 10 L Production Tank Operation with 10 ppm Lipolase® 100L (Genencor) added to the fermentor, extractant: Virgin Cognis Emery® 610 SOYA Fatty Acid (virgin soy bean oil fatty acid). The liquid solvent and non-solvent material was separated in a Sorval RC-12 centrifuge, and all Analytical methods.

Example 18

Experimental Identifier GLNOR1051 included: 10 L Pre-Seed Flask Growth, 10 L Propagation Tank Liquefaction, 10 L Propagation Tank Operation, 10 L Production Tank Liquefaction, 10 L Production Tank Operation with 4 ppm Lipolase® 100L (Genencor) added to the fermentor, extractant: Virgin Cognis Emery® 610 SOYA Fatty Acid (virgin soy bean oil fatty acid). The liquid solvent and non-solvent material was separated in a Sorval RC-12 centrifuge, and all Analytical methods.

Example 19

Identifier 2011Y029 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, 2 L Recycled Soy Bean Oil Fatty Acid Addition (Recycled Cognis Emery® 610 SOYA Fatty Acid and fatty acid butyl ester from Example 56A—50% v/v solvent load), 2 L Fermentation Vessel Operating Conditions, and all Analytical methods.

Example 20

Identifier 2011Y030 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, added 0.4 L/L (post-inoculation volume) Virgin Cognis Emery® 610 SOYA Fatty Acids that included 20-30% fatty acid butyl esters, 2 L Fermentation Vessel Operating Conditions, and all Analytical methods.

Example 21

Identifier 2011Y031 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, 2 L Recycled Soy Bean Oil Fatty Acid Addition (Recycled Cognis Emery® 610 SOYA Fatty Acid and fatty acid butyl ester from Example 56B—10% v/v solvent load), 2 L Fermentation Vessel Operating Conditions, and all Analytical methods.

Example 22

Identifier 2011Y032 included: 2 L Pre-Seed Flask Growth, 2 L Fermentation Preparation, 2 L Liquefaction, 2 L Additions Prior to Inoculation, 2 L Fermentation Vessel Inoculation, 2 L Lipase Addition After Inoculation at a final concentration of 10 ppm, added 0.4 L/L (post-inoculation volume) Virgin Cognis Emery® 610 SOYA Fatty Acids, 2 L Fermentation Vessel Operating Conditions, and all Analytical methods.

and a trace element solution, 1 mL/L, which contains in 1 L water, 15 g EDTA, 4.5 g zinc sulfate heptahydrate, 0.8 g manganese chloride dehydrate, 0.3 g cobalt chloride hexahydrate, 0.3 g copper sulfate pentahydrate, 0.4 g disodium molybdenum dehydrate, 4.5 g calcium chloride dihydrate, 3 g iron sulfate heptahydrate, 1 g boric acid, 0.1 g potassium iodide. The pH was adjusted to 5.5, and then the medium filter sterilized through an 0.22µ sterile filter apparatus.

Preparation of the 10 L Fermentor for Biomass Production

A single vial of the isobutanologen PNY2205 was aseptically transferred to 15 mL seed medium in a 125 mL vented flask for over night growth at 30° C. and 260 rpm shaking. The culture was aseptically transferred to 500 mL of the same medium in a 2 L baffled, vented flask for over night growth at 30° C. and 260 rpm shaking, and transferred to a prepared 10 L Sartorius C fermentor (Sartorius AG, Goettingen, Germany) when the culture reached $OD_{600}$ 7.

A 10 L Sartorius C fermentor was prepared with 6 L initial volume of growth medium. The growth medium composition and preparation was as follows: prior to sterilization, ammonium sulfate, 1 g/L; potassium phosphate monobasic, 5 g/L; magnesium sulfate, heptahydrate, 2 g/L; yeast extract (Amberex™ 695), 2 g/L; Antifoam Sigma 204, 0.5 mL/L; biotin, 100 µg/L; and 1 mL/L trace element solution (prepared in 1 L water: 15 g EDTA, 4.5 g zinc sulfate heptahydrate, 0.8 g manganese chloride dehydrate, 0.3 g cobalt chloride hexahydrate, 0.3 g copper sulfate pentahydrate, 0.4 g disodium molybdenum dehydrate, 4.5 g calcium chloride dihydrate, 3 g iron sulfate heptahydrate, 1 g boric acid, 0.1 g potassium iodide). After steam sterilization at 121° C. in place, the vessel was cooled, and 60 g of the feed medium was added. The feed medium was prepared as follows: sucrose, 50%

TABLE 6

| Exp. ID | Lipase ppm | Max Cell Count × $10^7$ | Solvent Loading Vol % | Max i-BuOH (aq) g/L | EOR Volumetric Rate g/L/hr | Extractant |
| --- | --- | --- | --- | --- | --- | --- |
| GLNOR 1050 | 10 | 21.3 | 28% | 6.9 | 0.97 | Virgin Soy Bean Oil Fatty Acid |
| GLNOR 1051 | 4 | 20.9 | 28% | 8.9 | 0.83 | Virgin Soy Bean Oil Fatty Acid |
| 2011Y029 | 10 | 20.9 | 50% | 8.2 | 0.85 | Recycled Soy Bean Oil Fatty Acid and Fatty Acid Butyl Ester |
| 2011Y030 | 10 | 24.4 | 40% | 9.8 | 0.88 | Virgin Soy Bean Oil Fatty Acid and Fatty Acid Butyl Ester |
| 2011Y031 | 10 | 9.8 | 10% | 12.7 | 0.42 | Recycled Soy Bean Oil Fatty Acid and Fatty Acid Butyl Ester |
| 2011Y032 | 10 | 26.5 | 40% | 6.8 | 0.94 | Virgin Soy Bean Oil Fatty Acid |

Example 23

The following example describes the production of isobutanol by fermentation using sucrose as a fermentable carbon source.

Generation of Biomass

Inoculum: A seed medium was prepared to initiate the growth of the isobutanologen. The composition of the seed medium was as follows: ammonium sulfate, 5 g/L; potassium phosphate monobasic, 3 g/L; magnesium sulfate heptahydrate, 0.5 g/L; ethanol, 3.2 g/L; yeast extract (BBL), 5 g/L; glucose, 10 g/L; MES buffer, 150 mmol/L; biotin, 50 µg/L;

solution, 2.97 L; biotin, 1.4 mg; 34 mL of the trace mineral solution; titrated to pH 7.5 with 5N sodium hydroxide and steam sterilized; post sterilization and cooling, 130 mL ethanol and 320 mL of a 20% (w/v) filter sterilized solution of yeast extract (Amberex™ 695) was added. The initial sugar concentration in the 10 L fermentor was thus 3.7 g/L sucrose, 0.8 g/L glucose, and 0.8 g/L fructose.

The fermentation was controlled at pH 5.5 (with ammonium hydroxide addition), 30° C., airflow at 2.0 standard liters per minute, dissolved oxygen at 30% by agitation control, and 0.5 barg back pressure. After inoculation, the sugar was consumed until the residual measurement of glucose was less than 0.1 g/L, and then the feed program began; this occurred at 11 hours elapsed fermentation time. The program was established to maintain sucrose limitation until $OD_{600}$ of 20 (approximately 8 g/L dry cell weight) was achieved, with a programmed growth rate of 0.1/hr. The actual measured growth rate in this experiment was 0.18/hr. The targeted $OD_{600}$ was reached after 20 hours fermentation time.

Once the target was achieved, the culture was harvested aseptically, and centrifuged in a Sorvall RC12BP centrifuge. The resulting pellet was resuspended to a final volume of 300 mL with isobutanol production medium, described below. This culture was used as the inoculum for the isobutanol production fermentors.

Isobutanol Production

Preparation of production fermentors: Two one liter glass Applikon (Applikon, Inc, Holland) fermentors associated with a Sartorius BioStat B Plus Twin control unit (Sartorius AG, Goettingen, Germany) were used for the isobutanol production. The fermentors were prepared with 1 L deionized water, and sterilized by autoclaving at 121° C. for 30 minutes. Once the fermentors cooled, the water was aseptically removed, and the volume of filter sterilized production medium, as indicated in Table 7, was added. The production medium composition was as follows: yeast nitrogen base without amino acids (Difco), 6.7 g/L; Yeast Synthetic Drop-out Medium Supplements without histidine, leucine, tryptophan, and uracil (Sigma), 2.70 g/L; tryptophan, 1.6 mg/L; leucine, 8 mg/L; ethanol, 2.8 g/L; Antifoam Sigma 204, 0.2 mL/L; sucrose, 25 g/L. Just before inoculation, filter sterilized lipase solution was as indicated in Table 7. The lipase solution was prepared by dilution of Lipolase® L100 (Sigma) in 10 mM potassium phosphate buffer, pH 7, to a final concentration of 1.25 mg protein/mL. The solution was prepared and stored for one day at 5° C. before addition to the fermentors.

TABLE 7

| Fermentor | Fermentation Broth (mL) | SOFA (mL) | lipase (mg/L) |
|---|---|---|---|
| A | 440 | 320 | 0 |
| B | 440 | 320 | 10 |
| C | 520 | 240 | 10 |
| D | 520 | 240 | 25 |

The fermentors were controlled at pH 5.2 (by addition of 20% potassium hydroxide), 30° C., airflow at 0.2 standard liters per minute, and dissolved oxygen at 3% by agitation control.

The fermentors were each inoculated with 40 mL of the concentrated biomass, to initial $OD_{600}$ 20-25 (approximately 8-10 g/L dry cell weight). An addition 4 mL of a filter sterilized vitamin solution (thiamine-HCl, 1 mg/mL; nicotinic acid, 1 mg/mL, in water) was added at inoculation, as was the volume of filter sterilized Soya Oil Fatty Acids (SOFA) indicated in Table 7. Samples (5-10 mL) were drawn every 2-3 hours, and assayed for glucose and sucrose by a YSI Select Biochemistry Analyzer (YSI, Inc., Yellow Springs, Ohio). As sucrose was consumed, a feed of 50% sucrose (w/w) was added to maintain a concentration of 5-30 g/L. The aqueous and organic phases of the samples were separated and analyzed by the HPLC method described above via an Agilent 1100 HPLC. For analysis of organic acids and alcohols, a Shodex® Sugar SH1011 column was used with 0.01 N sulfuric acid mobile phase. For analysis of sucrose, glucose, and fructose, a BioRad Aminex® HPX-87N column with 0.01 M $Na_2HPO_4$ (pH 8) mobile phase was used.

Figure 6:
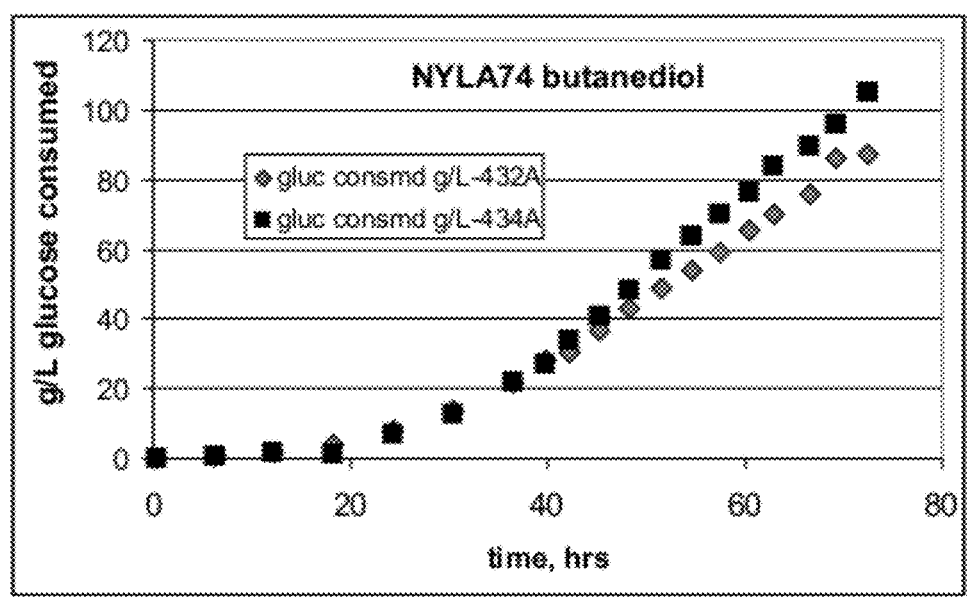

Each of the fermentors with lipase added had lower concentrations of isobutanol in the aqueous phase and free isobutanol in the solvent phase. The aqueous and solvent phase concentrations of isobutanol are shown in FIG. 6. Addition of more lipase at the same solvent loading also resulted in lower aqueous titers of isobutanol and lower free isobutanol in the solvent, and more isobutanol as FABE.

Figure 7:
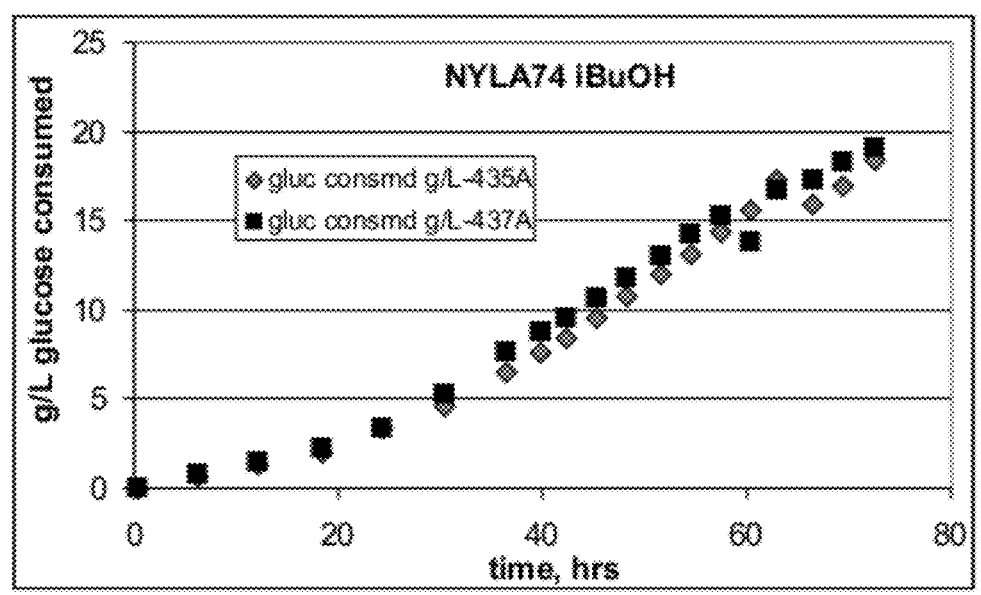
FIG. 7 shows the effective titer of isobutanol, g/L, over time. Effective titer in this example was calculated as described in the text, based on the initial volume of aqueous fermentor broth after inoculation.

The cultivations which included lipase resulted in a higher effective titer of isobutanol than the control fermentor without lipase. FIG. 7 shows the effective titer of isobutanol. In this example, the effective titer was calculated based on the initial measured weight of broth in the fermentor after inoculation and the initial measured weight of solvent charged to the fermentor. The solvent density was assumed to be 0.88 g/mL and the aqueous broth density 1.00 g/mL throughout the fermentation. Addition of more lipase at the lower solvent loading did result in higher effective titers of isobutanol (D vs C), but not as much as increasing the relative volume of solvent (C vs B).

Figure 8:
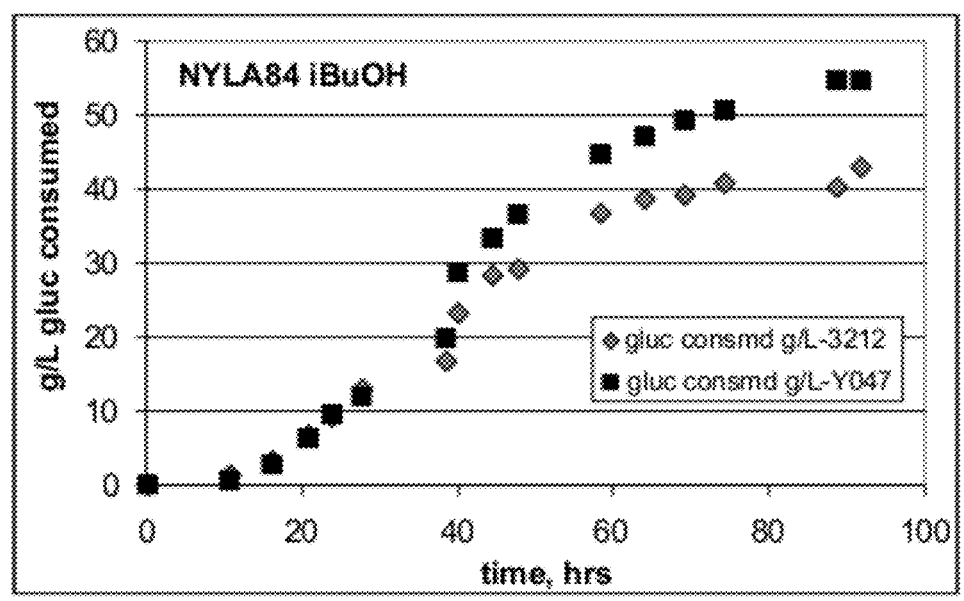
FIG. 8 shows the consumption of sugars, reported in glucose equivalents, over time.

Sugar consumed, calculated in glucose equivalents, was higher in fermentors with lipase added, shown in FIG. 8. Glucose equivalents consumed is calculated from the measured sugars fed and remaining in the fermentor, with each mole of sucrose counted as two moles of glucose and each mole of fructose counted as one mole of glucose, then converted to grams via the molecular weight of glucose. The concentration of glucose equivalents consumed is also calculated on the basis of the initial volume of fermentation broth after inoculation.

Example 24

Lipase Treatment of Liquefied Corn Mash for Simultaneous Saccharification and Fermentation with In-Situ Product Removal Using Oleyl Alcohol Samples of broth and oleyl alcohol taken from fermentations run as described above in Examples 1, 2, and 3 were analyzed for wt % lipid (derivatized as fatty acid methyl esters, FAME) and for wt % free fatty acid (FFA, derivatized as fatty acid methyl esters, FAME) according to the method described by E. G. Bligh and W. J. Dyer (Canadian Journal of Biochemistry and Physiology, 37:911-17, 1959, hereafter Reference 1). The liquefied corn mash that was prepared for each of the three fermentations was also analyzed for wt % lipid and for wt % FFA after treatment with Lipolase® 100 L (Novozymes) (10 ppm of Lipolase® total soluble protein (BCA protein analysis, Sigma Aldrich)) per kg of liquefaction reaction mass containing 30 wt % ground corn kernels). No lipase was added to the liquefied corn mash in Example 1 (control), and the fermentations described in Examples 2 and 3 containing liquefied corn mash treated with lipase (no heat inactivation of lipase) were identical except that no ethanol was added to the fermentation described in Example 3.

The % FFA in lipase-treated liquefied corn mash prepared for fermentations run as described in Examples 2 and 3 was 88% and 89%, respectively, compared to 31% without lipase treatment (Example 1). At 70 h (end of run (EOR)), the concentration of FFA in the OA phase of fermentations run as described in Examples 2 and 3 (containing active lipase) was 14% and 20%, respectively, and the corresponding increase in lipids (measured as corn oil fatty acid methyl ester derivatives) was determined by GC/MS to be due to the lipase-catalyzed esterification of COFA by OA, where COFA was first produced by lipase-catalyzed hydrolysis of corn oil in the liquefied corn mash; the production of oleyl palmitate, oleyl stearate, and oleyl oleate was confirmed by GC/MS, and a fourth ester was tentatively identified as oleyl linoleate. Results for FFA and lipid analysis are shown in Table 8.

TABLE 8

Lipid and free fatty acid content of fermentations containing oleyl alcohol as ISPR extractant and active lipase

| fermentation | lipase | time (h), sample | lipids (wt %) | FFA (wt %) | lipids (g) | FFA (g) | lipids + FFA (g) | % FFA |
|---|---|---|---|---|---|---|---|---|
| Example 1 | none | liq. mash | 0.61 | 0.28 | 5.3 | 2.4 | 7.7 | 31 |
| Example 1 | none | 0.8 h, broth | 0.49 | 0.22 | 5.5 | 2.5 | 8.0 | 31 |
| Example 1 | none | 31 h, broth | 0.19 | 0.03 | 2.1 | 0.3 | 2.4 | 13 |
| Example 1 | none | 31 h, OA | 0.36 | 0.21 | 3.4 | 2.0 | 5.3 | 37 |
| Example 1 | none | 70 h, broth | 0.15 | 0.03 | 1.7 | 0.3 | 2.0 | 15 |
| Example 1 | none | 70 h, OA | 0.57 | 0.25 | 5.3 | 2.3 | 7.7 | 31 |
| Example 2 | 10 ppm | liq. mash | 0.13 | 0.97 | 1.1 | 8.5 | 9.6 | 88 |
| Example 2 | 10 ppm | 0.8 h, broth | 0.15 | 0.62 | 1.7 | 7.0 | 8.7 | 81 |
| Example 2 | 10 ppm | 31 h, broth | 0.16 | 0.05 | 1.8 | 0.5 | 2.3 | 23 |
| Example 2 | 10 ppm | 31 h, OA | 0.37 | 0.23 | 3.5 | 2.2 | 5.7 | 38 |
| Example 2 | 10 ppm | 70 h, broth | 0.17 | 0.02 | 1.9 | 0.3 | 2.2 | 13 |
| Example 2 | 10 ppm | 70 h, OA | 0.60 | 0.10 | 5.7 | 1.0 | 6.7 | 14 |
| Example 3 | 10 ppm | liq. mash | 0.12 | 0.97 | 1.0 | 8.5 | 9.5 | 89 |
| Example 3 | 10 ppm | 0.8 h, broth | 0.32 | 0.40 | 3.6 | 4.5 | 8.1 | 56 |
| Example 3 | 10 ppm | 31 h, broth | 0.17 | 0.05 | 1.9 | 0.6 | 2.5 | 24 |
| Example 3 | 10 ppm | 31 h, OA | 0.38 | 0.22 | 3.6 | 2.1 | 5.7 | 37 |
| Example 3 | 10 ppm | 70 h, broth | 0.15 | 0.02 | 1.7 | 0.2 | 1.9 | 13 |
| Example 3 | 10 ppm | 70 h, OA | 0.46 | 0.12 | 4.4 | 1.1 | 5.6 | 20 |

Example 25

Heat Inactivation of Lipase in Lipase-Treated Liquefied Corn Mash to Limit Production of Oleyl Alcohol Esters of Corn Oil Free Fatty Acids Tap water (918.4 g) was added to a jacketed 2-L resin kettle, then 474.6 g wet weight (417.6 g dry weight) of ground whole corn kernels (1.0 mm screen on hammer mill) was added with stirring. The mixture was heated to 55° C. with stirring at 300 rpm, and the pH adjusted to 5.8 with 2 N sulfuric acid. To the mixture was added 14.0 g of an aqueous solution containing 0.672 g of Spezyme®-FRED L (Genencor®, Palo Alto, Calif.), and the temperature of the mixture increased to 85° C. with stirring at 600 rpm and pH 5.8. After 120 minutes at 85° C., the mixture was cooled to 50° C. and 45.0 mL aliquots of the resulting liquefied corn mash were transferred to 50-mL polypropylene centrifuge tubes and stored frozen at −80° C.

In a first reaction, 50 g of liquefied corn mash prepared as described above was mixed with 10 ppm Lipolase® 100 L (Novozymes) for 6 h at 55° C. and with no inactivation of lipase at 85° C. for 1 h, the mixture was cooled to 30° C. In a second reaction, 50 g of liquefied corn mash was mixed with 10 ppm Lipolase® for 6 h at 55° C., then heated to 85° C. for 1 h (lipase inactivation), then cooled to 30° C. In a third reaction, 50 g of liquefied corn mash without added lipase was mixed for 6 h at 55° C., and with no heating at 85° C. for 1 h, the mixture was cooled to 30° C., 38 g of oleyl alcohol was added, and the resulting mixture stirred for 73 h at 30° C. In a fourth reaction, 50 g of liquefied corn mash without added lipase was mixed for 6 h at 55° C., then heated to 85° C. for 1 h, then cooled to 30° C. Each of the four reaction mixtures was sampled at 6 h, then 38 g of oleyl alcohol added, and the resulting mixtures stirred at 30° C. and sampled at 25 h and 73 h. Samples (both liquefied mash and oleyl alcohol (OA)) were analyzed for wt % lipid (derivatized as fatty acid methyl esters, FAME) and for wt % free fatty acid (FFA, derivatized as fatty acid methyl esters, FAME) according to the method described by Reference 1.

The % FFA in the OA phase of the second reaction run with heat inactivation of lipase prior to OA addition was 99% at 25 h and 95% at 73 h, compared to only 40% FFA and 21% FFA at 25 h and 73 h, respectively, when the lipase in lipase-treated liquefied corn mash was not heat inactivated (first reaction). No significant change in % FFA was observed in the two control reactions without added lipase. Results are shown in Table 9.

TABLE 9

Lipid and free fatty acid content of a mixture of liquefied corn mash and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm active lipase, no 85° C. heat treatment | 6 h, liq. mash | 0.08 | 0.71 | 41 | 345 | 386 | 89 |
| | 25 h, liq. mash | 0.22 | 0.06 | 105 | 27 | 132 | 20 |
| | 25 h, OA | 0.58 | 0.39 | 212 | 143 | 355 | 40 |
| | 73 h, liq. mash | 0.25 | 0.05 | 121 | 22 | 143 | 18 |
| | 73 h, OA | 0.91 | 0.24 | 333 | 88 | 420 | 21 |
| 10 ppm inactive lipase, 85° C. heat treatment | 6 h, liq. mash | 0.06 | 0.45 | 28 | 224 | 252 | 89 |
| | 25 h, liq. mash | 0.10 | 0.11 | 49 | 54 | 103 | 53 |
| | 25 h, OA | 0.02 | 0.96 | 8 | 366 | 374 | 99 |
| | 73 h, liq. mash | 0.24 | 0.15 | 117 | 72 | 189 | 62 |
| | 73 h, OA | 0.06 | 1.11 | 23 | 424 | 447 | 95 |

TABLE 9-continued

Lipid and free fatty acid content of a mixture of liquefied corn mash
and oleyl alcohol in the presence or absence of active or heat-inactivated lipase

| reaction conditions | time (h), sample | lipids (wt %) | FFA (wt %) | lipids (mg) | FFA (mg) | lipid + FFA (mg) | % FFA |
|---|---|---|---|---|---|---|---|
| no lipase, no 85° C. heat treatment | 6 h, liq. mash | 0.80 | 0.40 | 401 | 199 | 599 | 33 |
|  | 25 h, liq. mash | 0.30 | 0.05 | 147 | 25 | 173 | 15 |
|  | 25 h, OA | 0.55 | 0.36 | 212 | 139 | 351 | 40 |
|  | 73 h, liq. mash | 0.23 | 0.05 | 117 | 26 | 143 | 23 |
|  | 73 h, OA | 0.79 | 0.42 | 305 | 162 | 467 | 34 |
| no lipase, 85° C. heat treatment | 6 h, liq. mash | 0.74 | 0.36 | 370 | 183 | 553 | 33 |
|  | 25 h, liq. mash | 0.31 | 0.05 | 156 | 27 | 183 | 15 |
|  | 25 h, OA | 0.60 | 0.35 | 233 | 136 | 369 | 37 |
|  | 73 h, liq. mash | 0.20 | 0.05 | 99 | 23 | 121 | 23 |
|  | 73 h, OA | 0.84 | 0.41 | 326 | 159 | 486 | 33 |

Example 26

Heat Inactivation of Lipase in Lipase-Treated Liquefied Corn Mash for Simultaneous Saccharification and Fermentation with In-Situ Product Removal Using Oleyl Alcohol Three fermentations were run as described above in Examples 4, 5, and 6. No lipase was added to the liquefied corn mash in Examples 4 and 6 prior to fermentation, and the Lipase Treatment of the liquefied corn mash in the fermentation described in Example 5 (using 7.2 ppm of Lipolase® total soluble protein) was followed immediately by Heat Inactivation Treatment (to completely inactivate the lipase), and subsequently followed by Nutrient Addition Prior to Inoculation and fermentation. The % FFA in liquefied corn mash prepared without lipase treatment for fermentations run as described in Examples 4 and 6 was 31% and 34%, respectively, compared to 89% with lipase treatment (Example 5). Over the course of the fermentations listed in Table 10, the concentration of FFA in the OA phase did not decrease in any of the three fermentations, including that containing heat-inactivated lipase. The % FFA in the OA phase of the fermentation run according to Example 5 (with heat inactivation of lipase prior to fermentation) was 95% at 70 h (end of run (EOR)), compared to only 33% FFA for the remaining two fermentations (Examples 4 and 6) where liquefied corn mash was not treated with lipase. Results are shown in Table 10.

TABLE 10

Lipid and free fatty acid content of
fermentations containing oleyl alcohol as ISPR extractant
and heat-inactivated lipase (after lipase treatment of liquefied mash)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 4 | none | liquefied mash | 0.65 | 0.30 | 7.2 | 3.3 | 10.4 | 31 |
| Example 4 | none | 0.2 h, broth | 0.56 | 0.28 | 6.6 | 3.3 | 9.9 | 33 |
| Example 4 | none | 4.3 h, broth | 0.28 | 0.09 | 3.3 | 1.0 | 4.4 | 24 |
| Example 4 | none | 4.3 h, OA | 0.45 | 0.27 | 4.0 | 2.4 | 6.4 | 37 |
| Example 4 | none | 30 h, broth | 0.17 | 0.05 | 2.0 | 0.6 | 2.7 | 24 |
| Example 4 | none | 30 h, OA | 0.63 | 0.29 | 5.7 | 2.6 | 8.3 | 32 |
| Example 4 | none | 53 h, broth | 0.13 | 0.04 | 1.5 | 0.5 | 2.0 | 23 |
| Example 4 | none | 53 h, OA | 0.67 | 0.32 | 6.0 | 2.9 | 8.9 | 32 |
| Example 4 | none | 70 h, broth | 0.13 | 0.04 | 1.5 | 0.4 | 1.9 | 23 |
| Example 4 | none | 70 h, OA | 0.64 | 0.31 | 5.8 | 2.8 | 8.5 | 33 |
| Example 5 | 7.2 ppm | liquefied mash | 0.11 | 0.89 | 1.3 | 9.9 | 11.2 | 89 |
| Example 5 | 7.2 ppm | 0.2 h, broth | 0.25 | 0.83 | 2.9 | 9.8 | 12.8 | 77 |
| Example 5 | 7.2 ppm | 4.3 h, broth | 0.14 | 0.17 | 1.6 | 2.1 | 3.7 | 56 |
| Example 5 | 7.2 ppm | 4.3 h, OA | 0.02 | 0.84 | 0.2 | 7.9 | 8.1 | 97 |
| Example 5 | 7.2 ppm | 30 h, broth | 0.08 | 0.18 | 1.0 | 2.1 | 3.1 | 68 |
| Example 5 | 7.2 ppm | 30 h, OA | 0.04 | 0.92 | 0.3 | 8.6 | 8.9 | 96 |
| Example 5 | 7.2 ppm | 53 h, broth | 0.07 | 0.11 | 0.9 | 1.3 | 2.2 | 61 |
| Example 5 | 7.2 ppm | 53 h, OA | 0.08 | 0.95 | 0.7 | 8.9 | 9.6 | 93 |
| Example 5 | 7.2 ppm | 70 h, broth | 0.08 | 0.10 | 0.9 | 1.2 | 2.1 | 55 |
| Example 5 | 7.2 ppm | 70 h, OA | 0.05 | 0.94 | 0.4 | 8.8 | 9.2 | 95 |
| Example 6 | none | liquefied mash | 0.66 | 0.34 | 7.3 | 3.8 | 11.1 | 34 |
| Example 6 | none | 0.2 h, broth | 0.63 | 0.34 | 7.6 | 4.0 | 11.6 | 34 |
| Example 6 | none | 4.3 h, broth | 0.33 | 0.10 | 3.9 | 1.2 | 5.1 | 23 |
| Example 6 | none | 4.3 h, OA | 0.45 | 0.27 | 4.0 | 2.4 | 6.4 | 38 |
| Example 6 | none | 30 h, broth | 0.17 | 0.06 | 2.1 | 0.8 | 2.8 | 26 |
| Example 6 | none | 30 h, OA | 0.69 | 0.33 | 6.2 | 3.0 | 9.1 | 32 |
| Example 6 | none | 53 h, broth | 0.14 | 0.05 | 1.6 | 0.5 | 2.2 | 25 |
| Example 6 | none | 53 h, OA | 0.72 | 0.35 | 6.4 | 3.1 | 9.5 | 33 |
| Example 6 | none | 70 h, broth | 0.15 | 0.05 | 1.8 | 0.6 | 2.4 | 25 |
| Example 6 | none | 70 h, OA | 0.70 | 0.34 | 6.2 | 3.0 | 9.2 | 33 |

Example 27

Lipase Treatment of Ground Whole Corn Kernels Prior to Liquefaction

Tap water (1377.6 g) was added into each of two jacketed 2-L resin kettles, then 711.9 g wet weight (625.8 g dry weight) of ground whole corn kernels (1.0 mm screen on hammer mill) was added to each kettle with stirring. Each mixture was heated to 55° C. with stirring at 300 rpm, and the pH adjusted to 5.8 with 2 N sulfuric acid. To each mixture was added 21.0 g of an aqueous solution containing 1.008 g of Spezyme®-FRED L (Genencor®, Palo Alto, Calif.). To one mixture was then added 10.5 mL of aqueous solution of Lipolase® 100L Solution (21 mg total soluble protein, 10 ppm lipase final concentration) and to the second mixture was added 1.05 mL of aqueous solution of Lipolase® 100L Solution (2.1 mg total soluble protein, 1.0 ppm lipase final concentration). Samples were withdrawn from each reaction mixture at 1 h, 2 h, 4 h and 6 h at 55° C., then the temperature of the mixture was increased to 85° C. with stirring at 600 rpm and pH 5.8, and a sample was taken when the mixture first reached 85° C. After 120 minutes at 85° C., a sample was taken and the mixtures were cooled to 50° C. and final samples of the resulting liquefied corn mash were transferred to 50-mL polypropylene centrifuge tubes; all samples were stored frozen at −80° C.

In two separate reactions, a 50 g sample of the 10 ppm lipase-treated liquefied corn mash or a 55 g sample of the 1.0 ppm lipase-treated liquefied corn mash prepared as described above was mixed with oleyl alcohol (OA) (38 g) at 30° C. for 20 h, then the liquefied mash and OA in each reaction mixture were separated by centrifugation and each phase analyzed for wt % lipid (derivatized as fatty acid methyl esters, FAME) and for wt % free fatty acid (FFA, derivatized as fatty acid methyl esters, FAME) according to the method described by Reference 1. The % FFA in the OA phase of the liquefied mash/OA mixture prepared using heat inactivation of 10 ppm lipase during liquefaction was 98% at 20 h, compared to only 62% FFA in the OA phase of the liquefied mash/OA mixture prepared using heat inactivation of 1.0 ppm lipase during liquefaction. Results are shown in Table 11.

Example 28

Lipase Screening for Treatment of Ground Whole Corn Kernels Prior to Liquefaction Seven reaction mixtures containing tap water (67.9 g) and ground whole corn kernels (35.1 g wet wt., ground with 1.0 mm screen using a hammer mill) at pH 5.8 were stirred at 55° C. in stoppered flasks. A 3-mL sample (t=0 h) was removed from each flask and the sample immediately frozen on dry ice, then ca. 0.5 mL of 10 mM sodium phosphate buffer (pH 7.0) containing 1 mg total soluble protein (10 ppm final concentration in reaction mixture) of one of the following lipases (Novozymes) were added to one of each flask: Lipolase® 100 L, Lipex® 100L, Lipoclean® 2000T, Lipozyme® CALB L, Novozyme® CALA L, and Palatase 20000L; no lipase was added to the seventh flask. The resulting mixtures were stirred at 55° C. in stoppered flasks, and 3-mL samples were withdrawn from each reaction mixture at 1 h, 2 h, 4 h and 6 h and immediately frozen in dry ice until analyzed for wt % lipid (derivatized as fatty acid methyl esters, FAME) and for wt % free fatty acid (FFA, derivatized as fatty acid methyl esters, FAME) according to the method described by Reference 1, and the percent free fatty acid content was calculated relative to the total combined concentrations of lipid and free fatty acid was determined for each sample. Results are shown in Table 12.

TABLE 12

Percent free fatty acid content (% FFA) of a mixture of ground whole corn kernels using lipase treatment at 55° C. prior to liquefaction

| | % FFA time | | | | |
|---|---|---|---|---|---|
| | 0 h | 1 h | 2 h | 4 h | 6 h |
| Lipolase ® 100L | 33 | 56 | 74 | 76 | 79 |
| Lipex ® 100L | 34 | 66 | 81 | 83 | 83 |
| Lipoclean ® 2000T | 38 | 55 | 73 | 69 | 65 |
| Lipozyme ® CALB L | 39 | 38 | 37 | 43 | 41 |

TABLE 11

Lipid and free fatty acid content of a mixture of liquefied corn mash and oleyl alcohol, using lipase treatment of ground corn suspension prior to liquefaction (heat inactivation of lipase during liquefaction)

| reaction conditions | time (h), sample | lipids (wt %) | FFA (wt %) | lipids (mg) | FFA (mg) | lipid + FFA (mg) | % FFA |
|---|---|---|---|---|---|---|---|
| 10 ppm lipase at 55° C. prior to liquefaction at 85° C., mix with OA for 20 h | 1 h, pre-liquefaction | 0.226 | 0.627 | 112 | 311 | 424 | 74 |
| | 2 h, pre-liquefaction | 0.199 | 0.650 | 99 | 323 | 422 | 77 |
| | 4 h, pre-liquefaction | 0.151 | 0.673 | 75 | 334 | 410 | 82 |
| | 6 h, pre-liquefaction | 0.101 | 0.700 | 50 | 348 | 398 | 87 |
| | 0 h, 85° C., liq. mash | 0.129 | 0.764 | 64 | 380 | 444 | 86 |
| | 2 h, 85° C., liq. mash | 0.129 | 0.751 | 64 | 373 | 437 | 85 |
| | 20 h, 30° C., liq. mash | 0.074 | 0.068 | 37 | 34 | 71 | 48 |
| | 20 h, 30° C., OA | 0.015 | 1.035 | 5.7 | 394 | 400 | 98 |
| 1.0 ppm lipase at 55° C. prior to liquefaction at 85° C., mix with OA for 20 h | 1 h, pre-liquefaction | 0.408 | 0.480 | 226 | 266 | 492 | 54 |
| | 2 h, pre-liquefaction | 0.401 | 0.424 | 222 | 235 | 457 | 51 |
| | 4 h, pre-liquefaction | 0.299 | 0.433 | 165 | 240 | 405 | 58 |
| | 6 h, pre-liquefaction | 0.346 | 0.453 | 192 | 251 | 442 | 57 |
| | 0 h, 85° C., liq. mash | 0.421 | 0.407 | 233 | 225 | 458 | 49 |
| | 2 h, 85° C., liq. mash | 0.424 | 0.429 | 235 | 237 | 472 | 50 |
| | 20 h, 30° C., liq. mash | 0.219 | 0.054 | 121 | 30 | 151 | 20 |
| | 20 h, 30° C., OA | 0.344 | 0.573 | 140 | 233 | 373 | 62 |

TABLE 12-continued

Percent free fatty acid content (% FFA) of a mixture of ground
whole corn kernels using lipase treatment at 55° C. prior to liquefaction

| | % FFA time | | | | |
|---|---|---|---|---|---|
| | 0 h | 1 h | 2 h | 4 h | 6 h |
| Novozyme ® CALA L | 37 | 40 | 44 | 44 | 45 |
| Palatase ® 20000L | 37 | 49 | 59 | 62 | 66 |
| no enzyme | 38 | 33 | 37 | 41 | 42 |

Example 29

Lipase Treatment of Ground Whole Corn Kernels Prior to Simultaneous Saccharification and Fermentation with In-Situ Product Removal Using Oleyl Alcohol Three fermentations were run as described above in Examples 7, 8, and 10. For fermentations run as described in Examples 7 and 10, lipase (10 ppm of Lipolase® total soluble protein) was added to the suspension of ground corn and heated at 55° C. for 6 h prior to Liquefaction to produce a liquefied corn mash containing heat-inactivated lipase. No lipase was added to the suspension of ground corn used to prepare liquefied corn mash for the fermentation described in Example 8, but the suspension was subjected to the same heating step at 55° C. prior to liquefaction. The % FFA in lipase-treated liquefied corn mash prepared for fermentations run as described in Examples 7 and 10 was 83% and 86%, respectively, compare to 41% without lipase treatment (Example 8). Over the course of the fermentations, the concentration of FFA did not decrease in any of the fermentations, including that containing heat-inactivated lipase. The % FFA in the OA phase of the fermentation run according to Examples 7 and 10 (with heat inactivation of lipase prior to fermentation) were each 97% at 70 h (end of run (EOR)), compared to only 49% FFA for the fermentation run according to Example 8 where ground whole corn kernels had not been treated with lipase prior to liquefaction. Results are shown in Table 13.

TABLE 13

Lipid and free fatty acid content of fermentations containing
oleyl alcohol as ISPR extractant and heat-inactivated lipase
(lipase treatment of ground corn suspension prior to liquefaction)

| fermentation | lipase | time (h), sample | lipids (wt %) | FFA (wt %) | lipids (g) | FFA (g) | lipid + FFA (g) | % FFA |
|---|---|---|---|---|---|---|---|---|
| Example 7 | 10 ppm | pre-lipase/pre-liq. | 0.65 | 0.22 | 7.1 | 2.4 | 9.4 | 25 |
| Example 7 | 10 ppm | post-lipase/pre-liq. | 0.22 | 0.65 | 2.4 | 7.0 | 9.5 | 74 |
| Example 7 | 10 ppm | liquefied mash | 0.17 | 0.79 | 1.8 | 8.5 | 10.3 | 83 |
| Example 7 | 10 ppm | 0.3 h, broth | 0.16 | 0.79 | 1.8 | 8.9 | 10.7 | 83 |
| Example 7 | 10 ppm | 4.8 h, broth | 0.14 | 0.31 | 1.6 | 3.5 | 5.1 | 69 |
| Example 7 | 10 ppm | 4.8 h, OA | 0.04 | 0.68 | 0.3 | 5.4 | 5.6 | 95 |
| Example 7 | 10 ppm | 29 h, broth | 0.10 | 0.12 | 1.2 | 1.3 | 2.5 | 53 |
| Example 7 | 10 ppm | 29 h, OA | 0.03 | 1.05 | 0.2 | 8.2 | 8.4 | 98 |
| Example 7 | 10 ppm | 53 h, broth | | | | | | |
| Example 7 | 10 ppm | 53 h, OA | 0.07 | 1.14 | 0.5 | 9.0 | 9.5 | 95 |
| Example 7 | 10 ppm | 70 h, broth | 0.11 | 0.07 | 1.2 | 0.8 | 2.0 | 39 |
| Example 7 | 10 ppm | 70 h, OA | 0.03 | 1.10 | 0.2 | 8.7 | 8.9 | 97 |
| Example 8 | none | pre-lipase/pre-liq. | 0.62 | 0.23 | 6.7 | 2.5 | 9.2 | 27 |
| Example 8 | none | post-lipase/pre-liq. | 0.57 | 0.26 | 6.2 | 2.8 | 9.0 | 31 |
| Example 8 | none | liquefied mash | 0.52 | 0.36 | 5.6 | 4.0 | 9.6 | 41 |
| Example 8 | none | 0.3 h, broth | 0.50 | 0.33 | 5.7 | 3.8 | 9.4 | 40 |
| Example 8 | none | 4.8 h, broth | 0.47 | 0.14 | 5.3 | 1.6 | 6.9 | 24 |
| Example 8 | none | 4.8 h, OA | 0.12 | 0.32 | 1.0 | 2.9 | 3.9 | 73 |
| Example 8 | none | 29 h, broth | 0.30 | 0.05 | 3.4 | 0.6 | 4.0 | 16 |
| Example 8 | none | 29 h, OA | 0.31 | 0.46 | 2.7 | 4.1 | 6.9 | 60 |
| Example 8 | none | 53 h, broth | | | | | | |
| Example 8 | none | 53 h, OA | 0.47 | 0.50 | 4.2 | 4.4 | 8.6 | 51 |
| Example 8 | none | 70 h, broth | 0.22 | 0.04 | 2.5 | 0.5 | 3.0 | 17 |
| Example 8 | none | 70 h, OA | 0.40 | 0.39 | 3.6 | 3.5 | 7.0 | 49 |
| Example 10 | 10 ppm | pre-lipase/pre-liq. | 0.67 | 0.23 | 7.4 | 2.5 | 9.9 | 25 |
| Example 10 | 10 ppm | post-lipase/pre-liq. | 0.19 | 0.69 | 2.1 | 7.6 | 9.7 | 78 |
| Example 10 | 10 ppm | liquefied mash | 0.14 | 0.85 | 1.6 | 9.4 | 11.0 | 86 |
| Example 10 | 10 ppm | 0.3 h, broth | 0.13 | 0.82 | 1.5 | 9.4 | 10.9 | 86 |
| Example 10 | 10 ppm | 4.8 h, broth | 0.11 | 0.29 | 1.3 | 3.3 | 4.6 | 72 |
| Example 10 | 10 ppm | 4.8 h, OA | 0.04 | 0.60 | 0.3 | 5.2 | 5.6 | 94 |
| Example 10 | 10 ppm | 29 h, broth | 0.09 | 0.14 | 1.0 | 1.6 | 2.6 | 61 |
| Example 10 | 10 ppm | 29 h, OA | 0.01 | 0.96 | 0.1 | 8.4 | 8.5 | 99 |
| Example 10 | 10 ppm | 53 h, broth | | | | | | |
| Example 10 | 10 ppm | 53 h, OA | 0.02 | 0.95 | 0.2 | 8.3 | 8.4 | 98 |
| Example 10 | 10 ppm | 70 h, broth | 0.09 | 0.08 | 1.1 | 0.9 | 1.9 | 45 |
| Example 10 | 10 ppm | 70 h, OA | 0.03 | 0.99 | 0.3 | 8.7 | 9.0 | 97 |

Example 30

Lipase Treatment of Ground Whole Corn Kernels or Liquefied Corn Mash for Simultaneous Saccharification and Fermentation with In-Situ Product Removal Using Corn Oil Fatty Acids (COFA)

Five fermentations were run as described above in Examples 9, 11, 12, 13, and 14. For the fermentations run as described in Examples 9, 13, and 14, lipase (10 ppm of Lipolase® total soluble protein) was added after Liquefaction and there was no heat-inactivation of lipase. Fermentations run as described in Examples 9 and 14 had 5 g/L of ethanol added prior to inoculation, whereas the fermentation run as described in Example 13 had no added ethanol. The fermentations run as described in Examples 11 and 12 employed the addition of 10 ppm Lipolase® total soluble protein to the suspension of ground corn prior to liquefaction, resulting in heat inactivation of lipase during liquefaction. The fermentation run as described in Example 11 had 5 g/L of ethanol added prior to inoculation, whereas the fermentation run as described in Example 12 had no added ethanol. The final total grams of isobutanol (i-BuOH) present in the COFA phase of the fermentations containing active lipase was significantly greater than the final total grams of i-BuOH (including i-BuOH present as FABE) present in the COFA phase of the fermentations containing inactive lipase. The final total grams of isobutanol (i-BuOH) present in the fermentation broths (aqueous phase) containing active lipase were only slightly less than the final total grams of i-BuOH present in the fermentation broths containing inactive lipase, such that the overall production of i-BuOH (as a combination of free i-BuOH and isobutyl esters of COFA (FABE)) was significantly greater in the presence of active lipase when compared to that obtained in the presence of heat-inactivated lipase. Results are shown in Tables 14 and 15.

TABLE 14

Dependence of the production of free isobutanol (i-BuOH) and isobutyl esters of COFA (FABE) in fermentations containing corn oil fatty acids (COFA) as ISPR extractant in presence (Examples 9, 13, and 14) or absence (Examples 11 and 12) of active lipase (COFA phase analysis)

| fermentation | fermentation time (h) | g i-BuOH/ kg COFA | g FABE/ kg COFA | g i-BuOH from FABE/ kg COFA | total g i-BuOH/ kg COFA |
|---|---|---|---|---|---|
| Example 9 | 4.5 | 2.4 | 0.0 | 0 | 2.4 |
| Example 9 | 28.8 | 5.4 | 70.9 | 16.5 | 22.0 |
| Example 9 | 52.4 | 8.9 | 199.0 | 46.4 | 55.3 |
| Example 9 | 69.3 | 4.9 | 230.9 | 53.9 | 69.3 |
| Example 11 | 6.6 | 2.3 | 0.0 | 0.0 | 2.3 |
| Example 11 | 53.5 | 25.1 | 2.9 | 0.6 | 25.7 |
| Example 11 | 71.1 | 24.4 | 6.3 | 1.4 | 25.8 |
| Example 12 | 6.6 | 2.3 | 0.0 | 0.0 | 2.3 |
| Example 12 | 53.5 | 12.8 | 1.6 | 0.4 | 13.2 |
| Example 12 | 71.1 | 12.8 | 3.0 | 0.7 | 13.5 |
| Example 13 | 6.6 | 2.3 | 0.0 | 0.0 | 2.3 |
| Example 13 | 53.5 | 4.9 | 72.1 | 16.0 | 20.9 |
| Example 13 | 71.1 | 4.6 | 91.4 | 20.3 | 24.9 |
| Example 14 | 6.6 | 2.1 | 0.0 | 0.0 | 2.1 |
| Example 14 | 53.5 | 9.8 | 197.2 | 43.8 | 53.6 |
| Example 14 | 71.1 | 4.9 | 244.5 | 54.3 | 59.2 |

TABLE 15

Dependence of the production of free isobutanol (i-BuOH) and isobutyl esters of COFA (FABE) in fermentations containing corn oil fatty acids (COFA) as ISPR extractant on presence (Examples 9, 13 and 14) or absence (Examples 11 and 12) of active lipase (fermentation broth analysis)

| sample | fermentation time (h) | g i-BuOH/ kg broth | g FABE/ kg broth | g i-BuOH from FABE/ kg broth | total g i-BuOH/ kg broth |
|---|---|---|---|---|---|
| Example 9 | 4.5 | 0.0 | 0.0 | 0 | 0 |
| Example 9 | 28.8 | 0.0 | 12.6 | 2.9 | 2.9 |
| Example 9 | 52.4 | 0.0 | 30.3 | 7.1 | 7.1 |
| Example 9 | 69.3 | 0.0 | 24.7 | 5.8 | 5.8 |
| Example 11 | 6.6 | 0.0 | 0.0 | 0 | 0.0 |
| Example 11 | 53.5 | 9.8 | 0.0 | 0 | 9.8 |
| Example 11 | 71.1 | 9.5 | 0.0 | 0 | 9.5 |
| Example 12 | 6.6 | 0.0 | 0.0 | 0 | 0 |
| Example 12 | 53.5 | 3.8 | 0.0 | 0.0 | 3.8 |
| Example 12 | 71.1 | 5.1 | 0.0 | 0.0 | 5.1 |
| Example 13 | 6.6 | 0.0 | 0.0 | 0 | 0 |
| Example 13 | 53.5 | 2.1 | 3.0 | 0.7 | 2.8 |
| Example 13 | 71.1 | 2.1 | 7.4 | 1.6 | 3.7 |
| Example 14 | 6.6 | 0.0 | 0.0 | 0 | 0.0 |
| Example 14 | 53.5 | 2.9 | 22.4 | 5.0 | 7.9 |
| Example 14 | 71.1 | 3.3 | 19.3 | 4.3 | 7.6 |

Example 31

Production of Iso-Butyl COFA Esters by Phospholipase-Catalyzed Reaction of Iso-Butanol and Corn Oil Fatty Acids (COFA)

Reaction mixtures containing aqueous 2-(N-morpholino) ethanesulfonic acid buffer (0.20 M, pH 5.3), isobutanol (2-methyl-1-propanol), phospholipase (Phospholipase A; SigmaAldrich, L3295-250) and corn oil fatty acids prepared from corn oil were stirred at 30° C. (Table 16), and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 17).

TABLE 16

Reaction conditions for conversion of isobutanol (i-BuOH) to isobutyl esters of corn oil fatty acids (i-BuO-COFA)

| reaction | MES buffer (0.2M) (g) | i-BuOH (g) | COFA (g) | lipase (ppm) |
|---|---|---|---|---|
| 1 | 46.1 | 3.6 | 14.7 | 10 |
| 2 | 46.1 | 3.6 | 14.7 | 3 |
| 3 | 46.1 | 3.6 | 14.7 | 0 |

TABLE 17

Weights of isobutanol (i-BuOH) and isobutyl esters of corn oil fatty acids (i-BuO-COFA) present in the aqueous fraction (AQ) and organic fraction (ORG) for reactions described in Table 16.

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 1.29 | 2.39 | 2.39 | 0.00 | 0.00 |
| 1 | 2 | 1.24 | 2.44 | 2.38 | 0.06 | 0.26 |
| 1 | 20 | 1.25 | 2.43 | 2.22 | 0.21 | 0.96 |

TABLE 17-continued

Weights of isobutanol (i-BuOH) and isobutyl esters of corn oil fatty acids (i-BuO-COFA) present in the aqueous fraction (AQ) and organic fraction (ORG) for reactions described in Table 16.

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 24 | 1.26 | 2.42 | 2.19 | 0.23 | 1.03 |
| 1 | 44 | 1.27 | 2.41 | 2.13 | 0.28 | 1.28 |
| 1 | 48 | 1.22 | 2.46 | 2.15 | 0.31 | 1.41 |
| 2 | 0.1 | 1.27 | 2.34 | 2.34 | 0.00 | 0.00 |
| 2 | 2 | 1.25 | 2.35 | 2.33 | 0.02 | 0.08 |
| 2 | 20 | 1.24 | 2.37 | 2.30 | 0.07 | 0.30 |
| 2 | 24 | 1.22 | 2.38 | 2.31 | 0.07 | 0.32 |
| 2 | 44 | 1.33 | 2.28 | 2.18 | 0.10 | 0.44 |
| 2 | 48 | 1.23 | 2.38 | 2.27 | 0.11 | 0.48 |
| 3 | 0.1 | 1.27 | 2.33 | 2.33 | 0.00 | 0.00 |
| 3 | 2 | 1.26 | 2.34 | 2.34 | 0.00 | 0.00 |
| 3 | 20 | 1.22 | 2.38 | 2.37 | 0.01 | 0.07 |
| 3 | 24 | 1.25 | 2.35 | 2.33 | 0.02 | 0.08 |
| 3 | 44 | 1.24 | 2.36 | 2.32 | 0.04 | 0.18 |
| 3 | 48 | 1.24 | 2.36 | 2.32 | 0.04 | 0.18 |

Example 32

Dependence of Isobutyl-COFA Ester Concentration on Aqueous/COFA Ratio in Lipase-Catalyzed Reactions Reaction mixtures containing aqueous 2-(N-morpholino)ethanesulfonic acid buffer (0.20 M, pH 5.2), isobutanol (2-methyl-1-propanol), lipase (Lipolase® 100 L; Novozymes) and corn oil fatty acids prepared from corn oil (Table 18) were stirred at 30° C., and samples were withdrawn from each reaction mixture at predetermined times, immediately centrifuged, and the aqueous and organic layers separated and analyzed for isobutanol (i-BuOH) and isobutyl esters of corn oil fatty acids (i-BuO-COFA) (Table 19).

TABLE 18

Reaction conditions for conversion of isobutanol (i-BuOH) to isobutyl esters of corn oil fatty acids (i-BuO-COFA)

| reaction # | MES buffer (0.2M) (g) | i-BuOH (g) | COFA (g) | lipase (ppm) |
|---|---|---|---|---|
| 1 | 45.96 | 3.6 | 43.4 | 10 |
| 2 | 45.96 | 3.6 | 21.7 | 10 |
| 3 | 45.96 | 3.6 | 10.85 | 10 |
| 4 | 45.96 | 3.6 | 43.4 | 4 |
| 5 | 45.96 | 3.6 | 43.4 | 0 |

TABLE 19

Weights of isobutanol (i-BuOH) and isobutyl esters of corn oil fatty acids (i-BuO-COFA) present in the aqueous fraction (AQ) and organic fraction (ORG) for reactions described in Table 18

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 0.1 | 0.77 | 2.83 | 2.77 | 0.05 | 0.24 |
| 1 | 1 | 0.76 | 2.84 | 2.58 | 0.25 | 1.13 |
| 1 | 2 | 0.74 | 2.86 | 2.41 | 0.44 | 2.00 |
| 1 | 4 | 0.66 | 2.94 | 2.05 | 0.89 | 4.03 |
| 1 | 6 | 0.63 | 2.97 | 1.43 | 1.54 | 6.93 |

TABLE 19-continued

Weights of isobutanol (i-BuOH) and isobutyl esters of corn oil fatty acids (i-BuO-COFA) present in the aqueous fraction (AQ) and organic fraction (ORG) for reactions described in Table 18

| reaction | time (h) | total i-BuOH (g) (AQ) | total i-BuOH (g) (ORG) | free i-BuOH (g) (ORG) | i-BuOH from i-BuO-COFA (g) (ORG) | i-BuO-COFA (g) (ORG) |
|---|---|---|---|---|---|---|
| 1 | 21.5 | 0.28 | 3.32 | 0.34 | 2.98 | 13.4 |
| 1 | 25.5 | 0.23 | 3.37 | 0.29 | 3.08 | 13.8 |
| 2 | 0.1 | 1.17 | 2.43 | 2.36 | 0.07 | 0.30 |
| 2 | 1 | 1.09 | 2.51 | 2.26 | 0.24 | 1.10 |
| 2 | 2 | 1.07 | 2.53 | 2.19 | 0.34 | 1.52 |
| 2 | 4 | 1.03 | 2.57 | 1.99 | 0.59 | 2.64 |
| 2 | 6 | 1.00 | 2.60 | 1.70 | 0.90 | 4.04 |
| 2 | 21.5 | 0.75 | 2.85 | 0.58 | 2.27 | 10.2 |
| 2 | 25.5 | 0.59 | 3.01 | 0.49 | 2.52 | 11.4 |
| 3 | 0.1 | 1.56 | 2.04 | 1.98 | 0.06 | 0.27 |
| 3 | 1 | 1.55 | 2.05 | 1.77 | 0.28 | 1.24 |
| 3 | 2 | 1.49 | 2.11 | 1.65 | 0.46 | 2.08 |
| 3 | 4 | 1.45 | 2.15 | 1.28 | 0.87 | 3.92 |
| 3 | 6 | 1.33 | 2.27 | 0.96 | 1.31 | 5.92 |
| 3 | 21.5 | 1.12 | 2.48 | 0.26 | 2.22 | 10.0 |
| 3 | 25.5 | 0.88 | 2.72 | 0.26 | 2.46 | 11.1 |
| 4 | 0.1 | 0.84 | 2.76 | 2.75 | 0.02 | 0.07 |
| 4 | 1 | 0.78 | 2.82 | 2.73 | 0.09 | 0.40 |
| 4 | 2 | 0.83 | 2.77 | 2.59 | 0.17 | 0.79 |
| 4 | 4 | 0.78 | 2.82 | 2.44 | 0.38 | 1.71 |
| 4 | 6 | 0.78 | 2.82 | 2.10 | 0.72 | 3.25 |
| 4 | 21.5 | 0.58 | 3.02 | 1.12 | 1.90 | 8.57 |
| 4 | 25.5 | 0.51 | 3.09 | 0.97 | 2.11 | 9.51 |
| 5 | 0.1 | 0.90 | 2.70 | 2.70 | 0.00 | 0.00 |
| 5 | 1 | 0.90 | 2.70 | 2.70 | 0.00 | 0.00 |
| 5 | 2 | 0.92 | 2.68 | 2.68 | 0.00 | 0.00 |
| 5 | 4 | 0.89 | 2.71 | 2.70 | 0.00 | 0.02 |
| 5 | 6 | 0.92 | 2.68 | 2.62 | 0.06 | 0.29 |
| 5 | 21.5 | 0.90 | 2.70 | 2.62 | 0.08 | 0.37 |
| 5 | 25.5 | 0.89 | 2.71 | 2.62 | 0.09 | 0.41 |

Example 33

Dependence of Butyl-COFA Ester Concentration on Esterification Alcohol in Lipase-Catalyzed Reactions Reaction mixtures containing aqueous 2-(N-morpholino)ethanesulfonic acid buffer (0.20 M, pH 5.2), isobutanol (2-methyl-1-propanol) or n-butanol, lipase (Lipolase® 100 L; Novozymes) and corn oil fatty acids prepared from corn oil (Table 20) were stirred at 30° C., and samples were withdrawn from each reaction mixture at predetermined times, immediately centrifuged, and the aqueous and organic layers separated and analyzed for isobutanol (i-BuOH) or n-butanol (n-BuOH) and isobutyl- or butyl esters of corn oil fatty acids (BuO-COFA) (Table 21).

TABLE 20

Reaction conditions for conversion of isobutanol (i-BuOH) or n-butanol (n-BuOH) to butyl esters of corn oil fatty acids (BuO-COFA)

| Reaction | butanol | MES buffer (0.2M) (g) | butanol (g) | COFA (g) | lipase (ppm) |
|---|---|---|---|---|---|
| 6 | iso-butanol | 45.96 | 3.6 | 13.5 | 10 |
| 7 | n-butanol | 45.96 | 3.6 | 13.5 | 10 |
| 8 | iso-butanol | 45.96 | 3.6 | 13.5 | 0 |
| 9 | isobutanol | 45.96 | 3.6 | 13.5 | 4 |

TABLE 21

Weights of isobutanol (i-BuOH) or n-butanol (n-BuOH) and butyl esters of corn oil fatty acids (BuO-COFA) present in the aqueous fraction (AQ) and organic fraction (ORG) for reactions described in Table 20

| reaction | time (h) | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
|---|---|---|---|---|---|---|
| 6 | 0.1 | 1.46 | 2.14 | 2.11 | 0.04 | 0.16 |
| 6 | 2 | 1.41 | 2.19 | 1.63 | 0.56 | 2.51 |
| 6 | 4 | 1.27 | 2.33 | 1.31 | 1.02 | 4.58 |
| 6 | 21 | 0.66 | 2.94 | 0.29 | 2.65 | 12.0 |
| 6 | 25 | 0.60 | 3.00 | 0.26 | 2.73 | 12.3 |
| 6 | 46 | 0.54 | 3.06 | 0.22 | 2.83 | 12.8 |

| reaction | time (h) | total n-BuOH (g) (AQ) | total n-BuOH (g) (ORG) | n-BuOH (g) (ORG) | n-BuOH from n-BuO-COFA (g) (ORG) | n-BuO-COFA (g) (ORG) |
|---|---|---|---|---|---|---|
| 7 | 0.1 | 1.31 | 2.29 | 2.26 | 0.03 | 0.11 |
| 7 | 2 | 1.26 | 2.34 | 1.89 | 0.45 | 2.03 |
| 7 | 4 | 1.20 | 2.40 | 1.66 | 0.74 | 3.35 |
| 7 | 21 | 0.81 | 2.79 | 0.50 | 2.29 | 10.3 |
| 7 | 25 | 0.77 | 2.83 | 0.40 | 2.43 | 11.0 |
| 7 | 46 | 0.50 | 3.10 | 0.23 | 2.87 | 12.9 |

| reaction | time (h) | total i-BuOH (g) (AQ) | total i-BuOH (g) (ORG) | i-BuOH (g) (ORG) | i-BuOH from i-BuO-COFA (g) (ORG) | i-BuO-COFA (g) (ORG) |
|---|---|---|---|---|---|---|
| 8 | 0.1 | 1.62 | 1.98 | 1.98 | 0.00 | 0.01 |
| 8 | 2 | 1.56 | 2.04 | 2.04 | 0.00 | 0.00 |
| 8 | 4 | 1.59 | 2.01 | 2.01 | 0.00 | 0.00 |
| 8 | 21 | 1.59 | 2.01 | 2.00 | 0.01 | 0.04 |
| 8 | 25 | 1.55 | 2.05 | 2.04 | 0.01 | 0.04 |
| 8 | 46 | 1.45 | 2.15 | 2.12 | 0.02 | 0.11 |
| 9 | 0.1 | 1.57 | 2.03 | 2.02 | 0.01 | 0.04 |
| 9 | 2 | 1.54 | 2.06 | 1.86 | 0.19 | 0.86 |
| 9 | 4 | 1.44 | 2.16 | 1.79 | 0.36 | 1.64 |
| 9 | 21 | 1.14 | 2.46 | 0.95 | 1.51 | 6.82 |
| 9 | 25 | 1.10 | 2.50 | 0.83 | 1.67 | 7.50 |
| 9 | 46 | 0.78 | 2.82 | 0.44 | 2.37 | 10.7 |

Example 34

Production of Iso-Butyl Oleate by Lipase-Catalyzed Reaction of Isobutanol and Oleic Acid Reaction mixtures containing aqueous 2-(N-morpholino) ethanesulfonic acid buffer (0.20 M, pH 5.2), isobutanol (2-methyl-1-propanol), lipase (0 ppm or 10 ppm Lipolase® 100 L; Novozymes) and oleic acid (Alfa Aesar) (Table 22) were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 23).

TABLE 22

Reaction conditions for conversion of isobutanol (i-BuOH) to iso-butyl oleate (i-BuO-oleate)

| reaction # | MES buffer (0.2M) (g) | i-BuOH (g) | oleic acid (g) | lipase (ppm) |
|---|---|---|---|---|
| 10 | 46.11 | 3.64 | 14.62 | 10 |
| 11 | 46.10 | 3.59 | 14.40 | 0 |

TABLE 23

Weights of isobutanol (i-BuOH) and iso-butyl oleate (i-BuO-COFA) present in the aqueous fraction (AQ) and organic fraction (ORG) for reactions described in Table 22

| reaction | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| 10 | 0.1 | 1.37 | 2.28 | 2.24 | 0.04 | 0.18 |
| 10 | 2 | 1.30 | 2.34 | 1.95 | 0.40 | 1.81 |
| 10 | 4 | 1.28 | 2.37 | 1.82 | 0.55 | 2.53 |
| 10 | 6 | 1.22 | 2.42 | 1.71 | 0.72 | 3.27 |
| 10 | 23 | 0.92 | 2.72 | 0.71 | 2.01 | 9.20 |
| 10 | 27 | 0.89 | 2.75 | 0.65 | 2.11 | 9.62 |
| 10 | 47 | 0.81 | 2.84 | 0.55 | 2.29 | 10.5 |
| 10 | 51 | 0.82 | 2.83 | 0.54 | 2.29 | 10.5 |
| 11 | 0.1 | 1.44 | 2.16 | 2.16 | 0.00 | 0.00 |
| 11 | 2 | 1.45 | 2.15 | 2.15 | 0.00 | 0.00 |
| 11 | 4 | 1.44 | 2.16 | 2.16 | 0.00 | 0.00 |
| 11 | 6 | 1.43 | 2.16 | 2.16 | 0.00 | 0.00 |
| 11 | 23 | 1.49 | 2.10 | 2.10 | 0.01 | 0.02 |
| 11 | 27 | 1.46 | 2.14 | 2.13 | 0.01 | 0.04 |
| 11 | 47 | 1.48 | 2.12 | 2.09 | 0.02 | 0.10 |
| 11 | 51 | 1.52 | 2.07 | 2.05 | 0.02 | 0.11 |

Example 35

Comparison of Production of Iso-Butyl Oleate by Lipase-Catalyzed Reactions of Isobutanol and Oleic Acid Reaction mixtures containing aqueous 2-(N-morpholino) ethanesulfonic acid buffer (MES, 0.20 M, pH 5.2), isobutanol (2-methyl-1-propanol), oleic acid (Alfa Aesar), and lipase (10 ppm) from Lipolase® 100L, Lipex® 100L, Lipozyme® CALB L, Novozyme® CALA L, Palatase® from Novozymes, or lipase (10 ppm) from Pseudomonas fluorescens, Pseudomonas cepacia, Mucor miehei, hog pancreas, Candida cylindracea, Rhizopus niveus, Candida antarctica, Rhizopus arrhizus or Aspergillus from SigmaAldrich (Table 24), were stirred at 30° C., and samples were withdrawn from each reaction mixture at predetermined times, immediately centrifuged, and the aqueous and organic layers separated and analyzed for isobutanol (i-BuOH) and iso-butyl oleate (i-BuO-oleate) (Table 25).

TABLE 24

Reaction conditions for conversion of isobutanol (i-BuOH) to iso-butyl oleate (i-BuO-oleate)

| MES buffer (0.2M) (g) | i-BuOH (g) | oleic acid (g) | lipase (ppm) |
|---|---|---|---|
| 46.105 | 3.601 | 13.72 | 10 |

TABLE 25

Weights of isobutanol (i-BuOH) and iso-butyl oleate (i-BuO-oleate) present in the aqueous fraction (AQ) and organic fraction (ORG) for reactions described in Table 24

| lipase | time (h) | total i-BuOH (g) (AQ) | total i-BuOH (g) (ORG) | i-BuOH (g) (ORG) | i-BuOH from i-BuO-oleate (g) (ORG) | i-BuO-oleate (g) (ORG) |
|---|---|---|---|---|---|---|
| Lipolase ® 100L | 23 | 0.92 | 2.72 | 0.71 | 2.01 | 9.20 |
| Lipex ® 100L | 23 | 0.65 | 2.95 | 0.30 | 2.65 | 12.09 |
| Lipozyme ® CALB L | 23 | 1.01 | 2.59 | 0.82 | 1.77 | 8.08 |
| Novozyme ® CALA L | 23 | 1.39 | 2.22 | 2.16 | 0.06 | 0.27 |
| Palatase ® | 23 | 1.27 | 2.33 | 1.43 | 0.91 | 4.14 |
| Pseudomonas fluorescens | 23 | 1.38 | 2.22 | 1.97 | 0.25 | 1.14 |
| Pseudomonas cepacia | 23 | 1.39 | 2.21 | 1.95 | 0.26 | 1.20 |
| Mucor miehei | 23 | 1.29 | 2.31 | 1.57 | 0.75 | 3.42 |
| hog pancreas | 23 | 1.40 | 2.20 | 2.19 | 0.01 | 0.04 |
| Candida cylindracea | 23 | 1.15 | 2.45 | 1.08 | 1.37 | 6.25 |
| Rhizopus niveus | 23 | 1.39 | 2.21 | 2.19 | 0.02 | 0.11 |
| Candida antarctica | 23 | 1.37 | 2.24 | 2.08 | 0.15 | 0.69 |
| Rhizopus arrhizus | 23 | 1.01 | 2.59 | 0.81 | 1.78 | 8.12 |
| Aspergillus | 23 | 1.36 | 2.24 | 2.06 | 0.18 | 0.82 |
| no lipase | 23 | 1.49 | 2.10 | 2.10 | 0.01 | 0.02 |

Example 36

Production of Ethyl-COFA Ester by Lipase-Catalyzed Reaction of Ethanol and Corn Oil Fatty Acids (COFA)

Reaction mixtures containing aqueous 2-(N-morpholino) ethanesulfonic acid buffer (0.20 M, pH 5.5), ethanol, lipase (Lipolase® 100 L or Lipozyme® CALB L; Novozymes) and corn oil fatty acids prepared from corn oil (Table 26) were stirred at 30° C., and samples were withdrawn while stirring from each reaction mixture at predetermined times, immediately centrifuged, and the aqueous and organic layers separated and analyzed for ethanol and ethyl esters of corn oil fatty acids (EtO-COFA) (Table 27).

TABLE 26

Reaction conditions for conversion of ethanol (EtOH) to ethyl esters of corn oil fatty acids (EtO-COFA)

| Reaction | MES buffer (0.2M) (g) | ethanol (g) | COFA (g) | lipase | lipase (ppm) |
|---|---|---|---|---|---|
| 12 | 46.11 | 3.60 | 14.48 | Lipolase ® 100L | 10 |
| 13 | 46.10 | 3.60 | 14.47 | Lipozyme ® CALB L | 10 |
| 14 | 46.11 | 3.61 | 14.47 | no lipase | 0 |

TABLE 27

Weights of ethanol (EtOH) and ethyl esters of corn oil fatty acids (EtO-COFA) present in the aqueous fraction (AQ) and organic fraction (ORG) for reactions described in Table 26

| reaction | time (h) | total EtOH (g) (AQ) | total EtOH (g) (ORG) | EtOH (g) (ORG) | EtOH from EtO-COFA (g) (ORG) | ETO-COFA (g) (ORG) |
|---|---|---|---|---|---|---|
| 12 | 0 | 2.94 | 0.655 | 0.634 | 0.021 | 0.01 |
| 12 | 2 | 3.09 | 0.504 | 0.105 | 0.398 | 0.81 |
| 12 | 20 | 2.74 | 0.854 | 0.030 | 0.824 | 4.46 |
| 12 | 24 | 2.43 | 1.167 | 0.032 | 1.135 | 5.25 |
| 12 | 44 | 2.37 | 1.230 | 0.022 | 1.208 | 7.28 |
| 12 | 48 | 2.24 | 1.360 | 0.022 | 1.338 | 7.63 |
| 13 | 0 | 2.94 | 0.659 | 0.635 | 0.024 | 0.01 |
| 13 | 2 | 2.83 | 0.773 | 0.074 | 0.699 | 1.88 |
| 13 | 20 | 2.10 | 1.501 | 0.000 | 1.501 | 9.72 |
| 13 | 24 | 2.07 | 1.532 | 0.000 | 1.532 | 10.14 |
| 13 | 44 | 1.94 | 1.673 | 0.014 | 1.659 | 10.93 |
| 13 | 48 | 1.72 | 1.882 | 0.016 | 1.865 | 11.05 |
| 14 | 0 | 2.96 | 0.646 | 0.624 | 0.023 | 0.01 |
| 14 | 2 | 2.93 | 0.679 | 0.661 | 0.018 | 0.01 |
| 14 | 20 | 2.75 | 0.857 | 0.779 | 0.079 | 0.02 |
| 14 | 24 | 2.87 | 0.738 | 0.662 | 0.075 | 0.03 |
| 14 | 44 | 2.79 | 0.813 | 0.688 | 0.126 | 0.04 |
| 14 | 48 | 2.82 | 0.785 | 0.671 | 0.114 | 0.05 |

Example 37

Production of Ethyl-COFA Ester by Lipase-Catalyzed Reaction of Ethanol and Corn Oil Fatty Acids (COFA) during Fermentation of Yeast The wild-type yeast strain CEN.PK113-7D was propagated overnight in medium containing yeast nitrogen base without amino acids (6.7 g/L), dextrose (25 g/L), and MES buffer (0.1 M at pH 5.5). The overnight culture was diluted into fresh medium such that the resulting optical density at 600 nm was 0.1. The diluted culture was aliquoted, 25 mL per flask, into six 250 mL sealed-cap shake flasks. Four of the cultures were supplemented with either of two lipase enzyme stock solutions (2 mg protein/mL 10 mM phosphate buffer (pH 7.0) of Lipozyme® CALB L or Lipolase® 100L) to a final lipase concentration of 10 ppm in the media. Corn oil fatty acids (COFA) were added at a 1:1 volume ratio to the aqueous culture in three of the flasks (no enzyme, CALB L, or Lipolase® 100L). One flask had no supplements. The cultures were grown in a temperature-controlled shaking incubator at 30° C. and a shaking speed of 250 rpm for 23 hours. Samples for cell mass determination were allowed to phase separate in 15 mL conical bottom tubes. The sample's optical density at 600 nm was measured at a 20-fold dilution in saline. Samples (5 mL aqueous or 10 mL culture/COFA emulsion) for chromatographic analysis were immediately centrifuged for 5 minutes at 4000 rpm in a TX-400 swinging bucket rotor in 15 mL conical bottom tubes. For aqueous samples, a 0.22 µm spin filter was used prior to analysis. Aqueous samples were analyzed on a Shodex SH1011 column with a SH-G guard column using 0.01 M sulfuric acid mobile phase at 50° C. and a flow rate of 0.5 mL per minute. Detection of sugars and alcohols was by Refractive Index and 210 nm absorption, and quantitation was performed using standard curves. Samples were taken of the aqueous culture (no added COFA) or culture/COFA emulsion, and analyzed as described in previous Examples for ethyl esters of COFA. Results are shown in Tables 28 and 29.

TABLE 28

Weights of ethanol (EtOH), glucose and fermentation byproducts present in the aqueous media (AQ) from 23 h fermentations

|  | glucose (g/L) | glycerol (g/L) | acetate (g/L) | acetoin (g/L) | EtOH (g/L) |
|---|---|---|---|---|---|
| Media | 0 | 0.62 | 1.01 | 0.08 | 9.98 |
| media + CALB L | 0 | 0.72 | 0.94 | 0.06 | 9.94 |
| media + Lipolase ® 100L | 0 | 0.61 | 0.99 | 0.05 | 9.87 |
| media + COFA | 0 | 0.68 | 0.32 | 0.15 | 7.73 |
| media + COFA + CALB L | 0 | 0.74 | 0.09 | 0.11 | 3.92 |
| media + COFA + Lipolase ® 100L | 0 | 0.63 | 0.23 | 0.18 | 7.19 |

TABLE 29

Weights of ethanol (EtOH) and ethyl esters of corn oil fatty acids (EtO-COFA) present in the aqueous fraction (AQ) and the organic fraction (ORG) for 23 h fermentations

| Reaction | EtOH (g/L) (AQ) | EtOH (g/L) (ORG) | EtOH from EtO-COFA (g/L) (ORG) | ETO-COFA (g/L) (ORG) |
|---|---|---|---|---|
| media + COFA | 6.7 | 0 | 0.18 | 1.2 |
| media + COFA + CALB L | 3.4 | 0 | 4.52 | 30.0 |
| media + COFA + Lipolase ® 100L | 6.1 | 0 | 0.72 | 4.8 |

Example 38

Production of Methyl-COFA Ester by Lipase-Catalyzed Reaction of Methanol and Corn Oil Fatty Acids (COFA)

Reaction mixtures containing aqueous 2-(N-morpholino) ethanesulfonic acid buffer (0.20 M, pH 5.5), methanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 30) were stirred at 30° C., and samples were withdrawn while stirring from each reaction mixture at predetermined times, immediately centrifuged, and the aqueous and organic layers separated and analyzed for ethanol and ethyl esters of corn oil fatty acids (EtO-COFA) (Table 31).

TABLE 30

Reaction conditions for conversion of methanol (MeOH) to methyl esters of corn oil fatty acids (MeO-COFA)

| Reaction | MES buffer (0.2M) (g) | methanol (g) | COFA (g) | lipase | lipase (ppm) |
|---|---|---|---|---|---|
| 15 | 46.11 | 3.60 | 14.51 | Lipolase ® 100L | 10 |
| 16 | 46.10 | 3.59 | 14.49 | Lipozyme ® CALB L | 10 |
| 17 | 46.11 | 3.60 | 14.49 | *R. arrhizus* | 10 |
| 18 | 46.10 | 3.60 | 14.48 | *C. cylindracea* | 10 |
| 19 | 46.10 | 3.60 | 14.51 | no lipase | 10 |

TABLE 31

Weights of methanol (MeOH) and methyl esters of corn oil fatty acids (MeO-COFA) present in the aqueous fraction (AQ) and organic fraction (ORG) for reactions described in Table 30

| reaction | time (h) | total MeOH (g) (AQ) | total MeOH (g) (ORG) | MeOH (g) (ORG) | MeOH from MeO-COFA (g) (ORG) | MeO-COFA (g) (ORG) |
|---|---|---|---|---|---|---|
| 15 | 0 | 3.33 | 0.26 | 0.05 | 0.01 | 0.02 |
| 15 | 2 | 3.09 | 0.50 | 0.05 | 0.13 | 0.16 |
| 15 | 4 | 3.09 | 0.51 | 0.04 | 0.33 | 0.73 |
| 15 | 20 | 2.81 | 0.79 | 0.04 | 0.70 | 3.03 |
| 15 | 24 | 2.72 | 0.87 | 0.04 | 0.79 | 3.47 |
| 15 | 44 | 2.53 | 1.06 | 0.03 | 1.00 | 4.97 |
| 15 | 48 | 2.48 | 1.12 | 0.03 | 1.05 | 5.18 |
| 16 | 0 | 3.07 | 0.53 | 0.04 | 0.02 | 0.02 |
| 16 | 2 | 3.01 | 0.59 | 0.04 | 0.20 | 0.22 |
| 16 | 4 | 2.92 | 0.67 | 0.03 | 0.56 | 1.32 |
| 16 | 20 | 2.54 | 1.06 | 0.03 | 0.99 | 5.25 |
| 16 | 24 | 2.43 | 1.16 | 0.03 | 1.09 | 5.90 |
| 16 | 44 | 2.28 | 1.32 | 0.02 | 1.27 | 7.63 |
| 16 | 48 | 2.22 | 1.37 | 0.03 | 1.32 | 7.89 |
| 17 | 0 | 3.09 | 0.52 | 0.04 | 0.02 | 0.02 |
| 17 | 2 | 3.05 | 0.56 | 0.06 | 0.05 | 0.06 |
| 17 | 4 | 2.98 | 0.63 | 0.04 | 0.25 | 0.24 |
| 17 | 20 | 3.03 | 0.57 | 0.04 | 0.32 | 0.49 |
| 17 | 24 | 2.98 | 0.63 | 0.04 | 0.35 | 0.52 |
| 17 | 44 | 2.99 | 0.62 | 0.04 | 0.38 | 0.62 |
| 17 | 48 | 2.94 | 0.67 | 0.04 | 0.40 | 0.61 |
| 18 | 0 | 3.17 | 0.43 | 0.05 | 0.02 | 0.02 |
| 18 | 2 | 3.12 | 0.49 | 0.04 | 0.02 | 0.02 |
| 18 | 4 | 2.96 | 0.64 | 0.00 | 0.64 | 1.24 |
| 18 | 20 | 2.64 | 0.96 | 0.03 | 0.89 | 3.97 |
| 18 | 24 | 2.58 | 1.03 | 0.03 | 0.95 | 4.49 |
| 18 | 44 | 2.37 | 1.23 | 0.03 | 1.18 | 6.40 |
| 18 | 48 | 2.30 | 1.30 | 0.03 | 1.25 | 6.71 |
| 19 | 0 | 3.08 | 0.52 | 0.04 | 0.03 | 0.02 |
| 19 | 2 | 3.08 | 0.52 | 0.04 | 0.02 | 0.02 |
| 19 | 4 | 3.04 | 0.56 | 0.04 | 0.03 | 0.02 |
| 19 | 20 | 3.08 | 0.53 | 0.04 | 0.03 | 0.03 |
| 19 | 24 | 3.04 | 0.56 | 0.05 | 0.03 | 0.04 |
| 19 | 44 | 3.01 | 0.59 | 0.04 | 0.06 | 0.04 |
| 19 | 48 | 2.95 | 0.65 | 0.05 | 0.06 | 0.04 |

Example 39

Production of 1-Propyl-COFA Ester by Lipase-Catalyzed Reaction of 1-Propanol and Corn Oil Fatty Acids (COFA)

Reaction mixtures containing aqueous 2-(N-morpholino) ethanesulfonic acid buffer (0.20 M, pH 5.5), 1-propanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 32) were stirred at 30° C., and samples were withdrawn while stirring from each reaction mixture at predetermined times, immediately centrifuged, and the aqueous and organic layers separated and analyzed for 1-propanol and 1-propyl esters of corn oil fatty acids (PrO-COFA) (Table 33).

TABLE 32

Reaction conditions for conversion of 1-propanol (PrOH) to 1-propyl esters of corn oil fatty acids (PrO-COFA)

| Reaction | MES buffer (0.2M) (g) | 1-propanol (g) | COFA (g) | lipase | lipase (ppm) |
|---|---|---|---|---|---|
| 20 | 46.11 | 3.60 | 14.47 | Lipolase ® 100L | 10 |
| 21 | 46.12 | 3.60 | 14.48 | Lipozyme ® CALB L | 10 |
| 22 | 46.10 | 3.60 | 14.48 | R. arrhizus | 10 |
| 23 | 46.13 | 3.62 | 14.49 | C. cylindracea | 10 |
| 24 | 46.13 | 3.60 | 14.48 | no lipase | 0 |

TABLE 33

Weights of 1-propanol (PrOH) and 1-propyl esters of corn oil fatty acids (PrO-COFA) present in the aqueous fraction (AQ) and organic fraction (ORG) for reactions described in Table 32

| reaction | time (h) | total PrOH (g) (AQ) | total PrOH (g) (ORG) | PrOH (g) (ORG) | PrOH from PrO-COFA (g) (ORG) | PrO-COFA (g) (ORG) |
|---|---|---|---|---|---|---|
| 20 | 0 | 2.54 | 1.05 | 0.80 | 0.00 | 0.02 |
| 20 | 2 | 2.39 | 1.20 | 0.70 | 0.11 | 0.44 |
| 20 | 4 | 2.00 | 1.60 | 0.61 | 0.55 | 1.88 |
| 20 | 20 | 1.65 | 1.95 | 0.31 | 1.50 | 6.96 |
| 20 | 24 | 1.51 | 2.08 | 0.28 | 1.69 | 7.97 |
| 20 | 44 | 1.13 | 2.46 | 0.16 | 2.23 | 11.09 |
| 20 | 48 | 1.09 | 2.51 | 0.15 | 2.29 | 11.27 |
| 21 | 0 | 2.44 | 1.16 | 0.79 | 0.00 | 0.02 |
| 21 | 2 | 2.38 | 1.22 | 0.65 | 0.13 | 0.49 |
| 21 | 4 | 2.07 | 1.53 | 0.52 | 0.73 | 2.94 |
| 21 | 20 | 1.16 | 2.43 | 0.17 | 2.18 | 10.80 |
| 21 | 24 | 1.08 | 2.51 | 0.16 | 2.28 | 11.26 |
| 21 | 44 | 1.00 | 2.60 | 0.13 | 2.40 | 11.86 |
| 21 | 48 | 0.98 | 2.62 | 0.13 | 2.42 | 11.91 |
| 22 | 0 | 2.49 | 1.11 | 0.80 | 0.00 | 0.02 |
| 22 | 2 | 2.42 | 1.18 | 0.76 | 0.10 | 0.38 |
| 22 | 4 | 2.23 | 1.37 | 0.71 | 0.29 | 1.08 |
| 22 | 20 | 2.09 | 1.51 | 0.56 | 0.71 | 2.96 |
| 22 | 24 | 2.06 | 1.54 | 0.54 | 0.77 | 3.17 |
| 22 | 44 | 1.87 | 1.73 | 0.47 | 0.58 | 1.75 |
| 22 | 48 | 1.88 | 1.73 | 0.46 | 0.60 | 1.82 |
| 23 | 0 | 2.49 | 1.13 | 0.80 | 0.00 | 0.02 |
| 23 | 2 | 2.45 | 1.17 | 0.77 | 0.07 | 0.29 |
| 23 | 4 | 2.35 | 1.27 | 0.71 | 0.21 | 0.82 |
| 23 | 20 | 2.00 | 1.61 | 0.50 | 0.89 | 3.74 |
| 23 | 24 | 1.93 | 1.68 | 0.49 | 0.99 | 4.23 |
| 23 | 44 | 1.57 | 2.04 | 0.33 | 1.56 | 6.83 |
| 23 | 48 | 1.49 | 2.13 | 0.31 | 1.67 | 7.33 |
| 24 | 0 | 2.49 | 1.11 | 0.81 | 0.00 | 0.02 |
| 24 | 2 | 2.47 | 1.13 | 0.81 | 0.00 | 0.02 |
| 24 | 4 | 2.38 | 1.21 | 0.78 | 0.01 | 0.03 |
| 24 | 20 | 2.46 | 1.14 | 0.79 | 0.01 | 0.05 |
| 24 | 24 | 2.42 | 1.17 | 0.79 | 0.01 | 0.05 |
| 24 | 44 | 2.41 | 1.19 | 0.76 | 0.02 | 0.09 |
| 24 | 48 | 2.32 | 1.28 | 0.77 | 0.03 | 0.10 |

Example 40

Production of 1-Pentyl-COFA Ester by Lipase-Catalyzed Reaction of 1-Pentanol and Corn Oil Fatty Acids (COFA)

Reaction mixtures containing aqueous 2-(N-morpholino)ethanesulfonic acid buffer (0.20 M, pH 5.5), 1-pentanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 34) were stirred at 30° C., and samples were withdrawn while stirring from each reaction mixture at predetermined times, immediately centrifuged, and the aqueous and organic layers separated and analyzed for 1-pentanol and 1-pentyl esters of corn oil fatty acids (PenO-COFA) (Table 35).

TABLE 34

Reaction conditions for conversion of 1-pentanol (PenOH) to 1-pentyl esters of corn oil fatty acids (PenO-COFA)

| Reaction | MES buffer (0.2M) (g) | 1-pentanol (g) | COFA (g) | lipase | lipase (ppm) |
|---|---|---|---|---|---|
| 25 | 46.11 | 3.60 | 14.47 | Lipolase ® 100L | 10 |
| 26 | 46.12 | 3.60 | 14.48 | Lipozyme ® CALB L | 10 |
| 27 | 46.10 | 3.60 | 14.48 | R. arrhizus | 10 |
| 28 | 46.13 | 3.62 | 14.49 | C. cylindracea | 10 |
| 29 | 46.13 | 3.60 | 14.48 | no lipase | 0 |

TABLE 35

Weights of 1-pentanol (PenOH) and 1-pentyl esters of corn oil fatty acids (PenO-COFA) present in the aqueous fraction (AQ) and organic fraction (ORG) for reactions described in Table 34

| reaction | time (h) | total PenOH (g) (AQ) | total PenOH (g) (ORG) | PenOH (g) (ORG) | PenOH from PenO-COFA (g) (ORG) | PenO-COFA (g) (ORG) |
|---|---|---|---|---|---|---|
| 25 | 0 | 0.364 | 3.238 | 3.091 | 0.002 | 0.006 |
| 25 | 2 | 0.339 | 3.264 | 2.745 | 0.446 | 1.760 |
| 25 | 4 | 0.373 | 3.229 | 2.761 | 0.557 | 2.196 |
| 25 | 20 | 0.336 | 3.266 | 1.833 | 1.002 | 3.953 |
| 25 | 24 | 0.325 | 3.277 | 1.575 | 1.257 | 4.960 |
| 25 | 44 | 0.226 | 3.377 | 0.921 | 2.383 | 9.400 |
| 25 | 48 | 0.206 | 3.396 | 0.723 | 2.524 | 9.957 |
| 26 | 0 | 0.364 | 3.243 | 3.105 | 0.002 | 0.006 |
| 26 | 2 | 0.317 | 3.290 | 2.462 | 0.512 | 2.019 |
| 26 | 4 | 0.320 | 3.287 | 2.287 | 0.652 | 2.574 |
| 26 | 20 | 0.130 | 3.477 | 0.387 | 3.007 | 11.860 |
| 26 | 24 | 0.094 | 3.513 | 0.215 | 3.251 | 12.823 |
| 26 | 44 | 0.075 | 3.532 | 0.165 | 3.312 | 13.067 |
| 26 | 48 | 0.081 | 3.526 | 0.165 | 3.326 | 13.120 |
| 27 | 0 | 0.384 | 3.216 | 3.102 | 0.002 | 0.006 |
| 27 | 2 | 0.356 | 3.244 | 2.957 | 0.437 | 1.725 |
| 27 | 4 | 0.333 | 3.267 | 2.912 | 0.388 | 1.532 |
| 27 | 20 | 0.363 | 3.237 | 2.664 | 0.433 | 1.707 |
| 27 | 24 | 0.367 | 3.233 | 2.597 | 0.665 | 2.623 |
| 27 | 44 | 0.366 | 3.234 | 2.473 | 0.549 | 2.166 |
| 27 | 48 | 0.347 | 3.253 | 2.473 | 0.559 | 2.205 |
| 28 | 0 | 0.369 | 3.244 | 3.086 | 0.002 | 0.006 |
| 28 | 2 | 0.329 | 3.284 | 2.523 | 0.435 | 1.717 |
| 28 | 4 | 0.332 | 3.281 | 2.496 | 0.493 | 1.944 |
| 28 | 20 | 0.304 | 3.309 | 1.575 | 1.321 | 5.209 |
| 28 | 24 | 0.270 | 3.343 | 1.292 | 1.868 | 7.367 |
| 28 | 44 | 0.186 | 3.427 | 0.596 | 2.722 | 10.735 |
| 28 | 48 | 0.162 | 3.451 | 0.509 | 2.846 | 11.224 |
| 29 | 0 | 0.375 | 3.239 | 3.102 | 0.001 | 0.006 |
| 29 | 2 | 0.366 | 3.248 | 3.117 | 0.009 | 0.034 |
| 29 | 4 | 0.377 | 3.237 | 3.099 | 0.023 | 0.089 |
| 29 | 20 | 0.380 | 3.234 | 3.092 | 0.032 | 0.125 |
| 29 | 24 | 0.379 | 3.235 | 3.058 | 0.039 | 0.154 |
| 29 | 44 | 0.374 | 3.240 | 3.013 | 0.053 | 0.209 |
| 29 | 48 | 0.373 | 3.241 | 2.950 | 0.059 | 0.233 |

Example 41

Production of 2-Methyl-1-Butyl-COFA Ester by Lipase-Catalyzed Reaction of 2-Methyl-1-Butanol and Corn Oil Fatty Acids (COFA)

Reaction mixtures containing aqueous 2-(N-morpholino) ethanesulfonic acid buffer (0.20 M, pH 5.5), 2-methyl-1-butanol, lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 36) were stirred at 30° C., and samples were withdrawn while stirring from each reaction mixture at predetermined times, immediately centrifuged, and the aqueous and organic layers separated and analyzed for 2-methyl-1-butanol and 2-methyl-1-butyl esters of corn oil fatty acids (MeBO-COFA) (Table 37).

TABLE 36

Reaction conditions for conversion of 2-methyl-1-butanol (MeBOH) to 2-methyl-1-butyl esters of corn oil fatty acids (MeBO-COFA)

| Reaction | MES buffer (0.2M) (g) | 2-methyl-1-butanol (g) | COFA (g) | lipase | lipase (ppm) |
|---|---|---|---|---|---|
| 30 | 46.27 | 3.60 | 14.48 | Lipolase ® 100L | 10 |
| 31 | 46.14 | 3.60 | 14.48 | Lipozyme ® CALB L | 10 |
| 32 | 46.12 | 3.60 | 14.47 | *R. arrhizus* | 10 |
| 33 | 46.11 | 3.49 | 14.47 | *C. cylindracea* | 10 |
| 34 | 46.18 | 3.60 | 14.47 | no lipase | 0 |

TABLE 37

Weights of 2-methyl-1-butanol (MeBOH) and 2-methyl-1-butyl esters of corn oil fatty acids (MeBO-COFA) present in the aqueous fraction (AQ) and organic fraction (ORG) for reactions described in Table 36

| reaction | time (h) | total MeBOH (g) (AQ) | total MeBOH (g) (ORG) | MeBOH (g) (ORG) | MeBOH from MeBO-COFA (g) (ORG) | MeBO-COFA (g) (ORG) |
|---|---|---|---|---|---|---|
| 30 | 0 | 0.000 | 3.603 | 3.103 | 0.002 | 0.008 |
| 30 | 2 | 0.009 | 3.593 | 2.919 | 0.630 | 2.484 |
| 30 | 4 | 0.058 | 3.545 | 2.766 | 0.673 | 2.653 |
| 30 | 20 | 0.005 | 3.598 | 2.041 | 1.331 | 5.250 |
| 30 | 24 | 0.029 | 3.574 | 1.967 | 1.418 | 5.594 |
| 30 | 44 | 0.017 | 3.585 | 1.218 | 2.174 | 8.577 |
| 30 | 48 | 0.008 | 3.595 | 1.099 | 2.085 | 8.224 |
| 31 | 0 | 0.000 | 3.595 | 3.129 | 0.003 | 0.010 |
| 31 | 2 | 0.003 | 3.592 | 2.665 | 0.692 | 2.730 |
| 31 | 4 | 0.012 | 3.583 | 2.510 | 0.839 | 3.308 |
| 31 | 20 | 0.001 | 3.594 | 1.408 | 1.932 | 7.622 |
| 31 | 24 | 0.005 | 3.590 | 1.293 | 2.082 | 8.214 |
| 31 | 44 | 0.006 | 3.589 | 0.970 | 2.437 | 9.612 |
| 31 | 48 | 0.007 | 3.588 | 0.918 | 2.495 | 9.840 |
| 32 | 0 | 0.000 | 3.597 | 3.100 | 0.003 | 0.011 |
| 32 | 2 | 0.017 | 3.580 | 2.855 | 0.588 | 2.321 |
| 32 | 4 | 0.000 | 3.597 | 2.783 | 0.675 | 2.664 |
| 32 | 20 | 0.000 | 3.597 | 2.392 | 1.027 | 4.051 |
| 32 | 24 | 0.000 | 3.597 | 2.337 | 1.081 | 4.266 |
| 32 | 44 | 0.001 | 3.596 | 2.209 | 1.191 | 4.697 |
| 32 | 48 | 0.000 | 3.597 | 2.174 | 1.216 | 4.798 |
| 33 | 0 | 0.000 | 3.597 | 3.093 | 0.002 | 0.008 |
| 33 | 2 | 0.001 | 3.596 | 1.756 | 1.398 | 5.514 |
| 33 | 4 | 0.003 | 3.594 | 2.116 | 1.026 | 4.046 |
| 33 | 20 | 0.027 | 3.570 | 0.607 | 2.865 | 11.302 |
| 33 | 24 | 0.000 | 3.597 | 0.429 | 3.097 | 12.216 |
| 33 | 44 | 0.007 | 3.590 | 0.205 | 3.345 | 13.194 |
| 33 | 48 | 0.003 | 3.594 | 0.202 | 3.353 | 13.228 |
| 34 | 0 | 0.000 | 3.485 | 3.014 | 0.003 | 0.011 |
| 34 | 2 | 0.000 | 3.485 | 2.991 | 0.021 | 0.083 |
| 34 | 4 | 0.000 | 3.485 | 3.020 | 0.012 | 0.046 |
| 34 | 20 | 0.000 | 3.485 | 2.970 | 0.029 | 0.115 |
| 34 | 24 | 0.002 | 3.483 | 2.949 | 0.037 | 0.148 |
| 34 | 44 | 0.000 | 3.485 | 2.912 | 0.047 | 0.185 |
| 34 | 48 | 0.000 | 3.485 | 2.909 | 0.051 | 0.200 |

Example 42

Production of Isopropyl-COFA Ester by Lipase-Catalyzed Reaction of Isopropanol and Corn Oil Fatty Acids (COFA)

Reaction mixtures containing aqueous 2-(N-morpholino) ethanesulfonic acid buffer (0.20 M, pH 5.5), isopropanol (2-propanol), lipase (Lipolase® 100 L (Novozymes), Lipozyme® CALB L (Novozymes), *Rhizopus arrhizus* lipase (SigmaAldrich), and *Candida cylindracea* lipase (SigmaAldrich) and corn oil fatty acids prepared from corn oil (Table 38) were stirred at 30° C., and samples were withdrawn while stirring from each reaction mixture at predetermined times, immediately centrifuged, and the aqueous and organic layers separated and analyzed for isopropanol and isopropyl esters of corn oil fatty acids (i-PrO-COFA) (Table 39).

TABLE 38

Reaction conditions for conversion of isopropanol (i-PrOH) to isopropyl esters of corn oil fatty acids (i-PrO-COFA)

| Reaction | MES buffer (0.2M) (g) | isopropanol (g) | COFA (g) | lipase | lipase (ppm) |
|---|---|---|---|---|---|
| 35 | 46.14 | 3.60 | 14.48 | Lipozyme ® CALB L | 10 |
| 36 | 46.11 | 3.49 | 14.47 | *C. cylindracea* | 10 |
| 37 | 46.18 | 3.60 | 14.47 | no lipase | 0 |

TABLE 39

Weights of isopropanol (i-PrOH) and isopropyl esters of corn oil fatty acids (i-PrO-COFA) present in the organic fraction (ORG) for reactions described in Table 38

| reaction | time (h) | i-PrOH from i-PRO-COFA (g) (ORG) | i-PrO-COFA (g) (ORG) |
|---|---|---|---|
| 35 | 0 | 0.001 | 0.00 |
| 35 | 2 | 0.013 | 0.07 |
| 35 | 4 | 0.038 | 0.20 |
| 35 | 20 | 0.132 | 0.71 |
| 35 | 24 | 0.177 | 0.94 |
| 35 | 44 | 0.291 | 1.55 |
| 35 | 48 | 0.301 | 1.61 |
| 36 | 0 | 0.001 | 0.01 |
| 36 | 2 | 0.051 | 0.27 |

TABLE 39-continued

Weights of isopropanol (i-PrOH) and isopropyl esters of corn oil fatty acids (i-PrO-COFA) present in the organic fraction (ORG) for reactions described in Table 38

| reaction | time (h) | i-PrOH from i-PRO-COFA (g) (ORG) | i-PrO-COFA (g) (ORG) |
|---|---|---|---|
| 36 | 4 | 0.163 | 0.87 |
| 36 | 20 | 0.532 | 2.84 |
| 36 | 24 | 0.652 | 3.48 |
| 36 | 44 | 0.916 | 4.89 |
| 36 | 48 | 0.959 | 5.12 |
| 37 | 0 | 0.001 | 0.01 |
| 37 | 2 | 0.001 | 0.01 |
| 37 | 4 | 0.003 | 0.02 |
| 37 | 20 | 0.009 | 0.05 |
| 37 | 24 | 0.011 | 0.06 |
| 37 | 44 | 0.016 | 0.09 |
| 37 | 48 | 0.023 | 0.12 |

Example 43

Comparison of Partition Coefficients for Isobutanol Between Water and Extractant Aqueous solutions of isobutanol (30 g/L) were mixed with corn oil fatty acids (COFA), or oleic acid or corn oil triglycerides, and their measured partition coefficients reported in the table relative to the measured partition coefficient for oleyl alcohol. Results are shown in Table 40.

TABLE 40

Relative partition coefficients for isobutanol (30 g/L) between water and extractant

| extractant | isobutanol partition coefficient, relative to oleyl alcohol |
|---|---|
| oleyl alcohol | 100% |
| corn oil fatty acids | 91% |
| corn oil fatty acid isobutyl esters | 43% |
| corn oil triglycerides | 10% |

Example 44

Production of Corn Oil Fatty Acids

A five-liter (5 L) round bottom flask equipped with a mechanical stirrer, thermocouple, heating mantle, condenser and nitrogen tee was charged with 750 g of crude corn oil (non-food grade, recovered from an ethanol fermentation facility), 2112 g of water and 285 g of 50% sodium hydroxide solution. Mixture was heated to 90° C. and held for two hours, during which time it became a single thick, emulsion-like single phase. At the end of this time, TLC shows no remaining corn oil in the mixture. The mixture was then cooled to 74° C. and 900 g of 25% sulfuric acid was added to acidify the mixture. It was then cooled to 50° C. and the aqueous layer was drained. The oil layer was washed twice with 1500 mL of 40° C. water and then once with 1 liter of saturated brine. It was dried over magnesium sulfate and filtered through Celite. Yield was 610 g of clear red oil. Titration for free fatty acids via AOCS method Ca 5a-40 shows a fatty acid content of 95% expressed as oleic acid. A sample was silanized by reacting 104 mg with 100 uL of N-methyl-N-(trimethylsilyl)trifluoroacetamide in 1 mL of dry pyridine. Gas chromatography-mass spectrometry (GCMS) analysis of the silanized product shows the presence of the TMS derivatives of the 16:0, 18:2, 18:1, 18:0, and 20:0 acids.

Example 45

Chemical Synthesis of FABE

A 3 L flask was equipped with a mechanical stirrer, thermocouple, nitrogen inlet, heating mantle and a condenser. The flask was charged with COFA (595 g) (prepared as in Example 44), isobutanol (595 g), and sulfuric acid (12 g). The mixture was refluxed for 1.5 hours at which time the condenser was removed and replaced with a still head. Distillate was collected over three hours with an initial head temperature of 90° C. and a final head temperature of 105° C. The mixture was then cooled to room temperature and 500 mL of DI water was added. The layers were separated and the organic layer was washed five times with 500 mL of DI water. It was then washed once with 500 mL of a 10% calcium chloride solution followed by six washings with 500 mL of DI water. The oil was then dried over magnesium sulfate and filtered through a bed of Celite yielding 601 g of a clear red oil. GC analysis shows the presence of 0.36 wt % of isobutanol. GC/MS analysis shows the presence of isobutyl palmitate, isobutyl stearate, isobutyl oleate, isobutyl linoleate, and isobutyl linolenate.

Example 46

Recovery of Butanol Using an Inorganic Acid Catalyst

A 1 liter round bottom flask with magnetic stirring and a 12" column packed with Rasching rings topped with a still head and nitrogen inlet was used. The flask was charged with 254 g FABE synthesized as in Example 45, 255 g COFA, 100 mL water, and 5 g sulfuric acid, and heated to a pot temperature of 93° C. Head temperature was equilibrated at 89.7° C. The first cut was collected with a reflux ratio that maintained the head temperature between 89 and 94° C.

The reaction was cooled and sat at room temperature for three days. GC analysis of the pot shows a total of 1 g of isobutanol in the pot. The distillation was restarted and three more cuts, each of 25 mL, were collected. One hundred (100) mL of water was added to the pot after collecting cut #2. Four cuts were collected and analyzed with the results shown in Table 41.

GC analysis was done using a Hewlett Packard 6890 GC using a 30 m FFAP column. Samples were dissolved in isopropanol and 1-pentanol was added as an internal standard. Standard curves were made for isobutanol, isobutyl palmitate, isobutyl stearate, isobutyl oleate, isobutyl linoleate, isobutyl linolenate, isobutyl arachidate, palmitic acid, stearic acid, oleic acid, linoleic acid and linolenic acid. FABE content is reported as the sum of the butyl esters and COFA content as the sum of the fatty acids.

TABLE 41

Composition analysis of cuts collected

| | i-BuOH mg/ml | mL | wt of i-BuOH |
|---|---|---|---|
| Cut 1 | 60 | 43 | 2.6 |
| Cut 2 | 41 | 23.4 | 1 |
| Cut 3 | 29 | 24.2 | 0.7 |
| Cut 4 | 30 | 27 | 0.8 |
| Total | | 117.6 | 5.1 |

Example 47

Recovery of Butanol Using an Organic Acid Catalyst

A 1 liter 3 neck round bottom flask equipped with magnetic stirrer, thermocouple, addition funnel and still head was used. The flask charged with 100 g FABE synthesized as in Example 45, 100 g COFA, 5 g p-toluenesulfonic acid, and 25 mL water. Isobutanol analysis of initial pot shows 1.1 g of isobutanol present (contaminant in FABE). The pot was heated to 125° C. When the pot reached 116° C. head temperature was 96° C., and 125 mL water was added over 2.5 hours. Six cuts were collected over the time that the water was added and they were analyzed by GC as in Example 46. Results are provided in Table 42.

TABLE 42

Composition analysis of cuts collected

| cut | pot temp | head temp | mL of water added | mg/ml i-BuOH in cut | mL | g i-BuOH in cut |
|---|---|---|---|---|---|---|
| #1 | 116 | 96 | 25 | 53 | 13 | 0.7 |
| #2 | 117 | 98 | 47 | 52 | 26 | 1.4 |
| #3 | 117 | 99 | 70 | 37 | 24 | 0.9 |
| #4 | 117 | 99 | 95 | 30 | 22 | 0.7 |
| #5 | 117 | 99 | 125 | 23 | 31 | 0.7 |
| #6 | 117 | 99 |  | 39 | 41 | 1.6 |
| Total |  |  |  |  |  | 5.9 |

Butanol analysis of the remaining still pot shows 0.9 g of free isobutanol present. The initial COFA:FABE mixture analyzed was 45 wt % FABE. The final pot analyzed was 32 wt % FABE.

Example 48

Hydrolysis of FABE with Water at High Temperature

A 1 liter autoclave was charged with FABE synthesized as in Example 45, 300 mL and 300 mL water. It was sealed and purged with nitrogen. Stirring was started and it was then heated to 250° C. over 45 minutes and samples were removed every hour after reaching temperature. The samples were analyzed by GC as in Example 46. The oil phase samples showed the compositions as a function of time shown in Table 43.

TABLE 43

Composition of organic phase of samples

| Time | wt % i-BuOH | wt % FABE | wt % COFA |
|---|---|---|---|
| 0 | 0 | 97 | 2 |
| 1 | 3 | 76 | 18 |
| 2 | 6 | 50 | 41 |
| 3 | 7 | 36 | 45 |
| 4 | 7 | 34 | 48 |
| 5 | 7 | 35 | 51 |

Example 49

Hydrolysis of FABE with Dilute Acid at High Temperature

A 1 liter autoclave was charged with 450 g of a 75/25 mixture of FABE synthesized as in Example 45 and COFA and with 150 g of 2% sulfuric acid. It was sealed and purged with nitrogen. Stirring was started and it was then heated to 225° C. over 45 minutes and samples were removed every hour after reaching temperature. The samples were analyzed by GC as in Example 46. The oil phase samples showed the compositions as a function of time shown in Table 44.

TABLE 44

Composition analysis of cuts collected

| Time (h) | wt % i-BuOH | wt % FABE | wt % COFA |
|---|---|---|---|
| 0 | 2.2 | 61.8 | 34.1 |
| 1 | 3.8 | 47.8 | 42.0 |
| 2 | 5.2 | 38.4 | 48.2 |
| 3 | 5.3 | 38.4 | 53.5 |
| 4 | 5.1 | 33.4 | 48.2 |
| 5 | 5.1 | 31.9 | 43.3 |
| 6 | 5.5 | 35.2 | 51.7 |

Example 50

Hydrolysis of FABE with Sulfuric Acid in Solvent at 100° C.

A solution of 5 g FABE synthesized as in Example 45, 5 g of 25% sulfuric acid, and 60 g of diethyleneglycol dimethyl ether was prepared. Ten (10) g of the solution was added to each of five vials which were then sealed. All of the vials were heated to 100° C. and one vial was removed from the heater and analyzed every hour. The resulting compositions were determined by GC (as described in Example 46) and are reported in Table 45.

TABLE 45

Composition analysis of cuts collected

| Time (h) | wt % i-BuOH | wt % FABE | wt % COFA |
|---|---|---|---|
| 0 | 0.11 | 5.74 | 0 |
| 1 | 1.1 | 1.72 | 1.23 |
| 2 | 1.32 | 0.96 | 1.77 |
| 3 | 1.35 | 0.76 | 1.8 |
| 4 | 1.38 | 0.7 | 1.81 |
| 5 | 1.37 | 0.72 | 1.82 |
| 15 | 1.37 | 0.84 | 2.12 |

Example 51

Hydrolysis of FABE by Reactive Distillation

A 12 liter flask was equipped with an insulated 2"×30" column topped with a feed inlet and a still head. The column was randomly packed with one liter of Pro-pak® (316 SS 0.16") still packing and 500 g of Amberlyst® 36 solid acid catalyst (Dow). The flask was charged with 6 liters of water and brought to a boil. The heat was controlled to have a water distillation rate of about 1.8 mL/min. FABE synthesized as per the method described in Example 45 was added to the top of the column at a rate of 2 g/min. The feed was continued for a total of 60 minutes. The distillation was continued for another 30 minutes. A total of 194 g of distillate was collected which contained 2.1 g of isobutanol. Based on the amount of FABE fed this represents a 9% conversion of FABE to butanol.

Example 52

Hydrolysis of FABE by Counter Current Steam

The apparatus as described in example 50 was modified by the addition of heat tape wrapped around the still column. The temperature in the upper half of the column was adjusted to 115° C. and the temperature in the lower half of the column was adjusted to 104° C. The pot was brought to a boil and the pot heat was adjusted until water was distilling at a rate of 1.5-2 mL/min. FABE (346 g) synthesized as per the method described in Example 45 was fed to the top of the packed column over a period of three hours while the distillation continued. After the feed period the distillation was continued for another 90 minutes. A total of 486 g of distillate was collected that contained 30.1 g of isobutanol. This represents a conversion of FABE to isobutanol of 39%.

Example 53

Hydrolysis Catalyzed by a Water Insoluble Organic Acid

A one liter 3 n round bottom flask equipped with an oil bath, mechanical stirrer, nitrogen inlet, subsurface water inlet, and a still head was charged with 150 g of FABE, 50 g water, and 5 g dodecylbenzene sulfonic acid. An oil bath was heated to 95-100° C. and a slow nitrogen sweep started. Distillate cuts were collected every half hour for a total of five hours. After three hours, water was fed to the still pot at a rate of 15 mL/hr. Distillate cuts were analyzed for isobutanol content by the GC method described in Example 46 and the results are shown in Table 46. Approximately 44% of the isobutanol contained in the FABE was collected over five hours.

TABLE 46

| Sample | Cumulative i-BuOH collected (g) |
|---|---|
| 1 | 0.80 |
| 2 | 1.47 |
| 3 | 2.46 |
| 4 | 3.99 |
| 5 | 5.71 |
| 6 | 7.75 |
| 7 | 9.16 |
| 8 | 10.33 |
| 9 | 13.76 |
| 10 | 14.37 |

Example 54

Hydrolysis Catalyzed by Solid Acid Catalyst

A one liter 3 n round bottom flask equipped with an oil bath, mechanical stirrer, subsurface nitrogen inlet, subsurface water inlet, and a still head was charged with 150 g of FABE and 50 g of dry Amberlyst 15 solid acid catalyst. The flask was heated to 110° C. with the oil bath and water was added via a syringe pump at a rate of 15 mL/hr. Distillation fractions were collected every half hour for a total of five hours. The fractions were analyzed for isobutanol content by the GC method described in Example 46 and the results are shown in Table 47. Approximately 44% of the theoretical amount of isobutanol contained in the FABE was collected over five hours.

TABLE 47

| Sample | Cumulative i-BuOH collected (g) |
|---|---|
| 1 | 0.3 |
| 2 | 0.9 |
| 3 | 2.3 |
| 4 | 3.4 |
| 5 | 4.4 |
| 6 | 5.5 |
| 7 | 6.3 |
| 8 | 6.9 |
| 9 | 7.4 |
| 10 | 8.0 |

Example 55

Hydrolysis Catalyzed by Water Soluble Organic Acid Catalyst

A one liter flask with mechanical stirrer, subsurface nitrogen inlet, subsurface water inlet, and a still head was charged with 200 g of FABE and 10 g of p-toluenesulfonic acid. The flask was stirred and heated to 110° C. with an oil bath at which time water was added at a rate of 20 mL/hr via a syringe pump. Still fractions were collected every half hour for a total of three hours. The fractions were analyzed for isobutanol content by the GC method described in Example 46 and the results are shown in Table 48. Approximately 30% of the theoretical amount of isobutanol contained in the FABE was collected over five hours.

TABLE 48

| Fraction | Cumulative amount of isobutanol |
|---|---|
| 1 | 1.0 |
| 2 | 4.0 |
| 3 | 7.2 |
| 4 | 9.5 |
| 5 | 11.8 |
| 6 | 13.4 |

Example 56

Hydrolysis of Solvent Phases from Fermentation

A. Solvent Phase 1

The solvent phase from the fermentation shown in Example 17 was analyzed by the GC method shown in Example 46 and the results are shown in Table 49. The analysis shows primarily FABE and fatty acids with a small amount of material with a retention time consistent with FAEE. Analysis of just the butyl esters and acids shows a ratio of 62% FABE and 39% fatty acids.

The solvent phase (1.25 liters, 1090 g) and 1.25 liters of water were charged to a one gallon autoclave. The autoclave was sealed and heated to 250° C. and held at temperature for four hours. The autoclave was then cooled and opened, giving an emulsion. The mixture was filtered through a bed of Celite and the layers were separated. The organic layer was washed three times with one liter of water. The sample was then heated to 50° C. and purged with nitrogen for six hours. GC analysis shows no i-BuOH and a ratio of 33% FABE and 67% fatty acids. An amber oil (993.9 g) was obtained. A detailed compositional analysis of the original solvent phase from fermentation Example 17 and the post-hydrolysis solvent phase is shown in Table 50.

B. Solvent Phase 2

The solvent phase from the fermentation shown in Example 18 was analyzed by the GC method shown in Example 46 and the results are shown in Table 49. The analysis shows primarily FABE and fatty acids with a small amount of material with a retention time consistent with FAEE. Analysis of just the butyl esters and acids shows a ratio of 45% FABE and 55% fatty acids.

The solvent (1.25 liters, 1100 g) and 1.25 liters of water charged to a one gallon autoclave. The autoclave was sealed and heated to 250° C. and held at temperature for four hours. The autoclave was then cooled and opened, giving an emulsion. The mixture was filtered through a bed of Celite and the layers were separated. The organic layer was washed three times with one liter of water. The sample was then heated to 50° C. and purged with nitrogen for six hours. GC analysis shows no i-BuOH and a ratio of 28% FABE and 72% fatty acids. An amber oil (720.5 g) was obtained.

TABLE 49

| Sample | Pre-hydrolysis | | Post-hydrolysis | |
|---|---|---|---|---|
| | FABE (%) | Fatty Acid (%) | FABE (%) | Fatty Acid (%) |
| Solvent Phase 1 | 62 | 39 | 33 | 67 |
| Solvent Phase 2 | 45 | 55 | 28 | 72 |

TABLE 50

| | Solvent Phase 1 (wt %) | Post Hydrolysis Composition (wt %) |
|---|---|---|
| Isobutyl palmitate | 7.28 | 4.24 |
| Isobutyl stearate | 3.41 | 2.25 |
| Isobutyl oleate | 13.92 | 7.69 |
| Isobutyl linoleate | 33.09 | 17.73 |
| Isobutyl linolenate | 2.78 | |
| Palmitic acid | 3.79 | 7.3 |
| Stearic acid | 2.58 | 4.07 |
| Oleic acid | 9.14 | 16.61 |
| Linoleic acid | 19.06 | 33.54 |
| Linolenic acid | 2.3 | 2.65 |

Example 57

Recovery of Product Alcohol

Hydrolysis Using a Lipase Catalyst

FABE was synthesized from corn oil fatty acid as per the method described in Example 44. Novozyme 435 (Novo 435, *Candida antarctica* lipase B, immobilized on an acrylic resin) was purchased from Sigma Aldrich (St. Louis, Mo.). *Candida antarctica* Lipase B was purchased from Novozymes (Franklinton, N.C.). t-BuOH, acetone, ethanol, methanol, and glycerol were all purchased from Sigma Aldrich (St. Louis, Mo.). For gas chromatography (GC) analysis, the gas chromatograph used was Hewlett Packard 5890 Series II GC chromatogram and methyl pentadecanoate was used as an internal standard.

A. Atmospheric pressure, 40° C.

To a mixture of 2 mL FABE and 5 mL water was added 40 mg Novozyme 435, and the reaction mixture was placed in a 20 mL vial and incubated at 40° C. in a rotary shaker (300 rpm). The reaction mixture was analyzed using GC during 24 h of the reaction, to generate the following % conversion profile given in Table 51:

TABLE 51

% Conversion Profile for Example 57A

| Reaction time (h) | % FABE conversion |
|---|---|
| 0 | 0 |
| 1 | 6.7 |
| 1.5 | 10.5 |
| 2 | 15.1 |
| 4 | 17.0 |
| 6 | 17.4 |
| 8 | 17.7 |
| 24 | 18.2 |

B. Atmospheric Pressure, 40° C., 65° C. and 80° C., No Organic Solvent

Together with part A of this example, these data show how equilibrium changes with temperature To a mixture of 1 mL FABE and 2 mL water was added 20 mg Novozyme 435 and the reaction mixture was rotated at 40° C. for 45 h in a 6 mL septum-capped vial. The reaction mixture was analyzed using GC to reveal 18.2% conversion of FABE at equilibrium.

To a mixture of 1 g FABE and 2 mL water was added 20 mg Novozyme 435, and the reaction mixture was rotated at 65° C. for 42 h in a 6 mL septum-capped vial. The reaction mixture was analyzed using GC to reveal 19.8% conversion of FABE at equilibrium.

To a mixture of 1 g FABE and 2 mL water was added 20 mg Novozyme 435, and the reaction mixture was rotated at 80° C. for 42 h in a 6 mL septum-capped vial. The reaction mixture was analyzed using GC to reveal 21.4% conversion of FABE at equilibrium.

C. Example Showing the Effect of Organic Solvent (t-BuOH) on the Equilibrium

To three reaction mixtures containing 0.25 mL FABE, 0.75 mL t-BuOH, and 0.1-0.3 mL water was added 20 mg Novozyme 435, and the mixtures, in 6 mL septum-capped vials, were left rotating at 40° C. overnight, at which point they had reached equilibrium. The reaction mixtures were analyzed using GC after 24 h of the reaction, to generate 77-82% FABE conversions given in Table 52. Replacing t-BuOH with 3-Me-3-pentanol under similar reaction conditions gave FABE hydrolysis yields of 70-80%.

TABLE 52

% Conversion Profile for Example 57C

| Reaction mixture | Novozyme 435 loading | % FABE conversion |
|---|---|---|
| 0.75 mL t-BuOH, 0.25 mL FABE, 0.1 g H$_2$O | 20 mg | 77% |
| 0.75 mL t-BuOH, 0.25 mL FABE, 0.2 g H$_2$O | 20 mg | 81% |
| 0.75 mL t-BuOH, 0.25 mL FABE, 0.3 g H$_2$O | 20 mg | 82% |

D. Acetone as Solvent

To three reaction mixtures containing 0.25 mL FABE, 0.75 mL acetone, and 0.1-0.3 mL water was added 20 mg Novozyme 435, and the mixtures, in 6 mL septum-capped vials, were left rotating at 40° C. overnight, at which point they had reached equilibrium. The reaction mixtures were analyzed using GC after 24 h of the reaction, to show 71-78% FABE conversions given in Table 53.

TABLE 53

% Conversion Profile for Example 57D

| Reaction mixture | Novozyme 435 loading | % FABE conversion |
|---|---|---|
| 0.75 mL acetone, 0.25 mL FABE, 0.1 g H$_2$O | 20 mg | 71% |
| 0.75 mL acetone, 0.25 mL FABE, 0.2 g H$_2$O | 20 mg | 74% |
| 0.75 mL acetone, 0.25 mL FABE, 0.3 g H$_2$O | 20 mg | 78% |

E. Example Showing the Effect of Removing i-BuOH During Hydrolysis on FABE Conversion—Nitrogen Purge at Atmospheric Pressure A 25 mL round bottom flask was charged with 2 mL FABE, 5 mL water, and 40 mg Novozyme 435. The reaction mixture was heated to 95° C., and the i-BuOH that was forming in the reaction was removed by bubbling nitrogen through the reaction mixture. Samples were taken from the mixture during the reaction, and the organic phase was analyzed using GC. Conversion of 94% was achieved after 6 h as shown in Table 54:

TABLE 54

FABE Conversion Profile for Example 57E

| Reaction time (h) | Mole % COFA in COFA + FABE |
|---|---|
| 0 | 1 |
| 1 | 62 |
| 2 | 76 |
| 3 | 86 |
| 4 | 90 |
| 6 | 94 |

F. Example Showing the Effect of Removing i-BuOH During Hydrolysis on the Conversion-Vacuum Distillation A 25 mL round bottom flask was charged with 3 mL FABE, 7.5 mL of water, and 60 mg Novozyme 435. The flask was attached to a vacuum distillation apparatus, and the pressure was set to 91 mm Hg. The reaction mixture was then heated to 74° C., and the i-BuOH that was forming in the reaction was distilled off. Samples were taken from the mixture during the reaction, and the organic phase was analyzed using GC. Conversion of 91% was achieved after 10 h as shown in Table 55.

TABLE 55

% Conversion Profile for Example 57F

| Reaction time (h) | % FABE conversion |
|---|---|
| 0 | 0 |
| 1 | 16 |
| 2 | 37 |
| 3 | 57 |
| 5 | 72 |
| 7 | 83 |
| 10 | 91 |

G. Example Showing the Effect of Removing i-BuOH During Hydrolysis on the Conversion-Vacuum Distillation Example-Varying FABE/COFA Starting Ratio: 23% FABE:77% COFA v/v A 25 mL round bottom flask was charged with 0.69 mL FABE, 2.31 mL COFA, 7.5 mL water, and 60 mg Novozyme 435. The flask was attached to a vacuum distillation apparatus, and the pressure was set to 91 mm Hg. The reaction mixture was then heated to 74° C., and the i-BuOH that was forming in the reaction was distilled off. Samples were taken from the mixture during the reaction, and the organic phase was analyzed using GC. Conversion of 98% was achieved after 10 h as shown in Table 56.

TABLE 56

FABE Conversion Profile for Example 57G

| Reaction time (h) | Mole % COFA in COFA + FABE |
|---|---|
| 0 | 77 |
| 1 | 83 |
| 2 | 86 |
| 3 | 90 |
| 4 | 92 |
| 6 | 93 |
| 7 | 96 |
| 10 | 98 |

H. Example Showing the Effect of Removing i-BuOH During Hydrolysis on the Conversion-Vacuum Distillation Example-Varying FABE/COFA Starting Ratio: 70% FABE:30% COFA v/v A 25 mL round bottom flask was charged with 2.1 mL FABE, 0.9 mL COFA, 7.5 mL water, and 60 mg Novozyme 435. The flask was attached to a vacuum distillation apparatus, and the pressure was set to 91 mm Hg. The reaction mixture was then heated to 74° C., and the i-BuOH that was forming in the reaction was distilled off. Samples were taken from the mixture during the reaction, and the organic phase was analyzed using GC. Conversion of 96% was achieved after 10 h as shown in Table 57:

TABLE 57

FABE Conversion Profile for Example 57H

| Reaction time (h) | Mole % COFA in COFA + FABE |
|---|---|
| 0 | 30 |
| 1 | 52 |
| 2 | 64 |
| 5 | 84 |
| 7 | 89 |
| 10 | 96 |

I. Example Showing the Free Cal B Enzyme in FABE Hydrolysis Under Vacuum Distillation Conditions Two round bottom flasks were charged with 3 mL (2.7 g) FABE and 7.5 mL H$_2$O each. To one mixture was added 5.9 mg *Candida antarctica* Lipase B, and to the other was added 0.59 mg enzyme. The reaction flasks were separately connected to the distillation apparatus and exposed to pressure of 91 mm Hg. The reaction mixtures were heated to 65-68° C. Samples were taken from the reaction mixtures over a ten-hour period, and analyzed using gas chromatography. The final FABE conversions were 96 and 78%, respectively. The experiments show that reducing the amount of enzyme concentration by a factor of ten reduces the rate and conversion by 3× and 18%, respectively. The results are shown in Table 58.

TABLE 58

FABE Conversion Profile for Example 57I

| Reaction time (h) | Mole % COFA in COFA + FABE with 5.9 mg CALB/ 2.7 g FABE | Mole % COFA in COFA + FABE with 0.59 mg CALB/ 2.7 g FABE |
|---|---|---|
| 0 | 0 | 0 |
| 1 | 44 | 21 |
| 2 | 62 | 31 |
| 6 | 89 | 61 |
| 10 | 96 | 78 |

Example 58

Recovery of Product Alcohol

Transesterification

FABE was synthesized from corn oil fatty acid as per the method described in Example 44; Novozyme 435 (*Candida antarctica* lipase B, immobilized on an acrylic resin) was purchased from Sigma Aldrich (St. Louis, Mo.). *Candida antarctica* Lipase B was purchased from Novozymes (Franklinton, N.C.). t-BuOH, acetone, ethanol, methanol, and glycerol were all purchased from Sigma Aldrich (St. Louis, Mo.). For GC analysis, the gas chromatograph used was Hewlett Packard 5890 Series II GC chromatogram and methyl pentadecanoate was used as an internal standard.

A. Testing Lipases—FABE to FAME

Reagents used were t-BuOH (Aldrich); MeOH (Aldrich); Novozyme 435 (Aldrich); PS30 (*Burkholderia cepacia*, Amano Enzymes, Inc, Elgin, Ill.); Lipolase® 100T (*Thermomyces lanuginosa*, immobilized on silica, Novozymes, Franklinton, N.C.); Lipolase® 100L (*Thermomyces lanuginosa*, Novozymes, Franklinton, N.C.); Lipozyme® TLIM (immobilized *Thermomyces lanuginosa*, Novozymes, Franklinton, N.C.); Lipoclean® 2000T (immobilized mixture of lipases; Novozymes, Franklinton, N.C.); NZL-103-LYO (Lipase from *Rhizomucor miehi*, Novozymes, Franklinton, N.C.

To a 6 mL vial was added 500 mg FABE (1.48 mmol), 400 μL t-BuOH, 60 μL MeOH (1.48 mmol), 3 μL water, and 2.5 mg lipase (see Table 57). The resulting mixture was placed in an incubator/shaker, and left at 40° C. overnight. GC analysis of the reaction mixture revealed the conversions from 9-56%. Results are shown in Table 59.

TABLE 59

Equilibrium concentrations [mg/mL] and % conversion of FABE→FAME using different lipases

| Lipase | FABE (mg/mL) | COFA (mg/mL) | i-BuOH (mg/mL) | % conversion |
|---|---|---|---|---|
| PS30 | 471 | 2.48 | 11.2 | 9.73% |
| NOVOZYME 435 | 224 | 16.8 | 63.7 | 56.30% |
| LTLIM | 266 | 15.9 | 67.7 | 53.50% |
| L100T | 455 | 1.8 | 8.9 | 8.80% |
| 2000T | 452 | 1.8 | 9.1 | 8.31% |
| NZL-103-LYO | 429 | 3.94 | 15.3 | 13.90% |

B. FABE to FAME Transformation—Optimizing the Amount of Methanol

To a 6 mL vial was added 500 mg FABE (1.48 mmol), 400 μL t-BuOH, 60-240 μL MeOH (1.48-5.92 mmol), 3 μL water, and 2.5 mg Novozyme 435. The resulting mixture was placed in an incubator/shaker, and left at 40° C. overnight. GC analysis of the reaction mixture revealed the conversions from 53-73% as shown in Table 60.

TABLE 60

% Conversion Profile for Example 58B

| MeOH eq's | FABE (mg/mL) | COFA (mg/mL) | i-BuOH (mg/mL) | % conversion |
|---|---|---|---|---|
| 1.2 | 232 | 2.4 | 66.9 | 56.64 |
| 1.4 | 168 | 2.4 | 70.4 | 65.50 |
| 1.6 | 167 | 0 | 72.1 | 66.17 |
| 1.8 | 184 | 0 | 80.3 | 66.41 |
| 2.0 | 131 | 0 | 72.4 | 71.46 |
| 2.2 | 134 | 1.2 | 81 | 73.25 |
| 2.4 | 136 | 0 | 80 | 72.71 |
| 2.6 | 161 | 0 | 78 | 68.70 |
| 2.8 | 168 | 0 | 73 | 66.31 |
| 3.0 | 155 | 0 | 74 | 68.38 |
| 3.2 | 180 | 0 | 73 | 64.75 |
| 3.4 | 161 | 0 | 78 | 68.70 |
| 3.6 | 192 | 0 | 66 | 60.89 |
| 3.8 | 236 | 0 | 63 | 54.74 |
| 4.0 | 243 | 0 | 61 | 53.21 |

C. Optimizing the Amount of Enzyme—FABE to FAME

To a 6 mL vial was added 500 mg FABE (1.48 mmol), 400 μL t-BuOH, 132 μL MeOH (3.26 mmol), and 5-25 mg Novozyme 435. The resulting mixture was placed in an incubator/shaker, and left at 40° C. overnight. GC analysis of the reaction mixture revealed the conversions from 76-79% as shown in Table 61.

TABLE 61

% Conversion Profile for Example 58C

| Novozyme 435 (mg) | FABE (mg/mL) | COFA (mg/mL) | i-BuOH (mg/mL) | % conversion |
|---|---|---|---|---|
| 5 mg | 129.4 | 0 | 88 | 75.49 |
| 7.5 mg | 119.3 | 0 | 89.2 | 77.21 |
| 10 mg | 110.9 | 0 | 89 | 78.43 |
| 12.5 mg | 109.2 | 0 | 84.9 | 77.89 |
| 15 mg | 112.4 | 0 | 86.1 | 77.63 |
| 17.5 mg | 108.4 | 0 | 87.4 | 78.51 |
| 20 mg | 115.6 | 0 | 91.8 | 78.25 |
| 22.5 mg | 108.6 | 0 | 87.7 | 78.53 |
| 25 mg | 111.6 | 0 | 89 | 78.32 |

D. Minimizing the Amount of Solvent (t-BuOH)—FABE to FAME

To a 6 mL vial was added 500 mg FABE (1.48 mmol), 0-300 μL t-BuOH, 132 μL MeOH (3.26 mmol), and 10 mg Novozyme 435. The resulting mixture was placed in an incubator/shaker, and left at 40° C. overnight. GC analysis of the reaction mixture revealed the conversions from 30-81% as shown in Table 62.

TABLE 62

% Conversion Profile for Example 58D

| Amount | FABE (mg/mL) | COFA (mg/mL) | i-BuOH (mg/mL) | % conversion | FAME (mg/mL) |
|---|---|---|---|---|---|
| 300 μL t-BuOH | 94.3 | 0 | 83 | 79.95 | 295 |
| 200 μL t-BuOH | 94.1 | 0 | 83.2 | 80.02 | 295 |
| 100 μL t-BuOH | 91.7 | 0 | 84.2 | 80.62 | 300 |
| 50 μL t-BuOH | 92.9 | 0 | 81 | 79.80 | 290.8 |
| <50 μL t-BuOH | 137 | 0 | 70.5 | 69.98 | 249.4 |
| no t-BuOH | 322.7 | 1.39 | 30.2 | 29.77 | 98.1 |

E. Minimization of the Amount of Solvent (3-Me-3-Pentanol)—FABE to FAME

To a 6 mL vial was added 500 mg FABE (1.48 mmol), 0-300 µL 3-Me-3-pentanol, 132 µL MeOH (3.26 mmol), and 10 mg Novozyme 435. The resulting mixture was placed in an incubator/shaker, and left at 40° C. overnight. GC analysis of the reaction mixture revealed the conversions from 30-78% as shown in Table 63.

TABLE 63

% Conversion Profile for Example 58E

| Amount | FABE (mg/mL) | COFA (mg/mL) | i-BuOH (mg/mL) | % Conversion | FAME (mg/mL) |
|---|---|---|---|---|---|
| 0.3 mL 3M3P | 115.6 | 3.75 | 81.4 | 76.13 | 296 |
| 0.2 mL 3M3P | 106.3 | 3.13 | 80 | 77.32 | 294 |
| 0.1 mL 3M3P | 104.8 | 2.36 | 80.8 | 77.74 | 296 |
| 0.05 mL 3M3P | 102.9 | 2.3 | 79.6 | 77.80 | 295 |
| soak 3M3P | 102.5 | 2.4 | 79.9 | 77.93 | 296 |
| no 3M3P | 322.7 | 1.39 | 30.2 | 29.77 | 98.1 |

F. Conversion of FABE to FAME without Solvent

To a mixture of FABE (500 mg, 1.48 mmol) and methanol (0.13 µL, 3.25 mmol) was added 40 mg Novozyme 435, and the reaction mixture was stirred at 40° C. overnight. The mixture was then filtered and analyzed by GC to reveal 76% conversion.

G. Enzyme Recycle—FABE to FAME

To a 6 mL vial was added 500 mg FABE (1.48 mmol), 400 µL t-BuOH, 132 µL MeOH (3.26 mmol), and 10 mg Novozyme 435. The resulting mixture was placed in an incubator/shaker, and left at 40° C. overnight. After that time, the reaction mixture was filtered and analyzed for conversion using GC, and the filter cake containing the immobilized enzyme, was used for another conversion of FABE to FAME. The process was repeated ten times (Table 64). The experiment shows that it is possible to recycle the enzyme up to ten times without the loss in conversion in the overnight reaction.

TABLE 64

% Conversion Profile for Enzyme Recycle in Example 58G Concentrations are in mg/mL

| FABE to FAME | FABE | COFA | i-BuOH | % Conversion | FAME |
|---|---|---|---|---|---|
| 1st | 115.8 | 5.29 | 82.1 | 76.26 | 298.1 |
| 2nd | 124 | 5.36 | 82.7 | 75.13 | 293.2 |
| 3rd | 112 | 4.82 | 85 | 77.47 | 303.1 |
| 4th | 111 | 9.06 | 85.1 | 77.64 | 306.3 |
| 5th | 99.4 | 5.1 | 82.1 | 78.91 | 284.5 |
| 6th | 98.2 | 6 | 81.2 | 78.93 | 283.8 |
| 7th | 115.6 | 6.8 | 78.9 | 75.56 | 262.7 |
| 8th | 114.8 | 6.5 | 77.6 | 75.38 | 257.2 |
| 9th | 99 | 5.7 | 78 | 78.12 | 241 |
| 10th | 109 | 8.6 | 73.7 | 75.39 | 226.7 |

H. Conversion of FABE to FAEE

To 6 mL septum-capped vials were added 0.8 mL FABE (2.08 mmol) and 0.2 mL EtOH (3.43 mmol), forming a single phase. No enzyme or 20 mg Novozyme 435 was added to the vials. The vials were then incubated at 25° C. and 40° C. in an incubator shaker (300 rpm) for 17 h after which the solution was analyzed by gas chromatography, giving the contents and percent conversion of FABE to FAEE shown in Table 65.

TABLE 65

| Sample | FABE (mg/mL) | i-BuOH (mg/mL) | COFA (mg/mL) | % Conversion |
|---|---|---|---|---|
| EtOH/FABE + enzyme, 25° C. | 93.2 | 38.5 | 0 | 41.6 |
| EtOH/FABE, no enzyme, 25° C. | 159.6 | 3.5 | 0.75 | 0 |
| EtOH/FABE + enzyme, 40° C. | 90 | 35.7 | 0 | 43.3 |
| EtOH/FABE, no enzyme, 40° C. | 158.7 | 3.1 | 0.75 | 0 |

Example 59

Glycerolysis of FABE

To a septum-capped 6 mL vial was added 0.75 mL t-BuOH, 0.25 mL FABE, 0.1 mL (0.126 g) glycerol+4 µL $H_2O$, enzyme 20 mg each, forming a single phase. The reactions were incubated with various lipases at 40° C. on a rotary shaker at 300 rpm. After 20 h, the samples were analyzed by gas chromatography, giving the contents shown in Table 66. A comparison of the COFA and FABE contents indicates that the products are i-BuOH and a mixture of COFA and acyl glycerol (~64% acyl glycerol/36% COFA on molar basis).

TABLE 66

Percent conversion of FABE to a mixture of COFA and acyl glycerol

| Lipase | FABE (mg/mL) | COFA (mg/mL) | i-BuOH (mg/mL) | Percent conversion of FABE |
|---|---|---|---|---|
| Amano PS-30 powder | 73 | 43 | 32 | 64% |
| IM-20, powder | 162.4 | 10.2 | 10.9 | 19% |
| Lipolase ® 100T immobilized | 190 | 0 | 4 | ~0% |
| Novozyme 435 immobilized | 73 | 39.5 | 30.8 | 64% |
| Lipozyme ® TL IM immobilized | 101.7 | 29 | 26.1 | 49% |
| Lipoclean ® 2000T immobilized | 200.9 | 0 | 3.9 | ~0% |

A. Dependence on Water and Glycerol/FABE

To 6 mL septum capped vials were added 0.75 mL t-BuOH, 0.25 mL FABE, 0.1 or 0.2 g glycerol+20 mg each of either Amano PS-30 or Novozyme 435, forming a single phase. No water was added. The reactions were incubated at 40° C. on a rotary shaker at 300 rpm. After 20 h, the samples were analyzed by gas chromatography, giving the contents shown in Table 67. A comparison of the COFA and FABE contents indicates that the products are i-BuOH and primarily acyl glycerol (mostly monoglyceride). Relative to the previous example, the percent of product in the form of acyl glycerol increases with the absence of added water and with the increase in glycerol/FABE (~91% acyl glycerol/9% COFA on molar basis with 1.6 glycerol/FABE, mole/mole and ~95% acyl glycerol/5% COFA on molar basis with 3.2 glycerol/FABE, mole/mole). The absence of added water eliminates the enzyme activity of Amano PS-30. The Novozyme 435 which has water in the acrylic resin (~3% w/w) to which it is immobilized is, however, still active.

TABLE 67

Percent conversion of FABE to acyl glyceride

| Lipase | Glycerol | FABE (mg/mL) | COFA (mg/mL) | i-BuOH (mg/mL) | Percent conversion of FABE |
|---|---|---|---|---|---|
| Amano PS-30 powder | 0.1 g | 209 | 1.2 | 4.4 | ~0% |
| Novozyme 435, immobilized | 0.1 g | 84.2 | 10.7 | 28.6 | 58% |
| Amano PS-30 powder | 0.2 g | 182 | 0.74 | 3.8 | ~0% |
| Novozyme 435 immobilized | 0.2 g | 61.5 | 7.1 | 30.6 | ~69% |

B. Dependence on Enzyme Concentration

To 6 mL septum capped vials was added 0.75 mL t-BuOH, 0.25 mL FABE, 0.2 g glycerol (glycerol/FABE 3.2/1, mole/mole)+2 or 20 mg of Novozyme 435 (Novo 435). No water was added. The reactions were incubated at 40° C. on a rotary shaker at 300 rpm and the reaction was followed as a function of time by gas chromatography. The yields are indicated in Table 68. Approximately 97% of the FABE that reacted was converted to acyl glycerol (mostly monoglyceride) on a mole basis.

TABLE 68

| Time (h) | % FABE conversion 2 mg Novo 435 | % FABE conversion 20 mg Novo 435 |
|---|---|---|
| 0 | 0 | 0 |
| 0.167 | | 13.2 |
| 0.333 | | 38 |
| 0.5 | 3.37 | 42.9 |
| 1 | 10.8 | 59.1 |
| 2 | 21.9 | 65.5 |
| 4 | 31.6 | 67.1 |
| 6.5 | 32.1 | |
| 7 | 45.7 | 67.1 |
| 24 | 64 | 67.3 |

The rate of the reaction is linear with enzyme concentration, with $t_{1/2}$ for 2 and 20 mg of Novozyme 435 of 208 and 20 minutes, respectively. The reaction, however, reaches nearly the same yield of FABE conversion after 24 h.

These last reactions were repeated with 0.75 mL of 3-methyl-3-pentanol replacing 0.75 mL of t-BuOH. The extent of FABE hydrolysis obtained after 24 h was the same for both solvents. The advantage of 3-methyl-3-pentanol is that with a boiling point of 122° C., the i-BuOH can be distilled off first in pure form (b.p. 108° C.). The 3-methyl-3-pentanol can then be distilled off and recycled for the hydrolysis reaction, leaving in the retentate acyl glycerol, COFA, and glycerol to be recycled to the fermentation tank for reuse in the generation of FABE. Tertiary alcohols act as a solvent alone and have the advantage of not reacting with the fatty acid to form fatty acid alkyl esters in the presence of CALB.

C. Glycerolysis of FABE (FABE to COFA+Acyl Glycerol) in the Absence of Organic Cosolvent—Dependence on Glycerol Concentration One gram (1 g) of FABE was mixed with 2 mL of 50, 70, 90, and 100% (w/w) glycerol and placed in a 6 mL septum-sealed vial in the presence of 20 mg Lipobond (Sprin Technologies, Trieste, Italy). The vial was tumbled end-over-end for 24 h at 62° C. With increasing glycerol concentration in the aqueous phase, the percent of the product in the form of acyl glycerol increases (Table 69, mostly monoglyceride). The extent of FABE conversion, however, does not show a dependence on the glycerol concentration.

TABLE 69

| Condition (% glycerol in aqueous phase) | % of FABE conversion | % of COFA in product (mole basis) | % of acyl glycerol in product (mole basis) |
|---|---|---|---|
| 50 | 18 | 100 | 0 |
| 70 | 17 | 84 | 16 |
| 90 | 17 | 34 | 66 |
| 100 | 17 | 3 | 97 |

Example 60

Conversion of COFA to FAEE and Monoacyl Glycerol

The following examples show that COFA can be esterified with EtOH or with glycerol at high yield under mild conditions using immobilized enzyme.

Novozyme 435 (*Candida antarctica* lipase B, immobilized on an acrylic resin) was purchased from Sigma Aldrich (St. Louis, Mo.). Acetone, t-BuOH, ethanol, methanol, and glycerol were all purchased from Sigma Aldrich (St. Louis, Mo.). For GC analysis, the gas chromatograph used was Hewlett Packard 5890 Series II GC chromatogram and methyl pentadecanoate was used as an internal standard.

A. Conversion of COFA to FAEE+i-BuOH using Ethanol

Corn oil fatty acid (COFA, 0.25 g) was dissolved in 2.0 mL EtOH forming a single phase. Twenty mg of *Candida antarctica* lipase B (CALB) immobilized on acrylic resin (Novozyme 435) was added (contains 1.7 mg of enzyme) and the suspension was incubated for 24 h on a rotary shaker (300 rpm) at 40° C. in a 6 mL glass vial sealed with a septum cap. The reaction went practically to completion with 98% of the COFA converted to FAEE (fatty acid ethyl ester). The GC analysis after 24 h showed 98% conversion of COFA to fatty acid ethyl ester as shown in Table 70.

TABLE 70

% Conversion Profile for Example 60A

| Reaction mix bp of EtOH = 78.1° C. | Novozyme 435 loading | % Conversion of COFA to FAEE | Phases |
|---|---|---|---|
| 2.0 mL EtOH + 0.25 g COFA Moles EtOH/ moles COFA = 38.7 | 20 mg (contains 1.7 mg CALB) | 98 | 1 throughout |

B. Conversion of COFA to Monoacylglycerides (MAG)+i-BuOH Using Glycerol

Corn oil fatty acid (COFA, 0.25 g) plus 0.325 g of glycerol were dissolved in 2.0 mL acetone. There was a large upper phase in which most of the components were dissolved and a small residual glycerol-containing phase. Twenty mg of *Candida antarctica* lipase B (CALB) immobilized on acrylic resin (Novozyme 435) was added (contains 1.7 mg of enzyme) and the suspension was incubated for 24 h on a rotary shaker (300 rpm) at 40° C. in a 6 mL glass vial sealed with a septum cap. GC of the upper phase indicated that 87% of the COFA had been converted to acyl glyceride (expected to be mostly mono-acylglyceride). Results are shown in Table 71.

TABLE 71

% Conversion Profile for Example 60B

| Reaction mix bp of acetone = 56° C. | Novozyme 435 loading | % Conversion of COFA to acyl glyceride (mostly MAG) | Phases |
|---|---|---|---|
| 2.0 mL acetone + 0.25 g COFA + 0.325 g glycerol Moles glycerol/ moles COFA = 4 | 20 mg (contains 1.7 mg CALB) | 87 | Minor glycerol phase throughout at 40° C. |

Example 61

Conversion of COFA to FAME

The following examples show that COFA can be esterified with MeOH, with EtOH, and with glycerol at high yield under mild conditions using immobilized lipase.

A. Conversion of COFA to FAME without Solvent

To a 6 mL vial was added 500 mg COFA (1.48 mmol), 132 µL of MeOH (3.26 mmol), and 10 mg Novozyme 435. The resulting mixture was placed in an incubator/shaker, and left at 40° C. overnight. GC analysis of the reaction mixture revealed 95% conversion.

B. Time Course Measurement of COFA to FAME Reaction

To a 6 mL vial was added 500 mg COFA (1.48 mmol), 132 µL of MeOH (3.26 mmol), and 10 mg Novozyme 435. The samples were incubated at 40° C. in an incubator/shaker and time points were taken during the reaction, and analyzed using GC. Results are shown in Table 72.

TABLE 72

| Time | COFA [mg/mL] | FAME [mg/mL] | Conversion [%] |
|---|---|---|---|
| 0 min | 377 | 0 | 0% |
| 10 min | 242.2 | 135 | 35% |
| 20 min | 173.6 | 231.8 | 56% |
| 30 min | 122.8 | 274.3 | 68% |
| 1 hr | 59.2 | 373.2 | 86% |
| 2 hr | 18.2 | 389.9 | 95% |
| 3 hr | 16.8 | 406.2 | 96% |
| 4 hr | 15.6 | 404.4 | 96% |
| 7 hr | 16 | 411.2 | 96% |

C. Adding More MeOH to the COFA→FAME Reaction

To a 6 mL vial was added 500 mg COFA (1.48 mmol), 180, 240, 300, or 1320 µL of MeOH (4.44, 5.92, 7.41, and 14.82 mmol), and 10 mg Novozyme 435. The resulting mixture was placed in an incubator/shaker, and left at 40° C. overnight. GC analysis of the reaction mixture revealed 96-97% conversion. The results are shown in Table 73.

TABLE 73

| MeOH [eq] | COFA [mg/mL] | FAME [mg/mL] | % Conversion |
|---|---|---|---|
| 3 | 13.26 | 377 | 96.44% |
| 4 | 13.15 | 398.9 | 96.65% |
| 5 | 12.12 | 391.8 | 96.85% |
| 10 | 12.65 | 399.5 | 96.78% |

Example 62

This example illustrated the removal of solids from stillage and extraction by desolventizer to recover fatty acids, esters, and triglycerides from the solids. During fermentation, solids are separated from whole stillage and fed to a desolventizer where they are contacted with 1.1 tons/hr of steam. The flow rates for the whole stillage wet cake (extractor feed), solvent, the extractor miscella, and extractor discharge solids are as shown in Table 74. Table values are short tons/hr.

TABLE 74

| | Solids from whole stillage | Solvent | Miscella | Extractor discharge solids |
|---|---|---|---|---|
| Fatty acids | 0.099 | 0 | 0.0982 | 0.001 |
| Undissolved solids | 17.857 | 0 | 0.0009 | 17.856 |
| Fatty acid butyl esters | 2.866 | 0 | 2.837 | 0.0287 |
| Hexane | 0 | 11.02 | 10.467 | 0.555 |
| Triglyceride | 0.992 | 0 | 0.982 | 0.0099 |
| Water | 29.762 | 0 | 29.464 | 0.297 |

Solids exiting the desolventizer are fed to a dryer. The vapor exiting the desolventizer contains 0.55 tons/hr of hexane and 1.102 tons/hr of water. This stream is condensed and fed to a decanter. The water-rich phase exiting the decanter contains about 360 ppm of hexane. This stream is fed to a distillation column where the hexane is removed from the water-rich stream. The hexane enriched stream exiting the top of the distillation column is condensed and fed to the decanter. The organic-rich stream exiting the decanter is fed to a distillation column. Steam (11.02 tons/hr) is fed to the bottom of the distillation column. The composition of the overhead and bottom products for this column are shown in Table 75. Table values are tons/hr.

TABLE 75

| | Bottoms | Overheads |
|---|---|---|
| Fatty acids | 0.0981 | 0 |
| Fatty acid butyl esters | 2.8232 | 0 |
| Hexane | 0.0011 | 11.12 |
| Triglyceride | 0.9812 | 0 |
| Water | 0 | 11.02 |

Example 63

Solids Extraction

Preparation of Hydrous Isobutanol

Into a 100 mL volumetric flask, 65 g of anhydrous reagent grade isobutanol (sourced from Aldrich) was combined with 10 g of distilled water and shaken until a clear colorless homogeneous phase resulted. Another 10 g of distilled water was added to the volumetric flask and shaken again resulting in two persistent clear colorless liquid layers. The top layer is considered to be hydrous isobutanol containing typically 20 wt % moisture and the bottom layer is predominantly water with typically 8 wt % dissolved alcohol.

Extraction Using Screen Filtration and Displacement Wash

A fermentation was completed using recycled fatty acid (Example 19). A 185 g portion representative of the resulting heterogeneous mixture was removed and passed through a 80 MESH screen dish supported and sealed within a Nalgene® plastic filter funnel over 5 minutes using slight vacuum (−20 in H2O) on the underside. The filtrate partitioned into 90.5 g of a reddish brown oil phase and 50.9 g of a hazy aqueous phase containing dispersed fines but no settling particulates. A wet cake remained on the screen dish. A sample of 1.5 g of this unwashed wet cake was removed and air dried. Hydrous isobutanol (23 g) was drawn from the top layer inside the volumetric flask and passed through the wet cake over 5 minutes while mild vacuum on the underside of the screen dish was maintained until no more liquid droplets were collected. The total filtrate mass of 18 g consisted of a small amount of an immiscible bottom hazy aqueous layer and a yellow clear hydrous isobutanol layer. The wet cake was removed from the screen dish and a total mass of 38.4 g was recovered. A sample of 1.5 g of this washed wet cake was removed and air dried. The dried sample of unwashed solids was analyzed and found to contain 53.35 wt % total fat on a triglyceride basis and the dried sample of washed solids was analyzed and found to contain 15.9 wt % total fat on a triglyceride basis.

Extraction Using Centrifugation and Reslurry Wash

A fermentation was completed using recycled fatty acid (Example 19). A 225 g portion representative of the resulting heterogeneous mixture was removed and centrifuged using a Beckman Coulter Allegra 64R machine at 10,000 rpm for 10 minutes. A clear reddish brown oil phase amounting to 67.2 g was decanted off. The remaining material was centrifuged again and 95.1 g of a cloudy aqueous centrate was decanted off. A 1.5 g sample of the wet solids was removed and air dried and 56.5 g were recovered and transferred to a 400 mL beaker. Hydrous isobutanol (20 g) drawn from the top layer inside the volumetric flask was added to the beaker to repulp the wet solids and stirring was carried out for 5 minutes. Another 32 g of hydrous isobutanol along with 32 g of the centrate were added and the solids were agitated in aqueous suspension beneath a quiescent organic layer for 5 minutes. The mixture was then centrifuged at 10,000 rpm for 10 minutes to decant off a clear yellow hydrous isobutanol layer and centrifuged again in order to isolate and dry a 1.5 g sample of washed wet solids. The dried sample of unwashed wet solids were analyzed and found to contain 21.6 wt % total fat on a triglyceride basis and the dried sample of washed wet solids were analyzed and found to contain 4.04 wt % total fat on a triglyceride basis.

Example 64

Removal of Corn Oil by Removing Undissolved Solids

Approximately 1000 g of liquefied corn mash was prepared in a 1 L glass, jacketed resin kettle. The kettle was set up with mechanical agitation, temperature control, and pH control. The following protocol was used: mixed ground corn with tap water (26 wt % corn on a dry basis), heated the slurry to 55° C. while agitating, adjusted pH to 5.8 with either NaOH or $H_2SO_4$, added alpha-amylase (0.02 wt % on a dry corn basis), continued heating to 85° C., adjusted pH to 5.8, held at 85° C. for 2 hrs while maintaining pH at 5.8, cool to 25° C. The corn used was whole kernel yellow corn from Pioneer (3335). It was ground in a hammer-mill using a 1 mm screen. The moisture content of the ground corn was measured to be about 11.7 wt %, and the starch content of the ground corn was measured to be about 71.4 wt % on a dry corn basis. The alpha-amylase enzyme was Liquozyme® SC DS from Novozymes (Franklinton, N.C.). The total amounts of the ingredients used were: 294.5 g of ground corn (11.7% moisture), 705.5 g of tap water, and 0.059 g of Liquozyme® SC DS. $H_2O$ (4.3 g) was added to dilute the enzyme, and a total of 2.3 g of 20% NaOH solution was added to control pH. About 952 g of mash was recovered. Note that there were losses due to mash sticking on walls of kettle and CF bottles.

The liquefied corn mash was centrifuged at 5000 rpm (7260 g's) for 30 minutes at 40° C. to remove the undissolved solids from the aqueous solution of oligosaccharides. Removing the solids by centrifugation also resulted in the removal of free corn oil as a separate organic liquid layer on top of the aqueous phase. Approximately 1.5 g of corn oil was recovered from the organic layer floating on top of the aqueous phase. It was determined by hexane extraction that the ground corn used to produce the liquefied mash contained about 3.5 wt % corn oil on a dry corn basis. This corresponds to about 9 g of corn oil fed to the liquefaction process with the ground corn.

Approximately 1 g of corn oil was recovered from the organic layer floating on top of the aqueous phase. About 617 g of liquefied starch solution was recovered leaving about 334 g of wet cake. The wet cake contained most of the undissolved solids that were in the liquefied mash. The liquefied starch solution contained about 0.2 wt % undissolved solids. The wet cake contained about 21 wt % undissolved solids. The wet cake was washed with 1000 g of tap water to remove the oligosaccharides still in the cake. This was done by mixing the cake with the water to form a slurry. The slurry was then centrifuged under the same conditions used to centrifuge the original mash in order to recover the washed solids. Removing the washed solids by centrifugation also resulted in the removal of some additional free corn oil as a separate organic liquid layer on top of the aqueous phase. Corn oil was recovered from the organic layer floating on top of the aqueous phase.

The wet solids were washed two more times using a 1000 g of tap water each time to remove essentially all of the liquefied starch. The final washed solids were dried in a vacuum oven overnight at 80° C. and about 20 inches Hg vacuum. The amount of corn oil remaining in the dry solids, presumably still in the germ, was determined by hexane extraction. It was measured that a 3.60 g sample of relatively dry solids (about 2 wt % moisture) contained 0.22 g of corn oil. This result corresponds to 0.0624 g corn oil/g dry solids. This was for washed solids which means there are no residual oligosaccharides in the wet solids. After centrifuging the liquefied corn mash to separate the layer of free corn oil and the aqueous solution of oligosaccharides from the wet cake, it was determined that about 334 g of wet cake containing about 21 wt % undissolved solids remained. This corresponds to the wet cake comprising about 70.1 g of undissolved solids. At 0.0624 g corn oil/g dry solids, the solids in the wet cake should contain about 4.4 g of corn oil.

Example 65

Lipid Analysis

Lipid analysis was conducted by conversion of the various fatty acid-containing compound classes to fatty acid methyl esters ("FAMEs") by transesterification. Glycerides and phospholipids were transesterified using sodium methoxide in methanol. Glycerides, phospholipids, and free fatty acids were transesterified using acetyl chloride in methanol. The resulting FAMEs were analyzed by gas chromatography using an Agilent 7890 GC fitted with a 30-m×0.25 mm (i.d.) OMEGAWAX™ (Supelco, SigmaAldrich, St. Louis, Mo.) column after dilution in toluene/hexane (2:3). The oven temperature was increased from 160° C. to 200° C. at 5° C./min then 200° C. to 250° C. (hold for 10 min) at 10° C./min. FAME peaks recorded via GC analysis were identified by their retention times, when compared to that of known methyl esters (MEs), and quantitated by comparing the FAME peak areas with that of the internal standard (C15:0 triglyceride, taken through the transesterification procedure with the sample) of known amount. Thus, the approximate amount (mg) of any fatty acid FAME ("mg FAME") is calculated according to the formula: (area of the FAME peak for the specified fatty acid/area of the 15:0 FAME peak)*(mg of the internal standard C15:0 FAME). The FAME result can then be corrected to mg of the corresponding fatty acid by dividing by the appropriate molecular weight conversion factor of 1.052. All internal and reference standards are obtained from Nu-Chek Prep, Inc.

The fatty acid results obtained for samples transesterified using sodium methoxide in methanol are converted to the corresponding triglyceride levels by multiplying the molecular weight conversion factor of 1.045. Triglycerides generally account for approximately 80 to 90% of the glycerides in the samples studies for this example, with the remainder being diglycerides. Monoglyceride and phospholipid contents are generally negligible. The total fatty acid results obtained for a sample transesterified using acetyl chloride in methanol are corrected for glyceride content by subtracting the fatty acids determined for the same sample using the sodium methoxide procedure. The result is the free fatty acid content of the sample.

The distribution of the glyceride content (monoglycerides, diglycerides, triglycerides, and phospholipids) is determined using thin layer chromatography. A solution of the oil dissolved in 6:1 chloroform/methanol is spotted near the bottom of a glass plate precoated with silica gel. The spot is then chromatographed up the plate using a 70:30:1 hexane/diethyl ether/acetic acid solvent system. Separated spots corresponding to monoglycerides, diglycerides, triglycerides, and phospholipids are then detected by staining the plate with iodine vapor. The spots are then scraped off the plate, transesterified using the acetyl chloride in methanol procedure, and analyzed by gas chromatography. The ratios of the totaled peak areas for each spot to the totaled peak areas for all the spots are the distribution of the various glycerides.

Example 66

This example illustrates the recovery of by-products from mash. Corn oil was separated from mash under the conditions described in Example 64 with the exception that a Tricanter® (three-phase centrifuge) centrifuge (Flottweg Z23-4, bowl diameter 230 mm, length to diameter ratio 4:1) was used with these conditions:

| | |
|---|---|
| Bowl Speed: | 5000 rpm |
| Differential Speed: | 10 rpm |
| Feed Rate: | 3 gpm |
| Phase Separator Disk: | 138 mm |
| Impeller Setting | 144 mm. |

The corn oil separate had 81% triglycerides, 6% free fatty acids, 4% diglyceride, and 5% total of phospholipids and monoglycerides as determined by the methods described in Example 65 and thin layer chromatography.

The solids separated from mash under the conditions described above had a moisture content of 58% as determined by weight loss upon drying and had 1.2% triglycerides and 0.27% free fatty acids as determined by the method described in Example 65.

The composition of solids separated from whole stillage, oil extracted between evaporator stages, by-product extractant and Condensed Distillers Solubles (CDS) in Table 78 were calculated assuming the composition of whole stillage shown in Table 76 and the assumptions in Table 77 (separation at Tricanter® (three-phase centrifuge) centrifuge). The values of Table 75 were obtained from an Aspen Plus® model (Aspen Technology, Inc., Burlington, Mass.). This model assumes that corn oil is not extracted from mash. It is estimated that the protein content on a dry basis of cells, dissolved solids, and suspended solids is approximately 50%, 22%, and 35.5%, respectively. The composition of by-product extractant is estimated to be 70.7% fatty acid and 29.3% fatty acid isobutyl ester on a dry basis.

TABLE 76

| Component | Mass % |
|---|---|
| Water | 57.386% |
| Cells | 0.502% |
| Fatty acids | 6.737% |
| Isobutyl esters of fatty acids | 30.817% |
| Triglyceride | 0.035% |
| Suspended solids | 0.416% |
| Dissolved solids | 4.107% |

TABLE 77

| | Hydrolyzer feed | Thin stillage | Solids |
|---|---|---|---|
| Organics | 99.175% | 0.75% | 0.08% |
| Water and dissolved solids | 1% | 96% | 3% |
| Suspended solids and cells | 1% | 2% | 97% |

TABLE 78

| Stream | C. protein | triglyceride | FFA | FABE |
|---|---|---|---|---|
| Whole stillage wet cake | 40% | trace | 0.5% | 2.2% |
| Oil at evaporator | 0% | 0.08% | 16.1% | 73.8% |
| CDS | 22% | trace % | 0.37% | 1.71% |

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for producing butyl esters comprising:
   a) providing an oil and converting at least a portion of the oil into carboxylic acid by contacting the oil with one or more enzymes, wherein the one or more enzymes are selected from an esterase, lipase, phospholipase, lysophospholipase, or a mixture thereof;
   b) providing the converted carboxylic acid to a fermentation process; and
   c) contacting butanol produced in the fermentation process with the provided carboxylic acid and at least one catalyst capable of esterifying the carboxylic acid with the butanol to form butyl esters of the carboxylic acid, wherein the catalyst is an enzyme selected from an esterase, lipase, phospholipase, lysophospholipase, or a mixture thereof; wherein the carboxylic acid in the fermentation process is present at a concentration sufficient to produce a two-phase mixture.

2. The method of claim 1, wherein the production of butanol and the production of butyl esters occur simultaneously or sequentially.

3. The method of claim 1, wherein a feedstock in the fermentation process comprises one or more fermentable sugars.

4. The method of claim 2, wherein the feedstock in the fermentation process comprises one or more fermentable sugars derived from corn grain, corn cobs, crop residues such as corn husks, corn stover, grasses, wheat, rye, wheat straw, barley, barley straw, hay, rice straw, switchgrass, waste paper, sugar cane bagasse, sorghum, sugar cane, soy, components obtained from milling of grains, cellulosic material, lignocellulosic material, trees, branches, roots, leaves, wood chips, sawdust, shrubs and bushes, vegetables, fruits, flowers, animal manure, and mixtures thereof.

5. The method of claim 1, wherein the carboxylic acid comprises fatty acids.

6. The method of claim 1, wherein the carboxylic acid comprises 12 to 22 carbons.

7. The method of claim 1, wherein the carboxylic acid is a mixture of carboxylic acids.

8. The method of claim 1, wherein the butyl esters of the carboxylic acid are butyl esters of fatty acids.

9. A method for producing butanol and butyl esters from a feedstock comprising:
   (a) providing a feedstock;
   (b) liquefying the feedstock to create a liquefied biomass comprising oligosaccharides;
   (c) separating the feedstock slurry to produce an aqueous stream comprising oligosaccharides, an oil stream, and solids;
   (d) adding the aqueous stream to a fermentation vessel containing a fermentation broth;
   (e) saccharifying the oligosaccharides of the aqueous stream;
   (f) fermenting the products of the oligosaccharide saccharification present in the aqueous stream to produce butanol and concurrently contacting the butanol with at least one carboxylic acid and at least one catalyst capable of esterifying the carboxylic acid with the butanol to form butyl esters of the carboxylic acid, wherein the catalyst is an enzyme selected from an esterase, lipase, phospholipase, lysophospholipase, or a mixture thereof,
   wherein the carboxylic acid is present at a concentration sufficient to produce a two-phase mixture;
   and optionally steps (e) and (f) occur concurrently.

10. A method for producing butanol and butyl esters from a feedstock comprising:
   (a) providing a feedstock;
   (b) liquefying the feedstock to create a liquefied biomass comprising oligosaccharides;
   (c) separating the feedstock slurry to produce a stream comprising oligosaccharides and oil, and solids;
   (d) adding the stream to a fermentation vessel containing a fermentation broth;
   (e) saccharifying the oligosaccharides of the stream;
   (f) fermenting the products of the oligosaccharide saccharification present in the stream to produce butanol and concurrently contacting the butanol with at least one carboxylic acid and at least one catalyst capable of esterifying the carboxylic acid with the butanol to form butyl esters of the carboxylic acid, wherein the catalyst is an enzyme selected from an esterase, lipase, phospholipase, lysophospholipase, or a mixture thereof,
   wherein the carboxylic acid is present at a concentration sufficient to produce a two-phase mixture;
   and optionally steps (e) and (f) occur concurrently.

11. The method of claim 9, wherein the carboxylic acid comprises fatty acids.

12. The method of claim 9, further comprising converting at least a portion of the oil into carboxylic acid by contacting the oil with one or more enzymes, wherein the one or more enzymes are selected from an esterase, lipase, phospholipase, lysophospholipase, or a mixture thereof.

13. The method of claim 12, wherein the carboxylic acid is added to the fermentation vessel.

14. The method of claim 12 wherein the carboxylic acid comprises fatty acids.

15. The method of claim 9, further comprising:
   adding the oil to the fermentation vessel and converting at least a portion of the oil into carboxylic acid by contacting the oil with one or more enzymes, wherein the one or more enzymes are selected from an esterase, lipase, phospholipase, lysophospholipase, or a mixture thereof.

16. The method of claim 10, wherein the carboxylic acid comprises fatty acids.

17. The method of claim 10, further comprising converting at least a portion of the oil into carboxylic acid by contracting the oil with one or more enzymes, wherein the one or more enzymes are selected from an esterase, lipase, phospholipase, lysophospholipase, or a mixture thereof.

18. The method of claim 17, wherein the carboxylic acid is added to the fermentation vessel.

19. The method of claim 17, wherein the carboxylic acid comprises fatty acids.

* * * * *

SEQUENCE LISTING

<160> NUMBER OF SEQ ID NOS: 202

<210> SEQ ID NO 1
<211> LENGTH: 11856
<212> TYPE: DNA
<213> ORGANISM: Artificial sequence
<220> FEATURE:
<223> OTHER INFORMATION: Plasmid

<400> SEQUENCE: 1

| | | | | | |
|---|---|---|---|---|---|
| tcccattacc | gacatttggg | cgctatacgt | gcatatgttc | atgtatgtat | ctgtatttaa | 60 |
| aacacttttg | tattattttt | cctcatatat | gtgtataggt | ttatacggat | gatttaatta | 120 |
| ttacttcacc | acccttttatt | tcaggctgat | atcttagcct | tgttactagt | tagaaaaaga | 180 |
| cattttgct | gtcagtcact | gtcaagagat | tcttttgctg | gcatttcttc | tagaagcaaa | 240 |
| aagagcgatg | cgtctttcc | gctgaaccgt | tccagcaaaa | aagactacca | acgcaatatg | 300 |
| gattgtcaga | atcatataaa | agagaagcaa | ataactcctt | gtcttgtatc | aattgcatta | 360 |
| taatatcttc | ttgttagtgc | aatatcatat | agaagtcatc | gaaatagata | ttaagaaaaa | 420 |
| caaactgtac | aatcaatcaa | tcaatcatcg | ctgaggatgt | tgacaaaagc | aacaaaagaa | 480 |
| caaaatccc | ttgtgaaaaa | cagaggggcg | gagcttgttg | ttgattgctt | agtggagcaa | 540 |
| ggtgtcacac | atgtatttgg | cattccaggt | gcaaaaattg | atgcggtatt | tgacgcttta | 600 |
| caagataaag | gacctgaaat | tatcgttgcc | cggcacgaac | aaaacgcagc | attcatggcc | 660 |
| caagcagtcg | gccgtttaac | tggaaaaccg | ggagtcgtgt | tagtcacatc | aggacccggt | 720 |
| gcctctaact | tggcaacagg | cctgctgaca | gcgaacactg | aaggagaccc | tgtcgttgcg | 780 |
| cttgctggaa | acgtgatccg | tgcagatcgt | ttaaaacgga | cacatcaatc | tttggataat | 840 |
| gcggcgctat | tccagccgat | tacaaaatac | agtgtagaag | ttcaagatgt | aaaaaatata | 900 |
| ccggaagctg | ttacaaatgc | atttaggata | gcgtcagcag | gcaggctgg | ggccgctttt | 960 |
| gtgagctttc | cgcaagatgt | tgtgaatgaa | gtcacaaata | cgaaaacgt | gcgtgctgtt | 1020 |
| gcagcgccaa | aactcggtcc | tgcagcagat | gatgcaatca | gtgcggccat | agcaaaaatc | 1080 |
| caaacagcaa | aacttcctgt | cgttttggtc | ggcatgaaag | gcggaagacc | ggaagcaatt | 1140 |
| aaagcggttc | gcaagctttt | gaaaaaggtt | cagcttccat | tgttgaaaac | atatcaagct | 1200 |
| gccggtaccc | tttctagaga | tttagaggat | caatattttg | gccgtatcgg | tttgttccgc | 1260 |
| aaccagcctg | gcgatttact | gctagagcag | gcagatgttg | ttctgacgat | cggctatgac | 1320 |
| ccgattgaat | atgatccgaa | attctggaat | atcaatggag | accggacaat | tatccattta | 1380 |
| gacgagatta | tcgctgacat | tgatcatgct | taccagcctg | atcttgaatt | gatcggtgac | 1440 |
| attccgtcca | cgatcaatca | tatcgaacac | gatgctgtga | agtggaatt | tgcagagcgt | 1500 |
| gagcagaaaa | tccttttctga | tttaaaacaa | tatatgcatg | aaggtgagca | ggtgcctgca | 1560 |
| gattggaaat | cagacagagc | gcaccctctt | gaaatcgtta | aagagttgcg | taatgcagtc | 1620 |
| gatgatcatg | ttacagtaac | ttgcgatatc | ggttcgcacg | ccatttggat | gtcacgttat | 1680 |
| ttccgcagct | acgagccgtt | aacattaatg | atcagtaacg | gtatgcaaac | actcggcgtt | 1740 |
| gcgcttcctt | gggcaatcgg | cgcttcattg | gtgaaaccgg | gagaaaaagt | ggtttctgtc | 1800 |
| tctggtgacg | gcggtttctt | attctcagca | atggaattag | agacagcagt | tcgactaaaa | 1860 |
| gcaccaattg | tacacattgt | atggaacgac | agcacatatg | acatggttgc | attccagcaa | 1920 |
| ttgaaaaaat | ataaccgtac | atctgcggtc | gatttcggaa | atatcgatat | cgtgaaatat | 1980 |
| gcggaaagct | tcggagcaac | tggcttgcgc | gtagaatcac | cagaccagct | ggcagatgtt | 2040 |

```
ctgcgtcaag gcatgaacgc tgaaggtcct gtcatcatcg atgtcccggt tgactacagt   2100
gataacatta atttagcaag tgacaagctt ccgaaagaat tcggggaact catgaaaacg   2160
aaagctctct agttaattaa tcatgtaatt agttatgtca cgcttacatt cacgccctcc   2220
ccccacatcc gctctaaccg aaaggaagg agttagacaa cctgaagtct aggtccctat    2280
ttattttttt atagttatgt tagtattaag aacgttattt atatttcaaa tttttctttt   2340
ttttctgtac agacgcgtgt acgcatgtaa cattatactg aaaaccttgc ttgagaaggt   2400
tttgggacgc tcgaaggctt taatttgcgg gcggccgcac ctggtaaaac ctctagtgga   2460
gtagtagatg taatcaatga agcggaagcc aaaagaccag agtagaggcc tatagaagaa   2520
actgcgatac cttttgtgat ggctaaacaa acagacatct ttttatatgt ttttacttct   2580
gtatatcgtg aagtagtaag tgataagcga atttggctaa gaacgttgta agtgaacaag   2640
ggacctcttt tgcctttcaa aaaggatta aatggagtta atcattgaga tttagttttc     2700
gttagattct gtatccctaa ataactccct tacccgacgg gaaggcacaa aagacttgaa   2760
taatagcaaa cggccagtag ccaagaccaa ataatactag agttaactga tggtcttaaa   2820
caggcattac gtggtgaact ccaagaccaa tatacaaaat atcgataagt tattcttgcc   2880
caccaattta aggagcctac atcaggacag tagtaccatt cctcagagaa gaggtataca   2940
taacaagaaa atcgcgtgaa caccttatat aacttagccc gttattgagc taaaaaacct   3000
tgcaaaattt cctatgaata agaatacttc agacgtgata aaaatttact ttctaactct   3060
tctcacgctg cccctatctg ttcttccgct ctaccgtgag aaataaagca tcgagtacgg   3120
cagttcgctg tcactgaact aaaacaataa ggctagttcg aatgatgaac ttgcttgctg   3180
tcaaacttct gagttgccgc tgatgtgaca ctgtgacaat aaattcaaac cggttatagc   3240
ggtctcctcc ggtaccggtt ctgccacctc caatagagct cagtaggagt cagaacctct   3300
gcggtggctg tcagtgactc atccgcgttt cgtaagttgt gcgcgtgcac atttcgcccg   3360
ttcccgctca tcttgcagca ggcggaaatt ttcatcacgc tgtaggacgc aaaaaaaaaa   3420
taattaatcg tacaagaatc ttggaaaaaa aattgaaaaa ttttgtataa agggatgac    3480 ctaacttgac tcaatggctt ttacacccag tattttccct ttccttgttt gttacaatta   3540
tagaagcaag acaaaaacat atagacaacc tattcctagg agttatattt tttaccccta   3600
ccagcaatat aagtaaaaaa ctgtttaaac agtatggcag ttacaatgta ttatgaagat   3660
gatgtagaag tatcagcact tgctggaaag caaattgcag taatcggtta tggttcacaa   3720
ggacatgctc acgcacagaa tttgcgtgat tctggtcaca acgttatcat tggtgtgcgc   3780
cacggaaaat cttttgataa agcaaagaa gatggctttg aaacatttga agtaggagaa    3840
gcagtagcta aagctgatgt tattatggtt ttggcaccag atgaacttca acaatccatt   3900
tatgaagagg acatcaaacc aaacttgaaa gcaggttcag cacttggttt tgctcacgga   3960
tttaatatcc attttggcta tattaaagta ccagaagacg ttgacgtctt tatggttgcg   4020
cctaaggctc caggtcacct tgtccgtcgg acttatactg aaggttttgg tacaccagct   4080
ttgtttgttt cacaccaaaa tgcaagtggt catgcgcgtg aaatcgcaat ggattgggcc   4140
aaaggaattg gttgtgctcg agtgggaatt attgaaacaa cttttaaaga agaaacagaa   4200
gaagatttgt ttggagaaca agctgttcta tgtggaggtt tgacagcact tgttgaagcc   4260
ggttttgaaa cactgacaga agctggatac gctggcgaat tggcttactt tgaagttttg   4320
cacgaaatga aattgattgt tgacctcatg tatgaaggtg gttttactaa aatgcgtcaa   4380
```

```
tccatctcaa atactgctga gtttggcgat tatgtgactg gtccacggat tattactgac    4440
gaagttaaaa agaatatgaa gcttgttttg gctgatattc aatctggaaa atttgctcaa    4500
gatttcgttg atgacttcaa agcggggcgt ccaaaattaa tagcctatcg cgaagctgca    4560
aaaaatcttg aaattgaaaa aattgggcca gagctacgtc aagcaatgcc attcacacaa    4620
tctggtgatg acgatgcctt taaaatctat cagtaaggcc ctgcaggcca gaggaaaata    4680
atatcaagtg ctggaaactt tttctcttgg aattttttgca acatcaagtc atagtcaatt    4740
gaattgaccc aatttcacat ttaagatttt tttttttttca tccgacatac atctgtacac    4800
taggaagccc tgttttttctg aagcagcttc aaatatatat attttttttaca tatttattat    4860
gattcaatga acaatctaat taaatcgaaa acaagaaccg aaacgcgaat aaataattta    4920
tttagatggt gacaagtgta taagtcctca tcgggacagc tacgatttct ctttcggttt    4980
tggctgagct actggttgct gtgacgcagc ggcattagcg cggcgttatg agctaccctc    5040
gtggcctgaa agatggcggg aataaagcgg aactaaaaat tactgactga gccatattga    5100
ggtcaatttg tcaactcgtc aagtcacgtt tggtggacgg cccctttcca acgaatcgta    5160
tatactaaca tgcgcgcgct tcctatatac acatatacat atatatatat atatatatgt    5220
gtgcgtgtat gtgtacacct gtatttaatt tccttactcg cgggttttttc ttttttctca    5280
attcttggct tcctctttct cgagcggacc ggatcctccg cggtgccggc agatctatttt    5340
aaatggcgcg ccgacgtcag gtggcacttt tcggggaaat gtgcgcggaa ccctatttg    5400
tttattttttc taaatacatt caaatatgta tccgctcatg agacaataac cctgataaat    5460
gcttcaataa tattgaaaaa ggaagagtat gagtattcaa catttccgtg tcgcccttat    5520
tcccttttttt gcggcatttt gccttcctgt ttttgctcac ccagaaacgc tggtgaaagt    5580
aaaagatgct gaagatcagt tgggtgcacg agtgggttac atcgaactgg atctcaacag    5640
cggtaagatc cttgagagtt ttcgccccga agaacgtttt ccaatgatga gcacttttaa    5700
agttctgcta tgtggcgcgg tattatcccg tattgacgcc gggcaagagc aactcggtcg    5760
ccgcatacac tattctcaga atgacttggt tgagtactca ccagtcacag aaaagcatct    5820
tacggatggc atgacagtaa gagaattatg cagtgctgcc ataaccatga gtgataacac    5880
tgcggccaac ttacttctga caacgatcgg aggaccgaag gagctaaccg ctttttttgca    5940
caacatgggg gatcatgtaa ctcgccttga tcgttgggaa ccggagctga atgaagccat    6000
accaaacgac gagcgtgaca ccacgatgcc tgtagcaatg gcaacaacgt tgcgcaaact    6060
attaactggc gaactactta ctctagcttc ccggcaacaa ttaatagact ggatggaggc    6120
ggataaagtt gcaggaccac ttctgcgctc ggcccttccg gctggctggt ttattgctga    6180
taaatctgga gccggtgagc gtgggtctcg cggtatcatt gcagcactgg ggccagatgg    6240
taagccctcc cgtatcgtag ttatctacac gacggggagt caggcaacta tggatgaacg    6300
aaatagacag atcgctgaga taggtgcctc actgattaag cattggtaac tgtcagacca    6360
agtttactca tatatacttt agattgattt aaaacttcat ttttaattta aaaggatcta    6420
ggtgaagatc cttttttgata atctcatgac caaaatccct aacgtgagt tttcgttcca    6480
ctgagcgtca gaccccgtag aaaagatcaa aggatcttct tgagatcctt ttttttctgcg    6540
cgtaatctgc tgcttgcaaa caaaaaaacc accgctacca gcggtggttt gtttgccgga    6600
tcaagagcta ccaactcttt ttccgaaggt aactggcttc agcagagcgc agataccaaa    6660
tactgttctt ctagtgtagc cgtagttagg ccaccacttc aagaactctg tagcaccgcc    6720
tacataccttc gctctgctaa tcctgttacc agtggctgct gccagtggcg ataagtcgtg    6780
```

```
tcttaccggg ttggactcaa gacgatagtt accggataag gcgcagcggt cgggctgaac   6840 gggggggttcg tgcacacagc ccagcttgga gcgaacgacc tacaccgaac tgagatacct   6900
acagcgtgag ctatgagaaa gcgccacgct tcccgaaggg agaaaggcgg acaggtatcc   6960
ggtaagcggc agggtcggaa caggagagcg cacgagggag cttccagggg gaaacgcctg   7020
gtatctttat agtcctgtcg ggtttcgcca cctctgactt gagcgtcgat ttttgtgatg   7080
ctcgtcaggg gggcggagcc tatggaaaaa cgccagcaac gcggccttttt tacgttcct    7140 ggccttttgc tggccttttg ctcacatgtt ctttcctgcg ttatcccctg attctgtgga   7200
taaccgtatt accgcctttg agtgagctga taccgctcgc cgcagccgaa cgaccgagcg   7260
cagcgagtca gtgagcgagg aagcggaaga gcgcccaata cgcaaaccgc ctctccccgc   7320
gcgttggccg attcattaat gcagctggca cgacaggttt cccgactgga aagcgggcag   7380
tgagcgcaac gcaattaatg tgagttagct cactcattag gcaccccagg ctttacactt   7440
tatgcttccg gctcgtatgt tgtgtggaat tgtgagcgga taacaatttc acacaggaaa   7500
cagctatgac catgattacg ccaagctttt tctttccaat ttttttttttt tcgtcattat    7560 aaaaatcatt acgaccgaga ttcccgggta ataactgata taattaaatt gaagctctaa   7620
tttgtgagtt tagtatacat gcatttactt ataatacagt tttttagttt tgctggccgc   7680
atcttctcaa atatgcttcc cagcctgctt ttctgtaacg ttcaccctct acctttagcat   7740 cccttccctt tgcaaatagt cctcttccaa caataataat gtcagatcct gtagagacca   7800
catcatccac ggttctatac tgttgaccca atgcgtctcc cttgtcatct aaacccacac   7860
cgggtgtcat aatcaaccaa tcgtaaccttt catctcttcc acccatgtct ctttgagcaa   7920
taaagccgat aacaaaatct ttgtcgctct tcgcaatgtc aacagtaccc ttagtatatt   7980
ctccagtaga tagggagccc ttgcatgaca attctgctaa catcaaaagg cctctaggtt   8040
cctttgttac ttcttctgcc gcctgcttca aaccgctaac aatacctggg cccaccacac   8100
cgtgtgcatt cgtaatgtct gcccattctg ctattctgta tacacccgca gagtactgca   8160
atttgactgt attaccaatg tcagcaaatt ttctgtcttc gaagagtaaa aaattgtact    8220
tggcggataa tgcctttagc ggcttaactg tgccctccat ggaaaaatca gtcaagatat   8280
ccacatgtgt ttttagtaaa caaattttgg gacctaatgc ttcaactaac tccagtaatt   8340
ccttggtggt acgaacatcc aatgaagcac acaagtttgt ttgcttttcg tgcatgatat   8400
taaatagctt ggcagcaaca ggactaggat gagtagcagc acgttcctta tatgtagctt   8460
tcgacatgat ttatcttcgt ttcctgcagg ttttttgttct gtgcagttgg gttaagaata   8520
ctgggcaatt tcatgtttct tcaacactac atatgcgtat atataccaat ctaagtctgt   8580
gctccttcct tcgttcttcc ttctgttcgg agattaccga atcaaaaaaa tttcaaggaa   8640
accgaaatca aaaaaagaa taaaaaaaaa atgatgaatt gaaaagcttg catgcctgca   8700
ggtcgactct agtatactcc gtctactgta cgatacactt ccgctcaggt ccttgtcctt   8760
taacgaggcc ttaccactct tttgttactc tattgatcca gctcagcaaa ggcagtgtga   8820
tctaagattc tatcttcgcg atgtagtaaa actagctaga ccgagaaaga gactagaaat   8880
gcaaaaggca cttctacaat ggctgccatc attattatcc gatgtgacgc tgcatttttt   8940
tttttttttt tttttttttt tttttttttt tttttttttt tttttgtac aaatatcata   9000 aaaaagaga atctttttaa gcaaggattt tcttaacttc ttcggcgaca gcatcaccga   9060
cttcggtggt actgttggaa ccacctaaat caccagttct gatacctgca tccaaaacct   9120
```

```
ttttaactgc atcttcaatg gctttacctt cttcaggcaa gttcaatgac aatttcaaca    9180
tcattgcagc agacaagata gtggcgatag ggttgacctt attctttggc aaatctggag    9240
cggaaccatg gcatggttcg tacaaaccaa atgcggtgtt cttgtctggc aaagaggcca    9300
aggacgcaga tggcaacaaa cccaaggagc ctgggataac ggaggcttca tcggagatga    9360
tatcaccaaa catgttgctg gtgattataa taccatttag gtgggttggg ttcttaacta    9420
ggatcatggc ggcagaatca atcaattgat gttgaacttt caatgtaggg aattcgttct    9480
tgatggtttc ctccacagtt tttctccata atcttgaaga ggccaaaaca ttagctttat    9540
ccaaggacca aataggcaat ggtggctcat gttgtagggc catgaaagcg gccattcttg    9600
tgattctttg cacttctgga acggtgtatt gttcactatc ccaagcgaca ccatcaccat    9660
cgtcttcctt tctcttacca aagtaaatac ctcccactaa ttctctaaca acaacgaagt    9720
cagtaccttt agcaaattgt ggcttgattg gagataagtc taaagagag tcggatgcaa    9780 agttacatgg tcttaagttg gcgtacaatt gaagttcttt acggattttt agtaaacctt    9840
gttcaggtct aacactaccg gtaccccatt taggaccacc cacagcacct aacaaaacgg    9900
catcagcctt cttggaggct tccagcgcct catctggaag tggaacacct gtagcatcga    9960
tagcagcacc accaattaaa tgattttcga aatcgaactt gacattggaa cgaacatcag   10020
aaatagcttt aagaaccta atggcttcgg ctgtgatttc ttgaccaacg tggtcacctg   10080 gcaaacgac gatcttctta gggcagaca ttacaatggt atatccttga aatatatata   10140
aaaaaaaaaa aaaaaaaaa aaaaaaaaat gcagcttctc aatgatattc gaatacgctt   10200
tgaggagata cagcctaata tccgacaaac tgttttacag atttacgatc gtacttgtta   10260
cccatcattg aattttgaac atccgaacct gggagttttc cctgaaacag atagtatatt   10320
tgaacctgta taataatata tagtctagcg ctttacggaa gacaatgtat gtatttcggt   10380
tcctggagaa actattgcat ctattgcata ggtaatcttg cacgtcgcat ccccggttca   10440
ttttctgcgt ttccatcttg cacttcaata gcatatcttt gttaacgaag catctgtgct   10500
tcattttgta gaacaaaaat gcaacgcgag agcgctaatt tttcaaacaa agaatctgag   10560
ctgcattttt acagaacaga aatgcaacgc gaaagcgcta ttttaccaac gaagaatctg   10620
tgcttcattt ttgtaaaaca aaaatgcaac gcgagagcgc taattttca aacaaagaat   10680 ctgagctgca tttttacaga acagaaatgc aacgcgagag cgctatttta ccaacaaaga   10740
atctatactt cttttttgtt ctacaaaaat gcatcccgag agcgctattt tctaacaaa   10800 gcatcttaga ttacttttt tctcctttgt gcgctctata atgcagtctc ttgataactt   10860
tttgcactgt aggtccgtta aggttagaag aaggctactt tggtgtctat tttctcttcc   10920
ataaaaaaag cctgactcca cttcccgcgt ttactgatta ctagcgaagc tgcgggtgca   10980
ttttttcaag ataaaggcat ccccgattat attctatacc gatgtggatt gcgcatactt   11040
tgtgaacaga aagtgatagc gttgatgatt cttcattggt cagaaaatta tgaacggttt   11100
cttctatttt gtctctatat actacgtata ggaaatgttt acattttcgt attgttttcg   11160
attcactcta tgaatagttc ttactacaat tttttgtct aaagagtaat actagagata   11220
aacataaaaa atgtagaggt cgagtttaga tgcaagttca aggagcgaaa ggtggatggg   11280
taggttatat agggatatag cacagagata tatagcaaag agatactttt gagcaatgtt   11340
tgtggaagcg gtattcgcaa tatttagta gctcgttaca gtccggtgcg ttttggttt    11400 tttgaaagtg cgtcttcaga gcgcttttgg ttttcaaaag cgctctgaag ttcctatact   11460
ttctagagaa taggaacttc ggaataggaa cttcaaagcg tttccgaaaa cgagcgcttc   11520
```

| | |
|---|---|
| cgaaaatgca acgcgagctg cgcacataca gctcactgtt cacgtcgcac ctatatctgc | 11580 |
| gtgttgcctg tatatatata tacatgagaa gaacggcata gtgcgtgttt atgcttaaat | 11640 |
| gcgtacttat atgcgtctat ttatgtagga tgaaaggtag tctagtacct cctgtgatat | 11700 |
| tatcccattc catgcggggt atcgtatgct tccttcagca ctacccttta gctgttctat | 11760 |
| atgctgccac tcctcaattg gattagtctc atccttcaat gctatcattt cctttgatat | 11820 |
| tggatcatat gcatagtacc gagaaactag aggatc | 11856 |

<210> SEQ ID NO 2
<211> LENGTH: 15539
<212> TYPE: DNA
<213> ORGANISM: Artificial sequence
<220> FEATURE:
<223> OTHER INFORMATION: Plasmid

<400> SEQUENCE: 2

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat attttttat gcctcggtaa tgattttcat | 360 |
| tttttttttt ccacctagcg gatgactctt ttttttcctt agcgattggc attatcacat | 420 |
| aatgaattat acattatata agtaatgtg atttcttcga agaatatact aaaaaatgag | 480 |
| caggcaagat aaacgaaggc aaagatgaca gagcagaaag ccctagtaaa gcgtattaca | 540 |
| aatgaaacca agattcagat tgcgatctct ttaaagggtg gtcccctagc gatagagcac | 600 |
| tcgatcttcc cagaaaaaga ggcagaagca gtagcagaac aggccacaca atcgcaagtg | 660 |
| attaacgtcc acacaggtat agggtttctg gaccatatga tacatgctct ggccaagcat | 720 |
| tccggctggt cgctaatcgt tgagtgcatt ggtgacttac acatagacga ccatcacacc | 780 |
| actgaagact gcgggattgc tctcggtcaa gcttttaaag aggccctagg ggccgtgcgt | 840 |
| ggagtaaaaa ggtttggatc aggatttgcg ccttttggatg aggcactttc cagagcggtg | 900 |
| gtagatctt cgaacaggcc gtacgcagtt gtcgaacttg gtttgcaaag ggagaaagta | 960 |
| ggagatctct cttgcgagat gatcccgcat tttcttgaaa gctttgcaga ggctagcaga | 1020 |
| attaccctcc acgttgattg tctgcgaggc aagaatgatc atcaccgtag tgagagtgcg | 1080 |
| ttcaaggctc ttgcggttgc cataagagaa gccacctcgc ccaatggtac caacgatgtt | 1140 |
| ccctccacca aagtgttct tatgtagtga caccgattat ttaaagctgc agcatacgat | 1200 |
| atatatacat gtgtatatat gtataccctat gaatgtcagt aagtatgtat acgaacagta | 1260 |
| tgatactgaa gatgacaagg taatgcatca ttctatacgt gtcattctga acgaggcgcg | 1320 |
| ctttccttttt ttcttttttgc ttttttcttt ttttttctctt gaactcgacg gatctatgcg | 1380 |
| gtgtgaaata ccgcacagat gcgtaaggag aaaataccgc atcaggaaat tgtaagcgtt | 1440 |
| aatattttgt taaattcgc gttaaatttt tgttaaatca gctcatttt taaccaatag | 1500 |
| gccgaaatcg gcaaaatccc ttataaatca aagaataga ccgagatagg gttgagtgtt | 1560 |
| gttccagttt ggaacaagag tccactatta agaacgtgg actccaacgt caagggcga | 1620 |
| aaaccgtct atcagggcga tggcccacta cgtgaaccat caccctaatc aagttttttg | 1680 |

```
gggtcgaggt gccgtaaagc actaaatcgg aaccctaaag ggagcccccg atttagagct    1740
tgacggggaa agccggcgaa cgtggcgaga aaggaaggga agaaagcgaa aggagcgggc    1800
gctagggcgc tggcaagtgt agcggtcacg ctgcgcgtaa ccaccacacc cgccgcgctt    1860
aatgcgccgc tacagggcgc gtccattcgc cattcaggct gcgcaactgt tgggaagggc    1920
gcggtgcggg cctcttcgct attacgccag ctggcgaaag ggggatgtgc tgcaaggcga    1980
ttaagttggg taacgccagg gttttcccag tcacgacgtt gtaaaacgac ggccagtgag    2040
cgcgcgtaat acgactcact atagggcgaa ttgggtaccg gccccccct cgaggtcgac     2100
ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tcctttcccc    2400
atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttcctttt tccattctag cagccgtcgg gaaaacgtgg catcctctct    2700
ttcgggctca attggagtca cgctgccgtg agcatcctct ctttccatat ctaacaactg    2760
agcacgtaac caatggaaaa gcatgagctt agcgttgctc caaaaagta ttggatggtt     2820
ataccatttt gtctgttctc ttctgacttt gactcctcaa aaaaaaaat ctacaatcaa     2880
cagatcgctt caattacgcc ctcacaaaaa cttttttcct tcttcttcgc ccacgttaaa    2940
ttttatccct catgttgtct aacggatttc tgcacttgat ttattataaa aagacaaaga    3000
cataatactt ctctatcaat ttcagttatt gttcttcctt gcgttattct tctgttcttc    3060
tttttctttt gtcatatata accataacca agtaatacat attcaaacta gtatgactga    3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact acatgacttt    3300
tggtaaacta gccaaagtcg gtgttaagga agctggtgct tggccagttc agttcggaac    3360
aatcacggtt tctgatggaa tcgccatggg aacccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccattttttg cttacggcgg aacaattgca cctggtaatt tagacggcaa    3600
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct cacccggctg aatccgcaga aaagaaagca gatattgaag aagctggtcg    3840
cgctgttgtc aaaatgctcg aaatgggctt aaaaccttct gacattttaa cgcgtgaagc    3900
ttttgaagat gctattactg taactatggc tctgggaggt tcaaccaact caacccttca    3960
cctcttagct attgccccatg ctgctaatgt ggaattgaca cttgatgatt tcaatacttt    4020
ccaagaaaaa gttcctcatt tggctgattt gaaaccttct ggtcaatatg tattccaaga    4080
```

```
cctttacaag gtcggagggg taccagcagt tatgaaatat ctccttaaaa atggcttcct    4140
tcatggtgac cgtatcactt gtactggcaa acagtcgct  gaaaatttga aggcttttga    4200
tgatttaaca cctggtcaaa aggttattat gccgcttgaa atcctaaac  gtgaagatgg    4260
tccgctcatt attctccatg gtaacttggc tccagacggt gccgttgcca agtttctgg     4320
tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttcccct tcatcaatga ttgttggtaa    4500
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttcactttg  atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
gaagcctgaa gaaactggca aaaaatgttg tcctggttgc tgtggttaag cggccgcgtt    4860
aattcaaatt aattgatata gttttttaat gagtattgaa tctgtttaga ataatggaa    4920
tattattttt atttatttat ttatattatt ggtcggctct tttcttctga aggtcaatga    4980
caaaatgata tgaaggaaat aatgatttct aaaattttac aacgtaagat atttttacaa    5040
aagcctagct catcttttgt catgcactat tttactcacg cttgaaatta acggccagtc    5100
cactgcggag tcatttcaaa gtcatcctaa tcgatctatc gttttgata  gctcattttg    5160
gagttcgcga ttgtcttctg ttattcacaa ctgttttaat ttttatttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tcttttaact    5340
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg gacgtgtcac tctacttcgc cttttccct  actccttta    5580
gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760
tgattttga  tattgtataa aaaaccaaa  tatgtataaa aaaagtgaat aaaaaatacc    5820
aagtatggag aaatatatta gaagtctata cgttaaacca cccgggcccc cctcgaggt    5880
cgacggtatc gataagcttg atatcgaatt cctgcagccc gggggatcca ctagttctag    5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat ttttttata  acttatttaa    6240
taataaaaat cataaatcat aagaaattcg cttactctta attaatcaaa aagttaaaat    6300
tgtacgaata gattcaccac ttcttaacaa atcaaaccct tcattgattt ctcgaatgg     6360
caatacatgt gtaattaaag gatcaagagc aaacttcttc gccataaagt cggcaacaag    6420
```

```
tttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga atcaactcc accgtttgac atttcagtaa ggacttcttg     6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg gaaaatccgc accctatcaa    6900 gcaaacttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaacctt ttccatcagc     7740 tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atccttttcca   8460 attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagatttta    8640 catttctggt gttgaaggga agatatgag ctatacagcg gaatttccat atcactcaga     8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
```

```
tgcgggagtt tttttcatgt agatgatact gactgcacgc aaatataggc atgatttata   8880
ggcatgattt gatggctgta ccgataggaa cgctaagagt aacttcagaa tcgttatcct   8940
ggcggaaaaa attcatttgt aaactttaaa aaaaaaagcc aatatcccca aaattattaa   9000
gagcgcctcc attattaact aaaatttcac tcagcatcca caatgtatca ggtatctact   9060
acagatatta catgtggcga aaaagacaag aacaatgcaa tagcgcatca agaaaaaaca   9120
caaagctttc aatcaatgaa tcgaaaatgt cattaaaata gtatataaat tgaaactaag   9180
tcataaagct ataaaagaa aatttattta aatgcaagat ttaaagtaaa ttcacggccc      9240
tgcaggcctc agctcttgtt ttgttctgca aataacttac ccatctttt caaaacttta     9300
ggtgcaccct cctttgctag aataagttct atccaataca tcctatttgg atctgcttga   9360
gcttctttca tcacggatac gaattcattt tctgttctca caattttgga cacaactctg   9420
tcttccgttg ccccgaaact ttctggcagt tttgagtaat tccacatagg aatgtcatta   9480
taactctggt tcggaccatg aatttccctc tcaaccgtgt aaccatcgtt attaatgata   9540
aagcagattg ggtttatctt ctctctaatg gctagtccta attcttggac agtcagttgc   9600
aatgatccat ctccgataaa caataaatgt ctagattctt tatctgcaat ttggctgcct   9660
agagctgcgg ggaaagtgta tcctatagat ccccacaagg gttgaccaat aaaatgtgat   9720
ttcgatttca gaaatataga tgaggcaccg aagaaagaag tgccttgttc agccacgatc   9780
gtctcattac tttgggtcaa attttcgaca gcttgccaca gtctatcttg tgacaacagc   9840
gcgttagaag gtacaaaatc ttcttgcttt ttatctatgt acttgccttt atattcaatt   9900
tcggacaagt caagaagaga tgatatcagg gattcgaagt cgaaattttg gattctttcg   9960
ttgaaaattt taccttcatc gatattcaag gaaatcattt tattttcatt aagatggtga  10020
gtaaatgcac ccgtactaga atcggtaagc tttacaccca acataagaat aaaatcagca  10080
gattccacaa attccttcaa gtttggctct gacagagtac cgttgtaaat ccccaaaaat  10140
gagggcaatg cttcatcaac agatgattta ccaaagttca aagtagtaat aggtaactta  10200
gtctttgaaa taaactgagt aacagtcttc tctaggccga acgatataat ttcatggcct  10260
gtgattacaa ttggtttctt ggcattcttc agactttcct gtattttgtt cagaatctct  10320
tgatcagatg tattcgacgt ggaattttcc ttcttaagag gcaaggatgg ttttcagcc   10380
ttagcggcag ctacatctac aggtaaattg atgtaaaccg gctttctttc ctttagtaag  10440
gcagacaaca ctctatcaat ttcaacagtt gcattctcgg ctgtcaataa agtcctggca  10500
gcagtaaccg gttcgtgcat cttcataaag tgcttgaaat caccatcagc caacgtatgg  10560
tgaacaaact taccttcgtt ctgcactttc gaggtaggag atcccacgat ctcaacaaca  10620
ggcaggttct cagcatagga gcccgctaag ccattaactg cggataattc gccaacacca  10680
aatgtagtca agaatgccgc agccttttc gttcttgcgt acccgtcggc catataggag  10740
gcatttaact cattagcatt tcccacccat ttcatatctt tgtgtgaaat aatttgatct  10800
agaaattgca aattgtagtc acctggtact ccgaatattt cttctatacc taattcgtgt  10860
aatctgtcca acagatagtc acctactgta tacattttgt ttactagttt atgtgtgttt  10920
attcgaaact aagttcttgg tgttttaaaa ctaaaaaaaa gactaactat aaaagtagaa  10980
tttaagaagt ttaagaaata gatttacaga attacaatca ataccaccg tctttatata   11040
cttattagtc aagtagggga ataatttcag ggaactggtt tcaacctttt ttttcagctt  11100
tttccaaatc agagagagca gaaggtaata gaaggtgtaa gaaaatgaga tagatacatg  11160
```

```
cgtgggtcaa ttgccttgtg tcatcattta ctccaggcag gttgcatcac tccattgagg  11220
ttgtgcccgt ttttttgcctg tttgtgcccc tgttctctgt agttgcgcta agagaatgga  11280
cctatgaact gatggttggt gaagaaaaca atattttggt gctgggattc ttttttttc   11340
tggatgccag cttaaaaagc gggctccatt atatttagtg gatgccagga ataaactgtt  11400
cacccagaca cctacgatgt tatatattct gtgtaacccg cccctatttt tgggcatgta  11460
cgggttacag cagaattaaa aggctaattt tttgactaaa taaagttagg aaaatcacta  11520
ctattaatta tttacgtatt cttgaaatg gcagtattga taatgataaa ctcgaactga   11580
aaaagcgtgt tttttattca aaatgattct aactccctta cgtaatcaag gaatcttttt  11640
gccttggcct ccgcgtcatt aaacttcttg ttgttgacgc taacattcaa cgctagtata  11700
tattcgtttt tttcaggtaa gttcttttca acgggtctta ctgatgaggc agtcgcgtct  11760
gaacctgtta agaggtcaaa tatgtcttct tgaccgtacg tgtcttgcat gttattagct  11820
ttgggaattt gcatcaagtc ataggaaaat ttaaatcttg gctctcttgg gctcaaggtg  11880
acaaggtcct cgaaaatagg gcgcgcccca ccgcggtgga gctccagctt ttgttccctt  11940
tagtgagggt taattgcgcg cttggcgtaa tcatggtcat agctgtttcc tgtgtgaaat  12000
tgttatccgc tcacaattcc acacaacata cgagccggaa gcataaagtg taaagcctgg  12060
ggtgcctaat gagtgagcta actcacatta attgcgttgc gctcactgcc cgctttccag  12120
tcgggaaacc tgtcgtgcca gctgcattaa tgaatcggcc aacgcgcggg gagaggcggt  12180
ttgcgtattg ggcgctcttc cgcttcctcg ctcactgact cgctgcgctc ggtcgttcgg  12240
ctgcggcgag cggtatcagc tcactcaaag gcggtaatac ggttatccac agaatcaggg  12300
gataacgcag gaaagaacat gtgagcaaaa ggccagcaaa aggccaggaa ccgtaaaaag  12360
gccgcgttgc tggcgttttt ccataggctc cgcccccctg acgagcatca caaaaatcga  12420
cgctcaagtc agaggtggcg aaacccgaca ggactataaa gataccaggc gtttccccct  12480
ggaagctccc tcgtgcgctc tcctgttccg accctgccgc ttaccggata cctgtccgcc  12540
tttctccctt cgggaagcgt ggcgctttct catagctcac gctgtaggta tctcagttcg  12600
gtgtaggtcg ttcgctccaa gctgggctgt gtgcacgaac cccccgttca gcccgaccgc  12660
tgcgccttat ccggtaacta tcgtcttgag tccaacccgg taagacacga cttatcgcca  12720
ctggcagcag ccactggtaa caggattagc agagcgaggt atgtaggcgg tgctacagag  12780
ttcttgaagt ggtggcctaa ctacggctac actagaagaa cagtatttgg tatctgcgct  12840
ctgctgaagc cagttacctt cggaaaaaga gttggtagct cttgatccgg caaacaaacc  12900
accgctggta gcggtggttt ttttgtttgc aagcagcaga ttacgcgcag aaaaaaagga  12960
tctcaagaag atcctttgat cttttctacg gggtctgacg ctcagtggaa cgaaaactca  13020
cgttaaggga ttttggtcat gagattatca aaaaggatct tcacctagat ccttttaaat  13080
taaaaatgaa gttttaaatc aatctaaagt atatatgagt aaacttggtc tgacagttac  13140
caatgcttaa tcagtgaggc acctatctca gcgatctgtc tatttcgttc atccatagtt  13200
gcctgactcc ccgtcgtgta gataactacg atacgggagg gcttaccatc tggccccagt  13260
gctgcaatga taccgcgaga cccacgctca ccggctccag atttatcagc aataaaccag  13320
ccagccggaa gggccgagcg cagaagtggt cctgcaactt tatccgcctc catccagtct  13380
attaattgtt gccgggaagc tagagtaagt agttcgccag ttaatagttt cgcaacgttg  13440
gttgccattg ctacaggcat cgtggtgtca cgctcgtcgt ttggtatggc ttcattcagc  13500
tccggttccc aacgatcaag gcgagttaca tgatccccca tgttgtgcaa aaaagcggtt  13560
```

```
agctccttcg gtcctccgat cgttgtcaga agtaagttgg ccgcagtgtt atcactcatg    13620
gttatggcag cactgcataa ttctcttact gtcatgccat ccgtaagatg cttttctgtg    13680
actggtgagt actcaaccaa gtcattctga gaatagtgta tgcggcgacc gagttgctct    13740
tgcccggcgt caatacggga taataccgcg ccacatagca gaactttaaa agtgctcatc    13800
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttccttttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt ttgtagaaca    14160
aaaatgcaac gcgagagcgc taattttttca acaaagaat ctgagctgca tttttacaga    14220
acagaaatgc aacgcgaaag cgctatttta ccaacgaaga atctgtgctt cattttgta    14280 aaacaaaaat gcaacgcgag agcgctaatt tttcaaacaa agaatctgag ctgcattttt    14340
acagaacaga aatgcaacgc gagagcgcta ttttaccaac aaagaatcta tacttctttt    14400
ttgttctaca aaaatgcatc ccgagagcgc tattttttcta caaagcatc ttagattact    14460 ttttttctcc tttgtgcgct ctataatgca gtctcttgat aacttttttgc actgtaggtc    14520 cgttaaggtt agaagaaggc tactttggtg tctattttct cttccataaa aaagcctga    14580 ctccacttcc cgcgtttact gattactagc gaagctgcgg gtgcatttttt tcaagataaa    14640 ggcatccccg attatattct ataccgatgt ggattgcgca tactttgtga acagaaagtg    14700
atagcgttga tgattcttca ttggtcagaa aattatgaac ggtttcttct attttgtctc    14760
tatatactac gtataggaaa tgtttacatt ttcgtattgt tttcgattca ctctatgaat    14820
agttcttact acaattttttt tgtctaaaga gtaatactag agataaacat aaaaaatgta    14880
gaggtcgagt ttagatgcaa gttcaaggag cgaaaggtgg atgggtaggt tatataggga    14940
tatagcacag agatatatag caaagagata cttttgagca atgtttgtgg aagcggtatt    15000 cgcaatatttt tagtagctcg ttacagtccg gtgcgttttt ggtttttttga aagtgcgtct    15060 tcagagcgct tttggttttc aaaagcgctc tgaagttcct atactttcta gaatagga    15120 acttcggaat aggaacttca aagcgtttcc gaaacgagc gcttccgaaa atgcaacgcg    15180
agctgcgcac atacagctca ctgttcacgt cgcacctata tctgcgtgtt gcctgtatat    15240
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc    15539
```

<210> SEQ ID NO 3
<211> LENGTH: 4586
<212> TYPE: DNA
<213> ORGANISM: Artificial sequence
<220> FEATURE:
<223> OTHER INFORMATION: Template

<400> SEQUENCE: 3

```
gggtaccgag ctcgaattca ctggccgtcg ttttacaacg tcgtgactgg gaaaaccctg       60
```

```
gcgttaccca acttaatcgc cttgcagcac atcccccttt cgccagctgg cgtaatagcg    120
aagaggcccg caccgatcgc ccttcccaac agttgcgcag cctgaatggc gaatggcgcc    180
tgatgcggta ttttctcctt acgcatctgt gcggtatttc acaccgcata tggtgcactc    240
tcagtacaat ctgctctgat gccgcatagt taagccagcc ccgacacccg ccaacacccg    300
ctgacgcgcc ctgacgggct tgtctgctcc cggcatccgc ttacagacaa gctgtgaccg    360
tctccgggag ctgcatgtgt cagaggtttt caccgtcatc accgaaacgc gcgagacgaa    420
agggcctcgt gatacgccta ttttttatagg ttaatgtcat gataataatg gtttcttaga    480
cgtcaggtgg cacttttcgg ggaaatgtgc gcggaacccc tatttgttta ttttctaaa    540
tacattcaaa tatgtatccg ctcatgagac aataaccctg ataaatgctt caataatatt    600
gaaaaaggaa gagtatgagt attcaacatt tccgtgtcgc ccttattccc ttttttgcgg    660
cattttgcct tcctgttttt gctcacccag aaacgctggt gaaagtaaaa gatgctgaag    720
atcagttggg tgcacgagtg ggttacatcg aactggatct caacagcggt aagatccttg    780
agagttttcg ccccgaagaa cgttttccaa tgatgagcac ttttaaagtt ctgctatgtg    840
gcgcggtatt atcccgtatt gacgccgggc aagagcaact cggtcgccgc atacactatt    900
ctcagaatga cttggttgag tactcaccag tcacagaaaa gcatcttacg gatggcatga    960
cagtaagaga attatgcagt gctgccataa ccatgagtga taacactgcg gccaacttac   1020
ttctgacaac gatcggagga ccgaaggagc taaccgcttt tttgcacaac atgggggatc   1080
atgtaactcg ccttgatcgt tgggaaccgg agctgaatga agccatacca aacgacgagc   1140
gtgacaccac gatgcctgta gcaatggcaa caacgttgcg caaactatta actggcgaac   1200
tacttactct agcttcccgg caacaattaa tagactggat ggaggcggat aaagttgcag   1260
gaccacttct gcgctcggcc cttccggctg gctggtttat tgctgataaa tctggagccg   1320
gtgagcgtgg gtctcgcggt atcattgcag cactggggcc agatggtaag ccctcccgta   1380
tcgtagttat ctacacgacg gggagtcagg caactatgga tgaacgaaat agacagatcg   1440
ctgagatagg tgcctcactg attaagcatt ggtaactgtc agaccaagtt tactcatata   1500
tactttagat tgatttaaaa cttcattttt aatttaaaag gatctaggtg aagatccttt   1560
ttgataatct catgaccaaa atcccttaac gtgagttttc gttccactga gcgtcagacc   1620
ccgtagaaaa gatcaaagga tcttcttgag atcctttttt tctgcgcgta atctgctgct   1680
tgcaaacaaa aaaaccaccg ctaccagcgg tggtttgttt gccggatcaa gagctaccaa   1740
ctcttttttcc gaaggtaact ggcttcagca gagcgcagat accaaatact gtccttctag   1800
tgtagccgta gttaggccac cacttcaaga actctgtagc accgcctaca tacctcgctc   1860
tgctaatcct gttaccagtg gctgctgcca gtggcgataa gtcgtgtctt accgggttgg   1920
actcaagacg atagttaccg gataaggcgc agcggtcggg ctgaacgggg ggttcgtgca   1980
cacagcccag cttggagcga acgacctaca ccgaactgag atacctacag cgtgagctat   2040
gagaaagcgc cacgcttccc gaagggagaa aggcggacag gtatccggta agcggcaggg   2100
tcggaacagg agagcgcacg agggagcttc caggggaaa cgcctggtat ctttatagtc   2160
ctgtcgggtt tcgccacctc tgacttgagc gtcgattttt gtgatgctcg tcaggggggc   2220
ggagcctatg gaaaaacgcc agcaacgcgg ccttttacg gttcctggcc ttttgctggc   2280
cttttgctca catgttcttt cctgcgttat cccctgattc tgtggataac cgtattaccg   2340
cctttgagtg agctgatacc gctcgccgca gccgaacgac cgagcgcagc gagtcagtga   2400
gcgaggaagc ggaagagcgc ccaatacgca aaccgcctct ccccgcgcgt tggccgattc   2460
```

```
attaatgcag ctggcacgac aggtttcccg actggaaagc gggcagtgag cgcaacgcaa    2520
ttaatgtgag ttagctcact cattaggcac cccaggcttt acactttatg cttccggctc    2580
gtatgttgtg tggaattgtg agcggataac aatttcacac aggaaacagc tatgaccatg    2640
attacgccaa gcttgcatgc ctgcaggtcg actctagagg atccccgcat tgcggattac    2700
gtattctaat gttcagataa cttcgtatag catacattat acgaagttat ctagggattc    2760
ataaccattt tctcaatcga attacacaga acacaccgta caaacctctc tatcataact    2820
acttaatagt cacacacgta ctcgtctaaa tacacatcat cgtcctacaa gttcatcaaa    2880
gtgttggaca gacaactata ccagcatgga tctcttgtat cggttctttt ctcccgctct    2940
ctcgcaataa caatgaacac tgggtcaatc atagcctaca caggtgaaca gagtagcgtt    3000
tatacagggt ttatacggtg attcctacgg caaaaatttt tcatttctaa aaaaaaaaag    3060
aaaaattttt ctttccaacg ctagaaggaa agaaaaatc taattaaatt gatttggtga    3120
ttttctgaga gttccctttt tcatatatcg aattttgaat ataaaaggag atcgaaaaaa    3180
tttttctatt caatctgttt tctggtttta tttgatagtt ttttttgtgta ttattattat    3240 ggattagtac tggtttatat gggtttttct gtataacttc ttttttatttt agtttgttta    3300 atcttatttt gagttacatt atagttccct aactgcaaga gaagtaacat taaaactcga    3360
gatgggtaag gaaaagactc acgtttcgag gccgcgatta aattccaaca tggatgctga    3420
tttatatggg tataaatggg ctcgcgataa tgtcgggcaa tcaggtgcga caatctatcg    3480
attgtatggg aagcccgatg cgccagagtt gtttctgaaa catggcaaag gtagcgttgc    3540
caatgatgtt acagatgaga tggtcagact aaactggctg acggaattta tgcctcttcc    3600
gaccatcaag catttttatcc gtactcctga tgatgcatgg ttactcacca ctgcgatccc    3660
cggcaaaaca gcattccagg tattagaaga atatcctgat tcaggtgaaa atattgttga    3720
tgcgctggca gtgttcctgc gccggttgca ttcgattcct gtttgtaatt gtccttttaa    3780
cagcgatcgc gtatttcgtc tcgctcaggc gcaatcacga atgaataacg gtttggttga    3840
tgcgagtgat tttgatgacg agcgtaatgg ctggcctgtt gaacaagtct ggaaagaaat    3900
gcataagctt ttgccattct caccggattc agtcgtcact catggtgatt tctcacttga    3960
taaccttatt tttgacgagg ggaaattaat aggttgtatt gatgttggac gagtcggaat    4020
cgcagaccga taccaggatc ttgccatcct atggaactgc ctcggtgagt tttctccttc    4080
attacagaaa cggctttttc aaaaatatgg tattgataat cctgatatga ataaattgca    4140
gtttcatttg atgctcgatg agtttttcta gtttaacttt gatactacta gattttttct    4200
cttcatttat aaaattttg gttataattg aagctttaga agtatgaaaa aatccttttt    4260
tttcattctt tgcaaccaaa ataagaagct tcttttattc attgaaatga tgaatataaa    4320
cctaacaaaa gaaaagact cgaatatcaa acattaaaaa aaaataaaag aggttatctg    4380
ttttcccatt tagttggagt ttgcattttc taatagatag aactctcaat taatgtggat    4440
ttagtttctc tgttcgtttt ttttgtttt gttctcactg tatttacatt tctatttagt    4500
atttagttat tcatataatc tataacttcg tatagcatac attatacgaa gttatccagt    4560
gatgatacaa cgagttagcc aaggtg                                         4586

<210> SEQ ID NO 4
<211> LENGTH: 80
<212> TYPE: DNA
<213> ORGANISM: Artificial sequence
<220> FEATURE:
```

```
<223> OTHER INFORMATION: Primer

<400> SEQUENCE: 4
ttccggtttc tttgaaattt ttttgattcg gtaatctccg agcagaagga gcattgcgga    60
ttacgtattc taatgttcag                                                80

<210> SEQ ID NO 5
<211> LENGTH: 81
<212> TYPE: DNA
<213> ORGANISM: Artificial sequence
<220> FEATURE:
<223> OTHER INFORMATION: Primer

<400> SEQUENCE: 5
gggtaataac tgatataatt aaattgaagc tctaatttgt gagtttagta caccttggct    60
aactcgttgt atcatcactg g                                              81

<210> SEQ ID NO 6
<211> LENGTH: 38
<212> TYPE: DNA
<213> ORGANISM: Artificial sequence
<220> FEATURE:
<223> OTHER INFORMATION: Primer

<400> SEQUENCE: 6
gcctcgagtt ttaatgttac ttctcttgca gttaggga                            38

<210> SEQ ID NO 7
<211> LENGTH: 31
<212> TYPE: DNA
<213> ORGANISM: Artificial sequence
<220> FEATURE:
<223> OTHER INFORMATION: Primer

<400> SEQUENCE: 7
gctaaattcg agtgaaacac aggaagacca g                                   31

<210> SEQ ID NO 8
<211> LENGTH: 90
<212> TYPE: DNA
<213> ORGANISM: Artificial sequence
<220> FEATURE:
<223> OTHER INFORMATION: Primer

<400> SEQUENCE: 8
gtattttggt agattcaatt ctctttccct ttccttttcc ttcgctcccc ttccttatca    60
gcattgcgga ttacgtattc taatgttcag                                     90

<210> SEQ ID NO 9
<211> LENGTH: 90
<212> TYPE: DNA
<213> ORGANISM: Artificial sequence
<220> FEATURE:
<223> OTHER INFORMATION: Primer

<400> SEQUENCE: 9
ttggttgggg gaaaagagg caacaggaaa gatcagaggg ggaggggggg ggagagtgtc     60
accttggcta actcgttgta tcatcactgg                                     90

<210> SEQ ID NO 10
<211> LENGTH: 21
<212> TYPE: DNA
<213> ORGANISM: Artificial sequence
```

```
<220> FEATURE:
<223> OTHER INFORMATION: Primer

<400> SEQUENCE: 10
tcggtgcggg cctcttcgct a                                              21

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
aatgtgagtt agctcactca t                                              21

<210> SEQ ID NO 12
<211> LENGTH: 57
<212> TYPE: DNA
<213> ORGANISM: Artificial sequence
<220> FEATURE:
<223> OTHER INFORMATION: Primer

<400> SEQUENCE: 12
aattggatcc ggcgcgccgt ttaaacggcc ggccaatgtg gctgtggttt cagggtc       57

<210> SEQ ID NO 13
<211> LENGTH: 49
<212> TYPE: DNA
<213> ORGANISM: Artificial sequence
<220> FEATURE:
<223> OTHER INFORMATION: Primer

<400> SEQUENCE: 13
aatttctaga ttaattaagc ggccgcaagg ccatgaagct ttttctttc                49

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
ttctcgacgt gggccttttt cttg                                           24

<210> SEQ ID NO 15
<211> LENGTH: 49
<212> TYPE: DNA
<213> ORGANISM: Artificial sequence
<220> FEATURE:
<223> OTHER INFORMATION: Primer

<400> SEQUENCE: 15
tgcagcttta aataatcggt gtcactactt tgccttcgtt tatcttgcc                49

<210> SEQ ID NO 16
<211> LENGTH: 49
<212> TYPE: DNA
<213> ORGANISM: Artificial sequence
<220> FEATURE:
<223> OTHER INFORMATION: Primer

<400> SEQUENCE: 16
gagcaggcaa gataaacgaa ggcaaagtag tgacaccgat tatttaaag                49
```

```
<210> SEQ ID NO 17
<211> LENGTH: 49
<212> TYPE: DNA
<213> ORGANISM: Artificial sequence
<220> FEATURE:
<223> OTHER INFORMATION: Primer

<400> SEQUENCE: 17
tatggaccct gaaaccacag ccacattgta accaccacga cggttgttg              49

<210> SEQ ID NO 18
<211> LENGTH: 49
<212> TYPE: DNA
<213> ORGANISM: Artificial sequence
<220> FEATURE:
<223> OTHER INFORMATION: Primer

<400> SEQUENCE: 18
tttagcaaca accgtcgtgg tggttacaat gtggctgtgg tttcagggt              49

<210> SEQ ID NO 19
<211> LENGTH: 49
<212> TYPE: DNA
<213> ORGANISM: Artificial sequence
<220> FEATURE:
<223> OTHER INFORMATION: Primer

<400> SEQUENCE: 19
ccagaaaccc tatacctgtg tggacgtaag gccatgaagc ttttctttt              49

<210> SEQ ID NO 20
<211> LENGTH: 49
<212> TYPE: DNA
<213> ORGANISM: Artificial sequence
<220> FEATURE:
<223> OTHER INFORMATION: Primer

<400> SEQUENCE: 20
attggaaaga aaagcttca tggccttacg tccacacagg tatagggtt              49

<210> SEQ ID NO 21
<211> LENGTH: 22
<212> TYPE: DNA
<213> ORGANISM: Artificial sequence
<220> FEATURE:
<223> OTHER INFORMATION: Primer

<400> SEQUENCE: 21
cataagaaca cctttggtgg ag                                           22

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
aggattatca ttcataagtt tc                                           22

<210> SEQ ID NO 23
<211> LENGTH: 23
<212> TYPE: DNA
<213> ORGANISM: Artificial sequence
<220> FEATURE:
<223> OTHER INFORMATION: Primer
```

```
<400> SEQUENCE: 23
ttcttggagc tgggacatgt ttg                                          23

<210> SEQ ID NO 24
<211> LENGTH: 22
<212> TYPE: DNA
<213> ORGANISM: Artificial sequence
<220> FEATURE:
<223> OTHER INFORMATION: Primer

<400> SEQUENCE: 24
tgatgatatt tcataaataa tg                                           22

<210> SEQ ID NO 25
<211> LENGTH: 23
<212> TYPE: DNA
<213> ORGANISM: Artificial sequence
<220> FEATURE:
<223> OTHER INFORMATION: Primer

<400> SEQUENCE: 25
atgcgtccat ctttacagtc ctg                                          23

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26
tacgtacgga ccaatcgaag tg                                           22

<210> SEQ ID NO 27
<211> LENGTH: 49
<212> TYPE: DNA
<213> ORGANISM: Artificial sequence
<220> FEATURE:
<223> OTHER INFORMATION: Primer

<400> SEQUENCE: 27
aattcgtttg agtacactac taatggcttt gttggcaata tgttttgc              49

<210> SEQ ID NO 28
<211> LENGTH: 49
<212> TYPE: DNA
<213> ORGANISM: Artificial sequence
<220> FEATURE:
<223> OTHER INFORMATION: Primer

<400> SEQUENCE: 28
atatagcaaa aacatattgc caacaaagcc attagtagtg tactcaaac             49

<210> SEQ ID NO 29
<211> LENGTH: 49
<212> TYPE: DNA
<213> ORGANISM: Artificial sequence
<220> FEATURE:
<223> OTHER INFORMATION: Primer

<400> SEQUENCE: 29
tatggaccct gaaccacag ccacattctt gttatttata aaaagacac              49

<210> SEQ ID NO 30
```

```
<211> LENGTH: 49
<212> TYPE: DNA
<213> ORGANISM: Artificial sequence
<220> FEATURE:
<223> OTHER INFORMATION: Primer

<400> SEQUENCE: 30
ctcccgtgtc tttttataaa taacaagaat gtggctgtgg tttcagggt          49

<210> SEQ ID NO 31
<211> LENGTH: 49
<212> TYPE: DNA
<213> ORGANISM: Artificial sequence
<220> FEATURE:
<223> OTHER INFORMATION: Primer

<400> SEQUENCE: 31
taccgtaggc gtccttagga aagatagaag gccatgaagc tttttcttt           49

<210> SEQ ID NO 32
<211> LENGTH: 49
<212> TYPE: DNA
<213> ORGANISM: Artificial sequence
<220> FEATURE:
<223> OTHER INFORMATION: Primer

<400> SEQUENCE: 32
attggaaaga aaaagcttca tggccttcta tctttcctaa ggacgccta           49

<210> SEQ ID NO 33
<211> LENGTH: 21
<212> TYPE: DNA
<213> ORGANISM: Artificial sequence
<220> FEATURE:
<223> OTHER INFORMATION: Primer

<400> SEQUENCE: 33
ttattgtttg gcatttgtag c                                         21

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
ccaagcatct cataaaccta tg                                        22

<210> SEQ ID NO 35
<211> LENGTH: 22
<212> TYPE: DNA
<213> ORGANISM: Artificial sequence
<220> FEATURE:
<223> OTHER INFORMATION: Primer

<400> SEQUENCE: 35
tgtgcagatg cagatgtgag ac                                        22

<210> SEQ ID NO 36
<211> LENGTH: 17
<212> TYPE: DNA
<213> ORGANISM: Artificial sequence
<220> FEATURE:
<223> OTHER INFORMATION: Primer

<400> SEQUENCE: 36
```

-continued

```
agttattgat accgtac                                                    17

<210> SEQ ID NO 37
<211> LENGTH: 19
<212> TYPE: DNA
<213> ORGANISM: Artificial sequence
<220> FEATURE:
<223> OTHER INFORMATION: Primer

<400> SEQUENCE: 37
cgagataccg taggcgtcc                                                  19

<210> SEQ ID NO 38
<211> LENGTH: 24
<212> TYPE: DNA
<213> ORGANISM: Artificial sequence
<220> FEATURE:
<223> OTHER INFORMATION: Primer

<400> SEQUENCE: 38
ttatgtatgc tcttctgact tttc                                            24

<210> SEQ ID NO 39
<211> LENGTH: 49
<212> TYPE: DNA
<213> ORGANISM: Artificial sequence
<220> FEATURE:
<223> OTHER INFORMATION: Primer

<400> SEQUENCE: 39
aataattaga gattaaatcg ctcattttt gccagtttct tcaggcttc                  49

<210> SEQ ID NO 40
<211> LENGTH: 49
<212> TYPE: DNA
<213> ORGANISM: Artificial sequence
<220> FEATURE:
<223> OTHER INFORMATION: Primer

<400> SEQUENCE: 40
agcctgaaga aactggcaaa aaatgagcga tttaatctct aattattag                 49

<210> SEQ ID NO 41
<211> LENGTH: 49
<212> TYPE: DNA
<213> ORGANISM: Artificial sequence
<220> FEATURE:
<223> OTHER INFORMATION: Primer

<400> SEQUENCE: 41
tatggaccct gaaccacag ccacattttt caatcattgg agcaatcat                  49

<210> SEQ ID NO 42
<211> LENGTH: 49
<212> TYPE: DNA
<213> ORGANISM: Artificial sequence
<220> FEATURE:
<223> OTHER INFORMATION: Primer

<400> SEQUENCE: 42
taaaatgatt gctccaatga ttgaaaaatg tggctgtggt ttcagggtc                 49

<210> SEQ ID NO 43
<211> LENGTH: 49
<212> TYPE: DNA
```

```
<213> ORGANISM: Artificial sequence
<220> FEATURE:
<223> OTHER INFORMATION: Primer

<400> SEQUENCE: 43
accgtaggtg ttgtttggga aagtggaagg ccatgaagct ttttctttc                49

<210> SEQ ID NO 44
<211> LENGTH: 49
<212> TYPE: DNA
<213> ORGANISM: Artificial sequence
<220> FEATURE:
<223> OTHER INFORMATION: Primer

<400> SEQUENCE: 44
ttggaaagaa aaagcttcat ggccttccac tttcccaaac aacacctac                49

<210> SEQ ID NO 45
<211> LENGTH: 23
<212> TYPE: DNA
<213> ORGANISM: Artificial sequence
<220> FEATURE:
<223> OTHER INFORMATION: Primer

<400> SEQUENCE: 45
ttattgctta gcgttggtag cag                                            23

<210> SEQ ID NO 46
<211> LENGTH: 21
<212> TYPE: DNA
<213> ORGANISM: Artificial sequence
<220> FEATURE:
<223> OTHER INFORMATION: Primer

<400> SEQUENCE: 46
tttttggtgg ttccggcttc c                                              21

<210> SEQ ID NO 47
<211> LENGTH: 22
<212> TYPE: DNA
<213> ORGANISM: Artificial sequence
<220> FEATURE:
<223> OTHER INFORMATION: Primer

<400> SEQUENCE: 47
aaagttggca tagcggaaac tt                                             22

<210> SEQ ID NO 48
<211> LENGTH: 16
<212> TYPE: DNA
<213> ORGANISM: Artificial sequence
<220> FEATURE:
<223> OTHER INFORMATION: Primer

<400> SEQUENCE: 48
gtcattgaca ccatct                                                    16

<210> SEQ ID NO 49
<211> LENGTH: 19
<212> TYPE: DNA
<213> ORGANISM: Artificial sequence
<220> FEATURE:
<223> OTHER INFORMATION: Primer

<400> SEQUENCE: 49
agagataccg taggtgttg                                                 19
```

<210> SEQ ID NO 50
<211> LENGTH: 33
<212> TYPE: DNA
<213> ORGANISM: Artificial sequence
<220> FEATURE:
<223> OTHER INFORMATION: Primer

<400> SEQUENCE: 50
aattggcgcg ccatgaaagc tctggtttat cac         33

<210> SEQ ID NO 51
<211> LENGTH: 49
<212> TYPE: DNA
<213> ORGANISM: Artificial sequence
<220> FEATURE:
<223> OTHER INFORMATION: Primer

<400> SEQUENCE: 51
tgaatcatga gttttatgtt aattagctca ggcagcgcct gcgttcgag         49

<210> SEQ ID NO 52
<211> LENGTH: 49
<212> TYPE: DNA
<213> ORGANISM: Artificial sequence
<220> FEATURE:
<223> OTHER INFORMATION: Primer

<400> SEQUENCE: 52
atcctctcga acgcaggcgc tgcctgagct aattaacata aaactcatg         49

<210> SEQ ID NO 53
<211> LENGTH: 34
<212> TYPE: DNA
<213> ORGANISM: Artificial sequence
<220> FEATURE:
<223> OTHER INFORMATION: Primer

<400> SEQUENCE: 53
aattgtttaa acaagtaaat aaattaatca gcat         34

<210> SEQ ID NO 54
<211> LENGTH: 49
<212> TYPE: DNA
<213> ORGANISM: Artificial sequence
<220> FEATURE:
<223> OTHER INFORMATION: Primer

<400> SEQUENCE: 54
acacaataca ataacaagaa gaacaaaatg aaagctctgg tttatcacg         49

<210> SEQ ID NO 55
<211> LENGTH: 49
<212> TYPE: DNA
<213> ORGANISM: Artificial sequence
<220> FEATURE:
<223> OTHER INFORMATION: Primer

<400> SEQUENCE: 55
agcgtataca tctgttggga aagtagaagg ccatgaagct ttttctttc         49

<210> SEQ ID NO 56
<211> LENGTH: 49
<212> TYPE: DNA
<213> ORGANISM: Artificial sequence
<220> FEATURE:

<223> OTHER INFORMATION: Primer

<400> SEQUENCE: 56
ttggaaagaa aaagcttcat ggccttctac tttcccaaca gatgtatac           49

<210> SEQ ID NO 57
<211> LENGTH: 22
<212> TYPE: DNA
<213> ORGANISM: Artificial sequence
<220> FEATURE:
<223> OTHER INFORMATION: Primer

<400> SEQUENCE: 57
ttattgttta gcgttagtag cg                                       22

<210> SEQ ID NO 58
<211> LENGTH: 72
<212> TYPE: DNA
<213> ORGANISM: Artificial sequence
<220> FEATURE:
<223> OTHER INFORMATION: Primer

<400> SEQUENCE: 58
cataatcaat ctcaaagaga acaacacaat acaataacaa gaagaacaaa atgaaagctc    60
tggtttatca cg                                                 72

<210> SEQ ID NO 59
<211> LENGTH: 21
<212> TYPE: DNA
<213> ORGANISM: Artificial sequence
<220> FEATURE:
<223> OTHER INFORMATION: Primer

<400> SEQUENCE: 59
taggcataat caccgaagaa g                                        21

<210> SEQ ID NO 60
<211> LENGTH: 21
<212> TYPE: DNA
<213> ORGANISM: Artificial sequence
<220> FEATURE:
<223> OTHER INFORMATION: Primer

<400> SEQUENCE: 60
aaaatggtaa gcagctgaaa g                                        21

<210> SEQ ID NO 61
<211> LENGTH: 17
<212> TYPE: DNA
<213> ORGANISM: Artificial sequence
<220> FEATURE:
<223> OTHER INFORMATION: Primer

<400> SEQUENCE: 61
agttgttaga actgttg                                             17

<210> SEQ ID NO 62
<211> LENGTH: 19
<212> TYPE: DNA
<213> ORGANISM: Artificial sequence
<220> FEATURE:
<223> OTHER INFORMATION: Primer

<400> SEQUENCE: 62
gacgatagcg tatacatct                                           19

<210> SEQ ID NO 63
<211> LENGTH: 22
<212> TYPE: DNA
<213> ORGANISM: Artificial sequence
<220> FEATURE:
<223> OTHER INFORMATION: Primer

<400> SEQUENCE: 63
cttagcctct agccatagcc at                                         22

<210> SEQ ID NO 64
<211> LENGTH: 23
<212> TYPE: DNA
<213> ORGANISM: Artificial sequence
<220> FEATURE:
<223> OTHER INFORMATION: Primer

<400> SEQUENCE: 64
ttagttttgc tggccgcatc ttc                                        23

<210> SEQ ID NO 65
<211> LENGTH: 21
<212> TYPE: DNA
<213> ORGANISM: Artificial sequence
<220> FEATURE:
<223> OTHER INFORMATION: Primer

<400> SEQUENCE: 65
cccattaata tactattgag a                                          21

<210> SEQ ID NO 66
<211> LENGTH: 7523
<212> TYPE: DNA
<213> ORGANISM: Artificial sequence
<220> FEATURE:
<223> OTHER INFORMATION: Plasmid

<400> SEQUENCE: 66
ccagcttttg ttcccttag tgagggttaa ttgcgcgctt ggcgtaatca tggtcatagc      60
tgtttcctgt gtgaaattgt tatccgctca caattccaca caacatagga gccggaagca     120
taaagtgtaa agcctggggt gcctaatgag tgaggtaact cacattaatt gcgttgcgct     180
cactgcccgc tttccagtcg ggaaacctgt cgtgccagct gcattaatga atcggccaac     240
gcgcggggag aggcggtttg cgtattgggc gctcttccgc ttcctcgctc actgactcgc     300
tgcgctcggt cgttcggctg cggcgagcgg tatcagctca ctcaaaggcg gtaatacggt     360
tatccacaga atcaggggat aacgcaggaa agaacatgtg agcaaaaggc cagcaaaagg     420
ccaggaaccg taaaaaggcc gcgttgctgg cgttttccca ggctccgccc ccctgacg      480 agcatcacaa aaatcgacgc tcaagtcaga ggtggcgaaa cccgacagga ctataaagat     540
accaggcgtt tcccctggaa gctccctcg tgcgctctcc tgttccgacc ctgccgctta     600
ccggatacct gtccgccttt ctcccttcgg gaagcgtggc gctttctcat agctcacgct     660
gtaggtatct cagttcggtg taggtcgttc gctccaagct gggctgtgtg cacgaacccc     720
ccgttcagcc cgaccgctgc gccttatccg gtaactatcg tcttgagtcc aacccggtaa     780
gacacgactt atcgccactg gcagcagcca ctggtaacag gattagcaga gcgaggtatg     840
taggcggtgc tacagagttc ttgaagtggt ggcctaacta cggctacact agaaggacag     900
tatttggtat ctgcgctctg ctgaagccag ttaccttcgg aaaaagagtt ggtagctctt     960

```
gatccggcaa acaaaccacc gctggtagcg gtggttttt tgtttgcaag cagcagatta    1020
cgcgcagaaa aaaaggatct caagaagatc ctttgatctt ttctacgggg tctgacgctc    1080
agtggaacga aaactcacgt taagggattt tggtcatgag attatcaaaa aggatcttca    1140
cctagatcct tttaaattaa aaatgaagtt ttaaatcaat ctaaagtata tatgagtaaa    1200
cttggtctga cagttaccaa tgcttaatca gtgaggcacc tatctcagcg atctgtctat    1260
ttcgttcatc catagttgcc tgactccccg tcgtgtagat aactacgata cgggagggct    1320
taccatctgg ccccagtgct gcaatgatac cgcgagaccc acgctcaccg gctccagatt    1380
tatcagcaat aaaccagcca gccggaaggg ccgagcgcag aagtggtcct gcaactttat    1440
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca tagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280
agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg catttttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta atgcagtc tcttgataac    2580
ttttttgcact gtaggtccgt taaggttaga agaaggctac tttggtgtct attttctctt    2640
ccataaaaaa agcctgactc cacttcccgc gtttactgat tactagcgaa gctgcgggtg    2700
cattttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca atttttttgt ctaaagagta atactagaga    2940
taaacataaa aaatgtagag gtcgagttta gatgcaagtt caaggagcga aaggtggatg    3000
ggtaggttat atagggatat agcacagaga tatatagcaa agagatactt ttgagcaatg    3060
tttgtggaag cggtattcgc aatattttag tagctcgtta cagtccggtg cgttttggt    3120
tttttgaaag tgcgtcttca gagcgctttt ggttttcaaa agcgctctga agttcctata    3180
ctttctagag aataggaact tcggaatagg aacttcaaag cgtttccgaa aacgagcgct    3240
tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
```

```
atgcgtactt atatgcgtct atttatgtag gatgaaaggt agtctagtac ctcctgtgat    3420
attatcccat tccatgcggg gtatcgtatg cttccttcag cactacccctt tagctgttct    3480 atatgctgcc actcctcaat tggattagtc tcatccttca atgctatcat ttcctttgat    3540
attggatcat ctaagaaacc attattatca tgacattaac ctataaaaat aggcgtatca    3600 cgaggcccett tcgtctcgcg cgtttcggtg atgacggtga aaacctctga cacatgcagc    3660
tcccggagac ggtcacagct tgtctgtaag cggatgccgg gagcagacaa gcccgtcagg    3720
gcgcgtcagc gggtgttggc gggtgtcggg gctggcttaa ctatgcggca tcagagcaga    3780
ttgtactgag agtgcaccat aaattcccgt tttaagagct tggtgagcgc taggagtcac    3840
tgccaggtat cgtttgaaca cggcattagt cagggaagtc ataacacagt cctttcccgc    3900
aatttctttt ttctattact cttggcctcc tctagtacac tctatatttt tttatgcctc    3960
ggtaatgatt ttcattttt ttttttcccct agcggatgac tctttttttt tcttagcgat    4020
tggcattatc acataatgaa ttatacatta tataaagtaa tgtgatttct tcgaagaata    4080
tactaaaaaa tgagcaggca agataaacga aggcaaagat gacagagcag aaagccctag    4140
taaagcgtat tacaaatgaa accaagattc agattgcgat ctctttaaag ggtggtcccc    4200
tagcgataga gcactcgatc ttcccagaaa aagaggcaga agcagtagca gaacaggcca    4260
cacaatcgca agtgattaac gtccacacag gtatagggtt tctggaccat atgatacatg    4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa agctttgcag    4620
aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt tttcttttg cttttttcttt tttttctct tgaactcgac    4980 ggatctatgc ggtgtgaaat accgcacaga tgcgtaagga gaaataccg catcaggaaa    5040 ttgtaaacgt taatatttg ttaaaattcg cgttaaattt tgttaaatc agctcatttt    5100 ttaaccaata ggccgaaatc ggcaaaatcc cttataaatc aaaagaatag accgagatag    5160
ggttgagtgt tgttccagtt tggaacaaga gtccactatt aaagaacgtg gactccaacg    5220
tcaaagggcg aaaaaccgtc tatcagggcg atggcccact acgtgaacca tcaccctaat    5280
caagtttttt ggggtcgagg tgccgtaaag cactaaatcg gaaccctaaa gggagccccc    5340
gatttagagc ttgacgggga agccggcga acgtggcgag aaaggaaggg aagaaagcga    5400
aaggagcggg cgctagggcg ctggcaagtg tagcggtcac gctgcgcgta accaccacac    5460
ccgccgcgct taatgcgccg ctacagggcg cgtcgcgcca ttcgccattc aggctgcgca    5520
actgttggga agggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg ggtaccgggc    5700
```

```
cccccctcga ggtattagaa gccgccgagc gggcgacagc cctccgacgg aagactctcc    5760
tccgtgcgtc ctcgtcttca ccggtcgcgt tcctgaaacg cagatgtgcc tcgcgccgca    5820
ctgctccgaa caataaagat tctacaatac tagcttttat ggttatgaag aggaaaaatt    5880
ggcagtaacc tggccccaca aaccttcaaa ttaacgaatc aaattaacaa ccataggatg    5940
ataatgcgat tagttttttta gccttatttc tggggtaatt aatcagcgaa gcgatgattt    6000
ttgatctatt aacagatata taaatggaaa agctgcataa ccactttaac taatactttc    6060
aacattttca gtttgtatta cttcttattc aaatgtcata aaagtatcaa caaaaaattg    6120
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgttttcact ggttatgcgg cggatccgaa agaaaacgt tgatgccggt    6540 gaacgtgcaa acaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta atatattgtca tgaactatat ccgtaacctg    7140
gatagtgaaa cagggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctcttttcctg    7320 taggtcaggt tgctttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                            7523
```

<210> SEQ ID NO 67
<211> LENGTH: 15456
<212> TYPE: DNA
<213> ORGANISM: Artificial sequence
<220> FEATURE:
<223> OTHER INFORMATION: Template

<400> SEQUENCE: 67

```
aaagagtaat actagagata aacataaaaa atgtagaggt cgagtttaga tgcaagttca      60
aggagcgaaa ggtggatggg taggttatat agggatatag cacagagata tatagcaaag     120
agatactttt gagcaatgtt tgtggaagcg gtattcgcaa tattttagta gctcgttaca     180
gtccggtgcg ttttttggttt tttgaaagtg cgtcttcaga gcgcttttgg ttttcaaaag     240
```

```
cgctctgaag ttcctatact ttctagagaa taggaacttc ggaataggaa cttcaaagcg    300
tttccgaaaa cgagcgcttc cgaaaatgca acgcgagctg cgcacataca gctcactgtt    360
cacgtcgcac ctatatctgc gtgttgcctg tatatatata tacatgagaa gaacggcata    420
gtgcgtgttt atgcttaaat gcgtacttat atgcgtctat ttatgtagga tgaaaggtag    480
tctagtacct cctgtgatat tatcccattc catgcggggt atcgtatgct tccttcagca    540
ctacccttta gctgttctat atgctgccac tcctcaattg gattagtctc atccttcaat    600
gctatcattt cctttgatat tggatcatac taagaaacca ttattatcat gacattaacc    660
tataaaaata ggcgtatcac gaggcccttt cgtctcgcgc gtttcggtga tgacggtgaa    720
aacctctgac acatgcagct cccggagacg gtcacagctt gtctgtaagc ggatgccggg    780
agcagacaag cccgtcaggg cgcgtcagcg ggtgttggcg ggtgtcgggg ctggcttaac    840
tatgcggcat cagagcagat tgtactgaga gtgcaccata aattcccgtt ttaagagctt    900
ggtgagcgct aggagtcact gccaggtatc gtttgaacac ggcattagtc agggaagtca    960
taacacagtc cttttcccgca attttctttt tctattactc ttggcctcct ctagtacact   1020
ctatattttt ttatgcctcg gtaatgattt tcattttttt ttttccacct agcggatgac   1080 tcttttttt tcttagcgat tggcattatc acataatgaa ttatacatta tataaagtaa   1140 tgtgattt ct tcgaagaata tactaaaaaa tgagcaggca agataaacga aggcaaagat   1200
gacagagcag aaagccctag taaagcgtat tacaaatgaa accaagattc agattgcgat   1260
ctctttaaag ggtggtcccc tagcgataga gcactcgatc ttcccagaaa aagaggcaga   1320
agcagtagca gaacaggcca cacaatcgca agtgattaac gtccacacag gtatagggtt   1380
tctggaccat atgatacatg ctctggccaa gcattccggc tggtcgctaa tcgttgagtg   1440
cattggtgac ttacacatag acgaccatca caccactgaa gactgcggga ttgctctcgg   1500
tcaagctttt aaagaggccc tagggggccgt gcgtggagta aaaaggtttg gatcaggatt   1560
tgcgcctttg gatgaggcac tttccagagc ggtggtagat ctttcgaaca ggccgtacgc   1620
agttgtcgaa cttggttttgc aaagggagaa gtaggagat ctctcttgcg agatgatccc   1680
gcattttctt gaaagctttg cagaggctag cagaattacc ctccacgttg attgtctgcg   1740
aggcaagaat gatcatcacc gtagtgagag tgcgttcaag gctcttgcgg ttgccataag   1800
agaagccacc tcgcccaatg gtaccaacga tgttccctcc accaaggtg ttcttatgta   1860 gtgacaccga ttatttaaag ctgcagcata cgatatatat acatgtgtat atatgtatac   1920
ctatgaatgt cagtaagtat gtatacgaac agtatgatac tgaagatgac aaggtaatgc   1980
atcattctat acgtgtcatt ctgaacgagg cgcgctttcc ttttttcttt ttgctttttc   2040 ttttttttc tcttgaactc gacgatcta tgcggtgtga ataccgcac agatgcgtaa    2100 ggagaaaata ccgcatcagg aaattgtaag cgttaatatt ttgttaaaat tcgcgttaaa   2160 ttttttgttaa atcagctcat tttttaacca ataggccgaa atcggcaaaa tcccttataa   2220
atcaaaagaa tagaccgaga tagggttgag tgttgttcca gtttggaaca agagtccact   2280
attaaagaac gtggactcca acgtcaaagg gcgaaaaacc gtctatcagg gcgatggccc   2340
actacgtgaa ccatcaccct aatcaagttt tttggggtcg aggtgccgta aagcactaaa   2400
tcggaaccct aaagggagcc ccgatttag agcttgacgg ggaaagccgg cgaacgtggc   2460
gagaaaggaa gggaagaaag cgaaaggagc gggcgctagg gcgctggcaa gtgtagcggt   2520
cacgctgcgc gtaaccacca cacccgccgc gcttaatgcg ccgctacagg gcgcgtccat   2580
```

```
tcgccattca ggctgcgcaa ctgttgggaa gggcgcggtg cgggcctctt cgctattacg   2640
ccagctggcg aaaggggggat gtgctgcaag gcgattaagt tgggtaacgc cagggttttc   2700
ccagtcacga cgttgtaaaa cgacggccag tgagcgcgcg taatacgact cactataggg   2760
cgaattgggt accgggcccc ccctcgaggt cgacggcgcg ccactggtag agagcgactt   2820
tgtatgcccc aattgcgaaa cccgcgatat ccttctcgat tctttagtac ccgaccagga   2880
caaggaaaag gaggtcgaaa cgttttttgaa gaaacaagag gaactacacg gaagctctaa   2940
agatggcaac cagccagaaa ctaagaaaat gaagttgatg gatccaactg gcaccgctgg   3000
cttgaacaac aataccagcc ttccaacttc tgtaaataac ggcggtacgc cagtgccacc   3060
agtaccgtta cctttcggta tacctccttt ccccatgttt ccaatgccct tcatgcctcc   3120
aacggctact atcacaaatc ctcatcaagc tgacgcaagc cctaagaaat gaataacaat   3180
actgacagta ctaaataatt gcctacttgg cttcacatac gttgcatacg tcgatataga   3240
taataatgat aatgacagca ggattatcgt aatacgtaat agctgaaaat ctcaaaaatg   3300
tgtgggtcat tacgtaaata atgataggaa tgggattctt ctattttttcc tttttccatt   3360
ctagcagccg tcgggaaaac gtggcatcct ctctttcggg ctcaattgga gtcacgctgc   3420
cgtgagcatc ctctctttcc atatctaaca actgagcacg taaccaatgg aaaagcatga   3480
gcttagcgtt gctccaaaaa agtattggat ggttaatacc atttgtctgt tctcttctga   3540
ctttgactcc tcaaaaaaaa aaatctacaa tcaacagatc gcttcaatta cgccctcaca   3600
aaaactttttt tccttcttct tcgcccacgt taaatttttat ccctcatgtt gtctaacgga   3660
tttctgcact tgatttatta taaaaagaca aagcataat acttctctat caatttcagt   3720
tattgttctt ccttgcgtta ttcttctgtt cttcttttttc ttttgtcata tataaccata   3780
accaagtaat acatattcaa actagtatga ctgacaaaaa aactcttaaa gacttaagaa   3840
atcgtagttc tgtttacgat tcaatggtta aatcacctaa tcgtgctatg ttgcgtgcaa   3900
ctggtatgca agatgaagac tttgaaaaac ctatcgtcgg tgtcatttca acttgggctg   3960
aaaacacacc ttgtaatatc cacttacatg actttggtaa actagccaaa gtcggtgtta   4020
aggaagctgg tgcttggcca gttcagttcg gaacaatcac ggtttctgat ggaatcgcca   4080
tgggaaccca aggaatgcgt ttctccttga catctcgtga tattattgca gattctattg   4140
aagcagccat gggaggtcat aatgcggatg cttttgtagc cattggcggt tgtgataaaa   4200
acatgcccgg ttctgttatc gctatggcta acatggatat cccagccatt tttgcttacg   4260
gcggaacaat tgcaccctgg aatttagacg gcaaagatat cgatttagtc tctgtctttg   4320
aaggtgtcgg ccattggaac cacggcgata tgaccaaaga agaagttaaa gctttggaat   4380
gtaatgcttg tccccggtcct ggaggctgcg gtggtatgta tactgctaac acaatggcga   4440
cagctattga agttttggga cttagccttc cgggttcatc ttctcacccg gctgaatccg   4500
cagaaaagaa agcagatatt gaagaagctg gtcgcgctgt tgtcaaaatg ctcgaaatgg   4560
gcttaaaacc ttctgacatt ttaacgcgtg aagcttttga agatgctatt actgtaacta   4620
tggctctggg aggttcaacc aactcaaccc ttcacctctt agctattgcc catgctgcta   4680
atgtggaatt gacacttgat gatttcaata cttttccaaga aaaagttcct catttggctg   4740
atttgaaacc ttctggtcaa tatgtattcc aagacctta caaggtcgga ggggtaccag   4800
cagttatgaa atatctcctt aaaaatggct tccttcatgg tgaccgtatc acttgtactg   4860
gcaaaacagt cgctgaaaat ttgaaggctt ttgatgattt aacacctggt caaaaggtta   4920
ttatgccgct tgaaaatcct aaacgtgaag atggtccgct cattattctc catggtaact   4980
```

| | |
|---|---|
| tggctccaga cggtgccgtt gccaaagttt ctggtgtaaa agtgcgtcgt catgtcggtc | 5040 |
| ctgctaaggt cttttaattct gaagaagaag ccattgaagc tgtcttgaat gatgatattg | 5100 |
| ttgatggtga tgttgttgtc gtacgttttg taggaccaaa gggcggtcct ggtatgcctg | 5160 |
| aaatgctttc cctttcatca atgattgttg gtaaagggca aggtgaaaaa gttgcccttc | 5220 |
| tgacagatgg ccgcttctca ggtggtactt atggtcttgt cgtgggtcat atcgctcctg | 5280 |
| aagcacaaga tggcggtcca atcgcctacc tgcaaacagg agacatagtc actattgacc | 5340 |
| aagacactaa ggaattacac tttgatatct ccgatgaaga gttaaaacat cgtcaagaga | 5400 |
| ccattgaatt gccaccgctc tattcacgcg gtatccttgg taaatatgct cacatcgttt | 5460 |
| cgtctgcttc taggggagcc gtaacagact tttggaagcc tgaagaaact ggcaaaaaat | 5520 |
| gttgtcctgg ttgctgtggt taagcggccg cgttaattca aattaattga tatagttttt | 5580 |
| taatgagtat tgaatctgtt tagaaataat ggaatattat ttttatttat ttatttatat | 5640 |
| tattggtcgg ctcttttctt ctgaaggtca atgacaaaat gatatgaagg aaataatgat | 5700 |
| ttctaaaatt ttacaacgta agatattttt acaaaagcct agctcatctt ttgtcatgca | 5760 |
| ctattttact cacgcttgaa attaacggcc agtccactgc ggagtcattt caaagtcatc | 5820 |
| ctaatcgatc tatcgttttt gatagctcat tttggagttc gcgattgtct tctgttattc | 5880 |
| acaactgttt taattttat ttcattctgg aactcttcga gttctttgta aagtctttca | 5940 |
| tagtagctta ctttatcctc caacatattt aacttcatgt caatttcggc tcttaaattt | 6000 |
| tccacatcat caagttcaac atcatctttt aacttgaatt tattctctag ctcttccaac | 6060 |
| caagcctcat tgctccttga tttactggtg aaaagtgata cactttgcgc gcaatccagg | 6120 |
| tcaaaacttt cctgcaaaga attcaccaat ttctcgacat catagtacaa tttgttttgt | 6180 |
| tctcccatca caatttaata tacctgatgg attcttatga agcgctgggt aatggacgtg | 6240 |
| tcactctact tcgcctttt ccctactcct tttagtacgg aagacaatgc taataaataa | 6300 |
| gagggtaata ataatattat taatcggcaa aaaagattaa acgccaagcg tttaattatc | 6360 |
| agaaagcaaa cgtcgtacca atccttgaat gcttcccaat tgtatattaa gagtcatcac | 6420 |
| agcaacatat tcttgttatt aaattaatta ttattgattt ttgatattgt ataaaaaaac | 6480 |
| caaatatgta taaaaaaagt gaataaaaaa taccaagtat ggagaaatat attagaagtc | 6540 |
| tatacgttaa accacccggg ccccccctcg aggtcgacgg tatcgataag cttgatatcg | 6600 |
| aattcctgca gcccggggga tccactagtt ctagagcggc cgctctagaa ctagtaccac | 6660 |
| aggtgttgtc ctctgaggac ataaaataca caccgagatt catcaactca ttgctggagt | 6720 |
| tagcatatct acaattgggt gaaatgggga gcgatttgca ggcatttgct cggcatgccg | 6780 |
| gtagaggtgt ggtcaataag agcgacctca tgctatacct gagaaagcaa cctgacctac | 6840 |
| aggaaagagt tactcaagaa taagaatttt cgttttaaaa cctaagagtc actttaaaat | 6900 |
| ttgtatacac ttattttttt tataacttat ttaataataa aaatcataaa tcataagaaa | 6960 |
| ttcgcttact cttaattaat caggcagcgc ctgcgttcga gaggatgatc ttcatcgcct | 7020 |
| tctccttggc gccattgagg aatacctgat aggcgtgctc gatctcggcc agctcgaagc | 7080 |
| gatgggtaat catcttcttc aacggaagct tgtcggtcga ggcgaccttc atcagcatgg | 7140 |
| gcgtcgtgtt cgtgttcacc agtcccgtgg tgatcgtcag gttcttgatc cagagcttct | 7200 |
| gaatctcgaa gtcaaccttg acgccatgca cgccgacgtt ggcgatgtgc gcgccgggct | 7260 |
| tgacgatctc ctggcagatg tcccaagtcg ccggtatgcc caccgcctcg atcgcaacat | 7320 |

```
cgactccctc tgccgcaatc ctatgcacgg cttcgacaac gttctccgtg ccggagttga    7380
tggtgtgcgt tgccccgagc tccttggcga gctggaggcg attctcgtcc atgtcgatca    7440
cgatgatggt cgagggggag tagaactggg cggtcaacag tacggacatg ccgacggggc    7500
ccgcgccgac aatagccacc gcatcgcccg gctggacatt cccatactgg acgccgattt    7560
cgtggccggt gggcaggatg tcgctcagca ggacggcgat ttcgtcgtca attgtctggg    7620
ggatcttgta gaggctgttg tcggcatgcg ggatgcggac gtattcggcc tgcacgccat    7680
cgatcatgta acccaggatc caccgccgt cgcggcaatg ggagtaaagc tgcttcttgc    7740
agtagtcgca cgagccgcaa gaagtgacgc aggaaatcag gaccttgtcg cctttcttga    7800
actgcgtgac actctcgccc acttcctcga tgacgcctac cccttcatgg cccaggatgc    7860
gcccgtcggc gacctctgga ttcttgcctt tgtagatgcc gagatccgtg ccgcagatcg    7920
tggtcttcaa aacccgtact actacatccg tgggcttttg aagggtgggc ttgggcttgt    7980
cttcaagcga gatcttgtgg tcaccgtgat aaaccagagc tttcatcctc agctattgta    8040
atatgtgtgt ttgtttggat tattaagaag aataattaca aaaaaaatta caaaggaagg    8100
taattacaac agaattaaga aaggacaaga aggaggaaga gaatcagttc attatttctt    8160
ctttgttata taacaaaccc aagtagcgat ttggccatac attaaaagtt gagaaccacc    8220
ctccctggca acagccacaa ctcgttacca ttgttcatca cgatcatgaa actcgctgtc    8280
agctgaaatt tcacctcagt ggatctctct ttttattctt catcgttcca ctaacctttt    8340
tccatcagct ggcagggaac ggaaagtgga atcccattta gcgagcttcc tcttttcttc    8400
aagaaaagac gaagcttgtg tgtgggtgcg cgcgctagta tctttccaca ttaagaaata    8460
taccataaag gttacttaga catcactatg ctatatata tatatatata tatatatgta    8520
acttagcacc atcgcgcgtg catcactgca tgtgttaacc gaaaagtttg gcgaacactt    8580
caccgacacg gtcatttaga tctgtcgtct gcattgcacg tcccttagcc ttaaatccta    8640
ggcgggagca ttctcgtgta attgtgcagc ctgcgtagca actcaacata gcgtagtcta    8700
cccagttttt caagggttta tcgttagaag attctcccct ttcttcctgc tcacaaatct    8760
taaagtcata cattgcacga ctaaatgcaa gcatgcggat cccccgggct gcaggaattc    8820
gatatcaagc ttatcgatac cgtcgactgg ccattaatct ttcccatatt agatttcgcc    8880
aagccatgaa agttcaagaa aggtctttag acgaattacc cttcatttct caaactggcg    8940
tcaagggatc ctggtatggt tttatcgttt tatttctggt tcttatagca tcgttttgga    9000
cttctctgtt cccattaggc ggttcaggag ccagcgcaga atcattcttt gaaggatact    9060
tatccttccc aattttgatt gtctgttacg ttggacataa actgtatact agaaattgga    9120
ctttgatggt gaaactagaa gatatggatc ttgataccgg cagaaaacaa gtagatttga    9180
ctcttcgtag ggaagaaatg aggattgagc gagaaacatt agcaaaaaga tccttcgtaa    9240
caagattttt acatttctgg tgttgaaggg aaagatatga gctatacagc ggaatttcca    9300
tatcactcag attttgttat ctaatttttt ccttcccacg tccgcgggaa tctgtgtata    9360
ttactgcatc tagatatatg ttatcttatc ttggcgcgta catttaattt tcaacgtatt    9420
ctataagaaa ttgcgggagt tttttcatg tagatgatac tgactgcacg caaatatagg    9480
catgatttat aggcatgatt tgatggctgt accgatagga acgctaagag taacttcaga    9540
atcgttatcc tggcggaaaa aattcatttg taaactttaa aaaaaaagc caatatcccc    9600
aaaattatta agagcgcctc cattattaac taaaatttca ctcagcatcc acaatgtatc    9660
aggtatctac tacagatatt acatgtggcg aaaaagacaa gaacaatgca atagcgcatc    9720
```

```
aagaaaaaac acaaagcttt caatcaatga atcgaaaatg tcattaaaat agtatataaa   9780
ttgaaactaa gtcataaagc tataaaaaga aaatttattt aaatgcaaga tttaaagtaa   9840
attcacggcc ctgcaggcct cagctcttgt tttgttctgc aaataactta cccatctttt   9900
tcaaaacttt aggtgcaccc tcctttgcta gaataagttc tatccaatac atcctatttg   9960
gatctgcttg agcttctttc atcacggata cgaattcatt ttctgttctc acaattttgg  10020
acacaactct gtcttccgtt gccccgaaac tttctggcag ttttgagtaa ttccacatag  10080
gaatgtcatt ataactctgg ttcggaccat gaatttccct ctcaaccgtg taaccatcgt  10140
tattaatgat aaagcagatt gggtttatct tctctctaat ggctagtcct aattcttgga  10200
cagtcagttg caatgatcca tctccgataa acaataaatg tctagattct ttatctgcaa  10260
tttggctgcc tagagctgcg gggaaagtgt atcctataga tccccacaag ggttgaccaa  10320
taaaatgtga tttcgatttc agaaatatag atgaggcacc gaagaaagaa gtgccttgtt  10380
cagccacgat cgtctcatta ctttgggtca aattttcgac agcttgccac agtctatctt  10440
gtgacaacag cgcgttagaa ggtacaaaat cttcttgctt tttatctatg tacttgcctt  10500
tatattcaat ttcggacaag tcaagaagag atgatatcag ggattcgaag tcgaaatttt  10560
ggattctttc gttgaaaatt ttaccttcat cgatattcaa ggaaatcatt ttattttcat  10620
taagatggtg agtaaatgca cccgtactag aatcggtaag ctttacaccc aacataagaa  10680
taaaatcagc agattccaca aattccttca gtttggctc tgacagagta ccgttgtaaa  10740
tccccaaaaa tgagggcaat gcttcatcaa cagatgattt accaaagttc aaagtagtaa  10800
taggtaactt agtctttgaa ataaactgag taacagtctt ctctaggccg aacgatataa  10860
tttcatggcc tgtgattaca attggtttct tggcattctt cagactttcc tgtattttgt  10920
tcagaatctc ttgatcagat gtattcgacg tggaatttc cttcttaaga ggcaaggatg  10980 gttttcagc cttagcggca gctacatcta caggtaaatt gatgtaaacc ggctttcttt  11040
cctttagtaa ggcagacaac actctatcaa tttcaacagt tgcattctcg gctgtcaata  11100
aagtcctggc agcagtaacc ggttcgtgca tcttcataaa gtgcttgaaa tcaccatcag  11160
ccaacgtatg gtgaacaaac ttaccttcgt tctgcacttt cgaggtagga gatcccacga  11220
tctcaacaac aggcaggttc tcagcatagg agcccgctaa gccattaact gcggataatt  11280
cgccaacacc aaatgtagtc aagaatgccg cagccttttt cgttcttgcg tacccgtcgg  11340
ccatatagga ggcatttaac tcattagcat ttcccaccca tttcatatct ttgtgtgaaa  11400
taatttgatc tagaaattgc aaattgtagt cacctggtac tccgaatatt tcttctatac  11460
ctaattcgtg taatctgtcc aacagatagt cacctactgt atacattttg tttactagtt  11520
tatgtgtgtt tattcgaaac taagttcttg gtgttttaaa actaaaaaaa agactaacta  11580
taaaagtaga atttaagaag tttaagaaat agatttacag aattacaatc aatacctacc  11640
gtctttatat acttattagt caagtagggg aataatttca gggaactggt ttcaaccttt  11700
tttttcagct ttttccaaat cagagagagc agaaggtaat agaaggtgta agaaaatgag  11760
atagatacat gcgtgggtca attgccttgt gtcatcattt actccaggca ggttgcatca  11820
ctccattgag gttgtgcccg ttttttgcct gtttgtgccc ctgttctctg tagttgcgct  11880
aagagaatgg acctatgaac tgatggttgg tgaagaaaac aatattttgg tgctgggatt  11940 ctttttttt ctggatgcca gcttaaaaag cgggctccat tatatttagt ggatgccagg  12000
aataaactgt tcacccagac acctacgatg ttatatattc tgtgtaaccc gccccctatt  12060
```

```
ttgggcatgt acgggttaca gcagaattaa aaggctaatt ttttgactaa ataaagttag   12120
gaaaatcact actattaatt atttacgtat tctttgaaat ggcagtattg ataatgataa   12180
actcgaactg aaaaagcgtg ttttttattc aaaatgattc taactcccct acgtaatcaa   12240
ggaatctttt tgccttggcc tccgcgtcat taaacttctt gttgttgacg ctaacattca   12300
acgctagtat atattcgttt ttttcaggta agttcttttc aacgggtctt actgatgagg   12360
cagtcgcgtc tgaacctgtt aagaggtcaa atatgtcttc ttgaccgtac gtgtcttgca   12420
tgttattagc tttgggaatt tgcatcaagt cataggaaaa tttaaatctt ggctctcttg   12480
ggctcaaggt gacaaggtcc tcgaaaatag ggcgcgcccc accgcggtgg agctccagct   12540
tttgttccct ttagtgaggg ttaattgcgc gcttggcgta atcatggtca tagctgtttc   12600
ctgtgtgaaa ttgttatccg ctcacaattc cacacaacat acgagccgga agcataaagt   12660
gtaaagcctg gggtgcctaa tgagtgagct aactcacatt aattgcgttg cgctcactgc   12720
ccgctttcca gtcgggaaac ctgtcgtgcc agctgcatta atgaatcggc caacgcgcgg   12780
ggagaggcgg tttgcgtatt gggcgctctt ccgcttcctc gctcactgac tcgctgcgct   12840
cggtcgttcg gctgcggcga gcggtatcag ctcactcaaa ggcggtaata cggttatcca   12900
cagaatcagg ggataacgca ggaaagaaca tgtgagcaaa aggccagcaa aaggccagga   12960
accgtaaaaa ggccgcgttg ctggcgtttt tccataggct ccgcccccct gacgagcatc   13020
acaaaaatcg acgctcaagt cagaggtggc gaaacccgac aggactataa agataccagg   13080
cgtttccccc tggaagctcc ctcgtgcgct ctcctgttcc gaccctgccg cttaccggat   13140
acctgtccgc ctttctccct tcgggaagcg tggcgctttc tcatagctca cgctgtaggt   13200
atctcagttc ggtgtaggtc gttcgctcca agctgggctg tgtgcacgaa ccccccgttc   13260
agcccgaccg ctgcgcctta tccggtaact atcgtcttga gtccaacccg gtaagacacg   13320
acttatcgcc actggcagca gccactggta acaggattag cagagcgagg tatgtaggcg   13380
gtgctacaga gttcttgaag tggtggccta actacggcta cactagaaga acagtatttg   13440
gtatctgcgc tctgctgaag ccagttacct tcggaaaaag agttggtagc tcttgatccg   13500
gcaaacaaac caccgctggt agcggtggtt ttttgtttg caagcagcag attacgcgca   13560
gaaaaaaagg atctcaagaa gatcctttga tcttttctac ggggtctgac gctcagtgga   13620
acgaaaactc acgttaaggg attttggtca tgagattatc aaaaaggatc ttcacctaga   13680
tccttttaaa ttaaaaatga agttttaaat caatctaaag tatatatgag taaacttggt   13740
ctgacagtta ccaatgctta atcagtgagg cacctatctc agcgatctgt ctatttcgtt   13800
catccatagt tgcctgactc cccgtcgtgt agataactac gatacgggag ggcttaccat   13860
ctggccccag tgctgcaatg ataccgcgag acccacgctc accggctcca gatttatcag   13920
caataaacca gccagccgga agggccgagc gcagaagtgg tcctgcaact ttatccgcct   13980
ccatccagtc tattaattgt tgccgggaag ctagagtaag tagttcgcca gttaatagtt   14040
tgcgcaacgt tgttgccatt gctacaggca tcgtggtgtc acgctcgtcg tttggtatgg   14100
cttcattcag ctccggttcc caacgatcaa ggcgagttac atgatccccc atgttgtgca   14160
aaaaagcggt tagctccttc ggtcctccga tcgttgtcag aagtaagttg gccgcagtgt   14220
tatcactcat ggttatggca gcactgcata attctcttac tgtcatgcca tccgtaagat   14280
gcttttctgt gactggtgag tactcaacca agtcattctg agaatagtgt atgcggcgac   14340
cgagttgctc ttgcccggcg tcaatacggg ataataccgc gccacatagc agaactttaa   14400
aagtgctcat cattggaaaa cgttcttcgg ggcgaaaact ctcaaggatc ttaccgctgt   14460
```

```
tgagatccag ttcgatgtaa cccactcgtg cacccaactg atcttcagca tcttttactt    14520
tcaccagcgt ttctgggtga gcaaaaacag gaaggcaaaa tgccgcaaaa aagggaataa    14580
gggcgacacg gaaatgttga atactcatac tcttccttt  tcaatattat tgaagcattt    14640
atcagggtta ttgtctcatg agcggataca tatttgaatg tatttagaaa aataaacaaa    14700 tagggggttcc gcgcacattt ccccgaaaag tgccacctga acgaagcatc tgtgcttcat    14760
tttgtagaac aaaaatgcaa cgcgagagcg ctaattttc  aaacaaagaa tctgagctgc    14820 attttttacag aacagaaatg caacgcgaaa gcgctatttt accaacgaag aatctgtgct    14880 tcattttgt  aaaacaaaaa tgcaacgcga gagcgctaat ttttcaaaca agaatctga     14940 gctgcatttt tacagaacag aaatgcaacg cgagagcgct attttaccaa caagaatct    15000 atacttcttt tttgttctac aaaaatgcat cccgagagcg ctattttct  aacaaagcat    15060 cttagattac tttttttctc ctttgtgcgc tctataatgc agtctcttga taacttttg     15120 cactgtaggt ccgttaaggt tagaagaagg ctactttggt gtctattttc tcttccataa    15180
aaaaagcctg actccacttc ccgcgtttac tgattactag cgaagctgcg ggtgcattt     15240 ttcaagataa aggcatcccc gattatattc tataccgatg tggattgcgc atactttgtg    15300
aacagaaagt gatagcgttg atgattcttc attggtcaga aaattatgaa cggtttcttc    15360
tattttgtct ctatatacta cgtataggaa atgtttacat tttcgtattg ttttcgattc    15420
actctatgaa tagttcttac tacaattttt ttgtct                              15456
```

```
<210> SEQ ID NO 68
<211> LENGTH: 1559
<212> TYPE: DNA
<213> ORGANISM: Artificial sequence
<220> FEATURE:
<223> OTHER INFORMATION: Template

<400> SEQUENCE: 68
```

```
gcattgcgga ttacgtattc taatgttcag taccgttcgt ataatgtatg ctatacgaag      60
ttatgcagat tgtactgaga gtgcaccata ccacctttc  aattcatcat tttttttta     120 ttctttttt  tgatttcggt ttccttgaaa tttttttgat tcggtaatct ccgaacagaa    180
ggaagaacga aggaaggagc acagacttag attggtatat atacgcatat gtagtgttga    240
agaaacatga aattgcccag tattcttaac ccaactgcac agaacaaaaa cctgcaggaa    300
acgaagataa atcatgtcga aagctacata taaggaacgt gctgctactc atcctagtcc    360
tgttgctgcc aagctatttta atatcatgca cgaaaagcaa acaaacttgt gtgcttcatt    420
ggatgttcgt accaccaagg aattactgga gttagttgaa gcattaggtc ccaaaatttg    480
tttactaaaa acacatgtgg atatcttgac tgatttttcc atggagggca cagttaagcc    540
gctaaaggca ttatccgcca agtacaattt tttactcttc gaagacagaa aatttgctga    600
cattggtaat acagtcaaat tgcagtactc tgcgggtgta tacagaatag cagaatgggc    660
agacattacg aatgcacacg gtgtggtggg cccaggtatt gttagcggtt tgaagcaggc    720
ggcagaagaa gtaacaaagg aacctagagg ccttttgatg ttagcagaat tgtcatgcaa    780
gggctcccta tctactggag aatatactaa gggtactgtt gacattgcga agagcgacaa    840
agattttgtt atcggcttta ttgctcaaag agacatgggt ggaagagatg aaggttacga    900
ttggttgatt atgacacccg gtgtgggttt agatgacaag ggagacgcat tgggtcaaca    960
gtatagaacc gtggatgatg tggtctctac aggatctgac attattattg ttggaagagg   1020
```

```
actatttgca aagggaaggg atgctaaggt agagggtgaa cgttacagaa aagcaggctg    1080
ggaagcatat ttgagaagat gcggccagca aaactaaaaa actgtattat aagtaaatgc    1140
atgtatacta aactcacaaa ttagagcttc aatttaatta tatcagttat taccctatgc    1200
ggtgtgaaat accgcacaga tgcgtaagga gaaataccg catcaggaaa ttgtaaacgt      1260
taatattttg ttaaaattcg cgttaaattt ttgttaaatc agctcatttt ttaaccaata    1320
ggccgaaatc ggcaaaatcc cttataaatc aaaagaatag accgagatag ggttgagtgt    1380
tgttccagtt tggaacaaga gtccactatt aaagaacgtg gactccaacg tcaaagggcg    1440
aaaaaccgtc tatcagggcg atggcccact acgtgaacca tcaccctaat caagataact    1500
tcgtataatg tatgctatac gaacggtacc agtgatgata caacgagtta gccaaggtg     1559
```

<210> SEQ ID NO 69
<211> LENGTH: 1047
<212> TYPE: DNA
<213> ORGANISM: Achromobacter xylosoxidans

<400> SEQUENCE: 69

```
atgaaagctc tggtttatca cggtgaccac aagatctcgc ttgaagacaa gcccaagccc     60
acccttcaaa agcccacgga tgtagtagta cgggttttga agaccacgat ctgcggcacg    120
gatctcggca tctacaaagg caagaatcca gaggtcgccg acgggcgcat cctgggccat    180
gaaggggtag gcgtcatcga ggaagtgggc gagagtgtca cgcagttcaa gaaaggcgac    240
aaggtcctga tttcctgcgt cacttcttgc ggctcgtgcg actactgcaa gaagcagctt    300
tactcccatt gccgcgacgg cgggtggatc ctgggttaca tgatcgatgg cgtgcaggcc    360
gaatacgtcc gcatcccgca tgccgacaac agcctctaca agatccccca gacaattgac    420
gacgaaatcg ccgtcctgct gagcgacatc ctgcccaccg ccacgaaaat cggcgtccag    480
tatgggaatg tccagccggg cgatgcggtg gctattgtcg gcgcgggccc cgtcggcatg    540
tccgtactgt tgaccgccca gttctactcc ccctcgacca tcatcgtgat cgacatggac    600
gagaatcgcc tccagctcgc caaggagctc ggggcaacgc acaccatcaa ctccggcacg    660
gagaacgttg tcgaagccgt gcataggatt gcggcagagg gagtcgatgt tgcgatcgag    720
gcggtgggca taccggcgac ttgggacatc tgccaggaga tcgtcaagcc cggcgcgcac    780
atcgccaacg tcggcgtgca tggcgtcaag gttgacttcg agattcagaa gctctggatc    840
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc    1020
atcctctcga acgcaggcgc tgcctga                                         1047
```

<210> SEQ ID NO 70
<211> LENGTH: 348
<212> TYPE: PRT
<213> ORGANISM: Achromobacter xylosoxidans

<400> SEQUENCE: 70

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45
```

Asn Pro Glu Val Ala Asp Gly Arg Ile Leu Gly His Glu Gly Val Gly
        50                  55                  60

Val Ile Glu Glu Val Gly Glu Ser Val Thr Gln Phe Lys Lys Gly Asp
 65                  70                  75                  80

Lys Val Leu Ile Ser Cys Val Thr Ser Cys Gly Ser Cys Asp Tyr Cys
                 85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 71
<211> LENGTH: 1644
<212> TYPE: DNA
<213> ORGANISM: artificial sequence
<220> FEATURE:
<223> OTHER INFORMATION: codon optimized L. lactis kivD coding region
      for S. cerevisiae expression

<400> SEQUENCE: 71
atgtatacag taggtgacta tctgttggac agattacacg aattaggtat agaagaaata    60
ttcggagtac caggtgacta caatttgcaa tttctagatc aaattatttc acacaaagat   120
atgaaatggg tgggaaatgc taatgagtta aatgcctcct atatggccga cgggtacgca   180
agaacgaaaa aggctgcggc attcttgact acatttggtg ttggcgaatt atccgcagtt   240
aatggcttag cgggctccta tgctgagaac ctgcctgttg ttgagatcgt gggatctcct   300
acctcgaaag tgcagaacga aggtaagttt gttcaccata cgttggctga tggtgatttc   360

```
aagcacttta tgaagatgca cgaaccggtt actgctgcca ggactttatt gacagccgag    420
aatgcaactg ttgaaattga tagagtgttg tctgccttac taaaggaaag aaagccggtt    480
tacatcaatt tacctgtaga tgtagctgcc gctaaggctg aaaaaccatc cttgcctctt    540
aagaaggaaa attccacgtc gaatacatct gatcaagaga ttctgaacaa atacaggaa     600 agtctgaaga atgccaagaa accaattgta atcacaggcc atgaaattat atcgttcggc    660
ctagagaaga ctgttactca gtttatttca aagactaagt tacctattac tactttgaac    720
tttggtaaat catctgttga tgaagcattg ccctcatttt tggggattta caacggtact    780
ctgtcagagc caaacttgaa ggaatttgtg aatctgctg attttattct tatgttgggt     840
gtaaagctta ccgattctag tacgggtgca tttactcacc atcttaatga aaataaaatg    900
atttccttga atatcgatga aggtaaaatt ttcaacgaaa gaatccaaaa tttcgacttc    960
gaatccctga tatcatctct tcttgacttg tccgaaattg aatataaagg caagtacata   1020
gataaaaagc aagaagattt tgtaccttct aacgcgctgt tgtcacaaga tagactgtgg   1080
caagctgtcg aaaatttgac ccaaagtaat gagacgatcg tggctgaaca aggcacttct   1140
ttcttcggtg cctcatctat atttctgaaa tcgaatcac attttattgg tcaacccttg     1200
tggggatcta taggatacac tttccccgca gctctaggca gccaaattgc agataaagaa   1260
tctagacatt tattgtttat cggagatgga tcattgcaac tgactgtcca agaattagga   1320
ctagccatta gagagaagat aaacccaatc tgctttatca ttaataacga tggttacacg   1380
gttgagaggg aaattcatgg tccgaaccag agttataatg acattcctat gtggaattac   1440
tcaaaactgc cagaaagttt cggggcaacg gaagacagag ttgtgtccaa aattgtgaga   1500
acagaaaatg aattcgtatc cgtgatgaaa gaagctcaag cagatccaaa taggatgtat   1560
tggatagaac ttattctagc aaaggagggt gcacctaaag ttttgaaaaa gatgggtaag   1620
ttatttgcag aacaaaacaa gagc                                          1644

<210> SEQ ID NO 72
<211> LENGTH: 753
<212> TYPE: DNA
<213> ORGANISM: Saccharomyces cerevisiae

<400> SEQUENCE: 72
gcatgcttgc atttagtcgt gcaatgtatg actttaagat ttgtgagcag gaagaaaagg     60
gagaatcttc taacgataaa cccttgaaaa actgggtaga ctacgctatg ttgagttgct    120
acgcaggctg cacaattaca cgagaatgct cccgcctagg atttaaggct aagggacgtg    180
caatgcagac gacagatcta aatgaccgtg tcggtgaagt gttcgccaaa cttttcggtt    240
aacacatgca gtgatgcacg cgcgatggtg ctaagttaca tatatatata tatagccata    300
gtgatgtcta agtaaccttt atggtatatt tcttaatgtg gaaagatact agcgcgcgca    360
cccacacaca agcttcgtct tttcttgaag aaaagaggaa gctcgctaaa tgggattcca    420
ctttccgttc cctgccagct gatggaaaaa ggttagtgga acgatgaaga ataaaagag    480 agatccactg aggtgaaatt tcagctgaca gcgagtttca tgatcgtgat gaacaatggt    540
aacgagttgt ggctgttgcc agggagggtg gttctcaact tttaatgtat ggccaaatcg    600
ctacttgggt ttgttatata acaaagaaga ataatgaac tgattctctt cctccttctt     660
gtcctttctt aattctgttg taattacctt cctttgtaat tttttttgta attattcttc    720
ttaataatcc aaacaaacac acatattaca ata                                 753
```

<210> SEQ ID NO 73
<211> LENGTH: 316
<212> TYPE: DNA
<213> ORGANISM: Saccharomyces cerevisiae

<400> SEQUENCE: 73

```
gagtaagcga atttcttatg atttatgatt tttattatta ataagttat aaaaaaata      60
agtgtataca aattttaaag tgactcttag gttttaaaac gaaaattctt attcttgagt   120
aactctttcc tgtaggtcag gttgctttct caggtatagc atgaggtcgc tcttattgac   180
cacacctcta ccggcatgcc gagcaaatgc ctgcaaatcg ctccccattt cacccaattg   240
tagatatgct aactccagca atgagttgat gaatctcggt gtgtatttta tgtcctcaga   300
ggacaacacc tgtggt                                                   316
```

<210> SEQ ID NO 74
<211> LENGTH: 30
<212> TYPE: DNA
<213> ORGANISM: artificial sequence
<220> FEATURE:
<223> OTHER INFORMATION: primer

<400> SEQUENCE: 74

```
ggaattcaca catgaaagct ctggtttatc                                     30
```

<210> SEQ ID NO 75
<211> LENGTH: 28
<212> TYPE: DNA
<213> ORGANISM: artificial sequence
<220> FEATURE:
<223> OTHER INFORMATION: primer

<400> SEQUENCE: 75

```
gcgtccaggg cgtcaaagat caggcagc                                       28
```

<210> SEQ ID NO 76
<211> LENGTH: 55
<212> TYPE: DNA
<213> ORGANISM: artificial sequence
<220> FEATURE:
<223> OTHER INFORMATION: primer

<400> SEQUENCE: 76

```
aaacaaacac acatattaca atagctgagg atgaaagctc tggtttatca cggtg         55
```

<210> SEQ ID NO 77
<211> LENGTH: 55
<212> TYPE: DNA
<213> ORGANISM: artificial sequence
<220> FEATURE:
<223> OTHER INFORMATION: primer

<400> SEQUENCE: 77

```
atcataagaa attcgcttac tcttaattaa tcaggcagcg cctgcgttcg agagg         55
```

<210> SEQ ID NO 78
<211> LENGTH: 8994
<212> TYPE: DNA
<213> ORGANISM: artificial sequence
<220> FEATURE:
<223> OTHER INFORMATION: constructed plasmid

<400> SEQUENCE: 78

```
ctagttctag agcggccgcc accgcggtgg agctccagct tttgttccct ttagtgaggg    60
```

```
ttaattgcgc gcttggcgta atcatggtca tagctgtttc ctgtgtgaaa ttgttatccg    120
ctcacaattc cacacaacat aggagccgga agcataaagt gtaaagcctg gggtgcctaa    180
tgagtgaggt aactcacatt aattgcgttg cgctcactgc ccgctttcca gtcgggaaac    240
ctgtcgtgcc agctgcatta atgaatcggc caacgcgcgg ggagaggcgg tttgcgtatt    300
gggcgctctt ccgcttcctc gctcactgac tcgctgcgct cggtcgttcg gctgcggcga    360
gcggtatcag ctcactcaaa ggcggtaata cggttatcca cagaatcagg ggataacgca    420
ggaaagaaca tgtgagcaaa aggccagcaa aaggccagga accgtaaaaa ggccgcgttg    480
ctggcgtttt tccataggct ccgcccccct gacgagcatc acaaaaatcg acgctcaagt    540
cagaggtggc gaaacccgac aggactataa agataccagg cgtttccccc tggaagctcc    600
ctcgtgcgct ctcctgttcc gaccctgccg cttaccggat acctgtccgc ctttctccct    660
tcgggaagcg tggcgctttc tcatagctca cgctgtaggt atctcagttc ggtgtaggtc    720
gttcgctcca agctgggctg tgtgcacgaa ccccccgttc agcccgaccg ctgcgcctta    780
tccggtaact atcgtcttga gtccaacccg gtaagacacg acttatcgcc actggcagca    840
gccactggta acaggattag cagagcgagg tatgtaggcg gtgctacaga gttcttgaag    900
tggtggccta actacggcta cactagaagg acagtatttg gtatctgcgc tctgctgaag    960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga acgaagcatc tgtgcttcat tttgtagaac aaaaatgcaa   2280
cgcgagagcg ctaattttt c aaacaaagaa tctgagctgc attttta cag aacagaaatg   2340 caacgcgaaa gcgctatttt accaacgaag aatctgtgct tcatttttgt aaaacaaaaa   2400
```

```
tgcaacgcga gagcgctaat ttttcaaaca aagaatctga gctgcatttt tacagaacag    2460
aaatgcaacg cgagagcgct attttaccaa caaagaatct atacttcttt tttgttctac    2520
aaaaatgcat cccgagagcg ctattttttct aacaaagcat cttagattac ttttttttctc   2580 ctttgtgcgc tctataatgc agtctcttga taacttttttg cactgtaggt ccgttaaggt   2640
tagaagaagg ctactttggt gtctatttttc tcttccataa aaaaagcctg actccacttc   2700
ccgcgtttac tgattactag cgaagctgcg ggtgcatttt ttcaagataa aggcatcccc    2760
gattatattc tataccgatg tggattgcgc atactttgtg aacagaaagt gatagcgttg    2820
atgattcttc attggtcaga aaattatgaa cggtttcttc tattttgtct ctatatacta    2880
cgtataggaa atgtttacat tttcgtattg ttttcgattc actctatgaa tagttcttac    2940
tacaattttt ttgtctaaag agtaatacta gagataaaca taaaaaatgt agaggtcgag    3000
tttagatgca agttcaagga gcgaaaggtg gatgggtagg ttatataggg atatagcaca    3060
gagatatata gcaaagagat acttttgagc aatgtttgtg gaagcggtat tcgcaatatt    3120
ttagtagctc gttacagtcc ggtgcgtttt tggttttttg aaagtgcgtc ttcagagcgc    3180
ttttggtttt caaaagcgct ctgaagttcc tatactttct agagaatagg aacttcggaa    3240
taggaacttc aaagcgtttc cgaaaacgag cgcttccgaa aatgcaacgc gagctgcgca    3300
catacagctc actgttcacg tcgcacctat atctgcgtgt tgcctgtata tatatataca    3360
tgagaagaac ggcatagtgc gtgtttatgc ttaaatgcgt acttatatgc gtctatttat    3420
gtaggatgaa aggtagtcta gtacctcctg tgatattatc ccattccatg cggggtatcg    3480
tatgcttcct tcagcactac cctttagctg ttctatatgc tgccactcct caattggatt    3540
agtctcatcc ttcaatgcta tcatttcctt tgatattgga tcatactaag aaaccattat    3600
tatcatgaca ttaacctata aaataggcg tatcacgagg cccttcgtc tcgcgcgttt    3660 cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggctgg cttaactatg cggcatcaga gcagattgta ctgagagtgc accatatcga    3840
ctacgtcgta aggccgtttc tgacagagta aaattcttga gggaactttc accattatgg    3900
gaaatgcttc aagaaggtat tgacttaaac tccatcaaat ggtcaggtca ttgagtgttt    3960
tttatttgtt gtatttttttt tttttagag aaaatcctcc aatatcaaat taggaatcgt    4020
agtttcatga ttttctgtta cacctaactt tttgtgtggt gccctcctcc ttgtcaatat    4080
taatgttaaa gtgcaattct ttttccttat cacgttgagc cattagtatc aatttgctta    4140
cctgtattcc tttactatcc tccttttttct ccttcttgat aaatgtatgt agattgcgta    4200
tatagtttcg tctaccctat gaacatattc cattttgtaa tttcgtgtcg tttctattat    4260
gaatttcatt tataaagttt atgtacaaat atcataaaaa aagagaatct ttttaagcaa    4320
ggattttctt aacttcttcg gcgacagcat caccgacttc ggtggtactg ttggaaccac    4380
ctaaatcacc agttctgata cctgcatcca aaaccttttt aactgcatct tcaatggcct    4440
taccttcttc aggcaagttc aatgacaatt tcaacatcat tgcagcagac aagatagtgg    4500
cgatagggtc aacctattc tttggcaaat ctggagcaga accgtggcat ggttcgtaca    4560
aaccaaatgc ggtgttcttg tctggcaaag aggccaagga cgcagatggc aacaaaccca    4620
aggaacctgg gataacggag gcttcatcgg agatgatatc accaaacatg ttgctggtga    4680
ttataatacc atttaggtgg gttgggttct taactaggat catggcggca gaatcaatca    4740
attgatgttg aaccttcaat gtagggaatt cgttcttgat ggtttcctcc acagtttttc    4800
```

```
tccataatct tgaagaggcc aaaagattag ctttatccaa ggaccaaata ggcaatggtg    4860
gctcatgttg tagggccatg aaagcggcca ttcttgtgat tctttgcact tctggaacgg    4920
tgtattgttc actatcccaa gcgacaccat caccatcgtc ttcctttctc ttaccaaagt    4980
aaatacctcc cactaattct ctgacaacaa cgaagtcagt acctttagca aattgtggct    5040
tgattggaga taagtctaaa agagagtcgg atgcaaagtt acatggtctt aagttggcgt    5100
acaattgaag ttctttacgg attttttagta aaccttgttc aggtctaaca ctaccggtac    5160
cccatttagg accagccaca gcacctaaca aaacggcatc aaccttcttg gaggcttcca    5220
gcgcctcatc tggaagtggg acacctgtag catcgatagc agcaccacca attaaatgat    5280
tttcgaaatc gaacttgaca ttggaacgaa catcagaaat agctttaaga accttaatgg    5340
cttcggctgt gatttcttga ccaacgtggt cacctggcaa aacgacgatc ttcttagggg    5400
cagacatagg ggcagacatt agaatggtat atccttgaaa tatatatata tattgctgaa    5460
atgtaaaagg taagaaaagt tagaaagtaa gacgattgct aaccacctat tggaaaaaac    5520
aataggtcct taaataatat tgtcaacttc aagtattgtg atgcaagcat ttagtcatga    5580
acgcttctct attctatatg aaaagccggt tccggcctct caccttttcct ttttctccca    5640 attttcagt tgaaaaggt atatgcgtca ggcgacctct gaaattaaca aaaaatttcc    5700
agtcatcgaa tttgattctg tgcgatagcg cccctgtgtg ttctcgttat gttgaggaaa    5760
aaaataatgg ttgctaagag attcgaactc ttgcatctta cgatacctga gtattcccac    5820
agttaactgc ggtcaagata tttcttgaat caggcgcctt agaccgctcg gccaaacaac    5880
caattacttg ttgagaaata gagtataatt atcctataaa tataacgttt ttgaacacac    5940
atgaacaagg aagtcaggga caattgattt tgaagagaat gtggattttg atgtaattgt    6000
tgggattcca ttttttaataa ggcaataata ttaggtatgt ggatatacta gaagttctcc    6060
tcgaccgtcg atatgcggtg tgaaataccg cacagatgcg taaggagaaa ataccgcatc    6120
aggaaattgt aaacgttaat attttgttaa aattcgcgtt aaattttgt taaatcagct    6180 catttttta ccaataggcc gaaatcggca aaatccctta taaatcaaaa gaatagaccg    6240
agatagggtt gagtgttgtt ccagtttgga acaagagtcc actattaaag aacgtggact    6300
ccaacgtcaa agggcgaaaa accgtctatc agggcgatgg cccactacgt gaaccatcac    6360
cctaatcaag ttttttgggg tcgaggtgcc gtaaagcact aaatcggaac cctaaaggga    6420
gcccccgatt tagagcttga cggggaaagc cggcgaacgt ggcgagaaag gaagggaaga    6480
aagcgaaagg agcgggcgct agggcgctgg caagtgtagc ggtcacgctg cgcgtaacca    6540
ccacacccgc cgcgcttaat gcgccgctac agggcgcgtc gcgccattcg ccattcaggc    6600
tgcgcaactg ttgggaaggg cgatcggtgc gggcctcttc gctattacgc cagctggcga    6660 aaggggatg tgctgcaagg cgattaagtt gggtaacgcc agggttttcc cagtcacgac    6720
gttgtaaaac gacggccagt gagcgcgcgt aatacgactc actatagggc gaattgggta    6780
ccgggccccc cctcgaggtc gacggtatcg ataagcttga tatcgaattc ctgcagcccg    6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
```

| | | | | | |
|---|---|---|---|---|---|
| tatatatata | tagccatagt | gatgtctaag | taacctttat | ggtatatttc | ttaatgtgga | 7200 |
| aagatactag | cgcgcgcacc | cacacacaag | cttcgtcttt | tcttgaagaa | aagaggaagc | 7260 |
| tcgctaaatg | ggattccact | ttccgttccc | tgccagctga | tggaaaaagg | ttagtggaac | 7320 |
| gatgaagaat | aaaagagag | atccactgag | gtgaaatttc | agctgacagc | gagtttcatg | 7380 |
| atcgtgatga | acaatggtaa | cgagttgtgg | ctgttgccag | ggagggtggt | tctcaacttt | 7440 |
| taatgtatgg | ccaaatcgct | acttgggttt | gttatataac | aaagaagaaa | taatgaactg | 7500 |
| attctcttcc | tccttcttgt | cctttcttaa | ttctgttgta | attaccttcc | tttgtaattt | 7560 |
| ttttgtaat | tattcttctt | aataatccaa | acaaacacac | atattacaat | agctagctga | 7620 |
| ggatgaaggc | attagtttat | catggggatc | acaaatttc | gttagaagac | aaaccaaaac | 7680 |
| ccactctgca | gaaaccaaca | gacgttgtgg | ttagggtgtt | gaaaacaaca | atttgcggta | 7740 |
| ctgacttggg | aatatacaaa | ggtaagaatc | ctgaagtggc | agatggcaga | atcctgggtc | 7800 |
| atgagggcgt | tggcgtcatt | gaagaagtgg | gcgaatccgt | gacacaattc | aaaaagggg | 7860 |
| ataaagtttt | aatctcctgc | gttactagct | gtggatcgtg | tgattattgc | aagaagcaac | 7920 |
| tgtattcaca | ctgtagagac | ggtggctgga | ttttaggtta | catgatcgac | ggtgtccaag | 7980 |
| ccgaatacgt | cagaatacca | catgctgaca | attcattgta | taagatcccg | caaactatcg | 8040 |
| atgatgaaat | tgcagtacta | ctgtccgata | ttttacctac | tggacatgaa | attggtgttc | 8100 |
| aatatggtaa | cgttcaacca | ggcgatgctg | tagcaattgt | aggagcaggt | cctgttggaa | 8160 |
| tgtcagtttt | gttaactgct | caattttact | cgcctagtac | cattattgtt | atcgacatgg | 8220 |
| acgaaaaccg | tttacaatta | gcgaaggagc | ttggggccac | acacactatt | aactccggta | 8280 |
| ctgaaaatgt | tgtcgaagct | gtgcatcgta | tagcagccga | aggagtggat | gtagcaatag | 8340 |
| aagctgttgg | tatacccgca | acctgggaca | tctgtcagga | aattgtaaaa | cccggcgctc | 8400 |
| atattgccaa | cgtgggagtt | catggtgtta | aggtggactt | tgaaattcaa | aagttgtgga | 8460 |
| ttaagaatct | aaccatcacc | actggtttgg | ttaacactaa | tactacccca | atgttgatga | 8520 |
| aggtagcctc | tactgataaa | ttgccttta | agaaaatgat | tactcacagg | tttgagttag | 8580 |
| ctgaaatcga | acacgcatat | caggtttct | tgaatggcgc | taaagaaaaa | gctatgaaga | 8640 |
| ttattctatc | taatgcaggt | gccgcctaat | taattaagag | taagcgaatt | tcttatgatt | 8700 |
| tatgatttt | attattaaat | aagttataaa | aaaataagt | gtatacaaat | tttaaagtga | 8760 |
| ctcttaggtt | ttaaaacgaa | aattcttatt | cttgagtaac | tctttcctgt | aggtcaggtt | 8820 |
| gctttctcag | gtatagcatg | aggtcgctct | tattgaccac | acctctaccg | gcatgccgag | 8880 |
| caaatgcctg | caaatcgctc | cccatttcac | ccaattgtag | atatgctaac | tccagcaatg | 8940 |
| agttgatgaa | tctcggtgtg | tattttatgt | cctcagagga | caacacctgt | ggta | 8994 |

<210> SEQ ID NO 79
<211> LENGTH: 2145
<212> TYPE: DNA
<213> ORGANISM: artificial sequence
<220> FEATURE:
<223> OTHER INFORMATION: constructed chimeric gene

<400> SEQUENCE: 79

| | | | | | |
|---|---|---|---|---|---|
| gcatgcttgc | atttagtcgt | gcaatgtatg | actttaagat | ttgtgagcag | gaagaaaagg | 60 |
| gagaatcttc | taacgataaa | cccttgaaaa | actgggtaga | ctacgctatg | ttgagttgct | 120 |
| acgcaggctg | cacaattaca | cgagaatgct | cccgcctagg | atttaaggct | aagggacgtg | 180 |
| caatgcagac | gacagatcta | aatgaccgtg | tcggtgaagt | gttcgccaaa | ctttcggtt | 240 |

```
aacacatgca gtgatgcacg cgcgatggtg ctaagttaca tatatatata tatatatata    300
tatagccata gtgatgtcta agtaacccttt atggtatatt tcttaatgtg gaaagatact   360
agcgcgcgca cccacacaca agcttcgtct tttcttgaag aaaagaggaa gctcgctaaa    420
tgggattcca ctttccgttc cctgccagct gatggaaaaa ggttagtgga acgatgaaga    480
ataaaaagag agatccactg aggtgaaatt tcagctgaca gcgagtttca tgatcgtgat    540
gaacaatggt aacgagttgt ggctgttgcc agggagggtg gttctcaact tttaatgtat    600
ggccaaatcg ctacttgggt ttgttatata acaagaaga aataatgaac tgattctctt    660
cctccttctt gtcctttctt aattctgttg taattacctt cctttgtaat ttttttttgta   720 attattcttc ttaataatcc aaacaaacac acatattaca atagctagct gaggatgaag    780
gcattagttt atcatgggga tcacaaaatt tcgttagaag acaaaccaaa acccactctg    840
cagaaaccaa cagacgttgt ggttagggtg ttgaaaacaa caatttgcgg tactgacttg    900
ggaatataca aagtaagaa tcctgaagtg gcagatggca gaatcctggg tcatgagggc    960
gttggcgtca ttgaagaagt gggcgaatcc gtgacacaat tcaaaaaggg ggataaagtt  1020
ttaatctcct gcgttactag ctgtggatcg tgtgattatt gcaagaagca actgtattca   1080
cactgtagag acgtggctg gattttaggt tacatgatcg acggtgtcca agccgaatac    1140
gtcagaatac cacatgctga caattcattg tataagatcc cgcaaactat cgatgatgaa   1200
attgcagtac tactgtccga tattttacct actggacatg aaattggtgt tcaatatggt   1260
aacgttcaac caggcgatgc tgtagcaatt gtaggagcag gtcctgttgg aatgtcagtt   1320
ttgttaactg ctcaatttta ctcgcctagt accattattg ttatcgacat ggacgaaaac   1380
cgtttacaat tagcgaagga gcttggggcc acacacacta ttaactccgg tactgaaaat   1440
gttgtcgaag ctgtgcatcg tatagcagcc gaaggagtgg atgtagcaat agaagctgtt   1500
ggtatacccg caacctggga catctgtcag gaaattgtaa acccggcgc tcatattgcc    1560 aacgtgggag ttcatggtgt taaggtggac tttgaaattc aaaagttgtg gattaagaat  1620
ctaaccatca ccactggttt ggttaacact aatactaccc caatgttgat gaaggtagcc   1680
tctactgata aattgccttt aaagaaaatg attactcaca ggtttgagtt agctgaaatc   1740
gaacacgcat atcaggtttt cttgaatggc gctaaagaaa aagctatgaa gattattcta   1800
tctaatgcag gtgccgccta attaattaag agtaagcgaa tttcttatga tttatgattt   1860
ttattattaa ataagttata aaaaaaataa gtgtatacaa attttaaagt gactcttagg    1920 tttaaaacg aaaattctta ttcttgagta actctttcct gtaggtcagg ttgctttctc   1980
aggtatagca tgaggtcgct cttattgacc acacctctac cggcatgccg agcaaatgcc    2040
tgcaaatcgc tccccatttc acccaattgt agatatgcta actccagcaa tgagttgatg   2100
aatctcggtg tgtattttat gtcctcagag gacaacacct gtggt                   2145
```

<210> SEQ ID NO 80
<211> LENGTH: 4280
<212> TYPE: DNA
<213> ORGANISM: artificial sequence
<220> FEATURE:
<223> OTHER INFORMATION: vector

<400> SEQUENCE: 80

```
ggggatcctc tagagtcgac ctgcaggcat gcaagcttgg cgtaatcatg gtcatagctg     60
tttcctgtgt gaaattgtta tccgctcaca attccacaca catacgagc cggaagcata    120
```

-continued

```
aagtgtaaag cctggggtgc ctaatgagtg agctaactca cattaattgc gttgcgctca      180
ctgcccgctt tccagtcggg aaacctgtcg tgccagctgc attaatgaat cggccaacgc      240
gcggggagag gcggtttgcg tattgggcgc tcttccgctt cctcgctcac tgactcgctg      300
cgctcggtcg ttcggctgcg gcgagcggta tcagctcact caaaggcggt aatacggtta      360
tccacagaat caggggataa cgcaggaaag aacatgtgag caaaaggcca gcaaaaggcc      420
aggaaccgta aaaaggccgc gttgctggcg ttttttccata ggctccgccc ccctgacgag      480
catcacaaaa atcgacgctc aagtcagagg tggcgaaacc cgacaggact ataaagatac      540
caggcgtttc ccctggaag ctccctcgtg cgctctcctg ttccgaccct gccgcttacc      600
ggatacctgt ccgcctttct cccttcggga agcgtggcgc tttctcatag ctcacgctgt      660
aggtatctca gttcggtgta ggtcgttcgc tccaagctgg gctgtgtgca cgaaccccc      720 gttcagcccg accgctgcgc cttatccggt aactatcgtc ttgagtccaa cccggtaaga      780
cacgacttat cgccactggc agcagccact ggtaacagga ttagcagagc gaggtatgta      840
ggcggtgcta cagagttctt gaagtggtgg cctaactacg gctacactag aaggacagta      900
tttggtatct gcgctctgct gaagccagtt accttcggaa aaagagttgg tagctcttga      960
tccggcaaac aaaccaccgc tggtagcggt ggtttttttg tttgcaagca gcagattacg     1020
cgcagaaaaa aaggatctca agaagatcct ttgatctttt ctacggggtc tgacgctcag     1080
tggaacgaaa actcacgtta agggattttg gtcatgagat tatcaaaaag gatcttcacc     1140
tagatccttt taaattaaaa atgaagtttt aaatcaatct aaagtatata tgagtaaact     1200
tggtctgaca gttaccaatg cttaatcagt gaggcaccta tctcagcgat ctgtctattt     1260
cgttcatcca tagttgcctg actccccgtc gtgtagataa ctacgatacg ggagggctta     1320
ccatctggcc ccagtgctgc aatgataccg cgagacccac gctcaccggc tccagattta     1380
tcagcaataa accagccagc cggaagggcc gagcgcagaa gtggtcctgc aactttatcc     1440
gcctccatcc agtctattaa ttgttgccgg gaagctagag taagtagttc gccagttaat     1500
agtttgcgca acgttgttgc cattgctaca ggcatcgtgg tgtcacgctc gtcgtttggt     1560
atggcttcat tcagctccgg ttcccaacga tcaaggcgag ttacatgatc ccccatgttg     1620
tgcaaaaaag cggttagctc cttcggtcct ccgatcgttg tcagaagtaa gttggccgca     1680
gtgttatcac tcatggttat ggcagcactg cataattctc ttactgtcat gccatccgta     1740
agatgctttt ctgtgactgg tgagtactca accaagtcat tctgagaata gtgtatgcgg     1800
cgaccgagtt gctcttgccc ggcgtcaata cgggataata ccgcgccaca tagcagaact     1860
ttaaaagtgc tcatcattgg aaaacgttct cggggcgaa aactctcaag gatcttaccg     1920
ctgttgagat ccagttcgat gtaacccact cgtgcaccca actgatcttc agcatctttt     1980
actttcacca gcgtttctgg gtgagcaaaa acaggaaggc aaaatgccgc aaaaaaggga     2040
ataagggcga cacggaaatg ttgaatactc atactcttcc ttttttcaata ttattgaagc     2100 atttatcagg gttattgtct catgagcgga tacatatttg aatgtattta gaaaaataaa     2160 caaataggg ttccgcgcac atttccccga aaagtgccac ctgacgtcta agaaaccatt     2220
attatcatga cattaaccta taaaaatagg cgtatcacga ggccctttcg tctcgcgcgt     2280
ttcggtgatg acggtgaaaa cctctgacac atgcagctcc cggagacggt cacagcttgt     2340
ctgtaagcgg atgccgggag cagacaagcc cgtcagggcg cgtcagcggg tgttggcggg     2400
tgtcggggct ggcttaacta tgcggcatca gagcagattg tactgagagt gcaccatatg     2460
cggtgtgaaa taccgcacag atgcgtaagg agaaaatacc gcatcaggcg ccattcgcca     2520
```

-continued

```
ttcaggctgc gcaactgttg ggaagggcga tcggtgcggg cctcttcgct attacgccag    2580
ctggcgaaag ggggatgtgc tgcaaggcga ttaagttggg taacgccagg ttttcccag    2640 tcacgacgtt gtaaaacgac ggccagtgaa ttcgagctcg gtaccccggg ctctgagaca    2700
gtagtaggtt agtcatcgct ctaccgacgc gcaggaaaag aaagaagcat tgcggattac    2760
gtattctaat gttcagcccg cggaacgcca gcaaatcacc acccatgcgc atgatactga    2820
gtcttgtaca cgctgggctt ccagtgtact gagagtgcac cataccacag cttttcaatt    2880
caattcatca ttttttttt attcttttt ttgatttcgg tttctttgaa attttttga    2940 ttcggtaatc tccgaacaga aggaagaacg aaggaaggag cacagactta gattggtata    3000
tatacgcata tgtagtgttg aagaaacatg aaattgccca gtattcttaa cccaactgca    3060
cagaacaaaa acctgcagga aacgaagata aatcatgtcg aaagctacat ataaggaacg    3120
tgctgctact catcctagtc ctgttgctgc caagctattt aatatcatgc acgaaaagca    3180
aacaaacttg tgtgcttcat tggatgttcg taccaccaag gaattactgg agttagttga    3240
agcattaggt cccaaaattt gtttactaaa acacatgtg gatatcttga ctgattttc    3300 catggagggc acagttaagc cgctaaaggc attatccgcc aagtacaatt ttttactctt    3360
cgaagacaga aaatttgctg acattggtaa tacagtcaaa ttgcagtact ctgcgggtgt    3420
atacagaata gcagaatggg cagacattac gaatgcacac ggtgtggtgg cccaggtat    3480 tgttagcggt ttgaagcagg cggcagaaga agtaacaaag gaacctagag gccttttgat    3540
gttagcagaa ttgtcatgca agggctccct atctactgga gaatatacta agggtactgt    3600
tgacattgcg aagagcgaca agatttttgt tatcggcttt attgctcaaa gagacatggg    3660
tggaagagat gaaggttacg attggttgat tatgacaccc ggtgtgggtt tagatgacaa    3720
gggagacgca ttgggtcaac agtatagaac cgtggatgat gtggtctcta caggatctga    3780
cattattatt gttggaagag gactatttgc aaagggaagg gatgctaagg tagagggtga    3840
acgttacaga aaagcaggct gggaagcata tttgagaaga tgcggccagc aaaactaaaa    3900
aactgtatta taagtaaatg catgtatact aaactcacaa attagagctt caatttaatt    3960
atatcagtta ttaccctatg cggtgtgaaa taccgcacag atgcgtaagg agaaaatacc    4020
gcatcaggaa attgtaaacg ttaatatttt gttaaaattc gcgttaaatt tttgttaaat    4080
cagctcattt tttaaccaat aggccgaaat cggcaaaatc ttcagcccgc ggaacgccag    4140
caaatcacca cccatgcgca tgatactgag tcttgtacac gctgggcttc cagtgatgat    4200
acaacgagtt agccaaggtg agcacggatg tctaaattag aattacgttt taatatcttt    4260
ttttccatat ctagggctag                                                 4280
```

<210> SEQ ID NO 81
<211> LENGTH: 30
<212> TYPE: DNA
<213> ORGANISM: artificial sequence
<220> FEATURE:
<223> OTHER INFORMATION: primer

<400> SEQUENCE: 81

```
gcatgcttgc atttagtcgt gcaatgtatg                                        30
```

<210> SEQ ID NO 82
<211> LENGTH: 54
<212> TYPE: DNA
<213> ORGANISM: artificial sequence
<220> FEATURE:

<223> OTHER INFORMATION: primer

<400> SEQUENCE: 82
gaacattaga atacgtaatc cgcaatgcac tagtaccaca ggtgttgtcc tctg        54

<210> SEQ ID NO 83
<211> LENGTH: 54
<212> TYPE: DNA
<213> ORGANISM: artificial sequence
<220> FEATURE:
<223> OTHER INFORMATION: primer

<400> SEQUENCE: 83
cagaggacaa cacctgtggt actagtgcat tgcggattac gtattctaat gttc        54

<210> SEQ ID NO 84
<211> LENGTH: 28
<212> TYPE: DNA
<213> ORGANISM: artificial sequence
<220> FEATURE:
<223> OTHER INFORMATION: primer

<400> SEQUENCE: 84
caccttggct aactcgttgt atcatcac                                     28

<210> SEQ ID NO 85
<211> LENGTH: 100
<212> TYPE: DNA
<213> ORGANISM: artificial sequence
<220> FEATURE:
<223> OTHER INFORMATION: primer

<400> SEQUENCE: 85
ttttaagccg aatgagtgac agaaaaagcc cacaacttat caagtgatat tgaacaaagg  60
gcgaaacttc gcatgcttgc atttagtcgt gcaatgtatg                       100

<210> SEQ ID NO 86
<211> LENGTH: 98
<212> TYPE: DNA
<213> ORGANISM: artificial sequence
<220> FEATURE:
<223> OTHER INFORMATION: primer

<400> SEQUENCE: 86
cccaattggt aaatattcaa caagagacgc gcagtacgta acatgcgaat tgcgtaattc  60
acggcgataa caccttggct aactcgttgt atcatcac                          98

<210> SEQ ID NO 87
<211> LENGTH: 29
<212> TYPE: DNA
<213> ORGANISM: artificial sequence
<220> FEATURE:
<223> OTHER INFORMATION: primer

<400> SEQUENCE: 87
caaaagccca tgtcccacac caaaggatg                                    29

<210> SEQ ID NO 88
<211> LENGTH: 26
<212> TYPE: DNA
<213> ORGANISM: artificial sequence
<220> FEATURE:
<223> OTHER INFORMATION: primer

<400> SEQUENCE: 88

-continued

```
caccatcgcg cgtgcatcac tgcatg                                          26

<210> SEQ ID NO 89
<211> LENGTH: 28
<212> TYPE: DNA
<213> ORGANISM: artificial sequence
<220> FEATURE:
<223> OTHER INFORMATION: primer

<400> SEQUENCE: 89
tcggtttttg caatatgacc tgtgggcc                                        28

<210> SEQ ID NO 90
<211> LENGTH: 22
<212> TYPE: DNA
<213> ORGANISM: artificial sequence
<220> FEATURE:
<223> OTHER INFORMATION: primer

<400> SEQUENCE: 90
gagaagatgc ggccagcaaa ac                                              22

<210> SEQ ID NO 91
<211> LENGTH: 2745
<212> TYPE: DNA
<213> ORGANISM: artificial sequence
<220> FEATURE:
<223> OTHER INFORMATION: constructed coding region-terminator segment

<400> SEQUENCE: 91
atgactgaca aaaaaactct taaagactta agaaatcgta gttctgttta cgattcaatg     60
gttaaatcac ctaatcgtgc tatgttgcgt gcaactggta tgcaagatga agactttgaa    120
aaacctatcg tcggtgtcat ttcaacttgg gctgaaaaca ccttgtaa tatccactta      180 catgactttg gtaaactagc caaagtcggt gttaaggaag ctggtgcttg gccagttcag    240
ttcggaacaa tcacggtttc tgatggaatc gccatgggaa cccaaggaat gcgtttctcc    300
ttgacatctc gtgatattat tgcagattct attgaagcag ccatgggagg tcataatgcg    360
gatgcttttg tagccattgg cggttgtgat aaaaacatgc ccggttctgt tatcgctatg    420
gctaacatgg atatcccagc catttttgct tacggcggaa caattgcacc tggtaattta    480
gacggcaaag atatcgattt agtctctgtc tttgaaggtg tcggccattg gaaccacggc    540
gatatgacca agaagaagt taaagctttg gaatgtaatg cttgtcccgg tcctggaggc    600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga catttttaacg    780 cgtgaagctt ttgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga accttctgg tcaatatgta    960 ttccaagacc tttacaaggt cggagggta ccagcagtta tgaaatatct ccttaaaaat   1020
ggcttccttc atggtgaccg tatcacttgt actggcaaaa cagtcgctga aaatttgaag   1080
gcttttgatg atttaaacac tggtcaaaag gttattatgc gcttgaaaa tcctaaacgt   1140 gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
```

```
gaagccattg aagctgtctt gaatgatgat attgttgatg gtgatgttgt tgtcgtacgt   1320
tttgtaggac caaagggcgg tcctggtatg cctgaaatgc tttcccttc atcaatgatt    1380 gttggtaaag ggcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gacttttgga agcctgaaga aactggcaaa aaatgttgtc ctggttgctg tggttaagcg   1740
gccgcgttaa ttcaaattaa ttgatatagt ttttaatga gtattgaatc tgtttagaaa    1800
taatggaata ttatttttat ttatttattt atattattgg tcggctcttt tcttctgaag   1860
gtcaatgaca aaatgatatg aaggaaataa tgatttctaa aattttacaa cgtaagatat   1920
ttttacaaaa gcctagctca tcttttgtca tgcactattt tactcacgct tgaaattaac   1980
ggccagtcca ctgcggagtc atttcaaagt catcctaatc gatctatcgt ttttgatagc   2040 tcatttttgga gttcgcgatt gtcttctgtt attcacaact gttttaattt ttatttcatt   2100
ctggaactct tcgagttctt tgtaaagtct ttcatagtag cttactttat cctccaacat   2160
atttaacttc atgtcaattt cggctcttaa attttccaca tcatcaagtt caacatcatc   2220
ttttaacttg aatttattct ctagctcttc caaccaagcc tcattgctcc ttgatttact   2280
ggtgaaaagt gatacacttt gcgcgcaatc caggtcaaaa cttttcctgca aagaattcac   2340 caatttctcg acatcatagt acaatttgtt ttgttctccc atcacaattt aatatacctg   2400
atggattctt atgaagcgct gggtaatgga cgtgtcactc tacttcgcct ttttccctac   2460 tcctttagt acgaagaca atgctaataa ataagagggt aataataata ttattaatcg      2520 gcaaaaaga ttaaacgcca agcgtttaat tatcagaaag caaacgtcgt accaatcctt    2580
gaatgcttcc caattgtata ttaagagtca tcacagcaac atattcttgt tattaaatta   2640
attattattg attttgata ttgtataaaa aaaccaaata tgtataaaaa aagtgaataa     2700
aaaataccaa gtatggagaa atatattaga agtctatacg ttaaa                   2745
```

<210> SEQ ID NO 92
<211> LENGTH: 27
<212> TYPE: DNA
<213> ORGANISM: artificial sequence
<220> FEATURE:
<223> OTHER INFORMATION: primer

<400> SEQUENCE: 92 gactttgga agcctgaaga aactggc                                         27

<210> SEQ ID NO 93
<211> LENGTH: 20
<212> TYPE: DNA
<213> ORGANISM: artificial sequence
<220> FEATURE:
<223> OTHER INFORMATION: primer

<400> SEQUENCE: 93
cttggcagca acaggactag                                                20

<210> SEQ ID NO 94
<211> LENGTH: 26
<212> TYPE: DNA
<213> ORGANISM: artificial sequence

```
<220> FEATURE:
<223> OTHER INFORMATION: primer

<400> SEQUENCE: 94
ccaggccaat tcaacagact gtcggc                                          26

<210> SEQ ID NO 95
<211> LENGTH: 2347
<212> TYPE: DNA
<213> ORGANISM: artificial sequence
<220> FEATURE:
<223> OTHER INFORMATION: constructed URA3 marker with flanking
      homologous repeat sequences for HIS gene replacement and marker
      excision

<400> SEQUENCE: 95
gcattgcgga ttacgtattc taatgttcag gtgctggaag aagagctgct taaccgccgc      60
gcccagggtg aagatccacg ctactttacc ctgcgtcgtc tggatttcgg cggctgtcgt     120
ctttcgctgg caacgccggt tgatgaagcc tgggacggtc cgctctcctt aaacggtaaa     180
cgtatcgcca cctcttatcc tcacctgctc aagcgttatc tcgaccagaa aggcatctct     240
tttaaatcct gcttactgaa cggttctgtt gaagtcgccc cgcgtgccgg actggcggat     300
gcgatttgcg atctggtttc caccggtgcc acgctggaag ctaacggcct gcgcgaagtc     360
gaagttatct atcgctcgaa agcctgcctg attcaacgcg atggcgaaat ggaagaatcc     420
aaacagcaac tgatcgacaa actgctgacc cgtattcagg gtgtgatcca ggcgcgcgaa     480
tcaaaataca tcatgatgca cgcaccgacc gaacgtctgg atgaagtcat ggtacctact     540
gagagtgcac cataccacag cttttcaatt caattcatca ttttttttttt attcttttt     600 ttgatttcgg tttctttgaa atttttttga ttcggtaatc tccgaacaga aggaagaacg     660
aaggaaggag cacagactta gattggtata tatacgcata tgtagtgttg aagaaacatg     720
aaattgccca gtattcttaa cccaactgca cagaacaaaa acctgcagga acgaagata     780 aatcatgtcg aaagctacat ataaggaacg tgctgctact catcctagtc ctgttgctgc     840
caagctattt aatatcatgc acgaaaagca aacaaacttg tgtgcttcat tggatgttcg     900
taccaccaag gaattactgg agttagttga agcattaggt cccaaaattt gtttactaaa     960
aacacatgtg gatatcttga ctgatttttc catggagggc acagttaagc cgctaaaggc    1020
attatccgcc aagtacaatt ttttactctt cgaagacaga aaatttgctg acattggtaa    1080
tacagtcaaa ttgcagtact ctgcgggtgt atacagaata gcagaatggg cagacattac    1140
gaatgcacac ggtgtggtgg gcccaggtat tgttagcggt ttgaagcagg cggcagaaga    1200
agtaacaaag gaacctagag gccttttgat gttagcagaa ttgtcatgca agggctccct    1260
atctactgga gaatatacta agggtactgt tgacattgcg aagagcgaca agatttttgt    1320
tatcggcttt attgctcaaa gagacatggg tggaagagat gaaggttacg attggttgat    1380
tatgacaccc ggtgtgggtt tagatgacaa gggagacgca ttgggtcaac agtatagaac    1440
cgtggatgat gtggtctcta caggatctga cattattatt gttggaagag gactatttgc    1500
aaagggaagg gatgctaagg tagagggtga acgttacaga aaagcaggct gggaagcata    1560
tttgagaaga tgcggccagc aaaactaaaa aactgtatta taagtaaatg catgtatact    1620
aaactcacaa attagagctt caatttaatt atatcagtta ttaccctatg cggtgtgaaa    1680
taccgcacag atgcgtaagg agaaaatacc gcatcaggaa attgtaaacg ttaatatttt    1740
gttaaaattc gcgttaaatt tttgttaaat cagctcattt tttaaccaat aggccgaaat    1800
```

-continued

```
cggcaaaatc tctagagtgc tggaagaaga gctgcttaac cgccgcgccc agggtgaaga    1860
tccacgctac tttaccctgc gtcgtctgga tttcggcggc tgtcgtcttt cgctggcaac    1920
gccggttgat gaagcctggg acggtccgct ctccttaaac ggtaaacgta tcgccacctc    1980
ttatcctcac ctgctcaagc gttatctcga ccagaaaggc atctctttta aatcctgctt    2040
actgaacggt tctgttgaag tcgccccgcg tgccggactg gcggatgcga tttgcgatct    2100
ggtttccacc ggtgccacgc tggaagctaa cggcctgcgc gaagtcgaag ttatctatcg    2160
ctcgaaagcc tgcctgattc aacgcgatgg cgaaatggaa gaatccaaac agcaactgat    2220
cgacaaactg ctgacccgta ttcagggtgt gatccaggcg cgcgaatcaa aatacatcat    2280
gatgcacgca ccgaccgaac gtctggatga agtcatccag tgatgataca acgagttagc    2340
caaggtg                                                              2347

<210> SEQ ID NO 96
<211> LENGTH: 80
<212> TYPE: DNA
<213> ORGANISM: artificial sequence
<220> FEATURE:
<223> OTHER INFORMATION: primer

<400> SEQUENCE: 96
cttcgaagaa tatactaaaa aatgagcagg caagataaac gaaggcaaag gcattgcgga    60
ttacgtattc taatgttcag                                                80

<210> SEQ ID NO 97
<211> LENGTH: 81
<212> TYPE: DNA
<213> ORGANISM: artificial sequence
<220> FEATURE:
<223> OTHER INFORMATION: primer

<400> SEQUENCE: 97
tatacacatg tatatatatc gtatgctgca gctttaaata atcggtgtca caccttggct    60
aactcgttgt atcatcactg g                                              81

<210> SEQ ID NO 98
<211> LENGTH: 26
<212> TYPE: DNA
<213> ORGANISM: artificial sequence
<220> FEATURE:
<223> OTHER INFORMATION: primer

<400> SEQUENCE: 98
gacttgaata atgcagcggc gcttgc                                         26

<210> SEQ ID NO 99
<211> LENGTH: 30
<212> TYPE: DNA
<213> ORGANISM: artificial sequence
<220> FEATURE:
<223> OTHER INFORMATION: primer

<400> SEQUENCE: 99
ccaccctctt caattagcta agatcatagc                                     30

<210> SEQ ID NO 100
<211> LENGTH: 25
<212> TYPE: DNA
<213> ORGANISM: artificial sequence
<220> FEATURE:
<223> OTHER INFORMATION: primer
```

```
<400> SEQUENCE: 100
aaaaattgat tctcatcgta aatgc                                              25

<210> SEQ ID NO 101
<211> LENGTH: 20
<212> TYPE: DNA
<213> ORGANISM: artificial sequence
<220> FEATURE:
<223> OTHER INFORMATION: primer

<400> SEQUENCE: 101
ctgcagcgag gagccgtaat                                                    20

<210> SEQ ID NO 102
<211> LENGTH: 90
<212> TYPE: DNA
<213> ORGANISM: artificial sequence
<220> FEATURE:
<223> OTHER INFORMATION: primer

<400> SEQUENCE: 102
atggttcatt taggtccaaa aaaaccacaa gccagaaagg gttccatggc cgatgtgcca        60
gcattgcgga ttacgtattc taatgttcag                                         90

<210> SEQ ID NO 103
<211> LENGTH: 91
<212> TYPE: DNA
<213> ORGANISM: artificial sequence
<220> FEATURE:
<223> OTHER INFORMATION: primer

<400> SEQUENCE: 103
ttaagcaccg atgataccaa cggacttacc ttcagcaatt ctttttttggg ccaaagcagc       60 caccttggct aactcgttgt atcatcactg g                                       91

<210> SEQ ID NO 104
<211> LENGTH: 24
<212> TYPE: DNA
<213> ORGANISM: artificial sequence
<220> FEATURE:
<223> OTHER INFORMATION: primer

<400> SEQUENCE: 104
ctaggatgag tagcagcacg ttcc                                               24

<210> SEQ ID NO 105
<211> LENGTH: 26
<212> TYPE: DNA
<213> ORGANISM: artificial sequence
<220> FEATURE:
<223> OTHER INFORMATION: primer

<400> SEQUENCE: 105
ccaattccgt gatgtctctt tgttgc                                             26

<210> SEQ ID NO 106
<211> LENGTH: 20
<212> TYPE: DNA
<213> ORGANISM: artificial sequence
<220> FEATURE:
<223> OTHER INFORMATION: primer

<400> SEQUENCE: 106
```

```
gtgaacgagt tcacaaccgc                                          20

<210> SEQ ID NO 107
<211> LENGTH: 22
<212> TYPE: DNA
<213> ORGANISM: artificial sequence
<220> FEATURE:
<223> OTHER INFORMATION: primer

<400> SEQUENCE: 107
gttcgttcca gaattatcac gc                                       22

<210> SEQ ID NO 108
<211> LENGTH: 28
<212> TYPE: DNA
<213> ORGANISM: artificial sequence
<220> FEATURE:
<223> OTHER INFORMATION: primer

<400> SEQUENCE: 108
ggatccgcat gcttgcattt agtcgtgc                                 28

<210> SEQ ID NO 109
<211> LENGTH: 20
<212> TYPE: DNA
<213> ORGANISM: artificial sequence
<220> FEATURE:
<223> OTHER INFORMATION: primer

<400> SEQUENCE: 109
gggatgcgga cgtattcggc                                          20

<210> SEQ ID NO 110
<211> LENGTH: 4506
<212> TYPE: DNA
<213> ORGANISM: Saccharomyces cerevisiae

<400> SEQUENCE: 110
atgtcgaata cccttataa ttcatctgtg ccttccattg catccatgac ccagtcttcg      60
gtctcaagaa gtcctaacat gcatacagca actacgcccg gtgccaacac cagctctaac     120
tctccaccct tgcacatgtc ttcagattcg tccaagatca agaggaagcg taacagaatt     180
ccgctcagtt gcaccatttg tcggaaaagg aaagtcaaat gtgacaaact cagaccacac     240
tgccagcagt gcactaaaac tggggtagcc catctctgcc actacatgga acagacctgg     300
gcagaagagg cagagaaaga attgctgaag gacaacgaat taagaagct tagggagcgc     360 gtaaaatctt tagaaaagac tctttctaag gtgcactctt ctccttcgtc taactccttg     420
aaaagttaca acactcccga gagcagcaac ctgtttatgg gtagcgatga acacaccacc     480
cttgttaatg caaatacagg ctctgcttcc tctgcctcgc atatgcatca gcaacaacag     540
caacagcagc aacaggaaca acaacaagac ttttccagaa gtgcgaacgc caacgcgaat     600
tcctcgtccc tttctatctc aaataaatat gacaacgatg agctggactt aactaaggac     660
tttgatcttt tgcatatcaa agtaacggaa accatccact aggtgccac ccactggttg      720 tctatcatga aaggtgaccc gtacctaaaa cttttgtggg gtcatatctt cgctatgagg     780
gaaaagttaa atgaatggta ctaccaaaaa aattcgtact ctaagctgaa gtcaagcaaa     840
tgtcccatca atcacgcgca agcgccgcct tctgccgctg ccgccgctac cagaaaatgt     900
cctgttgatc actccgcgtt ttcgtctggc atggtggccc caaggaggga gactcctctt     960
cctaggaaat gtccagttga ccacaccatg ttctcttcgg gaatgattcc tcccagagag    1020
```

```
gacacttcgt cccagaagag gtgtcccgtt gaccacacca tgtattccgc aggaatgatg    1080
ccgcccaagg acgagacacc ttccccattt tccactaaag ctatgataga ccataacaag    1140
catacaatga atccgcctca gtcaaaatgt cctgtggacc atagaaacta tatgaaggat    1200
tatccctctg acatggcaaa ttcttcttcg aacccggcaa gtcgttgccc cattgaccat    1260
tcaagcatga aaatacagc ggccttacca gcttcaacgc acaataccat cccacaccac    1320
caaccacagt ccggatctca tgctcgttcg catcccgcac aaagcaggaa acatgattcc    1380
tacatgacag aatctgaagt cctcgcaaca ctttgtgaga tgttgccacc aaagcgcgtc    1440
atcgcattat tcatcgagaa attcttcaaa catttatacc ctgccattcc aatcttagat    1500
gaacagaatt tcaaaaatca cgtgaatcaa atgctttcgt tgtcttcgat gaatcccaca    1560
gttaacaact tggtatgag catgccatct tcatctacac tagagaacca acccataaca    1620
caaatcaatc ttccaaaact ttccgattct tgtaacttag gtattctgat aataatcttg    1680
agattgacat ggctatccat accttctaat tcctgcgaag tcgacctggg agaagaaagt    1740
ggctcatttt tagtgcccaa cgaatctagc aatatgtctg catctgcatt gacctcgatg    1800
gctaaagaag aatcacttct gctaaagcat gagacaccgg tcgaggcact ggagctatgt    1860
caaaaatact tgattaaatt cgatgaactt tctagtattt ccaataacaa cgttaattta    1920
accacggtgc agtttgccat tttttacaac ttctatatga aaagtgcctc taatgatttg    1980
actaccttga caaataccaa caacactggc atggccaatc ctggtcacga ttccgagtct    2040
caccagatcc tattgtccaa tattactcaa atggcctta gttgtgggtt acacagagac    2100
cctgataatt ttcctcaatt aaacgctacc attccagcaa ccagccagga cgtgtctaac    2160
aacgggagca aaaggcaaa ccctagcacc aatccaactt tgaataacaa catgtctgct    2220
gccactacca acagcagtag cagatctggc agtgctgatt caagaagtgg ttctaacct    2280 gtgaacaaga aggaaaatca ggttagtatc gaaagattta acacacttg gaggaaaatt    2340 tggtattaca ttgttagcat ggatgttaac caatctcttt ccctggggag ccctcgacta    2400
ctaagaaatc tgagggattt cagcgataca aagctaccaa gtgcgtcaag gattgattat    2460
gttcgcgata tcaaagagtt aatcattgtg aagaatttta ctctttttt ccaaattgat    2520 ttgtgtatta ttgctgtatt aaatcacatt ttgaatgttt cttagcaag aagcgtgaga    2580 aaatttgaac tggattcatt gattaattta ttgaaaaatc tgacctatgg tactgagaat    2640
gtcaatgatg tagtgagctc cttgatcaac aaagggttat taccaacttc ggaaggtggt    2700
tctgtagatt caaataatga tgaaatttac ggtctaccga aactacccga tattctaaac    2760
catggtcaac ataaccaaaa cttgtatgct gatggaagaa atacttctag tagtgatata    2820
gataagaaat tggaccttcc tcacgaatct acaacgagag ctctattctt ttccaagcat    2880
atgacaatta gaatgttgct gtacttattg aactacattt tgtttactca ttatgaacca    2940
atgggcagtg aagatcctgg tactaatatc ctagctaagg agtacgctca agaggcatta    3000
aattttgcca tggatggcta cagaaactgc atgattttct tcaacaatat cagaaacacc    3060
aattcactat tcgattacat gaatgttatc ttgtcttacc cttgttggga cattggacat    3120
cgttctttac aatttatcgt ttgtttgatc ctgagagcta aatgtggccc attgactggt    3180
atgcgtgaat catcgatcat tactaatggt acatcaagtg gatttaatag ttcggtagaa    3240
gatgaggacg tcaaagttaa acaagaatct tctgatgaat tgaaaaaga cgatttcatg    3300 aaagatgtaa atttggattc aggcgattca ttagcagaga ttctaatgtc aagaatgctg    3360
```

-continued

| | |
|---|---|
| ctatttcaaa aactaacaaa acaactatca aagaagtaca actacgctat tcgtatgaac | 3420 |
| aaatccactg gattctttgt ctctttacta gatacacctt caaagaaatc agactcgaaa | 3480 |
| tcgggtggta gttcattcat gttgggtaat tggaaacatc caaaggtttc aaacatgagc | 3540 |
| ggatttcttg ctggtgacaa agaccaatta cagaaatgcc ccgtgtacca agatgcgctg | 3600 |
| gggtttgtta gtccaaccgg tgctaatgaa ggttctgctc cgatgcaagg catgtcctta | 3660 |
| cagggctcta ctgctaggat gggagggacc cagttgccac caattagatc atacaaacct | 3720 |
| atcacgtaca caagtagtaa tctacgtcgt atgaatgaaa cgggtgaggc agaagctaag | 3780 |
| agaagaagat ttaatgatgg ctatattgat aataatagta acaacgatat acctagagga | 3840 |
| atcagcccaa aaccttcaaa tgggctatca tcggtgcagc cactattatc gtcattttcc | 3900 |
| atgaaccagc taacgggggg taccattcca acggttccat cgttaaccaa cattacttca | 3960 |
| caaatgggag ctttaccatc tttagatagg atcaccacta atcaaataaa tttgccagac | 4020 |
| ccatctagag atgaagcatt tgacaactcc atcaagcaaa tgacgcctat gacaagtgca | 4080 |
| ttcatgaatg ctaatactac aattccaagt tcaactttaa acgggaatat gaacatgaat | 4140 |
| ggagctggaa ctgcgaatac agatacaagt gccaacggca gtgctttatc gacactgaca | 4200 |
| agcccacaag gctcagactt agcatccaat tctgctacac agtataaacc tgacttagaa | 4260 |
| gacttttga tgcaaaattc taactttaat gggctaatga taaatccttc cagtctggta | 4320 |
| gaagttgttg gtggatacaa cgatcctaat aaccttggaa gaaatgacgc ggttgatttt | 4380 |
| ctacccgttg ataatgttga aattgatggt gttggaataa aaatcaacta tcatctacta | 4440 |
| actagtattt acgttactag tatattatca tatacggtgt tagaagatga cgcaaatgat | 4500 |
| gagaaa | 4506 |

<210> SEQ ID NO 111
<211> LENGTH: 99
<212> TYPE: DNA
<213> ORGANISM: artificial sequence
<220> FEATURE:
<223> OTHER INFORMATION: primer

<400> SEQUENCE: 111

| | |
|---|---|
| tcctttctca attattattt tctactcata acctcacgca aaataacaca gtcaaatcaa | 60 |
| tcaaagtatg actgacaaaa aaactcttaa agacttaag | 99 |

<210> SEQ ID NO 112
<211> LENGTH: 77
<212> TYPE: DNA
<213> ORGANISM: artificial sequence
<220> FEATURE:
<223> OTHER INFORMATION: primer

<400> SEQUENCE: 112

| | |
|---|---|
| gaacattaga atacgtaatc cgcaatgctt ctttcttttc cgtttaacgt atagacttct | 60 |
| aatatatttc tccatac | 77 |

<210> SEQ ID NO 113
<211> LENGTH: 45
<212> TYPE: DNA
<213> ORGANISM: artificial sequence
<220> FEATURE:
<223> OTHER INFORMATION: primer

<400> SEQUENCE: 113

| | |
|---|---|
| aaacggaaaa gaaagaagca ttgcggatta cgtattctaa tgttc | 45 |

<210> SEQ ID NO 114
<211> LENGTH: 88
<212> TYPE: DNA
<213> ORGANISM: artificial sequence
<220> FEATURE:
<223> OTHER INFORMATION: primer

<400> SEQUENCE: 114

```
tatttttcgt tacataaaaa tgcttataaa actttaacta ataattagag attaaatcgc    60
caccttggct aactcgttgt atcatcac                                       88
```

<210> SEQ ID NO 115
<211> LENGTH: 1713
<212> TYPE: DNA
<213> ORGANISM: Streptococcus mutans

<400> SEQUENCE: 115

```
atgactgaca aaaaaactct taaagactta agaaatcgta gttctgttta cgattcaatg    60
gttaaatcac ctaatcgtgc tatgttgcgt gcaactggta tgcaagatga agactttgaa   120
aaacctatcg tcggtgtcat ttcaacttgg gctgaaaaca caccttgtaa tatccactta   180
catgactttg gtaaactagc caaagtcggt gttaaggaag ctggtgcttg gccagttcag   240
ttcggaacaa tcacggtttc tgatggaatc gccatgggaa cccaaggaat gcgtttctcc   300
ttgacatctc gtgatattat tgcagattct attgaagcag ccatgggagg tcataatgcg   360
gatgcttttg tagccattgg cggttgtgat aaaaacatgc ccggttctgt tatcgctatg   420
gctaacatgg atatcccagc cattttttgct tacggcggaa caattgcacc tggtaattta   480
gacggcaaag atatcgattt agtctctgtc tttgaaggtg tcggccattg gaaccacggc   540
gatatgacca agaagaagt taaagctttg gaatgtaatg cttgtcccgg tcctggaggc   600
tgcggtggta tgtatactgc taacacaatg gcgacagcta ttgaagtttt gggacttagc   660
cttccgggtt catcttctca cccggctgaa tccgcagaaa agaaagcaga tattgaagaa   720
gctggtcgcg ctgttgtcaa aatgctcgaa atgggcttaa aaccttctga cattttaacg   780
cgtgaagctt ttgaagatgc tattactgta actatggctc tgggaggttc aaccaactca   840
acccttcacc tcttagctat tgcccatgct gctaatgtgg aattgacact tgatgatttc   900
aatactttcc aagaaaaagt tcctcatttg gctgatttga accttctgg tcaatatgta   960 ttccaagacc tttacaaggt cggagggggta ccagcagtta tgaaatatct ccttaaaaat  1020
ggcttccttc atggtgaccg tatcacttgt actggcaaaa cagtcgctga aaatttgaag  1080
gcttttgatg atttaacacc tggtcaaaag gttattatgc cgcttgaaaa tcctaaacgt  1140
gaagatggtc cgctcattat tctccatggt aacttggctc cagacggtgc cgttgccaaa  1200
gtttctggtg taaaagtgcg tcgtcatgtc ggtcctgcta aggtctttaa ttctgaagaa  1260
gaagccattg aagctgtctt gaatgatgat attgttgatg gtgatgttgt tgtcgtacgt  1320
tttgtaggac caaagggcgg tcctggtatg cctgaaatgc tttcccttc atcaatgatt  1380 gttggtaaag ggcaaggtga aaagttgcc cttctgacag atggccgctt ctcaggtggt  1440
acttatggtc ttgtcgtggg tcatatcgct cctgaagcac aagatggcgg tccaatcgcc  1500
tacctgcaaa caggagacat agtcactatt gaccaagaca ctaaggaatt acactttgat  1560
atctccgatg aagagttaaa acatcgtcaa gagaccattg aattgccacc gctctattca  1620
cgcggtatcc ttggtaaata tgctcacatc gtttcgtctg cttctagggg agccgtaaca  1680
```

-continued

```
gacttttgga agcctgaaga aactggcaaa aaa                          1713
```

<210> SEQ ID NO 116
<211> LENGTH: 571
<212> TYPE: PRT
<213> ORGANISM: Streptococcus mutans

<400> SEQUENCE: 116

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365
```

```
Gln Lys Val Ile Met Pro Leu Glu Asn Pro Lys Arg Glu Asp Gly Pro
    370                 375                 380
Leu Ile Ile Leu His Gly Asn Leu Ala Pro Asp Gly Ala Val Ala Lys
385                 390                 395                 400
Val Ser Gly Val Lys Val Arg Arg His Val Gly Pro Ala Lys Val Phe
                405                 410                 415
Asn Ser Glu Glu Glu Ala Ile Glu Ala Val Leu Asn Asp Asp Ile Val
            420                 425                 430
Asp Gly Asp Val Val Val Arg Phe Val Gly Pro Lys Gly Gly Pro
        435                 440                 445
Gly Met Pro Glu Met Leu Ser Leu Ser Ser Met Ile Val Gly Lys Gly
    450                 455                 460
Gln Gly Glu Lys Val Ala Leu Leu Thr Asp Gly Arg Phe Ser Gly Gly
465                 470                 475                 480
Thr Tyr Gly Leu Val Val Gly His Ile Ala Pro Glu Ala Gln Asp Gly
                485                 490                 495
Gly Pro Ile Ala Tyr Leu Gln Thr Gly Asp Ile Val Thr Ile Asp Gln
            500                 505                 510
Asp Thr Lys Glu Leu His Phe Asp Ile Ser Asp Glu Glu Leu Lys His
        515                 520                 525
Arg Gln Glu Thr Ile Glu Leu Pro Pro Leu Tyr Ser Arg Gly Ile Leu
    530                 535                 540
Gly Lys Tyr Ala His Ile Val Ser Ser Ala Ser Arg Gly Ala Val Thr
545                 550                 555                 560
Asp Phe Trp Lys Pro Glu Glu Thr Gly Lys Lys
                565                 570

<210> SEQ ID NO 117
<211> LENGTH: 548
<212> TYPE: PRT
<213> ORGANISM: Lactococcus lactis

<400> SEQUENCE: 117

Met Tyr Thr Val Gly Asp Tyr Leu Leu Asp Arg Leu His Glu Leu Gly
1               5                   10                  15
Ile Glu Glu Ile Phe Gly Val Pro Gly Asp Tyr Asn Leu Gln Phe Leu
            20                  25                  30
Asp Gln Ile Ile Ser His Lys Asp Met Lys Trp Val Gly Asn Ala Asn
        35                  40                  45
Glu Leu Asn Ala Ser Tyr Met Ala Asp Gly Tyr Ala Arg Thr Lys Lys
    50                  55                  60
Ala Ala Ala Phe Leu Thr Thr Phe Gly Val Gly Glu Leu Ser Ala Val
65                  70                  75                  80
Asn Gly Leu Ala Gly Ser Tyr Ala Glu Asn Leu Pro Val Val Glu Ile
                85                  90                  95
Val Gly Ser Pro Thr Ser Lys Val Gln Asn Glu Gly Lys Phe Val His
            100                 105                 110
His Thr Leu Ala Asp Gly Asp Phe Lys His Phe Met Lys Met His Glu
        115                 120                 125
Pro Val Thr Ala Ala Arg Thr Leu Leu Thr Ala Glu Asn Ala Thr Val
    130                 135                 140
Glu Ile Asp Arg Val Leu Ser Ala Leu Leu Lys Glu Arg Lys Pro Val
145                 150                 155                 160
Tyr Ile Asn Leu Pro Val Asp Val Ala Ala Ala Lys Ala Glu Lys Pro
                165                 170                 175
```

```
Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
            210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Lys Met Gly Lys Leu Phe Ala Glu
            530                 535                 540

Gln Asn Lys Ser
545

<210> SEQ ID NO 118
<211> LENGTH: 1125
<212> TYPE: DNA
<213> ORGANISM: artificial sequence
<220> FEATURE:
```

<223> OTHER INFORMATION: horse ADH coding region codon optimized for S. cerevisiae expression

<400> SEQUENCE: 118

```
atgtcaacag ccggtaaagt tattaagtgt aaagcggcag ttttgtggga agagaaaaag    60
ccgtttagca tagaagaagt agaagtagcg ccaccaaaag cacacgaggt tagaatcaag   120
atggttgcca ccggaatctg tagatccgac gaccatgtgg tgagtggcac tctagttact   180
cctttgccag taatcgcggg acacgaggct gccggaatcg ttgaatccat aggtgaaggt   240
gttaccactg ttcgtcctgg tgataaagtg atcccactgt tcactcctca atgtggtaag   300
tgtagagtct gcaaacatcc tgagggtaat ttctgcctta aaaatgattt gtctatgcct   360
agaggtacta tgcaggatgg tacaagcaga tttacatgca gagggaaacc tatacaccat   420
ttccttggta cttctacatt ttcccaatac acagtggtgg acgagatatc tgtcgctaaa   480
atcgatgcag cttcaccact ggaaaaagtt tgcttgatag ggtgcggatt ttccaccggt   540
tacggttccg cagttaaagt tgcaaaggtt acacagggtt cgacttgtgc agtattcggt   600
ttaggaggag taggactaag cgttattatg gggtgtaaag ctgcaggcgc agcgaggatt   660
ataggtgtag acatcaataa ggacaaattt gcaaaagcta aggaggtcgg ggctactgaa   720
tgtgttaacc ctcaagatta taagaaacca atacaagaag tccttactga aatgtcaaac   780
ggtggagttg atttctcttt tgaagttata ggccgtcttg atactatggt aactgcgttg   840
tcctgctgtc aagaggcata tggagtcagt gtgatcgtag gtgttcctcc tgattcacaa   900
aatttgtcga tgaatcctat gctgttgcta agcggtcgta catggaaggg agctatattt   960
ggcggtttta agagcaagga tagtgttcca aaacttgttg ccgactttat ggcgaagaag  1020
tttgctcttg atcctttaat tacacatgta ttgccattcg agaaaatcaa tgaagggttt  1080
gatttgttaa gaagtggtga atctattcgt acaattttaa ctttt             1125
```

<210> SEQ ID NO 119
<211> LENGTH: 375
<212> TYPE: PRT
<213> ORGANISM: Equus caballus

<400> SEQUENCE: 119

```
Met Ser Thr Ala Gly Lys Val Ile Lys Cys Lys Ala Ala Val Leu Trp
1               5                   10                  15

Glu Glu Lys Lys Pro Phe Ser Ile Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
```

```
            145                 150                 155                 160
Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Val Gly Leu Ser Val
        195                 200                 205

Ile Met Gly Cys Lys Ala Ala Gly Ala Ala Arg Ile Ile Gly Val Asp
210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
                260                 265                 270

Leu Asp Thr Met Val Thr Ala Leu Ser Cys Cys Gln Glu Ala Tyr Gly
            275                 280                 285

Val Ser Val Ile Val Gly Val Pro Pro Asp Ser Gln Asn Leu Ser Met
        290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
                340                 345                 350

Phe Glu Lys Ile Asn Glu Gly Phe Asp Leu Leu Arg Ser Gly Glu Ser
            355                 360                 365

Ile Arg Thr Ile Leu Thr Phe
        370                 375

<210> SEQ ID NO 120
<211> LENGTH: 643
<212> TYPE: DNA
<213> ORGANISM: Saccharomyces cerevisiae

<400> SEQUENCE: 120
gaaatgaata acaatactga cagtactaaa taattgccta cttggcttca catacgttgc       60
atacgtcgat atagataata atgataatga cagcaggatt atcgtaatac gtaatagttg      120
aaaatctcaa aaatgtgtgg gtcattacgt aaataatgat aggaatggga ttcttctatt      180 tttcctttt ccattctagc agccgtcggg aaaacgtggc atcctctctt tcgggctcaa       240
ttggagtcac gctgccgtga gcatcctctc tttccatatc taacaactga gcacgtaacc      300
aatggaaaag catgagctta gcgttgctcc aaaaaagtat tggatggtta ataccatttg      360
tctgttctct tctgactttg actcctcaaa aaaaaaaaat ctacaatcaa cagatcgctt      420
caattacgcc ctcacaaaaa cttttttcct tcttcttcgc ccacgttaaa ttttatccct      480
catgttgtct aacggatttc tgcacttgat ttattataaa aagacaaaga cataatactt      540
ctctatcaat ttcagttatt gttcttcctt gcgttattct tctgttcttc tttttctttt      600
gtcatatata accataacca agtaatacat attcaaatct aga                        643

<210> SEQ ID NO 121
<211> LENGTH: 9089
<212> TYPE: DNA
<213> ORGANISM: artificial sequence
```

<220> FEATURE:
<223> OTHER INFORMATION: constructed plasmid

<400> SEQUENCE: 121

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accataccac agcttttcaa ttcaattcat cattttttt ttattctttt ttttgatttc    240
ggtttctttg aaattttttt gattcggtaa tctccgaaca aaggaagaa cgaaggaagg    300
agcacagact tagattggta tatatacgca tatgtagtgt tgaagaaaca tgaaattgcc   360
cagtattctt aacccaactg cacagaacaa aaacctgcag gaaacgaaga taaatcatgt   420
cgaaagctac atataaggaa cgtgctgcta ctcatcctag tcctgttgct gccaagctat   480
ttaatatcat gcacgaaaag caaacaaact tgtgtgcttc attggatgtt cgtaccacca   540
aggaattact ggagttagtt gaagcattag gtcccaaaat ttgtttacta aaaacacatg   600
tggatatctt gactgatttt tccatggagg gcacagttaa gccgctaaag gcattatccg   660
ccaagtacaa tttttactc ttcgaagaca gaaaatttgc tgacattggt aatacagtca    720
aattgcagta ctctgcgggt gtatacagaa tagcagaatg gcagacatt acgaatgcac    780
acggtgtggt gggcccaggt attgttagcg gtttgaagca ggcggcagaa gaagtaacaa   840
aggaacctag aggcctttg atgttagcag aattgtcatg caagggctcc ctatctactg    900
gagaatatac taagggtact gttgacattg cgaagagcga caagattttt gttatcggct   960
ttattgctca aagagacatg ggtggaagag atgaaggtta cgattggttg attatgacac  1020
ccggtgtggg tttagatgac aagggagacg cattgggtca acagtataga accgtggatg  1080
atgtggtctc tacaggatct gacattatta ttgttggaag aggactattt gcaaagggaa  1140
gggatgctaa ggtagaggt gaacgttaca gaaaagcagg ctgggaagca tatttgagaa   1200
gatgcggcca gcaaaactaa aaaactgtat tataagtaaa tgcatgtata ctaaactcac  1260
aaattagagc ttcaatttaa ttatatcagt tattaccta tgcggtgtga aataccgcac    1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatgcccc actacgtgaa ccatcaccct aatcaagttt tttggggtcg aggtgccgta   1620
aagcactaaa tcggaaccct aaagggagcc ccgatttag agcttgacgg ggaaagccgg    1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggccccccct cgaggtcgac tggccattaa   2040
tctttcccat attagatttc gccaagccat gaaagttcaa gaaaggtctt tagacgaatt   2100
acccttcatt tctcaaactg gcgtcaaggg atcctgtat ggtttatcg ttttattct     2160
ggttcttata gcatcgtttt ggacttctct gttcccatta ggcggttcag gagccagcgc   2220
```

```
agaatcattc tttgaaggat acttatcctt tccaattttg attgtctgtt acgttggaca    2280
taaactgtat actagaaatt ggactttgat ggtgaaacta aagatatgg atcttgatac     2340
cggcagaaaa caagtagatt tgactcttcg tagggaagaa atgaggattg agcgagaaac    2400
attagcaaaa agatccttcg taacaagatt tttacatttc tggtgttgaa gggaaagata    2460
tgagctatac agcggaattt ccatatcact cagattttgt tatctaattt tttccttccc    2520
acgtccgcgg gaatctgtgt atattactgc atctagatat atgttatctt atcttggcgc    2580
gtacatttaa ttttcaacgt attctataag aaattgcggg agtttttttc atgtagatga    2640
tactgactgc acgcaaatat aggcatgatt tataggcatg atttgatggc tgtaccgata    2700
ggaacgctaa gagtaacttc agaatcgtta tcctggcgga aaaaattcat ttgtaaactt    2760
taaaaaaaaa agccaatatc cccaaaatta ttaagagcgc ctccattatt aactaaaatt    2820
tcactcagca tccacaatgt atcaggtatc tactacagat attacatgtg gcgaaaaga    2880
caagaacaat gcaatagcgc atcaagaaaa acacaaagc tttcaatcaa tgaatcgaaa     2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tctttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg gttttttacca tacccgggcc    3780
acccgtaccg cacaacaatt ttatggatgg atgtttgata atagcgtcta aacttttccat   3840
agttgggttc tttatagtag tgacaaggtt ttcaggtcca ccacagctaa ttatggcttt    3900
gtttatcatt tctactgcga aagcgacaca cttttttggcg catgggtgac cattaaatac    3960
aactgcattc cccgcagcta tcataccat agaattgcag ataacggttt ctgttggatt     4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt attttcggtga ttattttctc   4260
tctttgttcc tttgtgtagt gtagggaaag aatctttttgt gcatgtactg cagaagaaat   4320
ggcattctca acatttttcaa atactccaaa acatgaagag ttatctttgt aattctttaa   4380
gttgatgttt tcaccattag tcttcacttt caagtctttg gtggttggga ttaaggtatc    4440
tttatccatg gtgtttgttt atgtgtgtttt attcgaaact aagttcttgg tgttttaaaa   4500
ctaaaaaaaa gactaactat aaaagtagaa tttaagaagt ttaagaaata gatttacaga    4560
attacaatca ataccaccg tctttatata cttattagtc aagtagggga ataatttcag     4620
```

```
ggaactggtt tcaaccttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt ttttgcctg tttgtgcccc    4800
tgttctctgt agttgcgcta agagaatgga cctatgaact gatggttggt gaagaaaaca    4860
atattttggt gctgggattc ttttttttc tggatgccag cttaaaaagc gggctccatt    4920
atatttagtg gatgccagga ataaactgtt cacccagaca cctacgatgt tatatattct    4980
gtgtaacccg cccctattt tgggcatgta cgggttacag cagaattaaa aggctaattt    5040
tttgactaaa taaagttagg aaaatcacta ctattaatta tttacgtatt ctttgaaatg    5100
gcagtattga taatgataaa ctcgaactga aaaagcgtgt ttttattca aaatgattct    5160
aactccctta cgtaatcaag gaatcttttt gccttggcct ccgcgtcatt aaacttcttg    5220
ttgttgacgc taacattcaa cgctagtata tattcgtttt tttcaggtaa gttctttca    5280
acgggtctta ctgatgaggc agtcgcgtct gaacctgtta agaggtcaaa tatgtcttct    5340
tgaccgtacg tgtcttgcat gttattagct ttgggaattt gcatcaagtc ataggaaaat    5400
ttaaatcttg gctctcttgg gctcaaggtg acaaggtcct cgaaaatagg gcgcgcccca    5460
ccgcggtgga gctccagctt ttgttccctt tagtgagggt taattgcgcg cttggcgtaa    5520
tcatggtcat agctgtttcc tgtgtgaaat tgttatccgc tcacaattcc acacaacata    5580
ggagccggaa gcataaagtg taaagcctgg ggtgcctaat gagtgaggta actcacatta    5640
attgcgttgc gctcactgcc cgctttccag tcgggaaacc tgtcgtgcca gctgcattaa    5700
tgaatcggcc aacgcgcggg gagaggcggt ttgcgtattg ggcgctcttc cgcttcctcg    5760
ctcactgact cgctgcgctc ggtcgttcgg ctgcggcgag cggtatcagc tcactcaaag    5820
gcggtaatac ggttatccac agaatcaggg gataacgcag gaaagaacat gtgagcaaaa    5880
ggccagcaaa aggccaggaa ccgtaaaaag gccgcgttgc tggcgttttt ccataggctc    5940
cgcccccctg acgagcatca aaaaatcga cgctcaagtc agaggtggcg aaacccgaca    6000
ggactataaa gataccaggc gtttccccct ggaagctccc tcgtgcgctc tcctgttccg    6060
accctgccgc ttaccggata cctgtccgcc tttctccctt cgggaagcgt ggcgctttct    6120
catagctcac gctgtaggta tctcagttcg gtgtaggtcg ttcgctccaa gctgggctgt    6180
gtgcacgaac cccccgttca gcccgaccgc tgcgccttat ccggtaacta tcgtcttgag    6240
tccaacccgg taagacacga cttatcgcca ctggcagcag ccactggtaa caggattagc    6300
agagcgaggt atgtaggcgg tgctacagag ttcttgaagt ggtggcctaa ctacggctac    6360
actagaagga cagtatttgg tatctgcgct ctgctgaagc cagttacctt cggaaaaaga    6420
gttggtagct cttgatccgg caaacaaacc accgctggta gcggtggttt ttttgtttgc    6480
aagcagcaga ttacgcgcag aaaaaaagga tctcaagaag atcctttgat cttttctacg    6540
gggtctgacg ctcagtggaa cgaaaactca cgttaaggga ttttggtcat gagattatca    6600
aaaaggatct tcacctagat ccttttaaat taaaaatgaa gttttaaatc aatctaaagt    6660
atatatgagt aaacttggtc tgacagttac caatgcttaa tcagtgaggc acctatctca    6720
gcgatctgtc tatttcgttc atccatagtt gcctgactcc ccgtcgtgta gataactacg    6780
atacgggagg gcttaccatc tggccccagt gctgcaatga taccgcgaga cccacgctca    6840
ccggctccag atttatcagc aataaaccag ccagccggaa gggccgagcg cagaagtggt    6900
cctgcaactt tatccgcctc catccagtct attaattgtt gccgggaagc tagagtaagt    6960
```

-continued

```
agttcgccag ttaatagttt gcgcaacgtt gttgccattg ctacaggcat cgtggtgtca    7020
cgctcgtcgt ttggtatggc ttcattcagc tccggttccc aacgatcaag gcgagttaca    7080
tgatccccca tgttgtgcaa aaaagcggtt agctccttcg gtcctccgat cgttgtcaga    7140
agtaagttgg ccgcagtgtt atcactcatg gttatggcag cactgcataa ttctcttact    7200
gtcatgccat ccgtaagatg cttttctgtg actggtgagt actcaaccaa gtcattctga    7260
gaatagtgta tgcggcgacc gagttgctct tgcccggcgt caatacggga taataccgcg    7320
ccacatagca gaactttaaa agtgctcatc attggaaaac gttcttcggg gcgaaaactc    7380
tcaaggatct taccgctgtt gagatccagt tcgatgtaac ccactcgtgc acccaactga    7440
tcttcagcat cttttacttt caccagcgtt tctgggtgag caaaaacagg aaggcaaaat    7500
gccgcaaaaa agggaataag ggcgacacgg aaatgttgaa tactcatact cttccttttt    7560
caatattatt gaagcattta tcagggttat tgtctcatga gcggatacat atttgaatgt    7620
atttagaaaa ataaacaaat aggggttccg cgcacatttc cccgaaaagt gccacctgaa    7680
cgaagcatct gtgcttcatt tgtagaaca aaaatgcaac gcgagagcgc taattttca    7740 aacaaagaat ctgagctgca tttttacaga acagaaatgc aacgcgaaag cgctatttta    7800
ccaacgaaga atctgtgctt catttttgta aaacaaaaat gcaacgcgag agcgctaatt    7860
tttcaaacaa gaatctgagc tgcatttttt acagaacaga aatgcaacgc gagagcgcta    7920
ttttaccaac aaagaatcta tacttctttt ttgttctaca aaaatgcatc ccgagagcgc    7980
tattttccta caaagcatc ttagattact tttttctcc tttgtgcgct ctataatgca    8040
gtctcttgat aactttttgc actgtaggtc cgttaaggtt agaagaaggc tactttggtg    8100
tctatttctc cttccataaa aaaagcctga ctccacttcc cgcgtttact gattactagc    8160
gaagctgcgg gtgcattttt tcaagataaa ggcatccccg attatattct ataccgatgt    8220
ggattgcgca tactttgtga acagaaagtg atagcgttga tgattcttca ttggtcagaa    8280
aattatgaac ggtttcttct attttgtctc tatatactac gtataggaaa tgtttacatt    8340
ttcgtattgt tttcgattca ctctatgaat agttcttact acaattttt tgtctaaaga    8400 gtaatactag agataaacat aaaaaatgta gaggtcgagt ttagatgcaa gttcaaggag    8460
cgaaaggtgg atgggtaggt tatataggga tatagcacag agatatatag caaagagata    8520
cttttgagca atgtttgtgg aagcggtatt cgcaatattt tagtagctcg ttacagtccg    8580
gtgcgttttt ggttttttga aagtgcgtct tcagagcgct tttggttttc aaaagcgctc    8640
tgaagttcct atactttcta gagaatagga acttcggaat aggaacttca aagcgtttcc    8700
gaaaacgagc gcttccgaaa atgcaacgcg agctgcgcac atacagctca ctgttcacgt    8760
cgcacctata tctgcgtgtt gcctgtatat atatatacat gagaagaacg gcatagtgcg    8820
tgtttatgct taaatgcgta cttatatgcg tctatttatg taggatgaaa ggtagtctag    8880
tacctcctgt gatattatcc cattccatgc ggggtatcgt atgcttcctt cagcactacc    8940
ctttagctgt tctatatgct gccactcctc aattggatta gtctcatcct tcaatgctat    9000
catttccttt gatattggat catactaaga aaccattatt atcatgacat aacctataa    9060 aaataggcgt atcacgaggc cctttcgtc                                     9089
```

<210> SEQ ID NO 122
<211> LENGTH: 1023
<212> TYPE: DNA
<213> ORGANISM: Saccharomyces cerevisiae

<400> SEQUENCE: 122

```
caccgcggtg gggcgcgccc tattttcgag gaccttgtca ccttgagccc aagagagcca    60
agatttaaat tttcctatga cttgatgcaa attcccaaag ctaataacat gcaagacacg   120
tacggtcaag aagacatatt tgacctctta acaggttcag acgcgactgc ctcatcagta   180
agacccgttg aaaagaactt acctgaaaaa acgaatata  tactagcgtt gaatgttagc   240
gtcaacaaca agaagtttaa tgacgcggag gccaaggcaa aaagattcct tgattacgta   300
agggagttag aatcattttg aataaaaaac acgcttttc  agttcgagtt tatcattatc   360
aatactgcca tttcaaagaa tacgtaaata attaatagta gtgattttcc taactttatt   420
tagtcaaaaa attagccttt taattctgct gtaacccgta catgcccaaa ataggggcg    480
ggttacacag aatatataac atcgtaggtg tctgggtgaa cagtttattc ctggcatcca   540
ctaaatataa tggagcccgc tttttaagct ggcatccaga aaaaaaaga  atcccagcac   600
caaaatattg ttttcttcac caaccatcag ttcataggtc cattctctta gcgcaactac   660
agagaacagg ggcacaaaca ggcaaaaaac gggcacaacc tcaatggagt gatgcaacct   720
gcctggagta aatgatgaca caaggcaatt gacccacgca tgtatctatc tcattttctt   780
acaccttcta ttaccttctg ctctctctga tttggaaaaa gctgaaaaaa aaggttgaaa   840
ccagttccct gaaattattc ccctacttga ctaataagta tataaagacg gtaggtattg   900
attgtaattc tgtaaatcta tttcttaaac ttcttaaatt ctactttat  agttagtctt   960
tttttagtt  ttaaaacacc aagaacttag tttcgaataa acacacataa actagtaaac  1020
aaa                                                                1023

<210> SEQ ID NO 123
<211> LENGTH: 21
<212> TYPE: DNA
<213> ORGANISM: artificial sequence
<220> FEATURE:
<223> OTHER INFORMATION: primer

<400> SEQUENCE: 123
caaaagctga gctccaccgc g                                              21

<210> SEQ ID NO 124
<211> LENGTH: 44
<212> TYPE: DNA
<213> ORGANISM: artificial sequence
<220> FEATURE:
<223> OTHER INFORMATION: primer

<400> SEQUENCE: 124
gtttactagt ttatgtgtgt ttattcgaaa ctaagttctt ggtg                     44

<210> SEQ ID NO 125

<400> SEQUENCE: 125

000

<210> SEQ ID NO 126
<211> LENGTH: 39
<212> TYPE: DNA
<213> ORGANISM: artificial sequence
<220> FEATURE:
<223> OTHER INFORMATION: primer

<400> SEQUENCE: 126
cacacatatt acaatagcta gctgaggatg aaagctctg                           39
```

<210> SEQ ID NO 127
<211> LENGTH: 39
<212> TYPE: DNA
<213> ORGANISM: artificial sequence
<220> FEATURE:
<223> OTHER INFORMATION: primer

<400> SEQUENCE: 127

| | |
|---|---|
| cagagctttc atcctcagct agctattgta atatgtgtg | 39 |

<210> SEQ ID NO 128
<211> LENGTH: 9491
<212> TYPE: DNA
<213> ORGANISM: artificial sequence
<220> FEATURE:
<223> OTHER INFORMATION: constructed plasmid

<400> SEQUENCE: 128

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tcttttttcta | 300 |
| ttactcttgg cctcctctag tacactctat attttttttat gcctcggtaa tgattttcat | 360 |
| tttttttttt cccctagcgg atgactcttt ttttttctta gcgattggca ttatcacata | 420 |
| atgaattata cattatataa agtaatgtga tttcttcgaa gaatatacta aaaaatgagc | 480 |
| aggcaagata aacgaaggca aagatgacag agcagaaagc cctagtaaag cgtattacaa | 540 |
| atgaaaccaa gattcagatt gcgatctctt taaagggtgg tcccctagcg atagagcact | 600 |
| cgatcttccc agaaaaagag gcagaagcag tagcagaaca ggccacacaa tcgcaagtga | 660 |
| ttaacgtcca cacaggtata gggtttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag cttttaaaga ggccctactg gcgcgtggag | 840 |
| taaaaaggtt tggatcagga tttgcgcctt ggatgaggc actttccaga gcggtggtag | 900 |
| atctttcgaa caggccgtac gcagttgtcg aacttggttt gcaaagggag aaagtaggag | 960 |
| atctctcttg cgagatgatc ccgcattttc ttgaaagctt tgcagaggct agcagaatta | 1020 |
| ccctccacgt tgattgtctg cgaggcaaga atgatcatca ccgtagtgag agtgcgttca | 1080 |
| aggctcttgc ggttgccata agagaagcca cctcgcccaa tggtaccaac gatgttccct | 1140 |
| ccaccaaagg tgttcttatg tagtgacacc gattatttaa agctgcagca tacgatatat | 1200 |
| atacatgtgt atatatgtat acctatgaat gtcagtaagt atgtatacga acagtatgat | 1260 |
| actgaagatg acaaggtaat gcatcattct atacgtgtca ttctgaacga ggcgcgcttt | 1320 |
| ccttttttct ttttgctttt tcttttttttt tctcttgaac tcgacggatc tatgcggtgt | 1380 |
| gaaataccgc acagatgcgt aaggagaaaa taccgcatca ggaaattgta aacgttaata | 1440 |
| ttttgttaaa attcgcgtta aatttttgtt aaatcagctc atttttttaac caataggccg | 1500 |
| aaatcggcaa aatcccttat aaatcaaaag aatagaccga gatagggttg agtgttgttc | 1560 |
| cagtttggaa caagagtcca ctattaaaga acgtggactc caacgtcaaa gggcgaaaaa | 1620 |
| ccgtctatca gggcgatggc ccactacgtg aaccatcacc ctaatcaagt ttttggggt | 1680 |

```
cgaggtgccg taaagcacta atcggaacc ctaaagggag ccccccgattt agagcttgac    1740 ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
gatcggtgcg ggcctcttcg ctattacgcc agctggcgaa aggggggatgt gctgcaaggc    1980 gattaagttg ggtaacgcca gggttttccc agtcacgacg ttgtaaaacg acggccagtg    2040
agcgcgcgta atacgactca ctatagggcg aattgggtac cgggccccc ctcgaggtcg    2100 acggcgcgcc actggtagag agcgactttg tatgccccaa ttgcgaaacc cgcgatatcc    2160
ttctcgattc tttagtaccc gaccaggaca aggaaaagga ggtcgaaacg ttttttgaaga    2220 aacaagagga actacacgga agctctaaag atggcaacca gccagaaact aagaaaatga    2280
agttgatgga tccaactggc accgctggct tgaacaacaa taccagcctt ccaacttctg    2340
taaataacgg cggtacgcca gtgccaccag taccgttacc tttcggtata cctccttttcc    2400 ccatgttttcc aatgcccttc atgcctccaa cggctactat cacaaatcct catcaagctg    2460
acgcaagccc taagaaatga ataacaaatac tgacagtact aaataattgc ctacttggct    2520
tcacatacgt tgcatacgtc gatatagata ataatgataa tgacagcagg attatcgtaa    2580
tacgtaatag ttgaaaatct caaaaatgtg tgggtcatta cgtaaataat gataggaatg    2640
ggattcttct atttttcctt tttccattct agcagccgtc gggaaaacgt ggcatcctct    2700
ctttcgggct caattggagt cacgctgccg tgagcatcct ctctttccat atctaacaac    2760
tgagcacgta accaatggaa aagcatgagc ttagcgttgc tccaaaaaag tattggatgg    2820
ttaataccat ttgtctgttc tcttctgact ttgactcctc aaaaaaaaaa aatctacaat    2880
caacagatcg cttcaattac gccctcacaa aaacttttttt ccttcttctt cgcccacgtt    2940 aaatttatc cctcatgttg tctaacggat ttctgcactt gatttattat aaaaagacaa    3000
agacataata cttctctatc aatttcagtt attgttcttc cttgcgttat tcttctgttc    3060
ttctttttct tttgtcatat ataaccataa ccaagtaata catattcaaa ctagtatgac    3120
tgacaaaaaa actcttaaag acttaagaaa tcgtagttct gtttacgatt caatggttaa    3180
atcacctaat cgtgctatgt tgcgtgcaac tggtatgcaa gatgaagact ttgaaaaacc    3240
tatcgtcggt gtcatttcaa cttgggctga aaacacacct tgtaatatcc acttacatga    3300
ctttggtaaa ctagccaaag tcggtgttaa ggaagctggt gcttggccag ttcagttcgg    3360
aacaatcacg gttctgatg gaatcgccat gggaacccaa ggaatgcgtt tctccttgac    3420
atctcgtgat attattgcag attctattga agcagccatg ggaggtcata atgcggatgc    3480
ttttgtagcc attggcggtt gtgataaaaa catgcccgt tctgttatcg ctatggctaa    3540
catggatatc ccagccattt tgcttacgg cggaacaatt gcacctggta atttagacgg    3600
caaagatatc gatttagtct ctgtctttga aggtgtcggc cattggaacc acggcgatat    3660
gaccaaagaa gaagttaaag ctttggaatg taatgcttgt cccggtcctg gaggctgcgg    3720
tggtatgtat actgctaaca caatggcgac agctattgaa gttttgggac ttagccttcc    3780
gggttcatct tctcacccgg ctgaatccgc agaaaagaaa gcagatattg aagaagctgg    3840
tcgcgctgtt gtcaaaatgc tcgaaatggg cttaaaacct tctgacattt taacgcgtga    3900
agcttttgaa gatgctatta ctgtaactat ggctctggga ggttcaacca actcaaccct    3960
tcacctctta gctattgccc atgctgctaa tgtggaattg acacttgatg atttcaatac    4020
tttccaagaa aaagttcctc atttggctga tttgaaacct tctggtcaat atgtattcca    4080
```

```
agacctttac aaggtcggag gggtaccagc agttatgaaa tatctcctta aaaatggctt    4140
ccttcatggt gaccgtatca cttgtactgg caaaacagtc gctgaaaatt tgaaggcttt    4200
tgatgattta acacctggtc aaaaggttat tatgccgctt gaaatcccta aacgtgaaga    4260
tggtccgctc attattctcc atggtaactt ggctccagac ggtgccgttg ccaaagtttc    4320
tggtgtaaaa gtgcgtcgtc atgtcggtcc tgctaaggtc tttaattctg aagaagaagc    4380
cattgaagct gtcttgaatg atgatattgt tgatggtgat gttgttgtcg tacgttttgt    4440
aggaccaaag ggcggtcctg gtatgcctga aatgcttttc ctttcatcaa tgattgttgg    4500
taaagggcaa ggtgaaaaag ttgcccttct gacagatggc cgcttctcag gtggtactta    4560
tggtcttgtc gtgggtcata tcgctcctga agcacaagat ggcggtccaa tcgcctacct    4620
gcaaacagga gacatagtca ctattgacca agacactaag gaattacact ttgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagtttttt aatgagtatt gaatctgttt agaaataatg    4920
gaatattatt tttatttatt tatttatatt attggtcggc tcttttcttc tgaaggtcaa    4980
tgacaaaatg atatgaagga ataatgatt tctaaaattt tacaacgtaa gatatttta     5040
caaaagccta gctcatcttt tgtcatgcac tattttactc acgcttgaaa ttaacggcca    5100
gtccactgcg gagtcatttc aaagtcatcc taatcgatct atcgttttg atagctcatt     5160
ttggagttcg cgattgtctt ctgttattca aactgtttt aattttatt tcattctgga     5220
actcttcgag ttctttgtaa agtctttcat agtagcttac tttatcctcc aacatattta    5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgtttttgtt ctcccatcac aatttaatat acctgatgga    5520
ttcttatgaa gcgctgggta atggacgtgt cactctactt cgccttttc cctactcctt    5580
ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaatata ttagaagtct atacgttaaa ccaccgcggt ggagctccag    5880
cttttgttcc ctttagtgag ggttaattgc gcgcttggcg taatcatggt catagctgtt    5940
tcctgtgtga attgttatc cgctcacaat tccacacaac ataggagccg aagcataaa      6000
gtgtaaagcc tggggtgcct aatgagtgag gtaactcaca ttaattgcgt tgcgctcact    6060
gcccgctttc cagtcgggaa acctgtcgtg ccagctgcat taatgaatcg gccaacgcgc    6120
ggggagaggc ggtttgcgta ttgggcgctc ttccgcttcc tcgctcactg actcgctgcg    6180
ctcggtcgtt cggctgcggc gagcggtatc agctcactca aaggcggtaa tacgttatc     6240
cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
```

```
ggcgtttccc cctggaagct ccctcgtgcg ctctcctgtt ccgaccctgc cgcttaccgg   6480
atacctgtcc gcctttctcc cttcgggaag cgtggcgctt tctcatagct cacgctgtag   6540
gtatctcagt tcggtgtagg tcgttcgctc caagctgggc tgtgtgcacg aaccccccgt   6600
tcagcccgac cgctgcgcct tatccggtaa ctatcgtctt gagtccaacc cggtaagaca   6660
cgacttatcg ccactggcag cagccactgg taacaggatt agcagagcga ggtatgtagg   6720
cggtgctaca gagttcttga agtggtggcc taactacggc tacactagaa ggacagtatt   6780
tggtatctgc gctctgctga agccagttac cttcggaaaa agagttggta gctcttgatc   6840
cggcaaacaa accaccgctg gtagcggtgg ttttttttgtt gcaagcagc agattacgcg   6900 cagaaaaaaa ggatctcaag aagatccttt gatcttttct acggggtctg acgctcagtg   6960
gaacgaaaac tcacgttaag ggattttggt catgagatta tcaaaaagga tcttcaccta   7020
gatcctttta aattaaaaat gaagttttaa atcaatctaa agtatatatg agtaaacttg   7080
gtctgacagt taccaatgct taatcagtga ggcacctatc tcagcgatct gtctatttcg   7140
ttcatccata gttgcctgac tccccgtcgt gtagataact acgatacggg agggcttacc   7200
atctggcccc agtgctgcaa tgataccgcg agacccacgc tcaccggctc cagatttatc   7260
agcaataaac cagccagccg aagggccgag cgcagaagt ggtcctgcaa ctttatccgc   7320
ctccatccag tctattaatt gttgccggga agctagagta agtagttcgc cagttaatag   7380
tttgcgcaac gttgttgcca ttgctacagg catcgtggtg tcacgctcgt cgtttggtat   7440
ggcttcattc agctccggtt cccaacgatc aaggcgagtt acatgatccc ccatgttgtg   7500
caaaaaagcg gttagctcct tcggtcctcc gatcgttgtc agaagtaagt tggccgcagt   7560
gttatcactc atggttatgg cagcactgca taattctctt actgtcatgc catccgtaag   7620
atgcttttct gtgactggtg agtactcaac caagtcattc tgagaatagt gtatgcggcg   7680
accgagttgc tcttgcccgg cgtcaatacg ggataatacc gcgccacata gcagaacttt   7740
aaaagtgctc atcattggaa aacgttcttc ggggcgaaaa ctctcaagga tcttaccgct   7800
gttgagatcc agttcgatgt aacccactcg tgcacccaac tgatcttcag catctttta c   7860 tttcaccagc gtttctgggt gagcaaaaac aggaaggcaa aatgccgcaa aaaagggaat   7920
aagggcgaca cggaaatgtt gaatactcat actcttcctt tttcaatatt attgaagcat   7980
ttatcagggt tattgtctca tgagcggata catatttgaa tgtatttaga aaataaaca   8040 aataggggtt ccgcgcacat ttccccgaaa agtgccacct gaacgaagca tctgtgcttc   8100
attttgtaga acaaaaatgc aacgcgagag cgctaatttt tcaaacaaag aatctgagct   8160
gcatttttac agaacagaaa tgcaacgcga aagcgctatt ttaccaacga agaatctgtg   8220
cttcattttt gtaaaacaaa aatgcaacgc gagagcgcta attttcaaa caagaatct   8280 gagctgcatt tttacagaac agaaatgcaa cgcgagagcg ctattttacc aacaaagaat   8340
ctatacttct tttttgttct acaaaaatgc atcccgagag cgctattttt ctaacaaagc   8400
atcttagatt acttttttc tcctttgtgc gctctataat gcagtctctt gataactttt   8460
tgcactgtag gtccgttaag gttagaagaa ggctactttg gtgtctattt tctcttccat   8520
aaaaaaagcc tgactccact tcccgcgttt actgattact agcgaagctg cgggtgcatt   8580
ttttcaagat aaaggcatcc ccgattatat tctataccga tgtggattgc gcatactttg   8640
tgaacagaaa gtgatagcgt tgatgattct tcattggtca gaaaattatg aacggtttct   8700 tctatttgt ctctatatac tacgtatagg aaatgtttac attttcgtat tgttttcgat   8760
tcactctatg aatagttctt actacaattt ttttgtctaa agagtaatac tagagataaa   8820
```

```
cataaaaaat gtagaggtcg agtttagatg caagttcaag gagcgaaagg tggatgggta    8880
ggttatatag ggatatagca cagagatata tagcaaagag atactttga gcaatgtttg    8940 tggaagcggt attcgcaata ttttagtagc tcgttacagt ccggtgcgtt tttggttttt    9000
tgaaagtgcg tcttcagagc gcttttggtt ttcaaaagcg ctctgaagtt cctatacttt    9060
ctagagaata ggaacttcgg aataggaact tcaaagcgtt tccgaaaacg agcgcttccg    9120
aaaatgcaac gcgagctgcg cacatacagc tcactgttca cgtcgcacct atatctgcgt    9180
gttgcctgta tatatatata catgagaaga acggcatagt gcgtgtttat gcttaaatgc    9240
gtacttatat gcgtctattt atgtaggatg aaaggtagtc tagtacctcc tgtgatatta    9300
tcccattcca tgcggggtat cgtatgcttc cttcagcact acccttagc tgttctatat    9360 gctgccactc ctcaattgga ttagtctcat ccttcaatgc tatcatttcc tttgatattg    9420
gatcatctaa gaaaccatta ttatcatgac attaacctat aaaaataggc gtatcacgag    9480
gccctttcgt c                                                         9491

<210> SEQ ID NO 129
<211> LENGTH: 1000
<212> TYPE: DNA
<213> ORGANISM: Saccharymoces cerevisiae

<400> SEQUENCE: 129
gttaattcaa attaattgat atagttttt aatgagtatt gaatctgttt agaaataatg      60
gaatattatt tttatttatt tatttatatt attggtcggc tcttttcttc tgaaggtcaa    120
tgacaaaatg atatgaagga ataatgatt tctaaaattt tacaacgtaa gatattttta    180
caaaagccta gctcatcttt tgtcatgcac tattttactc acgcttgaaa ttaacggcca    240
gtccactgcg gagtcatttc aaagtcatcc taatcgatct atcgtttttg atagctcatt    300
ttggagttcg cgattgtctt ctgttattca caactgtttt aatttttatt tcattctgga    360
actcttcgag ttctttgtaa agtctttcat agtagcttac tttatcctcc aacatatttg    420
acttcatgtc aatttcggct cttaaatttt ccacatcatc aagttcaaca tcatctttta    480
acttgaattt attctctagc tcttccaacc aagcctcatt gctccttgat ttactggtga    540
aaagtgatac actttgcgcg caatccaggt caaaactttc ctgcaaagaa ttcaccaatt    600
tctcgacatc atagtacaat ttgttttgtt ctcccatcac aatttaatat acctgatgga    660
ttcttatgaa gcgctgggta atggacgtgt cactctactt cgccttttc cctactcctt    720 ttagtacgga agacaatgct aataaataag agggtaataa taatattatt aatcggcaaa    780
aaagattaaa cgccaagcgt ttaattatca gaaagcaaac gtcgtaccaa tccttgaatg    840
cttcccaatt gtatattaag agtcatcaca gcaacatatt cttgttatta aattaattat    900
tattgatttt tgatattgta taaaaaaacc aaatatgtat aaaaaaagtg aataaaaaat    960
accaagtatg gagaaatata ttagaagtct atacgttaaa                         1000

<210> SEQ ID NO 130
<211> LENGTH: 16387
<212> TYPE: DNA
<213> ORGANISM: Artificial sequence
<220> FEATURE:
<223> OTHER INFORMATION: Plasmid

<400> SEQUENCE: 130
gatcctctag tttctcggta ctatgcatat gatccaatat caaaggaaat gatagcattg     60
```

-continued

```
aaggatgaga ctaatccaat tgaggagtgg cagcatatag aacagctaaa gggtagtgct    120
gaaggaagca tacgataccc cgcatggaat gggataatat cacaggaggt actagactac    180
ctttcatcct acataaatag acgcatataa gtacgcattt aagcataaac acgcactatg    240
ccgttcttct catgtatata tatatacagg caacacgcag ataggtgc gacgtgaaca      300 gtgagctgta tgtgcgcagc tcgcgttgca ttttcggaag cgctcgtttt cggaaacgct    360
ttgaagttcc tattccgaag ttcctattct ctagaaagta taggaacttc agagcgcttt    420
tgaaaaccaa aagcgctctg aagacgcact ttcaaaaaac caaaaacgca ccggactgta    480
acgagctact aaaatattgc gaataccgct tccacaaaca ttgctcaaaa gtatctcttt    540
gctatatatc tctgtgctat atccctatat aacctaccca tccacctttc gctccttgaa    600
cttgcatcta aactcgacct ctacatttt tatgtttatc tctagtatta ctctttagac     660
aaaaaaattg tagtaagaac tattcataga gtgaatcgaa aacaatacga aaatgtaaac    720
atttcctata cgtagtatat agagacaaaa tagaagaaac cgttcataat tttctgacca    780
atgaagaatc atcaacgcta tcactttctg ttcacaaagt atgcgcaatc cacatcggta    840
tagaatataa tcggggatgc ctttatcttg aaaaaatgca cccgcagctt cgctagtaat    900
cagtaaacgc gggaagtgga gtcaggcttt ttttatggaa gagaaaatag acaccaaagt    960
agccttcttc taaccttaac ggacctacag tgcaaaaagt tatcaagaga ctgcattata    1020
gagcgcacaa aggagaaaaa aagtaatcta agatgctttg ttagaaaaat agcgctctcg    1080
ggatgcattt ttgtagaaca aaaagaagt atagattctt tgttggtaaa atagcgctct     1140
cgcgttgcat ttctgttctg taaaaatgca gctcagattc tttgtttgaa aaattagcgc    1200
tctcgcgttg catttttgtt ttacaaaaat gaagcacaga ttcttcgttg gtaaaatagc    1260
gctttcgcgt tgcatttctg ttctgtaaaa atgcagctca gattctttgt ttgaaaaatt    1320
agcgctctcg cgttgcattt ttgttctaca aaatgaagca cagatgcttc gttaacaaag    1380
atatgctatt gaagtgcaag atggaaacgc agaaaatgaa ccggggatgc gacgtgcaag    1440
attacctatg caatagatgc aatagttttct ccaggaaccg aaatacatac attgtcttcc    1500
gtaaagcgct agactatata ttattataca ggttcaaata tactatctgt ttcagggaaa    1560
actcccaggt tcggatgttc aaaattcaat gatgggtaac aagtacgatc gtaaatctgt    1620
aaaacagttt gtcggatatt aggctgtatc tcctcaaagc gtattcgaat atcattgaga    1680
agctgcattt tttttttttt tttttttttt tttttttata tatatttcaa ggatatacca    1740
ttgtaatgtc tgcccctaag aagatcgtcg ttttgccagg tgaccacgtt ggtcaagaaa    1800
tcacagccga agccattaag gttcttaaag ctatttctga tgttcgttcc aatgtcaagt    1860
tcgatttcga aaatcattta attggtggtg ctgctatcga tgctacaggt gttccacttc    1920
cagatgaggc gctggaagcc tccaagaagg ctgatgccgt tttgttaggt gctgtgggtg    1980
gtcctaaatg gggtaccggt agtgttagac ctgaacaagg tttactaaaa atccgtaaag    2040
aacttcaatt gtacgccaac ttaagaccat gtaactttgc atccgactct cttttagact    2100
tatctccaat caagccacaa tttgctaaag gtactgactt cgttgttgtt agagaattag    2160
tgggaggtat ttactttggt aagagaaagg aagacgatgg tgatggtgtc gcttgggata    2220
gtgaacaata caccgttcca gaagtgcaaa gaatcacaag aatggccgct ttcatggccc    2280
tacaacatga gccaccattg cctatttggt ccttggataa agctaatgtt ttggcctctt    2340
caagattatg gagaaaaact gtggaggaaa ccatcaagaa cgaattccct acattgaaag    2400
ttcaacatca attgattgat tctgccgcca tgatcctagt taagaaccca acccacctaa    2460
```

```
atggtattat aatcaccagc aacatgtttg gtgatatcat ctccgatgaa gcctccgtta   2520
tcccaggctc cttgggtttg ttgccatctg cgtccttggc ctctttgcca gacaagaaca   2580
ccgcatttgg tttgtacgaa ccatgccatg gttccgctcc agatttgcca aagaataagg   2640
tcaaccctat cgccactatc ttgtctgctg caatgatgtt gaaattgtca ttgaacttgc   2700
ctgaagaagg taaagccatt gaagatgcag ttaaaaaggt tttggatgca ggtatcagaa   2760
ctggtgattt aggtggttcc aacagtacca ccgaagtcgg tgatgctgtc gccgaagaag   2820
ttaagaaaat ccttgcttaa aaagattctc tttttttatg atatttgtac aaaaaaaaa   2880
aaaaaaaaaa aaaaaaaaaa aaaaaaaaa aaaaaaaaaa aatgcagcgt cacatcggat   2940
aataatgatg gcagccattg tagaagtgcc ttttgcattt ctagtctctt tctcggtcta   3000
gctagtttta ctacatcgcg aagatagaat cttagatcac actgcctttg ctgagctgga   3060
tcaatagagt aacaaaagag tggtaaggcc tcgttaaagg acaaggacct gagcggaagt   3120
gtatcgtaca gtagacggag tatactagag tcgacctgca ggcatgcaag cttttcaatt   3180
catcattttt tttttattct tttttttgat ttcggtttcc ttgaaatttt tttgattcgg   3240
taatctccga acagaaggaa gaacgaagga aggagcacag acttagattg gtatatatac   3300
gcatatgtag tgttgaagaa acatgaaatt gcccagtatt cttaacccaa ctgcacagaa   3360
caaaaacctg caggaaacga agataaatca tgtcgaaagc tacatataag gaacgtgctg   3420
ctactcatcc tagtcctgtt gctgccaagc tatttaatat catgcacgaa aagcaaacaa   3480
acttgtgtgc ttcattggat gttcgtacca ccaaggaatt actggagtta gttgaagcat   3540
taggtcccaa aatttgttta ctaaaaacac atgtggatat cttgactgat ttttccatgg   3600
agggcacagt taagccgcta aaggcattat ccgccaagta caatttttta ctcttcgaag   3660
acagaaaatt tgctgacatt ggtaatacag tcaaattgca gtactctgcg ggtgtataca   3720
gaatagcaga atgggcagac attacgaatg cacacggtgt ggtgggccca ggtattgtta   3780
gcggtttgaa gcaggcggca gaagaagtaa caaaggaacc tagaggcctt ttgatgttag   3840
cagaattgtc atgcaagggc tccctatcta ctggagaata tactaagggt actgttgaca   3900
ttgcgaagag cgacaaagat tttgttatcg gctttattgc tcaaagagac atgggtggaa   3960
gagatgaagg ttacgattgg ttgattatga caccccggtgt gggtttagat gacaagggag   4020
acgcattggg tcaacagtat agaaccgtgg atgatgtggg ctctacagga tctgacatta   4080
ttattgttgg aagaggacta tttgcaaagg gaagggatgc taaggtagag ggtgaacgtt   4140
acagaaaagc aggctgggaa gcatatttga aagatgcgg ccagcaaaac taaaaaactg   4200
tattataagt aaatgcatgt atactaaact cacaaattag agcttcaatt taattatatc   4260
agttattacc cgggaatctc ggtcgtaatg attttttataa tgacgaaaaa aaaaaaattg   4320
gaaagaaaaa gcttggcgta atcatggtca tagctgtttc ctgtgtgaaa ttgttatccg   4380
ctcacaattc cacacaacat acgagccgga agcataaagt gtaaagcctg gggtgcctaa   4440
tgagtgagct aactcacatt aattgcgttg cgctcactgc ccgctttcca gtcgggaaac   4500
ctgtcgtgcc agctgcatta atgaatcggc caacgcgcgg ggagaggcgg tttgcgtatt   4560
gggcgctctt ccgcttcctc gctcactgac tcgctgcgct cggtcgttcg gctgcggcga   4620
gcggtatcag ctcactcaaa ggcggtaata cggttatcca cagaatcagg ggataacgca   4680
ggaaagaaca tgtgagcaaa aggccagcaa aaggccagga accgtaaaaa ggccgcgttg   4740
ctggcgtttt tccataggct ccgcccccct gacgagcatc acaaaaatcg acgctcaagt   4800
```

```
cagaggtggc gaaacccgac aggactataa agataccagg cgtttccccc tggaagctcc    4860
ctcgtgcgct ctcctgttcc gaccctgccg cttaccggat acctgtccgc ctttctccct    4920
tcgggaagcg tggcgctttc tcatagctca cgctgtaggt atctcagttc ggtgtaggtc    4980
gttcgctcca agctgggctg tgtgcacgaa ccccccgttc agcccgaccg ctgcgcctta    5040
tccggtaact atcgtcttga gtccaacccg gtaagacacg acttatcgcc actggcagca    5100
gccactggta acaggattag cagagcgagg tatgtaggcg gtgctacaga gttcttgaag    5160
tggtggccta actacggcta cactagaaga acagtatttg gtatctgcgc tctgctgaag    5220
ccagttacct tcggaaaaag agttggtagc tcttgatccg gcaaacaaac caccgctggt    5280
agcggtggtt ttttttgtttg caagcagcag attacgcgca gaaaaaaagg atctcaagaa    5340
gatcctttga tcttttctac ggggtctgac gctcagtgga acgaaaactc acgttaaggg    5400
attttggtca tgagattatc aaaaaggatc ttcacctaga tccttttaaa ttaaaaatga    5460
agttttaaat caatctaaag tatatatgag taaacttggt ctgacagtta ccaatgctta    5520
atcagtgagg cacctatctc agcgatctgt ctatttcgtt catccatagt tgcctgactc    5580
cccgtcgtgt agataactac gatacgggag ggcttaccat ctggccccag tgctgcaatg    5640
ataccgcgag acccacgctc accggctcca gatttatcag caataaacca gccagccgga    5700
agggccgagc gcagaagtgg tcctgcaact ttatccgcct ccatccagtc tattaattgt    5760
tgccgggaag ctagagtaag tagttcgcca gttaatagtt tgcgcaacgt tgttgccatt    5820
gctacaggca tcgtggtgtc acgctcgtcg tttggtatgg cttcattcag ctccggttcc    5880
caacgatcaa ggcgagttac atgatccccc atgttgtgca aaaaagcggt tagctccttc    5940
ggtcctccga tcgttgtcag aagtaagttg gccgcagtgt tatcactcat ggttatggca    6000
gcactgcata attctcttac tgtcatgcca tccgtaagat gcttttctgt gactggtgag    6060
tactcaacca agtcattctg agaatagtgt atgcggcgac cgagttgctc ttgcccggcg    6120
tcaatacggg ataataccgc gccacatagc agaactttaa aagtgctcat cattggaaaa    6180
cgttcttcgg ggcgaaaact ctcaaggatc ttaccgctgt tgagatccag ttcgatgtaa    6240
cccactcgtg cacccaactg atcttcagca tcttttactt tcaccagcgt ttctgggtga    6300
gcaaaaacag gaaggcaaaa tgccgcaaaa aagggaataa gggcgacacg gaaatgttga    6360
atactcatac tcttcctttt tcaatattat tgaagcattt atcagggtta ttgtctcatg    6420
agcggataca tatttgaatg tatttagaaa aataaacaaa taggggttcc gcgcacattt    6480
ccccgaaaag tgccacctga cgtctaagaa accattatta tcatgacatt aacctataaa    6540
aataggcgta tcacgaggcc ctttcgtctc gcgcgtttcg gtgatgacgg tgaaaacctc    6600
tgacacatgc agctcccgga gacggtcaca gcttgtctgt aagcggatgc cgggagcaga    6660
caagcccgtc agggcgcgtc agcgggtgtt ggcgggtgtc ggggctggct taactatgcg    6720
gcatcagagc agattgtact gagagtgcac cataaaattg taaacgttaa tattttgtta    6780
aaattcgcgt taaattttg ttaaatcagc tcattttta accaatagac cgaaatcggc    6840
aaaatccctt ataaatcaaa agaatagccc gagatagagt tgagtgttgt tccagtttgg    6900
aacaagagtc cactattaaa gaacgtggac tccaacgtca aagggcgaaa aaccgtctat    6960
cagggcgatg gcccactacg tgaaccatca cccaaatcaa gttttttggg gtcgaggtgc    7020
cgtaaagcac taaatcggaa ccctaaaggg agccccccgat ttagagcttg acggggaaag    7080
ccggcgaacg tggcgagaaa ggaagggaag aaagcgaaag gagcgggcgc taaggcgctg    7140
gcaagtgtag cggtcacgct gcgcgtaacc accacacccg ccgcgcttaa tgcgccgcta    7200
```

-continued

```
cagggcgcgt actatggttg cttgacgta tgcggtgtga aataccgcac agatgcgtaa     7260
ggagaaaata ccgcatcagg cgccattcgc cattcaggct gcgcaactgt tgggaagggc     7320
gatcggtgcg ggcctcttcg ctattacgcc agctggcgaa aggggatgt gctgcaaggc      7380 gattaagttg ggtaacgcca gggttttccc agtcacgacg ttgtaaaacg acggccagtg     7440
aattcgagct ccaccgcgga tagatctgaa atgaataaca atactgacag tactaaataa     7500
ttgcctactt ggcttcacat acgttgcata cgtcgatata gataataatg ataatgacag     7560
caggattatc gtaatacgta atagttgaaa atctcaaaaa tgtgtgggtc attacgtaaa     7620
taatgatagg aatgggattc ttctattttt ccttttttcca ttctagcagc cgtcgggaaa    7680
acgtggcatc ctctctttcg ggctcaattg gagtcacgct gccgtgagca tcctctcttt     7740
ccatatctaa caactgagca cgtaaccaat ggaaaagcat gagcttagcg ttgctccaaa     7800
aaagtattgg atggttaata ccatttgtct gttctcttct gactttgact cctcaaaaaa     7860
aaaaaatcta caatcaacag atcgcttcaa ttacgccctc acaaaaactt ttttccttct     7920
tcttcgccca cgttaaattt tatccctcat gttgtctaac ggattctgc acttgattta      7980 ttataaaaag acaaagacat aatacttctc tatcaatttc agttattgtt cttccttgcg     8040
ttattcttct gttcttcttt ttcttttgtc atatataacc ataaccaagt aatacatatt     8100
caaatctaga gctgaggatg ttgaagcaaa tcaacttcgg tggtactgtt gaaaccgtct     8160 acgaagagc tgactggcca agagaaaagt tgttggacta cttcaagaac gacactttg      8220 ctttgatcgg ttacggttcc caaggttacg gtcaaggtt gaacttgaga acaacggtt       8280 tgaacgttat cattggtgtc cgtaaagatg gtgcttcttg gaaggctgcc atcgaagacg     8340
gttgggttcc aggcaagaac ttgttcactg ttgaagatgc tatcaagaga ggtagttacg     8400
ttatgaactt gttgtccgat gccgctcaat cagaaacctg gcctgctatc aagccattgt     8460
tgaccaaggg taagactttg tacttctccc acggtttctc cccagtcttc aaggacttga     8520
ctcacgttga accaccaaag gacttagatg ttatcttggt tgctccaaag ggttccggta     8580
gaactgtcag atcttttgttc aaggaaggtc gtggtattaa ctcttcttac gccgtctgga    8640
acgatgtcac cggtaaggct cacgaaaagg cccaagcttt ggccgttgcc attggttccg     8700
gttacgttta ccaaaccact tcgaaagag aagtcaactc tgacttgtac ggtgaaagag      8760
gttgtttaat gggtggtatc cacggtatgt tcttggctca atacgacgtc ttgagagaaa     8820
acggtcactc cccatctgaa gctttcaacg aaaccgtcga agaagctacc caatctctat     8880
acccattgat cggtaagtac ggtatggatt acatgtcgac tgcttgttcc accaccgcca     8940
gaagaggtgc tttggactgg tacccaatct tcaagaatgc ttgaagcct gttttccaag      9000 acttgtacga atctaccaag aacggtaccg aaaccaagag atctttggaa ttcaactctc     9060
aacctgacta cagagaaaag ctagaaaagg aattagacac catcagaaac atggaaatct     9120
ggaaggttgg taaggaagtc agaaagttga accagaaaa ccaataatta ttaatcatg       9180 taattagtta tgtcacgctt acattcacgc cctcccccca catccgctct aaccgaaaag     9240
gaaggagtta gacaacctga agtctaggtc cctatttatt ttttatagt tatgttagta     9300 ttaagaacgt tattttatt tcaaatttt cttttttttc tgtacagacg cgtgtacgca      9360
tgtaacatta tactgaaaac cttgcttgag aaggttttgg gacgctcgaa ggctttaatt    9420
tgcgggcggc cgctctagag agttgttagc aacctttgt ttcttttgag ctggttcaga     9480
cattatgtac acgtatatgt gacgagttcg agaagtattt tactatcgta ctaaattta     9540
```

```
cctgaaaaat tatatactcg agaaagagga agccaagaat tgagaaaaaa gaaaaacccg   9600
cgagtaagga aattaaatac aggtgtacac atacacgcac acatatatat atatatatat   9660
atgtatatgt gtatataaga agcgcgcgca tgttagtata tacgattcgt tggaaagggg   9720
ccgtccacca aacgtgactt gacgagttga caaattgacc tcaatatggc tcagtcagta   9780 attttttagtt ccgctttatt cccgccatct ttcaggccac gagggtagct cataacgccg   9840
cgctaatgcc gctgcgtcac agcaaccagt agctcagcca aaaccgaaag agaaatcgta   9900
gctgtcccga tgaggactta tacacttgtc accatctaaa taaattattt attcgcgttt   9960
cggttcttgt tttcgattta attagattgt tcattgaatc ataataaata tgtaaaaaat  10020
atatatattt gaagctgctt cagaaaaaca gggcttccta gtgtacagat gtatgtcgga  10080
tgaaaaaaaa aaaatcttaa atgtgaaatt gggtcaattc aattgactat gacttgatgt  10140
tgcaaaaatt ccaagagaaa aagtttccag cacttgatat tattttcctc tttaattttt  10200
cgccttgtct acgatcttat tagcaccgat ccagggcatc atagacctta actgttcacc  10260
aataatttcg ataccatgtg ctgcattgtt tcttctttta gcagtcatac tcgggtaacc  10320
cgtagcgcct tcacttatga acatcttagc gtattcaccg tcctggatac gtttcaaggc  10380
atttctcatg gcttgtcttg attctgcgtt aatgacttca ggtccggtga catactcacc  10440
atattctgca ttatttgaaa tggaatagtt catattagct ataccacctt catacattaa  10500
gtctactatc aacttcaatt catgtagaca ttcgaagtat gccatttcgg gagcgtaccc  10560
tgcttcgaca agcgtctcaa agcctgcttt aaccaattca acagttcctc cgcacagaac  10620
cgcttgttct ccaaataaat ctgtctcagt ctcgtcttta aaagtggttt ctattatacc  10680
cgttctcccg ccaccaactc ctgctgcgta gcttaaagct acattcttag cgtttccgct  10740
tgcgtcttgg tatatagcga tcaaatctgg aataccacca cccttaacaa attcgctcct  10800
aacagtatgc cccggagcct taggtgcaat cataataacg tccaaatctg ccctggggac  10860
tacttgattg taatgaatgg caaatccatg actgaaggcc aaggtagcgc ccttcttaat  10920
gtttggttct atttcatttt tgtacaattg cgattgaaat tcatctggcg ttaaaatcat  10980
gactaaatca gcgccggcaa cagccgctgc aacatctgtg actttcaagc catgtgcttc  11040
agcctttgca acgtagcac tacctttcct cagacctact gtcacgtcga ccccagaatc  11100
tttcaagtta caggcttgtg cgtgtccttg ggaaccatat cctataatag caaccttctt  11160
tccctggatg atgctcagat cgcagtcttt atcgtaaaac accttcatgt tttattttt  11220 acttatattg ctggtagggt aaaaaaatat aactcctagg aataggttgt ctatatgttt  11280
ttgtcttgct tctataattg taacaaacaa ggaaagggaa aatactgggt gtaaaagcca  11340
ttgagtcaag ttaggtcatc cctttttatac aaaattttc aatttttttt ccaagattct  11400
tgtacgatta attatttttt ttttgcgtcc tacagcgtga tgaaaatttc cgcctgctgc  11460
aagatgagcg ggaacgggcg aaatgtgcac gcgcacaact tacgaaacgc ggatgagtca  11520
ctgacagcca ccgcagaggt tctgactcct actgagctct attggaggtg cagaaccgg  11580 taccggagga gaccgctata accggtttga atttattgtc acagtgtcac atcagcggca  11640
actcagaagt ttgacagcaa gcaagttcat cattcgaact agccttattg ttttagttca  11700
gtgacagcga actgccgtac tcgatgcttt atttctcacg gtagagcgga agaacagata  11760
ggggcagcgt gagaagagtt agaaagtaaa ttttttatcac gtctgaagta ttcttattca  11820
taggaaattt tgcaaggttt tttagctcaa taacgggcta agttatataa ggtgttcacg  11880
cgattttctt gttatgtata cctcttctct gaggaatggt actactgtcc tgatgtaggc  11940
```

```
tccttaaatt ggtgggcaag aataacttat cgatattttg tatattggtc ttggagttca    12000
ccacgtaatg cctgtttaag accatcagtt aactctagta ttatttggtc ttggctactg    12060
gccgtttgct attattcaag tcttttgtgc cttcccgtcg ggtaagggag ttatttaggg    12120
atacagaatc taacgaaaac taaatctcaa tgattaactc catttaatcc tttttgaaa     12180 ggcaaaagag gtcccttgtt cacttacaac gttcttagcc aaattcgctt atcacttact    12240
acttcacgat atacagaagt aaaaacatat aaaaagatgt ctgtttgttt agccatcaca    12300
aaaggtatcg cagtttcttc tataggcctc tactctggtc ttttggcttc cgcttcattg    12360
attacatcta ctactccact agaggtttta acaggatctc taaaaacatc gatatcgtct    12420
ctgcgttcca atcctacggt gaatatattt ccaagcaatt cactgaagaa gaaagagaag    12480
atgttgtgga acatgcatgc ccaggtcctg gttcttgtgg tggtatgtat actgccaaca    12540
caatggcttc tgccgctgaa gtgctaggtt tgaccattcc aaactcctct tccttcccag    12600
ccgtttccaa ggagaagtta gctgagtgtg acaacattgg tgaatacatc aagaagacaa    12660
tggaattggg tattttacct cgtgatatcc tcacaaaaga ggcttttgaa aacgccatta    12720
cttatgtcgt tgcaaccggt gggtccacta atgctgtttt gcatttggtg gctgttgctc    12780
actctgcggg tgtcaagttg tcaccagatg atttccaaag aatcagtgat actacaccat    12840
tgatcggtga cttcaaaacct tctggtaaat acgtcatggc cgatttgatt aacgttggtg    12900
gtacccaatc tgtgattaag tatctatatg aaaacaacat gttgcacggt aacacaatga    12960
ctgttaccgg tgacactttg gcagaacgtg caaagaaagc accaagccta cctgaaggac    13020
aagagattat taagccactc tcccacccaa tcaaggccaa cggtcacttg caaattctgt    13080
acggttcatt ggcaccaggt ggagctgtgg gtaaaattac cggtaaggaa ggtacttact    13140
tcaagggtag agcacgtgtg ttcgaagagg aaggtgcctt tattgaagcc ttggaaagag    13200
gtgaaatcaa gaagggtgaa aaaaccgttg ttgttatcag atatgaaggt ccaagaggtg    13260
caccaggtat gcctgaaatg ctaaagcctt cctctgctct gatgggttac ggtttgggta    13320
aagatgttgc attgttgact gatggtagat tctctggtgg ttctcacggg ttcttaatcg    13380
gccacattgt tcccgaagcc gctgaaggtg gtcctatcgg gttggtcaga gacggcgatg    13440
agattatcat tgatgctgat aataacaaga ttgacctatt agtctctgat aaggaaatgg    13500
ctcaacgtaa acaaagttgg gttgcacctc cacctcgtta cacaagaggt actctatcca    13560
agtatgctaa gttggtttcc aacgcttcca acggttgtgt tttagatgct tgattaatta    13620
agagtaagcg aatttcttat gatttatgat ttttattat aaataagtta taaaaaaaat    13680
aagtgtatac aaattttaaa gtgactctta ggttttaaaa cgaaaattct tattcttgag    13740
taactctttc ctgtaggtca ggttgctttc tcaggtatag catgaggtcg ctcttattga    13800
ccacacctct accggcatgc cgagcaaatg cctgcaaatc gctccccatt tcacccaatt    13860
gtagatatgc taactccagc aatgagttga tgaatctcgg tgtgtatttt atgtcctcag    13920
aggacaacac ctgtggtact agttctagag cggccgcccg caaattaaag ccttcgagcg    13980
tcccaaaacc ttctcaagca aggttttcag tataatgtta catgcgtaca cgcgtctgta    14040
cagaaaaaaa agaaaaattt gaaatataaa taacgttctt aatactaaca taactataaa    14100
aaataaaata gggacctaga cttcaggttg tctaactcct tccttttcgg ttagagcgga    14160 tgtggggggga gggcgtgaat gtaagcgtga cataactaat tacatgatta attaactaga    14220
gagctttcgt tttcatgagt tccccgaatt cttttcggaag cttgtcactt gctaaattaa    14280
```

-continued

```
tgttatcact gtagtcaacc gggacatcga tgatgacagg accttcagcg ttcatgcctt      14340
gacgcagaac atctgccagc tggtctggtg attctacgcg caagccagtt gctccgaagc      14400
tttccgcata tttcacgata tcgatatttc cgaaatcgac cgcagatgta cggttatatt      14460
ttttcaattg ctggaatgca accatgtcat atgtgctgtc gttccataca atgtgtacaa      14520
ttggtgcttt tagtcgaact gctgtctcta attccattgc tgagaataag aaaccgccgt      14580
caccagagac agaaaccact ttttctcccg gtttcaccaa tgaagcgccg attgcccaag      14640
gaagcgcaac gccgagtgtt tgcataccgt tactgatcat taatgttaac ggctcgtagc      14700
tgcggaaata acgtgacatc caaatggcgt gcgaaccgat atcgcaagtt actgtaacat      14760
gatcatcgac tgcattacgc aactctttaa cgatttcaag agggtgcgct ctgtctgatt      14820
tccaatctgc aggcacctgc tcaccttcat gcatatattg ttttaaatca gaaaggattt      14880
tctgctcacg ctctgcaaat tccactttca cagcatcgtg ttcgatatga ttgatcgtgg      14940
acggaatgtc accgatcaat tcaagatcag gctggtaagc atgatcaatg tcagcgataa      15000
tctcgtctaa atggataatt gtccggtctc cattgatatt ccagaatttc ggatcatatt      15060
caatcgggtc atagccgatc gtcagaacaa catctgcctg ctctagcagt aaatcgccag      15120
gctggttgcg gaacaaaccg atacggccaa aatattgatc ctctaaatct ctagaaaggg      15180
taccggcagc ttgatatgtt tcaacaaatg gaagctgaac cttttcaaa agcttgcgaa       15240 ccgctttaat tgcttccggt cttccgcctt tcatgccgac caaaacgaca ggaagttttg      15300
ctgtttggat ttttgctatg gccgcactga ttgcatcatc tgctgcagga ccgagttttg      15360
gcgctgcaac agcacgcacg tttttcgtat ttgtgacttc attcacaaca tcttgcggaa      15420
agctcacaaa agcggcccca gcctgccctg ctgacgctat cctaaatgca tttgtaacag      15480
cttccggtat attttttaca tcttgaactt ctacactgta ttttgtaatc ggctggaata      15540
gcgccgcatt atccaaagat tgatgtgtcc gttttaaacg atctgcacgg atcacgtttc      15600
cagcaagcgc aacgacaggg tctccttcag tgttcgctgt cagcaggcct gttgccaagt      15660
tagaggcacc cggtcctgat gtgactaaca cgactcccgg ttttccagtt aaacggccga      15720
ctgcttgggc catgaatgct gcgttttgtt cgtgccgggc aacgataatt tcaggtcctt      15780
tatcttgtaa agcgtcaaat accgcatcaa tttttgcacc tggaatgcca aatacatgtg      15840
tgacaccttg ctccactaag caatcaacaa caagctccgc ccctctgttt ttcacaaggg      15900
atttttgttc ttttgttgct tttgtcaaca tcctcagcga tgattgattg attgattgta      15960
cagtttgttt ttcttaatat ctatttcgat gacttctata tgatattgca ctaacaagaa      16020
gatattataa tgcaattgat acaagacaag gagttatttg cttctctttt atatgattct      16080
gacaatccat attgcgttgg tagtcttttt tgctggaacg gttcagcgga aaagacgcat      16140
cgctcttttt gcttctagaa gaaatgccag caaaagaatc tcttgacagt gactgacagc      16200
aaaaatgtct ttttctaact agtaacaagg ctaagatatc agcctgaaat aaagggtggt      16260
gaagtaataa ttaaatcatc cgtataaacc tatacacata tatgaggaaa aataatacaa      16320
aagtgtttta aatacagata catacatgaa catatgcacg tatagcgccc aaatgtcggt      16380
aatggga                                                               16387
```

<210> SEQ ID NO 131
<211> LENGTH: 1188
<212> TYPE: DNA
<213> ORGANISM: Saccharomyces cerevisiae

<400> SEQUENCE: 131

```
atgttgagaa ctcaagccgc cagattgatc tgcaactccc gtgtcatcac tgctaagaga    60
acctttgctt tggccacccg tgctgctgct tacagcagac cagctgcccg tttcgttaag   120
ccaatgatca ctacccgtgg tttgaagcaa atcaacttcg gtggtactgt tgaaaccgtc   180
tacgaaagag ctgactggcc aagagaaaag ttgttggact acttcaagaa cgacactttt   240
gctttgatcg gttacggttc ccaaggttac ggtcaaggtt tgaacttgag agacaacggt   300
ttgaacgtta tcattggtgt ccgtaaagat ggtgcttctt ggaaggctgc catcgaagac   360
ggttgggttc caggcaagaa cttgttcact gttgaagatg ctatcaagag aggtagttac   420
gttatgaact tgttgtccga tgccgctcaa tcagaaacct ggcctgctat caagccattg   480
ttgaccaagg gtaagacttt gtacttctcc cacggtttct ccccagtctt caaggacttg   540
actcacgttg aaccaccaaa ggacttagat gttatcttgg ttgctccaaa gggttccggt   600
agaactgtca gatctttgtt caaggaaggt cgtggtatta actcttctta cgccgtctgg   660
aacgatgtca ccggtaaggc tcacgaaaag gcccaagctt tggccgttgc cattggttcc   720
ggttacgttt accaaaccac tttcgaaaga gaagtcaact ctgacttgta cggtgaaaga   780
ggttgtttaa tgggtggtat ccacggtatg ttcttggctc aatacgacgt cttgagagaa   840
aacggtcact ccccatctga agctttcaac gaaaccgtcg aagaagctac ccaatctcta   900
tacccattga tcggtaagta cggtatggat tacatgtacg atgcttgttc caccaccgcc   960
agaagaggtg ctttggactg gtacccaatc ttcaagaatg ctttgaagcc tgttttccaa  1020
gacttgtacg aatctaccaa gaacggtacc gaaaccaaga gatctttgga attcaactct  1080
caacctgact acagagaaaa gctagaaaag gaattagaca ccatcagaaa catggaaatc  1140
tggaaggttg gtaaggaagt cagaaagttg agaccagaaa accaataa              1188
```

<210> SEQ ID NO 132
<211> LENGTH: 1014
<212> TYPE: DNA
<213> ORGANISM: Pseudomonas fluorescens

<400> SEQUENCE: 132

```
atgaaagttt tctacgataa agactgcgac ctgtcgatca tccaaggtaa gaaagttgcc    60
atcatcggct acggttccca gggccacgct caagcatgca acctgaagga ttccggcgta   120
gacgtgactg ttggcctgcg taaaggctcg gctaccgttg ccaaggctga gcccacggc   180 ttgaaagtga ccgacgttgc tgcagccgtt gccggtgccg acttggtcat gatcctgacc   240
ccggacgagt tccagtccca gctgtacaag aacgaaatcg agccgaacat caagaagggc   300
gccactctgg ccttctccca cggcttcgcg atccactaca accaggttgt gcctcgtgcc   360
gacctcgacg tgatcatgat cgcgccgaag gctccaggcc acaccgtacg ttccgagttc   420
gtcaagggcg gtggtattcc tgacctgatc gcgatctacc aggacgcttc cggcaacgcc   480
aagaacgttg ccctgtccta cgccgcaggc gtgggcggcg ccgtaccgg catcatcgaa   540 accaccttca aggacgagac tgaaaccgac ctgttcggtg agcaggctgt tctgtgtggc   600
ggtaccgtcg agctggtcaa agccggtttc gaaaccctgg ttgaagctgg ctacgctcca   660
gaaatggcct acttcgagtg cctgcacgaa ctgaagctga tcgttgacct catgtacgaa   720
ggcggtatcg ccaacatgaa ctactcgatc tccaacaacg ctgaatacgg cgagtacgtg   780
actggtccag aagtcatcaa cgccgaatcc cgtcaggcca tgcgcaatgc tctgaagcgc   840
atccaggacg gcgaatacgc gaagatgttc atcagcgaag gcgctaccgg ctacccatcg   900
```

```
atgaccgcca agcgtcgtaa caacgctgct cacggtatcg aaatcatcgg cgagcaactg      960
cgctcgatga tgccttggat cggtgccaac aaaatcgtcg acaaagccaa gaac           1014
```

<210> SEQ ID NO 133
<211> LENGTH: 250
<212> TYPE: DNA
<213> ORGANISM: Saccharomyces cerevisiae

<400> SEQUENCE: 133

```
ccgcaaatta agccttcga gcgtcccaaa accttctcaa gcaaggtttt cagtataatg       60
ttacatgcgt acacgcgtct gtacagaaaa aaagaaaaaa tttgaaatat aaataacgtt      120
cttaatacta acataactat aaaaaaataa atagggacct agacttcagg ttgtctaact      180
ccttcctttt cggttagagc ggatgtgggg ggagggcgtg aatgtaagcg tgacataact      240
aattacatga                                                            250
```

<210> SEQ ID NO 134
<211> LENGTH: 1181
<212> TYPE: DNA
<213> ORGANISM: Saccharomyces cerevisiae

<400> SEQUENCE: 134

```
taaaacctct agtggagtag tagatgtaat caatgaagcg gaagccaaaa gaccagagta       60
gaggcctata gaagaaactg cgatacccttt tgtgatggct aaacaaacag acatcttttt     120
atatgttttt acttctgtat atcgtgaagt agtaagtgat aagcgaattt ggctaagaac      180
gttgtaagtg aacaagggac ctcttttgcc tttcaaaaaa ggattaaatg gagttaatca      240
ttgagattta gttttcgtta gattctgtat ccctaaataa ctcccttacc cgacgggaag      300
gcacaaaaga cttgaataat agcaaacggc cagtagccaa gaccaaataa tactagagtt      360
aactgatggt cttaaacagg cattacgtgg tgaactccaa gaccaatata caaaatatcg      420
ataagttatt cttgcccacc aatttaagga gcctacatca ggacagtagt accattcctc      480
agagaagagg tatacataac aagaaaatcg cgtgaacacc ttatataact tagcccgtta      540
ttgagctaaa aaaccttgca aaatttccta tgaataagaa tacttcagac gtgataaaaa      600
tttactttct aactcttctc acgctgcccc tatctgttct tccgctctac cgtgagaaat      660
aaagcatcga gtacggcagt tcgctgtcac tgaactaaaa caataaggct agttcgaatg      720
atgaacttgc ttgctgtcaa acttctgagt tgccgctgat gtgacactgt gacaataaat      780
tcaaaccggt tatagcggtc tcctccggta ccggttctgc cacctccaat agagctcagt      840
aggagtcaga acctctgcgg tggctgtcag tgactcatcc gcgtttcgta agttgtgcgc      900
gtgcacattt cgcccgttcc cgctcatctt gcagcaggcg gaaattttca tcacgctgta      960
ggacgcaaaa aaaaaataat taatcgtaca agaatcttgg aaaaaaaatt gaaaaatttt     1020
gtataaaagg gatgacctaa cttgactcaa tggcttttac acccagtatt ttcccttttcc    1080 ttgtttgtta caattataga agcaagacaa aaacatatag acaacctatt cctaggagtt     1140 atatttttt acccctaccag caatataagt aaaaaactag t                          1181
```

<210> SEQ ID NO 135
<211> LENGTH: 759
<212> TYPE: DNA
<213> ORGANISM: Saccharomyces cerevisiae

<400> SEQUENCE: 135

```
ggccctgcag gcctatcaag tgctggaaac ttttttctctt ggaatttttg caacatcaag      60
```

```
tcatagtcaa ttgaattgac ccaatttcac atttaagatt ttttttttt catccgacat      120 acatctgtac actaggaagc cctgttttc tgaagcagct tcaaatatat atatttttta      180
catatttatt atgattcaat gaacaatcta attaaatcga aaacaagaac cgaaacgcga      240
ataaataatt tatttagatg gtgacaagtg tataagtcct catcgggaca gctacgattt      300
ctctttcggt tttggctgag ctactggttg ctgtgacgca gcggcattag cgcggcgtta      360
tgagctaccc tcgtggcctg aaagatggcg ggaataaagc ggaactaaaa attactgact      420
gagccatatt gaggtcaatt tgtcaactcg tcaagtcacg tttggtggac ggccccttc       480 caacgaatcg tatatactaa catgcgcgcg cttcctatat acacatatac atatatatat      540
atatatatat gtgtgcgtgt atgtgtacac ctgtatttaa tttccttact cgcgggtttt      600
tcttttttct caattcttgg cttcctcttt ctcgagtata taattttca ggtaaaattt       660 agtacgatag taaaatactt ctcgaactcg tcacatatac gtgtacataa tgtctgaacc      720
agctcaaaag aaacaaaagg ttgctaacaa ctctctaga                             759

<210> SEQ ID NO 136
<211> LENGTH: 643
<212> TYPE: DNA
<213> ORGANISM: Saccharomyces cerevisiae

<400> SEQUENCE: 136
gaaatgaata acaatactga cagtactaaa taattgccta cttggcttca catacgttgc       60
atacgtcgat atagataata atgataatga cagcaggatt atcgtaatac gtaatagttg      120
aaaatctcaa aaatgtgtgg gtcattacgt aaataatgat aggaatggga ttcttctatt      180 tttcctttt ccattctagc agccgtcggg aaaacgtggc atcctctctt tcgggctcaa       240
ttggagtcac gctgccgtga gcatcctctc tttccatatc taacaactga gcacgtaacc      300
aatggaaaag catgagctta gcgttgctcc aaaaaagtat tggatggtta ataccatttg      360
tctgttctct tctgacttg actcctcaaa aaaaaaaaat ctacaatcaa cagatcgctt       420
caattacgcc ctcacaaaaa ctttttcct tcttcttcgc ccacgttaaa ttttatccct       480
catgttgtct aacggatttc tgcacttgat ttattataaa aagacaaaga cataatactt      540
ctctatcaat ttcagttatt gttcttcctt gcgttattct tctgttcttc ttttctttt       600 gtcatatata accataacca agtaatacat attcaaatct aga                        643

<210> SEQ ID NO 137
<211> LENGTH: 1716
<212> TYPE: DNA
<213> ORGANISM: Bacillus subtilis

<400> SEQUENCE: 137
atgttgacaa aagcaacaaa agaacaaaaa tcccttgtga aaaacagagg ggcggagctt       60
gttgttgatt gcttagtgga gcaaggtgtc acacatgtat ttggcattcc aggtgcaaaa      120
attgatgcgg tatttgacgc tttacaagat aaaggacctg aaattatcgt tgcccggcac      180
gaacaaaacg cagcattcat ggcccaagca gtcggccgtt taactggaaa accgggagtc      240
gtgttagtca catcaggacc gggtgcctct aacttggcaa caggcctgct gacagcgaac      300
actgaaggag accctgtcgt tgcgcttgct ggaaacgtga tccgtgcaga tcgtttaaaa      360
cggacacatc aatctttgga taatgcggcg ctattccagc cgattacaaa atacagtgta      420
gaagttcaag atgtaaaaaa tataccggaa gctgttacaa atgcatttag gatagcgtca      480
```

-continued

```
gcagggcagg ctggggccgc ttttgtgagc tttccgcaag atgttgtgaa tgaagtcaca    540
aatacgaaaa acgtgcgtgc tgttgcagcg ccaaaactcg gtcctgcagc agatgatgca    600
atcagtgcgg ccatagcaaa atccaaaca gcaaaacttc ctgtcgtttt ggtcggcatg     660
aaaggcggaa gaccggaagc aattaaagcg gttcgcaagc ttttgaaaaa ggttcagctt    720
ccatttgttg aaacatatca agctgccggt accctttcta gagatttaga ggatcaatat    780
tttggccgta tcggtttgtt ccgcaaccag cctggcgatt tactgctaga gcaggcagat    840
gttgttctga cgatcggcta tgacccgatt gaatatgatc cgaaattctg gaatatcaat    900
ggagaccgga caattatcca tttagacgag attatcgctg acattgatca tgcttaccag    960
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa agtggttttc tgtctctggt gacggcggtt tcttattctc agcaatggaa   1380
ttagagacag cagttcgact aaaagcacca attgtacaca ttgtatggaa cgacagcaca   1440
tatgacatgg ttgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                             1716
```

<210> SEQ ID NO 138
<211> LENGTH: 571
<212> TYPE: PRT
<213> ORGANISM: Bacillus subtilis

<400> SEQUENCE: 138

```
Met Leu Thr Lys Ala Thr Lys Glu Gln Lys Ser Leu Val Lys Asn Arg
 1               5                  10                  15

Gly Ala Glu Leu Val Val Asp Cys Leu Val Glu Gln Gly Val Thr His
             20                  25                  30

Val Phe Gly Ile Pro Gly Ala Lys Ile Asp Ala Val Phe Asp Ala Leu
         35                  40                  45

Gln Asp Lys Gly Pro Glu Ile Ile Val Ala Arg His Glu Gln Asn Ala
     50                  55                  60

Ala Phe Met Ala Gln Ala Val Gly Arg Leu Thr Gly Lys Pro Gly Val
 65                  70                  75                  80

Val Leu Val Thr Ser Gly Pro Gly Ala Ser Asn Leu Ala Thr Gly Leu
                 85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160
```

```
Ala Gly Gln Ala Gly Ala Ala Phe Val Ser Phe Pro Gln Asp Val Val
            165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ile Ala Lys Ile
            195                 200                 205

Gln Thr Ala Lys Leu Pro Val Val Leu Val Gly Met Lys Gly Gly Arg
            210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
            245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
            275                 280                 285

Pro Ile Glu Tyr Asp Pro Lys Phe Trp Asn Ile Asn Gly Asp Arg Thr
            290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
            355                 360                 365

Asp Trp Lys Ser Asp Arg Ala His Pro Leu Glu Ile Val Lys Glu Leu
            370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
            435                 440                 445

Ser Gly Asp Gly Gly Phe Leu Phe Ser Ala Met Glu Leu Glu Thr Ala
            450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
            485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
            515                 520                 525

Leu Arg Gln Gly Met Asn Ala Glu Gly Pro Val Ile Ile Asp Val Pro
            530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570
```

<210> SEQ ID NO 139
<211> LENGTH: 448
<212> TYPE: DNA
<213> ORGANISM: Saccharomyces cerevisiae

<400> SEQUENCE: 139

| | | | | | |
|---|---|---|---|---|---|
| cccattaccg | acatttgggc | gctatacgtg | catatgttca | tgtatgtatc | tgtatttaaa | 60 |
| acactttttgt | attattttc | ctcatatatg | tgtataggtt | tatacggatg | atttaattat | 120 |
| tacttcacca | cccttttattt | caggctgata | tcttagcctt | gttactagtt | agaaaaagac | 180 |
| attttttgctg | tcagtcactg | tcaagagatt | cttttgctgg | catttcttct | agaagcaaaa | 240 |
| agagcgatgc | gtcttttccg | ctgaaccgtt | ccagcaaaaa | agactaccaa | cgcaatatgg | 300 |
| attgtcagaa | tcatataaaa | gagaagcaaa | taactccttg | tcttgtatca | attgcattat | 360 |
| aatatcttct | tgttagtgca | atatcatata | gaagtcatcg | aaatagatat | taagaaaaac | 420 |
| aaactgtaca | atcaatcaat | caatcatc | | | | 448 |

<210> SEQ ID NO 140
<211> LENGTH: 16387
<212> TYPE: DNA
<213> ORGANISM: artificial sequence
<220> FEATURE:
<223> OTHER INFORMATION: plasmid construct

<400> SEQUENCE: 140

| | | | | | |
|---|---|---|---|---|---|
| tcccattacc | gacatttggg | cgctatacgt | gcatatgttc | atgtatgtat | ctgtatttaa | 60 |
| aacactttttg | tattattttt | cctcatatat | gtgtataggt | ttatacggat | gatttaatta | 120 |
| ttacttcacc | acccttttatt | tcaggctgat | atcttagcct | tgttactagt | tagaaaaaga | 180 |
| cattttttgct | gtcagtcact | gtcaagagat | tcttttgctg | gcatttcttc | tagaagcaaa | 240 |
| aagagcgatg | cgtcttttcc | gctgaaccgt | tccagcaaaa | aagactacca | acgcaatatg | 300 |
| gattgtcaga | atcatataaa | agagaagcaa | ataactcctt | gtcttgtatc | aattgcatta | 360 |
| taatatcttc | ttgttagtgc | aatatcatat | agaagtcatc | gaaatagata | ttaagaaaaa | 420 |
| caaactgtac | aatcaatcaa | tcaatcatcg | ctgaggatgt | tgacaaaagc | aacaaaagaa | 480 |
| caaaaatccc | ttgtgaaaaa | cagaggggcg | gagcttgttg | ttgattgctt | agtggagcaa | 540 |
| ggtgtcacac | atgtatttgg | cattccaggt | gcaaaaattg | atgcggtatt | tgacgcttta | 600 |
| caagataaag | gacctgaaat | tatcgttgcc | cggcacgaac | aaaacgcagc | attcatggcc | 660 |
| caagcagtcg | gccgtttaac | tggaaaaccg | ggagtcgtgt | tagtcacatc | aggacccggt | 720 |
| gcctctaact | tggcaacagg | cctgctgaca | gcgaacactg | aaggagaccc | tgtcgttgcg | 780 |
| cttgctggaa | acgtgatccg | tgcagatcgt | ttaaaacgga | cacatcaatc | tttggataat | 840 |
| gcggcgctat | tccagccgat | tacaaaatac | agtgtagaag | ttcaagatgt | aaaaaatata | 900 |
| ccggaagctg | ttacaaatgc | atttaggata | gcgtcagcag | gcaggctgg | ggccgctttt | 960 |
| gtgagctttc | cgcaagatgt | tgtgaatgaa | gtcacaaata | cgaaaaacgt | gcgtgctgtt | 1020 |
| gcagcgccaa | aactcggtcc | tgcagcagat | gatgcaatca | gtgcggccat | agcaaaaatc | 1080 |
| caaacagcaa | aacttcctgt | cgttttggtc | ggcatgaaag | gcggaagacc | ggaagcaatt | 1140 |
| aaagcggttc | gcaagctttt | gaaaaaggtt | cagcttccat | tgttgaaac | atatcaagct | 1200 |
| gccggtaccc | tttctagaga | tttagaggat | caatattttg | gccgtatcgg | tttgttccgc | 1260 |
| aaccagcctg | gcgattact | gctagagcag | gcagatgttg | ttctgacgat | cggctatgac | 1320 |
| ccgattgaat | atgatccgaa | attctggaat | atcaatggag | accggacaat | tatccattta | 1380 |

-continued

```
gacgagatta tcgctgacat tgatcatgct taccagcctg atcttgaatt gatcggtgac    1440
attccgtcca cgatcaatca tatcgaacac gatgctgtga agtggaatt tgcagagcgt     1500 gagcagaaaa tcctttctga tttaaaacaa tatatgcatg aaggtgagca ggtgcctgca    1560
gattggaaat cagacagagc gcaccctctt gaaatcgtta aagagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaagaat tcggggaact catgaaaacg      2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280
ttattttttt atagttatgt tagtattaag aacgttattt atatttcaaa tttttctttt    2340
ttttctgtac agacgcgtgt acgcatgtaa cattatactg aaaaccttgc ttgagaaggt    2400
tttgggacgc tcgaaggctt taatttgcgg gcggccgctc tagaactagt accacaggtg    2460
ttgtcctctg aggacataaa atacacaccg agattcatca actcattgct ggagttagca    2520
tatctacaat tgggtgaaat ggggagcgat ttgcaggcat ttgctcggca tgccggtaga    2580
ggtgtggtca ataagagcga cctcatgcta tacctgagaa agcaacctga cctacaggaa    2640
agagttactc aagaataaga atttcgttt taaaacctaa gagtcacttt aaaatttgta     2700
tacacttatt tttttataa cttatttaat aataaaaatc ataaatcata agaaattcgc     2760
ttactcttaa ttaatcaagc atctaaaaca caaccgttgg aagcgttgga accaacttaa    2820
gcatacttgg atagagtacc tcttgtgtaa cgaggtggag gtgcaaccca actttgttta    2880
cgttgagcca tttccttatc agagactaat aggtcaatct tgttattatc agcatcaatg    2940
ataatctcat cgccgtctct gaccaacccg ataggaccac cttcagcggc ttcgggaaca    3000
atgtggccga ttaagaaccc gtgagaacca ccagagaatc taccatcagt caacaatgca    3060
acatctttac ccaaaccgta acccatcaga gcagaggaag ctttagcat tcaggcata      3120 cctggtgcac ctcttggacc ttcatatctg ataacaacaa cggttttttc acccttcttg    3180
atttcacctc tttccaaggc ttcaataaag gcaccttcct cttcgaacac acgtgctcta    3240
cccttgaagt aagtaccttc cttaccggta attttaccca cagctccacc tggtgccaat    3300
gaaccgtaca gaatttgcaa gtgaccgttg gccttgattg ggtgggagag tggcttaata    3360
atctcttgtc cttcaggtag gcttggtgct ttctttgcac gttctgccaa agtgtcaccg    3420
gtaacagtca ttgtgttacc gtgcaacatg ttgttttcat atagatactt aatcacagat    3480
tgggtaccac caacgttaat caaatcggcc atgacgtatt taccagaagg tttgaagtca    3540
ccgatcaatg gtgtagtatc actgattctt tggaaatcat ctggtgacaa cttgacaccc    3600
gcagagtgag caacagccac caaatgcaaa acagcattag tggacccacc ggttgcaacg    3660
acataagtaa tggcgttttc aaaagcctct tttgtgagga tatcacgagg taaaataccc    3720
```

```
aattccattg tcttcttgat gtattcacca atgttgtcac actcagctaa cttctccttg   3780
gaaacggctg ggaaggaaga ggagtttgga atggtcaaac ctagcacttc agcggcagaa   3840
gccattgtgt tggcagtata cataccacca caagaaccag gacctgggca tgcatgttcc   3900
acaacatctt ctctttcttc ttcagtgaat tgcttggaaa tatattcacc gtaggattgg   3960
aacgcagaga cgatatcgat gttttagag atcctgttaa aacctctagt ggagtagtag    4020
atgtaatcaa tgaagcggaa gccaaaagac cagagtagag gcctatagaa gaaactgcga   4080
tacctttgt gatggctaaa caaacagaca tcttttttata tgttttact tctgtatatc    4140
gtgaagtagt aagtgataag cgaatttggc taagaacgtt gtaagtgaac aagggacctc   4200
ttttgccttt caaaaagga ttaaatggag ttaatcattg agatttagtt ttcgttagat    4260
tctgtatccc taaataactc ccttacccga cgggaaggca caaagacttt gaataatagc   4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aaataattaa   4980
tcgtacaaga atcttggaaa aaaaattgaa aaattttgta taaagggat gacctaactt    5040
gactcaatgc ttttacacc cagtattttc cctttccttg tttgttacaa ttatagaagc    5100
aagacaaaaa catatagaca acctattcct aggagttata tttttttacc ctaccagcaa   5160
tataagtaaa aaactagtat gaaggtgttt tacgataaag actgcgatct gagcatcatc   5220
cagggaaaga aggttgctat tataggatat ggttcccaag gacacgcaca agccttgaac   5280
ttgaaagatt ctggggtcga cgtgacagta ggtctgtata aaggtgctgc tgatgcagca   5340
aaggctgaag cacatggctt taaagtcaca gatgttgcag cggctgttgc tggcgctgat   5400
ttagtcatga tttttaattcc agatgaattt caatcgcaat tgtacaaaaa tgaaatagaa   5460
ccaaacatta agaagggcgc taccttggcc ttcagtcatg gatttgccat tcattacaat   5520
caagtagtcc ccagggcaga tttggacgtt attatgattg cacctaaggc tccgggcat    5580
actgttagga gcgaatttgt taagggtggt ggtattccag atttgatcgc tatataccaa   5640
gacgttagcg gaaacgctaa gaatgtagct ttaagctacg cagcaggagt tggtggcggg   5700
agaacgggta atagaaaac cacttttaaa gacgagactg agacagattt atttggagaa    5760
caagcggttc tgtgcggagg aactgttgaa ttggttaaag caggctttga gacgcttgtc   5820
gaagcagggt acgctcccga aatggcatac ttcgaatgtc tacatgaatt gaagttgata   5880
gtagacttaa tgtatgaagg tggtatagct aatatgaact attccatttc aaataatgca   5940
gaatatggtg agtatgtcac cggacctgaa gtcattaacg cagaatcaag acaagccatg   6000
agaaatgcct tgaaacgtat ccaggacggt gaatacgcta agatgttcat aagtgaaggc   6060
gctacgggtt acccgagtat gactgctaaa agaagaaaca atgcagcaca tggtatcgaa   6120
```

```
attattggtg aacagttaag gtctatgatg ccctggatcg gtgctaataa gatcgtagac    6180
aaggcgaaaa attaaggccc tgcaggccta tcaagtgctg gaaactttt  ctcttggaat    6240
ttttgcaaca tcaagtcata gtcaattgaa ttgacccaat ttcacattta agattttttt    6300
tttttcatcc gacatacatc tgtacactag gaagccctgt ttttctgaag cagcttcaaa    6360
tatatatatt ttttacatat ttattatgat tcaatgaaca atctaattaa atcgaaaaca    6420
agaaccgaaa cgcgaataaa taatttattt agatggtgac aagtgtataa gtcctcatcg    6480
ggacagctac gatttctctt tcggttttgg ctgagctact ggttgctgtg acgcagcggc    6540
attagcgcgg cgttatgagc taccctcgtg gcctgaaaga tggcgggaat aaagcggaac    6600
taaaaattac tgactgagcc atattgaggt caatttgtca actcgtcaag tcacgtttgg    6660
tggacggccc cttccaacg  aatcgtatat actaacatgc gcgcgcttcc tatatacaca    6720
tatacatata tatatatata tatatgtgtg cgtgtatgtg tacacctgta tttaatttcc    6780
ttactcgcgg gttttctttt tttctcaatt cttggcttcc tctttctcga gtatataatt    6840
tttcaggtaa aatttagtac gatagtaaaa tacttctcga actcgtcaca tatacgtgta    6900
cataatgtct gaaccagctc aaaagaaaca aaggttgct  aacaactctc tagagcggcc    6960
gcccgcaaat taagccttc  gagcgtccca aaaccttctc aagcaaggtt ttcagtataa    7020
tgttacatgc gtcacgcgt  ctgtacagaa aaaaagaaa  aatttgaaat ataaataacg    7080
ttcttaatac taacataact ataaaaaaat aaataggac  ctagacttca ggttgtctaa    7140
ctccttcctt ttcggttaga gcggatgtgg ggggagggcg tgaatgtaag cgtgacataa    7200
ctaattacat gattaattaa ttattggttt tctggtctca actttctgac ttccttacca    7260
accttccaga tttccatgtt tctgatggtg tctaattcct ttttctagctt ttctctgtag    7320
tcaggttgag agttgaattc caaagatctc ttggtttcgg taccgttctt ggtagattcg    7380
tacaagtctt ggaaaacagg cttcaaagca ttcttgaaga ttgggtacca gtccaaagca    7440
cctcttctgg cggtggtgga acaagcatcg tacatgtaat ccataccgta cttaccgatc    7500
aatgggtata gagattgggt agcttcttcg acggtttcgt tgaaagcttc agatggggag    7560
tgaccgtttt ctctcaagac gtcgtattga gccaagaaca taccgtggat accacccatt    7620
aaacaacctc tttcaccgta caagtcagag ttgacttctc tttcgaaagt ggtttggtaa    7680
acgtaaccgg aaccaatggc aacggccaaa gcttgggcct tttcgtgagc cttaccggtg    7740
acatcgttcc agacggcgta agaagagtta ataccacgac cttccttgaa caaagatctg    7800
acagttctac cggaaccctt tggagcaacc aagataacat ctaagtcctt tggtggttca    7860
acgtgagtca agtccttgaa gactgggag  aaaccgtggg agaagtacaa agtcttaccc    7920
ttggtcaaca atggcttgat agcaggccag gtttctgatt gagcggcatc ggacaacaag    7980
ttcataacgt aactacctct cttgatagca tcttcaacag tgaacaagtt cttgcctgga    8040
acccaaccgt cttcgatggc agccttccaa gaagcaccat ctttacggac accaatgata    8100
acgttcaaac cgttgtctct caagttcaaa ccttgaccgt aaccttggga accgtaaccg    8160
atcaaagcaa aagtgtcgtt cttgaagtag tccaacaact tttctcttgg ccagtcagct    8220
ctttcgtaga cggtttcaac agtaccaccg aagttgattt gcttcaacat cctcagctct    8280
agatttgaat atgtattact tggttatggt tatatatgac aaaagaaaaa gaagaacaga    8340
agaataacgc aaggaagaac aataactgaa attgatagag aagtattatg tctttgtctt    8400
tttataataa atcaagtgca gaaatccgtt agacaacatg agggataaaa tttaacgtgg    8460
```

```
gcgaagaaga aggaaaaaag tttttgtgag ggcgtaattg aagcgatctg ttgattgtag    8520
atttttttt tttgaggagt caaagtcaga agagaacaga caaatggtat taaccatcca    8580
atactttttt ggagcaacgc taagctcatg cttttccatt ggttacgtgc tcagttgtta    8640
gatatggaaa gagaggatgc tcacggcagc gtgactccaa ttgagcccga aagagaggat    8700
gccacgtttt cccgacggct gctagaatgg aaaaaggaaa aatagaagaa tcccattcct    8760
atcattattt acgtaatgac ccacacattt ttgagatttt caactattac gtattacgat    8820
aatcctgctg tcattatcat tattatctat atcgacgtat gcaacgtatg tgaagccaag    8880
taggcaatta tttagtactg tcagtattgt tattcatttc agatctatcc gcggtggagc    8940
tcgaattcac tggccgtcgt tttacaacgt cgtgactggg aaaaccctgg cgttacccaa    9000
cttaatcgcc ttgcagcaca tccccctttc gccagctggc gtaatagcga agaggcccgc    9060
accgatcgcc cttcccaaca gttgcgcagc ctgaatggcg aatggcgcct gatgcggtat    9120
tttctcctta cgcatctgtg cggtatttca caccgcatac gtcaaagcaa ccatagtacg    9180
cgccctgtag cggcgcatta agcgcggcgg gtgtggtggt tacgcgcagc gtgaccgcta    9240
cacttgccag cgccttagcg cccgctcctt tcgctttctt cccttccttt ctcgccacgt    9300
tcgccggctt tccccgtcaa gctctaaatc ggggcctccc tttagggttc cgatttagtg    9360
ctttacggca cctcgacccc aaaaaacttg atttgggtga tggttcacgt agtgggccat    9420
cgccctgata gacggttttt cgccctttga cgttggagtc cacgttcttt aatagtggac    9480
tcttgttcca aactggaaca acactcaact ctatctcggg ctattctttt gatttataag    9540
ggattttgcc gatttcggtc tattggttaa aaaatgagct gatttaacaa aaatttaacg    9600
cgaattttaa caaaatatta acgtttacaa ttttatggtg cactctcagt acaatctgct    9660
ctgatgccgc atagttaagc cagccccgac acccgccaac accgctgac  gcgccctgac    9720
gggcttgtct gctcccggca tccgcttaca gacaagctgt gaccgtctcc gggagctgca    9780
tgtgtcagag gttttcaccg tcatcaccga acgcgcgag  acgaaagggc ctcgtgatac    9840
gcctatttt  ataggttaat gtcatgataa taatggtttc ttagacgtca ggtggcactt    9900
ttcggggaaa tgtgcgcgga acccctattt gtttatttt  ctaaatacat tcaaatatgt    9960
atccgctcat gagacaataa ccctgataaa tgcttcaata atattgaaaa aggaagagta   10020
tgagtattca acatttccgt gtcgccctta ttcccttttt tgcggcattt tgccttcctg   10080
tttttgctca cccagaaacg ctggtgaaag taaaagatgc tgaagatcag ttgggtgcac   10140
gagtgggtta catcgaactg gatctcaaca gcggtaagat ccttgagagt tttcgccccg   10200
aagaacgttt tccaatgatg agcactttta aagttctgct atgtggcgcg gtattatccc   10260
gtattgacgc cgggcaagag caactcggtc gccgcataca ctattctcag aatgacttgg   10320
ttgagtactc accagtcaca gaaaagcatc ttacggatgg catgacagta agagaattat   10380
gcagtgctgc cataaccatg agtgataaca ctgcggccaa cttacttctg acaacgatcg   10440
gaggaccgaa ggagctaacc gcttttttgc acaacatggg ggatcatgta actcgccttg   10500
atcgttggga accggagctg aatgaagcca taccaaacga cgagcgtgac accacgatgc   10560
ctgtagcaat ggcaacaacg ttgcgcaaac tattaactgg cgaactactt actctagctt   10620
cccggcaaca attaatagac tggatggagg cggataaagt tgcaggacca cttctgcgct   10680
cggcccttcc ggctggctgg tttattgctg ataaatctgg agccggtgag cgtgggtctc   10740
gcggtatcat tgcagcactg gggccagatg gtaagccctc ccgtatcgta gttatctaca   10800
cgacggggag tcaggcaact atggatgaac gaaatagaca gatcgctgag ataggtgcct   10860
```

```
cactgattaa gcattggtaa ctgtcagacc aagtttactc atatatactt tagattgatt     10920
taaaacttca tttttaattt aaaaggatct aggtgaagat cctttttgat aatctcatga     10980
ccaaaatccc ttaacgtgag ttttcgttcc actgagcgtc agaccccgta gaaaagatca     11040
aaggatcttc ttgagatcct ttttttctgc gcgtaatctg ctgcttgcaa acaaaaaaac     11100
caccgctacc agcggtggtt tgtttgccgg atcaagagct accaactctt tttccgaagg     11160
taactggctt cagcagagcg cagataccaa atactgttct tctagtgtag ccgtagttag     11220
gccaccactt caagaactct gtagcaccgc ctacatacct cgctctgcta atcctgttac     11280
cagtggctgc tgccagtggc gataagtcgt gtcttaccgg gttggactca agacgatagt     11340
taccggataa ggcgcagcgg tcgggctgaa cggggggttc gtgcacacag cccagcttgg     11400
agcgaacgac ctacaccgaa ctgagatacc tacagcgtga gctatgagaa agcgccacgc     11460
ttcccgaagg gagaaaggcg gacaggtatc cggtaagcgg cagggtcgga acaggagagc     11520
gcacgaggga gcttccaggg ggaaacgcct ggtatcttta tagtcctgtc gggtttcgcc     11580
acctctgact tgagcgtcga ttttttgtga tgctcgtcag ggggcggagc ctatggaaaa     11640
acgccagcaa cgcggccttt ttacggttcc tggccttttg ctggccttttt gctcacatgt     11700
tctttcctgc gttatcccct gattctgtgg ataaccgtat taccgccttt gagtgagctg     11760
ataccgctcg ccgcagccga acgaccgagc gcagcgagtc agtgagcgag gaagcggaag     11820
agcgcccaat acgcaaaccg cctctccccg cgcgttggcc gattcattaa tgcagctggc     11880
acgacaggtt tcccgactgg aaagcgggca gtgagcgcaa cgcaattaat gtgagttagc     11940
tcactcatta ggcacccag gctttacact ttatgcttcc ggctcgtatg ttgtgtggaa     12000
ttgtgagcgg ataacaattt cacacaggaa acagctatga ccatgattac gccaagcttt     12060
ttcttttccaa tttttttttt ttcgtcatta taaaaatcat tacgaccgag attcccgggt     12120
aataactgat ataattaaat tgaagctcta atttgtgagt ttagtataca tgcatttact     12180
tataatacag ttttttagtt ttgctggccg catcttctca aatatgcttc ccagcctgct     12240
tttctgtaac gttcaccctc taccttagca tcccttccct ttgcaaatag tcctcttcca     12300
acaataataa tgtcagatcc tgtagagacc acatcatcca cggttctata ctgttgaccc     12360
aatgcgtctc ccttgtcatc taaacccaca ccgggtgtca taatcaacca atcgtaacct     12420
tcatctcttc cacccatgtc tctttgagca ataaagccga taacaaaatc tttgtcgctc     12480
ttcgcaatgt caacagtacc cttagtatat tctccagtag ataggagcc cttgcatgac     12540
aattctgcta acatcaaaag gcctctaggt tcctttgtta cttcttctgc cgcctgcttc     12600
aaaccgctaa caatacctgg gcccaccaca ccgtgtgcat tcgtaatgtc tgcccattct     12660
gctattctgt atacacccgc agagtactgc aatttgactg tattaccaat gtcagcaaat     12720
tttctgtctt cgaagagtaa aaaattgtac ttggcggata atgcctttag cggcttaact     12780
gtgccctcca tggaaaaatc agtcaagata tccacatgtg tttttagtaa acaaattttg     12840
ggacctaatg cttcaactaa ctccagtaat tccttggtgg tacgaacatc caatgaagca     12900
cacaagtttg tttgcttttc gtgcatgata ttaaatagct tggcagcaac aggactagga     12960
tgagtagcag cacgttcctt atatgtagct ttcgacatga tttatcttcg tttcctgcag     13020
gttttttgttc tgtgcagttg ggttaagaat actgggcaat ttcatgtttc ttcaacacta     13080
catatgcgta tatataccaa tctaagtctg tgctccttcc ttcgttcttc cttctgttcg     13140
gagattaccg aatcaaaaaa atttcaagga aaccgaaatc aaaaaaaaga ataaaaaaaa     13200
```

```
aatgatgaat tgaaaagctt gcatgcctgc aggtcgactc tagtatactc cgtctactgt   13260
acgatacact tccgctcagg tccttgtcct ttaacgaggc cttaccactc ttttgttact   13320
ctattgatcc agctcagcaa aggcagtgtg atctaagatt ctatcttcgc gatgtagtaa   13380
aactagctag accgagaaag agactagaaa tgcaaaaggc acttctacaa tggctgccat   13440
cattattatc cgatgtgacg ctgcattttt tttttttttt tttttttttt tttttttttt   13500
tttttttttt ttttttttgta caaatatcat aaaaaaagag aatctttta agcaaggatt   13560 ttcttaactt cttcggcgac agcatcaccg acttcggtgg tactgttgga accacctaaa   13620
tcaccagttc tgatacctgc atccaaaacc ttttaactg catcttcaat ggctttacct   13680
tcttcaggca agttcaatga caatttcaac atcattgcag cagacaagat agtggcgata   13740
gggttgacct tattctttgg caaatctgga gcggaaccat ggcatggttc gtacaaacca   13800
aatgcggtgt tcttgtctgg caaagaggcc aaggacgcag atggcaacaa acccaaggag   13860
cctgggataa cggaggcttc atcggagatg atatccaccaa acatgttgct ggtgattata   13920
ataccattta ggtgggttgg gttcttaact aggatcatgg cggcagaatc aatcaattga   13980
tgttgaactt tcaatgtagg gaattcgttc ttgatggttt cctccacagt tttctccat   14040 aatcttgaag aggccaaaac attagcttta tccaaggacc aaataggcaa tggtggctca   14100
tgttgtaggg ccatgaaagc ggccattctt gtgattcttt gcacttctgg aacggtgtat   14160
tgttcactat cccaagcgac accatcacca tcgtcttcct ttctcttacc aaagtaaata   14220
cctcccacta attctctaac aacaacgaag tcagtacctt tagcaaattg tggcttgatt   14280
ggagataagt ctaaaagaga gtcggatgca aagttcatg gtcttaagtt ggcgtacaat   14340
tgaagttctt tacggatttt tagtaaacct tgttcaggtc taacactacc ggtaccccat   14400
ttaggaccac ccacagcacc taacaaaacg gcatcagcct tcttggaggc ttccagcgcc   14460
tcatctggaa gtggaacacc tgtagcatcg atagcagcac caccaattaa atgattttcg   14520
aaatcgaact tgacattgga acgaacatca gaaatagctt taagaacctt aatggcttcg   14580
gctgtgattt cttgaccaac gtggtcacct ggcaaaacga cgatcttctt aggggcagac   14640
attacaatgg tatatccttg aaatatatat aaaaaaaaaa aaaaaaaaa aaaaaaaaa   14700 tgcagcttct caatgatatt cgaatacgct ttgaggagat acagcctaat atccgacaaa   14760
ctgttttaca gatttacgat cgtacttgtt acccatcatt gaattttgaa catccgaacc   14820
tgggagtttt ccctgaaaca gatagtatat ttgaacctgt ataataatat atagtctagc   14880 gcttacgga agacaatgta tgtatttcgg ttcctggaga aactattgca tctattgcat   14940
aggtaatctt gcacgtcgca tccccggttc attttctgcg tttccatctt gcacttcaat   15000
agcatatctt tgttaacgaa gcatctgtgc ttcattttgt agaacaaaaa tgcaacgcga   15060
gagcgctaat ttttcaaaca aagaatctga gctgcatttt tacagaacag aaatgcaacg   15120
cgaaagcgct attttaccaa cgaagaatct gtgcttcatt tttgtaaaac aaaaatgcaa   15180
cgcgagagcg ctaattttc aaacaaagaa tctgagctgc attttacag aacagaaatg   15240 caacgcgaga gcgctatttt accaacaaag aatctatact tcttttttgt tctacaaaaa   15300
tgcatcccga gagcgctatt tttctaacaa agcatcttag attacttttt ttctcctttg   15360
tgcgctctat aatgcagtct cttgataact ttttgcactg taggtccgtt aaggttagaa   15420
gaaggctact ttggtgtcta ttttctcttc cataaaaaaa gcctgactcc acttcccgcg   15480
tttactgatt actagcgaag ctgcgggtgc attttttcaa gataaaggca tccccgatta   15540
tattctatac cgatgtggat tgcgcatact ttgtgaacag aaagtgatag cgttgatgat   15600
```

```
tcttcattgg tcagaaaatt atgaacggtt tcttctatttt tgtctctata tactacgtat      15660
aggaaatgtt tacattttcg tattgttttc gattcactct atgaatagtt cttactacaa      15720 ttttttttgtc taaagagtaa tactagagat aaacataaaa aatgtagagg tcgagtttag     15780
atgcaagttc aaggagcgaa aggtggatgg gtaggttata tagggatata gcacagagat      15840
atatagcaaa gagatacttt tgagcaatgt ttgtggaagc ggtattcgca atattttagt      15900
agctcgttac agtccggtgc gttttttggtt ttttgaaagt gcgtcttcag agcgttttg     15960 gttttcaaaa gcgctctgaa gttcctatac tttctagaga ataggaactt cggaatagga      16020
acttcaaagc gtttccgaaa acgagcgctt ccgaaaatgc aacgcgagct gcgcacatac      16080
agctcactgt tcacgtcgca cctatatctg cgtgttgcct gtatatatat atacatgaga      16140
agaacggcat agtgcgtgtt tatgcttaaa tgcgtactta tatgcgtcta tttatgtagg     16200
atgaaaggta gtctagtacc tcctgtgata ttatcccatt ccatgcgggg tatcgtatgc      16260
ttccttcagc actaccctttt agctgttcta tatgctgcca ctcctcaatt ggattagtct    16320
catccttcaa tgctatcatt tcctttgata ttggatcata tgcatagtac cgagaaacta     16380
gaggatc                                                               16387

<210> SEQ ID NO 141
<211> LENGTH: 2237
<212> TYPE: DNA
<213> ORGANISM: Artificial sequence
<220> FEATURE:
<223> OTHER INFORMATION: Fragment

<400> SEQUENCE: 141
ttatgtatgc tcttctgact tttcgtgtga tgaggctcgt ggaaaaaatg aataatttat        60
gaatttgaga acaattttgt gttgttacgg tattttacta tggaataatc aatcaattga      120
ggattttatg caaatatcgt ttgaatattt ttccgaccct ttgagtactt ttcttcataa      180
ttgcataata ttgtccgctg cccctttttc tgttagacgg tgtcttgatc tacttgctat      240
cgttcaacac caccttattt tctaactatt tttttttag ctcatttgaa tcagcttatg       300
gtgatggcac attttttgcat aaacctagct gtcctcgttg aacataggaa aaaaaaatat    360
ataaacaagg ctcttttcact ctccttgcaa tcagatttgg gtttgttccc tttatttttca  420 tatttcttgt catattcctt tctcaattat tattttctac tcataacctc acgcaaaata      480
acacagtcaa atcaatcaaa atgactgaca aaaaaactct taaagactta agaaatcgta     540
gttctgttta cgattcaatg gttaaatcac ctaatcgtgc tatgttgcgt gcaactggta      600
tgcaagatga agactttgaa aaacctatcg tcggtgtcat ttcaacttgg gctgaaaaca     660
caccttgtaa tatccactta catgactttg gtaaactagc caaagtcggt gttaaggaag     720
ctggtgcttg gccagttcag ttcggaacaa tcacggtttc tgatggaatc gccatgggaa     780
cccaaggaat gcgtttctcc ttgacatctc gtgatattat tgcagattct attgaagcag     840
ccatgggagg tcataatgcg gatgcttttg tagccattgg cggttgtgat aaaaacatgc     900
ccggttctgt tatcgctatg gctaacatgg atatcccagc cattttttgct tacggcggaa   960 caattgcacc tggtaatttta gacggcaaag atatcgattt agtctctgtc tttgaaggtg   1020
tcggccattg gaaccacggc gatatgacca agaagaagt taaagctttg gaatgtaatg    1080
cttgtcccgg tcctggaggc tgcggtggta tgtatactgc taacacaatg gcgcagcta   1140 ttgaagtttt gggacttagc cttccgggtt catcttctca cccggctgaa tccgcagaaa    1200
```

```
agaaagcaga tattgaagaa gctggtcgcg ctgttgtcaa aatgctcgaa atgggcttaa   1260
aaccttctga cattttaacg cgtgaagctt ttgaagatgc tattactgta actatggctc   1320
tgggaggttc aaccaactca acccttcacc tcttagctat tgcccatgct gctaatgtgg   1380
aattgacact tgatgatttc aatactttcc aagaaaaagt tcctcatttg gctgatttga   1440
aaccttctgg tcaatatgta ttccaagacc tttacaaggt cggaggggta ccagcagtta   1500
tgaaatatct ccttaaaaat ggcttccttc atggtgaccg tatcacttgt actggcaaaa   1560
cagtcgctga aaatttgaag gcttttgatg atttaacacc tggtcaaaag gttattatgc   1620
cgcttgaaaa tcctaaacgt gaagatggtc cgctcattat tctccatggt aacttggctc   1680
cagacggtgc cgttgccaaa gtttctggtg taaaagtgcg tcgtcatgtc ggtcctgcta   1740
aggtctttaa ttctgaagaa gaagccattg aagctgtctt gaatgatgat attgttgatg   1800
gtgatgttgt tgtcgtacgt tttgtaggac caaagggcgg tcctggtatg cctgaaatgc   1860 tttcccttc atcaatgatt gttggtaaag ggcaaggtga aaaagttgcc cttctgacag   1920
atggccgctt ctcaggtggt acttatggtc ttgtcgtggg tcatatcgct cctgaagcac   1980
aagatggcgg tccaatcgcc tacctgcaaa caggagacat agtcactatt gaccaagaca   2040
ctaaggaatt acactttgat atctccgatg aagagttaaa acatcgtcaa gagaccattg   2100
aattgccacc gctctattca cgcggtatcc ttggtaaata tgctcacatc gtttcgtctg   2160
cttctagggg agccgtaaca gacttttgga agcctgaaga aactggcaaa aaatgagcga   2220
tttaatctct aattatt                                                 2237

<210> SEQ ID NO 142
<211> LENGTH: 4420
<212> TYPE: DNA
<213> ORGANISM: Artificial sequence
<220> FEATURE:
<223> OTHER INFORMATION: Cassette

<400> SEQUENCE: 142
ttatgtatgc tcttctgact tttcgtgtga tgaggctcgt ggaaaaaatg aataatttat     60
gaatttgaga acaattttgt gttgttacgg tattttacta tggaataatc aatcaattga    120
ggattttatg caaatatcgt ttgaatattt ttccgaccct ttgagtactt tcttcataa     180 ttgcataata ttgtccgctg ccccttttc tgttagacgg tgtcttgatc tacttgctat    240
cgttcaacac caccttattt tctaactatt ttttttttag ctcatttgaa tcagcttatg    300
gtgatggcac attttttgcat aaacctagct gtcctcgttg aacataggaa aaaaaaatat   360
ataaacaagg ctcttttcact ctccttgcaa tcagatttgg gtttgttccc tttattttca   420 tattttcttgt catattcctt tctcaattat tatttctac tcataacctc acgcaaaata    480
acacagtcaa atcaatcaaa atgactgaca aaaaaactct taagactta agaaatcgta    540 gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca    660
caccttgtaa tatccactta catgactttg gtaaactagc caaagtcggt gttaaggaag    720
ctggtgcttg gccagttcag ttcggaacaa tcacggtttc tgatgggaatc gccatgggaa   780 cccaaggaat gcgtttctcc ttgacatctc gtgatattat tgcagattct attgaagcag    840
ccatgggagg tcataatgcg gatgcttttg tagccattgg cggttgtgat aaaaacatgc    900
ccggttctgt tatcgctatg gctaacatgg atatcccagc catttttgct tacggcggaa    960
caattgcacc tggtaattta gacggcaaag atatcgattt agtctctgtc tttgaaggtg   1020
```

```
tcggccattg gaaccacggc gatatgacca agaagaagt taaagctttg gaatgtaatg    1080
cttgtcccgg tcctggaggc tgcggtggta tgtatactgc taacacaatg gcgacagcta    1140
ttgaagtttt gggacttagc cttccgggtt catcttctca cccggctgaa tccgcagaaa    1200
agaaagcaga tattgaagaa gctggtcgcg ctgttgtcaa aatgctcgaa atgggcttaa    1260
aaccttctga cattttaacg cgtgaagctt ttgaagatgc tattactgta actatggctc    1320
tgggaggttc aaccaactca acccttcacc tcttagctat tgcccatgct gctaatgtgg    1380
aattgacact tgatgatttc aatactttcc aagaaaagt tcctcatttg gctgatttga    1440
aaccttctgg tcaatatgta ttccaagacc tttacaaggt cggaggggta ccagcagtta    1500
tgaaatatct ccttaaaaat ggcttccttc atggtgaccg tatcacttgt actggcaaaa    1560
cagtcgctga aaatttgaag gcttttgatg atttaacacc tggtcaaaag gttattatgc    1620
cgcttgaaaa tcctaaacgt gaagatggtc cgctcattat tctccatggt aacttggctc    1680
cagacggtgc cgttgccaaa gtttctggtg taaaagtgcg tcgtcatgtc ggtcctgcta    1740
aggtctttaa ttctgaagaa gaagccattg aagctgtctt gaatgatgat attgttgatg    1800
gtgatgttgt tgtcgtacgt tttgtaggac caaagggcgg tcctggtatg cctgaaatgc    1860
tttccctttc atcaatgatt gttggtaaag ggcaaggtga aaaagttgcc cttctgacag    1920
atggccgctt ctcaggtggt acttatggtc ttgtcgtggg tcatatcgct cctgaagcac    1980
aagatggcgg tccaatcgcc tacctgcaaa caggagacat agtcactatt gaccaagaca    2040
ctaaggaatt acactttgat atctccgatg aagagttaaa acatcgtcaa gagaccattg    2100
aattgccacc gctctattca cgcggtatcc ttggtaaata tgctcacatc gtttcgtctg    2160
cttctagggg agccgtaaca gacttttgga agcctgaaga aactggcaaa aaatgagcga    2220
tttaatctct aattattagt taaagtttta taagcatttt tatgtaacga aaaataaatt    2280
ggttcatatt attactgcac tgtcacttac catggaaaga ccagacaaga agttgccgac    2340
agtctgttga attggcctgg ttaggcttaa gtctgggtcc gcttctttac aaatttggag    2400
aatttctctt aaacgatatg tatattcttt tcgttggaaa agatgtcttc caaaaaaaaa    2460
accgatgaat tagtggaacc aaggaaaaaa aaagaggtat ccttgattaa ggaacactgt    2520
ttaaacagtg tggttccaa aaccctgaaa ctgcattagt gtaatagaag actagacacc    2580
tcgatacaaa taatggttac tcaattcaaa actgccagcg aattcgactc tgcaattgct    2640
caagacaagc tagttgtcgt agatttctac gcccacttggt gcggtccatg taaaatgatt    2700
gctccaatga ttgaaaaatg tggctgtggt ttcagggtcc ataaagcttt tcaattcatc    2760
tttttttttt ttgttctttt ttttgattcc ggtttctttg aaatttttt gattcggtaa    2820 tctccgagca aaggaagaa cgaaggaagg agcacagact tagattggta tatatacgca    2880
tatgtggtgt tgaagaaaca tgaaattgcc cagtattctt aacccaactg cacagaacaa    2940
aaacctgcag gaaacgaaga taatcatgt cgaaagctac atataaggaa cgtgctgcta    3000
ctcatcctag tcctgttgct gccaagctat ttaatatcat gcacgaaaag caaacaaact    3060
tgtgtgcttc attggatgtt cgtaccacca aggaattact ggagttagtt gaagcattag    3120
gtcccaaaat ttgtttacta aaaacacatg tggatatctt gactgatttt tccatggagg    3180
gcacagttaa gccgctaaag gcattatccg ccaagtacaa ttttttactc ttcgaagaca    3240
gaaaatttgc tgacattggt aatacagtca aattgcagta ctctgcgggt gtatacagaa    3300
tagcagaatg ggcagacatt acgaatgcac acggtgtggt gggcccaggt attgttagcg    3360
```

```
gtttgaagca ggcggcggaa gaagtaacaa aggaacctag aggccttttg atgttagcag    3420
aattgtcatg caagggctcc ctagctactg gagaatatac taagggtact gttgacattg    3480
cgaagagcga caaagatttt gttatcggct ttattgctca aagagacatg ggtggaagag    3540
atgaaggtta cgattggttg attatgacac ccggtgtggg tttagatgac aagggagacg    3600
cattgggtca acagtataga accgtggatg atgtggtctc tacaggatct gacattatta    3660
ttgttggaag aggactattt gcaaagggaa gggatgctaa ggtagagggt gaacgttaca    3720
gaaaagcagg ctgggaagca tatttgagaa gatgcggcca gcaaaactaa aaaactgtat    3780
tataagtaaa tgcatgtata ctaaactcac aaattagagc ttcaatttaa ttatatcagt    3840
tattacccgg gaatctcggt cgtaatgatt tctataatga cgaaaaaaaa aaaattggaa    3900
agaaaaagct tcatggcctt ccactttccc aaacaacacc tacggtatct ctcaagtctt    3960
atggggttcc attggtttca ccactggtgc taccttgggt gctgctttcg ctgctgaaga    4020
aattgatcca agaagagag ttatcttatt cattggtgac ggttcttttgc aattgactgt    4080 tcaagaaatc tccaccatga tcagatgggg cttgaagcca tacttgttcg tcttgaacaa    4140
cgatggttac accattgaaa agttgattca cggtccaaag gctcaataca acgaaattca    4200
aggttgggac cacctatcct tgttgccaac tttcggtgct aaggactatg aaacccacag    4260
agtcgctacc accggtgaat gggacaagtt gacccaagac aagtctttca cgacaactc    4320 taagatcaga atgattgaaa tcatgttgcc agtcttcgat gctccacaaa acttggttga    4380
acaagctaag ttgactgctg ctaccaacgc taagcaataa                            4420

<210> SEQ ID NO 143
<211> LENGTH: 3521
<212> TYPE: DNA
<213> ORGANISM: Artificial sequence
<220> FEATURE:
<223> OTHER INFORMATION: Cassette

<400> SEQUENCE: 143
aaggaaataa agcaaataac aataacacca ttattttaat tttttttcta ttactgtcgc      60
taacacctgt atggttgcaa ccaggtgaga atccttctga tgcatacttt atgcgtttat     120
gcgttttgcg ccccttggaa aaaaattgat tctcatcgta aatgcatact acatgcgttt     180
atgggaaaag cctccatatc caaggtcgc gtttctttta gaaaaactaa tacgtaaacc     240
tgcattaagg taagattata tcagaaaatg tgttgcaaga aatgcattat gcaattttt     300 gattatgaca atctctcgaa agaaatttca tatgatgaga cttgaataat gcagcggcgc     360
ttgctaaaag aacttgtata taagagctgc cattctcgat caatatactg tagtaagtcc     420
tttcctctct ttcttattac acttatttca cataatcaat ctcaaagaga acaacacaat     480
acaataacaa gaagaacaaa atgaaagctc tggtttatca cggtgaccac aagatctcgc     540
ttgaagacaa gcccaagccc acccttcaaa agcccacgga tgtagtagta cgggttttga     600
agaccacgat ctgcggcacg gatctcggca tctacaaagg caagaatcca gaggtcgccg     660
acgggcgcat cctgggccat gaaggggtag gcgtcatcga ggaagtgggc gagagtgtca     720
cgcagttcaa gaaaggcgac aaggtcctga tttcctgcgt cacttcttgc ggctcgtgcg     780
actactgcaa gaagcagctt tactcccatt gccgcgacgg cggtggatc ctgggttaca     840 tgatcgatgg cgtgcaggcc gaatacgtcc gcatcccgca tgccgacaac agcctctaca     900 agatcccca gacaattgac gacgaaatcg ccgtcctgct gagcgacatc ctgcccaccg     960
gccacgaaat cggcgtccag tatgggaatg tccagccggg cgatgcggtg ctattgtcg    1020
```

```
gcgcgggccc cgtcggcatg tccgtactgt tgaccgccca gttctactcc ccctcgacca   1080
tcatcgtgat cgacatggac gagaatcgcc tccagctcgc caaggagctc ggggcaacgc   1140
acaccatcaa ctccggcacg gagaacgttg tcgaagccgt gcataggatt gcggcagagg   1200
gagtcgatgt tgcgatcgag gcggtgggca taccggcgac ttgggacatc tgccaggaga   1260
tcgtcaagcc cggcgcgcac atcgccaacg tcggcgtgca tggcgtcaag gttgacttcg   1320
agattcagaa gctctggatc aagaacctga cgatcaccac gggactggtg aacacgaaca   1380
cgacgcccat gctgatgaag gtcgcctcga ccgacaagct tccgttgaag aagatgatta   1440
cccatcgctt cgagctggcc gagatcgagc acgcctatca ggtattcctc aatggcgcca   1500
aggagaaggc gatgaagatc atcctctcga acgcaggcgc tgcctgagct aattaacata   1560
aaactcatga ttcaacgttt gtgtattttt ttacttttga aggttataga tgtttaggta   1620
aataattggc atagatatag ttttagtata ataaatttct gatttggttt aaaatatcaa   1680 ctatttttt tcacatatgt tcttgtaatt acttttctgt cctgtcttcc aggttaaaga   1740
ttagcttcta atattttagg tggtttatta tttaattta tgctgattaa tttatttact   1800
tgtttaaacg gccggccaat gtggctgtgg tttcagggtc cataaagctt ttcaattcat   1860
cttttttttt tttgttcttt tttttgattc cggtttcttt gaaattttt tgattcggta   1920 atctccgagc agaaggaaga acgaaggaag gagcacagac ttagattggt atatatacgc   1980
atatgtggtg ttgaagaaac atgaaattgc ccagtattct taacccaact gcacagaaca   2040
aaaacctgca ggaaacgaag ataaatcatg tcgaaagcta catataagga acgtgctgct   2100
actcatccta gtcctgttgc tgccaagcta tttaatatca tgcacgaaaa gcaaacaaac   2160
ttgtgtgctt cattggatgt tcgtaccacc aaggaattac tggagttagt tgaagcatta   2220
ggtcccaaaa tttgtttact aaaaacacat gtggatatct tgactgattt ttccatggag   2280
ggcacagtta agccgctaaa ggcattatcc gccaagtaca attttttact cttcgaagac   2340
agaaaatttg ctgacattgg taatacagtc aaattgcagt actctgcggg tgtatacaga   2400
atagcagaat gggcagacat tacgaatgca cacggtgtgg tgggcccagg tattgttagc   2460
ggtttgaagc aggcggcgga agaagtaaca aaggaaccta gaggcctttt gatgttagca   2520
gaattgtcat gcaagggctc cctagctact ggagaatata ctaagggtac tgttgacatt   2580
gcgaagagcg acaaagattt tgttatcggc tttattgctc aaagagacat gggtggaaga   2640
gatgaaggtt acgattggtt gattatgaca cccggtgtgg gtttagatga caagggagac   2700
gcattgggtc aacagtatag aaccgtggat gatgtggtct ctacaggatc tgacattatt   2760
attgttggaa gaggactatt tgcaagggga agggatgcta aggtagaggg tgaacgttac   2820
agaaaagcag gctgggaagc atatttgaga agatgcggcc agcaaaacta aaaaactgta   2880
ttataagtaa atgcatgtat actaaactca caaattagag cttcaattta attatatcag   2940
ttattacccg ggaatctcgg tcgtaatgat ttctataatg acgaaaaaaa aaaaattgga   3000
aagaaaaagc ttcatggcct tctactttcc caacagatgt atacgctatc gtccaagtct   3060 tgtgggttc cattggtttc acagtcggcg ctctattggg tgctactatg gccgctgaag   3120
aacttgatcc aaagaagaga gttatttat tcattggtga cggttctcta caattgactg   3180
ttcaagaaat ctctaccatg attagatggg gtttgaagcc atacattttt gtcttgaata   3240
acaacggtta caccattgaa aaattgattc acggtcctca tgccgaatat aatgaaattc   3300
aaggttggga ccacttggcc ttattgccaa cttttggtgc tagaaactac gaaacccaca   3360
```

```
gagttgctac cactggtgaa tgggaaaagt tgactcaaga caaggacttc caagacaact    3420
ctaagattag aatgattgaa gttatgttgc cagtctttga tgctccacaa aacttggtta    3480
aacaagctca attgactgcc gctactaacg ctaaacaata a                       3521
```

<210> SEQ ID NO 144
<211> LENGTH: 571
<212> TYPE: PRT
<213> ORGANISM: Bacillus subtilis

<400> SEQUENCE: 144

```
Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350
```

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 145
<211> LENGTH: 340
<212> TYPE: PRT
<213> ORGANISM: Lactococcus lactis

<400> SEQUENCE: 145

Met Ala Val Thr Met Tyr Tyr Glu Asp Asp Val Glu Val Ser Ala Leu
1               5                   10                  15

Ala Gly Lys Gln Ile Ala Val Ile Gly Tyr Gly Ser Gln Gly His Ala
            20                  25                  30

His Ala Gln Asn Leu Arg Asp Ser Gly His Asn Val Ile Ile Gly Val
        35                  40                  45

Arg His Gly Lys Ser Phe Asp Lys Ala Lys Glu Asp Gly Phe Glu Thr
    50                  55                  60

Phe Glu Val Gly Glu Ala Val Ala Lys Ala Asp Val Ile Met Val Leu
65                  70                  75                  80

Ala Pro Asp Glu Leu Gln Gln Ser Ile Tyr Glu Glu Asp Ile Lys Pro
                85                  90                  95

Asn Leu Lys Ala Gly Ser Ala Leu Gly Phe Ala His Gly Phe Asn Ile
            100                 105                 110

His Phe Gly Tyr Ile Lys Val Pro Glu Asp Val Asp Val Phe Met Val
        115                 120                 125

Ala Pro Lys Ala Pro Gly His Leu Val Arg Arg Thr Tyr Thr Glu Gly
    130                 135                 140

Phe Gly Thr Pro Ala Leu Phe Val Ser His Gln Asn Ala Ser Gly His

```
                145                 150                 155                 160
Ala Arg Glu Ile Ala Met Asp Trp Ala Lys Gly Ile Gly Cys Ala Arg
            165                 170                 175
Val Gly Ile Ile Glu Thr Thr Phe Lys Glu Thr Glu Glu Asp Leu
        180                 185                 190
Phe Gly Glu Gln Ala Val Leu Cys Gly Gly Leu Thr Ala Leu Val Glu
        195                 200                 205
Ala Gly Phe Glu Thr Leu Thr Glu Ala Gly Tyr Ala Gly Glu Leu Ala
        210                 215                 220
Tyr Phe Glu Val Leu His Glu Met Lys Leu Ile Val Asp Leu Met Tyr
225                 230                 235                 240
Glu Gly Gly Phe Thr Lys Met Arg Gln Ser Ile Ser Asn Thr Ala Glu
            245                 250                 255
Phe Gly Asp Tyr Val Thr Gly Pro Arg Ile Ile Thr Asp Glu Val Lys
        260                 265                 270
Lys Asn Met Lys Leu Val Leu Ala Asp Ile Gln Ser Gly Lys Phe Ala
        275                 280                 285
Gln Asp Phe Val Asp Asp Phe Lys Ala Gly Arg Pro Lys Leu Ile Ala
        290                 295                 300
Tyr Arg Glu Ala Ala Lys Asn Leu Glu Ile Glu Lys Ile Gly Ala Glu
305                 310                 315                 320
Leu Arg Gln Ala Met Pro Phe Thr Gln Ser Gly Asp Asp Ala Phe
            325                 330                 335
Lys Ile Tyr Gln
            340

<210> SEQ ID NO 146
<211> LENGTH: 571
<212> TYPE: PRT
<213> ORGANISM: Streptococcus mutans

<400> SEQUENCE: 146

Met Thr Asp Lys Lys Thr Leu Lys Asp Leu Arg Asn Arg Ser Ser Val
1               5                   10                  15
Tyr Asp Ser Met Val Lys Ser Pro Asn Arg Ala Met Leu Arg Ala Thr
            20                  25                  30
Gly Met Gln Asp Glu Asp Phe Glu Lys Pro Ile Val Gly Val Ile Ser
        35                  40                  45
Thr Trp Ala Glu Asn Thr Pro Cys Asn Ile His Leu His Asp Phe Gly
    50                  55                  60
Lys Leu Ala Lys Val Gly Val Lys Glu Ala Gly Ala Trp Pro Val Gln
65                  70                  75                  80
Phe Gly Thr Ile Thr Val Ser Asp Gly Ile Ala Met Gly Thr Gln Gly
                85                  90                  95
Met Arg Phe Ser Leu Thr Ser Arg Asp Ile Ile Ala Asp Ser Ile Glu
            100                 105                 110
Ala Ala Met Gly Gly His Asn Ala Asp Ala Phe Val Ala Ile Gly Gly
        115                 120                 125
Cys Asp Lys Asn Met Pro Gly Ser Val Ile Ala Met Ala Asn Met Asp
    130                 135                 140
Ile Pro Ala Ile Phe Ala Tyr Gly Gly Thr Ile Ala Pro Gly Asn Leu
145                 150                 155                 160
Asp Gly Lys Asp Ile Asp Leu Val Ser Val Phe Glu Gly Val Gly His
                165                 170                 175
```

Trp Asn His Gly Asp Met Thr Lys Glu Val Lys Ala Leu Glu Cys
                180                 185                 190

Asn Ala Cys Pro Gly Pro Gly Cys Gly Gly Met Tyr Thr Ala Asn
            195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Lys Met Leu Glu Met Gly Leu Lys Pro Ser
                245                 250                 255

Asp Ile Leu Thr Arg Glu Ala Phe Glu Asp Ala Ile Thr Val Thr Met
                260                 265                 270

Ala Leu Gly Gly Ser Thr Asn Ser Thr Leu His Leu Leu Ala Ile Ala
                275                 280                 285

His Ala Ala Asn Val Glu Leu Thr Leu Asp Asp Phe Asn Thr Phe Gln
290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
                340                 345                 350

Lys Thr Val Ala Glu Asn Leu Lys Ala Phe Asp Asp Leu Thr Pro Gly
                355                 360                 365

Gln Lys Val Ile Met Pro Leu Glu Asn Pro Lys Arg Glu Asp Gly Pro
                370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
                420                 425                 430

Asp Gly Asp Val Val Val Arg Phe Val Gly Pro Lys Gly Gly Pro
                435                 440                 445

Gly Met Pro Glu Met Leu Ser Leu Ser Ser Met Ile Val Gly Lys Gly
450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
                500                 505                 510

Asp Thr Lys Glu Leu His Phe Asp Ile Ser Asp Glu Glu Leu Lys His
                515                 520                 525

Arg Gln Glu Thr Ile Glu Leu Pro Pro Leu Tyr Ser Arg Gly Ile Leu
                530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570

<210> SEQ ID NO 147
<211> LENGTH: 548
<212> TYPE: PRT

-continued

<213> ORGANISM: Lactococcus lactis

<400> SEQUENCE: 147

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

```
Trp Gly Ser Ile Gly Tyr Thr Phe Pro Ala Leu Gly Ser Gln Ile
                405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 148
<211> LENGTH: 375
<212> TYPE: PRT
<213> ORGANISM: Equus caballus

<400> SEQUENCE: 148

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
            20                  25                  30

Lys Ala His Glu Val Arg Ile Lys Met Val Ala Thr Gly Ile Cys Arg
        35                  40                  45

Ser Asp Asp His Val Val Ser Gly Thr Leu Val Thr Pro Leu Pro Val
    50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220
```

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
            245                 250                 255

Glu Met Ser Asn Gly Gly Val Asp Phe Ser Phe Glu Val Ile Gly Arg
        260                 265                 270

Leu Asp Thr Met Val Thr Ala Leu Ser Cys Cys Gln Glu Ala Tyr Gly
    275                 280                 285

Val Ser Val Ile Val Gly Val Pro Pro Asp Ser Gln Asn Leu Ser Met
290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
            325                 330                 335

Met Ala Lys Lys Phe Ala Leu Asp Pro Leu Ile Thr His Val Leu Pro
        340                 345                 350

Phe Glu Lys Ile Asn Glu Gly Phe Asp Leu Leu Arg Ser Gly Glu Ser
    355                 360                 365

Ile Arg Thr Ile Leu Thr Phe
370                 375

<210> SEQ ID NO 149
<211> LENGTH: 348
<212> TYPE: PRT
<213> ORGANISM: Achromobacter xylosoxidans

<400> SEQUENCE: 149

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val

```
Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
            245                 250                 255

Pro Gly Ala His Ile Ala Asn Val Gly Val His Gly Val Lys Val Asp
        260                 265                 270

Phe Glu Ile Gln Lys Leu Trp Ile Lys Asn Leu Thr Ile Thr Thr Gly
    275                 280                 285

Leu Val Asn Thr Asn Thr Thr Pro Met Leu Met Lys Val Ala Ser Thr
290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345
```

<210> SEQ ID NO 150
<211> LENGTH: 2686
<212> TYPE: DNA
<213> ORGANISM: Artificial sequence
<220> FEATURE:
<223> OTHER INFORMATION: Plasmid

<400> SEQUENCE: 150

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cgagctcggt | acccggggat | 420 |
| cctctagagt | cgacctgcag | gcatgcaagc | ttggcgtaat | catggtcata | gctgtttcct | 480 |
| gtgtgaaatt | gttatccgct | cacaattcca | cacaacatac | gagccggaag | cataaagtgt | 540 |
| aaagcctggg | gtgcctaatg | agtgagctaa | ctcacattaa | ttgcgttgcg | ctcactgccc | 600 |
| gctttccagt | cgggaaacct | gtcgtgccag | ctgcattaat | gaatcggcca | acgcgcgggg | 660 |
| agaggcggtt | tgcgtattgg | gcgctcttcc | gcttcctcgc | tcactgactc | gctgcgctcg | 720 |
| gtcgttcggc | tgcggcgagc | ggtatcagct | cactcaaagg | cggtaatacg | gttatccaca | 780 |
| gaatcagggg | ataacgcagg | aaagaacatg | tgagcaaaag | gccagcaaaa | ggccaggaac | 840 |
| cgtaaaaagg | ccgcgttgct | ggcgtttttc | cataggctcc | gcccccctga | cgagcatcac | 900 |
| aaaaatcgac | gctcaagtca | gaggtggcga | aacccgacag | gactataaag | ataccaggcg | 960 |
| tttccccctg | gaagctccct | cgtgcgctct | cctgttccga | ccctgccgct | taccggatac | 1020 |
| ctgtccgcct | ttctcccttc | gggaagcgtg | gcgctttctc | atagctcacg | ctgtaggtat | 1080 |
| ctcagttcgg | tgtaggtcgt | tcgctccaag | ctgggctgtg | tgcacgaacc | cccgttcag | 1140 |
| cccgaccgct | gcgccttatc | cggtaactat | cgtcttgagt | ccaacccggt | aagacacgac | 1200 |
| ttatcgccac | tggcagcagc | cactggtaac | aggattagca | gagcgaggta | tgtaggcggt | 1260 |
| gctacagagt | tcttgaagtg | gtggcctaac | tacggctaca | ctagaaggac | agtatttggt | 1320 |

```
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatccccat gttgtgcaaa     2040 aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacggga ataccgcgc cacatagcag aactttaaaa      2280
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttcctttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                   2686
```

<210> SEQ ID NO 151
<211> LENGTH: 1685
<212> TYPE: DNA
<213> ORGANISM: Artificial sequence
<220> FEATURE:
<223> OTHER INFORMATION: Cassette

<400> SEQUENCE: 151

```
gtattttggt agattcaatt ctctttccct ttccttttcc ttcgctcccc ttccttatca      60
gcattgcgga ttacgtattc taatgttcag ataacttcgt atagcataca ttatacgaag    120
ttatgcagat tgtactgaga gtgcaccata ccacagcttt tcaattcaat tcatcatttt    180
ttttttattc ttttttttga tttcggtttc tttgaaattt ttttgattcg gtaatctccg    240
aacagaagga agaacgaagg aaggagcaca gacttagatt ggtatatata cgcatatgta    300
gtgttgaaga acatgaaat tgcccagtat tcttaaccca actgcacaga acaaaaacct     360
gcaggaaacg aagataaatc atgtcgaaag ctacatataa ggaacgtgct gctactcatc    420
ctagtcctgt tgctgccaag ctatttaata tcatgcacga aaagcaaaca aacttgtgtg    480
cttcattgga tgttcgtacc accaaggaat tactggagtt agttgaagca ttaggtccca    540
aaatttgttt actaaaaaca catgtggata tcttgactga tttttccatg gagggcacag    600
ttaagccgct aaaggcatta tccgccaagt acaatttttt actcttcgaa gacagaaaat    660
```

-continued

| | |
|---|---|
| ttgctgacat tggtaataca gtcaaattgc agtactctgc gggtgtatac agaatagcag | 720 |
| aatgggcaga cattacgaat gcacacggtg tggtgggccc aggtattgtt agcggtttga | 780 |
| agcaggcggc agaagaagta acaaaggaac ctagaggcct tttgatgtta gcagaattgt | 840 |
| catgcaaggg ctccctatct actggagaat atactaaggg tactgttgac attgcgaaga | 900 |
| gcgacaaaga ttttgttatc ggctttattg ctcaaagaga catgggtgga agagatgaag | 960 |
| gttacgattg gttgattatg acacccggtg tgggtttaga tgacaaggga gacgcattgg | 1020 |
| gtcaacagta tagaaccgtg gatgatgtgg tctctacagg atctgacatt attattgttg | 1080 |
| gaagaggact atttgcaaag ggaagggatg ctaaggtaga gggtgaacgt tacagaaaag | 1140 |
| caggctggga agcatatttg agaagatgcg gccagcaaaa ctaaaaaact gtattataag | 1200 |
| taaatgcatg tatactaaac tcacaaatta gagcttcaat ttaattatat cagttattac | 1260 |
| cctatgcggt gtgaaatacc gcacagatgc gtaaggagaa ataccgcat caggaaattg | 1320 |
| taaacgttaa tattttgtta aaattcgcgt taaattttg ttaaatcagc tcatttttta | 1380 |
| accaataggc cgaaatcggc aaaatccctt ataaatcaaa agaatagacc gagataqggt | 1440 |
| tgagtgttgt tccagtttgg aacaagagtc cactattaaa gaacgtggac tccaacgtca | 1500 |
| aagggcgaaa aaccgtctat cagggcgatg gcccactacg tgaaccatca ccctaatcaa | 1560 |
| gataacttcg tatagcatac attatacgaa gttatccagt gatgatacaa cgagttagcc | 1620 |
| aaggtgacac tctcccccccc cctcccccctc tgatctttcc tgttgcctct tttccccca | 1680 |
| accaa | 1685 |

<210> SEQ ID NO 152
<211> LENGTH: 22
<212> TYPE: DNA
<213> ORGANISM: Artificial Sequence
<220> FEATURE:
<223> OTHER INFORMATION: Primer oBP594

<400> SEQUENCE: 152

| | |
|---|---|
| agctgtctcg tgttgtgggt tt | 22 |

<210> SEQ ID NO 153
<211> LENGTH: 49
<212> TYPE: DNA
<213> ORGANISM: Artificial Sequence
<220> FEATURE:
<223> OTHER INFORMATION: Primer oBP595

<400> SEQUENCE: 153

| | |
|---|---|
| cttaataata gaacaatatc atcctttacg ggcatcttat agtgtcgtt | 49 |

<210> SEQ ID NO 154
<211> LENGTH: 49
<212> TYPE: DNA
<213> ORGANISM: Artificial Sequence
<220> FEATURE:
<223> OTHER INFORMATION: Primer oBP596

<400> SEQUENCE: 154

| | |
|---|---|
| gcgccaacga cactataaga tgcccgtaaa ggatgatatt gttctatta | 49 |

<210> SEQ ID NO 155
<211> LENGTH: 49
<212> TYPE: DNA
<213> ORGANISM: Artificial Sequence
<220> FEATURE:
<223> OTHER INFORMATION: Primer oBP597

<400> SEQUENCE: 155
tatggaccct gaaaccacag ccacattgca acgacgacaa tgccaaacc         49

<210> SEQ ID NO 156
<211> LENGTH: 49
<212> TYPE: DNA
<213> ORGANISM: Artificial Sequence
<220> FEATURE:
<223> OTHER INFORMATION: Primer oBP598

<400> SEQUENCE: 156
tccttggttt ggcattgtcg tcgttgcaat gtggctgtgg tttcagggt         49

<210> SEQ ID NO 157
<211> LENGTH: 49
<212> TYPE: DNA
<213> ORGANISM: Artificial Sequence
<220> FEATURE:
<223> OTHER INFORMATION: Primer oBP599

<400> SEQUENCE: 157
atcctctcgc ggagtccctg ttcagtaaag gccatgaagc ttttttcttt         49

<210> SEQ ID NO 158
<211> LENGTH: 49
<212> TYPE: DNA
<213> ORGANISM: Artificial Sequence
<220> FEATURE:
<223> OTHER INFORMATION: Primer oBP600

<400> SEQUENCE: 158
attggaaaga aaaagcttca tggcctttac tgaacaggga ctccgcgag         49

<210> SEQ ID NO 159
<211> LENGTH: 22
<212> TYPE: DNA
<213> ORGANISM: Artificial Sequence
<220> FEATURE:
<223> OTHER INFORMATION: Primer oBP601

<400> SEQUENCE: 159
tcataccaca atcttagacc at         22

<210> SEQ ID NO 160
<211> LENGTH: 21
<212> TYPE: DNA
<213> ORGANISM: Artificial Sequence
<220> FEATURE:
<223> OTHER INFORMATION: Primer oBP602

<400> SEQUENCE: 160
tgttcaaacc cctaaccaac c         21

<210> SEQ ID NO 161
<211> LENGTH: 22
<212> TYPE: DNA
<213> ORGANISM: Artificial Sequence
<220> FEATURE:
<223> OTHER INFORMATION: Primer oBP603

<400> SEQUENCE: 161
tgttcccaca atctattacc ta         22

<210> SEQ ID NO 162

```
<211> LENGTH: 21
<212> TYPE: DNA
<213> ORGANISM: Artificial Sequence
<220> FEATURE:
<223> OTHER INFORMATION: Primer oBP605

<400> SEQUENCE: 162
tactgaacag ggactccgcg a                                             21

<210> SEQ ID NO 163
<211> LENGTH: 21
<212> TYPE: DNA
<213> ORGANISM: Artificial Sequence
<220> FEATURE:
<223> OTHER INFORMATION: Primer oBP606

<400> SEQUENCE: 163
tcataccaca atcttagacc a                                             21

<210> SEQ ID NO 164
<211> LENGTH: 34
<212> TYPE: DNA
<213> ORGANISM: Artificial Sequence
<220> FEATURE:
<223> OTHER INFORMATION: Primer oBP562

<400> SEQUENCE: 164
aattgtttaa acatgtatac agtaggtgac tatc                               34

<210> SEQ ID NO 165
<211> LENGTH: 49
<212> TYPE: DNA
<213> ORGANISM: Artificial Sequence
<220> FEATURE:
<223> OTHER INFORMATION: Primer oBP563

<400> SEQUENCE: 165
aatcataaat cataagaaat tcgcttatca gctcttgttt tgttctgca               49

<210> SEQ ID NO 166
<211> LENGTH: 49
<212> TYPE: DNA
<213> ORGANISM: Artificial Sequence
<220> FEATURE:
<223> OTHER INFORMATION: Primer oBP564

<400> SEQUENCE: 166
ttatttgcag aacaaaacaa gagctgataa gcgaatttct tatgattta               49

<210> SEQ ID NO 167
<211> LENGTH: 34
<212> TYPE: DNA
<213> ORGANISM: Artificial Sequence
<220> FEATURE:
<223> OTHER INFORMATION: Primer oBP565

<400> SEQUENCE: 167
aattggccgg ccaaaaaaag catgcacgta taca                               34

<210> SEQ ID NO 168
<211> LENGTH: 32
<212> TYPE: DNA
<213> ORGANISM: Artificial Sequence
<220> FEATURE:
<223> OTHER INFORMATION: Primer oBP505

<400> SEQUENCE: 168
```

-continued

```
aattgagctc actgtagccc tagacttgat ag                                        32
```

<210> SEQ ID NO 169
<211> LENGTH: 35
<212> TYPE: DNA
<213> ORGANISM: Artificial Sequence
<220> FEATURE:
<223> OTHER INFORMATION: Primer oBP506

<400> SEQUENCE: 169

```
aattggcgcg cctgtatatg agatagttga ttgta                                     35
```

<210> SEQ ID NO 170
<211> LENGTH: 35
<212> TYPE: DNA
<213> ORGANISM: Artificial Sequence
<220> FEATURE:
<223> OTHER INFORMATION: Primer oBP507

<400> SEQUENCE: 170

```
aattttaatt aagtctaggt tctttggctg ttcaa                                     35
```

<210> SEQ ID NO 171
<211> LENGTH: 33
<212> TYPE: DNA
<213> ORGANISM: Artificial Sequence
<220> FEATURE:
<223> OTHER INFORMATION: Primer oBP508

<400> SEQUENCE: 171

```
aattgtcgac tttagaagtg tcaacaacgt atc                                       33
```

<210> SEQ ID NO 172
<211> LENGTH: 8366
<212> TYPE: DNA
<213> ORGANISM: Artificial Sequence
<220> FEATURE:
<223> OTHER INFORMATION: pRS316-UAS(PGK1)-PFBA1-GUS

<400> SEQUENCE: 172

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accacgcttt tcaattcaat tcatcatttt ttttttattc ttttttttga tttcggtttc   240
tttgaaattt ttttgattcg gtaatctccg aacagaagga agaacgaagg aaggagcaca   300
gacttagatt ggtatatata cgcatatgta gtgttgaaga acatgaaat tgcccagtat    360
tcttaaccca actgcacaga acaaaaacct gcaggaaacg aagataaatc atgtcgaaag   420
ctacatataa ggaacgtgct gctactcatc ctagtcctgt tgctgccaag ctatttaata   480
tcatgcacga aaagcaaaca aacttgtgtg cttcattgga tgttcgtacc accaaggaat   540
tactggagtt agttgaagca ttaggtccca aaatttgttt actaaaaaca catgtggata   600
tcttgactga ttttttccatg gagggcacag ttaagccgct aaaggcatta tccgccaagt   660
acaatttttt actcttcgaa gacagaaaat ttgctgacat tggtaataca gtcaaattgc    720
agtactctgc gggtgtatac agaatagcag aatgggcaga cattacgaat gcacacggtg    780
tggtgggccc aggtattgtt agcggtttga agcaggcggc agaagaagta acaaaggaac   840
ctagaggcct tttgatgtta gcagaattgt catgcaaggg ctccctatct actggagaat   900
```

```
atactaaggg tactgttgac attgcgaaga gcgacaaaga ttttgttatc ggctttattg    960
ctcaaagaga catgggtgga agagatgaag gttacgattg gttgattatg acacccggtg   1020
tgggtttaga tgacaaggga gacgcattgg gtcaacagta tagaaccgtg gatgatgtgg   1080
tctctacagg atctgacatt attattgttg gaagaggact atttgcaaag gaagggatg    1140
ctaaggtaga gggtgaacgt tacagaaaag caggctggga agcatatttg agaagatgcg   1200
gccagcaaaa ctaaaaaact gtattataag taaatgcatg tatactaaac tcacaaatta   1260
gagcttcaat ttaattatat cagttattac cctgcggtgt gaaataccgc acagatgcgt   1320
aaggagaaaa taccgcatca ggaaattgta acgttaata ttttgttaaa attcgcgtta    1380
aattttgtt aaatcagctc atttttaac caataggccg aaatcggcaa atcccttat     1440
aaatcaaaag aatagaccga gatagggttg agtgttgttc cagtttggaa caagagtcca   1500
ctattaaaga acgtggactc caacgtcaaa gggcgaaaaa ccgtctatca gggcgatggc   1560
ccactacgtg aaccatcacc ctaatcaagt tttttggggt cgaggtgccg taaagcacta   1620
aatcggaacc ctaaagggag cccccgattt agagcttgac ggggaaagcc ggcgaacgtg   1680
gcgagaaagg aagggaagaa agcgaaagga gcgggcgcta gggcgctggc aagtgtagcg   1740
gtcacgctgc gcgtaaccac cacacccgcc gcgcttaatg cgccgctaca gggcgcgtcg   1800
cgccattcgc cattcaggct gcgcaactgt tgggaagggc gatcggtgcg ggcctcttcg   1860
ctattacgcc agctggcgaa gggggggatgt gctgcaaggc gattaagttg ggtaacgcca   1920
gggttttccc agtcacgacg ttgtaaaacg acggccagtg aattgtaata cgactcacta   1980
tagggcgaat tggagctcca ccgcggtggt ttaacgtata gacttctaat atatttctcc   2040
atacttggta tttttattc acttttttta tacatatttg gtttttttat acaatatcaa    2100
aaatcaataa taattaattt aataacaaga atatgttgct gtgatgactc ttaatataca   2160
attgggaagc attcaaggat tggtacgacg tttgctttct gataattaaa cgcttggcgt   2220
ttaatctttt ttgccgatta ataatattat tattaccctc ttatttatta gcattgtctt   2280
ccgtactaaa aggagtaggg aaaaaggcga agtagagtga cacgtccatt acccagcgct   2340
tcataagaat ccatcaggta tattaaattg tgatgggaga acaaaacaaa ttgtactatg   2400
atgtcgagaa attggtgaat tctttgcagg aaagttttga cctggattgc gcgcaaagtg   2460
tatcactttt caccagtaaa tcaaggagca atgaggcttg gttggaagag ctagagaata   2520
aattcaagtt aaaagatgat gttgaacttg atgatgtgga aaatttaaga gccgaaattg   2580
acatgaagtt aaatatgttg gaggataaag taagctacta tgaaagactt tacaaagaac   2640
tcgaagagtt ccagaatgaa ataaaaatta aaacagttgt gaataacaga agacaatcgc   2700
gaactccaaa atgagctatc aaaaacgata atcgattag gatgactttg aaatgactcc    2760
gcagtggact ggccgttaat ttcaagcgtg agtaaaatag tgcatgacaa aagatgagct   2820
aggcttttgt aaaaatatct tacgttgtaa aattttagaa atcattattt ccttcatatc   2880
attttgtcat tgaccttcag aagaaaagag ccgaccaata atataaataa ataaataaaa   2940
ataatattcc attatttcta aacagattca atactcatta aaaaactata tcaattaatt   3000
tgaattaacg cggccgctct agttaattaa tcattgtttg cctccctgct gcggttttc    3060
accgaagttc atgccagtcc agcgttttg cagcagaaaa gccgccgact tcggtttgcg    3120
gtcgcgagtg aagatccctt tcttgttacc gccaacgcgc aatatgcctt gcgaggtcgc   3180
aaaatcggcg aaattccata cctgttcacc gacgacggcg ctgacgcgat caaagacgcg   3240
gtgatacata tccagccatg cacactgata ctcttcactc cacatgtcgg tgtacattga   3300
```

```
gtgcagcccg gctaacgtat ccacgccgta ttcggtgatg ataatcggct gatgcagttt    3360
ctcctgccag gccagaagtt cttttttccag taccttctct gccgtttcca aatcgccgct    3420
ttggacatac catccgtaat aacggttcag gcacagcaca tcaaagagat cgctgatggt    3480
atcggtgtga gcgtcgcaga acattacatt gacgcaggtg atcggacgcg tcgggtcgag    3540
tttacgcgtt gcttccgcca gtggcgcgaa atattcccgt gcaccttgcg gacgggtatc    3600
cggttcgttg gcaatactcc acatcaccac gcttgggtgg ttttttgtcac gcgctatcag    3660 ctctttaatc gcctgtaagt gcgcttgctg agtttccccg ttgactgcct cttcgctgta    3720
cagttctttc ggcttgttgc ccgcttcgaa accaatgcct aaagagaggt taaagccgac    3780
agcagcagtt tcatcaatca ccacgatgcc atgttcatct gcccagtcga gcatctcttc    3840
agcgtaaggg taatgcgagg tacgtaggaa gttggcccca atccagtcca ttaatgcgtg    3900
gtcgtgcacc atcagcacgt tatcgaatcc tttgccacgc aagtccgcat cttcatgacg    3960
accaaagcca gtaaagtaga acggtttgtg gttaatcagg aactgttcgc ccttcactgc    4020
cactgaccgg atgccgacgc gaagcgggta gatatcacac tctgtctggc ttttggctgt    4080
gacgcacagt tcatagagat aaccttcacc cggttgccag aggtgcggat tcaccacttg    4140
caaagtcccg ctagtgcctt gtccagttgc aaccacctgt tgatccgcat cacgcagttc    4200
aacgctgaca tcaccattgg ccaccacctg ccagtcaaca gacgcgtggt tacagtcttg    4260
cgcgacatgc gtcaccacgg tgatatcgtc cacccaggtg ttcggcgtgg tgtagagcat    4320
tacgctgcga tggattccgg catagttaaa gaaatcatgg aagtaagact gcttttttctt    4380 gccgttttcg tcggtaatca ccattcccgg cgggatagtc tgccagttca gttcgttgtt    4440
cacacaaacg gtgatacgta cacttttccc ggcaataaca tacggcgtga catcggcttc    4500
aaatggagta tagccgccct gatgctccat cacttcctga ttattgaccc acactttgcc    4560
gtaatgagtg accgcatcga aacgcagcac gatacgctgg cctgcccaac ctttcggtat    4620
aaagacttcg cgctgatacc agacgttgcc cgcataatta cgaatatctg catcggcgaa    4680
ctgatcgtta aaactgcctg gcacagcaat tgcccggctt tcttgtaacg cgctttccca    4740
ccaacgctga tcaattccac agttttcgcg atccagacta aatgcccaca ggccgtcgag    4800
ttttttgatt tcacgggttg gggtttctac aggacgtacc atactagttt gaatatgtat    4860
tacttggtta tggttatata tgacaaaaga aaaagaagaa cagaagaata acgcaaggaa    4920
gaacaataac tgaaattgat agagaagtat tatgtctttg tcttttttata ataaatcaag    4980 tgcagaaatc cgttagacaa catgagggat aaaatttaac gtgggcgaag aagaaggaaa    5040 aaagttttg tgagggcgta attgaagcga tctgttgatt gtagatttttt tttttttgag    5100 gagtcaaagt cagaagagaa cagacaaatg gtattaacca tccaatactt ttttggagca    5160
acgctaagct catgcttttc cattggttac gtgctcagtt gttagatatg gaagagagg    5220 atgctcacgg cagcgtgact ccaattgagc ccgaaagaga ggatgccacg ttttcccgac    5280
ggctgctaga atggaaaaag gaaaaataga agaatcccat tcctatcatt atttacgtaa    5340
tgacccacac attttttgaga ttttcaacta ttacgtatta cgataatcct gctgtcatta    5400
tcattattat ctatatcgac gtatgcaacg tatgtgaagc caagtaggcg tcgacaggac    5460
cttgttgtgt gacgaaattg gaagctgcaa tcaataggaa gacaggaagt cgagcgtgtc    5520
tgggtttttt cagtttttgtt ctttttgcaa acaaatcacg agcgacggta attggtaccc    5580
agcttttgtt ccctttagtg agggttaatt ccgagcttgg cgtaatcatg gtcatagctg    5640
```

```
tttcctgtgt gaaattgtta tccgctcaca attccacaca acataggagc cggaagcata   5700
aagtgtaaag cctggggtgc ctaatgagtg aggtaactca cattaattgc gttgcgctca   5760
ctgcccgctt ccagtcggg aaacctgtcg tgccagctgc attaatgaat cggccaacgc   5820
gcggggagag gcggtttgcg tattgggcgc tcttccgctt cctcgctcac tgactcgctg   5880
cgctcggtcg ttcggctgcg gcgagcggta tcagctcact caaaggcggt aatacggtta   5940
tccacagaat caggggataa cgcaggaaag aacatgtgag caaaaggcca gcaaaaggcc   6000
aggaaccgta aaaaggccgc gttgctggcg ttttccata ggctcggccc ccctgacgag    6060
catcacaaaa atcgacgctc aagtcagagg tggcgaaacc cgacaggact ataaagatac   6120
caggcgttcc cccctggaag ctccctcgtg cgctctcctg ttccgaccct gccgcttacc   6180
ggatacctgt ccgcctttct cccttcggga agcgtggcgc tttctcaatg ctcacgctgt   6240
aggtatctca gttcggtgta ggtcgttcgc tccaagctgg gctgtgtgca cgaaccccc    6300
gttcagcccg accgctgcgc cttatccggt aactatcgtc ttgagtccaa cccggtaaga   6360
cacgacttat cgccactggc agcagccact ggtaacagga ttagcagagc gaggtatgta   6420
ggcggtgcta cagagttctt gaagtggtgg cctaactacg gctacactag aaggacagta   6480
tttggtatct gcgctctgct gaagccagtt accttcggaa aaagagttgg tagctcttga   6540
tccggcaaac aaaccaccgc tggtagcggt ggtttttttg tttgcaagca gcagattacg   6600
cgcagaaaaa aaggatctca agaagatcct ttgatctttt ctacggggtc tgacgctcag   6660
tggaacgaaa actcacgtta agggattttg gtcatgagat tatcaaaaag gatcttcacc   6720
tagatccttt taaattaaaa atgaagtttt aaatcaatct aaagtatata tgagtaaact   6780
tggtctgaca gttaccaatg cttaatcagt gaggcaccta tctcagcgat ctgtctattt   6840
cgttcatcca tagttgcctg actgcccgtc gtgtagataa ctacgatacg ggagggctta   6900
ccatctggcc ccagtgctgc aatgataccg cgagacccac gctcaccggc tccagattta   6960
tcagcaataa accagccagc cggaagggcc gagcgcagaa gtggtcctgc aactttatcc   7020
gcctccatcc agtctattaa ttgttgccgg gaagctagag taagtagttc gccagttaat   7080
agtttgcgca acgttgttgc cattgctaca ggcatcgtgg tgtcacgctc gtcgtttggt   7140
atggcttcat tcagctccgg ttcccaacga tcaaggcgag ttacatgatc ccccatgttg   7200
tgaaaaaaag cggttagctc cttcggtcct ccgatcgttg tcagaagtaa gttggccgca   7260
gtgttatcac tcatggttat ggcagcactg cataattctc ttactgtcat gccatccgta   7320
agatgctttt ctgtgactgg tgagtactca accaagtcat tctgagaata gtgtatgcgg   7380
cgaccgagtt gctcttgccc ggcgtcaata cgggataata ccgcgccaca tagcagaact   7440
ttaaaagtgc tcatcattgg aaaacgttct cggggcgaa aactctcaag gatcttaccg    7500
ctgttgagat ccagttcgat gtaacccact cgtgcaccca actgatcttc agcatctttt   7560
actttcacca gcgtttctgg gtgagcaaaa acaggaaggc aaaatgccgc aaaaagggga   7620
ataagggcga cacggaaatg ttgaatactc atactcttcc ttttcaata ttattgaagc    7680
atttatcagg gttattgtct catgagcgga tacatatttg aatgtattta gaaaaataaa   7740
caaatagggg ttccgcgcac atttccccga aaagtgccac ctgggtcctt tcatcacgt    7800
gctataaaaa taattataat ttaaattttt taatataaat ataaaatta aaaatagaaa    7860
gtaaaaaaag aaattaaaga aaaaatagtt tttgttttcc gaagatgtaa aagactctag   7920
ggggatcgcc aacaaatact acctttatc ttgctcttcc tgctctcagg tattaatgcc    7980
gaattgtttc atcttgtctg tgtagaagac cacacacgaa aatcctgtga ttttacattt   8040
```

```
tacttatcgt taatcgaatg tatatctatt taatctgctt ttcttgtcta ataaatatat    8100
atgtaaagta cgcttttgt tgaaatttt taaacctttg tttattttt tttcttcatt      8160 ccgtaactct tctaccttct ttatttactt tctaaaatcc aaatacaaaa cataaaaata    8220
aataaacaca gagtaaattc ccaaattatt ccatcattaa aagatacgag gcgcgtgtaa    8280
gttacaggca agcgatccgt cctaagaaac cattattatc atgacattaa cctataaaaa    8340
taggcgtatc acgaggccct ttcgtc                                          8366
```

<210> SEQ ID NO 173
<211> LENGTH: 34
<212> TYPE: DNA
<213> ORGANISM: Artificial Sequence
<220> FEATURE:
<223> OTHER INFORMATION: Primer oBP674

<400> SEQUENCE: 173

```
aattggcgcg ccaattaccg tcgctcgtga tttg                                 34
```

<210> SEQ ID NO 174
<211> LENGTH: 34
<212> TYPE: DNA
<213> ORGANISM: Artificial Sequence
<220> FEATURE:
<223> OTHER INFORMATION: Primer oBP675

<400> SEQUENCE: 174

```
aattgtttaa acttgaatat gtattacttg gtta                                 34
```

<210> SEQ ID NO 175
<211> LENGTH: 22
<212> TYPE: DNA
<213> ORGANISM: Artificial Sequence
<220> FEATURE:
<223> OTHER INFORMATION: Primer oBP495

<400> SEQUENCE: 175

```
ggagatatac aatagaacag at                                              22
```

<210> SEQ ID NO 176
<211> LENGTH: 22
<212> TYPE: DNA
<213> ORGANISM: Artificial Sequence
<220> FEATURE:
<223> OTHER INFORMATION: Primer oBP496

<400> SEQUENCE: 176

```
tagcaatggg gttttttca gt                                               22
```

<210> SEQ ID NO 177
<211> LENGTH: 725
<212> TYPE: DNA
<213> ORGANISM: Artificial Sequence
<220> FEATURE:
<223> OTHER INFORMATION: UAS(PGK1)-FBA1p

<400> SEQUENCE: 177

```
aattaccgtc gctcgtgatt tgtttgcaaa aagaacaaaa ctgaaaaaac ccagacacgc    60
tcgacttcct gtcttcctat tgattgcagc ttccaatttc gtcacacaac aaggtcctgt   120
cgacgcctac ttggcttcac atacgttgca tacgtcgata tagataataa tgataatgac   180
agcaggatta tcgtaatacg taatagttga aaatctcaaa aatgtgtggg tcattacgta   240
```

-continued

| | |
|---|---|
| aataatgata ggaatgggat tcttctattt ttccttttc cattctagca gccgtcggga | 300 |
| aaacgtggca tcctctcttt cgggctcaat tggagtcacg ctgccgtgag catcctctct | 360 |
| ttccatatct aacaactgag cacgtaacca atggaaaagc atgagcttag cgttgctcca | 420 |
| aaaaagtatt ggatggttaa taccatttgt ctgttctctt ctgactttga ctcctcaaaa | 480 |
| aaaaaaaatc tacaatcaac agatcgcttc aattacgccc tcacaaaaac ttttttcctt | 540 |
| cttcttcgcc cacgttaaat tttatccctc atgttgtcta acggatttct gcacttgatt | 600 |
| tattataaaa agacaaagac ataatacttc tctatcaatt tcagttattg ttcttccttg | 660 |
| cgttattctt ctgttcttct ttttcttttg tcatatataa ccataaccaa gtaatacata | 720 |
| ttcaa | 725 |

<210> SEQ ID NO 178
<211> LENGTH: 47
<212> TYPE: DNA
<213> ORGANISM: Artificial Sequence
<220> FEATURE:
<223> OTHER INFORMATION: Primer T-FBA1(SalI)

<400> SEQUENCE: 178

| | |
|---|---|
| attctacgta cgtcgacgcc tacttggctt cacatacgtt gcatacg | 47 |

<210> SEQ ID NO 179
<211> LENGTH: 49
<212> TYPE: DNA
<213> ORGANISM: Artificial Sequence
<220> FEATURE:
<223> OTHER INFORMATION: Primer B-FBA1(SpeI)

<400> SEQUENCE: 179

| | |
|---|---|
| gtatcaaata ctagtttgaa tatgtattac ttggttatgg ttatatatg | 49 |

<210> SEQ ID NO 180
<211> LENGTH: 10494
<212> TYPE: DNA
<213> ORGANISM: Artificial Sequence
<220> FEATURE:
<223> OTHER INFORMATION: pWS358-PGK1p-GUS

<400> SEQUENCE: 180

| | |
|---|---|
| tcgcgcgttt cggtgatgac ggtgaaaacc tctgacacat gcagctcccg gagacggtca | 60 |
| cagcttgtct gtaagcggat gccggagca gacaagcccg tcagggcgcg tcagcgggtg | 120 |
| ttggcgggtg tcggggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tcttttttcta | 300 |
| ttactcttgg cctcctctag tacactctat atttttttat gcctcggtaa tgattttcat | 360 |
| ttttttttt cccctagcgg atgactcttt ttttttctta gcgattggca ttatcacata | 420 |
| atgaattata cattatataa agtaatgtga tttcttcgaa gaatatacta aaaaatgagc | 480 |
| aggcaagata aacgaaggca aagatgacag agcagaaagc cctagtaaag cgtattacaa | 540 |
| atgaaaccaa gattcagatt gcgatctctt taagggtgg tccctagcg atagagcact | 600 |
| cgatcttccc agaaaaagag gcagaagcag tagcagaaca ggccacacaa tcgcaagtga | 660 |
| ttaacgtcca cacaggtata gggtttctgg accatatgct agggattcat aaccattttc | 720 |
| tcaatcgaat tacacagaac acaccgtaca aacctctcta tcataactac ttaatagtca | 780 |
| cacacgtact cgtctaaata cacatcatcg tcctacaagt tcatcaaagt gttggacaga | 840 |

```
caactatacc agcatggatc tcttgtatcg gttcttttct cccgctctct cgcaataaca      900
atgaacactg ggtcaatcat agcctacaca ggtgaacaga gtagcgttta tacagggttt      960
atacggtgat tcctacggca aaaattttc atttctaaaa aaaaaagaa aaattttct        1020
ttccaacgct agaaggaaaa gaaaaatcta attaaattga tttggtgatt ttctgagagt     1080
tccctttttc atatatcgaa ttttgaatat aaaggagat cgaaaaatt tttctattca       1140
atctgttttc tggttttatt tgatagtttt tttgtgtatt attattatgg attagtactg     1200
gtttatatgg gtttttctgt ataacttctt tttattttag tttgtttaat cttattttga    1260
gttacattat agttccctaa ctgcaagaga agtaacatta aaactcgaga tgggtaagga     1320
aaagactcac gtttcgaggc cgcgattaaa ttccaacatg gatgctgatt tatatgggta    1380
taaatgggct cgcgataatg tcgggcaatc aggtgcgaca atctatcgat tgtatgggaa    1440
gcccgatgcg ccagagttgt ttctgaaaca tggcaaaggt agcgttgcca atgatgttac    1500
agatgagatg gtcagactaa actggctgac ggaatttatg cctcttccga ccatcaagca    1560
ttttatccgt actcctgatg atgcatggtt actcaccact gcgatccccg gcaaaacagc    1620
attccaggta ttagaagaat atcctgattc aggtgaaaat attgttgatg cgctggcagt    1680
gttcctgcgc cggttgcatt cgattcctgt ttgtaattgt cctttaaca gcgatcgcgt     1740
atttcgtctc gctcaggcgc aatcacgaat gaataacggt ttggttgatg cgagtgattt    1800
tgatgacgag cgtaatggct ggcctgttga acaagtctgg aaagaaatgc ataagctttt    1860
gccattctca ccggattcag tcgtcactca tggtgatttc tcacttgata accttatttt    1920
tgacgagggg aaattaatag gttgtattga tgttggacga gtcggaatcg cagaccgata    1980
ccaggatctt gccatcctat ggaactgcct cggtgagttt tctccttcat acagaaacg    2040
gctttttcaa aaatatggta ttgataatcc tgatatgaat aaattgcagt tcatttgat    2100
gctcgatgag ttttttctaag tttaacttga tactactaga tttttttctct tcatttataa   2160
aatttttggt tataattgaa gctttagaag tatgaaaaaa tccttttttt tcattctttg    2220
caaccaaaat aagaagcttc ttttattcat tgaaatgatg aatataaacc taacaaaaga    2280
aaagactcg aatatcaaac attaaaaaaa aataaaagag gttatctgtt ttcccattta     2340
gttggagttt gcattttcta atagatagaa ctctcaatta atgtggattt agtttctctg    2400
ttcgctgcag catacgatat atatacatgt gtatatatgt ataccatgta atgtcagtaa    2460
gtatgtatac gaacagtatg atactgaaga tgacaaggta atgcatcatt ctatacgtgt    2520
cattctgaac gaggcgcgct ttccttttt ctttttgctt tttctttttt tttctcttga    2580
actcgacgga tctatgcggt gtgaaatacc gcacagatgc gtaaggagaa ataccgcat    2640
caggaaattg taaacgttaa tattttgtta aaattcgcgt taaattttg ttaaatcagc    2700
tcatttttta accaataggc cgaaatcggc aaaatccctt ataaatcaaa agaatagacc    2760
gagatagggt tgagtgttgt tccagtttgg aacaagagtc cactattaaa gaacgtggac    2820
tccaacgtca agggcgaaaa accgtctat caggcgatg gcccactacg tgaaccatca     2880
ccctaatcaa gttttttggg gtcgaggtgc cgtaaagcac taaatcggaa ccctaaaggg    2940
agccccgat ttagagcttg acggggaaag ccggcgaacg tggcgagaaa ggaaagggaag    3000
aaagcgaaag gagcgggcgc tagggcgctg gcaagtgtag cggtcacgct gcgcgtaacc    3060
accacaccccg ccgcgcttaa tgcgccgcta caggggcgcgt cgcgccattc gccattcagg   3120
ctgcgcaact gttgggaagg gcgatcggtg cgggcctctt cgctattacg ccagctggcg    3180
```

```
aaaggggat  gtgctgcaag  gcgattaagt  tgggtaacgc  cagggttttc  ccagtcacga    3240
cgttgtaaaa  cgacggccag  tgagcgcgcg  taatacgact  cactataggg  cgaattgggt    3300
accgggcccc  ccctcgaggt  cgacgtgagt  aaggaaagag  tgaggaacta  tcgcatacct    3360
gcatttaaag  atgccgattt  gggcgcgaat  cctttatttt  ggcttcaccc  tcatactatt    3420
atcagggcca  gaaaaaggaa  gtgtttccct  ccttcttgaa  ttgatgttac  cctcataaag    3480
cacgtggcct  cttatcgaga  aagaaattac  cgtcgctcgt  gatttgtttg  caaaaagaac    3540
aaaactgaaa  aaacccagac  acgctcgact  tcctgtcttc  ctattgattg  cagcttccaa    3600
tttcgtcaca  caacaaggtc  ctagcgacgg  ctcacaggtt  ttgtaacaag  caatcgaagg    3660
ttctggaatg  gcgggaaagg  gtttagtacc  acatgctatg  atgcccactg  tgatctccag    3720
agcaaagttc  gttcgatcgt  actgttactc  tctctctttc  aaacagaatt  gtccgaatcg    3780
tgtgacaaca  acagcctgtt  ctcacacact  cttttcttct  aaccaagggg  gtggtttagt    3840
ttagtagaac  ctcgtgaaac  ttacatttac  atatatataa  acttgcataa  attggtcaat    3900
gcaagaaata  catatttggt  cttttctaat  tcgtagtttt  tcaagttctt  agatgctttc    3960
ttttctctt   tttacagat   catcaaggaa  gtaattatct  acttttttaca  acaaatataa    4020
aacaactagt  atggtacgtc  ctgtagaaac  cccaacccgt  gaaatcaaaa  aactcgacgg    4080
cctgtgggca  ttcagtctgg  atcgcgaaaa  ctgtggaatt  gatcagcgtt  ggtgggaaag    4140
cgcgttacaa  gaaagccggg  caattgctgt  gccaggcagt  tttaacgatc  agttcgccga    4200
tgcagatatt  cgtaattatg  cgggcaacgt  ctggtatcag  cgcgaagtct  ttataccgaa    4260
aggttgggca  ggccagcgta  tcgtgctgcg  tttcgatgcg  gtcactcatt  acggcaaagt    4320
gtgggtcaat  aatcaggaag  tgatggagca  tcagggcggc  tatactccat  ttgaagccga    4380
tgtcacgccg  tatgttattg  ccgggaaaag  tgtacgtatc  accgtttgtg  tgaacaacga    4440
actgaactgg  cagactatcc  cgccgggaat  ggtgattacc  gacgaaaacg  gcaagaaaaa    4500
gcagtcttac  ttccatgatt  tctttaacta  tgccggaatc  catcgcagcg  taatgctcta    4560
caccacgccg  aacacctggg  tggacgatat  caccgtggtg  acgcatgtcg  cgcaagactg    4620
taaccacgcg  tctgttgact  ggcaggtggt  ggccaatggt  gatgtcagcg  ttgaactgcg    4680
tgatgcggat  caacaggtgg  ttgcaactgg  acaaggcact  agcgggactt  tgcaagtggt    4740
gaatccgcac  ctctggcaac  cgggtgaagg  ttatctctat  gaactgtgcg  tcacagccaa    4800
aagccagaca  gagtgtgata  tctacccgct  tcgcgtcggc  atccggtcag  tggcagtgaa    4860
gggcgaacag  ttcctgatta  ccacaaaacc  gttctacttt  actggctttg  gtcgtcatga    4920
agatgcggac  ttgcgtggca  aaggattcga  taacgtgctg  atggtgcacg  accacgcatt    4980
aatggactgg  attggggcca  actcctaccg  tacctcgcat  tacccttacg  ctgaagagat    5040
gctcgactgg  gcagatgaac  atggcatcgt  ggtgattgat  gaaactgctg  ctgtcggctt    5100
taacctctct  ttaggcattg  gtttcgaagc  gggcaacaag  ccgaaagaac  tgtacagcga    5160
agaggcagtc  aacgggaaa   ctcagcaagc  gcacttacag  gcgattaaag  agctgatagc    5220
gcgtgacaaa  aaccacccaa  gcgtggtgat  gtggagtatt  gccaacgaac  cggatacccg    5280
tccgcaaggt  gcacgggaat  atttcgcgcc  actggcggaa  gcaacgcgta  aactcgaccc    5340
gacgcgtccg  atcacctgcg  tcaatgtaat  gttctgcgac  gctcacaccg  ataccatcag    5400
cgatctcttt  gatgtgctgt  gcctgaaccg  ttattacgga  tggtatgtcc  aaagcgcgca    5460
tttgaaaacg  gcagagaagg  tactggaaaa  agaacttctg  gcctggcagg  agaaactgca    5520
tcagccgatt  atcatcaccg  aatacggcgt  ggatacgtta  gccgggctgc  actcaatgta    5580
```

```
caccgacatg tggagtgaag agtatcagtg tgcatggctg gatatgtatc accgcgtctt    5640
tgatcgcgtc agcgccgtcg tcggtgaaca ggtatggaat tcgccgatt ttgcgacctc     5700 gcaaggcata ttgcgcgttg gcggtaacaa gaaagggatc ttcactcgcg accgcaaacc    5760
gaagtcggcg gcttttctgc tgcaaaaacg ctggactggc atgaacttcg gtgaaaaacc    5820
gcagcaggga ggcaaacaat gattaattaa ctagagcggc cgcgttaatt caaattaatt    5880
gatatagttt tttaatgagt attgaatctg tttagaaata tggaatatt attttattt      5940 atttatttat attattggtc ggctcttttc ttctgaaggt caatgacaaa atgatatgaa    6000
ggaaataatg atttctaaaa ttttacaacg taagatattt ttacaaaagc ctagctcatc    6060
ttttgtcatg cactatttta ctcacgcttg aaattaacgg ccagtccact gcggagtcat    6120
ttcaaagtca tcctaatcga tctatcgttt ttgatagctc attttggagt tcgcgattgt    6180
cttctgttat tcacaactgt tttaatttttt atttcattct ggaactcttc gagttctttg    6240
taaagtcttt catagtagct tactttatcc tccaacatat ttaacttcat gtcaatttcg    6300
gctcttaaat tttccacatc atcaagttca acatcatctt ttaacttgaa tttattctct    6360
agctcttcca accaagcctc attgctcctt gatttactgg tgaaaagtga tacactttgc    6420
gcgcaatcca ggtcaaaact ttcctgcaaa gaattcacca atttctcgac atcatagtac    6480
aatttgtttt gttctcccat cacaatttaa tatacctgat ggattcttat gaagcgctgg    6540
gtaatggacg tgtcactcta cttcgccttt ttccctactc cttttagtac ggaagacaat    6600
gctaataaat aagagggtaa taataatatt attaatcggc aaaaaagatt aaacgccaag    6660
cgtttaatta tcagaaagca acgtcgtac caatccttga atgcttccca attgtatatt     6720
aagagtcatc acagcaacat attcttgtta ttaaattaat tattattgat ttttgatatt    6780
gtataaaaaa accaaatatg tataaaaaaa gtgaataaaa aataccaagt atggagaaat    6840
atattagaag tctatacgtt aaaccaccgc ggtggagctc cagcttttgt tccctttagt    6900
gagggttaat tgcgcgcttg gcgtaatcat ggtcatagct gtttcctgtg tgaaattgtt    6960
atccgctcac aattccacac aacataggag ccggaagcat aaagtgtaaa gcctggggtg    7020
cctaatgagt gaggtaactc acattaattg cgttgcgctc actgcccgct ttccagtcgg    7080
gaaacctgtc gtgccagctg cattaatgaa tcggccaacg cgcggggaga ggcggtttgc    7140
gtattgggcg ctcttccgct tcctcgctca ctgactcgct gcgctcggtc gttcggctgc    7200
ggcgagcggt atcagctcac tcaaaggcgg taatacggtt atccacagaa tcaggggata    7260
acgcaggaaa gaacatgtga gcaaaaggcc agcaaaaggc caggaaccgt aaaaaggccg    7320
cgttgctggc gtttttccat aggctccgcc ccctgacga gcatcacaaa aatcgacgct     7380
caagtcagag gtggcgaaac ccgacaggac tataaagata ccaggcgttt ccccctggaa    7440
gctccctcgt gcgctctcct gttccgaccc tgccgcttac cggatacctg tccgcctttc    7500
tcccttcggg aagcgtggcg ctttctcata gctcacgctg taggtatctc agttcggtgt    7560
aggtcgttcg ctccaagctg ggctgtgtgc acgaaccccc cgttcagccc gaccgctgcg    7620
ccttatccgg taactatcgt cttgagtcca acccggtaag acacgactta tcgccactgg    7680
cagcagccac tggtaacagg attagcagag cgaggtatgt aggcggtgct acagagttct    7740
tgaagtggtg gcctaactac ggctacacta aaggacagt atttggtatc tgcgctctgc     7800
tgaagccagt taccttcgga aaagagttg gtagctcttg atccggcaaa caaaccaccg     7860
ctggtagcgg tggttttttt gtttgcaagc agcagattac gcgcagaaaa aaggatctc     7920
```

```
aagaagatcc tttgatcttt tctacggggt ctgacgctca gtggaacgaa aactcacgtt    7980
aagggatttt ggtcatgaga ttatcaaaaa ggatcttcac ctagatcctt ttaaattaaa    8040
aatgaagttt taaatcaatc taaagtatat atgagtaaac ttggtctgac agttaccaat    8100
gcttaatcag tgaggcacct atctcagcga tctgtctatt tcgttcatcc atagttgcct    8160
gactccccgt cgtgtagata actacgatac gggagggctt accatctggc cccagtgctg    8220
caatgatacc gcgagaccca cgctcaccgg ctccagattt atcagcaata aaccagccag    8280
ccggaagggc cgagcgcaga agtggtcctg caactttatc cgcctccatc cagtctatta    8340
attgttgccg ggaagctaga gtaagtagtt cgccagttaa tagtttgcgc aacgttgttg    8400
ccattgctac aggcatcgtg gtgtcacgct cgtcgtttgg tatggcttca ttcagctccg    8460
gttcccaacg atcaaggcga gttacatgat cccccatgtt gtgcaaaaaa gcggttagct    8520
ccttcggtcc tccgatcgtt gtcagaagta agttggccgc agtgttatca ctcatggtta    8580
tggcagcact gcataattct cttactgtca tgccatccgt aagatgcttt tctgtgactg    8640
gtgagtactc aaccaagtca ttctgagaat agtgtatgcg gcgaccgagt tgctcttgcc    8700
cggcgtcaat acgggataat accgcgccac atagcagaac tttaaaagtg ctcatcattg    8760
gaaaacgttc ttcggggcga aaactctcaa ggatcttacc gctgttgaga tccagttcga    8820
tgtaacccac tcgtgcaccc aactgatctt cagcatcttt tactttcacc agcgtttctg    8880
ggtgagcaaa aacaggaagg caaaatgccg caaaaaaggg aataagggcg acacggaaat    8940
gttgaatact catactcttc cttttttcaat attattgaag catttatcag ggttattgtc    9000
tcatgagcgg atacatattt gaatgtattt agaaaaataa acaaatagggg gttccgcgca    9060 catttccccg aaaagtgcca cctgaacgaa gcatctgtgc ttcattttgt agaacaaaaa    9120
tgcaacgcga gagcgctaat ttttcaaaca agaatctga gctgcatttt tacagaacag    9180
aaatgcaacg cgaaagcgct attttaccaa cgaagaatct gtgcttcatt tttgtaaaac    9240
aaaaatgcaa cgcgagagcg ctaattttc aaacaaagaa tctgagctgc attttttacag    9300 aacagaaatg caacgcgaga gcgctatttt accaacaaag aatctatact ctttttttgt    9360
tctacaaaaa tgcatcccga gagcgctatt tttctaacaa agcatcttag attacttttt    9420
ttctcctttg tgcgctctat aatgcagtct cttgataact ttttgcactg taggtccgtt    9480
aaggttagaa gaaggctact tggtgtcta ttttctcttc cataaaaaaa gcctgactcc    9540
acttcccgcg tttactgatt actagcgaag ctgcgggtgc attttttcaa gataaaggca    9600
tccccgatta tattctatac cgatgtggat tgcgcatact ttgtgaacag aaagtgatag    9660
cgttgatgat tcttcattgg tcagaaaatt atgaacggtt tcttctattt tgtctctata    9720
tactacgtat aggaaatgtt tacattttcg tattgttttc gattcactct atgaatagtt    9780
cttactacaa tttttttgtc taaagagtaa tactagagat aaacataaaa aatgtagagg    9840
tcgagtttag atgcaagttc aaggagcgaa aggtggatgg gtaggttata tagggatata    9900
gcacagagat atatagcaaa gagatacttt tgagcaatgt ttgtggaagc ggtattcgca    9960
atattttagt agctcgttac agtccggtgc gttttttggtt ttttgaaagt gcgtcttcag   10020
agcgcttttg gttttcaaaa gcgctctgaa gttcctatac tttctagaga ataggaactt   10080
cggaatagga acttcaaagc gtttccgaaa acgagcgctt ccgaaaatgc aacgcgagct   10140
gcgcacatac agctcactgt tcacgtcgca cctatatctg cgtgttgcct gtatatatat   10200
atacatgaga agaacggcat agtgcgtgtt tatgcttaaa tgcgtactta tatgcgtcta   10260
tttatgtagg atgaaaggta gtctagtacc tcctgtgata ttatcccatt ccatgcgggg   10320
```

```
tatcgtatgc ttccttcagc actacccttt agctgttcta tatgctgcca ctcctcaatt    10380
ggattagtct catccttcaa tgctatcatt tcctttgata ttggatcatc taagaaacca    10440
ttattatcat gacattaacc tataaaaata ggcgtatcac gaggcccttt cgtc          10494
```

```
<210> SEQ ID NO 181
<211> LENGTH: 43
<212> TYPE: DNA
<213> ORGANISM: Artificial Sequence
<220> FEATURE:
<223> OTHER INFORMATION: Primer T-U/PGK1(KpnI)

<400> SEQUENCE: 181
actacagatg gtaccaatta ccgtcgctcg tgatttgttt gca                      43
```

```
<210> SEQ ID NO 182
<211> LENGTH: 45
<212> TYPE: DNA
<213> ORGANISM: Artificial Sequence
<220> FEATURE:
<223> OTHER INFORMATION: Primer B-U/PGK1(SalI)

<400> SEQUENCE: 182
agcatccttg tcgacaggac cttgttgtgt gacgaaattg gaagc                    45
```

```
<210> SEQ ID NO 183
<211> LENGTH: 20
<212> TYPE: DNA
<213> ORGANISM: Artificial Sequence
<220> FEATURE:
<223> OTHER INFORMATION: Primer N98SeqF1

<400> SEQUENCE: 183
cgtgttagtc acatcaggac                                                20
```

```
<210> SEQ ID NO 184
<211> LENGTH: 22
<212> TYPE: DNA
<213> ORGANISM: Artificial Sequence
<220> FEATURE:
<223> OTHER INFORMATION: Primer N99SeqR2

<400> SEQUENCE: 184
catcgactgc attacgcaac tc                                             22
```

```
<210> SEQ ID NO 185
<211> LENGTH: 20
<212> TYPE: DNA
<213> ORGANISM: Artificial Sequence
<220> FEATURE:
<223> OTHER INFORMATION: Primer N98SeqF4

<400> SEQUENCE: 185
ggtttctgtc tctggtgacg                                                20
```

```
<210> SEQ ID NO 186
<211> LENGTH: 30
<212> TYPE: DNA
<213> ORGANISM: Artificial Sequence
<220> FEATURE:
<223> OTHER INFORMATION: Primer N1111

<400> SEQUENCE: 186
tatttgtatc gaggtgtcta gtcttctatt                                     30
```

<210> SEQ ID NO 187
<211> LENGTH: 30
<212> TYPE: DNA
<213> ORGANISM: Artificial Sequence
<220> FEATURE:
<223> OTHER INFORMATION: Primer N1110

<400> SEQUENCE: 187
gcgatttaat ctctaattat tagttaaagt                                30

<210> SEQ ID NO 188
<211> LENGTH: 38
<212> TYPE: DNA
<213> ORGANISM: Artificial Sequence
<220> FEATURE:
<223> OTHER INFORMATION: Primer BK468

<400> SEQUENCE: 188
gcctcgagtt ttaatgttac ttctcttgca gttaggga                       38

<210> SEQ ID NO 189
<211> LENGTH: 22
<212> TYPE: DNA
<213> ORGANISM: Artificial Sequence
<220> FEATURE:
<223> OTHER INFORMATION: Primer N160SeqF5

<400> SEQUENCE: 189
cctgaagtct aggtccctat tt                                        22

<210> SEQ ID NO 190
<211> LENGTH: 7589
<212> TYPE: DNA
<213> ORGANISM: Artificial Sequence
<220> FEATURE:
<223> OTHER INFORMATION: pUC19-kan::pdc1::FBA-alsS::TRX1 (clone A)

<400> SEQUENCE: 190
tatttgtatc gaggtgtcta gtcttctatt acactaatgc agtttcaggg ttttggaaac    60
cacactgttt aaacagtgtt ccttaatcaa ggatacctct tttttttttcc ttggttccac   120 taattcatcg gttttttttt tggaagacat cttttccaac gaaaagaata tacatatcgt   180
ttaagagaaa ttctccaaat ttgtaaagaa gcggacccag acttaaggcc gcccgcaaat   240
taaagccttc gagcgtccca aaaccttctc aagcaaggtt ttcagtataa tgttacatgc   300
gtacacgcgt ctgtacagaa aaaaagaaa aatttgaaat ataaataacg ttcttaatac   360
taacataact ataaaaaaat aaatagggac ctagacttca ggttgtctaa ctccttcctt   420
ttcggttaga gcggatgtgg ggggagggcg tgaatgtaag cgtgacataa ctaattacat   480
gattaattaa ctagagagct ttcgttttca tgagttcccc gaattctttc ggaagcttgt   540
cacttgctaa attaatgtta tcactgtagt caacccgggac atcgatgatg acaggacctt   600
cagcgttcat gccttgacgc agaacatctg ccagctggtc tggtgattct acgcgcaagc   660
cagttgctcc gaagctttcc gcatatttca cgatatcgat atttccgaaa tcgaccgcag   720
atgtacggtt atatttttc aattgctgga atgcaaccat gtcatatgtg ctgtcgttcc   780
atacaatgtg tacaattggt gcttttagtc gaactgctgt ctctaattcc attgctgaga   840
ataagaaacc gccgtcacca gagacagaaa ccacttttc tcccggtttc accaatgaag   900
cgccgattgc ccaaggaagc gcaacgccga gtgtttgcat accgttactg atcattaatg   960
ttaacggctc gtagctgcgg aaataacgtg acatccaaat ggcgtgcgaa ccgatatcgc  1020

```
aagttactgt aacatgatca tcgactgcat tacgcaactc tttaacgatt tcaagagggt    1080
gcgctctgtc tgatttccaa tctgcaggca cctgctcacc ttcatgcata tattgtttta    1140
aatcagaaag gattttctgc tcacgctctg caaattccac tttcacagca tcgtgttcga    1200
tatgattgat cgtggacgga atgtcaccga tcaattcaag atcaggctgg taagcatgat    1260
caatgtcagc gataatctcg tctaaatgga taattgtccg gtctccattg atattccaga    1320
atttcggatc atattcaatc gggtcatagc cgatcgtcag aacaacatct gcctgctcta    1380
gcagtaaatc gccaggctgg ttgcggaaca aaccgatacg ccaaaatat tgatcctcta     1440 aatctctaga aagggtaccg gcagcttgat atgtttcaac aaatggaagc tgaacctttt    1500
tcaaaagctt gcgaaccgct ttaattgctt ccggtcttcc gcctttcatg ccgaccaaaa    1560
cgacaggaag ttttgctgtt tggatttttg ctatggccgc actgattgca tcatctgctg    1620
caggaccgag ttttggcgct gcaacagcac gcacgttttt cgtatttgtg acttcattca    1680
caacatcttg cggaaagctc acaaaagcgg ccccagcctg ccctgctgac gctatcctaa    1740
atgcatttgt aacagcttcc ggtatatttt ttacatcttg aacttctaca ctgtattttg    1800
taatcggctg gaatagcgcc gcattatcca aagattgatg tgtccgtttt aaacgatctg    1860
cacggatcac gtttccagca agcgcaacga cagggtctcc ttcagtgttc gctgtcagca    1920
ggcctgttgc caagttagag cacccggtc ctgatgtgac taacacgact cccggttttc     1980
cagttaaacg gccgactgct tgggccatga atgctgcgtt ttgttcgtgc cgggcaacga    2040
taatttcagg tcctttatct tgtaaagcgt caaataccgc atcaattttt gcacctggaa    2100
tgccaaatac atgtgtgaca ccttgctcca ctaagcaatc aacaacaagc tccgcccctc    2160 tgttttcac aagggatttt tgttcttttg ttgcttttgt caacatcctc agctctagat      2220
ttgaatatgt attacttggt tatggttata tatgacaaaa gaaaagaag aacagaagaa      2280 taacgcaagg aagaacaata actgaaattg atagagaagt attatgtctt tgtctttta      2340 taataaatca agtgcagaaa tccgttagac aacatgaggg ataaaattta acgtgggcga    2400
agaagaagga aaaagttttt tgtgagggcg taattgaagc gatctgttga ttgtagattt     2460 ttttttttttg aggagtcaaa gtcagaagag aacagacaaa tggtattaac catccaatac   2520 tttttttggag caacgctaag ctcatgcttt tccattggtt acgtgctcag ttgttagata   2580
tggaaagaga ggatgctcac ggcagcgtga ctccaattga gcccgaaaga gaggatgcca    2640
cgttttcccg acggctgcta gaatggaaaa aggaaaaata gaagaatccc attcctatca    2700
ttatttacgt aatgacccac acatttttga gatttcaac tattacgtat tacgataatc     2760
ctgctgtcat tatcattatt atctatatcg acgtatgcaa cgtatgtgaa gccaagtagg    2820
caattattta gtactgtcag tattgttatt catttcagat cttaagccta accaggccaa    2880
ttcaacagac tgtcggcaac ttcttgtctg gtctttccat ggtaagtgac agtgcagtaa    2940
taatatgaac caatttattt ttcgttacat aaaaatgctt ataaaacttt aactaataat    3000
tagagattaa atcgcaaacg gccgactcta gaggatcccc caccttggct aactcgttgt    3060
atcatcactg gataacttcg tatagcatac attatacgaa gttatctagg gattcataac    3120
cattttctca atcgaattac acagaacaca ccgtacaaac ctctctatca taactactta    3180
atagtcacac acgtactcgt ctaaatacac atcatcgtcc tacaagttca tcaaagtgtt    3240
ggacagacaa ctataccagc atggatctct tgtatcggtt cttttctccc gctctctcgc    3300
aataacaatg aacactgggt caatcatagc ctacacaggt gaacagagta gcgtttatac    3360
```

| | |
|---|---|
| agggtttata cggtgattcc tacggcaaaa attttccatt tctaaaaaaa aaaagaaaaa | 3420 |
| tttttctttc caacgctaga aggaaaagaa aaatctaatt aaattgattt ggtgattttc | 3480 |
| tgagagttcc cttttcata tatcgaattt tgaatataaa aggagatcga aaaaatttt | 3540 |
| ctattcaatc tgttttctgg ttttatttga tagtttttt gtgtattatt attatggatt | 3600 |
| agtactggtt tatatgggtt tttctgtata acttctttt attttagttt gtttaatctt | 3660 |
| attttgagtt acattatagt tccctaactg caagagaagt aacattaaaa ctcgagatgg | 3720 |
| gtaaggaaaa gactcacgtt tcgaggccgc gattaaattc caacatggat gctgatttat | 3780 |
| atgggtataa atgggctcgc gataatgtcg ggcaatcagg tgcgacaatc tatcgattgt | 3840 |
| atgggaagcc cgatgcgcca gagttgtttc tgaaacatgg caaaggtagc gttgccaatg | 3900 |
| atgttacaga tgagatggtc agactaaact ggctgacgga atttatgcct cttccgacca | 3960 |
| tcaagcattt tatccgtact cctgatgatg catggttact caccactgcg atccccggca | 4020 |
| aaacagcatt ccaggtatta gaagaatatc ctgattcagg tgaaaatatt gttgatgcgc | 4080 |
| tggcagtgtt cctgcgccgg ttgcattcga ttcctgtttg taattgtcct tttaacagcg | 4140 |
| atcgcgtatt tcgtctcgct caggcgcaat cacgaatgaa taacggtttg gttgatgcga | 4200 |
| gtgattttga tgacgagcgt aatggctggc ctgttgaaca agtctggaaa gaaatgcata | 4260 |
| agcttttgcc attctcaccg gattcagtcg tcactcatgg tgatttctca cttgataacc | 4320 |
| ttatttttga cgaggggaaa ttaataggtt gtattgatgt tggacgagtc ggaatcgcag | 4380 |
| accgatacca ggatcttgcc atcctatgga actgcctcgg tgagttttct ccttcattac | 4440 |
| agaaacggct ttttcaaaaa tatggtattg ataatcctga tatgaataaa ttgcagtttc | 4500 |
| atttgatgct cgatgagttt ttctaagttt aacttgatac tactagattt tttctcttca | 4560 |
| tttataaaat ttttggttat aattgaagct ttagaagtat gaaaaaatcc ttttttttca | 4620 |
| ttctttgcaa ccaaaataag aagcttcttt tattcattga aatgatgaat ataaacctaa | 4680 |
| caaaagaaaa agactcgaat atcaaacatt aaaaaaaaat aaaagaggtt atctgttttc | 4740 |
| ccatttagtt ggagtttgca ttttctaata gatagaactc tcaattaatg tggatttagt | 4800 |
| ttctctgttc gataacttcg tatagcatac attatacgaa gttatctgaa cattagaata | 4860 |
| cgtaatccgc aatgcggggc cgcttaatta atctagagtc gacctgcagg catgcaagct | 4920 |
| tggcgtaatc atggtcatag ctgtttcctg tgtgaaattg ttatccgctc acaattccac | 4980 |
| acaacatacg agccggaagc ataaagtgta agcctggggg tgcctaatga gtgagctaac | 5040 |
| tcacattaat tgcgttgcgc tcactgcccg ctttccagtc gggaaacctg tcgtgccagc | 5100 |
| tgcattaatg aatcggccaa cgcgcgggga gaggcggttt gcgtattggg cgctcttccg | 5160 |
| cttcctcgct cactgactcg ctgcgctcgg tcgttcggct gcggcgagcg gtatcagctc | 5220 |
| actcaaaggc ggtaatacgg ttatccacag aatcagggga taacgcagga aagaacatgt | 5280 |
| gagcaaaagg ccagcaaaag gccaggaacc gtaaaaaggc cgcgttgctg gcgtttttcc | 5340 |
| ataggctccg cccccctgac gagcatcaca aaaatcgacg ctcaagtcag aggtggcgaa | 5400 |
| acccgacagg actataaaga taccaggcgt ttccccctgg aagctccctc gtgcgctctc | 5460 |
| ctgttccgac cctgccgctt accggatacc tgtccgcctt ctcccttcg ggaagcgtgg | 5520 |
| cgctttctca tagctcacgc tgtaggtatc tcagttcggt gtaggtcgtt cgctccaagc | 5580 |
| tgggctgtgt gcacgaaccc cccgttcagc ccgaccgctg cgccttatcc ggtaactatc | 5640 |
| gtcttgagtc caacccggta agacacgact tatcgccact ggcagcagcc actggtaaca | 5700 |
| ggattagcag agcgaggtat gtaggcggtg ctacagagtt cttgaagtgg tggcctaact | 5760 |

```
acggctacac tagaaggaca gtatttggta tctgcgctct gctgaagcca gttaccttcg    5820
gaaaaagagt tggtagctct tgatccggca aacaaaccac cgctggtagc ggtggttttt    5880
ttgtttgcaa gcagcagatt acgcgcagaa aaaaggatc tcaagaagat cctttgatct     5940
tttctacggg gtctgacgct cagtggaacg aaaactcacg ttaagggatt ttggtcatga    6000
gattatcaaa aaggatcttc acctagatcc ttttaaatta aaaatgaagt tttaaatcaa    6060
tctaaagtat atatgagtaa acttggtctg acagttacca atgcttaatc agtgaggcac    6120
ctatctcagc gatctgtcta tttcgttcat ccatagttgc ctgactcccc gtcgtgtaga    6180
taactacgat acgggagggc ttaccatctg gccccagtgc tgcaatgata ccgcgagacc    6240
cacgctcacc ggctccagat ttatcagcaa taaaccagcc agccggaagg gccgagcgca    6300
gaagtggtcc tgcaacttta tccgcctcca tccagtctat taattgttgc cgggaagcta    6360
gagtaagtag ttcgccagtt aatagtttgc gcaacgttgt tgccattgct acaggcatcg    6420
tggtgtcacg ctcgtcgttt ggtatggctt cattcagctc cggttcccaa cgatcaaggc    6480
gagttacatg atcccccatg ttgtgcaaaa aagcggttag ctccttcggt cctccgatcg    6540
ttgtcagaag taagttggcc gcagtgttat cactcatggt tatggcagca ctgcataatt    6600
ctcttactgt catgccatcc gtaagatgct tttctgtgac tggtgagtac tcaaccaagt    6660
cattctgaga atagtgtatg cggcgaccga gttgctcttg cccggcgtca atacgggata    6720
ataccgcgcc acatagcaga actttaaaag tgctcatcat tggaaaacgt tcttcggggc    6780
gaaaactctc aaggatctta ccgctgttga gatccagttc gatgtaaccc actcgtgcac    6840
ccaactgatc ttcagcatct tttactttca ccagcgtttc tgggtgagca aaaacaggaa    6900
ggcaaaatgc cgcaaaaaag gaataagggc gacacggaa atgttgaata ctcatactct    6960
tcctttttca atattattga agcatttatc agggttattg tctcatgagc ggatacatat    7020
ttgaatgtat ttagaaaaat aaacaaatag gggttccgcg cacatttccc cgaaaagtgc    7080
cacctgacgt ctaagaaacc attattatca tgacattaac ctataaaaat aggcgtatca    7140
cgaggccctt tcgtctcgcg cgtttcggtg atgacggtga aaacctctga cacatgcagc    7200
tcccggagac ggtcacagct tgtctgtaag cggatgccgg gagcagacaa gcccgtcagg    7260
gcgcgtcagc gggtgttggc gggtgtcggg gctggcttaa ctatgcggca tcagagcaga    7320
ttgtactgag agtgcaccat atgcggtgtg aaataccgca cagatgcgta aggagaaaat    7380
accgcatcag gcgccattcg ccattcaggc tgcgcaactg ttgggaaggg cgatcggtgc    7440
gggcctcttc gctattacgc cagctggcga aggggggatg tgctgcaagg cgattaagtt    7500
gggtaacgcc agggttttcc cagtcacgac gttgtaaaac gacggccagt gaattcgagc    7560
tcggtacccg gggatccggc gcgccgttt                                      7589
```

<210> SEQ ID NO 191
<211> LENGTH: 38
<212> TYPE: DNA
<213> ORGANISM: Artificial Sequence
<220> FEATURE:
<223> OTHER INFORMATION: Primer N191

<400> SEQUENCE: 191

```
atccgcggat agatctccca ttaccgacat ttgggcgc                              38
```

<210> SEQ ID NO 192
<211> LENGTH: 9593
<212> TYPE: DNA

<213> ORGANISM: Artificial Sequence
<220> FEATURE:
<223> OTHER INFORMATION: pYZ090 alsS

<400> SEQUENCE: 192

```
ggccgcacct ggtaaaacct ctagtggagt agtagatgta atcaatgaag cggaagccaa    60
aagaccagag tagaggccta tagaagaaac tgcgatacct tttgtgatgg ctaaacaaac   120
agacatcttt ttatatgttt ttacttctgt atatcgtgaa gtagtaagtg ataagcgaat   180
ttggctaaga acgttgtaag tgaacaaggg acctcttttg cctttcaaaa aaggattaaa   240
tggagttaat cattgagatt tagttttcgt tagattctgt atccctaaat aactcccttag  300
cccgacggga aggcacaaaa gacttgaata atagcaaacg gccagtagcc aagaccaaat   360
aatactagag ttaactgatg gtcttaaaca ggcattacgt ggtgaactcc aagaccaata   420
tacaaaatat cgataagtta ttcttgccca ccaatttaag gagcctacat caggacagta   480
gtaccattcc tcagagaaga ggtatacata acaagaaaat cgcgtgaaca ccttatataa   540
cttagcccgt tattgagcta aaaaaccttg caaaatttcc tatgaataag aatacttcag   600
acgtgataaa aatttacttt ctaactcttc tcacgctgcc cctatctgtt cttccgctct   660
accgtgagaa ataaagcatc gagtacggca gttcgctgtc actgaactaa acaataagg    720
ctagttcgaa tgatgaactt gcttgctgtc aaacttctga gttgccgctg atgtgacact   780
gtgacaataa attcaaaccg gttatagcgg tctcctccgg taccggttct gccacctcca   840
atagagctca gtaggagtca gaacctctgc ggtggctgtc agtgactcat ccgcgtttcg   900
taagttgtgc gcgtgcacat ttcgcccgtt cccgctcatc ttgcagcagg cggaaatttt   960
catcacgctg taggacgcaa aaaaaaaata attaatcgta caagaatctt ggaaaaaaaa  1020
ttgaaaaatt ttgtataaaa gggatgacct aacttgactc aatggctttt acacccagta  1080
ttttcccttt ccttgtttgt tacaattata gaagcaagac aaaaacatat agacaaccta  1140
ttcctaggag ttatattttt ttaccctacc agcaatataa gtaaaaaact gtttaaacag  1200
tatggcagtt acaatgtatt atgaagatga tgtagaagta tcagcacttg ctggaaagca  1260
aattgcagta atcggttatg gttcacaagg acatgctcac gcacagaatt tgcgtgattc  1320
tggtcacaac gttatcattg gtgtgcgcca cggaaaatct tttgataaag caaagaaga   1380
tggcttttgaa acatttgaag taggagaagc agtagctaaa gctgatgtta ttatggtttt  1440
ggcaccagat gaacttcaac aatccatttta tgaagaggac atcaaaccaa acttgaaagc  1500
aggttcagca cttggttttg ctcacggatt aatatccat tttggctata ttaaagtacc   1560
agaagacgtt gacgtcttta tggttgcgcc taaggctcca ggtcaccttg tccgtcggac  1620
ttatactgaa ggttttggta caccagcttt gtttgtttca caccaaaatg caagtggtca  1680
tgcgcgtgaa atcgcaatgg attgggccaa aggaattggt tgtgctcgag tgggaattat  1740
tgaaacaact tttaaagaag aaacagaaga gatttgtttt ggagaacaag ctgttctatg  1800
tggaggtttg acagcacttg ttgaagccgg ttttgaaaca ctgacagaag ctggatacgc  1860
tggcgaattg gcttactttg aagttttgca cgaaatgaaa ttgattgttg acctcatgta  1920
tgaaggtggt tttactaaaa tgcgtcaatc catctcaaat actgctgagt ttggcgatta  1980
tgtgactggt ccacggatta ttactgacga agttaaaaag aatatgaagc ttgttttggc  2040
tgatattcaa tctggaaaat ttgctcaaga tttcgttgat gacttcaaag cggggcgtcc  2100
aaaattaata gcctatcgcg aagctgcaaa aaatcttgaa attgaaaaaa ttggggcaga  2160
gctacgtcaa gcaatgccat tcacacaatc tggtgatgac gatgcctttta aaatctatca  2220
```

```
gtaaggccct gcaggccaga ggaaaataat atcaagtgct ggaaacttt tctcttggaa      2280 ttttttgcaac atcaagtcat agtcaattga attgacccaa tttcacattt aagatttttt   2340
tttttccatc cgacatacat ctgtacacta ggaagccctg ttttctgaa gcagcttcaa     2400 atatatatat ttttacata tttattatga ttcaatgaac aatctaatta aatcgaaaac     2460
aagaaccgaa acgcgaataa ataatttatt tagatggtga caagtgtata agtcctcatc   2520
gggacagcta cgatttctct ttcggttttg gctgagctac tggttgctgt gacgcagcgg   2580
cattagcgcg gcgttatgag ctaccctcgt ggcctgaaag atggcgggaa taaagcggaa   2640
ctaaaaatta ctgactgagc catattgagg tcaatttgtc aactcgtcaa gtcacgtttg   2700
gtggacggcc cctttccaac gaatcgtata tactaacatg cgcgcgcttc ctatatacac   2760
atatacatat atatatatat atatatgtgt gcgtgtatgt gtacacctgt atttaatttc   2820
cttactcgcg ggttttcctt tttctcaat tcttggcttc ctctttctcg agcggaccgg    2880
atcctccgcg gtgccggcag atctatttaa atggcgcgcc gacgtcaggt ggcacttttc   2940
ggggaaatgt gcgcggaacc cctatttgtt tattttccta aatacattca aatatgtatc   3000
cgctcatgag acaataaccc tgataaatgc ttcaataata ttgaaaaagg aagagtatga   3060
gtattcaaca tttccgtgtc gcccttattc ccttttttgc ggcattttgc cttcctgttt   3120
ttgctcaccc agaaacgctg gtgaaagtaa aagatgctga agatcagttg ggtgcacgag   3180
tgggttacat cgaactggat ctcaacagcg gtaagatcct tgagagtttt cgccccgaag   3240
aacgttttcc aatgatgagc actttaaaag ttctgctatg tggcgcggta ttatcccgta   3300
ttgacgccgg gcaagagcaa ctcggtcgcc gcatacacta ttctcagaat gacttggttg   3360
agtactcacc agtcacagaa aagcatctta cggatggcat gacagtaaga gaattatgca   3420
gtgctgccat aaccatgagt gataacactg cggccaactt acttctgaca acgatcggag   3480
gaccgaagga gctaaccgct ttttgcaca acatggggga tcatgtaact cgccttgatc     3540
gttgggaacc ggagctgaat gaagccatac caaacgacga gcgtgacacc acgatgcctg   3600
tagcaatggc aacaacgttg cgcaaactat taactggcga actacttact ctagcttccc   3660
ggcaacaatt aatagactgg atggaggcgg ataaagttgc aggaccactt ctgcgctcgg   3720
cccttccggc tggctggttt attgctgata atctggagc cggtgagcgt gggtctcgcg    3780
gtatcattgc agcactgggg ccagatggta agccctcccg tatcgtagtt atctacacga   3840
cggggagtca ggcaactatg gatgaacgaa atagacagat cgctgagata ggtgcctcac   3900
tgattaagca ttggtaactg tcagaccaag tttactcata tatactttag attgatttaa   3960
aacttcattt ttaatttaaa aggatctagg tgaagatcct ttttgataat ctcatgacca   4020
aaatccctta acgtgagttt tcgttccact gagcgtcaga ccccgtagaa aagatcaaag   4080
gatcttcttg agatcctttt tttctgcgcg taatctgctg cttgcaaaca aaaaaaccac   4140
cgctaccagc ggtggtttgt ttgccggatc aagagctacc aactcttttt ccgaaggtaa   4200
ctggcttcag cagagcgcag ataccaaata ctgttcttct agtgtagccg tagttaggcc   4260
accacttcaa gaactctgta gcaccgccta catacctcgc tctgctaatc ctgttaccag   4320
tggctgctgc cagtggcgat aagtcgtgtc ttaccgggtt ggactcaaga cgatagttac   4380
cggataaggc gcagcggtcg ggctgaacgg ggggttcgtg cacacagccc agcttggagc   4440
gaacgaccta caccgaactg agatacctac agcgtgagct atgagaaagc gccacgcttc   4500
ccgaagggag aaaggcggac aggtatccgg taagcggcag ggtcggaaca ggagagcgca   4560
```

```
cgagggagct tccagggga aacgcctggt atctttatag tcctgtcggg tttcgccacc    4620
tctgacttga gcgtcgattt ttgtgatgct cgtcaggggg gcggagccta tggaaaaacg    4680
ccagcaacgc ggccttttta cggttcctgg ccttttgctg gccttttgct cacatgttct    4740
ttcctgcgtt atccctgat  tctgtggata accgtattac cgcctttgag tgagctgata    4800
ccgctcgccg cagccgaacg accgagcgca gcgagtcagt gagcgaggaa gcggaagagc    4860
gcccaatacg caaaccgcct ctccccgcgc gttggccgat tcattaatgc agctggcacg    4920
acaggtttcc cgactggaaa gcgggcagtg agcgcaacgc aattaatgtg agttagctca    4980
ctcattaggc accccaggct ttacacttta tgcttccggc tcgtatgttg tgtggaattg    5040
tgagcggata acaatttcac acaggaaaca gctatgacca tgattacgcc aagcttttc     5100
tttccaattt tttttttttc gtcattataa aaatcattac gaccgagatt cccgggtaat    5160
aactgatata attaaattga agctctaatt tgtgagttta gtatacatgc atttacttat    5220
aatacagttt tttagttttg ctggccgcat cttctcaaat atgcttccca gcctgctttt    5280
ctgtaacgtt caccctctac cttagcatcc cttccctttg caaatagtcc tcttccaaca    5340
ataataatgt cagatcctgt agagaccaca tcatccacgg ttctatactg ttgacccaat    5400
gcgtctccct tgtcatctaa acccacaccg ggtgtcataa tcaaccaatc gtaaccttca    5460
tctcttccac ccatgtctct tgagcaataa agccgataa  caaatctttt gtcgctcttc    5520
gcaatgtcaa cagtacccttt agtatattct ccagtagata gggagcccttt gcatgacaat    5580
tctgctaaca tcaaaaggcc tctaggttcc tttgttactt cttctgccgc ctgcttcaaa    5640
ccgctaacaa tacctgggcc caccacaccg tgtgcattcg taatgtctgc ccattctgct    5700
attctgtata cacccgcaga gtactgcaat ttgactgtat taccaatgtc agcaaatttt    5760
ctgtcttcga agagtaaaa  attgtacttg gcggataatg cctttagcgg cttaactgtg    5820
ccctccatgg aaaaatcagt caagatatcc acatgtgttt ttagtaaaca aatttttggga   5880
cctaatgctt caactaactc cagtaattcc ttggtggtac gaacatccaa tgaagcacac    5940
aagtttgttt gcttttcgtg catgatatta aatagcttgg cagcaacagg actaggatga    6000
gtagcagcac gttccttata tgtagctttc gacatgattt atcttcgttt cctgcaggtt    6060
tttgttctgt gcagttgggt taagaatact gggcaatttc atgtttcttc aacactacat    6120
atgcgtatat ataccaatct aagtctgtgc tccttccttc gttcttcctt ctgttcggag    6180
attaccgaat caaaaaaatt tcaaggaaac cgaaatcaaa aaaagaata  aaaaaaaaat    6240
gatgaattga aaagcttgca tgcctgcagg tcgactctag tatactccgt ctactgtacg    6300
atacacttcc gctcaggtcc ttgtccttta acgaggcctt accactcttt tgttactcta    6360
ttgatccagc tcagcaaagg cagtgtgatc taagattcta tcttcgcgat gtagtaaaac    6420
tagctagacc gagaaagaga ctagaaatgc aaaaggcact tctacaatgg ctgccatcat    6480
tattatccga tgtgacgctg cattttttt ttttttttt  ttttttttt  tttttttttt    6540
tttttttttt ttttgtacaa atatcataaa aaagagaat  cttttaagc  aaggattttc    6600
ttaacttctt cggcgacagc atcaccgact tcggtggtac tgttggaacc acctaaatca    6660
ccagttctga tacctgcatc caaaccctt  ttaactgcat cttcaatggc tttaccttct    6720
tcaggcaagt tcaatgacaa tttcaacatc attgcagcag acaagatagt ggcgataggg    6780
ttgaccttat tctttggcaa atctggagcg gaaccatggc atggttcgta caaaccaaat    6840
gcggtgttct tgtctggcaa agaggccaag gacgcagatg gcaacaaacc caaggagcct    6900
gggataacgg aggcttcatc ggagatgata tcaccaaaca tgttgctggt gattataata    6960
```

```
ccatttaggt gggttgggtt cttaactagg atcatggcgg cagaatcaat caattgatgt   7020
tgaactttca atgtagggaa ttcgttcttg atggtttcct ccacagtttt tctccataat   7080
cttgaagagg ccaaaacatt agctttatcc aaggaccaaa taggcaatgg tggctcatgt   7140
tgtagggcca tgaaagcggc cattcttgtg attctttgca cttctggaac ggtgtattgt   7200
tcactatccc aagcgacacc atcaccatcg tcttcctttc tcttaccaaa gtaaatacct   7260
cccactaatt ctctaacaac aacgaagtca gtacctttag caaattgtgg cttgattgga   7320
gataagtcta aaagagagtc ggatgcaaag ttacatggtc ttaagttggc gtacaattga   7380 agttcttac ggattttag taaaccttgt tcaggtctaa cactaccggt accccattta     7440
ggaccaccca cagcacctaa caaaacggca tcagccttct tggaggcttc cagcgcctca   7500
tctggaagtg aacacctgt agcatcgata gcagcaccac caattaaatg attttcgaaa    7560
tcgaacttga cattggaacg aacatcagaa atagctttaa gaaccttaat ggcttcggct   7620
gtgatttctt gaccaacgtg gtcacctggc aaaacgacga tcttcttagg ggcagacatt   7680
acaatggtat atccttgaaa tatatataaa aaaaaaaaa aaaaaaaaa aaaaaatgc      7740 agcttctcaa tgatattcga atacgctttg aggagataca gcctaatatc cgacaaactg   7800
ttttacagat ttacgatcgt acttgttacc catcattgaa ttttgaacat ccgaacctgg   7860
gagttttccc tgaaacagat agtatatttg aacctgtata ataatatata gtctagcgct   7920
ttacggaaga caatgtatgt atttcggttc ctggagaaac tattgcatct attgcatagg   7980
taatcttgca cgtcgcatcc ccggttcatt ttctgcgttt ccatcttgca cttcaatagc   8040
atatctttgt taacgaagca tctgtgcttc attttgtaga acaaaaatgc aacgcgagag   8100
cgctaatttt tcaaacaaag aatctgagct gcattttac agaacagaaa tgcaacgcga    8160
aagcgctatt ttaccaacga gaatctgtg cttcatttt gtaaacaaa aatgcaacgc      8220 gagagcgcta attttcaaa caaagaatct gagctgcatt tttacagaac agaaatgcaa    8280
cgcgagagcg ctattttacc aacaaagaat ctatacttct tttttgttct acaaaaatgc   8340
atcccgagag cgctatttt ctaacaaagc atcttagatt acttttttc tcctttgtgc     8400 gctctataat gcagtctctt gataactttt tgcactgtag gtccgttaag gttagaagaa   8460
ggctactttg gtgtctattt tctcttccat aaaaaaagcc tgactccact tcccgcgttt   8520
actgattact agcgaagctg cgggtgcatt ttttcaagat aaaggcatcc ccgattatat   8580
tctataccga tgtggattgc gcatactttg tgaacagaaa gtgatagcgt tgatgattct   8640
tcattggtca gaaaattatg aacggttct tctattttgt ctctatatac tacgtatagg    8700
aaatgtttac attttcgtat tgttttcgat tcactctatg aatagttctt actacaattt   8760
ttttgtctaa agagtaatac tagagataaa cataaaaaat gtagaggtcg agtttagatg   8820
caagttcaag gagcgaaagg tggatgggta ggttatatag ggatatagca cagagatata   8880
tagcaaagag atacttttga gcaatgtttg tggaagcggt attcgcaata ttttagtagc   8940
tcgttacagt ccggtgcgtt tttggttttt tgaaagtgcg tcttcagagc gcttttggtt   9000
ttcaaaagcg ctctgaagtt cctatacttt ctagagaata ggaacttcgg aataggaact   9060
tcaaagcgtt tccgaaaacg agcgcttccg aaaatgcaac gcgagctgcg cacatacagc   9120
tcactgttca cgtcgcacct atatctgcgt gttgcctgta tatatatata catgagaaga   9180
acggcatagt gcgtgtttat gcttaaatgc gtacttatat gcgtctattt atgtaggatg   9240
aaaggtagtc tagtacctcc tgtgatatta tcccattcca tgcgggtat cgtatgcttc    9300
```

| | | |
|---|---|---|
| cttcagcact acccttttagc tgttctatat gctgccactc ctcaattgga ttagtctcat | 9360 | |
| ccttcaatgc tatcatttcc tttgatattg gatcatatgc atagtaccga gaaactagag | 9420 | |
| gatctcccat taccgacatt tgggcgctat acgtgcatat gttcatgtat gtatctgtat | 9480 | |
| ttaaaacact tttgtattat ttttcctcat atatgtgtat aggtttatac ggatgattta | 9540 | |
| attattactt caccacccctt tatttcaggc tgatatctta gccttgttac tag | 9593 | |

<210> SEQ ID NO 193
<211> LENGTH: 22
<212> TYPE: DNA
<213> ORGANISM: Artificial Sequence
<220> FEATURE:
<223> OTHER INFORMATION: Primer oBP556

<400> SEQUENCE: 193
tattttcgag gaccttgtca cc    22

<210> SEQ ID NO 194
<211> LENGTH: 25
<212> TYPE: DNA
<213> ORGANISM: Artificial Sequence
<220> FEATURE:
<223> OTHER INFORMATION: Primer oBP561

<400> SEQUENCE: 194
tggccattaa tctttcccat attag    25

<210> SEQ ID NO 195
<211> LENGTH: 12896
<212> TYPE: DNA
<213> ORGANISM: Artificial Sequence
<220> FEATURE:
<223> OTHER INFORMATION: pBP915

<400> SEQUENCE: 195

| | | |
|---|---|---|
| tcgcgcgttt cggtgatgac ggtgaaaacc tctgacacat gcagctcccg gagacggtca | 60 | |
| cagcttgtct gtaagcggat gccggagcaa gacaagcccg tcagggcgcg tcagcgggtg | 120 | |
| ttggcgggtg tcgggctgg cttaactatg cggcatcaga gcagattgta ctgagagtgc | 180 | |
| accataaatt cccgttttaa gagcttggtg agcgctagga gtcactgcca ggtatcgttt | 240 | |
| gaacacggca ttagtcaggg aagtcataac acagtccttt ccgcaatttt cttttttcta | 300 | |
| ttactcttgg cctcctctag tacactctat atttttttat gcctcggtaa tgattttcat | 360 | |
| tttttttttt ccacctagcg gatgactctt tttttttctt agcgattggc attatcacat | 420 | |
| aatgaattat acattatata agtaatgtg atttcttcga agaatatact aaaaaatgag | 480 | |
| caggcaagat aaacgaaggc aaagatgaca gagcagaaag ccctagtaaa gcgtattaca | 540 | |
| aatgaaacca agattcagat tgcgatctct ttaaagggtg gtcccctagc gatagagcac | 600 | |
| tcgatcttcc cagaaaaaga ggcagaagca gtagcagaac aggccacaca atcgcaagtg | 660 | |
| attaacgtcc acacaggtat agggtttctg gaccatatga tacatgctct ggccaagcat | 720 | |
| tccggctggt cgctaatcgt tgagtgcatt ggtgacttac acatagacga ccatcacacc | 780 | |
| actgaagact gcgggattgc tctcggtcaa gcttttaaag aggccctagg ggccgtgcgt | 840 | |
| ggagtaaaaa ggtttggatc aggatttgcg cctttggatg aggcactttc cagagcggtg | 900 | |
| gtagatcttt cgaacaggcc gtacgcagtt gtcgaacttg gtttgcaaag ggagaaagta | 960 | |
| ggagatctct cttgcgagat gatcccgcat tttcttgaaa gctttgcaga ggctagcaga | 1020 | |
| attaccctcc acgttgattg tctgcgaggc aagaatgatc atcaccgtag tgagagtgcg | 1080 | |

```
ttcaaggctc ttgcggttgc cataagagaa gccacctcgc ccaatggtac caacgatgtt    1140
ccctccacca aaggtgttct tatgtagtga caccgattat ttaaagctgc agcatacgat    1200
atatatacat gtgtatatat gtatacctat gaatgtcagt aagtatgtat acgaacagta    1260
tgatactgaa gatgacaagg taatgcatca ttctatacgt gtcattctga acgaggcgcg    1320
cttccctttt ttcttttgc ttttctttt tttttctctt gaactcgacg gatctatgcg    1380
gtgtgaaata ccgcacagat gcgtaaggag aaaataccgc atcaggaaat tgtaagcgtt    1440 aatatttgt taaaattcgc gttaaatttt tgttaaatca gctcattttt taaccaatag    1500
gccgaaatcg gcaaaatccc ttataaatca aagaataga ccgagatagg gttgagtgtt    1560
gttccagttt ggaacaagag tccactatta agaacgtgg actccaacgt caaagggcga    1620
aaaaccgtct atcagggcga tggcccacta cgtgaaccat caccctaatc aagttttttg    1680
gggtcgaggt gccgtaaagc actaaatcgg aaccctaaag ggagccccg atttagagct    1740 tgacggggaa agccggcgaa cgtggcgaga aggaaggga agaaagcgaa aggagcgggc    1800
gctagggcgc tggcaagtgt agcggtcacg ctgcgcgtaa ccaccacacc cgccgcgctt    1860
aatgcgccgc tacagggcgc gtccattcgc cattcaggct gcgcaactgt tgggaagggc    1920
gcggtgcggg cctcttcgct attacgccag ctggcgaaag ggggatgtgc tgcaaggcga    1980
ttaagttggg taacgccagg ttttcccag tcacgacgtt gtaaaacgac ggccagtgag    2040
cgcgcgtaat acgactcact atagggcgaa ttgggtaccg ggccccccct cgaggtcgac    2100
ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tccttttcccc    2400 atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat tttccttt tccattctag cagccgtcgg gaaaacgtgg catcctctct    2700
ttcgggctca attggagtca cgctgccgtg agcatcctct ctttccatat ctaacaactg    2760
agcacgtaac caatggaaaa gcatgagctt agcgttgctc caaaaagta ttggatggtt    2820 aataccattt gtctgttctc ttctgacttt gactcctcaa aaaaaaaat ctacaatcaa    2880 cagatcgctt caattacgcc ctcacaaaaa ctttttcct tcttcttcgc ccacgttaaa    2940
ttttatccct catgttgtct aacggatttc tgcacttgat ttattataaa aagacaaaga    3000
cataatactt ctctatcaat ttcagttatt gttcttcctt gcgttattct tctgttcttc    3060
tttttctttt gtcatatata accataacca agtaatacat attcaaacta gtatgactga    3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact tacatgactt    3300 tggtaaaacta gccaaagtcg gtgttaagga agctggtgct tggccagttc agttcggaac    3360
aatcacggtt tctgatggaa tcgccatggg aacccaagga atgcgtttct ccttgacatc    3420
```

```
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccattttg cttacggcgg aacaattgca cctggtaatt tagacggcaa    3600
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct cacccggctg aatccgcaga aaagaaagca gatattgaag aagctggtcg    3840
cgctgttgtc aaaatgctcg aaatgggctt aaaaccttct gacattttaa cgcgtgaagc    3900
ttttgaagat gctattactg taactatggc tctgggaggt tcaaccaact caaccccttca    3960 cctcttagct attgcccatg ctgctaatgt ggaattgaca cttgatgatt caatactttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa acagtcgct gaaaatttga aggcttttga    4200
tgatttaaca cctggtcaaa aggttattat gccgcttgaa atcctaaac gtgaagatgg    4260 tccgctcatt attctccatg gtaacttggc tccagacggt gccgttgcca agtttctgg    4320 tgtaaaagtg cgtcgtcatg tcggtcctgc taaggtcttt aattctgaag aagaagccat    4380
tgaagctgtc ttgaatgatg atattgttga tggtgatgtt ttgtcgtac gttttgtagg    4440 accaaagggc ggtcctggta tgcctgaaat gctttcccct tcatcaatga ttgttggtaa    4500
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttacactttg atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
gaagcctgaa gaaactggca aaaaatgttg tcctggttgc tgtggttaag cggccgcgtt    4860
aattcaaatt aattgatata gttttttaat gagtattgaa tctgtttaga aataatggaa    4920
tattattttt atttatttat ttatattatt ggtcggctct tttcttctga aggtcaatga    4980
caaaatgata tgaaggaaat aatgatttct aaaatttac aacgtaagat attttttacaa    5040 aagcctagct catcttttgt catgcactat tttactcacg cttgaaatta acggccagtc    5100
cactgcggag tcatttcaaa gtcatcctaa tcgatctatc gttttgata gctcattttg    5160 gagttcgcga ttgtcttctg ttattcacaa ctgttttaat tttatttca ttctggaact    5220 cttcgagttc tttgtaaagt ctttcatagt agcttacttt atcctccaac atatttaact    5280
tcatgtcaat ttcggctctt aaattttcca catcatcaag ttcaacatca tctttaact    5340 tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg gacgtgtcac tctacttcgc cttttcccct actcctttta    5580
gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760 tgattttga tattgtataa aaaaccaaa tatgtataaa aaagtgaat aaaaaatacc    5820
```

```
aagtatggag aaatatatta gaagtctata cgttaaacca cccgggcccc ccctcgaggt    5880
cgacggtatc gataagcttg atatcgaatt cctgcagccc gggggatcca ctagttctag    5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat tttttttata acttatttaa    6240
taataaaaat cataaatcat aagaaattcg cttactctta attaatcaaa aagttaaaat    6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaccggtg gaaaatccgc accctatcaa    6900
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140 gatcactta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc    7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt ttccatcagc    7740
tggcagggaa cggaaagtgg aatcccattt agcgagcttc ctctttttctt caagaaagaa    7800 cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagttttc    8100 aagggtttat cgttagaaga ttctcccttt tcttcctgct cacaaatctt aaagtcatac    8160
```

| | |
|---|---|
| attgcacgac taaatgcaag catgcggatc ccccgggctg caggaattcg atatcaagct | 8220 |
| tatcgatacc gtcgactggc cattaatctt tcccatatta gatttcgcca agccatgaaa | 8280 |
| gttcaagaaa ggtctttaga cgaattaccc ttcatttctc aaactggcgt caagggatcc | 8340 |
| tggtatggtt ttatcgtttt atttctggtt cttatagcat cgttttggac ttctctgttc | 8400 |
| ccattaggcg gttcaggagc cagcgcagaa tcattctttg aaggatactt atcctttcca | 8460 |
| attttgattg tctgttacgt tggacataaa ctgtatacta gaaattggac tttgatggtg | 8520 |
| aaactagaag atatggatct tgataccggc agaaaacaag tagatttgac tcttcgtagg | 8580 |
| gaagaaatga ggattgagcg agaaacatta gcaaaaagat ccttcgtaac aagatttta | 8640 |
| catttctggt gttgaaggga agatatgag ctatacagcg gaatttccat atcactcaga | 8700 |
| ttttgttatc taattttttc cttcccacgt ccgcgggaat ctgtgtatat tactgcatct | 8760 |
| agatatatgt tatcttatct tggcgcgtac atttaatttt caacgtattc tataagaaat | 8820 |
| tgcgggagtt tttttcatgt agatgatact gactgcacgc aaataggc atgatttata | 8880 |
| ggcatgattt gatggctgta ccgataggaa cgctaagagt aacttcagaa tcgttatcct | 8940 |
| ggcggaaaaa attcatttgt aaactttaaa aaaaaaagcc aatatcccca aaattattaa | 9000 |
| gagcgcctcc attattaact aaaatttcac tcagcatcca caatgtatca ggtatctact | 9060 |
| acagatatta catgtggcga aaaagacaag aacaatgcaa tagcgcatca agaaaaaaca | 9120 |
| caaagctttc aatcaatgaa tcgaaaatgt cattaaaata gtatataaat tgaaactaag | 9180 |
| tcataaagct ataaaagaa aatttattta atcttggct ctcttgggct caaggtgaca | 9240 |
| aggtcctcga aaatagggcg cgccccaccg cggtggagct ccagcttttg ttccctttag | 9300 |
| tgagggttaa ttgcgcgctt ggcgtaatca tggtcatagc tgtttcctgt gtgaaattgt | 9360 |
| tatccgctca caattccaca caacatacga gccggaagca taaagtgtaa agcctggggt | 9420 |
| gcctaatgag tgagctaact cacattaatt gcgttgcgct cactgcccgc tttccagtcg | 9480 |
| ggaaacctgt cgtgccagct gcattaatga atcggccaac gcgcggggag aggcggtttg | 9540 |
| cgtattgggc gctcttccgc ttcctcgctc actgactcgc tgcgctcggt cgttcggctg | 9600 |
| cggcgagcgg tatcagctca ctcaaaggcg gtaatacggt tatccacaga atcaggggat | 9660 |
| aacgcaggaa agaacatgtg agcaaaaggc cagcaaaagg ccaggaaccg taaaaaggcc | 9720 |
| gcgttgctgg cgttttcca taggctccgc cccctgacg agcatcacaa aaatcgacgc | 9780 |
| tcaagtcaga ggtggcgaaa cccgacagga ctataaagat accaggcgtt tcccctgga | 9840 |
| agctccctcg tgcgctctcc tgttccgacc ctgccgctta ccggatacct gtccgccttt | 9900 |
| ctcccttcgg gaagcgtggc gctttctcat agctcacgct gtaggtatct cagttcggtg | 9960 |
| taggtcgttc gctccaagct gggctgtgtg cacgaacccc ccgttcagcc cgaccgctgc | 10020 |
| gccttatccg gtaactatcg tcttgagtcc aacccggtaa gacacgactt atcgccactg | 10080 |
| gcagcagcca ctggtaacag gattagcaga gcgaggtatg taggcggtgc tacagagttc | 10140 |
| ttgaagtggt ggcctaacta cggctacact agaagaacag tatttggtat ctgcgctctg | 10200 |
| ctgaagccag ttaccttcgg aaaaagagtt ggtagctctt gatccggcaa acaaaccacc | 10260 |
| gctggtagcg gtggtttttt tgtttgcaag cagcagatta cgcgcagaaa aaaggatct | 10320 |
| caagaagatc ctttgatctt ttctacgggg tctgacgctc agtggaacga aaactcacgt | 10380 |
| taagggattt tggtcatgag attatcaaaa aggatcttca cctagatcct tttaaattaa | 10440 |
| aaatgaagtt ttaaatcaat ctaaagtata tatgagtaaa cttggtctga cagttaccaa | 10500 |
| tgcttaatca gtgaggcacc tatctcagcg atctgtctat ttcgttcatc catagttgcc | 10560 |

```
tgactcccg tcgtgtagat aactacgata cgggagggct taccatctgg ccccagtgct   10620
gcaatgatac cgcgagaccc acgctcaccg gctccagatt tatcagcaat aaaccagcca   10680
gccggaaggg ccgagcgcag aagtggtcct gcaactttat ccgcctccat ccagtctatt   10740
aattgttgcc gggaagctag agtaagtagt tcgccagtta atagtttgcg caacgttgtt   10800
gccattgcta caggcatcgt ggtgtcacgc tcgtcgtttg gtatggcttc attcagctcc   10860
ggttcccaac gatcaaggcg agttacatga tcccccatgt tgtgcaaaaa agcggttagc   10920
tccttcggtc ctccgatcgt tgtcagaagt aagttggccg cagtgttatc actcatggtt   10980
atggcagcac tgcataattc tcttactgtc atgccatccg taagatgctt ttctgtgact   11040
ggtgagtact caaccaagtc attctgagaa tagtgtatgc ggcgaccgag ttgctcttgc   11100
ccggcgtcaa tacgggataa taccgcgcca catagcagaa ctttaaaagt gctcatcatt   11160
ggaaaacgtt cttcggggcg aaaactctca aggatcttac cgctgttgag atccagttcg   11220
atgtaaccca ctcgtgcacc caactgatct tcagcatctt ttactttcac cagcgtttct   11280
gggtgagcaa aaacaggaag gcaaaatgcc gcaaaaaagg aataagggc gacacggaaa   11340 tgttgaatac tcatactctt ccttttcaa tattattgaa gcatttatca gggttattgt   11400
ctcatgagcg gatacatatt tgaatgtatt tagaaaaata aacaaatagg ggttccgcgc   11460
acatttcccc gaaaagtgcc acctgaacga agcatctgtg cttcattttg tagaacaaaa   11520
atgcaacgcg agagcgctaa ttttcaaac aaagaatctg agctgcattt ttacagaaca   11580
gaaatgcaac gcgaaagcgc tattttacca acgaagaatc tgtgcttcat ttttgtaaaa   11640
caaaaatgca acgcgagagc gctaattttt caaacaaaga atctgagctg cattttaca   11700 gaacagaaat gcaacgcgag agcgctattt taccaacaaa gaatctatac ttcttttttg   11760
ttctacaaaa atgcatcccg agagcgctat ttttctaaca aagcatctta gattacttttt   11820 tttctccttt gtgcgctcta taatgcagtc tcttgataac ttttttgcact gtaggtccgt   11880 taaggttaga agaaggctac tttggtgtct attttctctt ccataaaaaa agcctgactc   11940
cacttcccgc gtttactgat tactagcgaa gctgcgggtg cattttttca agataaaggc   12000
atccccgatt atattctata ccgatgtgga ttgcgcatac tttgtgaaca gaaagtgata   12060
gcgttgatga ttcttcattg gtcagaaaat tatgaacggt ttcttctatt ttgtctctat   12120
atactacgta taggaaatgt ttacattttc gtattgtttt cgattcactc tatgaatagt   12180
tcttactaca attttttttgt ctaaagagta atactagaga taaacataaa aaatgtagag   12240
gtcgagttta gatgcaagtt caaggagcga aaggtggatg ggtaggttat atagggatat   12300
agcacagaga tatatagcaa agagatactt ttgagcaatg tttgtggaag cggtattcgc   12360 aatatttta g tagctcgtta cagtccggtg cgttttggt tttttgaaag tgcgtcttca   12420
gagcgctttt ggttttcaaa agcgctctga agttcctata ctttctagag aataggaact   12480
tcggaatagg aacttcaaag cgtttccgaa aacgagcgct tccgaaaatg caacgcgagc   12540
tgcgcacata cagctcactg ttcacgtcgc acctatatct gcgtgttgcc tgtatatata   12600
tatacatgag aagaacggca tagtgcgtgt ttatgcttaa atgcgtactt atatgcgtct   12660
atttatgtag gatgaaaggt agtctagtac ctcctgtgat attatcccat tccatgcggg   12720
gtatcgtatg cttccttcag cactacccctt tagctgttct atatgctgcc actcctcaat   12780
tggattagtc tcatccttca atgctatcat ttcctttgat attggatcat actaagaaac   12840
cattattatc atgacattaa cctataaaaa taggcgtatc acgaggccct ttcgtc       12896
```

<210> SEQ ID NO 196
<211> LENGTH: 3015
<212> TYPE: DNA
<213> ORGANISM: Artificial Sequence
<220> FEATURE:
<223> OTHER INFORMATION: FBA1-alsS- CYCt in Chr. XII; Upstream region = nt 1-154; FBA1 promoter = nt 155-802; alsS CDS = nt; CYC1 terminator = nt 2534-2788; Downstream region = nt 2790-3015

<400> SEQUENCE: 196

```
gcgatttaat ctctaattat tagttaaagt tttataagca tttttatgta acgaaaaata    60
aattggttca tattattact gcactgtcac ttaccatgga agaccagac aagaagttgc    120 cgacagtctg ttgaattggc ctggttaggc ttaagatctg aaatgaataa caatactgac   180
agtactaaat aattgcctac ttggcttcac atacgttgca tacgtcgata tagataataa    240
tgataatgac agcaggatta tcgtaatacg taatagttga aaatctcaaa aatgtgtggg    300
tcattacgta aataatgata ggaatgggat tcttctattt ttccttttc cattctagca    360 gccgtcggga aaacgtggca tcctctcttt cgggctcaat tggagtcacg ctgccgtgag    420
catcctctct ttccatatct aacaactgag cacgtaacca atggaaaagc atgagcttag    480
cgttgctcca aaaagtatt ggatggttaa taccatttgt ctgttctctt ctgactttga     540
ctcctcaaaa aaaaaaatc tacaatcaac agatcgcttc aattacgccc tcacaaaaac    600
ttttttcctt cttcttcgcc cacgttaaat tttatccctc atgttgtcta acggatttct    660
gcacttgatt tattataaaa agacaaagac ataatacttc tctatcaatt tcagttattg    720
ttcttccttg cgttattctt ctgttcttct ttttcttttg tcatatataa ccataaccaa    780
gtaatacata ttcaaatcta gagctgagga tgttgacaaa agcaacaaaa gaacaaaaat    840
cccttgtgaa aaacagaggg gcggagcttg ttgttgattg cttagtggag caaggtgtca    900
cacatgtatt tggcattcca ggtgcaaaaa ttgatgcggt atttgacgct ttacaagata    960
aaggacctga aattatcgtt gcccggcacg aacaaaacgc agcattcatg cccaagcag    1020 tcggccgttt aactggaaaa ccgggagtcg tgttagtcac atcaggaccg ggtgcctcta    1080
acttggcaac aggcctgctg acagcgaaca ctgaaggaga ccctgtcgtt gcgcttgctg    1140
gaaacgtgat ccgtgcagat cgtttaaaac ggacacatca atctttggat aatgcggcgc    1200
tattccagcc gattacaaaa tacagtgtag aagttcaaga tgtaaaaaat ataccggaag    1260
ctgttacaaa tgcatttagg atagcgtcag cagggcaggc tggggccgct tttgtgagct    1320
ttccgcaaga tgttgtgaat gaagtcacaa atacgaaaaa cgtgcgtgct gttgcagcgc    1380
caaaactcgg tcctgcagca gatgatgcaa tcagtgcggc catagcaaaa atccaaacag    1440
caaaacttcc tgtcgttttg gtcggcatga aggcggaag accggaagca attaaagcgg    1500
ttcgcaagct tttgaaaaag gttcagcttc catttgttga acatatcaa gctgccggta    1560 ccctttctag agatttagag gatcaatatt ttggccgtat cggtttgttc cgcaaccagc    1620
ctggcgattt actgctagag caggcagatg ttgttctgac gatcggctat gacccgattg    1680
aatatgatcc gaaattctgg aatatcaatg gagaccggac aattatccat ttagacgaga    1740
ttatcgctga cattgatcat gcttaccagc ctgatcttga attgatcggt gacattccgt    1800
ccacgatcaa tcatatcgaa cacgatgctg tgaaagtgga atttgcagag cgtgagcaga    1860
aaatcctttc tgatttaaaa caatatatgc atgaaggtga gcaggtgcct gcagattgga    1920
aatcagacag agcgcaccct cttgaaatcg ttaaagagtt gcgtaatgca gtcgatgatc    1980
atgttacagt aacttgcgat atcggttcgc acgccatttg gatgtcacgt atttccgca    2040
```

```
gctacgagcc gttaacatta atgatcagta acggtatgca aacactcggc gttgcgcttc    2100
cttgggcaat cggcgcttca ttggtgaaac cgggagaaaa agtggtttct gtctctggtg    2160
acggcggttt cttattctca gcaatggaat tagagacagc agttcgacta aaagcaccaa    2220
ttgtacacat tgtatggaac gacagcacat atgacatggt tgcattccag caattgaaaa    2280
aatataaccg tacatctgcg gtcgatttcg gaaatatcga tatcgtgaaa tatgcggaaa    2340
gcttcggagc aactggcttg cgcgtagaat caccagacca gctggcagat gttctgcgtc    2400
aaggcatgaa cgctgaaggt cctgtcatca tcgatgtccc ggttgactac agtgataaca    2460
ttaatttagc aagtgacaag cttccgaaag aattcgggga actcatgaaa acgaaagctc    2520
tctagttaat taatcatgta attagttatg tcacgcttac attcacgccc tccccccaca    2580
tccgctctaa ccgaaaagga aggagttaga caacctgaag tctaggtccc tatttatttt    2640
tttatagtta tgttagtatt aagaacgtta tttatatttc aaatttttct tttttttctg    2700
tacagacgcg tgtacgcatg taacattata ctgaaaacct tgcttagaag gttttggga    2760
cgctcgaagg ctttaatttg cgggcggcct taagtctggg tccgcttctt tacaaatttg    2820
gagaatttct cttaaacgat atgtatattc ttttcgttgg aaaagatgtc ttccaaaaaa    2880
aaaaccgatg aattagtgga accaaggaaa aaaaagagg tatccttgat taaggaacac    2940
tgtttaaaca gtgtggtttc caaaaccctg aaactgcatt agtgtaatag aagactagac    3000
acctcgatac aaata                                                    3015

<210> SEQ ID NO 197
<211> LENGTH: 2900
<212> TYPE: DNA
<213> ORGANISM: Artificial Sequence
<220> FEATURE:
<223> OTHER INFORMATION: fra2delta::PDC1-hADH-ADHt; Upstream region =
      nt 1-300; PDC1 promoter = nt 309-1178; hADH coding region = nt
      1179-2306; ADH1 terminator = nt 2315-2630; Downstream region = nt
      2639-2900

<400> SEQUENCE: 197
gttagcatcc acagcttctt gagcaactga cttcgtgagg tctacagtca aaaggacctt      60
tgttttagcg tttgcatcgg cagtggtgac ttgtgcagtg gaacaatcga tgagaagacc     120
cgtattgtcc cagctcttgt ctgcgtactt tgagggtag aacttggtaa tgctacgcac      180
aagtttgtcc aattgtgctc tagtaatagc tctgctcatt gcgtttcggt ggactcttgt     240
tctgtttcct tccgactgtg tattggaata agttttttcgg tgtttatatat atacatatat   300
ggcgcgcccc gcacgccgaa atgcatgcaa gtaacctatt caaagtaata tctcatacat     360
gtttcatgag gtaacaaca tgcgactggg tgagcatatg ttccgctgat gtgatgtgca      420
agataaacaa gcaaggcaga aactaacttc ttcttcatgt aataaacaca ccccgcgttt     480
atttacctat ctctaaactt caacaccta tatcataact aatattcttt gagataagca     540
cactgcaccc ataccttcct taaaaacgta gcttccagtt tttggtggtt ccggcttcct    600
tcccgattcc gcccgctaaa cgcatatttt tgttgcctgg tggcatttgc aaaatgcata    660
acctatgcat ttaaaagatt atgtatgctc ttctgactt tcgtgtgatg aggctcgtgg    720
aaaaaatgaa taatttatga atttgagaac aattttgtgt tgttacggta ttttactatg    780
gaataatcaa tcaattgagg attttatgca aatatcgttt gaatattttt ccgaccccttt  840
gagtactttt cttcataatt gcataatatt gtccgctgcc ccttttttctg ttagacggtg    900
tcttgatcta cttgctatcg ttcaacacca ccttattttc taactatttt ttttttagct    960
```

```
catttgaatc agcttatggt gatggcacat ttttgcataa acctagctgt cctcgttgaa    1020
cataggaaaa aaaatatat aaacaaggct ctttcactct ccttgcaatc agatttgggt    1080
ttgttccctt tattttcata tttcttgtca tattcctttc tcaattatta ttttctactc    1140
ataacctcac gcaaaataac acagtcaaat caatcaaaat gtcaacagcc ggtaaagtta    1200
ttaagtgtaa agcggcagtt ttgtgggaag agaaaaagcc gtttagcata gaagaagtag    1260
aagtagcgcc accaaaagca cacgaggtta gaatcaagat ggttgccacc ggaatctgta    1320
gatccgacga ccatgtggtg agtggcactc tagttactcc tttgccagta atcgcgggac    1380
acgaggctgc cggaatcgtt gaatccatag gtgaaggtgt taccactgtt cgtcctggtg    1440
ataaagtgat cccactgttc actcctcaat gtggtaagtg tagagtctgc aaacatcctg    1500
agggtaattt ctgccttaaa aatgatttgt ctatgcctag aggtactatg caggatggta    1560
caagcagatt tacatgcaga gggaaaccta tacaccattt ccttggtact tctacatttt    1620
cccaatacac agtggtggac gagatatctg tcgctaaaat cgatgcagct tcaccactgg    1680
aaaaagtttg cttgataggg tgcggatttt ccaccggtta cggttccgca gttaaagttg    1740
caaaggttac acagggttcg acttgtgcag tattcggttt aggaggagta ggactaagcg    1800
ttattatggg gtgtaaagct gcaggcgcag cgaggattat aggtgtagac atcaataagg    1860
acaaatttgc aaaagctaag gaggtcgggg ctactgaatg tgttaaccct caagattata    1920
agaaaccaat acaagaagtc cttactgaaa tgtcaaacgg tggagttgat ttctcttttg    1980
aagttatagg ccgtcttgat actatggtaa ctgcgttgtc ctgctgtcaa gaggcatatg    2040
gagtcagtgt gatcgtaggt gttcctcctg attcacaaaa tttgtcgatg aatcctatgc    2100
tgttgctaag cggtcgtaca tggaaggag ctatatttgg cggttttaag agcaaggata    2160
gtgttccaaa acttgttgcc gactttatgg cgaagaagtt tgctcttgat cctttaatta    2220
cacatgtatt gccattcgag aaaatcaatg aagggtttga tttgttaaga agtggtgaat    2280
ctattcgtac aatttttaact ttttgattaa ttaagagtaa gcgaatttct tatgatttat    2340
gatttttatt attaaataag ttataaaaaa aataagtgta tacaaatttt aaagtgactc    2400
ttaggtttta aaacgaaaat tcttattctt gagtaactct ttcctgtagg tcaggttgct    2460
ttctcaggta tagcatgagg tcgctcttat tgaccacacc tctaccggca tgccgagcaa    2520
atgcctgcaa atcgctcccc atttcaccca attgtagata tgctaactcc agcaatgagt    2580
tgatgaatct cggtgtgtat tttatgtcct cagaggacaa cacctgtggt gtttaaacaa    2640
aggatgatat tgttctatta ttaagtttcg aaaggagacg gcattgaatc ttttttggcat    2700 agacgatttt gctttcttac gttatttaca tcggagagta tgtatttgtg tagttatgta    2760
cttagatatg taacttaatt taatgatatg gtgggggggct atcctccatg ccccatttcc    2820
agttatttga aggttcttgc gagttcaaac ctatgaagta aaacggtttc tttttagatg    2880
tatctttctt ggagtccaaa                                                2900
```

<210> SEQ ID NO 198
<211> LENGTH: 2656
<212> TYPE: DNA
<213> ORGANISM: Artificial Sequence
<220> FEATURE:
<223> OTHER INFORMATION: yprcdelta15delta ::PDC5-hADH-ADHt; Upstream
      region = nt 1-150; PDC5 promoter = nt 159-696; hADH coding
      region = nt 697-1824; ADH1 terminator = nt 1833-2148; Downstream
      region = nt 2157-2656

<400> SEQUENCE: 198

```
ccaaaaggaa tattgggtca gatgaatgga cgcgaatgca agacagaagt ccaaatcacg      60
tcaagacaaa gaaagaaaga aagaaaaact aacacattaa tgtagtttta aaatttcaaa     120
tccgaacaac agagcatagg gtttcgcaaa ggcgcgccta tttgtaatac gtatacgaat     180
tccttcaaca aaggccaagg aaataaagca aataacaata acaccattat tttaatttt     240 tttctattac tgtcgctaac acctgtatgg ttgcaaccag gtgagaatcc ttctgatgca     300
tactttatgc gtttatgcgt tttgcgcccc ttggaaaaaa attgattctc atcgtaaatg     360
catactacat gcgtttatgg gaaaagcctc catatccaaa ggtcgcgttt cttttagaaa     420
aactaatacg taaacctgca ttaaggtaag attatatcag aaaatgtgtt gcaagaaatg     480
cattatgcaa ttttttgatt atgacaatct ctcgaaagaa atttcatatg atgagacttg     540
aataatgcag cggcgcttgc taaaagaact tgtatataag agctgccatt ctcgatcaat     600
atactgtagt aagtcctttc ctctctttct tattcacactt atttcacata atcaatctca     660
aagagaacaa cacaatacaa taacaagaag aacaaaatgt caacagccgg taaagttatt     720
aagtgtaaag cggcagtttt gtgggaagag aaaaagccgt ttagcataga agaagtagaa     780
gtagcgccac caaaagcaca cgaggttaga atcaagatgg ttgccaccgg aatctgtaga     840
tccgacgacc atgtggtgag tggcactcta gttactcctt tgccagtaat cgcgggacac     900
gaggctgccg gaatcgttga atccataggt gaaggtgtta ccactgttcg tcctggtgat     960
aaagtgatcc cactgttcac tcctcaatgt ggtaagtgta gagtctgcaa acatcctgag    1020
ggtaatttct gccttaaaaa tgatttgtct atgcctagag gtactatgca ggatggtaca    1080
agcagattta catgcagagg gaaacctata caccatttcc ttggtacttc tacattttcc    1140
caatacacag tggtggacga gatatctgtc gctaaaatcg atgcagcttc accactggaa    1200
aaagtttgct tgatagggtg cggattttcc accggttacg gttccgcagt taagttgca    1260 aaggttacac agggttcgac ttgtgcagta ttcggtttag gaggagtagg actaagcgtt    1320
attatggggt gtaaagctgc aggcgcagcg aggattatag gtgtagacat caataaggac    1380
aaatttgcaa aagctaagga ggtcggggct actgaatgtg ttaaccctca agattataag    1440
aaaccaatac aagaagtcct tactgaaatg tcaaacggtg gagttgattt ctcttttgaa    1500
gttataggcc gtcttgatac tatggtaact gcgttgtcct gctgtcaaga ggcatatgga    1560
gtcagtgtga tcgtaggtgt tcctcctgat tcacaaaatt tgtcgatgaa tcctatgctg    1620
ttgctaagcg gtcgtacatg gaagggagct atatttggcg gttttaagag caaggatagt    1680
gttccaaaac ttgttgccga ctttatggcg aagaagtttg ctcttgatcc tttaattaca    1740
catgtattgc cattcgagaa aatcaatgaa gggtttgatt tgttaagaag tggtgaatct    1800
attcgtacaa ttttaacttt ttgattaatt aagagtaagc gaatttctta tgatttatga    1860 ttttattat taaataagtt ataaaaaaaa taagtgtata caaatttaa agtgactctt    1920 aggttttaaa acgaaaattc ttattcttga gtaactcttt cctgtaggtc aggttgcttt    1980
ctcaggtata gcatgaggtc gctcttattg accacacctc taccggcatg ccgagcaaat    2040
gcctgcaaat cgctccccat ttcacccaat tgtagatatg ctaactccag caatgagttg    2100
atgaatctcg gtgtgtattt tatgtcctca gaggacaaca cctgtggtgt ttaaacaatg    2160
gaaggtcggg atgagcatat acaagcacta agaagaacaa tacagaactc tacacggtat    2220
tattgtgcta caagctcgag taaaaccgag tgttttgacg atactaacgt tgttaagaaa    2280
gtaacttgtt atcaaactca ttaccaactt gtgattaatt ggtgaataat atgataattg    2340
```

```
tcgaaattcc attgttggta aagcctataa tattatgtat acagattata ctagaaattc    2400
tctcgagaat ataagaatcc ccaaaattga atcggtattt ctacatacta atattaccat    2460
tacttctcct ttcgttttat atgtttcatt cctattacat tatcgatctt tgcatttcag    2520
cttccattat atttgatgtc tgttttatgt ccccacgtta caccgcatgt gacagtatac    2580
tagtaacatg agtgctaccg aatagatgac attttagact ttcattccaa caacttggtt    2640
gacagaatgt tacgta                                                    2656

<210> SEQ ID NO 199
<211> LENGTH: 451
<212> TYPE: DNA
<213> ORGANISM: Artificial Sequence
<220> FEATURE:
<223> OTHER INFORMATION: ymr226c delta; Upstream region = nt 1-250;
      Downstream region = nt 251-451

<400> SEQUENCE: 199
gatgatgcta tttggtgcag agggtgatga gtaagttctc tttatcatct atatattact      60
cttatacact atacgactct actctatgac gtatagcatt gatatatatt aaggcacgac     120
accgattttt cttatcggag cgatataaaa agctgaagaa aggaggatag atgaaacagc     180
atggcgcata gaaagtgttc aagctcacta gtaaaggcgg gaaatagaac attgagaacg     240
tattttgata acctagctaa actaagtaaa tctgtatact ttttatacat gtaagacttt     300
ttagctattt cattcttccc tgaaccgttt tgcgcgattc tacggaatat accggcgaaa     360
taaaagagat aaacttatgg atcctcaaat agaggatgaa cagatgtgaa gaagaaacga     420
gcttaattat atcttcgcca tgataactaa a                                   451

<210> SEQ ID NO 200
<211> LENGTH: 1128
<212> TYPE: DNA
<213> ORGANISM: Artificial Sequence
<220> FEATURE:
<223> OTHER INFORMATION: ald6 delta::loxP; Upstream region = nt 1-500;
      loxP site = nt 551-584; Downstream region = nt 678-1128

<400> SEQUENCE: 200
tgatctgatg cgctttgcat atctcatatt ccttcactag cataaaaatc caaaaaaaaa      60
gaatatttag gccgaatgga attattcgta acgtcatacg aaaaaagttt caattcgtac     120
aatgcctggc atgttcattc gaatataagg ccgccgcctt ccagtcaggg tagccaaaag     180
tataatcccg ggtggaaact aaactaaaaa ccgtactcac aactttccgc ggacgctaac     240
agacaaatag acacactatc aggtcaggaa ctgccgtcac atacgacact gccctcacg     300 taagggcatg atagaattgg attatgtaaa aggtgaagat accattgtag aagcaaccag     360
cacgtcgccg tggctgatga ggtctcctct tgcccgggcc gcagaaaaga ggggcagtgg     420 cctgttttc gacataaatg aggggcatgg ccagcaccga gacgtcattg ttgcatatgg     480
cgtatccaag ccgaaacggc ggtaccgcaa gggcgaattc accttggcta actcgttgta     540
tcatcactgg ataacttcgt ataatgtatg ctatacgaag ttatctgaac attagaatac     600
gtaatccgca atgcggatcc tctagagtcg acctgcaggc atgctcgagc ggccgccagt     660
gtgatggata tctgcagaat tcgcccttgc cgatcgtgta ccaacctgca tttctttccg     720
tcatatacac aaaatacttt catataaact tacttggtct tacgtcataa ataaatatgt     780
atacatataa attaaaaaat ttggtttttat attttacaa aaagaatcgt ttacttcatt     840
tctccctttt aagcgataca atccatgaaa aaagagaaaa agagagaaca ggcttgtgcc     900
```

```
ttctttaaaa catcccacac aaaatcatat tgaattgaat tttacatctt aagctagtgt    960
acaacaactg ctatatccaa agaaaactaa cgtggaccgc ttttagagtt gagaaaaagg   1020
tttgaaaaaa atagcaatac aaagacttgt ttcatatata aaatacaggg agcacattga   1080
gctaatataa cataaacact gcgaaccaat tccaatcaaa aggtacac               1128
```

<210> SEQ ID NO 201
<211> LENGTH: 9612
<212> TYPE: DNA
<213> ORGANISM: Artificial Sequence
<220> FEATURE:
<223> OTHER INFORMATION: pLH702

<400> SEQUENCE: 201

```
aaacagtatg gaagaatgta agatggctaa gatttactac caagaagact gtaacttgtc     60
cttgttggat ggtaagacta tcgccgttat cggttacggt tctcaaggtc acgctcatgc    120
cctgaatgct aaggaatccg gttgtaacgt tatcattggt ttatacgaag gtgctaagga    180
ttggaaaaga gctgaagaac aaggtttcga agtctacacc gctgctgaag ctgctaagaa    240
ggctgacatc attatgatct tgatcaacga tgaaaagcag gctaccatgt acaaaaacga    300
catcgaacca acttggaagc cggtaacatg ttgatgttc gctcacggtt tcaacatcca    360
tttcggttgt attgttccac caaggacgt tgatgtcact atgatcgctc aaagggtcc    420 aggtcacacc gttagatccg aatacgaaga aggtaaaggt gtcccatgct ggttgctgt    480 cgaacaagac gctactggca aggctttgga tatggctttg gcctacgctt tagccatcgg    540
tggtgctaga gccggtgtct ggaaaactac cttcagaacc gaaactgaaa ccgacttgtt    600
cggtgaacaa gctgtttat gtggtggtgt ctgcgctttg atgcaggccg gttttgaaac    660
cttggttgaa gccggttacg acccaagaaa cgcttacttc gaatgtatcc acgaaatgaa    720
gttgatcgtt gacttgatct accaatctgg ttttctccggt atgcgttact ctatctccaa    780
cactgctgaa tacggtgact acattaccgg tccaaagatc attactgaag ataccaagaa    840
ggctatgaag aagattttgt ctgacattca agatggtacc tttgccaagg acttcttggt    900
tgacatgtct gatgctggtt cccaggtcca cttcaaggct atgagaaagt ggcctccga    960 acacccagct gaagttgtcg gtgaagaaat tagatccttg tactcctggt ccgacgaaga   1020
caagttgatt aacaactgat attttcctct ggccctgcag gcctatcaag tgctggaaac   1080 ttttttctctt ggaattttttg caacatcaag tcatagtcaa ttgaattgac ccaatttcac   1140
atttaagatt tttttttttt catccgacat acatctgtac actaggaagc ctgttttttc   1200
tgaagcagct tcaaatatat atattttta catatttatt atgattcaat gaacaatcta   1260
attaaatcga aacaagaac cgaaacgcga ataataatt tatttagatg gtgacaagtg   1320
tataagtcct catcgggaca gctacgattt ctctttcggt tttggctgag ctactggttg   1380
ctgtgacgca gcggcattag cgcggcgtta tgagctaccc tcgtggcctg aaagatggcg   1440
ggaataaagc ggaactaaaa attactgact gagccatatt gaggtcaatt tgtcaactcg   1500
tcaagtcacg tttggtggac ggccccttc caacgaatcg tatatactaa catgcgcgcg   1560
cttcctatat acacatatac atatatatat atatatatat gtgtgcgtgt atgtgtacac   1620
ctgtatttaa tttccttact cgcgggtttt tcttttttct caattcttgg cttcctctt   1680 ctcgagcgga ccgatcctc cgcggtgccg gcagatctat ttaaatggcg cgccgacgtc   1740
aggtggcact tttcggggaa atgtgcgcgg aaccccctatt tgtttatttt tctaaataca   1800
```

```
ttcaaatatg tatccgctca tgagacaata accctgataa atgcttcaat aatattgaaa    1860
aaggaagagt atgagtattc aacatttccg tgtcgccctt attccctttt ttgcggcatt    1920
ttgccttcct gttttttgctc acccagaaac gctggtgaaa gtaaaagatg ctgaagatca    1980
```
(corrected line 1920: `ttgccttcct gtttttgctc acccagaaac gctggtgaaa gtaaaagatg ctgaagatca    1980`)

```
gttgggtgca cgagtgggtt acatcgaact ggatctcaac agcggtaaga tccttgagag    2040
ttttcgcccc gaagaacgtt ttccaatgat gagcactttt aaagttctgc tatgtggcgc    2100
ggtattatcc cgtattgacg ccgggcaaga gcaactcggt cgccgcatac actattctca    2160
gaatgacttg gttgagtact caccagtcac agaaaagcat cttacggatg gcatgacagt    2220
aagagaatta tgcagtgctg ccataaccat gagtgataac actgcggcca acttacttct    2280
gacaacgatc ggaggaccga aggagctaac cgcttttttg cacaacatgg ggatcatgt     2340
aactcgcctt gatcgttggg aaccggagct gaatgaagcc ataccaaacg acgagcgtga    2400
caccacgatg cctgtagcaa tggcaacaac gttgcgcaaa ctattaactg gcgaactact    2460
tactctagct tcccggcaac aattaataga ctggatggag gcggataaag ttgcaggacc    2520
acttctgcgc tcggcccttc cggctggctg gtttattgct gataaatctg gagccggtga    2580
gcgtgggtct cgcggtatca ttgcagcact ggggccagat ggtaagccct cccgtatcgt    2640
agttatctac acgacgggga gtcaggcaac tatggatgaa cgaaatagac agatcgctga    2700
gataggtgcc tcactgatta agcattggta actgtcagac caagtttact catatatact    2760
ttagattgat ttaaaacttc atttttaatt taaaaggatc taggtgaaga tcctttttga    2820
taatctcatg accaaaatcc cttaacgtga gttttcgttc cactgagcgt cagaccccgt    2880
agaaaagatc aaaggatctt cttgagatcc tttttttctg cgcgtaatct gctgcttgca    2940
aacaaaaaaa ccaccgctac cagcggtggt ttgtttgccg gatcaagagc taccaactct    3000
ttttccgaag gtaactggct tcagcagagc gcagatacca atactgttc ttctagtgta     3060
gccgtagtta ggccaccact tcaagaactc tgtagcaccg cctacatacc tcgctctgct    3120
aatcctgtta ccagtggctg ctgccagtgg cgataagtcg tgtcttaccg ggttggactc    3180
aagacgatag ttaccggata aggcgcagcg gtcgggctga acggggggtt cgtgcacaca    3240
gcccagcttg gagcgaacga cctacaccga actgagatac ctacagcgtg agctatgaga    3300
aagcgccacg cttcccgaag ggagaaaggc ggacaggtat ccggtaagcg cagggtcgg    3360
aacaggagag cgcacgaggg agcttccagg gggaaacgcc tggtatcttt atagtcctgt    3420
cgggtttcgc cacctctgac ttgagcgtcg attttttgtga tgctcgtcag gggggcggag    3480
cctatggaaa aacgccagca acgcggcctt tttacggttc ctggccttt gctggccttt     3540
tgctcacatg ttctttcctg cgttatcccc tgattctgtg ataaccgta ttaccgcctt     3600
tgagtgagct gataccgctc gccgcagccg aacgaccgag cgcagcgagt cagtgagcga    3660
ggaagcggaa gagcgcccaa tacgcaaacc gcctctcccc gcgcgttggc cgattcatta    3720
atgcagctgg cacgacaggt ttcccgactg gaaagcgggc agtgagcgca acgcaattaa    3780
tgtgagttag ctcactcatt aggcaccca ggctttacac tttatgcttc cggctcgtat     3840
gttgtgtgga attgtgagcg ataacaatt tcacacagga acagctatg accatgatta     3900
cgccaagctt ttctttcca atttttttt tttcgtcatt ataaaaatca ttacgaccga     3960
gattcccggg taataactga tataattaaa ttgaagctct aatttgtgag tttagtatac    4020
atgcatttac ttataataca gttttttagt tttgctggcc gcatcttctc aaatatgctt    4080
cccagcctgc ttttctgtaa cgttcaccct ctacctagc atcccttccc tttgcaaata    4140
gtcctcttcc aacaataata atgtcagatc ctgtagagac cacatcatcc acggttctat    4200
```

-continued

```
actgttgacc caatgcgtct cccttgtcat ctaaacccac accgggtgtc ataatcaacc    4260
aatcgtaacc ttcatctctt ccacccatgt ctctttgagc aataaagccg ataacaaaat    4320
ctttgtcgct cttcgcaatg tcaacagtac ccttagtata ttctccagta gatagggagc    4380
ccttgcatga caattctgct aacatcaaaa ggcctctagg ttcctttgtt acttcttctg    4440
ccgcctgctt caaccgctta acaatacctg ggcccaccac accgtgtgca ttcgtaatgt    4500
ctgcccattc tgctattctg tatacacccg cagagtactg caatttgact gtattaccaa    4560
tgtcagcaaa ttttctgtct tcgaagagta aaaaattgta cttggcggat aatgccttta    4620
gcggcttaac tgtgccctcc atggaaaaat cagtcaagat atccacatgt gtttttagta    4680
aacaaatttt gggacctaat gcttcaacta actccagtaa ttccttggtg gtacgaacat    4740
ccaatgaagc acacaagttt gtttgctttt cgtgcatgat attaaatagc ttggcagcaa    4800
caggactagg atgagtagca gcacgttcct tatatgtagc tttcgacatg atttatcttc    4860
gtttcctgca ggttttttgtt ctgtgcagtt gggttaagaa tactgggcaa tttcatgttt    4920
cttcaacact acatatgcgt atatatacca atctaagtct gtgctccttc cttcgttctt    4980
ccttctgttc ggagattacc gaatcaaaaa aatttcaagg aaaccgaaat caaaaaaaag    5040
aataaaaaaa aaatgatgaa ttgaaaagct tgcatgcctg caggtcgact ctagtatact    5100
ccgtctactg tacgatacac ttccgctcag gtccttgtcc tttaacgagg ccttaccact    5160
cttttgttac tctattgatc cagctcagca aaggcagtgt gatctaagat tctatcttcg    5220
cgatgtagta aaactagcta gaccgagaaa gagactagaa atgcaaaagg cacttctaca    5280
atggctgcca tcattattat ccgatgtgac gctgcatttt tttttttttt tttttttttt    5340
tttttttttt tttttttttt tttttttttgt acaaatatca taaaaaaaga gaatcttttt    5400
aagcaaggat tttcttaact tcttcggcga cagcatcacc gacttcggtg gtactgttgg    5460
aaccacctaa atcaccagtt ctgatacctg catccaaaac cttttttaact gcatcttcaa    5520 tggctttacc ttcttcaggc aagttcaatg acaatttcaa catcattgca gcagacaaga    5580
tagtggcgat agggttgacc ttattctttg gcaaatctgg agcggaacca tggcatggtt    5640
cgtacaaacc aaatgcggtg ttcttgtctg gcaaagaggc caaggacgca gatggcaaca    5700
aacccaagga gcctgggata acggaggctt catcggagat gatatcacca aacatgttgc    5760
tggtgattat aataccattt aggtgggttg ggttcttaac taggatcatg gcggcagaat    5820
caatcaattg atgttgaact ttcaatgtag ggaattcgtt cttgatggtt cctccacag    5880 tttttctcca taatcttgaa gaggccaaaa cattagcttt atccaaggac caaataggca    5940
atggtggctc atgttgtagg gccatgaaag cggccattct tgtgattctt gcacttctg    6000 gaacggtgta ttgttcacta tcccaagcga caccatcacc atcgtcttcc tttctcttac    6060
caaagtaaat acctcccact aattctctaa caacaacgaa gtcagtacct ttagcaaatt    6120
gtggcttgat tggagataag tctaaaagag agtcggatgc aaagttacat ggtcttaagt    6180
tggcgtacaa ttgaagttct ttacggattt ttagtaaacc ttgttcaggt ctaacactac    6240
cggtacccca tttaggacca cccacagcac ctaacaaaac ggcatcagcc ttcttggagg    6300
cttccagcgc ctcatctgga agtggaacac ctgtagcatc gatagcagca ccaccaatta    6360
aatgattttc gaatcgaact tgacattgg aacgaacatc agaaatagct ttaagaacct    6420
taatggcttc ggctgtgatt tcttgaccaa cgtggtcacc tggcaaaacg acgatcttct    6480
taggggcaga cattacaatg gtatatcctt gaaatatata taaaaaaaaa aaaaaaaaaa    6540
```

-continued

```
aaaaaaaaaa atgcagcttc tcaatgatat tcgaatacgc tttgaggaga tacagcctaa    6600
tatccgacaa actgtttac agatttacga tcgtacttgt tacccatcat tgaattttga     6660
acatccgaac ctgggagttt tccctgaaac agatagtata tttgaacctg tataataata    6720
tatagtctag cgctttacgg aagacaatgt atgtatttcg gttcctggag aaactattgc    6780
atctattgca taggtaatct tgcacgtcgc atccccggtt cattttctgc gtttccatct    6840
tgcacttcaa tagcatatct ttgttaacga agcatctgtg cttcattttg tagaacaaaa    6900
atgcaacgcg agagcgctaa ttttcaaac aaagaatctg agctgcattt ttacagaaca     6960
gaaatgcaac gcgaaagcgc tattttacca acgaagaatc tgtgcttcat ttttgtaaaa    7020
caaaaatgca acgcgagagc gctaatttt caaacaaaga atctgagctg cattttaca     7080
gaacagaaat gcaacgcgag agcgctattt taccaacaaa gaatctatac ttcttttttg    7140
ttctacaaaa atgcatcccg agagcgctat ttttctaaca aagcatctta gattactttt    7200
tttctccttt gtgcgctcta taatgcagtc tcttgataac ttttttgcact gtaggtccgt   7260
taaggttaga agaaggctac tttggtgtct atttctctt ccataaaaaa agcctgactc     7320
cacttcccgc gtttactgat tactagcgaa gctgcgggtg cattttttca agataaaggc    7380
atccccgatt atattctata ccgatgtgga ttgcgcatac tttgtgaaca gaaagtgata    7440
gcgttgatga ttcttcattg gtcagaaaat tatgaacggt ttcttctatt ttgtctctat    7500
atactacgta taggaaatgt ttacattttc gtattgtttt cgattcactc tatgaatagt    7560
tcttactaca atttttttgt ctaaagagta atactagaga taaacataaa aaatgtagag    7620
gtcgagttta gatgcaagtt caaggagcga aaggtggatg ggtaggttat atagggatat    7680
agcacagaga tatatagcaa agagatactt ttgagcaatg tttgtggaag cggtattcgc    7740
aatattttag tagctcgtta cagtccggtg cgttttggt tttttgaaag tgcgtcttca     7800
gagcgctttt ggttttcaaa agcgctctga agttcctata cttttctagag aataggaact   7860
tcggaatagg aacttcaaag cgtttccgaa aacgagcgct tccgaaaatg caacgcgagc    7920
tgcgcacata cagctcactg ttcacgtcgc acctatatct gcgtgttgcc tgtatatata    7980
tatacatgag aagaacggca tagtgcgtgt ttatgcttaa atgcgtactt atatgcgtct    8040
atttatgtag gatgaaaggt agtctagtac ctcctgtgat attatcccat tccatgcggg    8100
gtatcgtatg cttccttcag cactacccct tagctgttct atatgctgcc actcctcaat    8160
tggattagtc tcatccttca atgctatcat ttccttgat attggatcat atgcatagta    8220
ccgagaaact agaggatctc ccattaccga catttgggcg ctatacgtgc atatgttcat    8280
gtatgtatct gtatttaaaa cacttttgta ttattttcc tcatatatgt gtataggttt    8340
atacggatga tttaattatt acttcaccac cctttatttc aggctgatat cttagccttg    8400
ttactagtca ccggtggcgg ccgcacctgg taaaacctct agtggagtag tagatgtaat    8460
caatgaagcg gaagccaaaa gaccagagta gaggcctata gaagaaactg cgatacccttt   8520
tgtgatggct aaacaaacag acatcttttt atatgttttt acttctgtat atcgtgaagt    8580
agtaagtgat aagcgaattt ggctaagaac gttgtaagtg aacaagggac ctcttttgcc    8640
tttcaaaaaa ggattaaatg gagttaatca ttgagattta gttttcgtta gattctgtat    8700
ccctaaataa ctcccttacc cgacgggaag gcacaaaaga cttgaataat agcaaacggc    8760
cagtagccaa gaccaaataa tactagagtt aactgatggt cttaaacagg cattacgtgg    8820
tgaactccaa gaccaatata caaaatatcg ataagttatt cttgcccacc aatttaagga    8880
gcctacatca ggacagtagt accattcctc agagaagagg tatacataac aagaaaatcg    8940
```

```
cgtgaacacc ttatataact tagcccgtta ttgagctaaa aaaccttgca aaatttccta    9000
tgaataagaa tacttcagac gtgataaaaa tttactttct aactcttctc acgctgcccc    9060
tatctgttct tccgctctac cgtgagaaat aaagcatcga gtacggcagt tcgctgtcac    9120
tgaactaaaa caataaggct agttcgaatg atgaacttgc ttgctgtcaa acttctgagt    9180
tgccgctgat gtgacactgt gacaataaat tcaaaccggt tatagcggtc tcctccggta    9240
ccggttctgc cacctccaat agagctcagt aggagtcaga acctctgcgg tggctgtcag    9300
tgactcatcc gcgtttcgta agttgtgcgc gtgcacattt cgcccgttcc cgctcatctt    9360
gcagcaggcg gaaattttca tcacgctgta ggacgcaaaa aaaaaataat taatcgtaca    9420
agaatcttgg aaaaaaaatt gaaaaatttt gtataaaagg gatgacctaa cttgactcaa    9480
tggcttttac acccagtatt ttcccttttcc ttgtttgtta caattataga agcaagacaa    9540
aaacatatag acaacctatt cctaggagtt atatttttt acccgtaccag caatataagt    9600 aaaaaactgt tt                                                        9612

<210> SEQ ID NO 202
<211> LENGTH: 7938
<212> TYPE: DNA
<213> ORGANISM: Artificial Sequence
<220> FEATURE:
<223> OTHER INFORMATION: pYZ067DkivDDhADH

<400> SEQUENCE: 202
tcgcgcgttt cggtgatgac ggtgaaaacc tctgacacat gcagctcccg gagacggtca      60
cagcttgtct gtaagcggat gccggagcag acaagcccg tcagggcgcg tcagcgggtg      120
ttggcgggtg tcggggctgg cttaactatg cggcatcaga gcagattgta ctgagagtgc      180
accataaatt cccgttttaa gagcttggtg agcgctagga gtcactgcca ggtatcgttt      240
gaacacggca ttagtcaggg aagtcataac acagtccttt cccgcaattt tctttttcta      300
ttactcttgg cctcctctag tacactctat attttttat gcctcggtaa tgattttcat      360 ttttttttt ccacctagcg gatgactctt tttttttctt agcgattggc attatcacat      420
aatgaattat acattatata agtaatgtg atttcttcga agaatatact aaaaaatgag      480
caggcaagat aaacgaaggc aaagatgaca gagcagaaag ccctagtaaa gcgtattaca      540
aatgaaacca agattcagat tgcgatctct ttaaagggtg gtcccctagc gatagagcac      600
tcgatcttcc cagaaaaaga ggcagaagca gtagcagaac aggccacaca atcgcaagtg      660
attaacgtcc acacaggtat agggtttctg gaccatatga tacatgctct ggccaagcat      720
tccggctggt cgctaatcgt tgagtgcatt ggtgacttac acatagacga ccatcacacc      780
actgaagact gcgggattgc tctcggtcaa gcttttaaag aggccctagg ggccgtgcgt      840
ggagtaaaaa ggtttggatc aggatttgcg ccttttggatg aggcactttc cagagcggtg      900
gtagatcttt cgaacaggcc gtacgcagtt gtcgaacttg gtttgcaaag ggagaaagta      960
ggagatctct cttgcgagat gatcccgcat tttcttgaaa gctttgcaga ggctagcaga     1020
attaccctcc acgttgattg tctgcgaggc aagaatgatc atcaccgtag tgagagtgcg     1080
ttcaaggctc ttgcggttgc cataagagaa gccacctcgc ccaatggtac caacgatgtt     1140
ccctccacca aaggtgttct tatgtagtga caccgattat ttaaagctgc agcatacgat     1200
atatatacat gtgtatatat gtataccgtat gaatgtcagt aagtatgtat acgaacagta     1260
tgatactgaa gatgacaagg taatgcatca ttctatacgt gtcattctga acgaggcgcg     1320
```

-continued

```
ctttcctttt ttcttttttgc ttttttcttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcattttt taaccaatag   1500
gccgaaatcg gcaaaatccc ttataaatca aagaataga ccgagatagg gttgagtgtt   1560
gttccagttt ggaacaagag tccactatta agaacgtgg actccaacgt caaagggcga   1620
aaaaccgtct atcagggcga tggcccacta cgtggccggc ttcacatacg ttgcatacgt   1680
cgatatagat aataatgata atgacagcag gattatcgta atacgtaata gctgaaaatc   1740
tcaaaaatgt gtgggtcatt acgtaaataa tgataggaat gggattcttc tattttcct   1800
ttttccattc tagcagccgt cgggaaaacg tggcatcctc tctttcgggc tcaattggag   1860
tcacgctgcc gtgagcatcc tctctttcca tatctaacaa ctgagcacgt aaccaatgga   1920
aaagcatgag cttagcgttg ctccaaaaaa gtattggatg gttaatacca tttgtctgtt   1980
ctcttctgac tttgactcct caaaaaaaaa aatctacaat caacagatcg cttcaattac   2040
gccctcacaa aaactttttt ccttcttctt cgcccacgtt aaattttatc cctcatgttg   2100
tctaacggat ttctgcactt gatttattat aaaaagacaa agacataata cttctctatc   2160
aatttcagtt attgttcttc cttgcgttat tcttctgttc ttcttttct tttgtcatat    2220
ataaccataa ccaagtaata catattcaaa cacgtgagta tgactgacaa aaaaactctt   2280
aaagacttaa gaaatcgtag ttctgtttac gattcaatgg ttaaatcacc taatcgtgct   2340
atgttgcgtg caactggtat gcaagatgaa gactttgaaa aacctatcgt cggtgtcatt   2400
tcaacttggg ctgaaaacac accttgtaat atccacttac atgactttgg taaactagcc   2460
aaagtcggtg ttaaggaagc tggtgcttgg ccagttcagt tcggaacaat cacggtttct   2520
gatggaatcg ccatgggaac ccaaggaatg cgtttctcct tgcacatctcg tgatattatt   2580
gcagattcta ttgaagcagc catgggaggt cataatgcgg atgcttttgt agccattggc   2640
ggttgtgata aaaacatgcc cggttctgtt atcgctatgg ctaacatgga tatcccagcc   2700
attttttgctt acggcggaac aattgcacct ggtaatttag acggcaaaga tatcgattta   2760
gtctctgtct ttgaaggtgt cggccattgg aaccacggcg atatgaccaa agaagaagtt   2820
aaagctttgg aatgtaatgc ttgtcccggt cctggaggct gcggtggtat gtatactgct   2880
aacacaatgg cgacagctat tgaagttttg gacttagcc ttccgggttc atcttctcac   2940
ccggctgaat ccgcagaaaa gaaagcagat attgaagaag ctggtcgcgc tgttgtcaaa   3000
atgctcgaaa tgggcttaaa accttctgac attttaacgc gtgaagcttt tgaagatgct   3060
attactgtaa ctatggctct gggaggttca accaactcaa cccttcacct cttagctatt   3120
gcccatgctg ctaatgtgga attgacactt gatgatttca atactttcca agaaaaagtt   3180
cctcatttgg ctgatttgaa accttctggt caatatgtat ccaagacct ttacaaggtc    3240
ggagggtac cagcagttat gaaatatctc cttaaaaatg gcttccttca tggtgaccgt   3300
atcacttgta ctggcaaaac agtcgctgaa aatttgaagg cttttgatga tttaacacct   3360
ggtcaaaagg ttattatgcc gcttgaaaat cctaaacgtg aagatggtcc gctcattatt   3420
ctccatggta acttggctcc agacggtgcc gttgccaaag tttctggtgt aaaagtgcgt   3480
cgtcatgtcg gtcctgctaa ggtctttaat tctgaagaag aagccattga agctgtcttg   3540
aatgatgata ttgttgatgg tgatgttgtt gtcgtacgtt ttgtaggacc aaagggcggt   3600
cctggtatgc ctgaaatgct ttcccttca tcaatgattg ttggtaaagg gcaaggtgaa    3660
aaagttgccc ttctgacaga tggccgcttc tcaggtggta cttatggtct tgtcgtgggt   3720
```

```
catatcgctc ctgaagcaca agatggcggt ccaatcgcct acctgcaaac aggagacata   3780
gtcactattg accaagacac taaggaatta cactttgata tctccgatga agagttaaaa   3840
catcgtcaag agaccattga attgccaccg ctctattcac gcggtatcct tggtaaatat   3900
gctcacatcg tttcgtctgc ttctagggga gccgtaacag acttttggaa gcctgaagaa   3960
actggcaaaa aatgttgtcc tggttgctgt ggttaagcgg ccgcgttaat tcaaattaat   4020
tgatatagtt ttttaatgag tattgaatct gtttagaaat aatggaatat tatttttatt   4080
tatttattta tattattggt cggctctttt cttctgaagg tcaatgacaa aatgatatga   4140
aggaaataat gatttctaaa attttacaac gtaagatatt tttacaaaag cctagctcat   4200
cttttgtcat gcactatttt actcacgctt gaaattaacg gccagtccac tgcggagtca   4260
tttcaaagtc atcctaatcg atctatcgtt tttgatagct cattttggag ttcgcgagga   4320
tcccagcttt tgttcccttt agtgagggtt aattgcgcgc ttggcgtaat catggtcata   4380
gctgtttcct gtgtgaaatt gttatccgct cacaattcca cacaacatac gagccggaag   4440
cataaagtgt aaagcctggg gtgcctaatg agtgagctaa ctcacattaa ttgcgttgcg   4500
ctcactgccc gctttccagt cgggaaacct gtcgtgccag ctgcattaat gaatcggcca   4560
acgcgcgggg agaggcggtt tgcgtattgg gcgctcttcc gcttcctcgc tcactgactc   4620
gctgcgctcg tcgttcggc tgcggcgagc ggtatcagct cactcaaagg cggtaatacg   4680
gttatccaca gaatcagggg ataacgcagg aaagaacatg tgagcaaaag gccagcaaaa   4740
ggccaggaac cgtaaaaagg ccgcgttgct ggcgtttttc cataggctcc gcccccctga   4800
cgagcatcac aaaaatcgac gctcaagtca gaggtggcga aacccgacag gactataaag   4860
ataccaggcg tttccccctg gaagctccct cgtgcgctct cctgttccga cctgccgct    4920
taccggatac ctgtccgcct ttctcccttc gggaagcgtg gcgctttctc atagctcacg   4980
ctgtaggtat ctcagttcgg tgtaggtcgt tcgctccaag ctgggctgtg tgcacgaacc   5040
ccccgttcag cccgaccgct gcgccttatc cggtaactat cgtcttgagt ccaacccggt   5100
aagacacgac ttatcgccac tggcagcagc cactggtaac aggattagca gagcgaggta   5160
tgtaggcggt gctacagagt tcttgaagtg gtggcctaac tacggctaca ctagaagaac   5220
agtatttggt atctgcgctc tgctgaagcc agttaccttc ggaaaaagag ttggtagctc   5280
ttgatccggc aaacaaacca ccgctggtag cggtggtttt tttgtttgca agcagcagat   5340
tacgcgcaga aaaaaaggat ctcaagaaga tcctttgatc ttttctacgg ggtctgacgc   5400
tcagtggaac gaaaactcac gttaagggat tttggtcatg agattatcaa aaaggatctt   5460
cacctagatc cttttaaatt aaaaatgaag ttttaaatca atctaaagta tatatgagta   5520
aacttggtct gacagttacc aatgcttaat cagtgaggca cctatctcag cgatctgtct   5580
atttcgttca tccatagttg cctgactccc cgtcgtgtag ataactacga tacgggaggg   5640
cttaccatct ggccccagtg ctgcaatgat accgcgagac ccacgctcac cggctccaga   5700
tttatcagca ataaaccagc cagccggaag ggccgagcgc agaagtggtc ctgcaacttt   5760
atccgcctcc atccagtcta ttaattgttg ccgggaagct agagtaagta gttcgccagt   5820
taatagtttg cgcaacgttg ttgccattgc tacaggcatc gtggtgtcac gctcgtcgtt   5880
tggtatggct tcattcagct ccggttccca acgatcaagg cgagttacat gatcccccat   5940
gttgtgcaaa aaagcggtta gctccttcgg tcctccgatc gttgtcagaa gtaagttggc   6000
cgcagtgtta tcactcatgg ttatggcagc actgcataat tctcttactg tcatgccatc   6060
```

-continued

```
cgtaagatgc ttttctgtga ctggtgagta ctcaaccaag tcattctgag aatagtgtat    6120
gcggcgaccg agttgctctt gcccggcgtc aatacgggat aataccgcgc cacatagcag    6180
aactttaaaa gtgctcatca ttggaaaacg ttcttcgggg cgaaaactct caaggatctt    6240
accgctgttg agatccagtt cgatgtaacc cactcgtgca cccaactgat cttcagcatc    6300
ttttactttc accagcgttt ctgggtgagc aaaaacagga aggcaaaatg ccgcaaaaaa    6360
gggaataagg gcgacacgga aatgttgaat actcatactc ttccttttc aatattattg     6420 aagcatttat cagggttatt gtctcatgag cggatacata tttgaatgta tttagaaaaa    6480
taaacaaata ggggttccgc gcacatttcc ccgaaaagtg ccacctgaac gaagcatctg    6540
tgcttcattt tgtagaacaa aaatgcaacg cgagagcgct aatttttcaa acaaagaatc    6600
tgagctgcat ttttacagaa cagaaatgca acgcgaaagc gctattttac caacgaagaa    6660
tctgtgcttc attttgtaa aacaaaaatg caacgcgaga gcgctaattt ttcaaacaaa     6720
gaatctgagc tgcattttta cagaacagaa atgcaacgcg agagcgctat tttaccaaca    6780
aagaatctat acttcttttt tgttctacaa aaatgcatcc cgagagcgct attttttctaa   6840 caaagcatct tagattactt tttttctcct ttgtgcgctc tataatgcag tctcttgata    6900 acttttttgca ctgtaggtcc gttaaggtta gaagaaggct actttggtgt ctattttctc   6960
ttccataaaa aaagcctgac tccacttccc gcgtttactg attactagcg aagctgcggg    7020 tgcattttt caagataaag gcatccccga ttatattcta taccgatgtg gattgcgcat     7080
actttgtgaa cagaaagtga tagcgttgat gattcttcat tggtcagaaa attatgaacg    7140
gtttcttcta ttttgtctct atatactacg tataggaaat gtttacattt tcgtattgtt    7200
ttcgattcac tctatgaata gttcttacta caattttttt gtctaaagag taatactaga    7260
gataaacata aaaaatgtag aggtcgagtt tagatgcaag ttcaaggagc gaaaggtgga    7320
tgggtaggtt atatagggat atagcacaga gatatatagc aaagagatac ttttgagcaa    7380
tgtttgtgga agcggtattc gcaatatttt agtagctcgt tacagtccgg tgcgtttttg    7440
gttttttgaa agtgcgtctt cagagcgctt ttggttttca aaagcgctct gaagttccta    7500
tactttctag agaataggaa cttcggaata ggaacttcaa agcgtttccg aaaacgagcg    7560
cttccgaaaa tgcaacgcga gctgcgcaca tacagctcac tgttcacgtc gcacctatat    7620
ctgcgtgttg cctgtatata tatatacatg agaagaacgg catagtgcgt gtttatgctt    7680
aaatgcgtac ttatatgcgt ctatttatgt aggatgaaag gtagtctagt acctcctgtg    7740
atattatccc attccatgcg gggtatcgta tgcttccttc agcactaccc tttagctgtt    7800
ctatatgctg ccactcctca attggattag tctcatcctt caatgctatc atttcctttg    7860
atattggatc atactaagaa accattatta tcatgacatt aacctataaa aataggcgta    7920
tcacgaggcc ctttcgtc                                                  7938
```